US012527571B2

(12) United States Patent
Adams et al.

(10) Patent No.: US 12,527,571 B2
(45) Date of Patent: Jan. 20, 2026

(54) SURGICAL INSTRUMENT COMPRISING A FIRING DRIVE INCLUDING A SELECTABLE LEVERAGE MECHANISM

(71) Applicant: Cilag GmbH International, Zug (CH)

(72) Inventors: Shane R. Adams, Lebanon, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 47 days.

(21) Appl. No.: 18/376,252

(22) Filed: Oct. 3, 2023

(65) Prior Publication Data

US 2024/0032913 A1 Feb. 1, 2024

Related U.S. Application Data

(62) Division of application No. 17/208,362, filed on Mar. 22, 2021, now Pat. No. 11,826,042.

(51) Int. Cl.

*A61B 17/068* (2006.01)
*A61B 17/072* (2006.01)
*A61B 17/00* (2006.01)

(52) U.S. Cl.

CPC ........ *A61B 17/0686* (2013.01); *A61B 17/072* (2013.01); *A61B 2017/00017* (2013.01); *A61B 2017/07257* (2013.01); *A61B 2017/07271* (2013.01)

(58) Field of Classification Search

CPC . A61B 17/068; A61B 17/0686; A61B 17/072; A61B 17/07207; A61B 2017/00017; A61B 2017/00407; A61B 2017/00398; A61B 2017/320052; A61B 2017/07257; A61B 2017/07271; A61B 2090/0801; A61B 2090/0811

USPC .......................................... 227/175.1–181.1

See application file for complete search history.

(56) References Cited

U.S. PATENT DOCUMENTS

| | | | |
|---|---|---|---|
| 66,052 | A | 6/1867 | Smith |
| 662,587 | A | 11/1900 | Blake |
| 670,748 | A | 3/1901 | Weddeler |
| 719,487 | A | 2/1903 | Minor |
| 804,229 | A | 11/1905 | Hutchinson |
| 903,739 | A | 11/1908 | Lesemann |
| 951,393 | A | 3/1910 | Hahn |
| 1,075,556 | A | 10/1913 | Fenoughty |
| 1,082,105 | A | 12/1913 | Anderson |
| 1,188,721 | A | 6/1916 | Bittner |

(Continued)

FOREIGN PATENT DOCUMENTS

| | | | |
|---|---|---|---|
| AU | 2012200594 | A1 | 2/2012 |
| AU | 2012203035 | A1 | 6/2012 |

(Continued)

OTHER PUBLICATIONS

ASTM procedure D2240-00, "Standard Test Method for Rubber Property-Durometer Hardness," (Published Aug. 2000).

(Continued)

*Primary Examiner* — Anna K Kinsaul
*Assistant Examiner* — Linda J. Hodge
(74) *Attorney, Agent, or Firm* — Lempia Summerfield Katz LLC

(57) ABSTRACT

A surgical instrument comprising a firing drive including a leverage selection mechanism is disclosed.

16 Claims, 65 Drawing Sheets

(56) References Cited

U.S. PATENT DOCUMENTS

| | | | |
|---|---|---|---|
| 1,306,107 | A | 6/1919 | Elliott |
| 1,314,601 | A | 9/1919 | McCaskey |
| 1,466,128 | A | 8/1923 | Hallenbeck |
| 1,677,337 | A | 7/1928 | Grove |
| 1,794,907 | A | 3/1931 | Kelly |
| 1,849,427 | A | 3/1932 | Hook |
| 1,912,783 | A | 6/1933 | Meyer |
| 1,944,116 | A | 1/1934 | Stratman |
| 1,954,048 | A | 4/1934 | Jeffrey et al. |
| 2,028,635 | A | 1/1936 | Wappler |
| 2,037,727 | A | 4/1936 | La Chapelle |
| 2,120,951 | A | 6/1938 | Hodgman |
| 2,132,295 | A | 10/1938 | Hawkins |
| 2,161,632 | A | 6/1939 | Nattenheimer |
| D120,434 | S | 5/1940 | Gold |
| 2,211,117 | A | 8/1940 | Hess |
| 2,214,870 | A | 9/1940 | West |
| 2,224,108 | A | 12/1940 | Ridgway |
| 2,224,882 | A | 12/1940 | Peck |
| 2,256,295 | A | 9/1941 | Schmid |
| 2,318,379 | A | 5/1943 | Davis et al. |
| 2,329,440 | A | 9/1943 | La Place |
| 2,377,581 | A | 6/1945 | Shaffrey |
| 2,406,389 | A | 8/1946 | Lee |
| 2,420,552 | A | 5/1947 | Morrill |
| 2,441,096 | A | 5/1948 | Happe |
| 2,448,741 | A | 9/1948 | Scott et al. |
| 2,450,527 | A | 10/1948 | Smith |
| 2,491,872 | A | 12/1949 | Neuman |
| 2,507,872 | A | 5/1950 | Unsinger |
| 2,526,902 | A | 10/1950 | Rublee |
| 2,527,256 | A | 10/1950 | Jackson |
| 2,578,686 | A | 12/1951 | Fish |
| 2,638,901 | A | 5/1953 | Sugarbaker |
| 2,674,149 | A | 4/1954 | Benson |
| 2,701,489 | A | 2/1955 | Osborn |
| 2,711,461 | A | 6/1955 | Happe |
| 2,724,289 | A | 11/1955 | Wight |
| 2,742,955 | A | 4/1956 | Dominguez |
| 2,804,848 | A | 9/1957 | O'Farrell et al. |
| 2,808,482 | A | 10/1957 | Zanichkowsky et al. |
| 2,825,178 | A | 3/1958 | Hawkins |
| 2,853,074 | A | 9/1958 | Olson |
| 2,856,192 | A | 10/1958 | Schuster |
| 2,887,004 | A | 5/1959 | Stewart |
| 2,957,353 | A | 10/1960 | Lewis |
| 2,959,974 | A | 11/1960 | Emrick |
| 3,026,744 | A | 3/1962 | Rouse |
| 3,032,769 | A | 5/1962 | Palmer |
| 3,035,256 | A | 5/1962 | Egbert |
| 3,060,972 | A | 10/1962 | Sheldon |
| 3,075,062 | A | 1/1963 | Iaccarino |
| 3,078,465 | A | 2/1963 | Bobrov |
| 3,079,606 | A | 3/1963 | Bobrov et al. |
| 3,080,564 | A | 3/1963 | Strekopitov et al. |
| 3,166,072 | A | 1/1965 | Sullivan, Jr. |
| 3,180,236 | A | 4/1965 | Beckett |
| 3,196,869 | A | 7/1965 | Scholl |
| 3,204,731 | A | 9/1965 | Bent et al. |
| 3,252,643 | A | 5/1966 | Strekopytov et al. |
| 3,266,494 | A | 8/1966 | Brownrigg et al. |
| 3,269,630 | A | 8/1966 | Fleischer |
| 3,269,631 | A | 8/1966 | Takaro |
| 3,275,211 | A | 9/1966 | Hirsch et al. |
| 3,315,863 | A | 4/1967 | O'Dea |
| 3,317,103 | A | 5/1967 | Cullen et al. |
| 3,317,105 | A | 5/1967 | Astafjev et al. |
| 3,357,296 | A | 12/1967 | Lefever |
| 3,359,978 | A | 12/1967 | Smith, Jr. |
| 3,377,893 | A | 4/1968 | Shorb |
| 3,480,193 | A | 11/1969 | Ralston |
| 3,490,675 | A | 1/1970 | Green et al. |
| 3,494,533 | A | 2/1970 | Green et al. |
| 3,499,591 | A | 3/1970 | Green |
| 3,503,396 | A | 3/1970 | Pierie et al. |
| 3,509,629 | A | 5/1970 | Kidokoro |
| 3,551,987 | A | 1/1971 | Wilkinson |
| 3,568,675 | A | 3/1971 | Harvey |
| 3,572,159 | A | 3/1971 | Tschanz |
| 3,583,393 | A | 6/1971 | Takahashi |
| 3,589,589 | A | 6/1971 | Akopov |
| 3,598,943 | A | 8/1971 | Barrett |
| 3,604,561 | A | 9/1971 | Mallina et al. |
| 3,608,549 | A | 9/1971 | Merrill |
| 3,616,278 | A | 10/1971 | Jansen |
| 3,618,842 | A | 11/1971 | Bryan |
| 3,635,394 | A | 1/1972 | Natelson |
| 3,638,652 | A | 2/1972 | Kelley |
| 3,640,317 | A | 2/1972 | Panfili |
| 3,643,851 | A | 2/1972 | Green et al. |
| 3,650,453 | A | 3/1972 | Smith, Jr. |
| 3,661,339 | A | 5/1972 | Shimizu |
| 3,661,666 | A | 5/1972 | Foster et al. |
| 3,662,939 | A | 5/1972 | Bryan |
| 3,685,250 | A | 8/1972 | Henry et al. |
| 3,688,966 | A | 9/1972 | Perkins et al. |
| 3,692,224 | A | 9/1972 | Astafiev et al. |
| 3,695,646 | A | 10/1972 | Mommsen |
| 3,709,221 | A | 1/1973 | Riely |
| 3,717,294 | A | 2/1973 | Green |
| 3,724,237 | A | 4/1973 | Wood |
| 3,726,755 | A | 4/1973 | Shannon |
| 3,727,904 | A | 4/1973 | Gabbey |
| 3,734,207 | A | 5/1973 | Fishbein |
| 3,740,994 | A | 6/1973 | De Carlo, Jr. |
| 3,744,495 | A | 7/1973 | Johnson |
| 3,746,002 | A | 7/1973 | Haller |
| 3,747,603 | A | 7/1973 | Adler |
| 3,747,692 | A | 7/1973 | Davidson |
| 3,751,902 | A | 8/1973 | Kingsbury et al. |
| 3,752,161 | A | 8/1973 | Bent |
| 3,797,494 | A | 3/1974 | Zaffaroni |
| 3,799,151 | A | 3/1974 | Fukaumi et al. |
| 3,808,452 | A | 4/1974 | Hutchinson |
| 3,815,476 | A | 6/1974 | Green et al. |
| 3,819,100 | A | 6/1974 | Noiles et al. |
| 3,821,919 | A | 7/1974 | Knohl |
| 3,822,818 | A | 7/1974 | Strekopytov et al. |
| 3,825,007 | A | 7/1974 | Rand |
| 3,826,978 | A | 7/1974 | Kelly |
| 3,836,171 | A | 9/1974 | Hayashi et al. |
| 3,837,555 | A | 9/1974 | Green |
| 3,841,474 | A | 10/1974 | Maier |
| 3,851,196 | A | 11/1974 | Hinds |
| 3,863,639 | A | 2/1975 | Kleaveland |
| 3,863,940 | A | 2/1975 | Cummings |
| 3,883,624 | A | 5/1975 | McKenzie et al. |
| 3,885,491 | A | 5/1975 | Curtis |
| 3,887,393 | A | 6/1975 | La Rue, Jr. |
| 3,892,228 | A | 7/1975 | Mitsui |
| 3,894,174 | A | 7/1975 | Cartun |
| 3,899,829 | A | 8/1975 | Storm et al. |
| 3,902,247 | A | 9/1975 | Fleer et al. |
| 3,940,844 | A | 3/1976 | Colby et al. |
| 3,944,163 | A | 3/1976 | Hayashi et al. |
| 3,950,686 | A | 4/1976 | Randall |
| 3,952,747 | A | 4/1976 | Kimmell, Jr. |
| 3,955,581 | A | 5/1976 | Spasiano et al. |
| 3,959,879 | A | 6/1976 | Sellers |
| RE28,932 | E | 8/1976 | Noiles et al. |
| 3,972,734 | A | 8/1976 | King |
| 3,973,179 | A | 8/1976 | Weber et al. |
| 3,981,051 | A | 9/1976 | Brumlik |
| 3,993,072 | A | 11/1976 | Zaffaroni |
| 3,999,110 | A | 12/1976 | Ramstrom et al. |
| 4,025,216 | A | 5/1977 | Hives |
| 4,027,746 | A | 6/1977 | Kine |
| 4,034,143 | A | 7/1977 | Sweet |
| 4,038,987 | A | 8/1977 | Komiya |
| 4,047,654 | A | 9/1977 | Alvarado |
| 4,054,108 | A | 10/1977 | Gill |
| 4,060,089 | A | 11/1977 | Noiles |
| 4,066,133 | A | 1/1978 | Voss |
| 4,085,337 | A | 4/1978 | Moeller |

(56) References Cited

U.S. PATENT DOCUMENTS 4,100,820 A 7/1978 Evett
4,106,446 A 8/1978 Yamada et al.
4,106,620 A 8/1978 Brimmer et al.
4,108,211 A 8/1978 Tanaka
4,111,206 A 9/1978 Vishnevsky et al.
4,127,227 A 11/1978 Green
4,129,059 A 12/1978 Van Eck
4,132,146 A 1/1979 Uhlig
4,135,517 A 1/1979 Reale
4,149,461 A 4/1979 Simeth
4,154,122 A 5/1979 Severin
4,160,857 A 7/1979 Nardella et al.
4,169,476 A 10/1979 Hiltebrandt
4,169,990 A 10/1979 Lerdman
4,180,285 A 12/1979 Reneau
4,185,701 A 1/1980 Boys
4,190,042 A 2/1980 Sinnreich
4,191,377 A * 3/1980 Burnside ............. G07F 17/3265 273/143 R
4,198,734 A 4/1980 Brumlik
4,198,982 A 4/1980 Fortner et al.
4,203,444 A 5/1980 Bonnell et al.
4,207,898 A 6/1980 Becht
4,213,562 A 7/1980 Garrett et al.
4,226,242 A 10/1980 Jarvik
4,239,431 A 12/1980 Davini
4,241,861 A 12/1980 Fleischer
4,244,372 A 1/1981 Kapitanov et al.
4,250,436 A 2/1981 Weissman
4,250,817 A 2/1981 Michel
4,261,244 A 4/1981 Becht et al.
4,272,002 A 6/1981 Moshofsky
4,272,662 A 6/1981 Simpson
4,274,304 A 6/1981 Curtiss
4,274,398 A 6/1981 Scott, Jr.
4,275,813 A 6/1981 Noiles
4,278,091 A 7/1981 Borzone
4,282,573 A 8/1981 Imai et al.
4,289,131 A 9/1981 Mueller
4,289,133 A 9/1981 Rothfuss
4,290,542 A 9/1981 Fedotov et al.
D261,356 S 10/1981 Robinson
4,293,604 A 10/1981 Campbell
4,296,654 A 10/1981 Mercer
4,296,881 A 10/1981 Lee
4,304,236 A 12/1981 Conta et al.
4,305,539 A 12/1981 Korolkov et al.
4,312,363 A 1/1982 Rothfuss et al.
4,312,685 A 1/1982 Riedl
4,317,451 A 3/1982 Cerwin et al.
4,319,576 A 3/1982 Rothfuss
4,321,002 A 3/1982 Froehlich
4,321,746 A 3/1982 Grinage
4,328,839 A 5/1982 Lyons et al.
4,331,277 A 5/1982 Green
4,340,331 A 7/1982 Savino
4,347,450 A 8/1982 Colligan
4,348,603 A 9/1982 Huber
4,349,028 A 9/1982 Green
4,350,151 A 9/1982 Scott
4,353,371 A 10/1982 Cosman
4,357,940 A 11/1982 Muller
4,361,057 A 11/1982 Kochera
4,366,544 A 12/1982 Shima et al.
4,369,013 A 1/1983 Abildgaard et al.
4,373,147 A 2/1983 Carlson, Jr.
4,376,380 A 3/1983 Burgess
4,379,457 A 4/1983 Gravener et al.
4,380,312 A 4/1983 Landrus
4,382,326 A 5/1983 Rabuse
4,383,634 A 5/1983 Green
4,389,963 A 6/1983 Pearson
4,393,728 A 7/1983 Larson et al.
4,394,613 A 7/1983 Cole
4,396,139 A 8/1983 Hall et al.
4,397,311 A 8/1983 Kanshin et al.
4,402,445 A 9/1983 Green
4,406,621 A 9/1983 Bailey
4,408,692 A 10/1983 Sigel et al.
4,409,057 A 10/1983 Molenda et al.
4,415,112 A 11/1983 Green
4,416,276 A 11/1983 Newton et al.
4,417,890 A 11/1983 Dennehey et al.
4,421,264 A 12/1983 Arter et al.
4,423,456 A 12/1983 Zaidenweber
4,425,915 A 1/1984 Ivanov
4,428,376 A 1/1984 Mericle
4,429,695 A 2/1984 Green
4,430,997 A 2/1984 DiGiovanni et al.
4,434,796 A 3/1984 Karapetian et al.
4,438,659 A 3/1984 Desplats
4,442,964 A 4/1984 Becht
4,448,194 A 5/1984 DiGiovanni et al.
4,451,743 A 5/1984 Suzuki et al.
4,452,376 A 6/1984 Klieman et al.
4,454,887 A 6/1984 Kruger
4,459,519 A 7/1984 Erdman
4,461,305 A 7/1984 Cibley
4,467,805 A 8/1984 Fukuda
4,468,597 A 8/1984 Baumard et al.
4,469,481 A 9/1984 Kobayashi
4,470,414 A 9/1984 Imagawa et al.
4,471,780 A 9/1984 Menges et al.
4,471,781 A 9/1984 Di Giovanni et al.
4,473,077 A 9/1984 Noiles et al.
4,475,679 A 10/1984 Fleury, Jr.
4,476,864 A 10/1984 Tezel
4,478,220 A 10/1984 Di Giovanni et al.
4,480,641 A 11/1984 Failla et al.
4,481,458 A 11/1984 Lane
4,483,562 A 11/1984 Schoolman
4,485,816 A 12/1984 Krumme
4,485,817 A 12/1984 Swiggett
4,486,928 A 12/1984 Tucker et al.
4,488,523 A 12/1984 Shichman
4,489,875 A 12/1984 Crawford et al.
4,493,983 A 1/1985 Taggert
4,494,057 A 1/1985 Hotta
4,499,895 A 2/1985 Takayama
4,500,024 A 2/1985 DiGiovanni et al.
D278,081 S 3/1985 Green
4,503,842 A 3/1985 Takayama
4,505,272 A 3/1985 Utyamyshev et al.
4,505,273 A 3/1985 Braun et al.
4,505,414 A 3/1985 Filipi
4,506,671 A 3/1985 Green
4,512,038 A 4/1985 Alexander et al.
4,514,477 A 4/1985 Kobayashi
4,520,817 A 6/1985 Green
4,522,327 A 6/1985 Korthoff et al.
4,523,707 A 6/1985 Blake, III et al.
4,526,174 A 7/1985 Froehlich
4,527,724 A 7/1985 Chow et al.
4,530,357 A 7/1985 Pawloski et al.
4,530,453 A 7/1985 Green
4,531,522 A 7/1985 Bedi et al.
4,532,927 A 8/1985 Miksza, Jr.
4,540,202 A 9/1985 Amphoux et al.
4,548,202 A 10/1985 Duncan
4,556,058 A 12/1985 Green
4,560,915 A 12/1985 Soultanian
4,565,109 A 1/1986 Tsay
4,565,189 A 1/1986 Mabuchi
4,566,620 A 1/1986 Green et al.
4,569,346 A 2/1986 Poirier
4,569,469 A 2/1986 Mongeon et al.
4,571,213 A 2/1986 Ishimoto
4,573,468 A 3/1986 Conta et al.
4,573,469 A 3/1986 Golden et al.
4,573,622 A 3/1986 Green et al.
4,576,165 A 3/1986 Green et al.
4,576,167 A 3/1986 Noiles
4,580,712 A 4/1986 Green
4,585,153 A 4/1986 Failla et al.

(56) References Cited

U.S. PATENT DOCUMENTS 4,586,501 A 5/1986 Claracq
4,586,502 A 5/1986 Bedi et al.
4,589,416 A 5/1986 Green
4,589,582 A 5/1986 Bilotti
4,589,870 A 5/1986 Citrin et al.
4,591,085 A 5/1986 Di Giovanni
RE32,214 E 7/1986 Schramm
4,597,753 A 7/1986 Turley
4,600,037 A 7/1986 Hatten
4,604,786 A 8/1986 Howie, Jr.
4,605,001 A 8/1986 Rothfuss et al.
4,605,004 A 8/1986 Di Giovanni et al.
4,606,343 A 8/1986 Conta et al.
4,607,636 A 8/1986 Kula et al.
4,607,638 A 8/1986 Crainich
4,608,980 A 9/1986 Aihara
4,608,981 A 9/1986 Rothfuss et al.
4,610,250 A 9/1986 Green
4,610,383 A 9/1986 Rothfuss et al.
4,612,933 A 9/1986 Brinkerhoff et al.
D286,180 S 10/1986 Korthoff
D286,442 S 10/1986 Korthoff et al.
4,617,893 A 10/1986 Donner et al.
4,617,914 A 10/1986 Ueda
4,617,935 A 10/1986 Cartmell et al.
4,619,262 A 10/1986 Taylor
4,619,391 A 10/1986 Sharkany et al.
4,624,401 A 11/1986 Gassner et al.
D287,278 S 12/1986 Spreckelmeier
4,628,459 A 12/1986 Shinohara et al.
4,628,636 A 12/1986 Folger
4,629,107 A 12/1986 Fedotov et al.
4,632,290 A 12/1986 Green et al.
4,633,861 A 1/1987 Chow et al.
4,633,874 A 1/1987 Chow et al.
4,634,419 A 1/1987 Kreizman et al.
4,635,638 A 1/1987 Weintraub et al.
4,641,076 A 2/1987 Linden
4,642,618 A 2/1987 Johnson et al.
4,642,738 A 2/1987 Meller
4,643,173 A 2/1987 Bell et al.
4,643,731 A 2/1987 Eckenhoff
4,646,722 A 3/1987 Silverstein et al.
4,646,745 A 3/1987 Noiles
4,651,734 A 3/1987 Doss et al.
4,652,820 A 3/1987 Maresca
4,654,028 A 3/1987 Suma
4,655,222 A 4/1987 Florez et al.
4,662,555 A 5/1987 Thornton
4,663,874 A 5/1987 Sano et al.
4,664,305 A 5/1987 Blake, III et al.
4,665,916 A 5/1987 Green
4,667,674 A 5/1987 Korthoff et al.
4,669,647 A 6/1987 Storace
4,671,278 A 6/1987 Chin
4,671,280 A 6/1987 Dorband et al.
4,671,445 A 6/1987 Barker et al.
4,672,964 A 6/1987 Dee et al.
4,675,944 A 6/1987 Wells
4,676,245 A 6/1987 Fukuda
4,679,460 A 7/1987 Yoshigai
4,679,719 A 7/1987 Kramer
4,684,051 A 8/1987 Akopov et al.
4,688,555 A 8/1987 Wardle
4,691,703 A 9/1987 Auth et al.
4,693,248 A 9/1987 Failla
4,698,579 A 10/1987 Richter et al.
4,700,703 A 10/1987 Resnick et al.
4,705,038 A 11/1987 Sjostrom et al.
4,708,141 A 11/1987 Inoue et al.
4,709,120 A 11/1987 Pearson
4,715,520 A 12/1987 Roehr, Jr. et al.
4,719,917 A 1/1988 Barrows et al.
4,721,099 A 1/1988 Chikama
4,722,340 A 2/1988 Takayama et al.
4,724,840 A 2/1988 McVay et al.
4,726,247 A 2/1988 Hormann
4,727,308 A 2/1988 Huljak et al.
4,728,020 A 3/1988 Green et al.
4,728,876 A 3/1988 Mongeon et al.
4,729,260 A 3/1988 Dudden
4,730,726 A 3/1988 Holzwarth
4,741,336 A 5/1988 Failla et al.
4,743,214 A 5/1988 Tai-Cheng
4,744,363 A 5/1988 Hasson
4,747,820 A 5/1988 Hornlein et al.
4,750,902 A 6/1988 Wuchinich et al.
4,752,024 A 6/1988 Green et al.
4,754,909 A 7/1988 Barker et al.
4,755,070 A 7/1988 Cerutti
4,761,326 A 8/1988 Barnes et al.
4,763,669 A 8/1988 Jaeger
4,767,044 A 8/1988 Green
D297,764 S 9/1988 Hunt et al.
4,773,420 A 9/1988 Green
4,777,780 A 10/1988 Holzwarth
4,781,186 A 11/1988 Simpson et al.
4,784,137 A 11/1988 Kulik et al.
4,787,387 A 11/1988 Burbank, III et al.
4,788,485 A 11/1988 Kawagishi et al.
D298,967 S 12/1988 Hunt
4,788,978 A 12/1988 Strekopytov et al.
4,790,225 A 12/1988 Moody et al.
4,790,314 A 12/1988 Weaver
4,805,617 A 2/1989 Bedi et al.
4,805,823 A 2/1989 Rothfuss
4,807,628 A 2/1989 Peters et al.
4,809,695 A 3/1989 Gwathmey et al.
4,815,460 A 3/1989 Porat et al.
4,817,643 A 4/1989 Olson
4,817,847 A 4/1989 Redtenbacher et al.
4,819,495 A 4/1989 Hormann
4,819,853 A 4/1989 Green
4,821,939 A 4/1989 Green
4,827,552 A 5/1989 Bojar et al.
4,827,911 A 5/1989 Broadwin et al.
4,828,542 A 5/1989 Hermann
4,828,944 A 5/1989 Yabe et al.
4,830,855 A 5/1989 Stewart
4,832,158 A 5/1989 Farrar et al.
4,833,937 A 5/1989 Nagano
4,834,096 A 5/1989 Oh et al.
4,834,720 A 5/1989 Blinkhorn
4,838,859 A 6/1989 Strassmann
4,844,068 A 7/1989 Arata et al.
4,848,637 A 7/1989 Pruitt
4,856,078 A 8/1989 Konopka
4,860,644 A 8/1989 Kohl et al.
4,862,891 A 9/1989 Smith
4,863,423 A 9/1989 Wallace
4,865,030 A 9/1989 Polyak
4,868,530 A 9/1989 Ahs
4,868,958 A 9/1989 Suzuki et al.
4,869,414 A 9/1989 Green et al.
4,869,415 A 9/1989 Fox
4,870,966 A 10/1989 Dellon et al.
4,873,977 A 10/1989 Avant et al.
4,875,486 A 10/1989 Rapoport et al.
4,880,015 A 11/1989 Nierman
4,890,613 A 1/1990 Golden et al.
4,892,244 A 1/1990 Fox et al.
4,893,622 A 1/1990 Green et al.
4,894,051 A 1/1990 Shiber
4,896,584 A 1/1990 Stoll et al.
4,896,678 A 1/1990 Ogawa
4,900,303 A 2/1990 Lemelson
4,903,697 A 2/1990 Resnick et al.
4,909,789 A 3/1990 Taguchi et al.
4,915,100 A 4/1990 Green
4,919,039 A * 4/1990 Nutter .................. F15B 15/061
91/40
4,919,679 A 4/1990 Averill et al.
4,921,479 A 5/1990 Grayzel
4,925,082 A 5/1990 Kim

(56) References Cited

U.S. PATENT DOCUMENTS

| | | | |
|---|---|---|---|
| 4,928,699 | A | 5/1990 | Sasai |
| 4,930,503 | A | 6/1990 | Pruitt |
| 4,930,674 | A | 6/1990 | Barak |
| 4,931,047 | A | 6/1990 | Broadwin et al. |
| 4,931,737 | A | 6/1990 | Hishiki |
| 4,932,960 | A | 6/1990 | Green et al. |
| 4,933,800 | A | 6/1990 | Yang |
| 4,933,843 | A | 6/1990 | Scheller et al. |
| D309,350 | S | 7/1990 | Sutherland et al. |
| 4,938,408 | A | 7/1990 | Bedi et al. |
| 4,941,623 | A | 7/1990 | Pruitt |
| 4,943,182 | A | 7/1990 | Hoblingre |
| 4,944,443 | A | 7/1990 | Oddsen et al. |
| 4,946,067 | A | 8/1990 | Kelsall |
| 4,948,327 | A | 8/1990 | Crupi, Jr. |
| 4,949,707 | A | 8/1990 | LeVahn et al. |
| 4,949,927 | A | 8/1990 | Madocks et al. |
| 4,950,268 | A | 8/1990 | Rink |
| 4,951,860 | A | 8/1990 | Peters et al. |
| 4,951,861 | A | 8/1990 | Schulze et al. |
| 4,954,960 | A | 9/1990 | Lo et al. |
| 4,955,959 | A | 9/1990 | Tompkins et al. |
| 4,957,212 | A | 9/1990 | Duck et al. |
| 4,962,681 | A | 10/1990 | Yang |
| 4,962,877 | A | 10/1990 | Hervas |
| 4,964,559 | A | 10/1990 | Deniega et al. |
| 4,964,863 | A | 10/1990 | Kanshin et al. |
| 4,965,709 | A | 10/1990 | Ngo |
| 4,970,656 | A | 11/1990 | Lo et al. |
| 4,973,274 | A | 11/1990 | Hirukawa |
| 4,973,302 | A | 11/1990 | Armour et al. |
| 4,976,173 | A | 12/1990 | Yang |
| 4,978,049 | A | 12/1990 | Green |
| 4,978,333 | A | 12/1990 | Broadwin et al. |
| 4,979,952 | A | 12/1990 | Kubota et al. |
| 4,984,564 | A | 1/1991 | Yuen |
| 4,986,808 | A | 1/1991 | Broadwin et al. |
| 4,987,049 | A | 1/1991 | Komamura et al. |
| 4,988,334 | A | 1/1991 | Hornlein et al. |
| 4,995,877 | A | 2/1991 | Ams et al. |
| 4,995,959 | A | 2/1991 | Metzner |
| 4,996,975 | A | 3/1991 | Nakamura |
| 5,001,649 | A | 3/1991 | Lo et al. |
| 5,002,543 | A | 3/1991 | Bradshaw et al. |
| 5,002,553 | A | 3/1991 | Shiber |
| 5,005,754 | A | 4/1991 | Van Overloop |
| 5,009,222 | A | 4/1991 | Her |
| 5,009,661 | A | 4/1991 | Michelson |
| 5,012,411 | A | 4/1991 | Policastro et al. |
| D316,875 | S | 5/1991 | Momot et al. |
| 5,014,898 | A | 5/1991 | Heidrich |
| 5,014,899 | A | 5/1991 | Presty et al. |
| 5,015,227 | A | 5/1991 | Broadwin et al. |
| 5,018,515 | A | 5/1991 | Gilman |
| 5,018,657 | A | 5/1991 | Pedlick et al. |
| 5,019,077 | A | 5/1991 | De Bastiani et al. |
| 5,024,652 | A | 6/1991 | Dumenek et al. |
| 5,024,671 | A | 6/1991 | Tu et al. |
| 5,025,559 | A | 6/1991 | McCullough |
| 5,027,834 | A | 7/1991 | Pruitt |
| 5,030,226 | A | 7/1991 | Green et al. |
| 5,031,814 | A | 7/1991 | Tompkins et al. |
| 5,033,552 | A | 7/1991 | Hu |
| 5,035,040 | A | 7/1991 | Kerrigan et al. |
| 5,037,018 | A | 8/1991 | Matsuda et al. |
| 5,038,109 | A | 8/1991 | Goble et al. |
| 5,038,247 | A | 8/1991 | Kelley et al. |
| 5,040,715 | A | 8/1991 | Green et al. |
| 5,042,707 | A | 8/1991 | Taheri |
| 5,056,953 | A | 10/1991 | Marot et al. |
| 5,060,658 | A | 10/1991 | Dejter, Jr. et al. |
| 5,061,269 | A | 10/1991 | Muller |
| 5,062,491 | A | 11/1991 | Takeshima et al. |
| 5,062,563 | A | 11/1991 | Green et al. |
| 5,065,929 | A | 11/1991 | Schulze et al. |
| 5,071,052 | A | 12/1991 | Rodak et al. |
| 5,071,430 | A | 12/1991 | de Salis et al. |
| 5,074,454 | A | 12/1991 | Peters |
| 5,077,506 | A | 12/1991 | Krause |
| 5,079,006 | A | 1/1992 | Urquhart |
| 5,080,556 | A | 1/1992 | Carreno |
| 5,083,695 | A | 1/1992 | Foslien et al. |
| 5,084,057 | A | 1/1992 | Green et al. |
| 5,088,979 | A | 2/1992 | Filipi et al. |
| 5,088,997 | A | 2/1992 | Delahuerga et al. |
| 5,089,606 | A | 2/1992 | Cole et al. |
| 5,094,247 | A | 3/1992 | Hernandez et al. |
| 5,098,004 | A | 3/1992 | Kerrigan |
| 5,098,360 | A | 3/1992 | Hirota |
| 5,100,042 | A | 3/1992 | Gravener et al. |
| 5,100,420 | A | 3/1992 | Green et al. |
| 5,100,422 | A | 3/1992 | Berguer et al. |
| 5,104,025 | A | 4/1992 | Main et al. |
| 5,104,397 | A | 4/1992 | Vasconcelos et al. |
| 5,104,400 | A | 4/1992 | Berguer et al. |
| 5,106,008 | A | 4/1992 | Tompkins et al. |
| 5,108,368 | A | 4/1992 | Hammerslag et al. |
| 5,109,722 | A | 5/1992 | Hufnagle et al. |
| 5,111,987 | A | 5/1992 | Moeinzadeh et al. |
| 5,116,349 | A | 5/1992 | Aranyi |
| D327,323 | S | 6/1992 | Hunt |
| 5,119,009 | A | 6/1992 | McCaleb et al. |
| 5,122,156 | A | 6/1992 | Granger et al. |
| 5,124,990 | A | 6/1992 | Williamson |
| 5,129,570 | A | 7/1992 | Schulze et al. |
| 5,135,483 | A | 8/1992 | Wagner et al. |
| 5,137,198 | A | 8/1992 | Nobis et al. |
| 5,139,513 | A | 8/1992 | Segato |
| 5,141,144 | A | 8/1992 | Foslien et al. |
| 5,142,932 | A | 9/1992 | Moya et al. |
| 5,151,102 | A | 9/1992 | Kamiyama et al. |
| 5,155,941 | A | 10/1992 | Takahashi et al. |
| 5,156,151 | A | 10/1992 | Imran |
| 5,156,315 | A | 10/1992 | Green et al. |
| 5,156,609 | A | 10/1992 | Nakao et al. |
| 5,156,614 | A | 10/1992 | Green et al. |
| 5,158,222 | A | 10/1992 | Green et al. |
| 5,158,567 | A | 10/1992 | Green |
| D330,699 | S | 11/1992 | Gill |
| 5,163,598 | A | 11/1992 | Peters et al. |
| 5,163,842 | A | 11/1992 | Nonomura |
| 5,164,652 | A | 11/1992 | Johnson et al. |
| 5,168,605 | A | 12/1992 | Bartlett |
| 5,170,925 | A | 12/1992 | Madden et al. |
| 5,171,247 | A | 12/1992 | Hughett et al. |
| 5,171,249 | A | 12/1992 | Stefanchik et al. |
| 5,171,253 | A | 12/1992 | Klieman |
| 5,173,053 | A | 12/1992 | Swanson et al. |
| 5,173,133 | A | 12/1992 | Morin et al. |
| 5,176,677 | A | 1/1993 | Wuchinich |
| 5,176,688 | A | 1/1993 | Narayan et al. |
| 5,180,375 | A | 1/1993 | Feibus |
| 5,181,514 | A | 1/1993 | Solomon et al. |
| 5,187,422 | A | 2/1993 | Izenbaard et al. |
| 5,188,102 | A | 2/1993 | Idemoto et al. |
| 5,188,111 | A | 2/1993 | Yates et al. |
| 5,188,126 | A | 2/1993 | Fabian et al. |
| 5,190,517 | A | 3/1993 | Zieve et al. |
| 5,190,544 | A | 3/1993 | Chapman et al. |
| 5,190,560 | A | 3/1993 | Woods et al. |
| 5,190,657 | A | 3/1993 | Heagle et al. |
| 5,192,288 | A | 3/1993 | Thompson et al. |
| 5,193,731 | A | 3/1993 | Aranyi |
| 5,195,505 | A | 3/1993 | Josefsen |
| 5,195,968 | A | 3/1993 | Lundquist et al. |
| 5,197,648 | A | 3/1993 | Gingold |
| 5,197,649 | A | 3/1993 | Bessler et al. |
| 5,197,966 | A | 3/1993 | Sommerkamp |
| 5,197,970 | A | 3/1993 | Green et al. |
| 5,200,280 | A | 4/1993 | Karasa |
| 5,201,750 | A | 4/1993 | Hocherl et al. |
| 5,205,459 | A | 4/1993 | Brinkerhoff et al. |
| 5,207,672 | A | 5/1993 | Roth et al. |
| 5,207,697 | A | 5/1993 | Carusillo et al. |

(56) References Cited

U.S. PATENT DOCUMENTS

| | | | |
|---|---|---|---|
| 5,209,747 | A | 5/1993 | Knoepfler |
| 5,209,756 | A | 5/1993 | Seedhom et al. |
| 5,211,649 | A | 5/1993 | Kohler et al. |
| 5,211,655 | A | 5/1993 | Hasson |
| 5,217,457 | A | 6/1993 | Delahuerga et al. |
| 5,217,478 | A | 6/1993 | Rexroth |
| 5,219,111 | A | 6/1993 | Bilotti et al. |
| 5,220,269 | A | 6/1993 | Chen et al. |
| 5,221,036 | A | 6/1993 | Takase |
| 5,221,281 | A | 6/1993 | Klicek |
| 5,222,945 | A | 6/1993 | Basnight |
| 5,222,963 | A | 6/1993 | Brinkerhoff et al. |
| 5,222,975 | A | 6/1993 | Crainich |
| 5,222,976 | A | 6/1993 | Yoon |
| 5,223,675 | A | 6/1993 | Taft |
| D337,962 | S | 8/1993 | Avitan |
| D338,729 | S | 8/1993 | Sprecklemeier et al. |
| 5,234,447 | A | 8/1993 | Kaster et al. |
| 5,236,269 | A | 8/1993 | Handy |
| 5,236,424 | A | 8/1993 | Imran |
| 5,236,440 | A | 8/1993 | Hlavacek |
| 5,236,629 | A | 8/1993 | Mahabadi et al. |
| 5,239,981 | A | 8/1993 | Anapliotis |
| 5,240,163 | A | 8/1993 | Stein et al. |
| 5,242,456 | A | 9/1993 | Nash et al. |
| 5,242,457 | A | 9/1993 | Akopov et al. |
| 5,244,462 | A | 9/1993 | Delahuerga et al. |
| 5,246,156 | A | 9/1993 | Rothfuss et al. |
| 5,246,443 | A | 9/1993 | Mai |
| 5,251,801 | A | 10/1993 | Ruckdeschel et al. |
| 5,253,793 | A | 10/1993 | Green et al. |
| 5,258,007 | A | 11/1993 | Spetzler et al. |
| 5,258,008 | A | 11/1993 | Wilk |
| 5,258,009 | A | 11/1993 | Conners |
| 5,258,010 | A | 11/1993 | Green et al. |
| 5,258,012 | A | 11/1993 | Luscombe et al. |
| 5,259,366 | A | 11/1993 | Reydel et al. |
| 5,259,835 | A | 11/1993 | Clark et al. |
| 5,260,637 | A | 11/1993 | Pizzi |
| 5,261,135 | A | 11/1993 | Mitchell |
| 5,261,877 | A | 11/1993 | Fine et al. |
| 5,261,922 | A | 11/1993 | Hood |
| 5,263,629 | A | 11/1993 | Trumbull et al. |
| 5,263,937 | A | 11/1993 | Shipp |
| 5,263,973 | A | 11/1993 | Cook |
| 5,264,218 | A | 11/1993 | Rogozinski |
| 5,268,622 | A | 12/1993 | Philipp |
| 5,269,794 | A | 12/1993 | Rexroth |
| 5,271,543 | A | 12/1993 | Grant et al. |
| 5,271,544 | A | 12/1993 | Fox et al. |
| RE34,519 | E | 1/1994 | Fox et al. |
| 5,275,322 | A | 1/1994 | Brinkerhoff et al. |
| 5,275,323 | A | 1/1994 | Schulze et al. |
| 5,275,608 | A | 1/1994 | Forman et al. |
| 5,279,416 | A | 1/1994 | Malec et al. |
| 5,281,216 | A | 1/1994 | Klicek |
| 5,281,400 | A | 1/1994 | Berry, Jr. |
| 5,282,806 | A | 2/1994 | Haber et al. |
| 5,282,826 | A | 2/1994 | Quadri |
| 5,282,829 | A | 2/1994 | Hermes |
| 5,284,128 | A | 2/1994 | Hart |
| 5,285,381 | A | 2/1994 | Iskarous et al. |
| 5,285,945 | A | 2/1994 | Brinkerhoff et al. |
| 5,286,253 | A | 2/1994 | Fucci |
| 5,289,963 | A | 3/1994 | McGarry et al. |
| 5,290,271 | A | 3/1994 | Jernberg |
| 5,290,310 | A | 3/1994 | Makower et al. |
| 5,291,133 | A | 3/1994 | Gokhale et al. |
| 5,292,053 | A | 3/1994 | Bilotti et al. |
| 5,293,024 | A | 3/1994 | Sugahara et al. |
| 5,297,714 | A | 3/1994 | Kramer |
| 5,300,087 | A | 4/1994 | Knopfler |
| 5,302,148 | A | 4/1994 | Heinz |
| 5,303,606 | A | 4/1994 | Kokinda |
| 5,304,204 | A | 4/1994 | Bregen |
| D347,474 | S | 5/1994 | Olson |
| 5,307,976 | A | 5/1994 | Olson et al. |
| 5,308,353 | A | 5/1994 | Beurrier |
| 5,308,358 | A | 5/1994 | Bond et al. |
| 5,308,576 | A | 5/1994 | Green et al. |
| 5,309,387 | A | 5/1994 | Mori et al. |
| 5,309,927 | A | 5/1994 | Welch |
| 5,312,023 | A | 5/1994 | Green et al. |
| 5,312,024 | A | 5/1994 | Grant et al. |
| 5,312,329 | A | 5/1994 | Beaty et al. |
| 5,313,935 | A | 5/1994 | Kortenbach et al. |
| 5,313,967 | A | 5/1994 | Lieber et al. |
| 5,314,424 | A | 5/1994 | Nicholas |
| 5,314,445 | A | 5/1994 | Heidmueller et al. |
| 5,314,466 | A | 5/1994 | Stern et al. |
| 5,318,221 | A | 6/1994 | Green et al. |
| 5,318,589 | A | 6/1994 | Lichtman |
| 5,320,627 | A | 6/1994 | Sorensen et al. |
| D348,930 | S | 7/1994 | Olson |
| 5,326,013 | A | 7/1994 | Green et al. |
| 5,329,923 | A | 7/1994 | Lundquist |
| 5,330,486 | A | 7/1994 | Wilk |
| 5,330,487 | A | 7/1994 | Thornton et al. |
| 5,330,502 | A | 7/1994 | Hassler et al. |
| 5,331,971 | A | 7/1994 | Bales et al. |
| 5,332,142 | A | 7/1994 | Robinson et al. |
| 5,333,422 | A | 8/1994 | Warren et al. |
| 5,333,772 | A | 8/1994 | Rothfuss et al. |
| 5,333,773 | A | 8/1994 | Main et al. |
| 5,334,183 | A | 8/1994 | Wuchinich |
| 5,336,130 | A | 8/1994 | Ray |
| 5,336,229 | A | 8/1994 | Noda |
| 5,336,232 | A | 8/1994 | Green et al. |
| 5,338,317 | A | 8/1994 | Hasson et al. |
| 5,339,799 | A | 8/1994 | Kami et al. |
| 5,341,724 | A | 8/1994 | Vatel |
| 5,341,807 | A | 8/1994 | Nardella |
| 5,341,810 | A | 8/1994 | Dardel |
| 5,342,380 | A | 8/1994 | Hood |
| 5,342,381 | A | 8/1994 | Tidemand |
| 5,342,385 | A | 8/1994 | Norelli et al. |
| 5,342,395 | A | 8/1994 | Jarrett et al. |
| 5,342,396 | A | 8/1994 | Cook |
| 5,343,382 | A | 8/1994 | Hale et al. |
| 5,343,391 | A | 8/1994 | Mushabac |
| 5,344,059 | A | 9/1994 | Green et al. |
| 5,344,060 | A | 9/1994 | Gravener et al. |
| 5,344,454 | A | 9/1994 | Clarke et al. |
| 5,346,504 | A | 9/1994 | Ortiz et al. |
| 5,348,259 | A | 9/1994 | Blanco et al. |
| 5,350,104 | A | 9/1994 | Main et al. |
| 5,350,355 | A | 9/1994 | Sklar |
| 5,350,388 | A | 9/1994 | Epstein |
| 5,350,391 | A | 9/1994 | Iacovelli |
| 5,350,400 | A | 9/1994 | Esposito et al. |
| 5,352,229 | A | 10/1994 | Goble et al. |
| 5,352,235 | A | 10/1994 | Koros et al. |
| 5,352,238 | A | 10/1994 | Green et al. |
| 5,353,798 | A | 10/1994 | Sieben |
| 5,354,215 | A | 10/1994 | Viracola |
| 5,354,250 | A | 10/1994 | Christensen |
| 5,354,303 | A | 10/1994 | Spaeth et al. |
| 5,355,897 | A | 10/1994 | Pietrafitta et al. |
| 5,356,006 | A | 10/1994 | Alpern et al. |
| 5,356,064 | A | 10/1994 | Green et al. |
| 5,358,506 | A | 10/1994 | Green et al. |
| 5,358,510 | A | 10/1994 | Luscombe et al. |
| 5,359,231 | A | 10/1994 | Flowers et al. |
| D352,780 | S | 11/1994 | Glaeser et al. |
| 5,359,993 | A | 11/1994 | Slater et al. |
| 5,360,305 | A | 11/1994 | Kerrigan |
| 5,360,428 | A | 11/1994 | Hutchinson, Jr. |
| 5,361,902 | A | 11/1994 | Abidin et al. |
| 5,364,001 | A | 11/1994 | Bryan |
| 5,364,002 | A | 11/1994 | Green et al. |
| 5,364,003 | A | 11/1994 | Williamson, IV |
| 5,366,133 | A | 11/1994 | Geiste |
| 5,366,134 | A | 11/1994 | Green et al. |
| 5,366,479 | A | 11/1994 | McGarry et al. |

(56) References Cited

U.S. PATENT DOCUMENTS 5,368,015 A 11/1994 Wilk
5,368,592 A 11/1994 Stern et al.
5,368,599 A 11/1994 Hirsch et al.
5,369,565 A 11/1994 Chen et al.
5,370,645 A 12/1994 Klicek et al.
5,372,124 A 12/1994 Takayama et al.
5,372,596 A 12/1994 Klicek et al.
5,372,602 A 12/1994 Burke
5,374,277 A 12/1994 Hassler
5,375,588 A 12/1994 Yoon
5,376,095 A 12/1994 Ortiz
5,379,933 A 1/1995 Green et al.
5,381,649 A 1/1995 Webb
5,381,782 A 1/1995 DeLaRama et al.
5,381,943 A 1/1995 Allen et al.
5,382,247 A 1/1995 Cimino et al.
5,383,460 A 1/1995 Jang et al.
5,383,738 A 1/1995 Herbermann
5,383,874 A 1/1995 Jackson et al.
5,383,880 A 1/1995 Hooven
5,383,881 A 1/1995 Green et al.
5,383,882 A 1/1995 Buess et al.
5,383,888 A 1/1995 Zvenyatsky et al.
5,383,895 A 1/1995 Holmes et al.
5,388,568 A 2/1995 van der Heide
5,388,748 A * 2/1995 Davignon ............... B65C 7/006
227/67
5,389,072 A 2/1995 Imran
5,389,098 A 2/1995 Tsuruta et al.
5,389,102 A 2/1995 Green et al.
5,389,104 A 2/1995 Hahnen et al.
5,391,180 A 2/1995 Tovey et al.
5,392,979 A 2/1995 Green et al.
5,395,030 A 3/1995 Kuramoto et al.
5,395,033 A 3/1995 Byrne et al.
5,395,034 A 3/1995 Allen et al.
5,395,312 A 3/1995 Desai
5,395,384 A 3/1995 Duthoit et al.
5,397,046 A 3/1995 Savage et al.
5,397,324 A 3/1995 Carroll et al.
5,400,267 A 3/1995 Denen et al.
5,403,276 A 4/1995 Schechter et al.
5,403,312 A 4/1995 Yates et al.
5,404,106 A 4/1995 Matsuda
5,404,870 A 4/1995 Brinkerhoff et al.
5,404,960 A 4/1995 Wada et al.
5,405,072 A 4/1995 Zlock et al.
5,405,073 A 4/1995 Porter
5,405,344 A 4/1995 Williamson et al.
5,405,360 A 4/1995 Tovey
5,407,293 A 4/1995 Crainich
5,408,409 A 4/1995 Glassman et al.
5,409,498 A 4/1995 Braddock et al.
5,409,703 A 4/1995 McAnalley et al.
D357,981 S 5/1995 Green et al.
5,411,481 A 5/1995 Allen et al.
5,411,508 A 5/1995 Bessler et al.
5,413,107 A 5/1995 Oakley et al.
5,413,267 A 5/1995 Solyntjes et al.
5,413,268 A 5/1995 Green et al.
5,413,272 A 5/1995 Green et al.
5,413,573 A 5/1995 Koivukangas
5,415,334 A 5/1995 Williamson et al.
5,415,335 A 5/1995 Knodell, Jr.
5,417,203 A 5/1995 Tovey et al.
5,417,361 A 5/1995 Williamson, IV
5,419,766 A 5/1995 Chang et al.
5,421,829 A 6/1995 Olichney et al.
5,422,567 A 6/1995 Matsunaga
5,423,471 A 6/1995 Mastri et al.
5,423,809 A 6/1995 Klicek
5,423,835 A 6/1995 Green et al.
5,425,355 A 6/1995 Kulick
5,425,745 A 6/1995 Green et al.
5,427,298 A 6/1995 Tegtmeier
5,431,322 A 7/1995 Green et al.
5,431,323 A 7/1995 Smith et al.
5,431,645 A 7/1995 Smith et al.
5,431,654 A 7/1995 Nic
5,431,666 A 7/1995 Sauer et al.
5,431,668 A 7/1995 Burbank, III et al.
5,433,721 A 7/1995 Hooven et al.
5,437,681 A 8/1995 Meade et al.
5,438,302 A 8/1995 Goble
5,438,997 A 8/1995 Sieben et al.
5,439,155 A 8/1995 Viola
5,439,156 A 8/1995 Grant et al.
5,439,479 A 8/1995 Shichman et al.
5,441,191 A 8/1995 Linden
5,441,193 A 8/1995 Gravener
5,441,483 A 8/1995 Avitall
5,441,494 A 8/1995 Ortiz
5,441,499 A 8/1995 Fritzsch
5,443,197 A 8/1995 Malis et al.
5,443,198 A 8/1995 Viola et al.
5,443,463 A 8/1995 Stern et al.
5,444,113 A 8/1995 Sinclair et al.
5,445,155 A 8/1995 Sieben
5,445,304 A 8/1995 Plyley et al.
5,445,604 A 8/1995 Lang
5,445,644 A 8/1995 Pietrafitta et al.
5,446,646 A 8/1995 Miyazaki
5,447,265 A 9/1995 Vidal et al.
5,447,417 A 9/1995 Kuhl et al.
5,447,513 A 9/1995 Davison et al.
5,449,355 A 9/1995 Rhum et al.
5,449,365 A 9/1995 Green et al.
5,449,370 A 9/1995 Vaitekunas
5,452,836 A 9/1995 Huitema et al.
5,452,837 A 9/1995 Williamson, IV et al.
5,454,378 A 10/1995 Palmer et al.
5,454,822 A 10/1995 Schob et al.
5,454,824 A 10/1995 Fontayne et al.
5,454,827 A 10/1995 Aust et al.
5,456,401 A 10/1995 Green et al.
5,456,917 A 10/1995 Wise et al.
5,458,279 A 10/1995 Plyley
5,458,579 A 10/1995 Chodorow et al.
5,462,215 A 10/1995 Viola et al.
5,464,013 A 11/1995 Lemelson
5,464,144 A 11/1995 Guy et al.
5,464,300 A 11/1995 Crainich
5,465,819 A 11/1995 Weilant et al.
5,465,894 A 11/1995 Clark et al.
5,465,895 A 11/1995 Knodel et al.
5,465,896 A 11/1995 Allen et al.
5,466,020 A 11/1995 Page et al.
5,467,911 A 11/1995 Tsuruta et al.
5,468,253 A 11/1995 Bezwada et al.
5,470,006 A 11/1995 Rodak
5,470,007 A 11/1995 Plyley et al.
5,470,008 A 11/1995 Rodak
5,470,009 A 11/1995 Rodak
5,470,010 A 11/1995 Rothfuss et al.
5,471,129 A 11/1995 Mann
5,472,132 A 12/1995 Savage et al.
5,472,442 A 12/1995 Klicek
5,473,204 A 12/1995 Temple
5,474,057 A 12/1995 Makower et al.
5,474,223 A 12/1995 Viola et al.
5,474,566 A 12/1995 Alesi et al.
5,474,570 A 12/1995 Kockerling et al.
5,474,738 A 12/1995 Nichols et al.
5,476,206 A 12/1995 Green et al.
5,476,479 A 12/1995 Green et al.
5,476,481 A 12/1995 Schondorf
5,478,003 A 12/1995 Green et al.
5,478,308 A 12/1995 Cartmell et al.
5,478,354 A 12/1995 Tovey et al.
5,480,089 A 1/1996 Blewett
5,480,409 A 1/1996 Riza
5,482,197 A 1/1996 Green et al.
5,483,630 A 1/1996 Unuma et al.
5,483,952 A 1/1996 Aranyi

(56) References Cited

U.S. PATENT DOCUMENTS 5,484,095 A 1/1996 Green et al.
5,484,398 A 1/1996 Stoddard
5,484,451 A 1/1996 Akopov et al.
5,485,947 A 1/1996 Olson et al.
5,485,952 A 1/1996 Fontayne
5,487,377 A 1/1996 Smith et al.
5,487,499 A 1/1996 Sorrentino et al.
5,487,500 A 1/1996 Knodel et al.
5,489,058 A 2/1996 Plyley et al.
5,489,256 A 2/1996 Adair
5,489,290 A 2/1996 Furnish
5,490,819 A 2/1996 Nicholas et al.
5,492,671 A 2/1996 Krafft
5,496,312 A 3/1996 Klicek
5,496,317 A 3/1996 Goble et al.
5,497,933 A 3/1996 DeFonzo et al.
5,498,164 A 3/1996 Ward et al.
5,498,838 A 3/1996 Furman
5,501,654 A 3/1996 Failla et al.
5,503,320 A 4/1996 Webster et al.
5,503,635 A 4/1996 Sauer et al.
5,503,638 A 4/1996 Cooper et al.
5,505,363 A 4/1996 Green et al.
5,507,425 A 4/1996 Ziglioli
5,507,426 A 4/1996 Young et al.
5,507,773 A 4/1996 Huitema et al.
5,508,080 A 4/1996 Sorimachi et al.
5,509,596 A 4/1996 Green et al.
5,509,916 A 4/1996 Taylor
5,509,918 A 4/1996 Romano
5,510,138 A 4/1996 Sanftleben et al.
5,511,564 A 4/1996 Wilk
5,514,129 A 5/1996 Smith
5,514,149 A 5/1996 Green et al.
5,514,157 A 5/1996 Nicholas et al.
5,518,163 A 5/1996 Hooven
5,518,164 A 5/1996 Hooven
5,520,609 A 5/1996 Moll et al.
5,520,634 A 5/1996 Fox et al.
5,520,678 A 5/1996 Heckele et al.
5,520,700 A 5/1996 Beyar et al.
5,522,817 A 6/1996 Sander et al.
5,522,831 A 6/1996 Sleister et al.
5,527,264 A 6/1996 Moll et al.
5,527,320 A 6/1996 Carruthers et al.
5,529,235 A 6/1996 Boiarski et al.
D372,086 S 7/1996 Grasso et al.
5,531,305 A 7/1996 Roberts et al.
5,531,744 A 7/1996 Nardella et al.
5,531,856 A 7/1996 Moll et al.
5,533,521 A 7/1996 Granger
5,533,581 A 7/1996 Barth et al.
5,533,661 A 7/1996 Main et al.
5,535,934 A 7/1996 Boiarski et al.
5,535,935 A 7/1996 Vidal et al.
5,535,937 A 7/1996 Boiarski et al.
5,540,375 A 7/1996 Bolanos et al.
5,540,705 A 7/1996 Meade et al.
5,541,376 A 7/1996 Ladtkow et al.
5,541,489 A 7/1996 Dunstan
5,542,594 A 8/1996 McKean et al.
5,542,945 A 8/1996 Fritzsch
5,542,949 A 8/1996 Yoon
5,543,119 A 8/1996 Sutter et al.
5,543,695 A 8/1996 Culp et al.
5,544,802 A 8/1996 Crainich
5,547,117 A 8/1996 Hamblin et al.
5,549,583 A 8/1996 Sanford et al.
5,549,621 A 8/1996 Bessler et al.
5,549,627 A 8/1996 Kieturakis
5,549,628 A 8/1996 Cooper et al.
5,549,637 A 8/1996 Crainich
5,551,622 A 9/1996 Yoon
5,553,624 A 9/1996 Francese et al.
5,553,675 A 9/1996 Pitzen et al.
5,553,765 A 9/1996 Knodel et al.
5,554,148 A 9/1996 Aebischer et al.
5,554,169 A 9/1996 Green et al.
5,556,020 A 9/1996 Hou
5,556,416 A 9/1996 Clark et al.
5,558,533 A 9/1996 Hashizawa et al.
5,558,665 A 9/1996 Kieturakis
5,558,671 A 9/1996 Yates
5,560,530 A 10/1996 Bolanos et al.
5,560,532 A 10/1996 DeFonzo et al.
5,561,881 A 10/1996 Klinger et al.
5,562,239 A 10/1996 Boiarski et al.
5,562,241 A 10/1996 Knodel et al.
5,562,682 A 10/1996 Oberlin et al.
5,562,690 A 10/1996 Green et al.
5,562,694 A 10/1996 Sauer et al.
5,562,701 A 10/1996 Huitema et al.
5,562,702 A 10/1996 Huitema et al.
5,563,481 A 10/1996 Krause
5,564,615 A 10/1996 Bishop et al.
5,569,161 A 10/1996 Ebling et al.
5,569,270 A 10/1996 Weng
5,569,284 A 10/1996 Young et al.
5,571,090 A 11/1996 Sherts
5,571,100 A 11/1996 Goble et al.
5,571,116 A 11/1996 Bolanos et al.
5,571,285 A 11/1996 Chow et al.
5,571,488 A 11/1996 Beerstecher et al.
5,573,169 A 11/1996 Green et al.
5,573,543 A 11/1996 Akopov et al.
5,574,431 A 11/1996 McKeown et al.
5,575,054 A 11/1996 Klinzing et al.
5,575,789 A 11/1996 Bell et al.
5,575,799 A 11/1996 Bolanos et al.
5,575,803 A 11/1996 Cooper et al.
5,575,805 A 11/1996 Li
5,577,654 A 11/1996 Bishop
5,578,052 A 11/1996 Koros et al.
5,579,978 A 12/1996 Green et al.
5,580,067 A 12/1996 Hamblin et al.
5,582,611 A 12/1996 Tsuruta et al.
5,582,617 A 12/1996 Klieman et al.
5,582,907 A 12/1996 Pall
5,583,114 A 12/1996 Barrows et al.
5,584,425 A 12/1996 Savage et al.
5,586,711 A 12/1996 Plyley et al.
5,588,579 A 12/1996 Schnut et al.
5,588,580 A 12/1996 Paul et al.
5,588,581 A 12/1996 Conlon et al.
5,591,170 A 1/1997 Spievack et al.
5,591,187 A 1/1997 Dekel
5,597,107 A 1/1997 Knodel et al.
5,599,151 A 2/1997 Daum et al.
5,599,279 A 2/1997 Slotman et al.
5,599,344 A 2/1997 Paterson
5,599,350 A 2/1997 Schulze et al.
5,599,852 A 2/1997 Scopelianos et al.
5,601,224 A 2/1997 Bishop et al.
5,601,573 A 2/1997 Fogelberg et al.
5,601,604 A 2/1997 Vincent
5,602,449 A 2/1997 Krause et al.
5,603,443 A 2/1997 Clark et al.
5,605,272 A 2/1997 Witt et al.
5,605,273 A 2/1997 Hamblin et al.
D378,500 S 3/1997 Nakai et al.
5,607,094 A 3/1997 Clark et al.
5,607,095 A 3/1997 Smith et al.
5,607,303 A 3/1997 Nakamura
5,607,433 A 3/1997 Polla et al.
5,607,436 A 3/1997 Pratt et al.
5,607,450 A 3/1997 Zvenyatsky et al.
5,607,474 A 3/1997 Athanasiou et al.
5,609,285 A 3/1997 Grant et al.
5,609,601 A 3/1997 Kolesa et al.
5,611,709 A 3/1997 McAnulty
5,611,813 A 3/1997 Lichtman
5,613,499 A 3/1997 Palmer et al.
5,613,937 A 3/1997 Garrison et al.
5,613,966 A 3/1997 Makower et al.

(56) References Cited

U.S. PATENT DOCUMENTS 5,614,887 A 3/1997 Buchbinder
5,615,820 A 4/1997 Viola
5,618,294 A 4/1997 Aust et al.
5,618,303 A 4/1997 Marlow et al.
5,618,307 A 4/1997 Donlon et al.
5,619,992 A 4/1997 Guthrie et al.
5,620,289 A 4/1997 Curry
5,620,326 A 4/1997 Younker
5,620,415 A 4/1997 Lucey et al.
5,620,452 A 4/1997 Yoon
5,624,398 A 4/1997 Smith et al.
5,624,452 A 4/1997 Yates
5,626,587 A 5/1997 Bishop et al.
5,626,595 A 5/1997 Sklar et al.
5,626,979 A 5/1997 Mitsui et al.
5,628,446 A 5/1997 Geiste et al.
5,628,743 A 5/1997 Cimino
5,628,745 A 5/1997 Bek
5,630,539 A 5/1997 Plyley et al.
5,630,540 A 5/1997 Blewett
5,630,541 A 5/1997 Williamson, IV et al.
5,630,782 A 5/1997 Adair
5,631,973 A 5/1997 Green
5,632,432 A 5/1997 Schulze et al.
5,632,433 A 5/1997 Grant et al.
5,633,374 A 5/1997 Humphrey et al.
5,634,584 A 6/1997 Okorocha et al.
5,636,779 A 6/1997 Palmer
5,636,780 A 6/1997 Green et al.
5,637,110 A 6/1997 Pennybacker et al.
5,638,582 A 6/1997 Klatt et al.
5,639,008 A 6/1997 Gallagher et al.
D381,077 S 7/1997 Hunt
5,643,291 A 7/1997 Pier et al.
5,643,293 A 7/1997 Kogasaka et al.
5,643,294 A 7/1997 Tovey et al.
5,643,319 A 7/1997 Green et al.
5,645,209 A 7/1997 Green et al.
5,647,526 A 7/1997 Green et al.
5,647,869 A 7/1997 Goble et al.
5,649,937 A 7/1997 Bito et al.
5,649,956 A 7/1997 Jensen et al.
5,651,491 A 7/1997 Heaton et al.
5,651,762 A 7/1997 Bridges
5,651,821 A 7/1997 Uchida
5,653,373 A 8/1997 Green et al.
5,653,374 A 8/1997 Young et al.
5,653,677 A 8/1997 Okada et al.
5,653,721 A 8/1997 Knodel et al.
5,653,748 A 8/1997 Strecker
5,655,698 A 8/1997 Yoon
5,656,917 A 8/1997 Theobald
5,657,417 A 8/1997 Di Troia
5,657,429 A 8/1997 Wang et al.
5,657,921 A 8/1997 Young et al.
5,658,238 A 8/1997 Suzuki et al.
5,658,281 A 8/1997 Heard
5,658,298 A 8/1997 Vincent et al.
5,658,300 A 8/1997 Bito et al.
5,658,307 A 8/1997 Exconde
5,662,258 A 9/1997 Knodel et al.
5,662,260 A 9/1997 Yoon
5,662,662 A 9/1997 Bishop et al.
5,662,667 A 9/1997 Knodel
5,664,404 A 9/1997 Ivanov et al.
5,665,085 A 9/1997 Nardella
5,667,517 A 9/1997 Hooven
5,667,526 A 9/1997 Levin
5,667,527 A 9/1997 Cook
5,667,864 A 9/1997 Landoll
5,669,544 A 9/1997 Schulze et al.
5,669,904 A 9/1997 Platt, Jr. et al.
5,669,907 A 9/1997 Platt, Jr. et al.
5,669,918 A 9/1997 Balazs et al.
5,672,945 A 9/1997 Krause
5,673,840 A 10/1997 Schulze et al.
5,673,841 A 10/1997 Schulze et al.
5,673,842 A 10/1997 Bittner et al.
5,674,184 A 10/1997 Hassler, Jr.
5,674,286 A 10/1997 D'Alessio et al.
5,678,748 A 10/1997 Plyley et al.
5,680,981 A 10/1997 Mililli et al.
5,680,982 A 10/1997 Schulze et al.
5,680,983 A 10/1997 Plyley et al.
5,681,341 A 10/1997 Lunsford et al.
5,683,349 A 11/1997 Makower et al.
5,683,432 A 11/1997 Goedeke et al.
5,685,474 A 11/1997 Seeber
5,686,090 A 11/1997 Schilder et al.
5,688,270 A 11/1997 Yates et al.
5,690,269 A 11/1997 Bolanos et al.
5,690,675 A 11/1997 Sawyer et al.
5,692,668 A 12/1997 Schulze et al.
5,693,020 A 12/1997 Rauh
5,693,042 A 12/1997 Boiarski et al.
5,693,051 A 12/1997 Schulze et al.
5,695,494 A 12/1997 Becker
5,695,502 A 12/1997 Pier et al.
5,695,504 A 12/1997 Gifford, III et al.
5,695,524 A 12/1997 Kelley et al.
5,697,542 A 12/1997 Knodel et al.
5,697,543 A 12/1997 Burdorff
5,697,909 A 12/1997 Eggers et al.
5,697,943 A 12/1997 Sauer et al.
5,700,265 A 12/1997 Romano
5,700,270 A 12/1997 Peyser et al.
5,700,276 A 12/1997 Benecke
5,702,387 A 12/1997 Arts et al.
5,702,408 A 12/1997 Wales et al.
5,702,409 A 12/1997 Rayburn et al.
5,704,087 A 1/1998 Strub
5,704,534 A 1/1998 Huitema et al.
5,704,792 A 1/1998 Sobhani
5,706,997 A 1/1998 Green et al.
5,706,998 A 1/1998 Plyley et al.
5,707,392 A 1/1998 Kortenbach
5,709,334 A 1/1998 Sorrentino et al.
5,709,335 A 1/1998 Heck
5,709,680 A 1/1998 Yates et al.
5,709,706 A 1/1998 Kienzle et al.
5,711,472 A 1/1998 Bryan
5,711,960 A 1/1998 Shikinami
5,712,460 A 1/1998 Carr et al.
5,713,128 A 2/1998 Schrenk et al.
5,713,505 A 2/1998 Huitema
5,713,895 A 2/1998 Lontine et al.
5,713,896 A 2/1998 Nardella
5,713,920 A 2/1998 Bezwada et al.
5,715,604 A 2/1998 Lanzoni
5,715,836 A 2/1998 Kliegis et al.
5,715,987 A 2/1998 Kelley et al.
5,715,988 A 2/1998 Palmer
5,716,352 A 2/1998 Viola et al.
5,716,366 A 2/1998 Yates
5,718,359 A 2/1998 Palmer et al.
5,718,360 A 2/1998 Green et al.
5,718,548 A 2/1998 Cotellessa
5,718,714 A 2/1998 Livneh
5,720,744 A 2/1998 Eggleston et al.
D393,067 S 3/1998 Geary et al.
5,724,025 A 3/1998 Tavori
5,725,536 A 3/1998 Oberlin et al.
5,725,554 A 3/1998 Simon et al.
5,728,110 A 3/1998 Vidal et al.
5,728,113 A 3/1998 Sherts
5,728,121 A 3/1998 Bimbo et al.
5,730,758 A 3/1998 Allgeyer
5,732,712 A 3/1998 Adair
5,732,821 A 3/1998 Stone et al.
5,732,871 A 3/1998 Clark et al.
5,732,872 A 3/1998 Bolduc et al.
5,733,308 A 3/1998 Daugherty et al.
5,735,445 A 4/1998 Vidal et al.
5,735,848 A 4/1998 Yates et al.

(56) References Cited

U.S. PATENT DOCUMENTS

| | | | |
|---|---|---|---|
| 5,735,874 | A | 4/1998 | Measamer et al. |
| 5,736,271 | A | 4/1998 | Cisar et al. |
| 5,738,474 | A | 4/1998 | Blewett |
| 5,738,629 | A | 4/1998 | Moll et al. |
| 5,738,648 | A | 4/1998 | Lands et al. |
| 5,741,271 | A | 4/1998 | Nakao et al. |
| 5,743,456 | A | 4/1998 | Jones et al. |
| 5,746,770 | A | 5/1998 | Zeitels et al. |
| 5,747,953 | A | 5/1998 | Philipp |
| 5,749,889 | A | 5/1998 | Bacich et al. |
| 5,749,893 | A | 5/1998 | Vidal et al. |
| 5,749,896 | A | 5/1998 | Cook |
| 5,749,968 | A | 5/1998 | Melanson et al. |
| 5,752,644 | A | 5/1998 | Bolanos et al. |
| 5,752,965 | A | 5/1998 | Francis et al. |
| 5,752,970 | A | 5/1998 | Yoon |
| 5,752,973 | A | 5/1998 | Kieturakis |
| 5,755,717 | A | 5/1998 | Yates et al. |
| 5,755,726 | A | 5/1998 | Pratt et al. |
| D395,645 | S | 6/1998 | Cappa et al. |
| 5,758,814 | A | 6/1998 | Gallagher et al. |
| 5,762,255 | A | 6/1998 | Chrisman et al. |
| 5,762,256 | A | 6/1998 | Mastri et al. |
| 5,762,458 | A | 6/1998 | Wang et al. |
| 5,765,565 | A | 6/1998 | Adair |
| 5,766,186 | A | 6/1998 | Faraz et al. |
| 5,766,188 | A | 6/1998 | Igaki |
| 5,766,205 | A | 6/1998 | Zvenyatsky et al. |
| 5,769,303 | A | 6/1998 | Knodel et al. |
| 5,769,640 | A | 6/1998 | Jacobus et al. |
| 5,769,748 | A | 6/1998 | Eyerly et al. |
| 5,769,791 | A | 6/1998 | Benaron et al. |
| 5,769,892 | A | 6/1998 | Kingwell |
| 5,772,099 | A | 6/1998 | Gravener |
| 5,772,379 | A | 6/1998 | Evensen |
| 5,772,578 | A | 6/1998 | Heimberger et al. |
| 5,772,659 | A | 6/1998 | Becker et al. |
| 5,773,991 | A | 6/1998 | Chen |
| 5,776,130 | A | 7/1998 | Buysse et al. |
| 5,778,939 | A | 7/1998 | Hok-Yin |
| 5,779,130 | A | 7/1998 | Alesi et al. |
| 5,779,131 | A | 7/1998 | Knodel et al. |
| 5,779,132 | A | 7/1998 | Knodel et al. |
| 5,782,396 | A | 7/1998 | Mastri et al. |
| 5,782,397 | A | 7/1998 | Koukline |
| 5,782,748 | A | 7/1998 | Palmer et al. |
| 5,782,749 | A | 7/1998 | Riza |
| 5,782,859 | A | 7/1998 | Nicholas et al. |
| 5,784,934 | A | 7/1998 | Izumisawa |
| 5,785,232 | A | 7/1998 | Vidal et al. |
| 5,785,647 | A | 7/1998 | Tompkins et al. |
| 5,787,897 | A | 8/1998 | Kieturakis |
| 5,791,231 | A | 8/1998 | Cohn et al. |
| 5,792,135 | A | 8/1998 | Madhani et al. |
| 5,792,162 | A | 8/1998 | Jolly et al. |
| 5,792,165 | A | 8/1998 | Klieman et al. |
| 5,792,573 | A | 8/1998 | Pitzen et al. |
| 5,794,834 | A | 8/1998 | Hamblin et al. |
| 5,796,188 | A | 8/1998 | Bays |
| 5,797,536 | A | 8/1998 | Smith et al. |
| 5,797,537 | A | 8/1998 | Oberlin et al. |
| 5,797,538 | A | 8/1998 | Heaton et al. |
| 5,797,637 | A | 8/1998 | Ervin |
| 5,797,900 | A | 8/1998 | Madhani et al. |
| 5,797,906 | A | 8/1998 | Rhum et al. |
| 5,797,927 | A | 8/1998 | Yoon |
| 5,797,941 | A | 8/1998 | Schulze et al. |
| 5,797,959 | A | 8/1998 | Castro et al. |
| 5,798,752 | A | 8/1998 | Buxton et al. |
| 5,799,857 | A | 9/1998 | Robertson et al. |
| 5,800,379 | A | 9/1998 | Edwards |
| 5,800,423 | A | 9/1998 | Jensen |
| 5,804,726 | A | 9/1998 | Geib et al. |
| 5,804,936 | A | 9/1998 | Brodsky et al. |
| 5,806,676 | A | 9/1998 | Wasgien |
| 5,807,241 | A | 9/1998 | Heimberger |
| 5,807,376 | A | 9/1998 | Viola et al. |
| 5,807,378 | A | 9/1998 | Jensen et al. |
| 5,807,393 | A | 9/1998 | Williamson, IV et al. |
| 5,809,441 | A | 9/1998 | McKee |
| 5,810,240 | A | 9/1998 | Robertson |
| 5,810,721 | A | 9/1998 | Mueller et al. |
| 5,810,811 | A | 9/1998 | Yates et al. |
| 5,810,846 | A | 9/1998 | Virnich et al. |
| 5,810,855 | A | 9/1998 | Rayburn et al. |
| 5,812,188 | A | 9/1998 | Adair |
| 5,813,813 | A | 9/1998 | Daum et al. |
| 5,814,055 | A | 9/1998 | Knodel et al. |
| 5,814,057 | A | 9/1998 | Oi et al. |
| 5,816,471 | A | 10/1998 | Plyley et al. |
| 5,817,084 | A | 10/1998 | Jensen |
| 5,817,091 | A | 10/1998 | Nardella et al. |
| 5,817,093 | A | 10/1998 | Williamson, IV et al. |
| 5,817,109 | A | 10/1998 | McGarry et al. |
| 5,817,119 | A | 10/1998 | Klieman et al. |
| 5,820,009 | A | 10/1998 | Melling et al. |
| 5,823,066 | A | 10/1998 | Huitema et al. |
| 5,824,333 | A | 10/1998 | Scopelianos et al. |
| 5,826,776 | A | 10/1998 | Schulze et al. |
| 5,827,271 | A | 10/1998 | Buysse et al. |
| 5,827,298 | A | 10/1998 | Hart et al. |
| 5,827,323 | A | 10/1998 | Klieman et al. |
| 5,829,662 | A | 11/1998 | Allen et al. |
| 5,830,598 | A | 11/1998 | Patterson |
| 5,833,690 | A | 11/1998 | Yates et al. |
| 5,833,695 | A | 11/1998 | Yoon |
| 5,833,696 | A | 11/1998 | Whitfield et al. |
| 5,836,503 | A | 11/1998 | Ehrenfels et al. |
| 5,836,960 | A | 11/1998 | Kolesa et al. |
| 5,839,369 | A | 11/1998 | Chatterjee et al. |
| 5,839,639 | A | 11/1998 | Sauer et al. |
| 5,841,284 | A | 11/1998 | Takahashi |
| 5,843,021 | A | 12/1998 | Edwards et al. |
| 5,843,096 | A | 12/1998 | Igaki et al. |
| 5,843,097 | A | 12/1998 | Mayenberger et al. |
| 5,843,122 | A | 12/1998 | Riza |
| 5,843,132 | A | 12/1998 | Ilvento |
| 5,843,169 | A | 12/1998 | Taheri |
| 5,846,254 | A | 12/1998 | Schulze et al. |
| 5,847,566 | A | 12/1998 | Marritt et al. |
| 5,849,011 | A | 12/1998 | Jones et al. |
| 5,849,020 | A | 12/1998 | Long et al. |
| 5,849,023 | A | 12/1998 | Mericle |
| 5,851,179 | A | 12/1998 | Ritson et al. |
| 5,851,212 | A | 12/1998 | Zirps et al. |
| 5,853,366 | A | 12/1998 | Dowlatshahi |
| 5,855,311 | A | 1/1999 | Hamblin et al. |
| 5,855,583 | A | 1/1999 | Wang et al. |
| 5,860,581 | A | 1/1999 | Robertson et al. |
| 5,860,975 | A | 1/1999 | Goble et al. |
| 5,865,361 | A | 2/1999 | Milliman et al. |
| 5,865,638 | A | 2/1999 | Trafton |
| 5,868,361 | A | 2/1999 | Rinderer |
| 5,868,664 | A | 2/1999 | Speier et al. |
| 5,868,760 | A | 2/1999 | McGuckin, Jr. |
| 5,868,790 | A | 2/1999 | Vincent et al. |
| 5,871,135 | A | 2/1999 | Williamson IV et al. |
| 5,873,885 | A | 2/1999 | Weidenbenner |
| 5,876,401 | A | 3/1999 | Schulze et al. |
| 5,878,193 | A | 3/1999 | Wang et al. |
| 5,878,607 | A | 3/1999 | Nunes et al. |
| 5,878,937 | A | 3/1999 | Green et al. |
| 5,878,938 | A | 3/1999 | Bittner et al. |
| 5,881,777 | A | 3/1999 | Bassi et al. |
| 5,881,943 | A | 3/1999 | Heck et al. |
| 5,891,094 | A | 4/1999 | Masterson et al. |
| 5,891,160 | A | 4/1999 | Williamson, IV et al. |
| 5,891,558 | A | 4/1999 | Bell et al. |
| 5,893,506 | A | 4/1999 | Powell |
| 5,893,835 | A | 4/1999 | Witt et al. |
| 5,893,855 | A | 4/1999 | Jacobs |
| 5,893,863 | A | 4/1999 | Yoon |
| 5,893,878 | A | 4/1999 | Pierce |
| 5,894,979 | A | 4/1999 | Powell |

(56) References Cited

U.S. PATENT DOCUMENTS 5,897,552 A 4/1999 Edwards et al.
5,897,562 A 4/1999 Bolanos et al.
5,899,824 A 5/1999 Kurtz et al.
5,899,914 A 5/1999 Zirps et al.
5,901,895 A 5/1999 Heaton et al.
5,902,312 A 5/1999 Frater et al.
5,903,117 A 5/1999 Gregory
5,904,647 A 5/1999 Ouchi
5,904,693 A 5/1999 Dicesare et al.
5,904,702 A 5/1999 Ek et al.
5,906,577 A 5/1999 Beane et al.
5,906,625 A 5/1999 Bito et al.
5,907,211 A 5/1999 Hall et al.
5,907,664 A 5/1999 Wang et al.
5,908,149 A 6/1999 Welch et al.
5,908,402 A 6/1999 Blythe
5,908,427 A 6/1999 McKean et al.
5,909,062 A 6/1999 Krietzman
5,911,353 A 6/1999 Bolanos et al.
5,915,616 A 6/1999 Viola et al.
5,916,225 A 6/1999 Kugel
5,918,791 A 7/1999 Sorrentino et al.
5,919,198 A 7/1999 Graves, Jr. et al.
5,921,956 A 7/1999 Grinberg et al.
5,922,001 A 7/1999 Yoon
5,922,003 A 7/1999 Anctil et al.
5,924,864 A 7/1999 Loge et al.
5,928,137 A 7/1999 Green
5,928,256 A 7/1999 Riza
5,931,847 A 8/1999 Bittner et al.
5,931,853 A 8/1999 McEwen et al.
5,937,951 A 8/1999 Izuchukwu et al.
5,938,667 A 8/1999 Peyser et al.
5,941,442 A 8/1999 Geiste et al.
5,941,890 A 8/1999 Voegele et al.
5,944,172 A 8/1999 Hannula
5,944,715 A 8/1999 Goble et al.
5,946,978 A 9/1999 Yamashita
5,947,984 A 9/1999 Whipple
5,947,996 A 9/1999 Logeman
5,948,030 A 9/1999 Miller et al.
5,948,429 A 9/1999 Bell et al.
5,951,301 A 9/1999 Younker
5,951,516 A 9/1999 Bunyan
5,951,552 A 9/1999 Long et al.
5,951,574 A 9/1999 Stefanchik et al.
5,951,575 A 9/1999 Bolduc et al.
5,951,581 A 9/1999 Saadat et al.
5,954,259 A 9/1999 Viola et al.
5,957,831 A 9/1999 Adair
5,964,394 A 10/1999 Robertson
5,964,774 A 10/1999 McKean et al.
5,966,126 A 10/1999 Szabo
5,971,916 A 10/1999 Koren
5,973,221 A 10/1999 Collyer et al.
D416,089 S 11/1999 Barton et al.
5,976,122 A 11/1999 Madhani et al.
5,977,746 A 11/1999 Hershberger et al.
5,980,248 A 11/1999 Kusakabe et al.
5,980,569 A 11/1999 Scirica
5,984,949 A 11/1999 Levin
5,988,479 A 11/1999 Palmer
5,990,379 A 11/1999 Gregory
5,993,464 A 11/1999 Knodel
5,993,466 A 11/1999 Yoon
5,997,528 A 12/1999 Bisch et al.
5,997,552 A 12/1999 Person et al.
6,001,108 A 12/1999 Wang et al.
6,003,517 A 12/1999 Sheffield et al.
6,004,319 A 12/1999 Goble et al.
6,004,335 A 12/1999 Vaitekunas et al.
6,007,521 A 12/1999 Bidwell et al.
6,010,054 A 1/2000 Johnson et al.
6,010,513 A 1/2000 Tormala et al.
6,010,520 A 1/2000 Pattison
6,012,494 A 1/2000 Balazs
6,013,076 A 1/2000 Goble et al.
6,013,991 A 1/2000 Philipp
6,015,406 A 1/2000 Goble et al.
6,015,417 A 1/2000 Reynolds, Jr.
6,017,322 A 1/2000 Snoke et al.
6,017,354 A 1/2000 Culp et al.
6,017,356 A 1/2000 Frederick et al.
6,018,227 A 1/2000 Kumar et al.
6,019,745 A 2/2000 Gray
6,019,780 A 2/2000 Lombardo et al.
6,022,352 A 2/2000 Vandewalle
6,023,275 A 2/2000 Horvitz et al.
6,023,641 A 2/2000 Thompson
6,024,708 A 2/2000 Bales et al.
6,024,741 A 2/2000 Williamson, IV et al.
6,024,748 A 2/2000 Manzo et al.
6,024,750 A 2/2000 Mastri et al.
6,024,764 A 2/2000 Schroeppel
6,027,501 A 2/2000 Goble et al.
6,030,384 A 2/2000 Nezhat
6,031,148 A 2/2000 Hayes et al.
6,032,849 A 3/2000 Mastri et al.
6,033,105 A 3/2000 Barker et al.
6,033,378 A 3/2000 Lundquist et al.
6,033,399 A 3/2000 Gines
6,033,427 A 3/2000 Lee
6,036,641 A 3/2000 Taylor et al.
6,036,667 A 3/2000 Manna et al.
6,037,724 A 3/2000 Buss et al.
6,037,927 A 3/2000 Rosenberg
6,039,126 A 3/2000 Hsieh
6,039,733 A 3/2000 Buysse et al.
6,039,734 A 3/2000 Goble
6,042,601 A 3/2000 Smith
6,042,607 A 3/2000 Williamson, IV et al.
6,043,626 A 3/2000 Snyder et al.
D422,545 S 4/2000 Palalau et al.
6,045,560 A 4/2000 McKean et al.
6,047,861 A 4/2000 Vidal et al.
6,049,145 A 4/2000 Austin et al.
6,050,172 A 4/2000 Corves et al.
6,050,472 A 4/2000 Shibata
6,050,989 A 4/2000 Fox et al.
6,050,990 A 4/2000 Tankovich et al.
6,050,996 A 4/2000 Schmaltz et al.
6,053,390 A 4/2000 Green et al.
6,053,899 A 4/2000 Slanda et al.
6,053,922 A 4/2000 Krause et al.
6,054,142 A 4/2000 Li et al.
6,055,062 A 4/2000 Dina et al.
RE36,720 E 5/2000 Green et al.
6,056,735 A 5/2000 Okada et al.
6,056,746 A 5/2000 Goble et al.
6,059,806 A 5/2000 Hoegerle
6,062,360 A 5/2000 Shields
6,063,020 A 5/2000 Jones et al.
6,063,025 A 5/2000 Bridges et al.
6,063,050 A 5/2000 Manna et al.
6,063,095 A 5/2000 Wang et al.
6,063,097 A 5/2000 Oi et al.
6,063,098 A 5/2000 Houser et al.
6,065,679 A 5/2000 Levie et al.
6,065,919 A 5/2000 Peck
6,066,132 A 5/2000 Chen et al.
6,066,144 A 5/2000 Wolf et al.
6,066,151 A 5/2000 Miyawaki et al.
6,068,627 A 5/2000 Orszulak et al.
6,071,233 A 6/2000 Ishikawa et al.
6,072,299 A 6/2000 Kurle et al.
6,074,386 A 6/2000 Goble et al.
6,074,401 A 6/2000 Gardiner et al.
6,075,441 A 6/2000 Maloney
6,077,280 A 6/2000 Fossum
6,077,286 A 6/2000 Cuschieri et al.
6,077,290 A 6/2000 Marini
6,079,606 A 6/2000 Milliman et al.
6,080,181 A 6/2000 Jensen et al.
6,082,577 A 7/2000 Coates et al.

(56) References Cited

U.S. PATENT DOCUMENTS 6,083,191 A 7/2000 Rose
6,083,223 A 7/2000 Baker
6,083,234 A 7/2000 Nicholas et al.
6,083,242 A 7/2000 Cook
6,086,544 A 7/2000 Hibner et al.
6,086,600 A 7/2000 Kortenbach
6,090,106 A 7/2000 Goble et al.
6,090,123 A 7/2000 Culp et al.
6,093,186 A 7/2000 Goble
6,094,021 A 7/2000 Noro et al.
D429,252 S 8/2000 Haitani et al.
6,099,537 A 8/2000 Sugai et al.
6,099,551 A 8/2000 Gabbay
6,102,271 A 8/2000 Longo et al.
6,102,926 A 8/2000 Tartaglia et al.
6,104,162 A 8/2000 Sainsbury et al.
6,104,304 A 8/2000 Clark et al.
6,106,511 A 8/2000 Jensen
6,109,500 A 8/2000 Alli et al.
6,110,187 A 8/2000 Donlon
6,113,618 A 9/2000 Nic
6,117,148 A 9/2000 Ravo et al.
6,117,158 A 9/2000 Measamer et al.
6,119,913 A 9/2000 Adams et al.
6,120,433 A 9/2000 Mizuno et al.
6,120,462 A 9/2000 Hibner et al.
6,123,241 A 9/2000 Walter et al.
6,123,701 A 9/2000 Nezhat
H1904 H 10/2000 Yates et al.
RE36,923 E 10/2000 Hiroi et al.
6,126,058 A 10/2000 Adams et al.
6,126,359 A 10/2000 Dittrich et al.
6,126,670 A 10/2000 Walker et al.
6,131,789 A 10/2000 Schulze et al.
6,131,790 A 10/2000 Piraka
6,132,368 A 10/2000 Cooper
6,134,962 A 10/2000 Sugitani
6,139,546 A 10/2000 Koenig et al.
6,142,149 A 11/2000 Steen
6,142,933 A 11/2000 Longo et al.
6,147,135 A 11/2000 Yuan et al.
6,148,979 A * 11/2000 Roach .................... F16D 43/16
74/577 M
6,149,660 A 11/2000 Laufer et al.
6,151,323 A 11/2000 O'Connell et al.
6,152,935 A 11/2000 Kammerer et al.
6,155,083 A 12/2000 Goeser et al.
6,155,473 A 12/2000 Tompkins et al.
6,156,056 A 12/2000 Kearns et al.
6,157,169 A 12/2000 Lee
6,157,303 A 12/2000 Bodie et al.
6,159,146 A 12/2000 El Gazayerli
6,159,200 A 12/2000 Verdura et al.
6,159,224 A 12/2000 Yoon
6,162,208 A 12/2000 Hipps
6,162,220 A 12/2000 Nezhat
6,162,537 A 12/2000 Martin et al.
6,165,175 A 12/2000 Wampler et al.
6,165,184 A 12/2000 Verdura et al.
6,165,188 A 12/2000 Saadat et al.
6,167,185 A 12/2000 Smiley et al.
6,168,605 B1 1/2001 Measamer et al.
6,171,305 B1 1/2001 Sherman
6,171,316 B1 1/2001 Kovac et al.
6,171,330 B1 1/2001 Benchetrit
6,173,074 B1 1/2001 Russo
6,174,308 B1 1/2001 Goble et al.
6,174,309 B1 1/2001 Wrublewski et al.
6,174,318 B1 1/2001 Bates et al.
6,175,290 B1 1/2001 Forsythe et al.
6,179,195 B1 1/2001 Adams et al.
6,179,776 B1 1/2001 Adams et al.
6,181,105 B1 1/2001 Cutolo et al.
6,182,673 B1 2/2001 Kindermann et al.
6,185,356 B1 2/2001 Parker et al.
6,186,142 B1 2/2001 Schmidt et al.
6,186,957 B1 2/2001 Milam
6,187,003 B1 2/2001 Buysse et al.
6,190,386 B1 2/2001 Rydell
6,193,129 B1 2/2001 Bittner et al.
6,197,042 B1 3/2001 Ginn et al.
6,200,311 B1 3/2001 Danek et al.
6,200,330 B1 3/2001 Benderev et al.
6,202,914 B1 3/2001 Geiste et al.
6,206,894 B1 3/2001 Thompson et al.
6,206,897 B1 3/2001 Jamiolkowski et al.
6,206,903 B1 3/2001 Ramans
6,206,904 B1 3/2001 Ouchi
6,209,414 B1 4/2001 Uneme
6,210,403 B1 4/2001 Klicek
6,211,626 B1 4/2001 Lys et al.
6,213,999 B1 4/2001 Platt, Jr. et al.
6,214,028 B1 4/2001 Yoon et al.
6,220,368 B1 4/2001 Ark et al.
6,221,007 B1 4/2001 Green
6,221,023 B1 4/2001 Matsuba et al.
6,223,100 B1 4/2001 Green
6,223,835 B1 5/2001 Habedank et al.
6,224,617 B1 5/2001 Saadat et al.
6,228,080 B1 5/2001 Gines
6,228,081 B1 5/2001 Goble
6,228,083 B1 5/2001 Lands et al.
6,228,084 B1 5/2001 Kirwan, Jr.
6,228,089 B1 5/2001 Wahrburg
6,228,098 B1 5/2001 Kayan et al.
6,231,565 B1 5/2001 Tovey et al.
6,234,178 B1 5/2001 Goble et al.
6,235,036 B1 5/2001 Gardner et al.
6,237,604 B1 5/2001 Burnside et al.
6,238,384 B1 5/2001 Peer
6,241,139 B1 6/2001 Milliman et al.
6,241,140 B1 6/2001 Adams et al.
6,241,723 B1 6/2001 Heim et al.
6,245,084 B1 6/2001 Mark et al.
6,248,116 B1 6/2001 Chevillon et al.
6,248,117 B1 6/2001 Blatter
6,249,076 B1 6/2001 Madden et al.
6,249,105 B1 6/2001 Andrews et al.
6,250,532 B1 6/2001 Green et al.
6,251,485 B1 6/2001 Harris et al.
D445,745 S 7/2001 Norman
6,254,534 B1 7/2001 Butler et al.
6,254,619 B1 7/2001 Garabet et al.
6,254,642 B1 7/2001 Taylor
6,258,107 B1 7/2001 Balazs et al.
6,261,246 B1 7/2001 Pantages et al.
6,261,286 B1 7/2001 Goble et al.
6,261,679 B1 7/2001 Chen et al.
6,264,086 B1 7/2001 McGuckin, Jr.
6,264,087 B1 7/2001 Whitman
6,264,617 B1 7/2001 Bales et al.
6,269,997 B1 8/2001 Balazs et al.
6,270,508 B1 8/2001 Klieman et al.
6,270,916 B1 8/2001 Sink et al.
6,273,252 B1 8/2001 Mitchell
6,273,876 B1 8/2001 Klima et al.
6,273,897 B1 8/2001 Dalessandro et al.
6,277,114 B1 8/2001 Bullivant et al.
6,280,407 B1 8/2001 Manna et al.
6,283,981 B1 9/2001 Beaupre
6,293,927 B1 9/2001 McGuckin, Jr.
6,293,942 B1 9/2001 Goble et al.
6,296,607 B1 10/2001 Milbocker
6,296,640 B1 10/2001 Wampler et al.
6,302,311 B1 10/2001 Adams et al.
6,302,743 B1 10/2001 Chiu et al.
6,305,891 B1 10/2001 Burlingame
6,306,134 B1 10/2001 Goble et al.
6,306,149 B1 10/2001 Meade
6,306,424 B1 10/2001 Vyakarnam et al.
6,309,397 B1 10/2001 Julian et al.
6,309,400 B2 10/2001 Beaupre
6,309,403 B1 10/2001 Minor et al.
6,312,435 B1 11/2001 Wallace et al.

(56) References Cited

U.S. PATENT DOCUMENTS 6,315,184 B1 11/2001 Whitman
6,317,616 B1 11/2001 Glossop
6,319,510 B1 11/2001 Yates
6,320,123 B1 11/2001 Reimers
6,322,494 B1 11/2001 Bullivant et al.
6,324,339 B1 11/2001 Hudson et al.
6,325,799 B1 12/2001 Goble
6,325,805 B1 12/2001 Ogilvie et al.
6,325,810 B1 12/2001 Hamilton et al.
6,328,498 B1 12/2001 Mersch
6,330,965 B1 12/2001 Milliman et al.
6,331,181 B1 12/2001 Tierney et al.
6,331,761 B1 12/2001 Kumar et al.
6,333,029 B1 12/2001 Vyakarnam et al.
6,334,860 B1 1/2002 Dorn
6,334,861 B1 1/2002 Chandler et al.
6,336,926 B1 1/2002 Goble
6,338,737 B1 1/2002 Toledano
6,338,738 B1 1/2002 Bellotti et al.
6,343,731 B1 2/2002 Adams et al.
6,346,077 B1 2/2002 Taylor et al.
6,348,061 B1 2/2002 Whitman
6,349,868 B1 2/2002 Mattingly et al.
D454,951 S 3/2002 Bon
6,352,503 B1 3/2002 Matsui et al.
6,352,532 B1 3/2002 Kramer et al.
6,355,699 B1 3/2002 Vyakarnam et al.
6,356,072 B1 3/2002 Chass
6,358,224 B1 3/2002 Tims et al.
6,358,263 B2 3/2002 Mark et al.
6,358,459 B1 3/2002 Ziegler et al.
6,361,542 B1 3/2002 Dimitriu et al.
6,364,828 B1 4/2002 Yeung et al.
6,364,877 B1 4/2002 Goble et al.
6,364,888 B1 4/2002 Niemeyer et al.
6,366,441 B1 4/2002 Ozawa et al.
6,370,981 B2 4/2002 Watarai
6,371,114 B1 4/2002 Schmidt et al.
6,373,152 B1 4/2002 Wang et al.
6,377,011 B1 4/2002 Ben-Ur
6,383,201 B1 5/2002 Dong
6,387,092 B1 5/2002 Burnside et al.
6,387,113 B1 5/2002 Hawkins et al.
6,387,114 B2 5/2002 Adams
6,391,038 B2 5/2002 Vargas et al.
6,392,854 B1 5/2002 O'Gorman
6,394,998 B1 5/2002 Wallace et al.
6,398,779 B1 6/2002 Buysse et al.
6,398,781 B1 6/2002 Goble et al.
6,398,797 B2 6/2002 Bombard et al.
6,402,766 B2 6/2002 Bowman et al.
6,402,780 B2 6/2002 Williamson, IV et al.
6,406,440 B1 6/2002 Stefanchik
6,406,472 B1 6/2002 Jensen
6,409,724 B1 6/2002 Penny et al.
H2037 H 7/2002 Yates et al.
6,412,639 B1 7/2002 Hickey
6,413,274 B1 7/2002 Pedros
6,415,542 B1 7/2002 Bates et al.
6,416,486 B1 7/2002 Wampler
6,416,509 B1 7/2002 Goble et al.
6,419,695 B1 7/2002 Gabbay
6,423,079 B1 7/2002 Blake, III
6,424,885 B1 7/2002 Niemeyer et al.
RE37,814 E 8/2002 Allgeyer
6,428,070 B1 8/2002 Takanashi et al.
6,428,487 B1 8/2002 Burdorff et al.
6,429,611 B1 8/2002 Li
6,430,298 B1 8/2002 Kettl et al.
6,432,065 B1 8/2002 Burdorff et al.
6,436,097 B1 8/2002 Nardella
6,436,107 B1 8/2002 Wang et al.
6,436,110 B2 8/2002 Bowman et al.
6,436,115 B1 8/2002 Beaupre
6,436,122 B1 8/2002 Frank et al.
6,439,439 B1 8/2002 Rickard et al.
6,439,446 B1 8/2002 Perry et al.
6,440,146 B2 8/2002 Nicholas et al.
6,441,577 B2 8/2002 Blumenkranz et al.
D462,758 S 9/2002 Epstein et al.
6,443,973 B1 9/2002 Whitman
6,445,530 B1 9/2002 Baker
6,447,518 B1 9/2002 Krause et al.
6,447,523 B1 9/2002 Middleman et al.
6,447,799 B1 9/2002 Ullman
6,447,864 B2 9/2002 Johnson et al.
6,450,391 B1 9/2002 Kayan et al.
6,450,989 B2 9/2002 Dubrul et al.
6,454,656 B2 9/2002 Brissette et al.
6,454,781 B1 9/2002 Witt et al.
6,457,338 B1 10/2002 Frenken
6,457,625 B1 10/2002 Tormala et al.
6,458,077 B1 10/2002 Boebel et al.
6,458,142 B1 10/2002 Faller et al.
6,458,147 B1 10/2002 Cruise et al.
6,460,627 B1 10/2002 Below et al.
6,463,824 B1 10/2002 Prell et al.
6,468,275 B1 10/2002 Wampler et al.
6,468,286 B2 10/2002 Mastri et al.
6,471,106 B1 10/2002 Reining
6,471,659 B2 10/2002 Eggers et al.
6,478,210 B2 11/2002 Adams et al.
6,482,063 B1 11/2002 Frigard
6,482,200 B2 11/2002 Shippert
6,482,217 B1 11/2002 Pintor et al.
6,485,490 B2 11/2002 Wampler et al.
6,485,503 B2 11/2002 Jacobs et al.
6,485,667 B1 11/2002 Tan
6,486,286 B1 11/2002 McGall et al.
6,488,196 B1 12/2002 Fenton, Jr.
6,488,197 B1 12/2002 Whitman
6,488,659 B1 12/2002 Rosenman
6,491,201 B1 12/2002 Whitman
6,491,690 B1 12/2002 Goble et al.
6,491,701 B2 12/2002 Tierney et al.
6,491,702 B2 12/2002 Heilbrun et al.
6,492,785 B1 12/2002 Kasten et al.
6,494,882 B1 12/2002 Lebouitz et al.
6,494,885 B1 12/2002 Dhindsa
6,494,888 B1 12/2002 Laufer et al.
6,494,896 B1 12/2002 D'Alessio et al.
6,498,480 B1 12/2002 Manara
6,500,176 B1 12/2002 Truckai et al.
6,500,189 B1 12/2002 Lang et al.
6,500,194 B2 12/2002 Benderev et al.
D468,749 S 1/2003 Friedman
6,503,139 B2 1/2003 Coral
6,503,257 B2 1/2003 Grant et al.
6,503,259 B2 1/2003 Huxel et al.
6,505,768 B2 1/2003 Whitman
6,506,197 B1 1/2003 Rollero et al.
6,506,399 B2 1/2003 Donovan
6,510,854 B2 1/2003 Goble
6,511,468 B1 1/2003 Cragg et al.
6,512,360 B1 1/2003 Goto et al.
6,514,252 B2 2/2003 Nezhat et al.
6,516,073 B1 2/2003 Schulz et al.
6,517,528 B1 2/2003 Pantages et al.
6,517,535 B2 2/2003 Edwards
6,517,565 B1 2/2003 Whitman et al.
6,517,566 B1 2/2003 Hovland et al.
6,520,971 B1 2/2003 Perry et al.
6,520,972 B2 2/2003 Peters
6,522,101 B2 2/2003 Malackowski
6,524,180 B1 2/2003 Simms et al.
6,525,499 B2 2/2003 Naganuma
D471,206 S 3/2003 Buzzard et al.
6,527,782 B2 3/2003 Hogg et al.
6,527,785 B2 3/2003 Sancoff et al.
6,530,942 B2 3/2003 Fogarty et al.
6,532,958 B1 3/2003 Buan et al.
6,533,157 B1 3/2003 Whitman
6,533,723 B1 3/2003 Lockery et al.
6,533,784 B2 3/2003 Truckai et al.

(56) References Cited

U.S. PATENT DOCUMENTS 6,535,764 B2 3/2003 Imran et al.
6,539,297 B2 3/2003 Weiberle et al.
D473,239 S 4/2003 Cockerill
6,539,816 B2 4/2003 Kogiso et al.
6,540,737 B2 4/2003 Bacher et al.
6,543,456 B1 4/2003 Freeman
6,545,384 B1 4/2003 Pelrine et al.
6,547,786 B1 4/2003 Goble
6,550,546 B2 4/2003 Thurler et al.
6,551,333 B2 4/2003 Kuhns et al.
6,554,844 B2 4/2003 Lee et al.
6,554,861 B2 4/2003 Knox et al.
6,555,770 B2 4/2003 Kawase
6,558,378 B2 5/2003 Sherman et al.
6,558,379 B1 5/2003 Batchelor et al.
6,558,429 B2 5/2003 Taylor
6,561,187 B2 5/2003 Schmidt et al.
6,565,560 B1 5/2003 Goble et al.
6,566,619 B2 5/2003 Gillman et al.
6,569,085 B2 5/2003 Kortenbach et al.
6,569,171 B2 5/2003 DeGuillebon et al.
6,569,173 B1 5/2003 Blatter et al.
6,572,629 B2 6/2003 Kalloo et al.
6,575,969 B1 6/2003 Rittman, III et al.
6,578,751 B2 6/2003 Hartwick
6,582,364 B2 6/2003 Butler et al.
6,582,427 B1 6/2003 Goble et al.
6,582,441 B1 6/2003 He et al.
6,583,533 B2 6/2003 Pelrine et al.
6,585,144 B2 7/2003 Adams et al.
6,585,664 B2 7/2003 Burdorff et al.
6,586,898 B2 7/2003 King et al.
6,587,750 B2 7/2003 Gerbi et al.
6,588,277 B2 7/2003 Giordano et al.
6,588,643 B2 7/2003 Bolduc et al.
6,588,931 B2 7/2003 Betzner et al.
6,589,118 B1 7/2003 Soma et al.
6,589,164 B1 7/2003 Flaherty
6,592,538 B1 7/2003 Hotchkiss et al.
6,592,572 B1 7/2003 Suzuta
6,592,597 B2 7/2003 Grant et al.
6,594,552 B1 7/2003 Nowlin et al.
6,595,914 B2 7/2003 Kato
6,596,296 B1 7/2003 Nelson et al.
6,596,304 B1 7/2003 Bayon et al.
6,596,432 B2 7/2003 Kawakami et al.
6,599,295 B1 7/2003 Tornier et al.
6,599,323 B2 7/2003 Melican et al.
D478,665 S 8/2003 Isaacs et al.
D478,986 S 8/2003 Johnston et al.
6,601,749 B2 8/2003 Sullivan et al.
6,602,252 B2 8/2003 Mollenauer
6,602,262 B2 8/2003 Griego et al.
6,603,050 B2 8/2003 Heaton
6,605,078 B2 8/2003 Adams
6,605,669 B2 8/2003 Awokola et al.
6,605,911 B1 8/2003 Klesing
6,607,475 B2 8/2003 Doyle et al.
6,611,793 B1 8/2003 Burnside et al.
6,613,069 B2 9/2003 Boyd et al.
6,616,686 B2 9/2003 Coleman et al.
6,619,529 B2 9/2003 Green et al.
6,620,111 B2 9/2003 Stephens et al.
6,620,161 B2 9/2003 Schulze et al.
6,620,166 B1 9/2003 Wenstrom, Jr. et al.
6,623,482 B2 9/2003 Pendekanti et al.
6,625,517 B1 9/2003 Bogdanov et al.
6,626,834 B2 9/2003 Dunne et al.
6,626,901 B1 9/2003 Treat et al.
6,626,938 B1 9/2003 Butaric et al.
H2086 H 10/2003 Amsler
6,629,630 B2 10/2003 Adams
6,629,974 B2 10/2003 Penny et al.
6,629,988 B2 10/2003 Weadock
6,635,838 B1 10/2003 Kornelson
6,636,412 B2 10/2003 Smith
6,638,108 B2 10/2003 Tachi
6,638,285 B2 10/2003 Gabbay
6,638,297 B1 10/2003 Huitema
RE38,335 E 11/2003 Aust et al.
6,641,528 B2 11/2003 Torii
6,644,532 B2 11/2003 Green et al.
6,645,201 B1 11/2003 Utley et al.
6,646,307 B1 11/2003 Yu et al.
6,648,816 B2 11/2003 Irion et al.
6,648,901 B2 11/2003 Fleischman et al.
6,652,595 B1 11/2003 Nicolo
D484,243 S 12/2003 Ryan et al.
D484,595 S 12/2003 Ryan et al.
D484,596 S 12/2003 Ryan et al.
6,656,177 B2 12/2003 Truckai et al.
6,656,193 B2 12/2003 Grant et al.
6,659,940 B2 12/2003 Adler
6,660,008 B1 12/2003 Foerster et al.
6,663,623 B1 12/2003 Oyama et al.
6,663,641 B1 12/2003 Kovac et al.
6,666,854 B1 12/2003 Lange
6,666,860 B1 12/2003 Takahashi
6,666,875 B1 12/2003 Sakurai et al.
6,667,825 B2 12/2003 Lu et al.
6,669,073 B2 12/2003 Milliman et al.
6,670,806 B2 12/2003 Wendt et al.
6,671,185 B2 12/2003 Duval
D484,977 S 1/2004 Ryan et al.
6,676,660 B2 1/2004 Wampler et al.
6,677,687 B2 1/2004 Ho et al.
6,679,269 B2 1/2004 Swanson
6,679,410 B2 1/2004 Wursch et al.
6,681,978 B2 1/2004 Geiste et al.
6,681,979 B2 1/2004 Whitman
6,682,527 B2 1/2004 Strul
6,682,528 B2 1/2004 Frazier et al.
6,682,544 B2 1/2004 Mastri et al.
6,685,698 B2 2/2004 Morley et al.
6,685,727 B2 2/2004 Fisher et al.
6,689,153 B1 2/2004 Skiba
6,692,507 B2 2/2004 Pugsley et al.
6,692,692 B2 2/2004 Stetzel
6,695,198 B2 2/2004 Adams et al.
6,695,199 B2 2/2004 Whitman
6,695,774 B2 2/2004 Hale et al.
6,695,849 B2 2/2004 Michelson
6,696,814 B2 2/2004 Henderson et al.
6,697,048 B2 2/2004 Rosenberg et al.
6,698,643 B2 3/2004 Whitman
6,699,177 B1 3/2004 Wang et al.
6,699,214 B2 3/2004 Gellman
6,699,235 B2 3/2004 Wallace et al.
6,704,210 B1 3/2004 Myers
6,705,503 B1 3/2004 Pedicini et al.
6,709,445 B2 3/2004 Boebel et al.
6,712,773 B1 3/2004 Viola
6,716,215 B1 4/2004 David et al.
6,716,223 B2 4/2004 Leopold et al.
6,716,232 B1 4/2004 Vidal et al.
6,716,233 B1 4/2004 Whitman
6,720,734 B2 4/2004 Norris
6,722,550 B1 4/2004 Ricordi et al.
6,722,552 B2 4/2004 Fenton, Jr.
6,723,087 B2 4/2004 O'Neill et al.
6,723,091 B2 4/2004 Goble et al.
6,723,106 B1 4/2004 Charles et al.
6,723,109 B2 4/2004 Solingen
6,726,651 B1 4/2004 Robinson et al.
6,726,697 B2 4/2004 Nicholas et al.
6,726,705 B2 4/2004 Peterson et al.
6,726,706 B2 4/2004 Dominguez
6,729,119 B2 5/2004 Schnipke et al.
6,731,976 B2 5/2004 Penn et al.
6,736,810 B2 5/2004 Hoey et al.
6,736,825 B2 5/2004 Blatter et al.
6,736,854 B2 5/2004 Vadurro et al.
6,740,030 B2 5/2004 Martone et al.
6,743,230 B2 6/2004 Lutze et al.

(56) References Cited

U.S. PATENT DOCUMENTS 6,744,385 B2 6/2004 Kazuya et al.
6,747,121 B2 6/2004 Gogolewski
6,747,300 B2 6/2004 Nadd et al.
6,749,560 B1 6/2004 Konstorum et al.
6,749,600 B1 6/2004 Levy
6,750,622 B2 6/2004 Simizu et al.
6,752,768 B2 6/2004 Burdorff et al.
6,752,816 B2 6/2004 Culp et al.
6,754,959 B1 6/2004 Guiette, III et al.
6,755,195 B1 6/2004 Lemke et al.
6,755,338 B2 6/2004 Hahnen et al.
6,755,825 B2 6/2004 Shoenman et al.
6,755,843 B2 6/2004 Chung et al.
6,756,705 B2 6/2004 Pulford, Jr.
6,758,846 B2 7/2004 Goble et al.
6,761,685 B2 7/2004 Adams et al.
6,762,339 B1 7/2004 Klun et al.
6,763,307 B2 7/2004 Berg et al.
6,764,445 B2 7/2004 Ramans et al.
6,766,957 B2 7/2004 Matsuura et al.
6,767,352 B2 7/2004 Field et al.
6,767,356 B2 7/2004 Kanner et al.
6,769,590 B2 8/2004 Vresh et al.
6,769,594 B2 8/2004 Orban, III
6,770,027 B2 8/2004 Banik et al.
6,770,070 B1 8/2004 Balbierz
6,770,072 B1 8/2004 Truckai et al.
6,770,078 B2 8/2004 Bonutti
6,773,409 B2 8/2004 Truckai et al.
6,773,437 B2 8/2004 Ogilvie et al.
6,773,438 B1 8/2004 Knodel et al.
6,773,458 B1 8/2004 Brauker et al.
6,775,575 B2 8/2004 Bommannan et al.
6,777,838 B2 8/2004 Miekka et al.
6,778,846 B1 8/2004 Martinez et al.
6,780,151 B2 8/2004 Grabover et al.
6,780,180 B1 8/2004 Goble et al.
6,783,524 B2 8/2004 Anderson et al.
6,784,775 B2 8/2004 Mandell et al.
6,786,382 B1 9/2004 Hoffman
6,786,864 B2 9/2004 Matsuura et al.
6,786,896 B1 9/2004 Madhani et al.
6,788,018 B1 9/2004 Blumenkranz
6,790,173 B2 9/2004 Saadat et al.
6,793,652 B1 9/2004 Whitman et al.
6,793,661 B2 9/2004 Hamilton et al.
6,793,663 B2 9/2004 Kneifel et al.
6,793,669 B2 9/2004 Nakamura et al.
6,796,921 B1 9/2004 Buck et al.
6,799,669 B2 10/2004 Fukumura et al.
6,801,009 B2 10/2004 Makaran et al.
6,802,822 B1 10/2004 Dodge
6,802,843 B2 10/2004 Truckai et al.
6,802,844 B2 10/2004 Ferree
6,805,273 B2 10/2004 Bilotti et al.
6,806,808 B1 10/2004 Watters et al.
6,806,867 B1 10/2004 Arruda et al.
6,808,525 B2 10/2004 Latterell et al.
6,810,359 B2 10/2004 Sakaguchi
6,814,154 B2 11/2004 Chou
6,814,741 B2 11/2004 Bowman et al.
6,817,508 B1 11/2004 Racenet et al.
6,817,509 B2 11/2004 Geiste et al.
6,817,974 B2 11/2004 Cooper et al.
6,818,018 B1 11/2004 Sawhney
6,819,269 B2 11/2004 Flick
6,820,791 B2 11/2004 Adams
6,821,273 B2 11/2004 Mollenauer
6,821,282 B2 11/2004 Perry et al.
6,821,284 B2 11/2004 Sturtz et al.
6,827,246 B2 12/2004 Sullivan et al.
6,827,712 B2 12/2004 Tovey et al.
6,827,725 B2 12/2004 Batchelor et al.
6,828,902 B2 12/2004 Casden
6,830,174 B2 12/2004 Hillstead et al.
6,831,629 B2 12/2004 Nishino et al.
6,832,998 B2 12/2004 Goble
6,834,001 B2 12/2004 Myono
6,835,173 B2 12/2004 Couvillon, Jr.
6,835,199 B2 12/2004 McGuckin, Jr. et al.
6,835,336 B2 12/2004 Watt
6,836,611 B2 12/2004 Popovic et al.
6,837,846 B2 1/2005 Jaffe et al.
6,837,883 B2 1/2005 Moll et al.
6,838,493 B2 1/2005 Williams et al.
6,840,423 B2 1/2005 Adams et al.
6,840,938 B1 1/2005 Morley et al.
6,841,967 B2 1/2005 Kim et al.
6,843,403 B2 1/2005 Whitman
6,843,789 B2 1/2005 Goble
6,843,793 B2 1/2005 Brock et al.
6,846,307 B2 1/2005 Whitman et al.
6,846,308 B2 1/2005 Whitman et al.
6,846,309 B2 1/2005 Whitman et al.
6,847,190 B2 1/2005 Schaefer et al.
6,849,071 B2 2/2005 Whitman et al.
6,850,817 B1 2/2005 Green
6,852,122 B2 2/2005 Rush
6,852,330 B2 2/2005 Bowman et al.
6,853,879 B2 2/2005 Sunaoshi
6,858,005 B2 2/2005 Ohline et al.
6,859,882 B2 2/2005 Fung
RE38,708 E 3/2005 Bolanos et al.
D502,994 S 3/2005 Blake, III
6,860,169 B2 3/2005 Shinozaki
6,861,142 B1 3/2005 Wilkie et al.
6,861,954 B2 3/2005 Levin
6,863,668 B2 3/2005 Gillespie et al.
6,863,694 B1 3/2005 Boyce et al.
6,863,924 B2 3/2005 Ranganathan et al.
6,866,178 B2 3/2005 Adams et al.
6,866,668 B2 3/2005 Giannetti et al.
6,866,671 B2 3/2005 Tierney et al.
6,867,248 B1 3/2005 Martin et al.
6,869,430 B2 3/2005 Balbierz et al.
6,869,435 B2 3/2005 Blake, III
6,872,214 B2 3/2005 Sonnenschein et al.
6,874,669 B2 4/2005 Adams et al.
6,876,850 B2 4/2005 Maeshima et al.
6,877,647 B2 4/2005 Green et al.
6,878,106 B1 4/2005 Herrmann
6,882,127 B2 4/2005 Konigbauer
6,883,199 B1 4/2005 Lundell et al.
6,884,392 B2 4/2005 Malkin et al.
6,884,428 B2 4/2005 Binette et al.
6,886,730 B2 5/2005 Fujisawa et al.
6,887,244 B1 5/2005 Walker et al.
6,887,710 B2 5/2005 Call et al.
6,889,116 B2 5/2005 Jinno
6,893,435 B2 5/2005 Goble
6,894,140 B2 5/2005 Roby
6,895,176 B2 5/2005 Archer et al.
6,899,538 B2 5/2005 Matoba
6,899,593 B1 5/2005 Moeller et al.
6,899,705 B2 5/2005 Niemeyer
6,899,915 B2 5/2005 Yelick et al.
6,905,057 B2 6/2005 Swayze et al.
6,905,497 B2 6/2005 Truckai et al.
6,905,498 B2 6/2005 Hooven
6,908,472 B2 6/2005 Wiener et al.
6,911,033 B2 6/2005 de Guillebon et al.
6,911,916 B1 6/2005 Wang et al.
6,913,579 B2 7/2005 Truckai et al.
6,913,608 B2 7/2005 Liddicoat et al.
6,913,613 B2 7/2005 Schwarz et al.
6,921,397 B2 7/2005 Corcoran et al.
6,921,412 B1 7/2005 Black et al.
6,923,093 B2 8/2005 Ullah
6,923,803 B2 8/2005 Goble
6,923,819 B2 8/2005 Meade et al.
6,925,849 B2 8/2005 Jairam
6,926,716 B2 8/2005 Baker et al.
6,927,315 B1 8/2005 Heinecke et al.
6,928,902 B1 8/2005 Eyssallenne

(56) References Cited

U.S. PATENT DOCUMENTS 6,929,641 B2 8/2005 Goble et al.
6,929,644 B2 8/2005 Truckai et al.
6,931,830 B2 8/2005 Liao
6,932,218 B2 8/2005 Kosann et al.
6,932,810 B2 8/2005 Ryan
6,936,042 B2 8/2005 Wallace et al.
6,936,948 B2 8/2005 Bell et al.
D509,297 S 9/2005 Wells
D509,589 S 9/2005 Wells
6,938,706 B2 9/2005 Ng
6,939,358 B2 9/2005 Palacios et al.
6,942,662 B2 9/2005 Goble et al.
6,942,674 B2 9/2005 Belef et al.
6,945,444 B2 9/2005 Gresham et al.
6,945,981 B2 9/2005 Donofrio et al.
6,949,196 B2 9/2005 Schmitz et al.
6,951,562 B2 10/2005 Zwirnmann
6,953,138 B1 10/2005 Dworak et al.
6,953,139 B2 10/2005 Milliman et al.
6,953,461 B2 10/2005 McClurken et al.
6,957,758 B2 10/2005 Aranyi
6,958,035 B2 10/2005 Friedman et al.
6,958,070 B2 10/2005 Witt et al.
D511,525 S 11/2005 Hernandez et al.
6,959,851 B2 11/2005 Heinrich
6,959,852 B2 11/2005 Shelton, IV et al.
6,960,107 B1 11/2005 Schaub et al.
6,960,163 B2 11/2005 Ewers et al.
6,960,220 B2 11/2005 Marino et al.
6,960,894 B2 11/2005 Carusillo et al.
6,962,587 B2 11/2005 Johnson et al.
6,963,792 B1 11/2005 Green
6,964,363 B2 11/2005 Wales et al.
6,966,907 B2 11/2005 Goble
6,966,909 B2 11/2005 Marshall et al.
6,968,908 B2 11/2005 Tokunaga et al.
6,969,385 B2 11/2005 Moreyra
6,969,395 B2 11/2005 Eskuri
6,971,988 B2 12/2005 Orban, III
6,972,199 B2 12/2005 Lebouitz et al.
6,974,435 B2 12/2005 Daw et al.
6,974,462 B2 12/2005 Sater
6,978,921 B2 12/2005 Shelton, IV et al.
6,978,922 B2 12/2005 Bilotti et al.
6,981,628 B2 1/2006 Wales
6,981,941 B2 1/2006 Whitman et al.
6,981,978 B2 1/2006 Gannoe
6,984,203 B2 1/2006 Tartaglia et al.
6,984,231 B2 1/2006 Goble et al.
6,986,451 B1 1/2006 Mastri et al.
6,988,649 B2 1/2006 Shelton, IV et al.
6,988,650 B2 1/2006 Schwemberger et al.
6,989,034 B2 1/2006 Hammer et al.
6,990,731 B2 1/2006 Haytayan
6,990,796 B2 1/2006 Schnipke et al.
6,991,146 B2 1/2006 Sinisi et al.
6,993,200 B2 1/2006 Tastl et al.
6,993,413 B2 1/2006 Sunaoshi
6,994,708 B2 2/2006 Manzo
6,995,729 B2 2/2006 Govari et al.
6,996,433 B2 2/2006 Burbank et al.
6,997,931 B2 2/2006 Sauer et al.
6,997,935 B2 2/2006 Anderson et al.
6,998,736 B2 2/2006 Lee et al.
6,998,816 B2 2/2006 Wieck et al.
6,999,821 B2 2/2006 Jenney et al.
7,000,818 B2 2/2006 Shelton, IV et al.
7,000,819 B2 2/2006 Swayze et al.
7,000,911 B2 2/2006 McCormick et al.
7,001,380 B2 2/2006 Goble
7,001,408 B2 2/2006 Knodel et al.
7,004,174 B2 2/2006 Eggers et al.
7,005,828 B2 2/2006 Karikomi
7,007,176 B2 2/2006 Goodfellow et al.
7,008,433 B2 3/2006 Voellmicke et al.
7,008,435 B2 3/2006 Cummins
7,009,039 B2 3/2006 Yayon et al.
7,011,213 B2 3/2006 Clark et al.
7,011,657 B2 3/2006 Truckai et al.
7,014,640 B2 3/2006 Kemppainen et al.
7,018,357 B2 3/2006 Emmons
7,018,390 B2 3/2006 Turovskiy et al.
7,021,399 B2 4/2006 Driessen
7,021,669 B1 4/2006 Lindermeir et al.
7,022,131 B1 4/2006 Derowe et al.
7,023,159 B2 4/2006 Gorti et al.
7,025,064 B2 4/2006 Wang et al.
7,025,732 B2 4/2006 Thompson et al.
7,025,743 B2 4/2006 Mann et al.
7,025,774 B2 4/2006 Freeman et al.
7,025,775 B2 4/2006 Gadberry et al.
7,028,570 B2 4/2006 Ohta et al.
7,029,435 B2 4/2006 Nakao
7,029,439 B2 4/2006 Roberts et al.
7,030,904 B2 4/2006 Adair et al.
7,032,798 B2 4/2006 Whitman et al.
7,032,799 B2 4/2006 Viola et al.
7,033,356 B2 4/2006 Latterell et al.
7,033,378 B2 4/2006 Smith et al.
7,035,716 B2 4/2006 Harris et al.
7,035,762 B2 4/2006 Menard et al.
7,036,680 B1 5/2006 Flannery
7,037,314 B2 5/2006 Armstrong
7,037,344 B2 5/2006 Kagan et al.
7,038,421 B2 5/2006 Trifilo
7,041,088 B2 5/2006 Nawrocki et al.
7,041,102 B2 5/2006 Truckai et al.
7,041,868 B2 5/2006 Greene et al.
7,043,852 B2 5/2006 Hayashida et al.
7,044,350 B2 5/2006 Kameyama et al.
7,044,352 B2 5/2006 Shelton, IV et al.
7,044,353 B2 5/2006 Mastri et al.
7,046,082 B2 5/2006 Komiya et al.
7,048,165 B2 5/2006 Haramiishi
7,048,687 B1 5/2006 Reuss et al.
7,048,716 B1 5/2006 Kucharczyk et al.
7,048,745 B2 5/2006 Tierney et al.
7,052,454 B2 5/2006 Taylor
7,052,494 B2 5/2006 Goble et al.
7,052,499 B2 5/2006 Steger et al.
7,055,730 B2 6/2006 Ehrenfels et al.
7,055,731 B2 6/2006 Shelton, IV et al.
7,056,123 B2 6/2006 Gregorio et al.
7,056,284 B2 6/2006 Martone et al.
7,056,330 B2 6/2006 Gayton
7,059,331 B2 6/2006 Adams et al.
7,059,508 B2 6/2006 Shelton, IV et al.
7,063,671 B2 6/2006 Couvillon, Jr.
7,063,712 B2 6/2006 Vargas et al.
7,064,509 B1 6/2006 Fu et al.
7,066,879 B2 6/2006 Fowler et al.
7,066,944 B2 6/2006 Laufer et al.
7,067,038 B2 6/2006 Trokhan et al.
7,070,083 B2 7/2006 Jankowski
7,070,559 B2 7/2006 Adams et al.
7,070,597 B2 7/2006 Truckai et al.
7,071,287 B2 7/2006 Rhine et al.
7,075,412 B1 7/2006 Reynolds et al.
7,075,770 B1 7/2006 Smith
7,077,856 B2 7/2006 Whitman
7,080,769 B2 7/2006 Vresh et al.
7,081,114 B2 7/2006 Rashid
7,081,318 B2 7/2006 Lee et al.
7,083,073 B2 8/2006 Yoshie et al.
7,083,075 B2 8/2006 Swayze et al.
7,083,571 B2 8/2006 Wang et al.
7,083,615 B2 8/2006 Peterson et al.
7,083,619 B2 8/2006 Truckai et al.
7,083,620 B2 8/2006 Jahns et al.
7,083,626 B2 8/2006 Hart et al.
7,086,267 B2 8/2006 Dworak et al.
7,087,049 B2 8/2006 Nowlin et al.
7,087,054 B2 8/2006 Truckai et al.
7,087,071 B2 8/2006 Nicholas et al.

(56) References Cited

U.S. PATENT DOCUMENTS 7,090,637 B2 8/2006 Danitz et al.
7,090,673 B2 8/2006 Dycus et al.
7,090,683 B2 8/2006 Brock et al.
7,090,684 B2 8/2006 McGuckin, Jr. et al.
7,091,191 B2 8/2006 Laredo et al.
7,091,412 B2 8/2006 Wang et al.
7,093,492 B2 8/2006 Treiber et al.
7,094,202 B2 8/2006 Nobis et al.
7,094,247 B2 8/2006 Monassevitch et al.
7,094,916 B2 8/2006 DeLuca et al.
7,096,972 B2 8/2006 Orozco, Jr.
7,097,089 B2 8/2006 Marczyk
7,097,644 B2 8/2006 Long
7,097,650 B2 8/2006 Weller et al.
7,098,794 B2 8/2006 Lindsay et al.
7,100,949 B2 9/2006 Williams et al.
7,101,187 B1 9/2006 Deconinck et al.
7,101,363 B2 9/2006 Nishizawa et al.
7,101,371 B2 9/2006 Dycus et al.
7,101,394 B2 9/2006 Hamm et al.
7,104,741 B2 9/2006 Krohn
7,108,695 B2 9/2006 Witt et al.
7,108,701 B2 9/2006 Evens et al.
7,108,709 B2 9/2006 Cummins
7,111,768 B2 9/2006 Cummins et al.
7,111,769 B2 9/2006 Wales et al.
7,112,201 B2 9/2006 Truckai et al.
7,112,214 B2 9/2006 Peterson et al.
RE39,358 E 10/2006 Goble
D530,339 S 10/2006 Hernandez et al.
7,114,642 B2 10/2006 Whitman
7,116,100 B1 10/2006 Mock et al.
7,118,020 B2 10/2006 Lee et al.
7,118,528 B1 10/2006 Piskun
7,118,563 B2 10/2006 Weckwerth et al.
7,118,582 B1 10/2006 Wang et al.
7,119,534 B2 10/2006 Butzmann
7,121,446 B2 10/2006 Arad et al.
7,121,773 B2 10/2006 Mikiya et al.
7,122,028 B2 10/2006 Looper et al.
7,125,403 B2 10/2006 Julian et al.
7,125,409 B2 10/2006 Truckai et al.
7,126,303 B2 10/2006 Farritor et al.
7,126,879 B2 10/2006 Snyder
7,128,253 B2 10/2006 Mastri et al.
7,128,254 B2 10/2006 Shelton, IV et al.
7,128,748 B2 10/2006 Mooradian et al.
7,131,445 B2 11/2006 Amoah
7,133,601 B2 11/2006 Phillips et al.
7,134,364 B2 11/2006 Kageler et al.
7,134,587 B2 11/2006 Schwemberger et al.
7,135,027 B2 11/2006 Delmotte
7,137,980 B2 11/2006 Buysse et al.
7,137,981 B2 11/2006 Long
7,139,016 B2 11/2006 Squilla et al.
7,140,527 B2 11/2006 Ehrenfels et al.
7,140,528 B2 11/2006 Shelton, IV
7,141,055 B2 11/2006 Abrams et al.
7,143,923 B2 12/2006 Shelton, IV et al.
7,143,924 B2 12/2006 Scirica et al.
7,143,925 B2 12/2006 Shelton, IV et al.
7,143,926 B2 12/2006 Shelton, IV et al.
7,146,191 B2 12/2006 Kerner et al.
7,147,138 B2 12/2006 Shelton, IV
7,147,139 B2 12/2006 Schwemberger et al.
7,147,140 B2 12/2006 Wukusick et al.
7,147,637 B2 12/2006 Goble
7,147,648 B2 12/2006 Lin
7,147,650 B2 12/2006 Lee
7,150,748 B2 12/2006 Ebbutt et al.
7,153,300 B2 12/2006 Goble
7,153,314 B2 12/2006 Laufer et al.
7,155,316 B2 12/2006 Sutherland et al.
7,156,846 B2 1/2007 Dycus et al.
7,156,863 B2 1/2007 Sonnenschein et al.
7,159,750 B2 1/2007 Racenet et al.
7,160,296 B2 1/2007 Pearson et al.
7,160,299 B2 1/2007 Baily
7,160,311 B2 1/2007 Blatter et al.
7,161,036 B2 1/2007 Oikawa et al.
7,161,580 B2 1/2007 Bailey et al.
7,162,758 B2 1/2007 Skinner
7,163,563 B2 1/2007 Schwartz et al.
7,166,117 B2 1/2007 Hellenkamp
7,166,133 B2 1/2007 Evans et al.
7,168,604 B2 1/2007 Milliman et al.
7,169,146 B2 1/2007 Truckai et al.
7,170,910 B2 1/2007 Chen et al.
7,171,279 B2 1/2007 Buckingham et al.
7,172,104 B2 2/2007 Scirica et al.
7,172,593 B2 2/2007 Trieu et al.
7,172,615 B2 2/2007 Morriss et al.
7,174,202 B2 2/2007 Bladen et al.
7,174,636 B2 2/2007 Lowe
7,177,533 B2 2/2007 McFarlin et al.
7,179,223 B2 2/2007 Motoki et al.
7,179,267 B2 2/2007 Nolan et al.
7,182,239 B1 2/2007 Myers
7,182,763 B2 2/2007 Nardella
7,183,737 B2 2/2007 Kitagawa
7,187,960 B2 3/2007 Abreu
7,188,758 B2 3/2007 Viola et al.
7,189,207 B2 3/2007 Viola
7,190,147 B2 3/2007 Gileff et al.
7,193,199 B2 3/2007 Jang
7,195,627 B2 3/2007 Amoah et al.
7,196,911 B2 3/2007 Takano et al.
D541,418 S 4/2007 Schechter et al.
7,197,965 B1 4/2007 Anderson
7,199,537 B2 4/2007 Okamura et al.
7,199,545 B2 4/2007 Oleynikov et al.
7,202,576 B1 4/2007 Dechene et al.
7,202,653 B2 4/2007 Pai
7,204,404 B2 4/2007 Nguyen et al.
7,204,835 B2 4/2007 Latterell et al.
7,205,959 B2 4/2007 Henriksson
7,206,626 B2 4/2007 Quaid, III
7,207,233 B2 4/2007 Wadge
7,207,471 B2 4/2007 Heinrich et al.
7,207,472 B2 4/2007 Wukusick et al.
7,207,556 B2 4/2007 Saitoh et al.
7,208,005 B2 4/2007 Frecker et al.
7,210,609 B2 5/2007 Leiboff et al.
7,211,081 B2 5/2007 Goble
7,211,084 B2 5/2007 Goble et al.
7,211,092 B2 5/2007 Hughett
7,211,979 B2 5/2007 Khatib et al.
7,213,736 B2 5/2007 Wales et al.
7,214,224 B2 5/2007 Goble
7,215,517 B2 5/2007 Takamatsu
7,217,285 B2 5/2007 Vargas et al.
7,220,260 B2 5/2007 Fleming et al.
7,220,272 B2 5/2007 Weadock
7,225,959 B2 6/2007 Patton et al.
7,225,963 B2 6/2007 Scirica
7,225,964 B2 6/2007 Mastri et al.
7,226,450 B2 6/2007 Athanasiou et al.
7,226,467 B2 6/2007 Lucatero et al.
7,228,505 B2 6/2007 Shimazu et al.
7,229,408 B2 6/2007 Douglas et al.
7,234,624 B2 6/2007 Gresham et al.
7,235,072 B2 6/2007 Sartor et al.
7,235,089 B1 6/2007 McGuckin, Jr.
7,235,302 B2 6/2007 Jing et al.
7,237,708 B1 7/2007 Guy et al.
7,238,195 B2 7/2007 Viola
7,238,901 B2 7/2007 Kim et al.
7,239,657 B1 7/2007 Gunnarsson
7,241,288 B2 7/2007 Braun
7,241,289 B2 7/2007 Braun
7,246,734 B2 7/2007 Shelton, IV
7,247,161 B2 7/2007 Johnston et al.
7,249,267 B2 7/2007 Chapuis
7,252,641 B2 8/2007 Thompson et al.

(56) References Cited

U.S. PATENT DOCUMENTS 7,252,660 B2 8/2007 Kunz
7,255,012 B2 8/2007 Hedtke
7,255,696 B2 8/2007 Goble et al.
7,256,695 B2 8/2007 Hamel et al.
7,258,262 B2 8/2007 Mastri et al.
7,258,546 B2 8/2007 Beier et al.
7,260,431 B2 8/2007 Libbus et al.
7,265,374 B2 9/2007 Lee et al.
7,267,677 B2 9/2007 Johnson et al.
7,267,679 B2 9/2007 McGuckin, Jr. et al.
7,272,002 B2 9/2007 Drapeau
7,273,483 B2 9/2007 Wiener et al.
7,273,488 B2 9/2007 Nakamura et al.
D552,623 S 10/2007 Vong et al.
7,275,674 B2 10/2007 Racenet et al.
7,276,044 B2 10/2007 Ferry et al.
7,276,068 B2 10/2007 Johnson et al.
7,278,562 B2 10/2007 Mastri et al.
7,278,563 B1 10/2007 Green
7,278,949 B2 10/2007 Bader
7,278,994 B2 10/2007 Goble
7,282,048 B2 10/2007 Goble et al.
7,283,096 B2 10/2007 Geisheimer et al.
7,286,850 B2 10/2007 Frielink et al.
7,287,682 B1 10/2007 Ezzat et al.
7,289,139 B2 10/2007 Amling et al.
7,293,685 B2 11/2007 Ehrenfels et al.
7,295,893 B2 11/2007 Sunaoshi
7,295,907 B2 11/2007 Lu et al.
7,296,722 B2 11/2007 Ivanko
7,296,724 B2 11/2007 Green et al.
7,297,149 B2 11/2007 Vitali et al.
7,300,373 B2 11/2007 Jinno et al.
7,300,431 B2 11/2007 Dubrovsky
7,300,450 B2 11/2007 Vleugels et al.
7,303,106 B2 12/2007 Milliman et al.
7,303,107 B2 12/2007 Milliman et al.
7,303,108 B2 12/2007 Shelton, IV
7,303,502 B2 12/2007 Thompson
7,303,556 B2 12/2007 Metzger
7,306,597 B2 12/2007 Manzo
7,308,998 B2 12/2007 Mastri et al.
7,311,238 B2 12/2007 Liu
7,311,709 B2 12/2007 Truckai et al.
7,313,430 B2 12/2007 Urquhart et al.
7,314,473 B2 1/2008 Jinno et al.
7,317,955 B2 1/2008 McGreevy
7,320,704 B2 1/2008 Lashinski et al.
7,322,859 B2 1/2008 Evans
7,322,975 B2 1/2008 Goble et al.
7,322,994 B2 1/2008 Nicholas et al.
7,324,572 B2 1/2008 Chang
7,326,203 B2 2/2008 Papineau et al.
7,326,213 B2 2/2008 Benderev et al.
7,328,828 B2 2/2008 Ortiz et al.
7,328,829 B2 2/2008 Arad et al.
7,330,004 B2 2/2008 DeJonge et al.
7,331,340 B2 2/2008 Barney
7,331,343 B2 2/2008 Schmidt et al.
7,331,403 B2 2/2008 Berry et al.
7,331,406 B2 2/2008 Wottreng, Jr. et al.
7,331,969 B1 2/2008 Inganas et al.
7,334,717 B2 2/2008 Rethy et al.
7,334,718 B2 2/2008 McAlister et al.
7,335,199 B2 2/2008 Goble et al.
7,335,401 B2 2/2008 Finke et al.
7,336,045 B2 2/2008 Clermonts
7,336,048 B2 2/2008 Lohr
7,336,183 B2 2/2008 Reddy et al.
7,336,184 B2 2/2008 Smith et al.
7,337,774 B2 3/2008 Webb
7,338,505 B2 3/2008 Belson
7,338,513 B2 3/2008 Lee et al.
7,341,554 B2 3/2008 Sekine et al.
7,341,555 B2 3/2008 Ootawara et al.
7,341,591 B2 3/2008 Grinberg
7,343,920 B2 3/2008 Toby et al.
7,344,532 B2 3/2008 Goble et al.
7,344,533 B2 3/2008 Pearson et al.
7,346,344 B2 3/2008 Fontaine
7,346,406 B2 3/2008 Brotto et al.
7,348,763 B1 3/2008 Reinhart et al.
7,348,875 B2 3/2008 Hughes et al.
RE40,237 E 4/2008 Bilotti et al.
7,351,258 B2 4/2008 Ricotta et al.
7,354,398 B2 4/2008 Kanazawa
7,354,440 B2 4/2008 Truckal et al.
7,354,447 B2 4/2008 Shelton, IV et al.
7,354,502 B2 4/2008 Polat et al.
7,357,287 B2 4/2008 Shelton, IV et al.
7,357,806 B2 4/2008 Rivera et al.
7,361,168 B2 4/2008 Makower et al.
7,361,195 B2 4/2008 Schwartz et al.
7,362,062 B2 4/2008 Schneider et al.
7,364,060 B2 4/2008 Milliman
7,364,061 B2 4/2008 Swayze et al.
7,367,485 B2 5/2008 Shelton, IV et al.
7,367,973 B2 5/2008 Manzo et al.
7,368,124 B2 5/2008 Chun et al.
7,371,210 B2 5/2008 Brock et al.
7,371,403 B2 5/2008 McCarthy et al.
7,375,493 B2 5/2008 Calhoon et al.
7,377,918 B2 5/2008 Amoah
7,377,928 B2 5/2008 Zubik et al.
7,378,817 B2 5/2008 Calhoon et al.
RE40,388 E 6/2008 Gines
D570,868 S 6/2008 Hosokawa et al.
7,380,695 B2 6/2008 Doll et al.
7,380,696 B2 6/2008 Shelton, IV et al.
7,384,403 B2 6/2008 Sherman
7,384,417 B2 6/2008 Cucin
7,386,365 B2 6/2008 Nixon
7,386,730 B2 6/2008 Uchikubo
7,388,217 B2 6/2008 Buschbeck et al.
7,388,484 B2 6/2008 Hsu
7,391,173 B2 6/2008 Schena
7,394,190 B2 7/2008 Huang
7,396,356 B2 7/2008 Mollenauer
7,397,364 B2 7/2008 Govari
7,398,707 B2 7/2008 Morley et al.
7,398,907 B2 7/2008 Racenet et al.
7,398,908 B2 7/2008 Holsten et al.
7,400,107 B2 7/2008 Schneider et al.
7,400,752 B2 7/2008 Zacharias
7,401,000 B2 7/2008 Nakamura
7,401,721 B2 7/2008 Holsten et al.
7,404,449 B2 7/2008 Bermingham et al.
7,404,508 B2 7/2008 Smith et al.
7,404,509 B2 7/2008 Ortiz et al.
7,404,822 B2 7/2008 Viart et al.
D575,793 S 8/2008 Ording
7,407,074 B2 8/2008 Ortiz et al.
7,407,075 B2 8/2008 Holsten et al.
7,407,076 B2 8/2008 Racenet et al.
7,407,077 B2 8/2008 Ortiz et al.
7,407,078 B2 8/2008 Shelton, IV et al.
7,408,310 B2 8/2008 Hong et al.
7,410,085 B2 8/2008 Wolf et al.
7,410,086 B2 8/2008 Ortiz et al.
7,410,483 B2 8/2008 Danitz et al.
7,413,563 B2 8/2008 Corcoran et al.
7,416,101 B2 8/2008 Shelton, IV et al.
7,418,078 B2 8/2008 Blanz et al.
RE40,514 E 9/2008 Mastri et al.
7,419,080 B2 9/2008 Smith et al.
7,419,081 B2 9/2008 Ehrenfels et al.
7,419,321 B2 9/2008 Tereschouk
7,419,495 B2 9/2008 Menn et al.
7,422,136 B1 9/2008 Marczyk
7,422,138 B2 9/2008 Bilotti et al.
7,422,139 B2 9/2008 Shelton, IV et al.
7,422,582 B2 9/2008 Malackowski et al.
7,424,965 B2 9/2008 Racenet et al.
7,427,607 B2 9/2008 Suzuki

(56) References Cited

U.S. PATENT DOCUMENTS

| | | | |
|---|---|---|---|
| D578,644 | S | 10/2008 | Shumer et al. |
| 7,430,772 | B2 | 10/2008 | Van Es |
| 7,430,849 | B1 | 10/2008 | Coutts et al. |
| 7,431,188 | B1 | 10/2008 | Marczyk |
| 7,431,189 | B2 | 10/2008 | Shelton, IV et al. |
| 7,431,230 | B2 | 10/2008 | McPherson et al. |
| 7,431,694 | B2 | 10/2008 | Stefanchik et al. |
| 7,431,730 | B2 | 10/2008 | Viola |
| 7,434,715 | B2 | 10/2008 | Shelton, IV et al. |
| 7,434,717 | B2 | 10/2008 | Shelton, IV et al. |
| 7,435,249 | B2 | 10/2008 | Buysse et al. |
| 7,438,209 | B1 | 10/2008 | Hess et al. |
| 7,438,718 | B2 | 10/2008 | Milliman et al. |
| 7,439,354 | B2 | 10/2008 | Lenges et al. |
| 7,441,684 | B2 | 10/2008 | Shelton, IV et al. |
| 7,441,685 | B1 | 10/2008 | Boudreaux |
| 7,442,201 | B2 | 10/2008 | Pugsley et al. |
| 7,443,547 | B2 | 10/2008 | Moreno et al. |
| D580,942 | S | 11/2008 | Oshiro et al. |
| 7,446,131 | B1 | 11/2008 | Liu et al. |
| 7,448,525 | B2 | 11/2008 | Shelton, IV et al. |
| 7,450,010 | B1 | 11/2008 | Gravelle et al. |
| 7,450,991 | B2 | 11/2008 | Smith et al. |
| 7,451,904 | B2 | 11/2008 | Shelton, IV |
| 7,455,208 | B2 | 11/2008 | Wales et al. |
| 7,455,676 | B2 | 11/2008 | Holsten et al. |
| 7,455,682 | B2 | 11/2008 | Viola |
| 7,455,687 | B2 | 11/2008 | Saunders et al. |
| D582,934 | S | 12/2008 | Byeon |
| 7,461,767 | B2 | 12/2008 | Viola et al. |
| 7,462,187 | B2 | 12/2008 | Johnston et al. |
| 7,464,845 | B2 | 12/2008 | Chou |
| 7,464,846 | B2 | 12/2008 | Shelton, IV et al. |
| 7,464,847 | B2 | 12/2008 | Viola et al. |
| 7,464,848 | B2 | 12/2008 | Green et al. |
| 7,464,849 | B2 | 12/2008 | Shelton, IV et al. |
| 7,467,740 | B2 | 12/2008 | Shelton, IV et al. |
| 7,467,849 | B2 | 12/2008 | Silverbrook et al. |
| 7,472,814 | B2 | 1/2009 | Mastri et al. |
| 7,472,815 | B2 | 1/2009 | Shelton, IV et al. |
| 7,472,816 | B2 | 1/2009 | Holsten et al. |
| 7,473,221 | B2 | 1/2009 | Ewers et al. |
| 7,473,253 | B2 | 1/2009 | Dycus et al. |
| 7,473,263 | B2 | 1/2009 | Johnston et al. |
| 7,476,237 | B2 | 1/2009 | Taniguchi et al. |
| 7,479,147 | B2 | 1/2009 | Honeycutt et al. |
| 7,479,608 | B2 | 1/2009 | Smith |
| 7,481,347 | B2 | 1/2009 | Roy |
| 7,481,348 | B2 | 1/2009 | Marczyk |
| 7,481,349 | B2 | 1/2009 | Holsten et al. |
| 7,481,824 | B2 | 1/2009 | Boudreaux et al. |
| 7,485,124 | B2 | 2/2009 | Kuhns et al. |
| 7,485,133 | B2 | 2/2009 | Cannon et al. |
| 7,485,142 | B2 | 2/2009 | Milo |
| 7,487,899 | B2 | 2/2009 | Shelton, IV et al. |
| 7,489,055 | B2 | 2/2009 | Jeong et al. |
| 7,490,749 | B2 | 2/2009 | Schall et al. |
| 7,491,232 | B2 | 2/2009 | Bolduc et al. |
| 7,492,261 | B2 | 2/2009 | Cambre et al. |
| 7,494,039 | B2 | 2/2009 | Racenet et al. |
| 7,494,460 | B2 | 2/2009 | Haarstad et al. |
| 7,494,499 | B2 | 2/2009 | Nagase et al. |
| 7,494,501 | B2 | 2/2009 | Ahlberg et al. |
| 7,497,137 | B2 | 3/2009 | Tellenbach et al. |
| 7,500,979 | B2 | 3/2009 | Hueil et al. |
| 7,501,198 | B2 | 3/2009 | Barlev et al. |
| 7,503,474 | B2 | 3/2009 | Hillstead et al. |
| 7,506,790 | B2 | 3/2009 | Shelton, IV |
| 7,506,791 | B2 | 3/2009 | Omaits et al. |
| 7,507,202 | B2 | 3/2009 | Schoellhorn |
| 7,510,107 | B2 | 3/2009 | Timm et al. |
| 7,510,534 | B2 | 3/2009 | Burdorff et al. |
| 7,510,566 | B2 | 3/2009 | Jacobs et al. |
| 7,513,407 | B1 | 4/2009 | Chang |
| 7,513,408 | B2 | 4/2009 | Shelton, IV et al. |
| 7,517,356 | B2 | 4/2009 | Heinrich |
| 7,524,320 | B2 | 4/2009 | Tierney et al. |
| 7,527,632 | B2 | 5/2009 | Houghton et al. |
| 7,530,984 | B2 | 5/2009 | Sonnenschein et al. |
| 7,530,985 | B2 | 5/2009 | Takemoto et al. |
| 7,533,790 | B1 | 5/2009 | Knodel et al. |
| 7,533,906 | B2 | 5/2009 | Luettgen et al. |
| 7,534,259 | B2 | 5/2009 | Lashinski et al. |
| 7,540,867 | B2 | 6/2009 | Jinno et al. |
| 7,540,872 | B2 | 6/2009 | Schechter et al. |
| 7,542,807 | B2 | 6/2009 | Bertolero et al. |
| 7,543,730 | B1 | 6/2009 | Marczyk |
| 7,544,197 | B2 | 6/2009 | Kelsch et al. |
| 7,546,939 | B2 | 6/2009 | Adams et al. |
| 7,546,940 | B2 | 6/2009 | Milliman et al. |
| 7,547,287 | B2 | 6/2009 | Boecker et al. |
| 7,547,312 | B2 | 6/2009 | Bauman et al. |
| 7,549,563 | B2 | 6/2009 | Mather et al. |
| 7,549,564 | B2 | 6/2009 | Boudreaux |
| 7,549,998 | B2 | 6/2009 | Braun |
| 7,552,854 | B2 | 6/2009 | Wixey et al. |
| 7,553,173 | B2 | 6/2009 | Kowalick |
| 7,553,275 | B2 | 6/2009 | Padget et al. |
| 7,554,343 | B2 | 6/2009 | Bromfield |
| 7,556,185 | B2 | 7/2009 | Viola |
| 7,556,186 | B2 | 7/2009 | Milliman |
| 7,556,647 | B2 | 7/2009 | Drews et al. |
| 7,559,449 | B2 | 7/2009 | Viola |
| 7,559,450 | B2 | 7/2009 | Wales et al. |
| 7,559,452 | B2 | 7/2009 | Wales et al. |
| 7,559,937 | B2 | 7/2009 | de la Torre et al. |
| 7,561,637 | B2 | 7/2009 | Jonsson et al. |
| 7,562,910 | B2 | 7/2009 | Kertesz et al. |
| 7,563,269 | B2 | 7/2009 | Hashiguchi |
| 7,563,862 | B2 | 7/2009 | Sieg et al. |
| 7,565,993 | B2 | 7/2009 | Milliman et al. |
| 7,566,300 | B2 | 7/2009 | Devierre et al. |
| 7,567,045 | B2 | 7/2009 | Fristedt |
| 7,568,603 | B2 | 8/2009 | Shelton, IV et al. |
| 7,568,604 | B2 | 8/2009 | Ehrenfels et al. |
| 7,568,619 | B2 | 8/2009 | Todd et al. |
| 7,572,285 | B2 | 8/2009 | Frey et al. |
| 7,572,298 | B2 | 8/2009 | Roller et al. |
| 7,575,144 | B2 | 8/2009 | Ortiz et al. |
| 7,578,825 | B2 | 8/2009 | Huebner |
| D600,703 | S | 9/2009 | LaManna et al. |
| D600,712 | S | 9/2009 | LaManna et al. |
| 7,582,086 | B2 | 9/2009 | Privitera et al. |
| 7,583,063 | B2 | 9/2009 | Dooley |
| 7,584,880 | B2 | 9/2009 | Racenet et al. |
| 7,586,289 | B2 | 9/2009 | Andruk et al. |
| 7,588,174 | B2 | 9/2009 | Holsten et al. |
| 7,588,175 | B2 | 9/2009 | Timm et al. |
| 7,588,176 | B2 | 9/2009 | Timm et al. |
| 7,588,177 | B2 | 9/2009 | Racenet |
| 7,591,783 | B2 | 9/2009 | Boulais et al. |
| 7,591,818 | B2 | 9/2009 | Bertolero et al. |
| 7,593,766 | B2 | 9/2009 | Faber et al. |
| 7,595,642 | B2 | 9/2009 | Doyle |
| D601,578 | S | 10/2009 | Poulet et al. |
| 7,597,229 | B2 | 10/2009 | Boudreaux et al. |
| 7,597,230 | B2 | 10/2009 | Racenet et al. |
| 7,597,693 | B2 | 10/2009 | Garrison |
| 7,597,699 | B2 | 10/2009 | Rogers |
| 7,598,972 | B2 | 10/2009 | Tomita |
| 7,600,663 | B2 | 10/2009 | Green |
| 7,604,118 | B2 | 10/2009 | Iio et al. |
| 7,604,150 | B2 | 10/2009 | Boudreaux |
| 7,604,151 | B2 | 10/2009 | Hess et al. |
| 7,604,668 | B2 | 10/2009 | Farnsworth et al. |
| 7,605,826 | B2 | 10/2009 | Sauer |
| 7,607,557 | B2 | 10/2009 | Shelton, IV et al. |
| 7,608,091 | B2 | 10/2009 | Goldfarb et al. |
| D604,325 | S | 11/2009 | Ebeling et al. |
| 7,611,038 | B2 | 11/2009 | Racenet et al. |
| 7,611,474 | B2 | 11/2009 | Hibner et al. |
| 7,615,003 | B2 | 11/2009 | Stefanchik et al. |
| 7,615,006 | B2 | 11/2009 | Abe |
| 7,615,067 | B2 | 11/2009 | Lee et al. |

(56) References Cited

U.S. PATENT DOCUMENTS 7,617,961 B2 11/2009 Viola
7,618,427 B2 11/2009 Ortiz et al.
D605,201 S 12/2009 Lorenz et al.
D606,992 S 12/2009 Liu et al.
D607,010 S 12/2009 Kocmick
7,624,902 B2 12/2009 Marczyk et al.
7,624,903 B2 12/2009 Green et al.
7,625,370 B2 12/2009 Hart et al.
7,625,388 B2 12/2009 Boukhny et al.
7,625,662 B2 12/2009 Vaisnys et al.
7,630,841 B2 12/2009 Comisky et al.
7,631,793 B2 12/2009 Rethy et al.
7,631,794 B2 12/2009 Rethy et al.
7,635,074 B2 12/2009 Olson et al.
7,635,922 B2 12/2009 Becker
7,637,409 B2 12/2009 Marczyk
7,637,410 B2 12/2009 Marczyk
7,638,958 B2 12/2009 Philipp et al.
7,639,598 B2 12/2009 Sovenyi
7,641,091 B2 1/2010 Olson et al.
7,641,092 B2 1/2010 Kruszynski et al.
7,641,093 B2 1/2010 Doll et al.
7,641,095 B2 1/2010 Viola
7,641,671 B2 1/2010 Crainich
7,644,016 B2 1/2010 Nycz et al.
7,644,484 B2 1/2010 Vereschagin
7,644,783 B2 1/2010 Roberts et al.
7,644,848 B2 1/2010 Swayze et al.
7,645,230 B2 1/2010 Mikkaichi et al.
7,648,055 B2 1/2010 Marczyk
7,648,457 B2 1/2010 Stefanchik et al.
7,648,519 B2 1/2010 Lee et al.
7,650,185 B2 1/2010 Maile et al.
7,651,017 B2 1/2010 Ortiz et al.
7,651,498 B2 1/2010 Shifrin et al.
7,654,431 B2 2/2010 Hueil et al.
7,655,003 B2 2/2010 Lorang et al.
7,655,004 B2 2/2010 Long
7,655,288 B2 2/2010 Bauman et al.
7,655,584 B2 2/2010 Biran et al.
7,656,131 B2 2/2010 Embrey et al.
7,658,311 B2 2/2010 Boudreaux
7,658,312 B2 2/2010 Vidal et al.
7,658,705 B2 2/2010 Melvin et al.
7,659,219 B2 2/2010 Biran et al.
7,661,448 B2 2/2010 Kim et al.
7,662,161 B2 2/2010 Briganti et al.
7,665,646 B2 2/2010 Prommersberger
7,665,647 B2 2/2010 Shelton, IV et al.
7,666,195 B2 2/2010 Kelleher et al.
7,669,746 B2 3/2010 Shelton, IV
7,669,747 B2 3/2010 Weisenburgh, II et al.
7,670,334 B2 3/2010 Hueil et al.
7,670,337 B2 3/2010 Young
7,673,780 B2 3/2010 Shelton, IV et al.
7,673,781 B2 3/2010 Swayze et al.
7,673,782 B2 3/2010 Hess et al.
7,673,783 B2 3/2010 Morgan et al.
7,674,253 B2 3/2010 Fisher et al.
7,674,255 B2 3/2010 Braun
7,674,263 B2 3/2010 Ryan
7,674,270 B2 3/2010 Layer
7,678,121 B1 3/2010 Knodel
7,682,307 B2 3/2010 Danitz et al.
7,682,367 B2 3/2010 Shah et al.
7,682,686 B2 3/2010 Curro et al.
7,686,201 B2 3/2010 Csiky
7,686,804 B2 3/2010 Johnson et al.
7,686,826 B2 3/2010 Lee et al.
7,688,028 B2 3/2010 Phillips et al.
7,690,547 B2 4/2010 Racenet et al.
7,691,098 B2 4/2010 Wallace et al.
7,691,103 B2 4/2010 Fernandez et al.
7,691,106 B2 4/2010 Schenberger et al.
7,694,864 B2 4/2010 Okada et al.
7,694,865 B2 4/2010 Scirica
7,695,485 B2 4/2010 Whitman et al.
7,695,493 B2 4/2010 Saadat et al.
7,699,204 B2 4/2010 Viola
7,699,835 B2 4/2010 Lee et al.
7,699,844 B2 4/2010 Utley et al.
7,699,846 B2 4/2010 Ryan
7,699,856 B2 4/2010 Van Wyk et al.
7,699,859 B2 4/2010 Bombard et al.
7,699,860 B2 4/2010 Huitema et al.
7,699,868 B2 4/2010 Frank et al.
7,703,653 B2 4/2010 Shah et al.
7,705,559 B2 4/2010 Powell et al.
7,706,853 B2 4/2010 Hacker et al.
7,708,180 B2 5/2010 Murray et al.
7,708,181 B2 5/2010 Cole et al.
7,708,182 B2 5/2010 Viola
7,708,758 B2 5/2010 Lee et al.
7,708,768 B2 5/2010 Danek et al.
7,709,136 B2 5/2010 Touchton et al.
7,712,182 B2 5/2010 Zeiler et al.
7,713,190 B2 5/2010 Brock et al.
7,713,542 B2 5/2010 Xu et al.
7,714,239 B2 5/2010 Smith
7,714,334 B2 5/2010 Lin
7,717,312 B2 5/2010 Beetel
7,717,313 B2 5/2010 Criscuolo et al.
7,717,846 B2 5/2010 Zirps et al.
7,717,873 B2 5/2010 Swick
7,717,915 B2 5/2010 Miyazawa
7,717,926 B2 5/2010 Whitfield et al.
7,718,180 B2 5/2010 Karp
7,718,556 B2 5/2010 Matsuda et al.
7,721,930 B2 5/2010 McKenna et al.
7,721,931 B2 5/2010 Shelton, IV et al.
7,721,932 B2 5/2010 Cole et al.
7,721,933 B2 5/2010 Ehrenfels et al.
7,721,934 B2 5/2010 Shelton, IV et al.
7,721,936 B2 5/2010 Shalton, IV et al.
7,722,527 B2 5/2010 Bouchier et al.
7,722,607 B2 5/2010 Dumbauld et al.
7,722,610 B2 5/2010 Viola et al.
7,725,214 B2 5/2010 Diolaiti
7,726,171 B2 6/2010 Langlotz et al.
7,726,537 B2 6/2010 Olson et al.
7,726,538 B2 6/2010 Holsten et al.
7,726,539 B2 6/2010 Holsten et al.
7,727,954 B2 6/2010 McKay
7,728,553 B2 6/2010 Carrier et al.
7,729,742 B2 6/2010 Govari
7,731,072 B2 6/2010 Timm et al.
7,731,073 B2 6/2010 Wixey et al.
7,731,724 B2 6/2010 Huitema et al.
7,735,703 B2 6/2010 Morgan et al.
7,735,704 B2 6/2010 Bilotti
7,736,254 B2 6/2010 Schena
7,736,306 B2 6/2010 Brustad et al.
7,736,356 B2 6/2010 Cooper et al.
7,736,374 B2 6/2010 Vaughan et al.
7,738,971 B2 6/2010 Swayze et al.
7,740,159 B2 6/2010 Shelton, IV et al.
7,742,036 B2 6/2010 Grant et al.
7,743,960 B2 6/2010 Whitman et al.
7,744,624 B2 6/2010 Bettuchi
7,744,627 B2 6/2010 Orban, III et al.
7,744,628 B2 6/2010 Viola
7,747,146 B2 6/2010 Milano et al.
7,748,587 B2 7/2010 Haramiishi et al.
7,748,632 B2 7/2010 Coleman et al.
7,749,204 B2 7/2010 Dhanaraj et al.
7,749,240 B2 7/2010 Takahashi et al.
7,751,870 B2 7/2010 Whitman
7,753,245 B2 7/2010 Boudreaux et al.
7,753,246 B2 7/2010 Scirica
7,753,904 B2 7/2010 Shelton, IV et al.
7,757,924 B2 7/2010 Gerbi et al.
7,758,594 B2 7/2010 Lamson et al.
7,758,612 B2 7/2010 Shipp
7,758,613 B2 7/2010 Whitman

(56) References Cited

U.S. PATENT DOCUMENTS 7,762,462 B2 7/2010 Gelbman
7,762,998 B2 7/2010 Birk et al.
D622,286 S 8/2010 Umezawa
7,766,207 B2 8/2010 Mather et al.
7,766,209 B2 8/2010 Baxter, III et al.
7,766,210 B2 8/2010 Shelton, IV et al.
7,766,821 B2 8/2010 Brunnen et al.
7,766,894 B2 8/2010 Weitzner et al.
7,770,658 B2 8/2010 Ito et al.
7,770,773 B2 8/2010 Whitman et al.
7,770,774 B2 8/2010 Mastri et al.
7,770,775 B2 8/2010 Shelton, IV et al.
7,770,776 B2 8/2010 Chen et al.
7,771,396 B2 8/2010 Stefanchik et al.
7,772,720 B2 8/2010 McGee et al.
7,772,725 B2 8/2010 Siman-Tov
7,775,972 B2 8/2010 Brock et al.
7,776,037 B2 8/2010 Odom
7,776,060 B2 8/2010 Mooradian et al.
7,776,065 B2 8/2010 Griffiths et al.
7,778,004 B2 8/2010 Nerheim et al.
7,779,614 B1 8/2010 McGonagle et al.
7,779,737 B2 8/2010 Newman, Jr. et al.
7,780,054 B2 8/2010 Wales
7,780,055 B2 8/2010 Scirica et al.
7,780,309 B2 8/2010 McMillan et al.
7,780,651 B2 8/2010 Madhani et al.
7,780,663 B2 8/2010 Yates et al.
7,780,685 B2 8/2010 Hunt et al.
7,782,382 B2 8/2010 Fujimura
7,784,662 B2 8/2010 Wales et al.
7,784,663 B2 8/2010 Shelton, IV
7,787,256 B2 8/2010 Chan et al.
7,789,283 B2 9/2010 Shah
7,789,875 B2 9/2010 Brock et al.
7,789,883 B2 9/2010 Takashino et al.
7,789,889 B2 9/2010 Zubik et al.
7,793,812 B2 9/2010 Moore et al.
7,794,475 B2 9/2010 Hess et al.
7,798,386 B2 9/2010 Schall et al.
7,799,039 B2 9/2010 Shelton, IV et al.
7,799,044 B2 9/2010 Johnston et al.
7,799,965 B2 9/2010 Patel et al.
7,803,151 B2 9/2010 Whitman
7,806,871 B2 10/2010 Li et al.
7,806,891 B2 10/2010 Nowlin et al.
7,810,690 B2 10/2010 Bilotti et al.
7,810,691 B2 10/2010 Boyden et al.
7,810,692 B2 10/2010 Hall et al.
7,810,693 B2 10/2010 Broehl et al.
7,811,275 B2 10/2010 Birk et al.
7,814,816 B2 10/2010 Alberti et al.
7,815,092 B2 10/2010 Whitman et al.
7,815,565 B2 10/2010 Stefanchik et al.
7,815,662 B2 10/2010 Spivey et al.
7,819,296 B2 10/2010 Hueil et al.
7,819,297 B2 10/2010 Doll et al.
7,819,298 B2 * 10/2010 Hall ..................... A61B 17/072
227/176.1
7,819,299 B2 10/2010 Shelton, IV et al.
7,819,799 B2 10/2010 Merril et al.
7,819,884 B2 10/2010 Lee et al.
7,819,885 B2 10/2010 Cooper
7,819,886 B2 10/2010 Whitfield et al.
7,819,894 B2 10/2010 Mitsuishi et al.
7,823,076 B2 10/2010 Borovsky et al.
7,823,592 B2 11/2010 Bettuchi et al.
7,823,760 B2 11/2010 Zemlok et al.
7,824,401 B2 11/2010 Manzo et al.
7,824,422 B2 11/2010 Benchetrit
7,824,426 B2 11/2010 Racenet et al.
7,828,189 B2 11/2010 Holsten et al.
7,828,794 B2 11/2010 Sartor
7,828,808 B2 11/2010 Hinman et al.
7,829,416 B2 11/2010 Kudou et al.
7,831,292 B2 11/2010 Quaid et al.
7,832,408 B2 11/2010 Shelton, IV et al.
7,832,611 B2 11/2010 Boyden et al.
7,832,612 B2 11/2010 Baxter, III et al.
7,833,234 B2 11/2010 Bailly et al.
7,835,823 B2 11/2010 Sillman et al.
7,836,400 B2 11/2010 May et al.
7,837,079 B2 11/2010 Holsten et al.
7,837,080 B2 11/2010 Schwemberger
7,837,081 B2 11/2010 Holsten et al.
7,837,425 B2 11/2010 Saeki et al.
7,837,685 B2 11/2010 Weinberg et al.
7,837,687 B2 11/2010 Harp
7,837,694 B2 11/2010 Tethrake et al.
7,838,789 B2 11/2010 Stoffers et al.
7,839,109 B2 11/2010 Carmen, Jr. et al.
7,840,253 B2 11/2010 Tremblay et al.
7,841,503 B2 11/2010 Sonnenschein et al.
7,842,025 B2 11/2010 Coleman et al.
7,842,028 B2 11/2010 Lee
7,843,158 B2 11/2010 Prisco
7,845,533 B2 12/2010 Marczyk et al.
7,845,534 B2 12/2010 Viola et al.
7,845,535 B2 12/2010 Scircia
7,845,536 B2 12/2010 Viola et al.
7,845,537 B2 12/2010 Shelton, IV et al.
7,845,538 B2 12/2010 Whitman
7,845,912 B2 12/2010 Sung et al.
7,846,085 B2 12/2010 Silverman et al.
7,846,149 B2 12/2010 Jankowski
7,846,161 B2 12/2010 Dumbauld et al.
7,848,066 B2 12/2010 Yanagishima
7,850,623 B2 12/2010 Griffin et al.
7,850,642 B2 12/2010 Moll et al.
7,850,982 B2 12/2010 Stopek et al.
7,853,813 B2 12/2010 Lee
7,854,735 B2 12/2010 Houser et al.
7,854,736 B2 12/2010 Ryan
7,857,183 B2 12/2010 Shelton, IV
7,857,184 B2 12/2010 Viola
7,857,185 B2 12/2010 Swayze et al.
7,857,186 B2 12/2010 Baxter, III et al.
7,857,813 B2 12/2010 Schmitz et al.
7,861,906 B2 1/2011 Doll et al.
7,862,502 B2 1/2011 Pool et al.
7,862,546 B2 1/2011 Conlon et al.
7,862,579 B2 1/2011 Ortiz et al.
7,866,525 B2 1/2011 Scirica
7,866,527 B2 1/2011 Hall et al.
7,866,528 B2 1/2011 Olson et al.
7,870,989 B2 1/2011 Viola et al.
7,871,418 B2 1/2011 Thompson et al.
7,871,440 B2 1/2011 Schwartz et al.
7,875,055 B2 1/2011 Cichocki, Jr.
7,877,869 B2 2/2011 Mehdizadeh et al.
7,879,063 B2 2/2011 Khosravi
7,879,070 B2 2/2011 Ortiz et al.
7,879,367 B2 2/2011 Heublein et al.
7,883,461 B2 2/2011 Albrecht et al.
7,883,465 B2 2/2011 Donofrio et al.
7,883,540 B2 2/2011 Niwa et al.
7,886,951 B2 2/2011 Hessler
7,886,952 B2 2/2011 Scirica et al.
7,887,530 B2 2/2011 Zemlok et al.
7,887,535 B2 2/2011 Lands et al.
7,887,536 B2 2/2011 Johnson et al.
7,887,563 B2 2/2011 Cummins
7,887,755 B2 2/2011 Mingerink et al.
7,891,531 B1 2/2011 Ward
7,891,532 B2 2/2011 Mastri et al.
7,892,200 B2 2/2011 Birk et al.
7,892,245 B2 2/2011 Liddicoat et al.
7,893,586 B2 2/2011 West et al.
7,896,214 B2 3/2011 Farascioni
7,896,215 B2 3/2011 Adams et al.
7,896,671 B2 3/2011 Kim et al.
7,896,869 B2 3/2011 DiSilvestro et al.
7,896,877 B2 3/2011 Hall et al.
7,896,895 B2 3/2011 Boudreaux et al.

(56) References Cited

U.S. PATENT DOCUMENTS 7,896,897 B2 3/2011 Gresham et al.
7,896,900 B2 3/2011 Frank et al.
7,898,198 B2 3/2011 Murphree
7,900,805 B2 3/2011 Shelton, IV et al.
7,900,806 B2 3/2011 Chen et al.
7,901,381 B2 3/2011 Birk et al.
7,905,380 B2 3/2011 Shelton, IV et al.
7,905,381 B2 3/2011 Baxter, III et al.
7,905,881 B2 3/2011 Masuda et al.
7,905,889 B2 3/2011 Catanese, III et al.
7,905,890 B2 3/2011 Whitfield et al.
7,905,902 B2 3/2011 Huitema et al.
7,909,039 B2 3/2011 Hur
7,909,191 B2 3/2011 Baker et al.
7,909,220 B2 3/2011 Viola
7,909,221 B2 3/2011 Viola et al.
7,909,224 B2 3/2011 Prommersberger
7,913,891 B2 3/2011 Doll et al.
7,913,893 B2 3/2011 Mastri et al.
7,914,521 B2 3/2011 Wang et al.
7,914,543 B2 3/2011 Roth et al.
7,914,551 B2 3/2011 Ortiz et al.
7,918,230 B2 4/2011 Whitman et al.
7,918,376 B1 4/2011 Knodel et al.
7,918,377 B2 4/2011 Measamer et al.
7,918,845 B2 4/2011 Saadat et al.
7,918,848 B2 4/2011 Lau et al.
7,918,861 B2 4/2011 Brock et al.
7,918,867 B2 4/2011 Dana et al.
7,922,061 B2 4/2011 Shelton, IV et al.
7,922,063 B2 4/2011 Zemlok et al.
7,922,743 B2 4/2011 Heinrich et al.
7,923,144 B2 4/2011 Kohn et al.
7,926,691 B2 4/2011 Viola et al.
7,926,692 B2 4/2011 Racenet et al.
7,927,328 B2 4/2011 Orszulak et al.
7,928,281 B2 4/2011 Augustine
7,930,040 B1 4/2011 Kelsch et al.
7,930,065 B2 4/2011 Larkin et al.
7,931,660 B2 4/2011 Aranyi et al.
7,931,695 B2 4/2011 Ringeisen
7,931,877 B2 4/2011 Steffens et al.
D638,028 S 5/2011 Cook et al.
7,934,630 B2 5/2011 Shelton, IV et al.
7,934,631 B2 5/2011 Balbierz et al.
7,934,896 B2 5/2011 Schnier
7,935,130 B2 5/2011 Williams
7,935,773 B2 5/2011 Hadba et al.
7,936,142 B2 5/2011 Otsuka et al.
7,938,307 B2 5/2011 Bettuchi
7,939,152 B2 5/2011 Haskin et al.
7,941,865 B2 5/2011 Seman, Jr. et al.
7,942,300 B2 5/2011 Rethy et al.
7,942,303 B2 5/2011 Shah
7,942,890 B2 5/2011 D'Agostino et al.
7,944,175 B2 5/2011 Mori et al.
7,945,792 B2 5/2011 Cherpantier
7,945,798 B2 5/2011 Carlson et al.
7,946,453 B2 5/2011 Voegele et al.
7,947,011 B2 5/2011 Birk et al.
7,948,381 B2 5/2011 Lindsay et al.
7,950,560 B2 5/2011 Zemlok et al.
7,950,561 B2 5/2011 Aranyi
7,950,562 B2 5/2011 Beardsley et al.
7,951,071 B2 5/2011 Whitman et al.
7,951,166 B2 5/2011 Orban, III et al.
7,952,464 B2 5/2011 Nikitin et al.
7,954,682 B2 6/2011 Giordano et al.
7,954,684 B2 6/2011 Boudreaux
7,954,685 B2 6/2011 Viola
7,954,686 B2 6/2011 Baxter, III et al.
7,954,687 B2 6/2011 Zemlok et al.
7,954,688 B2 6/2011 Argentine et al.
7,955,253 B2 6/2011 Ewers et al.
7,955,257 B2 6/2011 Frasier et al.
7,955,322 B2 6/2011 Devengenzo et al.
7,955,327 B2 6/2011 Sartor et al.
7,955,380 B2 6/2011 Chu et al.
7,959,050 B2 6/2011 Smith et al.
7,959,051 B2 6/2011 Smith et al.
7,959,052 B2 6/2011 Sonnenschein et al.
7,963,432 B2 6/2011 Knodel et al.
7,963,433 B2 6/2011 Whitman et al.
7,963,913 B2 6/2011 Devengenzo et al.
7,963,963 B2 6/2011 Francischelli et al.
7,963,964 B2 6/2011 Santilli et al.
7,964,206 B2 6/2011 Suokas et al.
7,966,236 B2 6/2011 Noriega et al.
7,966,269 B2 6/2011 Bauer et al.
7,966,799 B2 6/2011 Morgan et al.
7,967,178 B2 6/2011 Scirica et al.
7,967,179 B2 6/2011 Olson et al.
7,967,180 B2 6/2011 Scirica
7,967,181 B2 6/2011 Viola et al.
7,967,791 B2 6/2011 Franer et al.
7,967,839 B2 6/2011 Flock et al.
7,972,298 B2 7/2011 Wallace et al.
7,972,315 B2 7/2011 Birk et al.
7,976,213 B2 7/2011 Bertolotti et al.
7,976,508 B2 7/2011 Hoag
7,976,563 B2 7/2011 Summerer
7,979,137 B2 7/2011 Tracey et al.
7,980,443 B2 7/2011 Scheib et al.
7,981,025 B2 7/2011 Pool et al.
7,981,102 B2 7/2011 Patel et al.
7,981,132 B2 7/2011 Dubrul et al.
7,987,405 B2 7/2011 Turner et al.
7,988,015 B2 8/2011 Mason et al.
7,988,026 B2 8/2011 Knodel et al.
7,988,027 B2 8/2011 Olson et al.
7,988,028 B2 8/2011 Farascioni et al.
7,988,779 B2 8/2011 Disalvo et al.
7,992,757 B2 8/2011 Wheeler et al.
7,993,360 B2 8/2011 Hacker et al.
7,994,670 B2 8/2011 Ji
7,996,064 B2 8/2011 Simon et al.
7,997,054 B2 8/2011 Bertsch et al.
7,997,468 B2 8/2011 Farascioni
7,997,469 B2 8/2011 Olson et al.
8,002,696 B2 8/2011 Suzuki
8,002,784 B2 8/2011 Jinno et al.
8,002,785 B2 8/2011 Weiss et al.
8,002,795 B2 8/2011 Beetel
8,006,365 B2 8/2011 Levin et al.
8,006,885 B2 8/2011 Marczyk
8,006,889 B2 8/2011 Adams et al.
8,007,370 B2 8/2011 Hirsch et al.
8,007,465 B2 8/2011 Birk et al.
8,007,479 B2 8/2011 Birk et al.
8,007,511 B2 8/2011 Brock et al.
8,007,513 B2 8/2011 Nalagatla et al.
8,008,598 B2 8/2011 Whitman et al.
8,010,180 B2 8/2011 Quaid et al.
8,011,550 B2 9/2011 Aranyi et al.
8,011,551 B2 * 9/2011 Marczyk .............. A61B 17/068
227/175.1
8,011,553 B2 9/2011 Mastri et al.
8,011,555 B2 9/2011 Tarinelli et al.
8,012,170 B2 9/2011 Whitman et al.
8,016,176 B2 9/2011 Kasvikis et al.
8,016,177 B2 9/2011 Bettuchi et al.
8,016,178 B2 9/2011 Olson et al.
8,016,849 B2 9/2011 Wenchell
8,016,855 B2 9/2011 Whitman et al.
8,016,858 B2 9/2011 Whitman
8,016,881 B2 9/2011 Furst
8,020,741 B2 9/2011 Cole et al.
8,020,742 B2 9/2011 Marczyk
8,020,743 B2 9/2011 Shelton, IV
8,021,375 B2 9/2011 Aldrich et al.
8,025,199 B2 9/2011 Whitman et al.
8,025,896 B2 9/2011 Malaviya et al.
8,028,835 B2 10/2011 Yasuda et al.
8,028,882 B2 10/2011 Viola

(56) References Cited

U.S. PATENT DOCUMENTS 8,028,883 B2 10/2011 Stopek
8,028,884 B2 10/2011 Sniffin et al.
8,028,885 B2 10/2011 Smith et al.
8,029,510 B2 10/2011 Hoegerle
8,031,069 B2 10/2011 Cohn et al.
8,033,438 B2 10/2011 Scirica
8,033,439 B2 10/2011 Racenet et al.
8,033,440 B2 10/2011 Wenchell et al.
8,033,442 B2 10/2011 Racenet et al.
8,034,077 B2 10/2011 Smith et al.
8,034,337 B2 10/2011 Simard
8,034,363 B2 10/2011 Li et al.
8,035,487 B2 10/2011 Malackowski
8,037,591 B2 10/2011 Spivey et al.
8,038,044 B2 10/2011 Viola
8,038,045 B2 10/2011 Bettuchi et al.
8,038,046 B2 10/2011 Smith et al.
8,038,686 B2 10/2011 Huitema et al.
8,043,207 B2 10/2011 Adams
8,043,328 B2 10/2011 Hahnen et al.
8,044,536 B2 10/2011 Nguyen et al.
8,044,604 B2 10/2011 Hagino et al.
8,047,236 B2 11/2011 Perry
8,048,503 B2 11/2011 Farnsworth et al.
8,052,024 B2 11/2011 Viola et al.
8,052,636 B2 11/2011 Moll et al.
8,052,697 B2 11/2011 Phillips
8,056,787 B2 11/2011 Boudreaux et al.
8,056,788 B2 11/2011 Mastri et al.
8,056,789 B1 11/2011 White et al.
8,057,508 B2 11/2011 Shelton, IV
8,058,771 B2 11/2011 Giordano et al.
8,060,250 B2 11/2011 Reiland et al.
8,061,014 B2 11/2011 Smith et al.
8,061,576 B2 11/2011 Cappola
8,062,236 B2 11/2011 Soltz
8,062,306 B2 11/2011 Nobis et al.
8,062,330 B2 11/2011 Prommersberger et al.
8,063,619 B2 11/2011 Zhu et al.
8,066,158 B2 11/2011 Vogel et al.
8,066,166 B2 11/2011 Demmy et al.
8,066,167 B2 11/2011 Measamer et al.
8,066,168 B2 11/2011 Vidal et al.
8,066,720 B2 11/2011 Knodel et al.
D650,074 S 12/2011 Hunt et al.
D650,789 S 12/2011 Arnold
8,070,033 B2 12/2011 Milliman et al.
8,070,034 B1 12/2011 Knodel
8,070,035 B2 12/2011 Holsten et al.
8,070,743 B2 12/2011 Kagan et al.
8,074,858 B2 12/2011 Marczyk
8,074,859 B2 12/2011 Kostrzewski
8,074,861 B2 12/2011 Ehrenfels et al.
8,075,476 B2 12/2011 Vargas
8,075,571 B2 12/2011 Vitali et al.
8,079,950 B2 12/2011 Stem et al.
8,079,989 B2 12/2011 Birk et al.
8,080,004 B2 12/2011 Downey et al.
8,083,118 B2 12/2011 Milliman et al.
8,083,119 B2 12/2011 Prommersberger
8,083,120 B2 12/2011 Shelton, IV et al.
8,084,001 B2 12/2011 Burns et al.
8,084,969 B2 12/2011 David et al.
8,085,013 B2 12/2011 Wei et al.
D652,048 S 1/2012 Joseph
8,087,562 B1 1/2012 Manoux et al.
8,087,563 B2 1/2012 Milliman et al.
8,089,509 B2 1/2012 Chatenever et al.
8,091,753 B2 1/2012 Viola
8,091,756 B2 1/2012 Viola
8,092,443 B2 1/2012 Bischoff
8,092,932 B2 1/2012 Phillips et al.
8,093,572 B2 1/2012 Kuduvalli
8,096,458 B2 1/2012 Hessler
8,096,459 B2 1/2012 Ortiz et al.
8,097,017 B2 1/2012 Viola
8,100,310 B2 1/2012 Zemlok
8,100,824 B2 1/2012 Hegeman et al.
8,100,872 B2 1/2012 Patel
8,102,138 B2 1/2012 Sekine et al.
8,102,278 B2 1/2012 Deck et al.
8,105,320 B2 1/2012 Manzo
8,105,350 B2 1/2012 Lee et al.
8,107,925 B2 1/2012 Natsuno et al.
8,108,033 B2 1/2012 Drew et al.
8,108,072 B2 1/2012 Zhao et al.
8,109,426 B2 2/2012 Milliman et al.
8,110,208 B1 2/2012 Hen
8,113,405 B2 2/2012 Milliman
8,113,407 B2 2/2012 Holsten et al.
8,113,408 B2 2/2012 Wenchell et al.
8,113,410 B2 2/2012 Hall et al.
8,114,017 B2 2/2012 Bacher
8,114,100 B2 2/2012 Smith et al.
8,114,345 B2 2/2012 Dlugos, Jr. et al.
8,118,206 B2 2/2012 Zand et al.
8,118,207 B2 2/2012 Racenet et al.
8,120,301 B2 2/2012 Goldberg et al.
8,122,128 B2 2/2012 Burke, II et al.
8,123,103 B2 2/2012 Milliman
8,123,523 B2 2/2012 Carron et al.
8,123,766 B2 2/2012 Bauman et al.
8,123,767 B2 2/2012 Bauman et al.
8,125,168 B2 2/2012 Johnson et al.
8,127,975 B2 3/2012 Olson et al.
8,127,976 B2 3/2012 Scirica et al.
8,128,624 B2 3/2012 Couture et al.
8,128,643 B2 3/2012 Aranyi et al.
8,128,645 B2 3/2012 Sonnenschein et al.
8,128,662 B2 3/2012 Altarac et al.
8,132,703 B2 3/2012 Milliman et al.
8,132,705 B2 3/2012 Viola et al.
8,132,706 B2 3/2012 Marczyk et al.
8,133,500 B2 3/2012 Ringeisen et al.
8,134,306 B2 3/2012 Drader et al.
8,136,711 B2 3/2012 Beardsley et al.
8,136,712 B2 3/2012 Zingman
8,136,713 B2 3/2012 Hathaway et al.
8,137,339 B2 3/2012 Jinno et al.
8,140,417 B2 3/2012 Shibata
8,141,762 B2 3/2012 Bedi et al.
8,141,763 B2 3/2012 Milliman
8,142,200 B2 3/2012 Crunkilton et al.
8,142,425 B2 3/2012 Eggers
8,142,461 B2 3/2012 Houser et al.
8,142,515 B2 3/2012 Therin et al.
8,143,520 B2 3/2012 Cutler
8,146,790 B2 4/2012 Milliman
8,147,421 B2 4/2012 Farquhar et al.
8,147,456 B2 4/2012 Fisher et al.
8,147,485 B2 4/2012 Wham et al.
8,152,041 B2 4/2012 Kostrzewski
8,152,756 B2 4/2012 Webster et al.
8,154,239 B2 4/2012 Katsuki et al.
8,157,145 B2 4/2012 Shelton, IV et al.
8,157,148 B2 4/2012 Scirica
8,157,150 B2 4/2012 Viola et al.
8,157,151 B2 4/2012 Ingmanson et al.
8,157,152 B2 4/2012 Holsten et al.
8,157,153 B2 4/2012 Shelton, IV et al.
8,157,793 B2 4/2012 Omori et al.
8,157,834 B2 4/2012 Conlon
8,161,977 B2 4/2012 Shelton, IV et al.
8,162,138 B2 4/2012 Bettenhausen et al.
8,162,197 B2 4/2012 Mastri et al.
8,162,668 B2 4/2012 Toly
8,162,933 B2 4/2012 Francischelli et al.
8,162,965 B2 4/2012 Reschke et al.
8,167,185 B2 5/2012 Shelton, IV et al.
8,167,622 B2 5/2012 Zhou
8,167,895 B2 5/2012 D'Agostino et al.
8,167,898 B1 5/2012 Schaller et al.
8,170,241 B2 5/2012 Roe et al.
8,172,004 B2 5/2012 Ho

(56) References Cited

U.S. PATENT DOCUMENTS

| | | | |
|---|---|---|---|
| 8,172,120 | B2 | 5/2012 | Boyden et al. |
| 8,172,122 | B2 | 5/2012 | Kasvikis et al. |
| 8,172,124 | B2 | 5/2012 | Shelton, IV et al. |
| 8,177,776 | B2 | 5/2012 | Humayun et al. |
| 8,177,797 | B2 | 5/2012 | Shimoji et al. |
| 8,179,705 | B2 | 5/2012 | Chapuis |
| 8,180,458 | B2 | 5/2012 | Kane et al. |
| 8,181,839 | B2 | 5/2012 | Beetel |
| 8,181,840 | B2 | 5/2012 | Milliman |
| 8,182,422 | B2 | 5/2012 | Bayer et al. |
| 8,182,444 | B2 | 5/2012 | Uber, III et al. |
| 8,183,807 | B2 | 5/2012 | Tsai et al. |
| 8,186,555 | B2 | 5/2012 | Shelton, IV et al. |
| 8,186,556 | B2 | 5/2012 | Viola |
| 8,186,558 | B2 | 5/2012 | Sapienza |
| 8,186,560 | B2 | 5/2012 | Hess et al. |
| 8,190,238 | B2 | 5/2012 | Moll et al. |
| D661,314 | S | 6/2012 | Marchetti |
| D661,315 | S | 6/2012 | Marchetti et al. |
| 8,191,752 | B2 | 6/2012 | Scirica |
| 8,192,350 | B2 | 6/2012 | Ortiz et al. |
| 8,192,460 | B2 | 6/2012 | Orban, III et al. |
| 8,192,651 | B2 | 6/2012 | Young et al. |
| 8,193,129 | B2 | 6/2012 | Tagawa et al. |
| 8,196,795 | B2 | 6/2012 | Moore et al. |
| 8,196,796 | B2 | 6/2012 | Shelton, IV et al. |
| 8,197,501 | B2 | 6/2012 | Shadeck et al. |
| 8,197,502 | B2 | 6/2012 | Smith et al. |
| 8,197,837 | B2 | 6/2012 | Jamiolkowski et al. |
| 8,201,720 | B2 | 6/2012 | Hessler |
| 8,201,721 | B2 | 6/2012 | Zemlok et al. |
| 8,202,549 | B2 | 6/2012 | Stucky et al. |
| 8,205,779 | B2 | 6/2012 | Ma et al. |
| 8,205,780 | B2 | 6/2012 | Sorrentino et al. |
| 8,205,781 | B2 | 6/2012 | Baxter, III et al. |
| 8,207,863 | B2 | 6/2012 | Neubauer et al. |
| 8,210,411 | B2 | 7/2012 | Yates et al. |
| 8,210,413 | B2 | 7/2012 | Whitman et al. |
| 8,210,414 | B2 | 7/2012 | Bettuchi et al. |
| 8,210,415 | B2 | 7/2012 | Ward |
| 8,210,416 | B2 | 7/2012 | Milliman et al. |
| 8,210,721 | B2 | 7/2012 | Chen et al. |
| 8,211,125 | B2 | 7/2012 | Spivey |
| 8,214,019 | B2 | 7/2012 | Govari et al. |
| 8,215,531 | B2 | 7/2012 | Shelton, IV et al. |
| 8,215,532 | B2 | 7/2012 | Marczyk |
| 8,215,533 | B2 | 7/2012 | Viola et al. |
| 8,220,468 | B2 | 7/2012 | Cooper et al. |
| 8,220,688 | B2 | 7/2012 | Laurent et al. |
| 8,220,690 | B2 | 7/2012 | Hess et al. |
| 8,221,402 | B2 | 7/2012 | Francischelli et al. |
| 8,221,424 | B2 | 7/2012 | Cha |
| 8,221,433 | B2 | 7/2012 | Lozier et al. |
| 8,225,799 | B2 | 7/2012 | Bettuchi |
| 8,225,979 | B2 | 7/2012 | Farascioni et al. |
| 8,226,553 | B2 | 7/2012 | Shelton, IV et al. |
| 8,226,635 | B2 | 7/2012 | Petrie et al. |
| 8,226,675 | B2 | 7/2012 | Houser et al. |
| 8,226,715 | B2 | 7/2012 | Hwang et al. |
| 8,227,946 | B2 | 7/2012 | Kim |
| 8,228,020 | B2 | 7/2012 | Shin et al. |
| 8,228,048 | B2 | 7/2012 | Spencer |
| 8,229,549 | B2 | 7/2012 | Whitman et al. |
| 8,230,235 | B2 | 7/2012 | Goodman et al. |
| 8,231,040 | B2 | 7/2012 | Zemlok et al. |
| 8,231,042 | B2 | 7/2012 | Hessler et al. |
| 8,231,043 | B2 | 7/2012 | Tarinelli et al. |
| 8,235,272 | B2 | 8/2012 | Nicholas et al. |
| 8,235,274 | B2 | 8/2012 | Cappola |
| 8,236,010 | B2 | 8/2012 | Ortiz et al. |
| 8,236,011 | B2 | 8/2012 | Harris et al. |
| 8,236,020 | B2 | 8/2012 | Smith et al. |
| 8,237,388 | B2 | 8/2012 | Jinno et al. |
| 8,240,536 | B2 | 8/2012 | Marczyk |
| 8,240,537 | B2 | 8/2012 | Marczyk |
| 8,241,271 | B2 | 8/2012 | Millman et al. |
| 8,241,284 | B2 | 8/2012 | Dycus et al. |
| 8,241,308 | B2 | 8/2012 | Kortenbach et al. |
| 8,241,322 | B2 | 8/2012 | Whitman et al. |
| 8,245,594 | B2 | 8/2012 | Rogers et al. |
| 8,245,898 | B2 | 8/2012 | Smith et al. |
| 8,245,899 | B2 | 8/2012 | Swensgard et al. |
| 8,245,900 | B2 | 8/2012 | Scirica |
| 8,245,901 | B2 | 8/2012 | Stopek |
| 8,246,608 | B2 | 8/2012 | Omori et al. |
| 8,246,637 | B2 | 8/2012 | Viola et al. |
| 8,251,921 | B2 | 8/2012 | Briggs et al. |
| 8,252,009 | B2 | 8/2012 | Weller et al. |
| D667,450 | S | 9/2012 | Eby et al. |
| 8,256,654 | B2 | 9/2012 | Bettuchi et al. |
| 8,256,655 | B2 | 9/2012 | Sniffin et al. |
| 8,256,656 | B2 | 9/2012 | Milliman et al. |
| 8,257,251 | B2 | 9/2012 | Shelton, IV et al. |
| 8,257,356 | B2 | 9/2012 | Bleich et al. |
| 8,257,386 | B2 | 9/2012 | Lee et al. |
| 8,257,391 | B2 | 9/2012 | Orban, III et al. |
| 8,257,634 | B2 | 9/2012 | Scirica |
| 8,258,745 | B2 | 9/2012 | Smith et al. |
| 8,261,958 | B1 | 9/2012 | Knodel |
| 8,262,560 | B2 | 9/2012 | Whitman |
| 8,262,655 | B2 | 9/2012 | Ghabrial et al. |
| 8,266,232 | B2 | 9/2012 | Piper et al. |
| 8,267,300 | B2 | 9/2012 | Boudreaux |
| 8,267,849 | B2 | 9/2012 | Wazer et al. |
| 8,267,924 | B2 | 9/2012 | Zemlok et al. |
| 8,267,946 | B2 | 9/2012 | Whitfield et al. |
| 8,267,951 | B2 | 9/2012 | Whayne et al. |
| 8,268,344 | B2 | 9/2012 | Ma et al. |
| 8,269,121 | B2 | 9/2012 | Smith |
| 8,272,553 | B2 | 9/2012 | Mastri et al. |
| 8,272,554 | B2 | 9/2012 | Whitman et al. |
| 8,272,918 | B2 | 9/2012 | Lam |
| 8,273,404 | B2 | 9/2012 | Dave et al. |
| 8,276,594 | B2 | 10/2012 | Shah |
| 8,276,801 | B2 | 10/2012 | Zemlok et al. |
| 8,276,802 | B2 | 10/2012 | Kostrzewski |
| 8,277,473 | B2 | 10/2012 | Sunaoshi et al. |
| 8,281,446 | B2 | 10/2012 | Moskovich |
| 8,281,973 | B2 | 10/2012 | Wenchell et al. |
| 8,281,974 | B2 | 10/2012 | Hessler et al. |
| 8,282,654 | B2 | 10/2012 | Ferrari et al. |
| 8,285,367 | B2 | 10/2012 | Hyde et al. |
| 8,286,723 | B2 | 10/2012 | Puzio et al. |
| 8,286,845 | B2 | 10/2012 | Perry et al. |
| 8,286,846 | B2 | 10/2012 | Smith et al. |
| 8,286,847 | B2 | 10/2012 | Taylor |
| 8,287,487 | B2 | 10/2012 | Estes |
| 8,287,522 | B2 | 10/2012 | Moses et al. |
| 8,287,561 | B2 | 10/2012 | Nunez et al. |
| 8,288,984 | B2 | 10/2012 | Yang |
| 8,289,403 | B2 | 10/2012 | Dobashi et al. |
| 8,290,883 | B2 | 10/2012 | Takeuchi et al. |
| 8,292,147 | B2 | 10/2012 | Viola |
| 8,292,148 | B2 | 10/2012 | Viola |
| 8,292,150 | B2 | 10/2012 | Bryant |
| 8,292,151 | B2 | 10/2012 | Viola |
| 8,292,152 | B2 | 10/2012 | Milliman et al. |
| 8,292,155 | B2 | 10/2012 | Shelton, IV et al. |
| 8,292,157 | B2 | 10/2012 | Smith et al. |
| 8,292,158 | B2 | 10/2012 | Sapienza |
| 8,292,801 | B2 | 10/2012 | Dejima et al. |
| 8,292,888 | B2 | 10/2012 | Whitman |
| 8,292,906 | B2 | 10/2012 | Taylor et al. |
| 8,294,399 | B2 | 10/2012 | Suzuki et al. |
| 8,298,161 | B2 | 10/2012 | Vargas |
| 8,298,189 | B2 | 10/2012 | Fisher et al. |
| 8,298,233 | B2 | 10/2012 | Mueller |
| 8,298,677 | B2 | 10/2012 | Wiesner et al. |
| 8,302,323 | B2 | 11/2012 | Fortier et al. |
| 8,303,621 | B2 | 11/2012 | Miyamoto et al. |
| 8,308,040 | B2 | 11/2012 | Huang et al. |
| 8,308,041 | B2 | 11/2012 | Kostrzewski |
| 8,308,042 | B2 | 11/2012 | Aranyi |
| 8,308,043 | B2 | 11/2012 | Bindra et al. |

(56) References Cited

U.S. PATENT DOCUMENTS

| | | | |
|---|---|---|---|
| 8,308,046 | B2 | 11/2012 | Prommersberger |
| 8,308,659 | B2 | 11/2012 | Scheibe et al. |
| 8,308,725 | B2 | 11/2012 | Bell et al. |
| 8,310,188 | B2 | 11/2012 | Nakai |
| 8,313,444 | B2 | 11/2012 | Thompson et al. |
| 8,313,496 | B2 | 11/2012 | Sauer et al. |
| 8,313,499 | B2 | 11/2012 | Magnusson et al. |
| 8,313,509 | B2 | 11/2012 | Kostrzewski |
| 8,317,070 | B2 | 11/2012 | Hueil et al. |
| 8,317,071 | B1 | 11/2012 | Knodel |
| 8,317,074 | B2 | 11/2012 | Ortiz et al. |
| 8,317,437 | B2 | 11/2012 | Merkley et al. |
| 8,317,744 | B2 | 11/2012 | Kirschenman |
| 8,317,790 | B2 | 11/2012 | Bell et al. |
| 8,319,002 | B2 | 11/2012 | Daniels et al. |
| D672,784 | S | 12/2012 | Clanton et al. |
| 8,322,455 | B2 | 12/2012 | Shelton, IV et al. |
| 8,322,589 | B2 | 12/2012 | Boudreaux |
| 8,322,590 | B2 | 12/2012 | Patel et al. |
| 8,322,901 | B2 | 12/2012 | Michelotti |
| 8,323,271 | B2 | 12/2012 | Humayun et al. |
| 8,323,789 | B2 | 12/2012 | Rozhin et al. |
| 8,324,585 | B2 | 12/2012 | McBroom et al. |
| 8,327,514 | B2 | 12/2012 | Kim |
| 8,328,061 | B2 | 12/2012 | Kasvikis |
| 8,328,062 | B2 | 12/2012 | Viola |
| 8,328,063 | B2 | 12/2012 | Milliman et al. |
| 8,328,064 | B2 | 12/2012 | Racenet et al. |
| 8,328,065 | B2 | 12/2012 | Shah |
| 8,328,802 | B2 | 12/2012 | Deville et al. |
| 8,328,823 | B2 | 12/2012 | Aranyi et al. |
| 8,333,313 | B2 | 12/2012 | Boudreaux et al. |
| 8,333,691 | B2 | 12/2012 | Schaaf |
| 8,333,764 | B2 | 12/2012 | Francischelli et al. |
| 8,333,779 | B2 | 12/2012 | Smith et al. |
| 8,334,468 | B2 | 12/2012 | Palmer et al. |
| 8,336,753 | B2 | 12/2012 | Olson et al. |
| 8,336,754 | B2 | 12/2012 | Cappola et al. |
| 8,342,377 | B2 | 1/2013 | Milliman et al. |
| 8,342,378 | B2 | 1/2013 | Marczyk et al. |
| 8,342,379 | B2 | 1/2013 | Whitman et al. |
| 8,342,380 | B2 | 1/2013 | Viola |
| 8,343,150 | B2 | 1/2013 | Artale |
| 8,347,978 | B2 | 1/2013 | Forster et al. |
| 8,348,118 | B2 | 1/2013 | Segura |
| 8,348,123 | B2 | 1/2013 | Scirica et al. |
| 8,348,124 | B2 | 1/2013 | Scirica |
| 8,348,125 | B2 | 1/2013 | Viola et al. |
| 8,348,126 | B2 | 1/2013 | Olson et al. |
| 8,348,127 | B2 | 1/2013 | Marczyk |
| 8,348,129 | B2 | 1/2013 | Bedi et al. |
| 8,348,130 | B2 | 1/2013 | Shah et al. |
| 8,348,131 | B2 | 1/2013 | Omaits et al. |
| 8,348,837 | B2 | 1/2013 | Wenchell |
| 8,348,948 | B2 | 1/2013 | Bahney |
| 8,348,959 | B2 | 1/2013 | Wolford et al. |
| 8,348,972 | B2 | 1/2013 | Soltz et al. |
| 8,349,987 | B2 | 1/2013 | Kapiamba et al. |
| 8,352,004 | B2 | 1/2013 | Mannheimer et al. |
| 8,353,437 | B2 | 1/2013 | Boudreaux |
| 8,353,438 | B2 | 1/2013 | Baxter, III et al. |
| 8,353,439 | B2 | 1/2013 | Baxter, III et al. |
| 8,356,740 | B1 | 1/2013 | Knodel |
| 8,357,144 | B2 | 1/2013 | Whitman et al. |
| 8,357,158 | B2 | 1/2013 | McKenna et al. |
| 8,357,161 | B2 | 1/2013 | Mueller |
| 8,359,174 | B2 | 1/2013 | Nakashima et al. |
| 8,360,296 | B2 | 1/2013 | Zingman |
| 8,360,297 | B2 | 1/2013 | Shelton, IV et al. |
| 8,360,298 | B2 | 1/2013 | Farascioni et al. |
| 8,360,299 | B2 | 1/2013 | Zemlok et al. |
| 8,361,501 | B2 | 1/2013 | DiTizio et al. |
| D676,866 | S | 2/2013 | Chaudhri |
| 8,365,972 | B2 | 2/2013 | Aranyi et al. |
| 8,365,973 | B1 | 2/2013 | White et al. |
| 8,365,975 | B1 | 2/2013 | Manoux et al. |
| 8,365,976 | B2 | 2/2013 | Hess et al. |
| 8,366,559 | B2 | 2/2013 | Papenfuss et al. |
| 8,366,719 | B2 | 2/2013 | Markey et al. |
| 8,366,787 | B2 | 2/2013 | Brown et al. |
| 8,368,327 | B2 | 2/2013 | Benning et al. |
| 8,369,056 | B2 | 2/2013 | Senriuchi et al. |
| 8,371,393 | B2 | 2/2013 | Higuchi et al. |
| 8,371,491 | B2 | 2/2013 | Huitema et al. |
| 8,371,492 | B2 | 2/2013 | Aranyi et al. |
| 8,371,493 | B2 | 2/2013 | Aranyi et al. |
| 8,371,494 | B2 | 2/2013 | Racenet et al. |
| 8,372,094 | B2 | 2/2013 | Bettuchi et al. |
| 8,374,723 | B2 | 2/2013 | Zhao et al. |
| 8,376,865 | B2 | 2/2013 | Forster et al. |
| 8,377,029 | B2 | 2/2013 | Nagao et al. |
| 8,377,044 | B2 | 2/2013 | Coe et al. |
| 8,377,059 | B2 | 2/2013 | Deville et al. |
| 8,381,828 | B2 | 2/2013 | Whitman et al. |
| 8,381,834 | B2 | 2/2013 | Barhitte et al. |
| 8,382,773 | B2 | 2/2013 | Whitfield et al. |
| 8,382,790 | B2 | 2/2013 | Uenohara et al. |
| D677,273 | S | 3/2013 | Randall et al. |
| 8,387,848 | B2 | 3/2013 | Johnson et al. |
| 8,388,633 | B2 | 3/2013 | Rousseau et al. |
| 8,389,588 | B2 | 3/2013 | Ringeisen et al. |
| 8,393,513 | B2 | 3/2013 | Jankowski |
| 8,393,514 | B2 | 3/2013 | Shelton, IV et al. |
| 8,393,516 | B2 | 3/2013 | Kostrzewski |
| 8,395,342 | B2 | 3/2013 | Prisco |
| 8,397,832 | B2 | 3/2013 | Blickle et al. |
| 8,397,971 | B2 | 3/2013 | Yates et al. |
| 8,397,972 | B2 | 3/2013 | Kostrzewski |
| 8,397,973 | B1 | 3/2013 | Hausen |
| 8,398,633 | B2 | 3/2013 | Mueller |
| 8,398,669 | B2 | 3/2013 | Kim |
| 8,398,673 | B2 | 3/2013 | Hinchliffe et al. |
| 8,398,674 | B2 | 3/2013 | Prestel |
| 8,400,108 | B2 | 3/2013 | Powell et al. |
| 8,400,851 | B2 | 3/2013 | Byun |
| 8,403,138 | B2 | 3/2013 | Weisshaupt et al. |
| 8,403,195 | B2 | 3/2013 | Beardsley et al. |
| 8,403,196 | B2 | 3/2013 | Beardsley et al. |
| 8,403,198 | B2 | 3/2013 | Sorrentino et al. |
| 8,403,832 | B2 | 3/2013 | Cunningham et al. |
| 8,403,926 | B2 | 3/2013 | Nobis et al. |
| 8,403,945 | B2 | 3/2013 | Whitfield et al. |
| 8,403,946 | B2 | 3/2013 | Whitfield et al. |
| 8,403,950 | B2 | 3/2013 | Palmer et al. |
| D679,726 | S | 4/2013 | Kobayashi |
| D680,646 | S | 4/2013 | Hunt et al. |
| 8,408,439 | B2 | 4/2013 | Huang et al. |
| 8,408,442 | B2 | 4/2013 | Racenet et al. |
| 8,409,079 | B2 | 4/2013 | Okamoto et al. |
| 8,409,174 | B2 | 4/2013 | Omori |
| 8,409,175 | B2 | 4/2013 | Lee et al. |
| 8,409,211 | B2 | 4/2013 | Baroud |
| 8,409,222 | B2 | 4/2013 | Whitfield et al. |
| 8,409,223 | B2 | 4/2013 | Sorrentino et al. |
| 8,409,234 | B2 | 4/2013 | Stahler et al. |
| 8,411,500 | B2 | 4/2013 | Gapihan et al. |
| 8,413,661 | B2 | 4/2013 | Rousseau et al. |
| 8,413,870 | B2 | 4/2013 | Pastorelli et al. |
| 8,413,871 | B2 | 4/2013 | Racenet et al. |
| 8,413,872 | B2 | 4/2013 | Patel |
| 8,414,469 | B2 | 4/2013 | Diolaiti |
| 8,414,577 | B2 | 4/2013 | Boudreaux et al. |
| 8,414,598 | B2 | 4/2013 | Brock et al. |
| 8,418,073 | B2 | 4/2013 | Mohr et al. |
| 8,418,906 | B2 | 4/2013 | Farascioni et al. |
| 8,418,907 | B2 | 4/2013 | Johnson et al. |
| 8,418,908 | B1 | 4/2013 | Beardsley |
| 8,418,909 | B2 | 4/2013 | Kostrzewski |
| 8,419,635 | B2 | 4/2013 | Shelton, IV et al. |
| 8,419,717 | B2 | 4/2013 | Diolaiti et al. |
| 8,419,747 | B2 | 4/2013 | Hinman et al. |
| 8,419,754 | B2 | 4/2013 | Laby et al. |
| 8,419,755 | B2 | 4/2013 | Deem et al. |
| 8,423,182 | B2 | 4/2013 | Robinson et al. |

(56) References Cited

U.S. PATENT DOCUMENTS 8,424,737 B2 4/2013 Scirica
8,424,739 B2 4/2013 Racenet et al.
8,424,740 B2 4/2013 Shelton, IV et al.
8,424,741 B2 4/2013 McGuckin, Jr. et al.
8,424,742 B2 4/2013 Bettuchi
8,425,600 B2 4/2013 Maxwell
8,427,430 B2 4/2013 Lee et al.
8,430,292 B2 4/2013 Patel et al.
8,430,892 B2 4/2013 Bindra et al.
8,430,898 B2 4/2013 Wiener et al.
D681,674 S 5/2013 Koehn et al.
8,435,257 B2 5/2013 Smith et al.
8,439,246 B1 5/2013 Knodel
8,439,830 B2 5/2013 McKinley et al.
8,444,036 B2 5/2013 Shelton, IV
8,444,037 B2 5/2013 Nicholas et al.
8,444,549 B2 5/2013 Viola et al.
8,449,536 B2 5/2013 Selig
8,449,560 B2 5/2013 Roth et al.
8,453,904 B2 6/2013 Eskaros et al.
8,453,906 B2 6/2013 Huang et al.
8,453,907 B2 6/2013 Laurent et al.
8,453,908 B2 6/2013 Bedi et al.
8,453,912 B2 6/2013 Mastri et al.
8,453,914 B2 6/2013 Laurent et al.
8,454,495 B2 6/2013 Kawano et al.
8,454,551 B2 6/2013 Allen et al.
8,454,628 B2 6/2013 Smith et al.
8,454,640 B2 6/2013 Johnston et al.
8,457,757 B2 6/2013 Cauller et al.
8,459,520 B2 6/2013 Giordano et al.
8,459,521 B2 6/2013 Zemlok et al.
8,459,524 B2 6/2013 Pribanic et al.
8,459,525 B2 6/2013 Yates et al.
8,460,207 B2 6/2013 Burdorff et al.
8,464,922 B2 6/2013 Marczyk
8,464,923 B2 6/2013 Shelton, IV
8,464,924 B2 6/2013 Gresham et al.
8,464,925 B2 6/2013 Hull et al.
8,465,475 B2 6/2013 Isbell, Jr.
8,465,502 B2 6/2013 Zergiebel
8,465,515 B2 6/2013 Drew et al.
8,469,254 B2 6/2013 Czernik et al.
8,469,946 B2 6/2013 Sugita
8,469,973 B2 6/2013 Meade et al.
8,470,355 B2 6/2013 Skalla et al.
D686,240 S 7/2013 Lin
D686,244 S 7/2013 Moriya et al.
8,474,677 B2 7/2013 Woodard, Jr. et al.
8,475,453 B2 7/2013 Marczyk et al.
8,475,454 B1 7/2013 Alshemari
8,475,474 B2 7/2013 Bombard et al.
8,479,968 B2 7/2013 Hodgkinson et al.
8,479,969 B2 7/2013 Shelton, IV
8,480,703 B2 7/2013 Nicholas et al.
8,483,509 B2 7/2013 Matsuzaka
8,485,412 B2 7/2013 Shelton, IV et al.
8,485,413 B2 7/2013 Scheib et al.
8,485,970 B2 7/2013 Widenhouse et al.
8,486,047 B2 7/2013 Stopek
8,487,199 B2 7/2013 Palmer et al.
8,487,487 B2 7/2013 Dietz et al.
8,490,851 B2 7/2013 Blier et al.
8,490,852 B2 7/2013 Viola
8,490,853 B2 7/2013 Criscuolo et al.
8,491,581 B2 7/2013 Deville et al.
8,491,603 B2 7/2013 Yeung et al.
8,491,624 B2 7/2013 Kerr et al.
8,496,153 B2 7/2013 Demmy et al.
8,496,154 B2 7/2013 Marczyk et al.
8,496,156 B2 7/2013 Sniffin et al.
8,496,683 B2 7/2013 Prommersberger et al.
8,498,691 B2 7/2013 Moll et al.
8,499,673 B2 8/2013 Keller
8,499,966 B2 8/2013 Palmer et al.
8,499,992 B2 8/2013 Whitman et al.
8,499,993 B2 8/2013 Shelton, IV et al.
8,499,994 B2 8/2013 D'Arcangelo
8,500,721 B2 8/2013 Jinno
8,500,762 B2 8/2013 Sholev et al.
8,502,091 B2 8/2013 Palmer et al.
8,505,799 B2 8/2013 Viola et al.
8,505,801 B2 8/2013 Ehrenfels et al.
8,505,802 B2 8/2013 Viola et al.
8,506,555 B2 8/2013 Ruiz Morales
8,506,557 B2 8/2013 Zemlok et al.
8,506,580 B2 8/2013 Zergiebel et al.
8,506,581 B2 8/2013 Wingardner, III et al.
8,511,308 B2 8/2013 Hecox et al.
8,512,359 B2 8/2013 Whitman et al.
8,512,402 B2 8/2013 Marczyk et al.
8,517,239 B2 8/2013 Scheib et al.
8,517,241 B2 8/2013 Nicholas et al.
8,517,243 B2 8/2013 Giordano et al.
8,517,244 B2 8/2013 Shelton, IV et al.
8,517,938 B2 8/2013 Eisenhardt et al.
8,518,024 B2 8/2013 Williams et al.
8,521,273 B2 8/2013 Kliman
8,523,042 B2 9/2013 Masiakos et al.
8,523,043 B2 9/2013 Ullrich et al.
8,523,787 B2 9/2013 Ludwin et al.
8,523,881 B2 9/2013 Cabiri et al.
8,523,882 B2 9/2013 Huitema et al.
8,523,900 B2 9/2013 Jinno et al.
8,529,588 B2 9/2013 Ahlberg et al.
8,529,599 B2 9/2013 Holsten
8,529,600 B2 9/2013 Woodard, Jr. et al.
8,529,819 B2 9/2013 Ostapoff et al.
8,531,153 B2 9/2013 Baarman et al.
8,532,747 B2 9/2013 Nock et al.
8,534,527 B2 9/2013 Brendel et al.
8,534,528 B2 9/2013 Shelton, IV
8,535,304 B2 9/2013 Sklar et al.
8,535,340 B2 9/2013 Allen
8,539,866 B2 9/2013 Nayak et al.
8,540,128 B2 9/2013 Shelton, IV et al.
8,540,129 B2 9/2013 Baxter, III et al.
8,540,130 B2 9/2013 Moore et al.
8,540,131 B2 9/2013 Swayze
8,540,133 B2 9/2013 Bedi et al.
8,540,646 B2 9/2013 Mendez-Coll
8,540,733 B2 9/2013 Whitman et al.
8,540,735 B2 9/2013 Mitelberg et al.
D690,614 S 10/2013 Mascadri et al.
8,550,984 B2 10/2013 Takemoto
8,551,076 B2 10/2013 Duval et al.
8,555,660 B2 10/2013 Takenaka et al.
8,556,151 B2 10/2013 Viola
8,556,918 B2 10/2013 Bauman et al.
8,556,935 B1 10/2013 Knodel et al.
8,560,147 B2 10/2013 Taylor et al.
8,561,617 B2 10/2013 Lindh et al.
8,561,870 B2 10/2013 Baxter, III et al.
8,561,871 B2 10/2013 Rajappa et al.
8,561,873 B2 10/2013 Ingmanson et al.
8,562,592 B2 10/2013 Conlon et al.
8,562,598 B2 10/2013 Falkenstein et al.
8,567,656 B2 10/2013 Shelton, IV et al.
8,568,416 B2 10/2013 Schmitz et al.
8,568,425 B2 10/2013 Ross et al.
D692,916 S 11/2013 Granchi et al.
8,573,459 B2 11/2013 Smith et al.
8,573,461 B2 11/2013 Shelton, IV et al.
8,573,462 B2 11/2013 Smith et al.
8,573,465 B2 11/2013 Shelton, IV
8,574,199 B2 11/2013 von Bulow et al.
8,574,263 B2 11/2013 Mueller
8,575,880 B2 11/2013 Grantz
8,575,895 B2 11/2013 Garrastacho et al.
8,579,176 B2 11/2013 Smith et al.
8,579,178 B2 11/2013 Holsten et al.
8,579,897 B2 11/2013 Vakharia et al.
8,579,937 B2 11/2013 Gresham
8,584,919 B2 11/2013 Hueil et al.

(56) References Cited

U.S. PATENT DOCUMENTS 8,584,920 B2 11/2013 Hodgkinson
8,584,921 B2 11/2013 Scirica
8,585,583 B2 11/2013 Sakaguchi et al.
8,585,598 B2 11/2013 Razzaque et al.
8,585,721 B2 11/2013 Kirsch
8,590,760 B2 11/2013 Cummins et al.
8,590,762 B2 11/2013 Hess et al.
8,590,764 B2 11/2013 Hartwick et al.
8,591,400 B2 11/2013 Sugiyama
D695,310 S 12/2013 Jang et al.
8,596,515 B2 12/2013 Okoniewski
8,597,745 B2 12/2013 Farnsworth et al.
8,599,450 B2 12/2013 Kubo et al.
8,602,125 B2 12/2013 King
8,602,287 B2 12/2013 Yates et al.
8,602,288 B2 12/2013 Shelton, IV et al.
8,603,077 B2 12/2013 Cooper et al.
8,603,089 B2 12/2013 Viola
8,603,110 B2 12/2013 Maruyama et al.
8,603,135 B2 12/2013 Mueller
8,608,043 B2 12/2013 Scirica
8,608,044 B2 12/2013 Hueil et al.
8,608,045 B2 12/2013 Smith et al.
8,608,046 B2 12/2013 Laurent et al.
8,608,745 B2 12/2013 Guzman et al.
8,613,383 B2 12/2013 Beckman et al.
8,613,384 B2 12/2013 Pastorelli et al.
8,616,427 B2 12/2013 Viola
8,616,431 B2 12/2013 Timm et al.
8,617,155 B2 12/2013 Johnson et al.
8,620,473 B2 12/2013 Diolaiti et al.
8,622,274 B2 1/2014 Yates et al.
8,622,275 B2 1/2014 Baxter, III et al.
8,627,993 B2 1/2014 Smith et al.
8,627,994 B2 1/2014 Zemlok et al.
8,627,995 B2 1/2014 Smith et al.
8,628,467 B2 1/2014 Whitman et al.
8,628,518 B2 1/2014 Blumenkranz et al.
8,628,544 B2 1/2014 Farascioni
8,628,545 B2 1/2014 Cabrera et al.
8,631,987 B2 1/2014 Shelton, IV et al.
8,631,992 B1 1/2014 Hausen et al.
8,631,993 B2 1/2014 Kostrzewski
8,632,462 B2 1/2014 Yoo et al.
8,632,525 B2 1/2014 Kerr et al.
8,632,535 B2 1/2014 Shelton, IV et al.
8,632,539 B2 1/2014 Twomey et al.
8,632,563 B2 1/2014 Nagase et al.
8,636,187 B2 1/2014 Hueil et al.
8,636,190 B2 1/2014 Zemlok et al.
8,636,191 B2 1/2014 Meagher
8,636,193 B2 1/2014 Whitman et al.
8,636,736 B2 1/2014 Yates et al.
8,636,766 B2 1/2014 Milliman et al.
8,639,936 B2 1/2014 Hu et al.
8,640,788 B2 2/2014 Dachs, II et al.
8,646,674 B2 2/2014 Schulte et al.
8,647,258 B2 2/2014 Aranyi et al.
8,652,120 B2 2/2014 Giordano et al.
8,652,151 B2 2/2014 Lehman et al.
8,652,155 B2 2/2014 Houser et al.
8,656,929 B2 2/2014 Miller et al.
8,657,174 B2 2/2014 Yates et al.
8,657,175 B2 2/2014 Sonnenschein et al.
8,657,176 B2 2/2014 Shelton, IV et al.
8,657,177 B2 2/2014 Scirica et al.
8,657,178 B2 2/2014 Hueil et al.
8,657,482 B2 2/2014 Malackowski et al.
8,657,808 B2 2/2014 McPherson et al.
8,657,814 B2 2/2014 Werneth et al.
8,657,821 B2 2/2014 Palermo
D701,238 S 3/2014 Lai et al.
8,662,370 B2 3/2014 Takei
8,663,106 B2 3/2014 Stivoric et al.
8,663,192 B2 3/2014 Hester et al.
8,663,245 B2 3/2014 Francischelli et al.
8,663,262 B2 3/2014 Smith et al.
8,663,270 B2 3/2014 Donnigan et al.
8,664,792 B2 3/2014 Rebsdorf
8,668,129 B2 3/2014 Olson
8,668,130 B2 3/2014 Hess et al.
8,672,206 B2 3/2014 Aranyi et al.
8,672,207 B2 3/2014 Shelton, IV et al.
8,672,208 B2 3/2014 Hess et al.
8,672,209 B2 3/2014 Crainich
8,672,922 B2 3/2014 Loh et al.
8,672,935 B2 3/2014 Okada et al.
8,672,951 B2 3/2014 Smith et al.
8,673,210 B2 3/2014 Deshays
8,675,820 B2 3/2014 Baic et al.
8,678,263 B2 3/2014 Viola
8,678,994 B2 3/2014 Sonnenschein et al.
8,679,093 B2 3/2014 Farra
8,679,098 B2 3/2014 Hart
8,679,114 B2 3/2014 Chapman et al.
8,679,137 B2 3/2014 Bauman et al.
8,679,154 B2 3/2014 Smith et al.
8,679,156 B2 3/2014 Smith et al.
8,679,454 B2 3/2014 Guire et al.
8,684,248 B2 4/2014 Milliman
8,684,249 B2 4/2014 Racenet et al.
8,684,250 B2 4/2014 Bettuchi et al.
8,684,253 B2 4/2014 Giordano et al.
8,684,962 B2 4/2014 Kirschenman et al.
8,685,004 B2 4/2014 Zemlock et al.
8,685,020 B2 4/2014 Weizman et al.
8,690,893 B2 4/2014 Deitch et al.
8,695,866 B2 4/2014 Leimbach et al.
8,696,665 B2 4/2014 Hunt et al.
8,701,958 B2 4/2014 Shelton, IV et al.
8,701,959 B2 4/2014 Shah
8,706,316 B1 4/2014 Hoevenaar
8,708,210 B2 4/2014 Zemlok et al.
8,708,211 B2 4/2014 Zemlok et al.
8,708,212 B2 4/2014 Williams
8,708,213 B2 4/2014 Shelton, IV et al.
8,709,012 B2 4/2014 Muller
8,712,549 B2 4/2014 Zdeblick et al.
8,714,352 B2 5/2014 Farascioni et al.
8,714,429 B2 5/2014 Demmy
8,714,430 B2 5/2014 Natarajan et al.
8,715,256 B2 5/2014 Greener
8,715,302 B2 5/2014 Ibrahim et al.
8,720,766 B2 5/2014 Hess et al.
8,721,630 B2 5/2014 Ortiz et al.
8,721,666 B2 5/2014 Schroeder et al.
8,727,197 B2 5/2014 Hess et al.
8,727,199 B2 5/2014 Wenchell
8,727,200 B2 5/2014 Roy
8,727,961 B2 5/2014 Ziv
8,728,099 B2 5/2014 Cohn et al.
8,728,119 B2 5/2014 Cummins
8,733,470 B2 5/2014 Matthias et al.
8,733,611 B2 5/2014 Milliman
8,733,612 B2 5/2014 Ma
8,733,613 B2 5/2014 Huitema et al.
8,733,614 B2 5/2014 Ross et al.
8,734,336 B2 5/2014 Bonadio et al.
8,734,359 B2 5/2014 Ibanez et al.
8,734,431 B2 5/2014 Shimada et al.
8,734,478 B2 5/2014 Widenhouse et al.
8,734,831 B2 5/2014 Kim et al.
8,739,033 B2 5/2014 Rosenberg
8,739,417 B2 6/2014 Tokunaga et al.
8,740,034 B2 6/2014 Morgan et al.
8,740,037 B2 6/2014 Shelton, IV et al.
8,740,038 B2 6/2014 Shelton, IV et al.
8,740,987 B2 6/2014 Geremakis et al.
8,746,529 B2 6/2014 Shelton, IV et al.
8,746,530 B2 6/2014 Giordano et al.
8,746,533 B2 6/2014 Whitman et al.
8,746,535 B2 6/2014 Shelton, IV et al.
8,747,238 B2 6/2014 Shelton, IV et al.
8,747,441 B2 6/2014 Konieczynski et al.

(56) References Cited

U.S. PATENT DOCUMENTS 8,752,264 B2 6/2014 Ackley et al.
8,752,699 B2 6/2014 Morgan et al.
8,752,747 B2 6/2014 Shelton, IV et al.
8,752,748 B2 6/2014 Whitman et al.
8,752,749 B2 6/2014 Moore et al.
8,753,664 B2 6/2014 Dao et al.
8,757,287 B2 6/2014 Mak et al.
8,757,465 B2 6/2014 Woodard, Jr. et al.
8,758,235 B2 6/2014 Jaworek
8,758,366 B2 6/2014 McLean et al.
8,758,391 B2 6/2014 Swayze et al.
8,758,438 B2 6/2014 Boyce et al.
8,763,875 B2 7/2014 Morgan et al.
8,763,876 B2 7/2014 Kostrzewski
8,763,877 B2 7/2014 Schall et al.
8,763,879 B2 7/2014 Shelton, IV et al.
8,764,732 B2 7/2014 Hartwell
8,765,942 B2 7/2014 Feraud et al.
8,770,458 B2 7/2014 Scirica
8,770,459 B2 7/2014 Racenet et al.
8,770,460 B2 7/2014 Belzer
8,771,169 B2 7/2014 Whitman et al.
8,771,260 B2 7/2014 Conlon et al.
8,777,004 B2 7/2014 Shelton, IV et al.
8,777,082 B2 7/2014 Scirica
8,777,083 B2 7/2014 Racenet et al.
8,777,898 B2 7/2014 Suon et al.
8,783,541 B2 7/2014 Shelton, IV et al.
8,783,542 B2 7/2014 Riestenberg et al.
8,783,543 B2 7/2014 Shelton, IV et al.
8,784,304 B2 7/2014 Mikkaichi et al.
8,784,404 B2 7/2014 Doyle et al.
8,784,415 B2 7/2014 Malackowski et al.
8,789,737 B2 7/2014 Hodgkinson et al.
8,789,739 B2 7/2014 Swensgard
8,789,740 B2 7/2014 Baxter, III et al.
8,789,741 B2 7/2014 Baxter, III et al.
8,790,658 B2 7/2014 Cigarini et al.
8,790,684 B2 7/2014 Dave et al.
D711,905 S 8/2014 Morrison et al.
8,794,098 B2 8/2014 Long
8,794,496 B2 8/2014 Scirica
8,794,497 B2 8/2014 Zingman
8,795,159 B2 8/2014 Moriyama
8,795,276 B2 8/2014 Dietz et al.
8,795,308 B2 8/2014 Valin
8,795,324 B2 8/2014 Kawai et al.
8,796,995 B2 8/2014 Cunanan et al.
8,800,681 B2 8/2014 Rousson et al.
8,800,837 B2 8/2014 Zemlok
8,800,838 B2 8/2014 Shelton, IV
8,800,839 B2 8/2014 Beetel
8,800,840 B2 8/2014 Jankowski
8,800,841 B2 8/2014 Ellerhorst et al.
8,801,710 B2 8/2014 Ullrich et al.
8,801,734 B2 8/2014 Shelton, IV et al.
8,801,735 B2 8/2014 Shelton, IV et al.
8,801,752 B2 8/2014 Fortier et al.
8,801,801 B2 8/2014 Datta et al.
8,806,973 B2 8/2014 Ross et al.
8,807,414 B2 8/2014 Ross et al.
8,808,161 B2 8/2014 Gregg et al.
8,808,164 B2 8/2014 Hoffman et al.
8,808,274 B2 8/2014 Hartwell
8,808,294 B2 8/2014 Fox et al.
8,808,308 B2 8/2014 Boukhny et al.
8,808,311 B2 8/2014 Heinrich et al.
8,808,325 B2 8/2014 Hess et al.
8,810,197 B2 8/2014 Juergens
8,811,017 B2 8/2014 Fujii et al.
8,813,866 B2 8/2014 Suzuki
8,814,024 B2 8/2014 Woodard, Jr. et al.
8,814,025 B2 8/2014 Miller et al.
8,814,836 B2 8/2014 Ignon et al.
8,815,594 B2 8/2014 Harris et al.
8,818,523 B2 8/2014 Olson et al.
8,820,603 B2 9/2014 Shelton, IV et al.
8,820,605 B2 9/2014 Shelton, IV
8,820,606 B2 9/2014 Hodgkinson
8,820,607 B2 9/2014 Marczyk
8,820,608 B2 9/2014 Miyamoto
8,821,514 B2 9/2014 Aranyi
8,822,934 B2 9/2014 Sayeh et al.
8,825,164 B2 9/2014 Tweden et al.
8,827,133 B2 9/2014 Shelton, IV et al.
8,827,134 B2 9/2014 Viola et al.
8,827,903 B2 9/2014 Shelton, IV et al.
8,828,046 B2 9/2014 Stefanchik et al.
8,831,779 B2 9/2014 Ortmaier et al.
8,833,219 B2 9/2014 Pierce
8,833,630 B2 9/2014 Milliman
8,833,632 B2 9/2014 Swensgard
8,834,353 B2 9/2014 Dejima et al.
8,834,465 B2 9/2014 Ramstein et al.
8,834,498 B2 9/2014 Byrum et al.
8,834,518 B2 9/2014 Faller et al.
8,840,003 B2 9/2014 Morgan et al.
8,840,004 B2 9/2014 Holsten et al.
8,840,603 B2 9/2014 Shelton, IV et al.
8,840,609 B2 9/2014 Stuebe
8,840,876 B2 9/2014 Eemeta et al.
8,844,789 B2 9/2014 Shelton, IV et al.
8,844,790 B2 9/2014 Demmy et al.
8,845,622 B2 9/2014 Paik et al.
8,851,215 B2 10/2014 Goto
8,851,354 B2 10/2014 Swensgard et al.
8,851,355 B2 10/2014 Aranyi et al.
8,852,174 B2 10/2014 Burbank
8,852,185 B2 10/2014 Twomey
8,852,199 B2 10/2014 Deslauriers et al.
8,852,218 B2 10/2014 Hughett, Sr. et al.
8,852,473 B1 10/2014 Tan
8,855,822 B2 10/2014 Bartol et al.
8,857,692 B2 10/2014 Shima et al.
8,857,693 B2 10/2014 Schuckmann et al.
8,857,694 B2 10/2014 Shelton, IV et al.
8,858,538 B2 10/2014 Belson et al.
8,858,547 B2 10/2014 Brogna
8,858,571 B2 10/2014 Shelton, IV et al.
8,858,590 B2 10/2014 Shelton, IV et al.
8,864,007 B2 10/2014 Widenhouse et al.
8,864,009 B2 10/2014 Shelton, IV et al.
8,864,010 B2 10/2014 Williams
8,864,750 B2 10/2014 Ross et al.
8,869,912 B2 10/2014 Roßkamp et al.
8,869,913 B2 10/2014 Matthias et al.
8,870,049 B2 10/2014 Amid et al.
8,870,050 B2 10/2014 Hodgkinson
8,870,867 B2 10/2014 Walberg et al.
8,870,912 B2 10/2014 Brisson et al.
8,871,829 B2 10/2014 Gerold et al.
D716,820 S 11/2014 Wood
8,875,971 B2 11/2014 Hall et al.
8,875,972 B2 11/2014 Weisenburgh, II et al.
8,876,698 B2 11/2014 Sakamoto et al.
8,876,857 B2 11/2014 Burbank
8,876,858 B2 11/2014 Braun
8,882,660 B2 11/2014 Phee et al.
8,882,792 B2 11/2014 Dietz et al.
8,884,560 B2 11/2014 Ito
8,887,979 B2 11/2014 Mastri et al.
8,888,688 B2 11/2014 Julian et al.
8,888,695 B2 11/2014 Piskun et al.
8,888,792 B2 11/2014 Harris et al.
8,888,809 B2 11/2014 Davison et al.
8,893,946 B2 11/2014 Boudreaux et al.
8,893,949 B2 11/2014 Shelton, IV et al.
8,894,634 B2 11/2014 Devengenzo et al.
8,894,647 B2 11/2014 Beardsley et al.
8,894,654 B2 11/2014 Anderson
8,899,460 B2 12/2014 Wojcicki
8,899,461 B2 12/2014 Farascioni
8,899,462 B2 12/2014 Kostrzewski et al.
8,899,463 B2 12/2014 Schall et al.

(56) References Cited

U.S. PATENT DOCUMENTS

| | | | |
|---|---|---|---|
| 8,899,464 | B2 | 12/2014 | Hueil et al. |
| 8,899,465 | B2 | 12/2014 | Shelton, IV et al. |
| 8,899,466 | B2 | 12/2014 | Baxter, III et al. |
| 8,900,267 | B2 | 12/2014 | Woolfson et al. |
| 8,905,287 | B2 | 12/2014 | Racenet et al. |
| 8,905,977 | B2 | 12/2014 | Shelton et al. |
| 8,910,846 | B2 | 12/2014 | Viola |
| 8,910,847 | B2 | 12/2014 | Nalagatla et al. |
| 8,911,426 | B2 | 12/2014 | Coppeta et al. |
| 8,911,448 | B2 | 12/2014 | Stein |
| 8,911,460 | B2 | 12/2014 | Neurohr et al. |
| 8,911,471 | B2 | 12/2014 | Spivey et al. |
| 8,912,746 | B2 | 12/2014 | Reid et al. |
| 8,915,842 | B2 | 12/2014 | Weisenburgh, II et al. |
| 8,920,368 | B2 | 12/2014 | Sandhu et al. |
| 8,920,433 | B2 | 12/2014 | Barrier et al. |
| 8,920,435 | B2 | 12/2014 | Smith et al. |
| 8,920,438 | B2 | 12/2014 | Aranyi et al. |
| 8,920,443 | B2 | 12/2014 | Hiles et al. |
| 8,920,444 | B2 | 12/2014 | Hiles et al. |
| 8,922,163 | B2 | 12/2014 | Macdonald |
| 8,925,782 | B2 | 1/2015 | Shelton, IV |
| 8,925,783 | B2 | 1/2015 | Zemlok et al. |
| 8,925,788 | B2 | 1/2015 | Hess et al. |
| 8,926,506 | B2 | 1/2015 | Widenhouse et al. |
| 8,926,598 | B2 | 1/2015 | Mollere et al. |
| 8,931,576 | B2 | 1/2015 | Iwata |
| 8,931,679 | B2 | 1/2015 | Kostrzewski |
| 8,931,680 | B2 | 1/2015 | Milliman |
| 8,931,682 | B2 | 1/2015 | Timm et al. |
| 8,931,692 | B2 | 1/2015 | Sancak |
| 8,936,614 | B2 | 1/2015 | Allen, IV |
| 8,937,408 | B2 | 1/2015 | Ganem et al. |
| 8,939,343 | B2 | 1/2015 | Milliman et al. |
| 8,939,344 | B2 | 1/2015 | Olson et al. |
| 8,939,898 | B2 | 1/2015 | Omoto |
| 8,944,069 | B2 | 2/2015 | Miller et al. |
| 8,945,095 | B2 | 2/2015 | Blumenkranz et al. |
| 8,945,098 | B2 | 2/2015 | Seibold et al. |
| 8,945,163 | B2 | 2/2015 | Voegele et al. |
| 8,955,732 | B2 | 2/2015 | Zemlok et al. |
| 8,956,342 | B1 | 2/2015 | Russo et al. |
| 8,956,390 | B2 | 2/2015 | Shah et al. |
| 8,958,860 | B2 | 2/2015 | Banerjee et al. |
| 8,960,519 | B2 | 2/2015 | Whitman et al. |
| 8,960,520 | B2 | 2/2015 | McCuen |
| 8,960,521 | B2 | 2/2015 | Kostrzewski |
| 8,961,191 | B2 | 2/2015 | Hanshew |
| 8,961,504 | B2 | 2/2015 | Hoarau et al. |
| 8,961,542 | B2 | 2/2015 | Whitfield et al. |
| 8,963,714 | B2 | 2/2015 | Medhal et al. |
| D725,674 | S | 3/2015 | Jung et al. |
| 8,967,443 | B2 | 3/2015 | McCuen |
| 8,967,444 | B2 | 3/2015 | Beetel |
| 8,967,446 | B2 | 3/2015 | Beardsley et al. |
| 8,967,448 | B2 | 3/2015 | Carter et al. |
| 8,968,276 | B2 | 3/2015 | Zemlok et al. |
| 8,968,308 | B2 | 3/2015 | Horner et al. |
| 8,968,312 | B2 | 3/2015 | Marczyk et al. |
| 8,968,337 | B2 | 3/2015 | Whitfield et al. |
| 8,968,340 | B2 | 3/2015 | Chowaniec et al. |
| 8,968,355 | B2 | 3/2015 | Malkowski et al. |
| 8,968,358 | B2 | 3/2015 | Reschke |
| 8,970,507 | B2 | 3/2015 | Holbein et al. |
| 8,973,803 | B2 | 3/2015 | Hall et al. |
| 8,973,804 | B2 | 3/2015 | Hess et al. |
| 8,973,805 | B2 | 3/2015 | Scirica et al. |
| 8,974,440 | B2 | 3/2015 | Farritor et al. |
| 8,974,542 | B2 | 3/2015 | Fujimoto et al. |
| 8,974,932 | B2 | 3/2015 | McGahan et al. |
| 8,978,954 | B2 | 3/2015 | Shelton, IV et al. |
| 8,978,955 | B2 | 3/2015 | Aronhalt et al. |
| 8,978,956 | B2 | 3/2015 | Schall et al. |
| 8,979,843 | B2 | 3/2015 | Timm et al. |
| 8,979,890 | B2 | 3/2015 | Boudreaux |
| 8,982,195 | B2 | 3/2015 | Claus et al. |
| 8,984,711 | B2 | 3/2015 | Ota et al. |
| 8,985,240 | B2 | 3/2015 | Winnard |
| 8,985,429 | B2 | 3/2015 | Balek et al. |
| 8,986,302 | B2 | 3/2015 | Aldridge et al. |
| 8,989,903 | B2 | 3/2015 | Weir et al. |
| 8,991,676 | B2 | 3/2015 | Hess et al. |
| 8,991,677 | B2 | 3/2015 | Moore et al. |
| 8,991,678 | B2 | 3/2015 | Wellman et al. |
| 8,992,042 | B2 | 3/2015 | Eichenholz |
| 8,992,422 | B2 | 3/2015 | Spivey et al. |
| 8,992,565 | B2 | 3/2015 | Brisson et al. |
| 8,996,165 | B2 | 3/2015 | Wang et al. |
| 8,998,058 | B2 | 4/2015 | Moore et al. |
| 8,998,059 | B2 | 4/2015 | Smith et al. |
| 8,998,060 | B2 | 4/2015 | Bruewer et al. |
| 8,998,061 | B2 | 4/2015 | Williams et al. |
| 8,998,939 | B2 | 4/2015 | Price et al. |
| 9,000,720 | B2 | 4/2015 | Stulen et al. |
| 9,002,518 | B2 | 4/2015 | Manzo et al. |
| 9,004,339 | B1 | 4/2015 | Park |
| 9,004,799 | B1 | 4/2015 | Tibbits |
| 9,005,230 | B2 | 4/2015 | Yates et al. |
| 9,005,238 | B2 | 4/2015 | DeSantis et al. |
| 9,005,243 | B2 | 4/2015 | Stopek et al. |
| 9,010,606 | B2 | 4/2015 | Aranyi et al. |
| 9,010,608 | B2 | 4/2015 | Casasanta, Jr. et al. |
| 9,010,611 | B2 | 4/2015 | Ross et al. |
| 9,011,437 | B2 | 4/2015 | Woodruff et al. |
| 9,011,439 | B2 | 4/2015 | Shalaby et al. |
| 9,011,471 | B2 | 4/2015 | Timm et al. |
| 9,014,856 | B2 | 4/2015 | Manzo et al. |
| 9,016,539 | B2 | 4/2015 | Kostrzewski et al. |
| 9,016,540 | B2 | 4/2015 | Whitman et al. |
| 9,016,541 | B2 | 4/2015 | Viola et al. |
| 9,016,542 | B2 | 4/2015 | Shelton, IV et al. |
| 9,016,545 | B2 | 4/2015 | Aranyi et al. |
| 9,017,331 | B2 | 4/2015 | Fox |
| 9,017,355 | B2 | 4/2015 | Smith et al. |
| 9,017,369 | B2 | 4/2015 | Renger et al. |
| 9,017,371 | B2 | 4/2015 | Whitman et al. |
| 9,017,849 | B2 | 4/2015 | Stulen et al. |
| 9,017,851 | B2 | 4/2015 | Felder et al. |
| D729,274 | S | 5/2015 | Clement et al. |
| D730,393 | S | 5/2015 | Bray et al. |
| 9,021,684 | B2 | 5/2015 | Lenker et al. |
| 9,023,014 | B2 | 5/2015 | Chowaniec et al. |
| 9,023,069 | B2 | 5/2015 | Kasvikis et al. |
| 9,023,071 | B2 | 5/2015 | Miller et al. |
| 9,026,347 | B2 | 5/2015 | Gadh et al. |
| 9,027,817 | B2 | 5/2015 | Milliman et al. |
| 9,028,468 | B2 | 5/2015 | Scarfogliero et al. |
| 9,028,494 | B2 | 5/2015 | Shelton, IV et al. |
| 9,028,495 | B2 | 5/2015 | Mueller et al. |
| 9,028,510 | B2 | 5/2015 | Miyamoto et al. |
| 9,028,511 | B2 | 5/2015 | Weller et al. |
| 9,028,519 | B2 | 5/2015 | Yates et al. |
| 9,028,529 | B2 | 5/2015 | Fox et al. |
| 9,030,166 | B2 | 5/2015 | Kano |
| 9,030,169 | B2 | 5/2015 | Christensen et al. |
| 9,033,203 | B2 | 5/2015 | Woodard, Jr. et al. |
| 9,033,204 | B2 | 5/2015 | Shelton, IV et al. |
| 9,034,505 | B2 | 5/2015 | Detry et al. |
| 9,038,881 | B1 | 5/2015 | Schaller et al. |
| 9,039,690 | B2 | 5/2015 | Kersten et al. |
| 9,039,694 | B2 | 5/2015 | Ross et al. |
| 9,039,720 | B2 | 5/2015 | Madan |
| 9,039,736 | B2 | 5/2015 | Scirica et al. |
| 9,040,062 | B2 | 5/2015 | Maeda et al. |
| 9,043,027 | B2 | 5/2015 | Durant et al. |
| 9,044,227 | B2 | 6/2015 | Shelton, IV et al. |
| 9,044,228 | B2 | 6/2015 | Woodard, Jr. et al. |
| 9,044,229 | B2 | 6/2015 | Scheib et al. |
| 9,044,230 | B2 | 6/2015 | Morgan et al. |
| 9,044,238 | B2 | 6/2015 | Orszulak |
| 9,044,241 | B2 | 6/2015 | Barner et al. |
| 9,044,261 | B2 | 6/2015 | Houser |
| 9,044,281 | B2 | 6/2015 | Pool et al. |
| 9,050,083 | B2 | 6/2015 | Yates et al. |

(56) References Cited

U.S. PATENT DOCUMENTS 9,050,084 B2 6/2015 Schmid et al.
9,050,089 B2 6/2015 Orszulak
9,050,100 B2 6/2015 Yates et al.
9,050,120 B2 6/2015 Swarup et al.
9,050,123 B2 6/2015 Krause et al.
9,050,176 B2 6/2015 Datta et al.
9,050,192 B2 6/2015 Mansmann
9,055,941 B2 6/2015 Schmid et al.
9,055,942 B2 6/2015 Balbierz et al.
9,055,943 B2 6/2015 Zemlok et al.
9,055,944 B2 6/2015 Hodgkinson et al.
9,055,961 B2 6/2015 Manzo et al.
9,060,770 B2 6/2015 Shelton, IV et al.
9,060,776 B2 6/2015 Yates et al.
9,060,794 B2 6/2015 Kang et al.
9,060,894 B2 6/2015 Wubbeling
9,061,392 B2 6/2015 Forgues et al.
9,070,068 B2 6/2015 Coveley et al.
D733,727 S 7/2015 Cojuangco et al.
9,072,515 B2 7/2015 Hall et al.
9,072,523 B2 7/2015 Houser et al.
9,072,535 B2 7/2015 Shelton, IV et al.
9,072,536 B2 7/2015 Shelton, IV et al.
9,078,653 B2 7/2015 Leimbach et al.
9,078,654 B2 7/2015 Whitman et al.
9,084,586 B2 7/2015 Hafner et al.
9,084,601 B2 7/2015 Moore et al.
9,084,602 B2 7/2015 Gleiman
9,086,875 B2 7/2015 Harrat et al.
9,089,317 B2 7/2015 Burdorff et al.
9,089,326 B2 7/2015 Krumanaker et al.
9,089,330 B2 7/2015 Widenhouse et al.
9,089,338 B2 7/2015 Smith et al.
9,089,352 B2 7/2015 Jeong
9,089,360 B2 7/2015 Messerly et al.
9,091,588 B2 7/2015 Lefler
D736,792 S 8/2015 Brinda et al.
9,095,339 B2 8/2015 Moore et al.
9,095,346 B2 8/2015 Houser et al.
9,095,362 B2 8/2015 Dachs, II et al.
9,095,367 B2 8/2015 Olson et al.
9,095,642 B2 8/2015 Harder et al.
9,096,033 B2 8/2015 Holop et al.
9,098,153 B2 8/2015 Shen et al.
9,099,863 B2 8/2015 Smith et al.
9,099,877 B2 8/2015 Banos et al.
9,099,922 B2 8/2015 Toosky et al.
9,101,358 B2 8/2015 Kerr et al.
9,101,359 B2 8/2015 Smith et al.
9,101,385 B2 8/2015 Shelton, IV et al.
9,101,475 B2 8/2015 Wei et al.
9,101,621 B2 8/2015 Zeldis
9,107,663 B2 8/2015 Swensgard
9,107,667 B2 8/2015 Hodgkinson
9,107,690 B2 8/2015 Bales, Jr. et al.
9,110,587 B2 8/2015 Kim et al.
9,113,862 B2 8/2015 Morgan et al.
9,113,864 B2 8/2015 Morgan et al.
9,113,865 B2 8/2015 Shelton, IV et al.
9,113,866 B2 8/2015 Felder et al.
9,113,868 B2 8/2015 Felder et al.
9,113,873 B2 8/2015 Marczyk et al.
9,113,874 B2 8/2015 Shelton, IV et al.
9,113,875 B2 8/2015 Viola et al.
9,113,876 B2 8/2015 Zemlok et al.
9,113,877 B1 8/2015 Whitman et al.
9,113,879 B2 8/2015 Felder et al.
9,113,880 B2 8/2015 Zemlok et al.
9,113,881 B2 8/2015 Scirica
9,113,883 B2 8/2015 Aronhalt et al.
9,113,884 B2 8/2015 Shelton, IV et al.
9,113,887 B2 8/2015 Behnke, II et al.
9,119,615 B2 9/2015 Felder et al.
9,119,657 B2 9/2015 Shelton, IV et al.
9,119,898 B2 9/2015 Bayon et al.
9,119,957 B2 9/2015 Gantz et al.
9,123,286 B2 9/2015 Park
9,124,097 B2 9/2015 Cruz
9,125,651 B2 9/2015 Mandakolathur Vasudevan et al.
9,125,654 B2 9/2015 Aronhalt et al.
9,125,662 B2 9/2015 Shelton, IV
9,126,317 B2 9/2015 Lawton et al.
9,131,835 B2 9/2015 Widenhouse et al.
9,131,940 B2 9/2015 Huitema et al.
9,131,950 B2 9/2015 Matthew
9,131,957 B2 9/2015 Skarbnik et al.
9,138,225 B2 9/2015 Huang et al.
9,138,226 B2 9/2015 Racenet et al.
9,144,455 B2 9/2015 Kennedy et al.
D740,414 S 10/2015 Katsura
D741,882 S 10/2015 Shmilov et al.
9,149,274 B2 10/2015 Spivey et al.
9,149,324 B2 10/2015 Huang et al.
9,149,325 B2 10/2015 Worrell et al.
9,153,994 B2 10/2015 Wood et al.
9,154,189 B2 10/2015 Von Novak et al.
9,161,753 B2 10/2015 Prior
9,161,769 B2 10/2015 Stoddard et al.
9,161,803 B2 10/2015 Yates et al.
9,161,807 B2 10/2015 Garrison
9,161,855 B2 10/2015 Rousseau et al.
9,164,271 B2 10/2015 Ebata et al.
9,167,960 B2 10/2015 Yamaguchi et al.
9,168,038 B2 10/2015 Shelton, IV et al.
9,168,039 B1 10/2015 Knodel
9,168,042 B2 10/2015 Milliman
9,168,054 B2 10/2015 Turner et al.
9,168,144 B2 10/2015 Rivin et al.
9,171,244 B2 10/2015 Endou et al.
9,179,832 B2 11/2015 Diolaiti
9,179,911 B2 11/2015 Morgan et al.
9,179,912 B2 11/2015 Yates et al.
9,180,223 B2 11/2015 Yu et al.
9,182,244 B2 11/2015 Luke et al.
9,186,046 B2 11/2015 Ramamurthy et al.
9,186,137 B2 11/2015 Farascioni et al.
9,186,140 B2 11/2015 Hiles et al.
9,186,142 B2 11/2015 Fanelli et al.
9,186,143 B2 11/2015 Timm et al.
9,186,148 B2 11/2015 Felder et al.
9,186,221 B2 11/2015 Burbank
9,192,376 B2 11/2015 Almodovar
9,192,380 B2 11/2015 (Tarinelli) Racenet et al.
9,192,384 B2 11/2015 Bettuchi
9,192,430 B2 11/2015 Rachlin et al.
9,192,434 B2 11/2015 Twomey et al.
9,193,045 B2 11/2015 Saur et al.
9,197,079 B2 11/2015 Yip et al.
D744,528 S 12/2015 Agrawal
D746,459 S 12/2015 Kaercher et al.
9,198,642 B2 12/2015 Storz
9,198,644 B2 12/2015 Balek et al.
9,198,661 B2 12/2015 Swensgard
9,198,662 B2 12/2015 Barton et al.
9,198,683 B2 12/2015 Friedman et al.
9,204,830 B2 12/2015 Zand et al.
9,204,877 B2 12/2015 Whitman et al.
9,204,878 B2 12/2015 Hall et al.
9,204,879 B2 12/2015 Shelton, IV
9,204,880 B2 12/2015 Baxter, III et al.
9,204,881 B2 12/2015 Penna
9,204,923 B2 12/2015 Manzo et al.
9,204,924 B2 12/2015 Marczyk et al.
9,211,120 B2 12/2015 Scheib et al.
9,211,121 B2 12/2015 Hall et al.
9,211,122 B2 12/2015 Hagerty et al.
9,216,013 B2 12/2015 Scirica et al.
9,216,019 B2 12/2015 Schmid et al.
9,216,020 B2 12/2015 Zhang et al.
9,216,030 B2 12/2015 Fan et al.
9,216,062 B2 12/2015 Duque et al.
9,220,500 B2 12/2015 Swayze et al.
9,220,501 B2 12/2015 Baxter, III et al.
9,220,502 B2 12/2015 Zemlok et al.

(56) References Cited

U.S. PATENT DOCUMENTS 9,220,504 B2 12/2015 Viola et al.
9,220,508 B2 12/2015 Dannaher
9,220,559 B2 12/2015 Worrell et al.
9,220,570 B2 12/2015 Kim et al.
D746,854 S 1/2016 Shardlow et al.
9,226,686 B2 1/2016 Blair
9,226,750 B2 1/2016 Weir et al.
9,226,751 B2 1/2016 Shelton, IV et al.
9,226,754 B2 1/2016 D'Agostino et al.
9,226,760 B2 1/2016 Shelton, IV
9,226,761 B2 1/2016 Burbank
9,226,767 B2 1/2016 Stulen et al.
9,226,799 B2 1/2016 Lightcap et al.
9,232,941 B2 1/2016 Mandakolathur Vasudevan et al.
9,232,945 B2 1/2016 Zingman
9,232,979 B2 1/2016 Parihar et al.
9,233,610 B2 1/2016 Kim et al.
9,237,891 B2 1/2016 Shelton, IV
9,237,892 B2 1/2016 Hodgkinson
9,237,895 B2 1/2016 McCarthy et al.
9,237,900 B2 1/2016 Boudreaux et al.
9,237,921 B2 1/2016 Messerly et al.
9,239,064 B2 1/2016 Helbig et al.
9,240,740 B2 1/2016 Zeng et al.
9,241,711 B2 1/2016 Ivanko
9,241,712 B2 1/2016 Zemlok et al.
9,241,714 B2 1/2016 Timm et al.
9,241,716 B2 1/2016 Whitman
9,241,731 B2 1/2016 Boudreaux et al.
9,241,758 B2 1/2016 Franer et al.
9,244,524 B2 1/2016 Inoue et al.
D748,668 S 2/2016 Kim et al.
D749,128 S 2/2016 Perez et al.
D749,623 S 2/2016 Gray et al.
D750,122 S 2/2016 Shardlow et al.
D750,129 S 2/2016 Kwon
9,254,131 B2 2/2016 Soltz et al.
9,254,170 B2 2/2016 Parihar et al.
9,259,265 B2 2/2016 Harris et al.
9,259,268 B2 2/2016 Behnke, II et al.
9,259,274 B2 2/2016 Prisco
9,259,275 B2 2/2016 Burbank
9,261,172 B2 2/2016 Solomon et al.
9,265,500 B2 2/2016 Sorrentino et al.
9,265,510 B2 2/2016 Dietzel et al.
9,265,516 B2 2/2016 Casey et al.
9,265,585 B2 2/2016 Wingardner et al.
9,271,718 B2 3/2016 Milad et al.
9,271,727 B2 3/2016 McGuckin, Jr. et al.
9,271,753 B2 3/2016 Butler et al.
9,271,799 B2 3/2016 Shelton, IV et al.
9,272,406 B2 3/2016 Aronhalt et al.
9,274,095 B2 3/2016 Humayun et al.
9,277,919 B2 3/2016 Timmer et al.
9,277,922 B2 3/2016 Carter et al.
9,277,969 B2 3/2016 Brannan et al.
9,282,962 B2 3/2016 Schmid et al.
9,282,963 B2 3/2016 Bryant
9,282,966 B2 3/2016 Shelton, IV et al.
9,282,974 B2 3/2016 Shelton, IV
9,283,028 B2 3/2016 Johnson
9,283,045 B2 3/2016 Rhee et al.
9,283,054 B2 3/2016 Morgan et al.
9,283,334 B2 3/2016 Mantell et al.
9,289,206 B2 3/2016 Hess et al.
9,289,207 B2 3/2016 Shelton, IV
9,289,210 B2 3/2016 Baxter, III et al.
9,289,211 B2 3/2016 Williams et al.
9,289,212 B2 3/2016 Shelton, IV et al.
9,289,225 B2 3/2016 Shelton, IV et al.
9,289,256 B2 3/2016 Shelton, IV et al.
9,293,757 B2 3/2016 Toussaint et al.
9,295,464 B2 3/2016 Shelton, IV et al.
9,295,465 B2 3/2016 Farascioni
9,295,466 B2 3/2016 Hodgkinson et al.
9,295,467 B2 3/2016 Scirica
9,295,468 B2 3/2016 Heinrich et al.
9,295,514 B2 3/2016 Shelton, IV et al.
9,295,522 B2 3/2016 Kostrzewski
9,295,565 B2 3/2016 McLean
9,295,784 B2 3/2016 Eggert et al.
D753,167 S 4/2016 Yu et al.
9,301,691 B2 4/2016 Hufnagel et al.
9,301,752 B2 4/2016 Mandakolathur Vasudevan et al.
9,301,753 B2 4/2016 Aldridge et al.
9,301,755 B2 4/2016 Shelton, IV et al.
9,301,759 B2 4/2016 Spivey et al.
9,301,811 B2 4/2016 Goldberg et al.
9,307,965 B2 4/2016 Ming et al.
9,307,986 B2 4/2016 Hall et al.
9,307,987 B2 4/2016 Swensgard et al.
9,307,988 B2 4/2016 Shelton, IV
9,307,989 B2 4/2016 Shelton, IV et al.
9,307,994 B2 4/2016 Gresham et al.
9,308,009 B2 4/2016 Madan et al.
9,308,011 B2 4/2016 Chao et al.
9,308,646 B2 4/2016 Lim et al.
9,313,915 B2 4/2016 Niu et al.
9,314,246 B2 4/2016 Shelton, IV et al.
9,314,247 B2 4/2016 Shelton, IV et al.
9,314,261 B2 4/2016 Bales, Jr. et al.
9,314,291 B2 4/2016 Schall et al.
9,314,339 B2 4/2016 Mansmann
9,314,908 B2 4/2016 Tanimoto et al.
9,320,518 B2 4/2016 Henderson et al.
9,320,520 B2 4/2016 Shelton, IV et al.
9,320,521 B2 4/2016 Shelton, IV et al.
9,320,523 B2 4/2016 Shelton, IV et al.
9,325,516 B2 4/2016 Pera et al.
D755,196 S 5/2016 Meyers et al.
D756,373 S 5/2016 Raskin et al.
D756,377 S 5/2016 Connolly et al.
D757,028 S 5/2016 Goldenberg et al.
9,326,767 B2 5/2016 Koch, Jr. et al.
9,326,768 B2 5/2016 Shelton, IV
9,326,769 B2 5/2016 Shelton, IV et al.
9,326,770 B2 5/2016 Shelton, IV et al.
9,326,771 B2 5/2016 Baxter, III et al.
9,326,788 B2 5/2016 Batross et al.
9,326,812 B2 5/2016 Waaler et al.
9,326,824 B2 5/2016 Inoue et al.
9,327,061 B2 5/2016 Govil et al.
9,331,721 B2 5/2016 Martinez Nuevo et al.
9,332,890 B2 5/2016 Ozawa
9,332,974 B2 5/2016 Henderson et al.
9,332,984 B2 5/2016 Weaner et al.
9,332,987 B2 5/2016 Leimbach et al.
9,333,040 B2 5/2016 Shellenberger et al.
9,333,082 B2 5/2016 Wei et al.
9,337,668 B2 5/2016 Yip
9,339,226 B2 5/2016 van der Walt et al.
9,339,342 B2 5/2016 Prisco et al.
9,345,477 B2 5/2016 Anim et al.
9,345,479 B2 5/2016 (Tarinelli) Racenet et al.
9,345,480 B2 5/2016 Hessler et al.
9,345,481 B2 5/2016 Hall et al.
9,345,503 B2 5/2016 Ishida et al.
9,351,726 B2 5/2016 Leimbach et al.
9,351,727 B2 5/2016 Leimbach et al.
9,351,728 B2 5/2016 Sniffin et al.
9,351,730 B2 5/2016 Schmid et al.
9,351,731 B2 5/2016 Carter et al.
9,351,732 B2 5/2016 Hodgkinson
9,352,071 B2 5/2016 Landgrebe et al.
D758,433 S 6/2016 Lee et al.
D759,063 S 6/2016 Chen
9,358,003 B2 6/2016 Hall et al.
9,358,004 B2 6/2016 Sniffin et al.
9,358,005 B2 6/2016 Shelton, IV et al.
9,358,015 B2 6/2016 Sorrentino et al.
9,358,031 B2 6/2016 Manzo
9,358,065 B2 6/2016 Ladtkow et al.
9,364,217 B2 6/2016 Kostrzewski et al.
9,364,219 B2 6/2016 Olson et al.

(56) References Cited

U.S. PATENT DOCUMENTS 9,364,220 B2 6/2016 Williams
9,364,223 B2 6/2016 Scirica
9,364,226 B2 6/2016 Zemlok et al.
9,364,228 B2 6/2016 Straehnz et al.
9,364,229 B2 6/2016 D'Agostino et al.
9,364,230 B2 6/2016 Shelton, IV et al.
9,364,231 B2 6/2016 Wenchell
9,364,233 B2 6/2016 Alexander, III et al.
9,364,279 B2 6/2016 Houser et al.
9,368,991 B2 6/2016 Qahouq
9,370,341 B2 6/2016 Ceniccola et al.
9,370,358 B2 6/2016 Shelton, IV et al.
9,370,361 B2 6/2016 Viola et al.
9,370,362 B2 6/2016 Petty et al.
9,370,364 B2 6/2016 Smith et al.
9,370,400 B2 6/2016 Parihar
9,375,206 B2 6/2016 Vidal et al.
9,375,218 B2 6/2016 Wheeler et al.
9,375,230 B2 6/2016 Ross et al.
9,375,232 B2 6/2016 Hunt et al.
9,375,255 B2 6/2016 Houser et al.
D761,309 S 7/2016 Lee et al.
9,381,058 B2 7/2016 Houser et al.
9,383,881 B2 7/2016 Day et al.
9,385,640 B2 7/2016 Sun et al.
9,386,983 B2 7/2016 Swensgard et al.
9,386,984 B2 7/2016 Aronhalt et al.
9,386,985 B2 7/2016 Koch, Jr. et al.
9,386,988 B2 7/2016 Baxter, III et al.
9,387,003 B2 7/2016 Kaercher et al.
9,392,885 B2 7/2016 Vogler et al.
9,393,015 B2 7/2016 Laurent et al.
9,393,017 B2 7/2016 Flanagan et al.
9,393,018 B2 7/2016 Wang et al.
9,393,354 B2 7/2016 Freedman et al.
9,396,369 B1 7/2016 Whitehurst et al.
9,396,669 B2 7/2016 Karkanias et al.
9,398,905 B2 7/2016 Martin
9,398,911 B2 7/2016 Auld
D763,277 S 8/2016 Ahmed et al.
D764,498 S 8/2016 Capela et al.
9,402,604 B2 8/2016 Williams et al.
9,402,625 B2 8/2016 Coleman et al.
9,402,626 B2 8/2016 Ortiz et al.
9,402,627 B2 8/2016 Stevenson et al.
9,402,629 B2 8/2016 Ehrenfels et al.
9,402,679 B2 8/2016 Ginnebaugh et al.
9,402,682 B2 8/2016 Worrell et al.
9,402,688 B2 8/2016 Min et al.
9,408,604 B2 8/2016 Shelton, IV et al.
9,408,605 B1 8/2016 Knodel et al.
9,408,606 B2 8/2016 Shelton, IV
9,408,622 B2 8/2016 Stulen et al.
9,408,668 B2 8/2016 Durant et al.
9,411,370 B2 8/2016 Benni et al.
9,413,128 B2 8/2016 Tien et al.
9,414,838 B2 8/2016 Shelton, IV et al.
9,414,849 B2 8/2016 Nagashimada
9,414,880 B2 8/2016 Monson et al.
9,420,967 B2 8/2016 Zand et al.
9,421,003 B2 8/2016 Williams et al.
9,421,014 B2 8/2016 Ingmanson et al.
9,421,030 B2 8/2016 Cole et al.
9,421,060 B2 8/2016 Monson et al.
9,421,062 B2 8/2016 Houser et al.
9,421,682 B2 8/2016 McClaskey et al.
9,427,223 B2 8/2016 Park et al.
9,427,231 B2 8/2016 Racenet et al.
9,429,204 B2 8/2016 Stefan et al.
D767,624 S 9/2016 Lee et al.
9,433,411 B2 9/2016 Racenet et al.
9,433,414 B2 9/2016 Chen et al.
9,433,418 B2 9/2016 Whitman et al.
9,433,419 B2 9/2016 Gonzalez et al.
9,433,420 B2 9/2016 Hodgkinson
9,439,649 B2 9/2016 Shelton, IV et al.
9,439,650 B2 9/2016 McGuckin, Jr. et al.
9,439,651 B2 9/2016 Smith et al.
9,439,668 B2 9/2016 Timm et al.
9,445,808 B2 9/2016 Woodard, Jr. et al.
9,445,813 B2 9/2016 Shelton, IV et al.
9,445,816 B2 9/2016 Swayze et al.
9,445,817 B2 9/2016 Bettuchi
9,446,226 B2 9/2016 Zilberman
9,451,938 B2 9/2016 Overes et al.
9,451,958 B2 9/2016 Shelton, IV et al.
9,452,020 B2 9/2016 Griffiths et al.
D768,152 S 10/2016 Gutierrez et al.
D768,156 S 10/2016 Frincke
D768,167 S 10/2016 Jones et al.
D769,315 S 10/2016 Scotti
D769,930 S 10/2016 Agrawal
9,461,340 B2 10/2016 Li et al.
9,463,012 B2 10/2016 Bonutti et al.
9,463,040 B2 10/2016 Jeong et al.
9,463,260 B2 10/2016 Stopek
9,468,438 B2 10/2016 Baber et al.
9,468,447 B2 10/2016 Aman et al.
9,470,297 B2 10/2016 Aranyi et al.
9,471,969 B2 10/2016 Zeng et al.
9,474,506 B2 10/2016 Magnin et al.
9,474,513 B2 10/2016 Ishida et al.
9,474,523 B2 10/2016 Meade et al.
9,474,528 B2 10/2016 Marczyk
9,474,540 B2 10/2016 Stokes et al.
9,474,581 B2 10/2016 Niemeyer
9,475,180 B2 10/2016 Eshleman et al.
9,477,649 B1 10/2016 Davidson et al.
D770,476 S 11/2016 Jitkoff et al.
D770,515 S 11/2016 Cho et al.
D771,116 S 11/2016 Dellinger et al.
D772,905 S 11/2016 Ingenlath
9,480,476 B2 11/2016 Aldridge et al.
9,480,492 B2 11/2016 Aranyi et al.
9,483,095 B2 11/2016 Tran et al.
9,486,186 B2 11/2016 Fiebig et al.
9,486,213 B2 11/2016 Altman et al.
9,486,214 B2 11/2016 Shelton, IV
9,486,215 B2 11/2016 Olson et al.
9,486,302 B2 11/2016 Boey et al.
9,488,197 B2 11/2016 Wi
9,492,146 B2 11/2016 Kostrzewski et al.
9,492,167 B2 11/2016 Shelton, IV et al.
9,492,170 B2 11/2016 Bear et al.
9,492,172 B2 11/2016 Weisshaupt et al.
9,492,189 B2 11/2016 Williams et al.
9,492,192 B2 11/2016 To et al.
9,492,237 B2 11/2016 Kang et al.
9,498,213 B2 11/2016 Marczyk et al.
9,498,219 B2 11/2016 Moore et al.
9,498,231 B2 11/2016 Haider et al.
9,504,455 B2 11/2016 Whitman et al.
9,504,483 B2 11/2016 Houser et al.
9,504,520 B2 11/2016 Worrell et al.
9,504,521 B2 11/2016 Deutmeyer et al.
9,504,528 B2 11/2016 Ivinson et al.
9,507,399 B2 11/2016 Chien
D774,547 S 12/2016 Capela et al.
D775,336 S 12/2016 Shelton, IV et al.
9,510,827 B2 12/2016 Kostrzewski
9,510,828 B2 12/2016 Yates et al.
9,510,830 B2 12/2016 Shelton, IV et al.
9,510,846 B2 12/2016 Sholev et al.
9,510,895 B2 12/2016 Houser et al.
9,510,925 B2 12/2016 Hotter et al.
9,515,366 B2 12/2016 Herbsommer et al.
9,517,063 B2 12/2016 Swayze et al.
9,517,065 B2 12/2016 Simms et al.
9,517,068 B2 12/2016 Shelton, IV et al.
9,517,326 B2 12/2016 Hinman et al.
9,519,341 B2 12/2016 Hasegawa et al.
9,521,996 B2 12/2016 Armstrong
9,522,003 B2 12/2016 Weir et al.
9,522,005 B2 12/2016 Williams et al.

(56) References Cited

U.S. PATENT DOCUMENTS

| | | | |
|---|---|---|---|
| 9,522,014 | B2 | 12/2016 | Nishizawa et al. |
| 9,522,029 | B2 | 12/2016 | Yates et al. |
| 9,526,481 | B2 | 12/2016 | Storz et al. |
| 9,526,499 | B2 | 12/2016 | Kostrzewski et al. |
| 9,526,563 | B2 | 12/2016 | Twomey |
| 9,526,564 | B2 | 12/2016 | Rusin |
| 9,526,921 | B2 | 12/2016 | Kimball et al. |
| D776,683 | S | 1/2017 | Gobinski et al. |
| D777,773 | S | 1/2017 | Shi |
| 9,532,783 | B2 | 1/2017 | Swayze et al. |
| 9,539,060 | B2 | 1/2017 | Lightcap et al. |
| 9,539,726 | B2 | 1/2017 | Simaan et al. |
| 9,545,253 | B2 | 1/2017 | Worrell et al. |
| 9,545,258 | B2 | 1/2017 | Smith et al. |
| 9,549,732 | B2 | 1/2017 | Yates et al. |
| 9,549,733 | B2 | 1/2017 | Knodel |
| 9,549,735 | B2 | 1/2017 | Shelton, IV et al. |
| 9,549,750 | B2 | 1/2017 | Shelton, IV et al. |
| 9,554,794 | B2 | 1/2017 | Baber et al. |
| 9,554,796 | B2 | 1/2017 | Kostrzewski |
| 9,554,803 | B2 | 1/2017 | Smith et al. |
| 9,554,812 | B2 | 1/2017 | Inkpen et al. |
| 9,554,854 | B2 | 1/2017 | Yates et al. |
| 9,559,624 | B2 | 1/2017 | Philipp |
| 9,561,013 | B2 | 2/2017 | Tsuchiya |
| 9,561,029 | B2 | 2/2017 | Scheib et al. |
| 9,561,030 | B2 | 2/2017 | Zhang et al. |
| 9,561,031 | B2 | 2/2017 | Heinrich et al. |
| 9,561,032 | B2 | 2/2017 | Shelton, IV et al. |
| 9,561,038 | B2 | 2/2017 | Shelton, IV et al. |
| 9,561,045 | B2 | 2/2017 | Hinman et al. |
| 9,561,072 | B2 | 2/2017 | Ko |
| 9,561,082 | B2 | 2/2017 | Yen et al. |
| 9,566,061 | B2 | 2/2017 | Aronhalt et al. |
| 9,566,062 | B2 | 2/2017 | Boudreaux |
| 9,566,064 | B2 | 2/2017 | Williams et al. |
| 9,566,065 | B2 | 2/2017 | Knodel |
| 9,566,067 | B2 | 2/2017 | Milliman et al. |
| 9,566,124 | B2 | 2/2017 | Prisco et al. |
| 9,572,552 | B1 | 2/2017 | Bodor et al. |
| 9,572,574 | B2 | 2/2017 | Shelton, IV et al. |
| 9,572,576 | B2 | 2/2017 | Hodgkinson et al. |
| 9,572,577 | B2 | 2/2017 | Lloyd et al. |
| 9,572,592 | B2 | 2/2017 | Price et al. |
| 9,574,644 | B2 | 2/2017 | Parihar |
| 9,579,039 | B2 | 2/2017 | Jansen et al. |
| 9,579,088 | B2 | 2/2017 | Farritor et al. |
| 9,579,143 | B2 | 2/2017 | Ullrich et al. |
| 9,579,158 | B2 | 2/2017 | Brianza et al. |
| D780,803 | S | 3/2017 | Gill et al. |
| D781,879 | S | 3/2017 | Butcher et al. |
| D782,530 | S | 3/2017 | Paek et al. |
| 9,585,550 | B2 | 3/2017 | Abel et al. |
| 9,585,657 | B2 | 3/2017 | Shelton, IV et al. |
| 9,585,658 | B2 | 3/2017 | Shelton, IV |
| 9,585,659 | B2 | 3/2017 | Viola et al. |
| 9,585,660 | B2 | 3/2017 | Laurent et al. |
| 9,585,662 | B2 | 3/2017 | Shelton, IV et al. |
| 9,585,663 | B2 | 3/2017 | Shelton, IV et al. |
| 9,585,672 | B2 | 3/2017 | Bastia |
| 9,590,433 | B2 | 3/2017 | Li |
| 9,592,050 | B2 | 3/2017 | Schmid et al. |
| 9,592,052 | B2 | 3/2017 | Shelton, IV |
| 9,592,053 | B2 | 3/2017 | Shelton, IV et al. |
| 9,592,054 | B2 | 3/2017 | Schmid et al. |
| 9,597,073 | B2 | 3/2017 | Sorrentino et al. |
| 9,597,075 | B2 | 3/2017 | Shelton, IV et al. |
| 9,597,078 | B2 | 3/2017 | Scirica et al. |
| 9,597,080 | B2 | 3/2017 | Milliman et al. |
| 9,597,104 | B2 | 3/2017 | Nicholas et al. |
| 9,597,143 | B2 | 3/2017 | Madan et al. |
| 9,603,595 | B2 | 3/2017 | Shelton, IV et al. |
| 9,603,598 | B2 | 3/2017 | Shelton, IV et al. |
| 9,603,599 | B2 | 3/2017 | Miller et al. |
| 9,603,991 | B2 | 3/2017 | Shelton, IV et al. |
| D783,658 | S | 4/2017 | Hurst et al. |
| 9,610,068 | B2 | 4/2017 | Kappel et al. |
| 9,610,079 | B2 | 4/2017 | Kamei et al. |
| 9,610,080 | B2 | 4/2017 | Whitfield et al. |
| 9,610,412 | B2 | 4/2017 | Zemlok et al. |
| 9,614,258 | B2 | 4/2017 | Takahashi et al. |
| 9,615,826 | B2 | 4/2017 | Shelton, IV et al. |
| 9,622,745 | B2 | 4/2017 | Ingmanson et al. |
| 9,622,746 | B2 | 4/2017 | Simms et al. |
| 9,629,623 | B2 | 4/2017 | Lytle, IV et al. |
| 9,629,626 | B2 | 4/2017 | Soltz et al. |
| 9,629,627 | B2 | 4/2017 | Kostrzewski et al. |
| 9,629,628 | B2 | 4/2017 | Aranyi |
| 9,629,629 | B2 | 4/2017 | Leimbach et al. |
| 9,629,631 | B2 | 4/2017 | Nicholas et al. |
| 9,629,632 | B2 | 4/2017 | Linder et al. |
| 9,629,652 | B2 | 4/2017 | Mumaw et al. |
| 9,629,814 | B2 | 4/2017 | Widenhouse et al. |
| D785,794 | S | 5/2017 | Magno, Jr. |
| D786,280 | S | 5/2017 | Ma |
| D786,896 | S | 5/2017 | Kim et al. |
| D787,547 | S | 5/2017 | Basargin et al. |
| D788,123 | S | 5/2017 | Shan et al. |
| D788,140 | S | 5/2017 | Hemsley et al. |
| 9,636,091 | B2 | 5/2017 | Beardsley et al. |
| 9,636,111 | B2 | 5/2017 | Wenchell |
| 9,636,112 | B2 | 5/2017 | Penna et al. |
| 9,636,113 | B2 | 5/2017 | Wenchell |
| 9,636,850 | B2 | 5/2017 | Stopek et al. |
| 9,641,122 | B2 | 5/2017 | Romanowich et al. |
| 9,642,620 | B2 | 5/2017 | Baxter, III et al. |
| 9,642,642 | B2 | 5/2017 | Lim |
| 9,649,096 | B2 | 5/2017 | Sholev |
| 9,649,110 | B2 | 5/2017 | Parihar et al. |
| 9,649,111 | B2 | 5/2017 | Shelton, IV et al. |
| 9,649,190 | B2 | 5/2017 | Mathies |
| 9,651,032 | B2 | 5/2017 | Weaver et al. |
| 9,655,613 | B2 | 5/2017 | Schaller |
| 9,655,614 | B2 | 5/2017 | Swensgard et al. |
| 9,655,615 | B2 | 5/2017 | Knodel et al. |
| 9,655,616 | B2 | 5/2017 | Aranyi |
| 9,655,624 | B2 | 5/2017 | Shelton, IV et al. |
| 9,661,991 | B2 | 5/2017 | Glossop |
| 9,662,108 | B2 | 5/2017 | Williams |
| 9,662,110 | B2 | 5/2017 | Huang et al. |
| 9,662,111 | B2 | 5/2017 | Holsten et al. |
| 9,662,116 | B2 | 5/2017 | Smith et al. |
| 9,662,130 | B2 | 5/2017 | Bartels et al. |
| 9,662,131 | B2 | 5/2017 | Omori et al. |
| D788,792 | S | 6/2017 | Alessandri et al. |
| D789,384 | S | 6/2017 | Lin et al. |
| D790,570 | S | 6/2017 | Butcher et al. |
| 9,668,728 | B2 | 6/2017 | Williams et al. |
| 9,668,729 | B2 | 6/2017 | Williams et al. |
| 9,668,732 | B2 | 6/2017 | Patel et al. |
| 9,668,733 | B2 | 6/2017 | Williams |
| 9,668,734 | B2 | 6/2017 | Kostrzewski et al. |
| 9,668,735 | B2 | 6/2017 | Beetel |
| 9,675,344 | B2 | 6/2017 | Combrowski et al. |
| 9,675,348 | B2 | 6/2017 | Smith et al. |
| 9,675,351 | B2 | 6/2017 | Hodgkinson et al. |
| 9,675,354 | B2 | 6/2017 | Weir et al. |
| 9,675,355 | B2 | 6/2017 | Shelton, IV et al. |
| 9,675,368 | B2 | 6/2017 | Guo et al. |
| 9,675,372 | B2 | 6/2017 | Laurent et al. |
| 9,675,375 | B2 | 6/2017 | Houser et al. |
| 9,675,405 | B2 | 6/2017 | Trees et al. |
| 9,675,819 | B2 | 6/2017 | Dunbar et al. |
| 9,681,870 | B2 | 6/2017 | Baxter, III et al. |
| 9,681,873 | B2 | 6/2017 | Smith et al. |
| 9,681,884 | B2 | 6/2017 | Clem et al. |
| 9,687,230 | B2 | 6/2017 | Leimbach et al. |
| 9,687,231 | B2 | 6/2017 | Baxter, III et al. |
| 9,687,232 | B2 | 6/2017 | Shelton, IV et al. |
| 9,687,233 | B2 | 6/2017 | Fernandez et al. |
| 9,687,236 | B2 | 6/2017 | Leimbach et al. |
| 9,687,237 | B2 | 6/2017 | Schmid et al. |
| 9,687,253 | B2 | 6/2017 | Detry et al. |
| 9,689,466 | B2 | 6/2017 | Kanai et al. |

(56) References Cited

U.S. PATENT DOCUMENTS 9,690,362 B2 6/2017 Leimbach et al.
9,693,772 B2 7/2017 Ingmanson et al.
9,693,774 B2 7/2017 Gettinger et al.
9,693,775 B2 7/2017 Agarwal et al.
9,693,777 B2 7/2017 Schellin et al.
9,700,309 B2 7/2017 Jaworek et al.
9,700,310 B2 7/2017 Morgan et al.
9,700,312 B2 7/2017 Kostrzewski et al.
9,700,314 B2 7/2017 Marczyk
9,700,315 B2 7/2017 Chen et al.
9,700,317 B2 7/2017 Aronhalt et al.
9,700,318 B2 7/2017 Scirica et al.
9,700,319 B2 7/2017 Motooka et al.
9,700,320 B2 7/2017 Dinardo et al.
9,700,321 B2 7/2017 Shelton, IV et al.
9,700,334 B2 7/2017 Hinman et al.
9,700,381 B2 7/2017 Amat Girbau
9,702,823 B2 7/2017 Maher et al.
9,706,674 B2 7/2017 Collins et al.
9,706,981 B2 7/2017 Nicholas et al.
9,706,991 B2 7/2017 Hess et al.
9,706,993 B2 7/2017 Hessler et al.
9,707,003 B2 7/2017 Hoell, Jr. et al.
9,707,005 B2 7/2017 Strobl et al.
9,707,026 B2 7/2017 Malackowski et al.
9,707,033 B2 7/2017 Parihar et al.
9,707,043 B2 7/2017 Bozung
9,707,684 B2 7/2017 Ruiz Morales et al.
9,713,466 B2 7/2017 Kostrzewski
9,713,468 B2 7/2017 Harris et al.
9,713,470 B2 7/2017 Scirica et al.
9,713,474 B2 7/2017 Lorenz
D795,919 S 8/2017 Bischoff et al.
9,717,497 B2 8/2017 Zerkle et al.
9,717,498 B2 8/2017 Aranyi et al.
9,718,190 B2 8/2017 Larkin et al.
9,722,236 B2 8/2017 Sathrum
9,724,091 B2 8/2017 Shelton, IV et al.
9,724,092 B2 8/2017 Baxter, III et al.
9,724,094 B2 8/2017 Baber et al.
9,724,095 B2 8/2017 Gupta et al.
9,724,096 B2 8/2017 Thompson et al.
9,724,098 B2 8/2017 Baxter, III et al.
9,724,118 B2 8/2017 Schulte et al.
9,724,163 B2 8/2017 Orban
9,730,692 B2 8/2017 Shelton, IV et al.
9,730,695 B2 8/2017 Leimbach et al.
9,730,697 B2 8/2017 Morgan et al.
9,730,717 B2 8/2017 Katsuki et al.
9,730,757 B2 8/2017 Brudniok
9,731,410 B2 8/2017 Hirabayashi et al.
9,733,663 B2 8/2017 Leimbach et al.
9,737,297 B2 8/2017 Racenet et al.
9,737,298 B2 8/2017 Isbell, Jr.
9,737,299 B2 8/2017 Yan
9,737,301 B2 8/2017 Baber et al.
9,737,302 B2 8/2017 Shelton, IV et al.
9,737,303 B2 8/2017 Shelton, IV et al.
9,737,323 B2 8/2017 Thapliyal et al.
9,737,365 B2 8/2017 Hegeman et al.
9,743,927 B2 8/2017 Whitman
9,743,928 B2 8/2017 Shelton, IV et al.
9,743,929 B2 8/2017 Leimbach et al.
D798,319 S 9/2017 Bergstrand et al.
9,750,498 B2 9/2017 Timm et al.
9,750,499 B2 9/2017 Leimbach et al.
9,750,501 B2 9/2017 Shelton, IV et al.
9,750,502 B2 9/2017 Scirica et al.
9,750,503 B2 9/2017 Milliman
9,750,639 B2 9/2017 Barnes et al.
9,751,176 B2 9/2017 McRoberts et al.
9,757,123 B2 9/2017 Giordano et al.
9,757,124 B2 9/2017 Schellin et al.
9,757,126 B2 9/2017 Cappola
9,757,128 B2 9/2017 Baber et al.
9,757,129 B2 9/2017 Williams
9,757,130 B2 9/2017 Shelton, IV
9,763,662 B2 9/2017 Shelton, IV et al.
9,763,668 B2 9/2017 Whitfield et al.
9,770,245 B2 9/2017 Swayze et al.
9,770,274 B2 9/2017 Pool et al.
D798,886 S 10/2017 Prophete et al.
D800,742 S 10/2017 Rhodes
D800,744 S 10/2017 Jitkoff et al.
D800,766 S 10/2017 Park et al.
D800,904 S 10/2017 Leimbach et al.
9,775,608 B2 10/2017 Aronhalt et al.
9,775,609 B2 10/2017 Shelton, IV et al.
9,775,610 B2 10/2017 Nicholas et al.
9,775,611 B2 10/2017 Kostrzewski
9,775,613 B2 10/2017 Shelton, IV et al.
9,775,614 B2 10/2017 Shelton, IV et al.
9,775,618 B2 10/2017 Bettuchi et al.
9,775,635 B2 10/2017 Takei
9,775,678 B2 10/2017 Lohmeier
9,782,169 B2 10/2017 Kimsey et al.
9,782,170 B2 10/2017 Zemlok et al.
9,782,180 B2 10/2017 Smith et al.
9,782,187 B2 10/2017 Zergiebel et al.
9,782,193 B2 10/2017 Thistle
9,782,214 B2 10/2017 Houser et al.
9,788,834 B2 10/2017 Schmid et al.
9,788,835 B2 10/2017 Morgan et al.
9,788,836 B2 10/2017 Overmyer et al.
9,788,847 B2 10/2017 Jinno
9,788,851 B2 10/2017 Dannaher et al.
9,788,902 B2 10/2017 Inoue et al.
9,795,379 B2 10/2017 Leimbach et al.
9,795,380 B2 10/2017 Shelton, IV et al.
9,795,381 B2 10/2017 Shelton, IV
9,795,382 B2 10/2017 Shelton, IV
9,795,383 B2 10/2017 Aldridge et al.
9,795,384 B2 10/2017 Weaner et al.
9,797,486 B2 10/2017 Zergiebel et al.
9,801,626 B2 10/2017 Parihar et al.
9,801,627 B2 10/2017 Harris et al.
9,801,628 B2 10/2017 Harris et al.
9,801,634 B2 10/2017 Shelton, IV et al.
9,801,679 B2 10/2017 Trees et al.
9,802,033 B2 10/2017 Hibner et al.
9,804,618 B2 10/2017 Leimbach et al.
D803,234 S 11/2017 Day et al.
D803,235 S 11/2017 Markson et al.
D803,850 S 11/2017 Chang et al.
9,808,244 B2 11/2017 Leimbach et al.
9,808,246 B2 11/2017 Shelton, IV et al.
9,808,247 B2 11/2017 Shelton, IV et al.
9,808,248 B2 11/2017 Hoffman
9,808,249 B2 11/2017 Shelton, IV
9,814,460 B2 11/2017 Kimsey et al.
9,814,462 B2 11/2017 Woodard, Jr. et al.
9,814,463 B2 11/2017 Williams et al.
9,814,530 B2 11/2017 Weir et al.
9,814,561 B2 11/2017 Forsell
9,815,118 B1 11/2017 Schmitt et al.
9,820,445 B2 11/2017 Simpson et al.
9,820,737 B2 11/2017 Beardsley et al.
9,820,738 B2 11/2017 Lytle, IV et al.
9,820,741 B2 11/2017 Kostrzewski
9,820,768 B2 11/2017 Gee et al.
9,825,455 B2 11/2017 Sandhu et al.
9,826,976 B2 11/2017 Parihar et al.
9,826,977 B2 11/2017 Leimbach et al.
9,826,978 B2 11/2017 Shelton, IV et al.
9,829,698 B2 11/2017 Haraguchi et al.
D806,108 S 12/2017 Day
9,833,235 B2 12/2017 Penna et al.
9,833,236 B2 12/2017 Shelton, IV et al.
9,833,238 B2 12/2017 Baxter, III et al.
9,833,239 B2 12/2017 Yates et al.
9,833,241 B2 12/2017 Huitema et al.
9,833,242 B2 12/2017 Baxter, III et al.
9,839,420 B2 12/2017 Shelton, IV et al.
9,839,421 B2 12/2017 Zerkle et al.

(56) References Cited

U.S. PATENT DOCUMENTS 9,839,422 B2 12/2017 Schellin et al.
9,839,423 B2 12/2017 Vendely et al.
9,839,427 B2 12/2017 Swayze et al.
9,839,428 B2 12/2017 Baxter, III et al.
9,839,429 B2 12/2017 Weisenburgh, II et al.
9,839,480 B2 12/2017 Pribanic et al.
9,839,481 B2 12/2017 Blumenkranz et al.
9,844,313 B2 12/2017 DiCarlo et al.
9,844,368 B2 12/2017 Boudreaux et al.
9,844,369 B2 12/2017 Huitema et al.
9,844,371 B2 12/2017 Scirica et al.
9,844,372 B2 12/2017 Shelton, IV et al.
9,844,373 B2 12/2017 Swayze et al.
9,844,374 B2 12/2017 Lytle, IV et al.
9,844,375 B2 12/2017 Overmyer et al.
9,844,376 B2 12/2017 Baxter, III et al.
9,844,379 B2 12/2017 Shelton, IV et al.
9,848,871 B2 12/2017 Harris et al.
9,848,873 B2 12/2017 Shelton, IV
9,848,875 B2 12/2017 Aronhalt et al.
9,848,877 B2 12/2017 Shelton, IV et al.
9,850,499 B2 12/2017 Baylink et al.
9,850,994 B2 12/2017 Schena
D808,989 S 1/2018 Ayvazian et al.
9,855,039 B2 1/2018 Racenet et al.
9,855,040 B2 1/2018 Kostrzewski
9,855,662 B2 1/2018 Ruiz Morales et al.
9,861,261 B2 1/2018 Shahinian
9,861,359 B2 1/2018 Shelton, IV et al.
9,861,361 B2 1/2018 Aronhalt et al.
9,861,362 B2 1/2018 Whitman et al.
9,861,366 B2 1/2018 Aranyi
9,861,382 B2 1/2018 Smith et al.
9,861,446 B2 1/2018 Lang
9,867,612 B2 1/2018 Parihar et al.
9,867,613 B2 1/2018 Marczyk et al.
9,867,615 B2 1/2018 Fanelli et al.
9,867,617 B2 1/2018 Ma
9,867,618 B2 1/2018 Hall et al.
9,867,620 B2 1/2018 Fischvogt et al.
9,868,198 B2 1/2018 Nicholas et al.
9,872,682 B2 1/2018 Hess et al.
9,872,683 B2 1/2018 Hopkins et al.
9,872,684 B2 1/2018 Hall et al.
9,872,722 B2 1/2018 Lech
9,877,718 B2 1/2018 Weir et al.
9,877,721 B2 1/2018 Schellin et al.
9,877,722 B2 1/2018 Schellin et al.
9,877,723 B2 1/2018 Hall et al.
9,877,776 B2 1/2018 Boudreaux
D810,099 S 2/2018 Riedel
9,883,843 B2 2/2018 Garlow
9,883,860 B2 2/2018 Leimbach et al.
9,883,861 B2 2/2018 Shelton, IV et al.
9,884,456 B2 2/2018 Schellin et al.
9,888,914 B2 2/2018 Martin et al.
9,888,919 B2 2/2018 Leimbach et al.
9,888,921 B2 2/2018 Williams et al.
9,888,924 B2 2/2018 Ebersole et al.
9,889,230 B2 2/2018 Bennett et al.
9,895,147 B2 2/2018 Shelton, IV
9,895,148 B2 2/2018 Shelton, IV et al.
9,895,813 B2 2/2018 Blumenkranz et al.
9,901,339 B2 2/2018 Farascioni
9,901,341 B2 2/2018 Kostrzewski
9,901,342 B2 2/2018 Shelton, IV et al.
9,901,344 B2 2/2018 Moore et al.
9,901,345 B2 2/2018 Moore et al.
9,901,346 B2 2/2018 Moore et al.
9,901,358 B2 2/2018 Faller et al.
9,901,406 B2 2/2018 State et al.
9,901,412 B2 2/2018 Lathrop et al.
D813,899 S 3/2018 Erant et al.
9,907,456 B2 3/2018 Miyoshi
9,907,552 B2 3/2018 Measamer et al.
9,907,553 B2 3/2018 Cole et al.
9,907,600 B2 3/2018 Stulen et al.
9,907,620 B2 3/2018 Shelton, IV et al.
9,913,641 B2 3/2018 Takemoto et al.
9,913,642 B2 3/2018 Leimbach et al.
9,913,644 B2 3/2018 McCuen
9,913,646 B2 3/2018 Shelton, IV
9,913,647 B2 3/2018 Weisenburgh, II et al.
9,913,648 B2 3/2018 Shelton, IV et al.
9,913,694 B2 3/2018 Brisson
9,913,733 B2 3/2018 Piron et al.
9,918,704 B2 3/2018 Shelton, IV et al.
9,918,714 B2 3/2018 Gibbons, Jr.
9,918,715 B2 3/2018 Menn
9,918,716 B2 3/2018 Baxter, III et al.
9,918,717 B2 3/2018 Czernik
9,918,730 B2 3/2018 Trees et al.
9,924,941 B2 3/2018 Burbank
9,924,942 B2 3/2018 Swayze et al.
9,924,943 B2 3/2018 Mohan Pinjala et al.
9,924,944 B2 3/2018 Shelton, IV et al.
9,924,945 B2 3/2018 Zheng et al.
9,924,946 B2 3/2018 Vendely et al.
9,924,947 B2 3/2018 Shelton, IV et al.
9,924,961 B2 3/2018 Shelton, IV et al.
9,931,106 B2 4/2018 Au et al.
9,931,116 B2 4/2018 Racenet et al.
9,931,117 B2 4/2018 Hathaway et al.
9,931,118 B2 4/2018 Shelton, IV et al.
9,931,120 B2 4/2018 Chen et al.
9,936,949 B2 4/2018 Measamer et al.
9,936,950 B2 4/2018 Shelton, IV et al.
9,936,951 B2 4/2018 Hufnagel et al.
9,936,952 B2 4/2018 Demmy
9,936,954 B2 4/2018 Shelton, IV et al.
9,937,626 B2 4/2018 Rockrohr
9,943,309 B2 4/2018 Shelton, IV et al.
9,943,310 B2 4/2018 Harris et al.
9,943,312 B2 4/2018 Posada et al.
9,949,754 B2 4/2018 Newhauser et al.
9,953,193 B2 4/2018 Butler et al.
D819,072 S 5/2018 Clediere
9,955,954 B2 5/2018 Destoumieux et al.
9,955,965 B2 5/2018 Chen et al.
9,955,966 B2 5/2018 Zergiebel
9,956,677 B2 5/2018 Baskar et al.
9,962,129 B2 5/2018 Jerebko et al.
9,962,157 B2 5/2018 Sapre
9,962,158 B2 5/2018 Hall et al.
9,962,159 B2 5/2018 Heinrich et al.
9,962,161 B2 5/2018 Scheib et al.
9,968,354 B2 5/2018 Shelton, IV et al.
9,968,355 B2 5/2018 Shelton, IV et al.
9,968,356 B2 5/2018 Shelton, IV et al.
9,968,397 B2 5/2018 Taylor et al.
9,974,529 B2 5/2018 Shelton, IV et al.
9,974,538 B2 5/2018 Baxter, III et al.
9,974,539 B2 5/2018 Yates et al.
9,974,541 B2 5/2018 Calderoni
9,974,542 B2 5/2018 Hodgkinson
9,980,713 B2 5/2018 Aronhalt et al.
9,980,724 B2 5/2018 Farascioni et al.
9,980,729 B2 5/2018 Moore et al.
9,980,740 B2 5/2018 Krause et al.
9,980,769 B2 5/2018 Trees et al.
D819,680 S 6/2018 Nguyen
D819,682 S 6/2018 Howard et al.
D819,684 S 6/2018 Dart
D820,307 S 6/2018 Jian et al.
D820,867 S 6/2018 Dickens et al.
9,987,000 B2 6/2018 Shelton, IV et al.
9,987,003 B2 6/2018 Timm et al.
9,987,005 B2 6/2018 Viola et al.
9,987,006 B2 6/2018 Morgan et al.
9,987,008 B2 6/2018 Scirica et al.
9,987,095 B2 6/2018 Chowaniec et al.
9,987,097 B2 6/2018 van der Weide et al.
9,987,099 B2 6/2018 Chen et al.
9,993,248 B2 6/2018 Shelton, IV et al.

(56) References Cited

U.S. PATENT DOCUMENTS 9,993,258 B2 6/2018 Shelton, IV et al.
9,993,284 B2 6/2018 Boudreaux
9,999,408 B2 6/2018 Boudreaux et al.
9,999,423 B2 6/2018 Schuckmann et al.
9,999,426 B2 6/2018 Moore et al.
9,999,431 B2 6/2018 Shelton, IV et al.
9,999,472 B2 6/2018 Weir et al.
10,004,497 B2 6/2018 Overmyer et al.
10,004,498 B2 6/2018 Morgan et al.
10,004,500 B2 6/2018 Shelton, IV et al.
10,004,501 B2 6/2018 Shelton, IV et al.
10,004,505 B2 6/2018 Moore et al.
10,004,506 B2 6/2018 Shelton, IV et al.
10,004,552 B1 6/2018 Kleyman et al.
D822,206 S 7/2018 Shelton, IV et al.
D823,858 S 7/2018 Li et al.
10,010,322 B2 7/2018 Shelton, IV et al.
10,010,324 B2 7/2018 Huitema et al.
10,010,395 B2 7/2018 Puckett et al.
10,013,049 B2 7/2018 Leimbach et al.
10,016,199 B2 7/2018 Baber et al.
10,016,656 B2 7/2018 Devor et al.
10,022,120 B2 7/2018 Martin et al.
10,022,123 B2 7/2018 Williams et al.
10,022,125 B2 7/2018 (Prommersberger) Stopek et al.
10,024,407 B2 7/2018 Aranyi et al.
10,028,742 B2 7/2018 Shelton, IV et al.
10,028,743 B2 7/2018 Shelton, IV et al.
10,028,744 B2 7/2018 Shelton, IV et al.
10,028,761 B2 7/2018 Leimbach et al.
10,029,108 B2 7/2018 Powers et al.
10,029,125 B2 7/2018 Shapiro et al.
10,034,344 B2 7/2018 Yoshida
10,034,668 B2 7/2018 Ebner
D826,405 S 8/2018 Shelton, IV et al.
10,039,440 B2 8/2018 Fenech et al.
10,039,529 B2 8/2018 Kerr et al.
10,039,532 B2 8/2018 Srinivas et al.
10,039,545 B2 8/2018 Sadowski et al.
10,041,822 B2 8/2018 Zemlok
10,045,769 B2 8/2018 Aronhalt et al.
10,045,776 B2 8/2018 Shelton, IV et al.
10,045,778 B2 8/2018 Yates et al.
10,045,779 B2 8/2018 Savage et al.
10,045,781 B2 8/2018 Cropper et al.
10,045,782 B2 8/2018 Murthy Aravalli
10,045,869 B2 8/2018 Forsell
10,046,904 B2 8/2018 Evans et al.
10,052,044 B2 8/2018 Shelton, IV et al.
10,052,099 B2 8/2018 Morgan et al.
10,052,100 B2 8/2018 Morgan et al.
10,052,102 B2 8/2018 Baxter, III et al.
10,052,104 B2 8/2018 Shelton, IV et al.
10,052,164 B2 8/2018 Overmyer
10,058,317 B2 8/2018 Fan et al.
10,058,327 B2 8/2018 Weisenburgh, II et al.
10,058,373 B2 8/2018 Takashino et al.
10,058,395 B2 8/2018 Devengenzo et al.
10,058,963 B2 8/2018 Shelton, IV et al.
10,064,620 B2 9/2018 Gettinger et al.
10,064,621 B2 9/2018 Kerr et al.
10,064,622 B2 9/2018 Murthy Aravalli
10,064,624 B2 9/2018 Shelton, IV et al.
10,064,639 B2 9/2018 Ishida et al.
10,064,642 B2 9/2018 Marczyk et al.
10,064,649 B2 9/2018 Golebieski et al.
10,064,688 B2 9/2018 Shelton, IV et al.
10,070,861 B2 9/2018 Spivey et al.
10,070,863 B2 9/2018 Swayze et al.
10,071,452 B2 9/2018 Shelton, IV et al.
10,076,325 B2 9/2018 Huang et al.
10,076,326 B2 9/2018 Yates et al.
10,076,340 B2 9/2018 Belagali et al.
10,080,552 B2 9/2018 Nicholas et al.
D830,550 S 10/2018 Miller et al.
D831,209 S 10/2018 Huitema et al.
D831,676 S 10/2018 Park et al.
D832,301 S 10/2018 Smith
10,085,624 B2 10/2018 Isoda et al.
10,085,643 B2 10/2018 Bandic et al.
10,085,728 B2 10/2018 Jogasaki et al.
10,085,746 B2 10/2018 Fischvogt
10,085,748 B2 10/2018 Morgan et al.
10,085,749 B2 10/2018 Cappola et al.
10,085,750 B2 10/2018 Zergiebel et al.
10,085,751 B2 10/2018 Overmyer et al.
10,085,754 B2 10/2018 Sniffin et al.
10,085,806 B2 10/2018 Hagn et al.
10,092,290 B2 10/2018 Yigit et al.
10,092,292 B2 10/2018 Boudreaux et al.
10,098,635 B2 10/2018 Burbank
10,098,636 B2 10/2018 Shelton, IV et al.
10,098,640 B2 10/2018 Bertolero et al.
10,098,642 B2 10/2018 Baxter, III et al.
10,099,303 B2 10/2018 Yoshida et al.
10,101,861 B2 10/2018 Kiyoto
10,105,126 B2 10/2018 Sauer
10,105,128 B2 10/2018 Cooper et al.
10,105,136 B2 10/2018 Yates et al.
10,105,139 B2 10/2018 Yates et al.
10,105,140 B2 10/2018 Malinouskas et al.
10,105,142 B2 10/2018 Baxter, III et al.
10,105,149 B2 10/2018 Haider et al.
10,106,932 B2 10/2018 Anderson et al.
10,111,657 B2 10/2018 McCuen
10,111,658 B2 10/2018 Chowaniec et al.
10,111,660 B2 10/2018 Hemmann
10,111,665 B2 10/2018 Aranyi et al.
10,111,679 B2 10/2018 Baber et al.
10,111,698 B2 10/2018 Scheib et al.
10,111,702 B2 10/2018 Kostrzewski
D833,608 S 11/2018 Miller et al.
10,117,649 B2 11/2018 Baxter, III et al.
10,117,650 B2 11/2018 Nicholas et al.
10,117,652 B2 11/2018 Schmid et al.
10,117,653 B2 11/2018 Leimbach et al.
10,117,654 B2 11/2018 Ingmanson et al.
10,123,798 B2 11/2018 Baxter, III et al.
10,123,845 B2 11/2018 Yeung
10,124,493 B2 11/2018 Rothfuss et al.
10,130,352 B2 11/2018 Widenhouse et al.
10,130,359 B2 11/2018 Hess et al.
10,130,360 B2 11/2018 Olson et al.
10,130,361 B2 11/2018 Yates et al.
10,130,363 B2 11/2018 Huitema et al.
10,130,366 B2 11/2018 Shelton, IV et al.
10,130,367 B2 11/2018 Cappola et al.
10,130,382 B2 11/2018 Gladstone
10,130,738 B2 11/2018 Shelton, IV et al.
10,130,830 B2 11/2018 Miret Carceller et al.
10,133,248 B2 11/2018 Fitzsimmons et al.
10,135,242 B2 11/2018 Baber et al.
10,136,879 B2 11/2018 Ross et al.
10,136,887 B2 11/2018 Shelton, IV et al.
10,136,889 B2 11/2018 Shelton, IV et al.
10,136,890 B2 11/2018 Shelton, IV et al.
10,136,891 B2 11/2018 Shelton, IV et al.
10,136,949 B2 11/2018 Felder et al.
D835,659 S 12/2018 Anzures et al.
D836,124 S 12/2018 Fan
10,143,474 B2 12/2018 Bucciaglia et al.
10,146,423 B1 12/2018 Reed et al.
10,149,679 B2 12/2018 Shelton, IV et al.
10,149,680 B2 12/2018 Parihar et al.
10,149,682 B2 12/2018 Shelton, IV et al.
10,149,683 B2 12/2018 Smith et al.
10,149,712 B2 12/2018 Manwaring et al.
10,152,789 B2 12/2018 Carnes et al.
10,154,841 B2 12/2018 Weaner et al.
10,159,481 B2 12/2018 Whitman et al.
10,159,482 B2 12/2018 Swayze et al.
10,159,483 B2 12/2018 Beckman et al.
10,159,506 B2 12/2018 Boudreaux et al.
10,161,816 B2 12/2018 Jackson et al.

(56) References Cited

U.S. PATENT DOCUMENTS

| | | | |
|---|---|---|---|
| 10,163,065 | B1 | 12/2018 | Koski et al. |
| 10,163,589 | B2 | 12/2018 | Zergiebel et al. |
| 10,164,466 | B2 | 12/2018 | Calderoni |
| D837,244 | S | 1/2019 | Kuo et al. |
| D837,245 | S | 1/2019 | Kuo et al. |
| 10,166,023 | B2 | 1/2019 | Vendely et al. |
| 10,166,025 | B2 | 1/2019 | Leimbach et al. |
| 10,166,026 | B2 | 1/2019 | Shelton, IV et al. |
| 10,172,611 | B2 | 1/2019 | Shelton, IV et al. |
| 10,172,615 | B2 | 1/2019 | Marczyk et al. |
| 10,172,616 | B2 | 1/2019 | Murray et al. |
| 10,172,617 | B2 | 1/2019 | Shelton, IV et al. |
| 10,172,618 | B2 | 1/2019 | Shelton, IV et al. |
| 10,172,619 | B2 | 1/2019 | Harris et al. |
| 10,172,620 | B2 | 1/2019 | Harris et al. |
| 10,172,636 | B2 | 1/2019 | Stulen et al. |
| 10,172,669 | B2 | 1/2019 | Felder et al. |
| 10,175,127 | B2 | 1/2019 | Collins et al. |
| 10,178,992 | B2 | 1/2019 | Wise et al. |
| 10,180,463 | B2 | 1/2019 | Beckman et al. |
| 10,182,813 | B2 | 1/2019 | Leimbach et al. |
| 10,182,815 | B2 | 1/2019 | Williams et al. |
| 10,182,816 | B2 | 1/2019 | Shelton, IV et al. |
| 10,182,818 | B2 | 1/2019 | Hensel et al. |
| 10,182,819 | B2 | 1/2019 | Shelton, IV |
| 10,182,868 | B2 | 1/2019 | Meier et al. |
| 10,188,385 | B2 | 1/2019 | Kerr et al. |
| 10,188,389 | B2 | 1/2019 | Vendely et al. |
| 10,188,393 | B2 | 1/2019 | Smith et al. |
| 10,188,394 | B2 | 1/2019 | Shelton, IV et al. |
| 10,190,888 | B2 | 1/2019 | Hryb et al. |
| D839,900 | S | 2/2019 | Gan |
| D841,667 | S | 2/2019 | Coren |
| 10,194,801 | B2 | 2/2019 | Elhawary et al. |
| 10,194,904 | B2 | 2/2019 | Viola et al. |
| 10,194,907 | B2 | 2/2019 | Marczyk et al. |
| 10,194,908 | B2 | 2/2019 | Duque et al. |
| 10,194,910 | B2 | 2/2019 | Shelton, IV et al. |
| 10,194,911 | B2 | 2/2019 | Miller et al. |
| 10,194,912 | B2 | 2/2019 | Scheib et al. |
| 10,194,913 | B2 | 2/2019 | Nalagatla et al. |
| 10,194,976 | B2 | 2/2019 | Boudreaux |
| 10,194,981 | B2 | 2/2019 | Margallo Balbas et al. |
| 10,194,992 | B2 | 2/2019 | Robinson |
| 10,201,348 | B2 | 2/2019 | Scheib et al. |
| 10,201,349 | B2 | 2/2019 | Leimbach et al. |
| 10,201,363 | B2 | 2/2019 | Shelton, IV |
| 10,201,364 | B2 | 2/2019 | Leimbach et al. |
| 10,201,365 | B2 | 2/2019 | Boudreaux et al. |
| 10,201,381 | B2 | 2/2019 | Zergiebel et al. |
| 10,206,605 | B2 | 2/2019 | Shelton, IV et al. |
| 10,206,676 | B2 | 2/2019 | Shelton, IV |
| 10,206,677 | B2 | 2/2019 | Harris et al. |
| 10,206,678 | B2 | 2/2019 | Shelton, IV et al. |
| 10,206,748 | B2 | 2/2019 | Burbank |
| 10,210,244 | B1 | 2/2019 | Branavan et al. |
| 10,211,586 | B2 | 2/2019 | Adams et al. |
| 10,213,198 | B2 | 2/2019 | Aronhalt et al. |
| 10,213,201 | B2 | 2/2019 | Shelton, IV et al. |
| 10,213,202 | B2 | 2/2019 | Flanagan et al. |
| 10,213,203 | B2 | 2/2019 | Swayze et al. |
| 10,213,204 | B2 | 2/2019 | Aranyi et al. |
| 10,213,262 | B2 | 2/2019 | Shelton, IV et al. |
| D842,328 | S | 3/2019 | Jian et al. |
| 10,219,811 | B2 | 3/2019 | Haider et al. |
| 10,219,832 | B2 | 3/2019 | Bagwell et al. |
| 10,220,522 | B2 | 3/2019 | Rockrohr |
| 10,226,239 | B2 | 3/2019 | Nicholas et al. |
| 10,226,249 | B2 | 3/2019 | Jaworek et al. |
| 10,226,250 | B2 | 3/2019 | Beckman et al. |
| 10,226,251 | B2 | 3/2019 | Scheib et al. |
| 10,226,274 | B2 | 3/2019 | Worrell et al. |
| 10,231,634 | B2 | 3/2019 | Zand et al. |
| 10,231,653 | B2 | 3/2019 | Bohm et al. |
| 10,231,734 | B2 | 3/2019 | Thompson et al. |
| 10,231,794 | B2 | 3/2019 | Shelton, IV et al. |
| 10,238,385 | B2 | 3/2019 | Yates et al. |
| 10,238,386 | B2 | 3/2019 | Overmyer et al. |
| 10,238,387 | B2 | 3/2019 | Yates et al. |
| 10,238,389 | B2 | 3/2019 | Yates et al. |
| 10,238,390 | B2 | 3/2019 | Harris et al. |
| 10,238,391 | B2 | 3/2019 | Leimbach et al. |
| D844,666 | S | 4/2019 | Espeleta et al. |
| D844,667 | S | 4/2019 | Espeleta et al. |
| D845,342 | S | 4/2019 | Espeleta et al. |
| D847,199 | S | 4/2019 | Whitmore |
| 10,244,991 | B2 | 4/2019 | Shademan et al. |
| 10,245,027 | B2 | 4/2019 | Shelton, IV et al. |
| 10,245,028 | B2 | 4/2019 | Shelton, IV et al. |
| 10,245,029 | B2 | 4/2019 | Hunter et al. |
| 10,245,030 | B2 | 4/2019 | Hunter et al. |
| 10,245,032 | B2 | 4/2019 | Shelton, IV |
| 10,245,033 | B2 | 4/2019 | Overmyer et al. |
| 10,245,034 | B2 | 4/2019 | Shelton, IV et al. |
| 10,245,035 | B2 | 4/2019 | Swayze et al. |
| 10,245,038 | B2 | 4/2019 | Hopkins et al. |
| 10,245,058 | B2 | 4/2019 | Omori et al. |
| 10,251,645 | B2 | 4/2019 | Kostrzewski |
| 10,251,648 | B2 | 4/2019 | Harris et al. |
| 10,251,649 | B2 | 4/2019 | Schellin et al. |
| 10,251,725 | B2 | 4/2019 | Valentine et al. |
| 10,258,322 | B2 | 4/2019 | Fanton et al. |
| 10,258,330 | B2 | 4/2019 | Shelton, IV et al. |
| 10,258,331 | B2 | 4/2019 | Shelton, IV et al. |
| 10,258,332 | B2 | 4/2019 | Schmid et al. |
| 10,258,333 | B2 | 4/2019 | Shelton, IV et al. |
| 10,258,336 | B2 | 4/2019 | Baxter, III et al. |
| 10,258,363 | B2 | 4/2019 | Worrell et al. |
| 10,258,418 | B2 | 4/2019 | Shelton, IV et al. |
| 10,264,797 | B2 | 4/2019 | Zhang et al. |
| 10,265,065 | B2 | 4/2019 | Shelton, IV et al. |
| 10,265,067 | B2 | 4/2019 | Yates et al. |
| 10,265,068 | B2 | 4/2019 | Harris et al. |
| 10,265,072 | B2 | 4/2019 | Shelton, IV et al. |
| 10,265,073 | B2 | 4/2019 | Scheib et al. |
| 10,265,074 | B2 | 4/2019 | Shelton, IV et al. |
| 10,265,090 | B2 | 4/2019 | Ingmanson et al. |
| 10,271,840 | B2 | 4/2019 | Sapre |
| 10,271,844 | B2 | 4/2019 | Valentine et al. |
| 10,271,845 | B2 | 4/2019 | Shelton, IV |
| 10,271,846 | B2 | 4/2019 | Shelton, IV et al. |
| 10,271,847 | B2 | 4/2019 | Racenet et al. |
| 10,271,849 | B2 | 4/2019 | Vendely et al. |
| 10,271,851 | B2 | 4/2019 | Shelton, IV et al. |
| D847,989 | S | 5/2019 | Shelton, IV et al. |
| D848,473 | S | 5/2019 | Zhu et al. |
| D849,046 | S | 5/2019 | Kuo et al. |
| 10,278,696 | B2 | 5/2019 | Gurumurthy et al. |
| 10,278,697 | B2 | 5/2019 | Shelton, IV et al. |
| 10,278,702 | B2 | 5/2019 | Shelton, IV et al. |
| 10,278,703 | B2 | 5/2019 | Nativ et al. |
| 10,278,707 | B2 | 5/2019 | Thompson et al. |
| 10,278,722 | B2 | 5/2019 | Shelton, IV et al. |
| 10,278,780 | B2 | 5/2019 | Shelton, IV |
| 10,285,694 | B2 | 5/2019 | Viola et al. |
| 10,285,695 | B2 | 5/2019 | Jaworek et al. |
| 10,285,696 | B2 | 5/2019 | Marczyk |
| 10,285,699 | B2 | 5/2019 | Vendely et al. |
| 10,285,700 | B2 | 5/2019 | Scheib |
| 10,285,705 | B2 | 5/2019 | Shelton, IV et al. |
| 10,285,724 | B2 | 5/2019 | Faller et al. |
| 10,285,750 | B2 | 5/2019 | Coulson et al. |
| 10,292,701 | B2 | 5/2019 | Scheib et al. |
| 10,292,704 | B2 | 5/2019 | Harris et al. |
| 10,292,707 | B2 | 5/2019 | Shelton, IV et al. |
| 10,293,100 | B2 | 5/2019 | Shelton, IV et al. |
| 10,293,553 | B2 | 5/2019 | Racenet et al. |
| 10,299,787 | B2 | 5/2019 | Shelton, IV |
| 10,299,788 | B2 | 5/2019 | Heinrich et al. |
| 10,299,789 | B2 | 5/2019 | Marczyk et al. |
| 10,299,790 | B2 | 5/2019 | Beardsley |
| 10,299,792 | B2 | 5/2019 | Huitema et al. |
| 10,299,817 | B2 | 5/2019 | Shelton, IV et al. |
| 10,299,818 | B2 | 5/2019 | Riva |

(56) References Cited

U.S. PATENT DOCUMENTS

| | | | |
|---|---|---|---|
| 10,299,878 | B2 | 5/2019 | Shelton, IV et al. |
| 10,303,851 | B2 | 5/2019 | Nguyen et al. |
| D850,617 | S | 6/2019 | Shelton, IV et al. |
| D851,676 | S | 6/2019 | Foss et al. |
| D851,762 | S | 6/2019 | Shelton, IV et al. |
| 10,307,159 | B2 | 6/2019 | Harris et al. |
| 10,307,160 | B2 | 6/2019 | Vendely et al. |
| 10,307,161 | B2 | 6/2019 | Jankowski |
| 10,307,163 | B2 | 6/2019 | Moore et al. |
| 10,307,170 | B2 | 6/2019 | Parfett et al. |
| 10,307,202 | B2 | 6/2019 | Smith et al. |
| 10,314,559 | B2 | 6/2019 | Razzaque et al. |
| 10,314,577 | B2 | 6/2019 | Laurent et al. |
| 10,314,578 | B2 | 6/2019 | Leimbach et al. |
| 10,314,579 | B2 | 6/2019 | Chowaniec et al. |
| 10,314,580 | B2 | 6/2019 | Scheib et al. |
| 10,314,582 | B2 | 6/2019 | Shelton, IV et al. |
| 10,314,584 | B2 | 6/2019 | Scirica et al. |
| 10,314,587 | B2 | 6/2019 | Harris et al. |
| 10,314,588 | B2 | 6/2019 | Turner et al. |
| 10,314,589 | B2 | 6/2019 | Shelton, IV et al. |
| 10,314,590 | B2 | 6/2019 | Shelton, IV et al. |
| 10,315,566 | B2 | 6/2019 | Choi et al. |
| 10,321,907 | B2 | 6/2019 | Shelton, IV et al. |
| 10,321,909 | B2 | 6/2019 | Shelton, IV et al. |
| 10,321,927 | B2 | 6/2019 | Hinman |
| 10,327,743 | B2 | 6/2019 | St. Goar et al. |
| 10,327,764 | B2 | 6/2019 | Harris et al. |
| 10,327,765 | B2 | 6/2019 | Timm et al. |
| 10,327,767 | B2 | 6/2019 | Shelton, IV et al. |
| 10,327,769 | B2 | 6/2019 | Overmyer et al. |
| 10,327,776 | B2 | 6/2019 | Harris et al. |
| 10,327,777 | B2 | 6/2019 | Harris et al. |
| D854,032 | S | 7/2019 | Jones et al. |
| D854,151 | S | 7/2019 | Shelton, IV et al. |
| 10,335,144 | B2 | 7/2019 | Shelton, IV et al. |
| 10,335,145 | B2 | 7/2019 | Harris et al. |
| 10,335,147 | B2 | 7/2019 | Rector et al. |
| 10,335,148 | B2 | 7/2019 | Shelton, IV et al. |
| 10,335,149 | B2 | 7/2019 | Baxter, III et al. |
| 10,335,150 | B2 | 7/2019 | Shelton, IV |
| 10,335,151 | B2 | 7/2019 | Shelton, IV et al. |
| 10,337,148 | B2 | 7/2019 | Rouse et al. |
| 10,342,533 | B2 | 7/2019 | Shelton, IV et al. |
| 10,342,535 | B2 | 7/2019 | Scheib et al. |
| 10,342,541 | B2 | 7/2019 | Shelton, IV et al. |
| 10,342,543 | B2 | 7/2019 | Shelton, IV et al. |
| 10,342,623 | B2 | 7/2019 | Huelman et al. |
| 10,349,937 | B2 | 7/2019 | Williams |
| 10,349,939 | B2 | 7/2019 | Shelton, IV et al. |
| 10,349,941 | B2 | 7/2019 | Marczyk et al. |
| 10,349,963 | B2 | 7/2019 | Fiksen et al. |
| 10,350,016 | B2 | 7/2019 | Burbank et al. |
| 10,357,246 | B2 | 7/2019 | Shelton, IV et al. |
| 10,357,247 | B2 | 7/2019 | Shelton, IV et al. |
| 10,357,248 | B2 | 7/2019 | Dalessandro et al. |
| 10,357,252 | B2 | 7/2019 | Harris et al. |
| 10,363,031 | B2 | 7/2019 | Alexander, III et al. |
| 10,363,033 | B2 | 7/2019 | Timm et al. |
| 10,363,036 | B2 | 7/2019 | Yates et al. |
| 10,363,037 | B2 | 7/2019 | Aronhalt et al. |
| D855,634 | S | 8/2019 | Kim |
| D856,359 | S | 8/2019 | Huang et al. |
| 10,368,838 | B2 | 8/2019 | Williams et al. |
| 10,368,861 | B2 | 8/2019 | Baxter, III et al. |
| 10,368,863 | B2 | 8/2019 | Timm et al. |
| 10,368,864 | B2 | 8/2019 | Harris et al. |
| 10,368,865 | B2 | 8/2019 | Harris et al. |
| 10,368,866 | B2 | 8/2019 | Wang et al. |
| 10,368,867 | B2 | 8/2019 | Harris et al. |
| 10,368,892 | B2 | 8/2019 | Stulen et al. |
| 10,374,544 | B2 | 8/2019 | Yokoyama et al. |
| 10,376,263 | B2 | 8/2019 | Morgan et al. |
| 10,383,626 | B2 | 8/2019 | Soltz |
| 10,383,628 | B2 | 8/2019 | Kang et al. |
| 10,383,629 | B2 | 8/2019 | Ross et al. |
| 10,383,630 | B2 | 8/2019 | Shelton, IV et al. |
| 10,383,631 | B2 | 8/2019 | Collings et al. |
| 10,383,633 | B2 | 8/2019 | Shelton, IV et al. |
| 10,383,634 | B2 | 8/2019 | Shelton, IV et al. |
| 10,390,823 | B2 | 8/2019 | Shelton, IV et al. |
| 10,390,825 | B2 | 8/2019 | Shelton, IV et al. |
| 10,390,828 | B2 | 8/2019 | Vendely et al. |
| 10,390,829 | B2 | 8/2019 | Eckert et al. |
| 10,390,830 | B2 | 8/2019 | Schulz |
| 10,390,841 | B2 | 8/2019 | Shelton, IV et al. |
| 10,390,897 | B2 | 8/2019 | Kostrzewski |
| D859,466 | S | 9/2019 | Okada et al. |
| D860,219 | S | 9/2019 | Rasmussen et al. |
| D861,035 | S | 9/2019 | Park et al. |
| 10,398,433 | B2 | 9/2019 | Boudreaux et al. |
| 10,398,434 | B2 | 9/2019 | Shelton, IV et al. |
| 10,398,436 | B2 | 9/2019 | Shelton, IV et al. |
| 10,398,460 | B2 | 9/2019 | Overmyer |
| 10,404,136 | B2 | 9/2019 | Oktavec et al. |
| 10,405,854 | B2 | 9/2019 | Schmid et al. |
| 10,405,857 | B2 | 9/2019 | Shelton, IV et al. |
| 10,405,859 | B2 | 9/2019 | Harris et al. |
| 10,405,863 | B2 | 9/2019 | Wise et al. |
| 10,405,914 | B2 | 9/2019 | Manwaring et al. |
| 10,405,932 | B2 | 9/2019 | Overmyer |
| 10,405,937 | B2 | 9/2019 | Black et al. |
| 10,413,155 | B2 | 9/2019 | Inoue |
| 10,413,291 | B2 | 9/2019 | Worthington et al. |
| 10,413,293 | B2 | 9/2019 | Shelton, IV et al. |
| 10,413,294 | B2 | 9/2019 | Shelton, IV et al. |
| 10,413,297 | B2 | 9/2019 | Harris et al. |
| 10,413,370 | B2 | 9/2019 | Yates et al. |
| 10,413,373 | B2 | 9/2019 | Yates et al. |
| 10,420,548 | B2 | 9/2019 | Whitman et al. |
| 10,420,549 | B2 | 9/2019 | Yates et al. |
| 10,420,550 | B2 | 9/2019 | Shelton, IV |
| 10,420,551 | B2 | 9/2019 | Calderoni |
| 10,420,552 | B2 | 9/2019 | Shelton, IV et al. |
| 10,420,553 | B2 | 9/2019 | Shelton, IV et al. |
| 10,420,554 | B2 | 9/2019 | Collings et al. |
| 10,420,555 | B2 | 9/2019 | Shelton, IV et al. |
| 10,420,558 | B2 | 9/2019 | Nalagatla et al. |
| 10,420,559 | B2 | 9/2019 | Marczyk et al. |
| 10,420,560 | B2 | 9/2019 | Shelton, IV et al. |
| 10,420,561 | B2 | 9/2019 | Shelton, IV et al. |
| 10,420,577 | B2 | 9/2019 | Chowaniec et al. |
| D861,707 | S | 10/2019 | Yang |
| D862,518 | S | 10/2019 | Niven et al. |
| D863,343 | S | 10/2019 | Mazlish et al. |
| D864,388 | S | 10/2019 | Barber |
| D865,174 | S | 10/2019 | Auld et al. |
| D865,175 | S | 10/2019 | Widenhouse et al. |
| 10,426,463 | B2 | 10/2019 | Shelton, IV et al. |
| 10,426,466 | B2 | 10/2019 | Contini et al. |
| 10,426,467 | B2 | 10/2019 | Miller et al. |
| 10,426,468 | B2 | 10/2019 | Contini et al. |
| 10,426,469 | B2 | 10/2019 | Shelton, IV et al. |
| 10,426,471 | B2 | 10/2019 | Shelton, IV et al. |
| 10,426,476 | B2 | 10/2019 | Harris et al. |
| 10,426,477 | B2 | 10/2019 | Harris et al. |
| 10,426,478 | B2 | 10/2019 | Shelton, IV et al. |
| 10,426,481 | B2 | 10/2019 | Aronhalt et al. |
| 10,426,555 | B2 | 10/2019 | Crowley et al. |
| 10,433,837 | B2 | 10/2019 | Worthington et al. |
| 10,433,839 | B2 | 10/2019 | Scheib et al. |
| 10,433,840 | B2 | 10/2019 | Shelton, IV et al. |
| 10,433,842 | B2 | 10/2019 | Amariglio et al. |
| 10,433,844 | B2 | 10/2019 | Shelton, IV et al. |
| 10,433,845 | B2 | 10/2019 | Baxter, III et al. |
| 10,433,846 | B2 | 10/2019 | Vendely et al. |
| 10,433,849 | B2 | 10/2019 | Shelton, IV et al. |
| 10,433,918 | B2 | 10/2019 | Shelton, IV et al. |
| 10,441,279 | B2 | 10/2019 | Shelton, IV et al. |
| 10,441,280 | B2 | 10/2019 | Timm et al. |
| 10,441,281 | B2 | 10/2019 | Shelton, IV et al. |
| 10,441,285 | B2 | 10/2019 | Shelton, IV et al. |
| 10,441,286 | B2 | 10/2019 | Shelton, IV et al. |
| 10,441,345 | B2 | 10/2019 | Aldridge et al. |

(56) References Cited

U.S. PATENT DOCUMENTS

| | | | |
|---|---|---|---|
| 10,441,369 | B2 | 10/2019 | Shelton, IV et al. |
| 10,448,948 | B2 | 10/2019 | Shelton, IV et al. |
| 10,448,950 | B2 | 10/2019 | Shelton, IV et al. |
| 10,448,952 | B2 | 10/2019 | Shelton, IV et al. |
| 10,456,122 | B2 | 10/2019 | Koltz et al. |
| 10,456,132 | B2 | 10/2019 | Gettinger et al. |
| 10,456,133 | B2 | 10/2019 | Yates et al. |
| 10,456,137 | B2 | 10/2019 | Vendely et al. |
| 10,456,140 | B2 | 10/2019 | Shelton, IV et al. |
| D865,796 | S | 11/2019 | Xu et al. |
| 10,463,367 | B2 | 11/2019 | Kostrzewski et al. |
| 10,463,369 | B2 | 11/2019 | Shelton, IV et al. |
| 10,463,370 | B2 | 11/2019 | Yates et al. |
| 10,463,371 | B2 | 11/2019 | Kostrzewski |
| 10,463,372 | B2 | 11/2019 | Shelton, IV et al. |
| 10,463,373 | B2 | 11/2019 | Mozdzierz et al. |
| 10,463,382 | B2 | 11/2019 | Ingmanson et al. |
| 10,463,383 | B2 | 11/2019 | Shelton, IV et al. |
| 10,463,384 | B2 | 11/2019 | Shelton, IV et al. |
| 10,470,762 | B2 | 11/2019 | Leimbach et al. |
| 10,470,763 | B2 | 11/2019 | Yates et al. |
| 10,470,764 | B2 | 11/2019 | Baxter, III et al. |
| 10,470,767 | B2 | 11/2019 | Gleiman et al. |
| 10,470,768 | B2 | 11/2019 | Harris et al. |
| 10,470,769 | B2 | 11/2019 | Shelton, IV et al. |
| 10,471,282 | B2 | 11/2019 | Kirk et al. |
| 10,471,576 | B2 | 11/2019 | Totsu |
| 10,471,607 | B2 | 11/2019 | Butt et al. |
| 10,478,181 | B2 | 11/2019 | Shelton, IV et al. |
| 10,478,182 | B2 | 11/2019 | Taylor |
| 10,478,185 | B2 | 11/2019 | Nicholas |
| 10,478,187 | B2 | 11/2019 | Shelton, IV et al. |
| 10,478,188 | B2 | 11/2019 | Harris et al. |
| 10,478,189 | B2 | 11/2019 | Bear et al. |
| 10,478,190 | B2 | 11/2019 | Miller et al. |
| 10,478,207 | B2 | 11/2019 | Lathrop |
| 10,482,292 | B2 | 11/2019 | Clouser et al. |
| 10,485,536 | B2 | 11/2019 | Ming et al. |
| 10,485,537 | B2 | 11/2019 | Yates et al. |
| 10,485,539 | B2 | 11/2019 | Shelton, IV et al. |
| 10,485,541 | B2 | 11/2019 | Shelton, IV et al. |
| 10,485,542 | B2 | 11/2019 | Shelton, IV et al. |
| 10,485,543 | B2 | 11/2019 | Shelton, IV et al. |
| 10,485,546 | B2 | 11/2019 | Shelton, IV et al. |
| 10,485,547 | B2 | 11/2019 | Shelton, IV et al. |
| D869,655 | S | 12/2019 | Shelton, IV et al. |
| D870,742 | S | 12/2019 | Cornell |
| 10,492,783 | B2 | 12/2019 | Shelton, IV et al. |
| 10,492,785 | B2 | 12/2019 | Overmyer et al. |
| 10,492,787 | B2 | 12/2019 | Smith et al. |
| 10,492,814 | B2 | 12/2019 | Snow et al. |
| 10,492,847 | B2 | 12/2019 | Godara et al. |
| 10,492,851 | B2 | 12/2019 | Hughett, Sr. et al. |
| 10,498,269 | B2 | 12/2019 | Zemlok et al. |
| 10,499,890 | B2 | 12/2019 | Shelton, IV et al. |
| 10,499,914 | B2 | 12/2019 | Huang et al. |
| 10,499,917 | B2 | 12/2019 | Scheib et al. |
| 10,499,918 | B2 | 12/2019 | Schellin et al. |
| 10,500,000 | B2 | 12/2019 | Swayze et al. |
| 10,500,004 | B2 | 12/2019 | Hanuschik et al. |
| 10,500,309 | B2 | 12/2019 | Shah et al. |
| 10,507,034 | B2 | 12/2019 | Timm |
| 10,508,720 | B2 | 12/2019 | Nicholas |
| 10,512,461 | B2 | 12/2019 | Gupta et al. |
| 10,512,462 | B2 | 12/2019 | Felder et al. |
| 10,512,464 | B2 | 12/2019 | Park et al. |
| 10,517,590 | B2 | 12/2019 | Giordano et al. |
| 10,517,592 | B2 | 12/2019 | Shelton, IV et al. |
| 10,517,594 | B2 | 12/2019 | Shelton, IV et al. |
| 10,517,595 | B2 | 12/2019 | Hunter et al. |
| 10,517,596 | B2 | 12/2019 | Hunter et al. |
| 10,517,599 | B2 | 12/2019 | Baxter, III et al. |
| 10,517,682 | B2 | 12/2019 | Giordano et al. |
| 10,524,784 | B2 | 1/2020 | Kostrzewski |
| 10,524,787 | B2 | 1/2020 | Shelton, IV et al. |
| 10,524,788 | B2 | 1/2020 | Vendely et al. |
| 10,524,789 | B2 | 1/2020 | Swayze et al. |
| 10,524,790 | B2 | 1/2020 | Shelton, IV et al. |
| 10,524,795 | B2 | 1/2020 | Nalagatla et al. |
| 10,524,870 | B2 | 1/2020 | Saraliev et al. |
| 10,531,874 | B2 | 1/2020 | Morgan et al. |
| 10,531,887 | B2 | 1/2020 | Shelton, IV et al. |
| 10,537,323 | B2 | 1/2020 | Racenet et al. |
| 10,537,324 | B2 | 1/2020 | Shelton, IV et al. |
| 10,537,325 | B2 | 1/2020 | Bakos et al. |
| 10,537,351 | B2 | 1/2020 | Shelton, IV et al. |
| 10,542,908 | B2 | 1/2020 | Mei et al. |
| 10,542,974 | B2 | 1/2020 | Yates et al. |
| 10,542,976 | B2 | 1/2020 | Calderoni et al. |
| 10,542,978 | B2 | 1/2020 | Chowaniec et al. |
| 10,542,979 | B2 | 1/2020 | Shelton, IV et al. |
| 10,542,982 | B2 | 1/2020 | Beckman et al. |
| 10,542,985 | B2 | 1/2020 | Zhan et al. |
| 10,542,988 | B2 | 1/2020 | Schellin et al. |
| 10,542,991 | B2 | 1/2020 | Shelton, IV et al. |
| D876,478 | S | 2/2020 | Sakata et al. |
| 10,548,504 | B2 | 2/2020 | Shelton, IV et al. |
| 10,548,593 | B2 | 2/2020 | Shelton, IV et al. |
| 10,548,600 | B2 | 2/2020 | Shelton, IV et al. |
| 10,548,673 | B2 | 2/2020 | Harris et al. |
| 10,561,412 | B2 | 2/2020 | Bookbinder et al. |
| 10,561,418 | B2 | 2/2020 | Richard et al. |
| 10,561,419 | B2 | 2/2020 | Beardsley |
| 10,561,420 | B2 | 2/2020 | Harris et al. |
| 10,561,422 | B2 | 2/2020 | Schellin et al. |
| 10,561,432 | B2 | 2/2020 | Estrella et al. |
| 10,561,474 | B2 | 2/2020 | Adams et al. |
| 10,562,160 | B2 | 2/2020 | Iwata et al. |
| 10,568,493 | B2 | 2/2020 | Blase et al. |
| 10,568,621 | B2 | 2/2020 | Shelton, IV et al. |
| 10,568,624 | B2 | 2/2020 | Shelton, IV et al. |
| 10,568,625 | B2 | 2/2020 | Harris et al. |
| 10,568,626 | B2 | 2/2020 | Shelton, IV et al. |
| 10,568,629 | B2 | 2/2020 | Shelton, IV et al. |
| 10,568,632 | B2 | 2/2020 | Miller et al. |
| 10,568,652 | B2 | 2/2020 | Hess et al. |
| 10,569,071 | B2 | 2/2020 | Harris et al. |
| D879,808 | S | 3/2020 | Harris et al. |
| D879,809 | S | 3/2020 | Harris et al. |
| 10,575,868 | B2 | 3/2020 | Hall et al. |
| 10,580,320 | B2 | 3/2020 | Kamiguchi et al. |
| 10,582,928 | B2 | 3/2020 | Hunter et al. |
| 10,588,231 | B2 | 3/2020 | Sgroi, Jr. et al. |
| 10,588,623 | B2 | 3/2020 | Schmid et al. |
| 10,588,625 | B2 | 3/2020 | Weaner et al. |
| 10,588,626 | B2 | 3/2020 | Overmyer et al. |
| 10,588,629 | B2 | 3/2020 | Malinouskas et al. |
| 10,588,630 | B2 | 3/2020 | Shelton, IV et al. |
| 10,588,631 | B2 | 3/2020 | Shelton, IV et al. |
| 10,588,632 | B2 | 3/2020 | Shelton, IV et al. |
| 10,588,633 | B2 | 3/2020 | Shelton, IV et al. |
| 10,589,410 | B2 | 3/2020 | Aho |
| 10,595,835 | B2 | 3/2020 | Kerr et al. |
| 10,595,862 | B2 | 3/2020 | Shelton, IV et al. |
| 10,595,882 | B2 | 3/2020 | Parfett et al. |
| 10,595,887 | B2 | 3/2020 | Shelton, IV et al. |
| 10,595,929 | B2 | 3/2020 | Boudreaux et al. |
| 10,603,036 | B2 | 3/2020 | Hunter et al. |
| 10,603,039 | B2 | 3/2020 | Vendely et al. |
| 10,603,041 | B2 | 3/2020 | Miller et al. |
| 10,603,117 | B2 | 3/2020 | Schings et al. |
| 10,603,128 | B2 | 3/2020 | Zergiebel et al. |
| D882,783 | S | 4/2020 | Shelton, IV et al. |
| 10,610,224 | B2 | 4/2020 | Shelton, IV et al. |
| 10,610,225 | B2 | 4/2020 | Reed et al. |
| 10,610,236 | B2 | 4/2020 | Baril |
| 10,610,313 | B2 | 4/2020 | Bailey et al. |
| 10,610,346 | B2 | 4/2020 | Schwartz |
| 10,614,184 | B2 | 4/2020 | Solki |
| 10,617,411 | B2 | 4/2020 | Williams |
| 10,617,412 | B2 | 4/2020 | Shelton, IV et al. |
| 10,617,413 | B2 | 4/2020 | Shelton, IV et al. |
| 10,617,414 | B2 | 4/2020 | Shelton, IV et al. |
| 10,617,416 | B2 | 4/2020 | Leimbach et al. |

(56) References Cited

U.S. PATENT DOCUMENTS

| | | | |
|---|---|---|---|
| 10,617,417 | B2 | 4/2020 | Baxter, III et al. |
| 10,617,418 | B2 | 4/2020 | Barton et al. |
| 10,617,420 | B2 | 4/2020 | Shelton, IV et al. |
| 10,617,438 | B2 | 4/2020 | O'Keefe et al. |
| 10,624,616 | B2 | 4/2020 | Mukherjee et al. |
| 10,624,630 | B2 | 4/2020 | Deville et al. |
| 10,624,633 | B2 | 4/2020 | Shelton, IV et al. |
| 10,624,634 | B2 | 4/2020 | Shelton, IV et al. |
| 10,624,635 | B2 | 4/2020 | Harris et al. |
| 10,624,709 | B2 | 4/2020 | Remm |
| 10,624,861 | B2 | 4/2020 | Widenhouse et al. |
| 10,625,062 | B2 | 4/2020 | Matlock et al. |
| 10,631,857 | B2 | 4/2020 | Kostrzewski |
| 10,631,858 | B2 | 4/2020 | Burbank |
| 10,631,859 | B2 | 4/2020 | Shelton, IV et al. |
| 10,631,860 | B2 | 4/2020 | Bakos et al. |
| 10,636,104 | B2 | 4/2020 | Mazar et al. |
| 10,639,018 | B2 | 5/2020 | Shelton, IV et al. |
| 10,639,034 | B2 | 5/2020 | Harris et al. |
| 10,639,035 | B2 | 5/2020 | Shelton, IV et al. |
| 10,639,036 | B2 | 5/2020 | Yates et al. |
| 10,639,037 | B2 | 5/2020 | Shelton, IV et al. |
| 10,639,038 | B2 | 5/2020 | Scott et al. |
| 10,639,089 | B2 | 5/2020 | Manwaring et al. |
| 10,639,115 | B2 | 5/2020 | Shelton, IV et al. |
| 10,642,633 | B1 | 5/2020 | Chopra et al. |
| 10,645,905 | B2 | 5/2020 | Gandola et al. |
| 10,646,220 | B2 | 5/2020 | Shelton, IV et al. |
| 10,646,292 | B2 | 5/2020 | Solomon et al. |
| 10,653,413 | B2 | 5/2020 | Worthington et al. |
| 10,653,417 | B2 | 5/2020 | Shelton, IV et al. |
| 10,653,435 | B2 | 5/2020 | Shelton, IV et al. |
| 10,660,640 | B2 | 5/2020 | Yates et al. |
| 10,667,408 | B2 | 5/2020 | Sgroi, Jr. et al. |
| D888,953 | S | 6/2020 | Baxter, III et al. |
| 10,667,808 | B2 | 6/2020 | Baxter, III et al. |
| 10,667,809 | B2 | 6/2020 | Bakos et al. |
| 10,667,810 | B2 | 6/2020 | Shelton, IV et al. |
| 10,667,811 | B2 | 6/2020 | Harris et al. |
| 10,667,818 | B2 | 6/2020 | McLain et al. |
| 10,674,895 | B2 | 6/2020 | Yeung et al. |
| 10,675,021 | B2 | 6/2020 | Harris et al. |
| 10,675,024 | B2 | 6/2020 | Shelton, IV et al. |
| 10,675,025 | B2 | 6/2020 | Swayze et al. |
| 10,675,026 | B2 | 6/2020 | Harris et al. |
| 10,675,028 | B2 | 6/2020 | Shelton, IV et al. |
| 10,675,035 | B2 | 6/2020 | Zingman |
| 10,675,080 | B2 | 6/2020 | Woloszko et al. |
| 10,675,102 | B2 | 6/2020 | Forgione et al. |
| 10,677,035 | B2 | 6/2020 | Balan et al. |
| 10,682,134 | B2 | 6/2020 | Shelton, IV et al. |
| 10,682,136 | B2 | 6/2020 | Harris et al. |
| 10,682,137 | B2 | 6/2020 | Stokes et al. |
| 10,682,138 | B2 | 6/2020 | Shelton, IV et al. |
| 10,682,141 | B2 | 6/2020 | Moore et al. |
| 10,682,142 | B2 | 6/2020 | Shelton, IV et al. |
| 10,687,806 | B2 | 6/2020 | Shelton, IV et al. |
| 10,687,809 | B2 | 6/2020 | Shelton, IV et al. |
| 10,687,810 | B2 | 6/2020 | Shelton, IV et al. |
| 10,687,812 | B2 | 6/2020 | Shelton, IV et al. |
| 10,687,813 | B2 | 6/2020 | Shelton, IV et al. |
| 10,687,817 | B2 | 6/2020 | Shelton, IV et al. |
| 10,687,819 | B2 | 6/2020 | Stokes et al. |
| 10,687,904 | B2 | 6/2020 | Harris et al. |
| 10,695,053 | B2 | 6/2020 | Hess et al. |
| 10,695,055 | B2 | 6/2020 | Shelton, IV et al. |
| 10,695,057 | B2 | 6/2020 | Shelton, IV et al. |
| 10,695,058 | B2 | 6/2020 | Lytle, IV et al. |
| 10,695,062 | B2 | 6/2020 | Leimbach et al. |
| 10,695,063 | B2 | 6/2020 | Morgan et al. |
| 10,695,074 | B2 | 6/2020 | Carusillo |
| 10,695,081 | B2 | 6/2020 | Shelton, IV et al. |
| 10,695,119 | B2 | 6/2020 | Smith |
| 10,695,123 | B2 | 6/2020 | Allen, IV |
| 10,695,187 | B2 | 6/2020 | Moskowitz et al. |
| D890,784 | S | 7/2020 | Shelton, IV et al. |
| D890,805 | S | 7/2020 | Echeverri et al. |
| 10,702,266 | B2 | 7/2020 | Parihar et al. |
| 10,702,267 | B2 | 7/2020 | Hess et al. |
| 10,702,270 | B2 | 7/2020 | Shelton, IV et al. |
| 10,702,271 | B2 | 7/2020 | Aranyi et al. |
| 10,705,660 | B2 | 7/2020 | Xiao |
| 10,709,446 | B2 | 7/2020 | Harris et al. |
| 10,709,468 | B2 | 7/2020 | Shelton, IV et al. |
| 10,709,469 | B2 | 7/2020 | Shelton, IV et al. |
| 10,709,495 | B2 | 7/2020 | Broderick et al. |
| 10,709,496 | B2 | 7/2020 | Moua et al. |
| 10,716,563 | B2 | 7/2020 | Shelton, IV et al. |
| 10,716,565 | B2 | 7/2020 | Shelton, IV et al. |
| 10,716,568 | B2 | 7/2020 | Hall et al. |
| 10,716,614 | B2 | 7/2020 | Yates et al. |
| 10,717,179 | B2 | 7/2020 | Koenig et al. |
| 10,722,232 | B2 | 7/2020 | Yates et al. |
| 10,722,233 | B2 | 7/2020 | Wellman |
| 10,722,292 | B2 | 7/2020 | Arya et al. |
| 10,722,293 | B2 | 7/2020 | Arya et al. |
| 10,722,317 | B2 | 7/2020 | Ward et al. |
| D893,717 | S | 8/2020 | Messerly et al. |
| 10,729,432 | B2 | 8/2020 | Shelton, IV et al. |
| 10,729,434 | B2 | 8/2020 | Harris et al. |
| 10,729,435 | B2 | 8/2020 | Richard |
| 10,729,436 | B2 | 8/2020 | Shelton, IV et al. |
| 10,729,443 | B2 | 8/2020 | Cabrera et al. |
| 10,729,458 | B2 | 8/2020 | Stoddard et al. |
| 10,729,501 | B2 | 8/2020 | Leimbach et al. |
| 10,729,509 | B2 | 8/2020 | Shelton, IV et al. |
| 10,736,616 | B2 | 8/2020 | Scheib et al. |
| 10,736,628 | B2 | 8/2020 | Yates et al. |
| 10,736,629 | B2 | 8/2020 | Shelton, IV et al. |
| 10,736,630 | B2 | 8/2020 | Huang et al. |
| 10,736,633 | B2 | 8/2020 | Vendely et al. |
| 10,736,634 | B2 | 8/2020 | Shelton, IV et al. |
| 10,736,636 | B2 | 8/2020 | Baxter, III et al. |
| 10,736,644 | B2 | 8/2020 | Windolf et al. |
| 10,736,702 | B2 | 8/2020 | Harris et al. |
| 10,737,398 | B2 | 8/2020 | Remirez et al. |
| 10,743,849 | B2 | 8/2020 | Shelton, IV et al. |
| 10,743,850 | B2 | 8/2020 | Hibner et al. |
| 10,743,851 | B2 | 8/2020 | Swayze et al. |
| 10,743,868 | B2 | 8/2020 | Shelton, IV et al. |
| 10,743,870 | B2 | 8/2020 | Hall et al. |
| 10,743,872 | B2 | 8/2020 | Leimbach et al. |
| 10,743,873 | B2 | 8/2020 | Overmyer et al. |
| 10,743,874 | B2 | 8/2020 | Shelton, IV et al. |
| 10,743,875 | B2 | 8/2020 | Shelton, IV et al. |
| 10,743,877 | B2 | 8/2020 | Shelton, IV et al. |
| 10,743,930 | B2 | 8/2020 | Nagtegaal |
| 10,751,048 | B2 | 8/2020 | Whitman et al. |
| 10,751,051 | B2 | 8/2020 | Weir et al. |
| 10,751,053 | B2 | 8/2020 | Harris et al. |
| 10,751,076 | B2 | 8/2020 | Laurent et al. |
| 10,751,104 | B2 | 8/2020 | Mistry et al. |
| 10,751,138 | B2 | 8/2020 | Giordano et al. |
| 10,758,226 | B2 | 9/2020 | Weir et al. |
| 10,758,229 | B2 | 9/2020 | Shelton, IV et al. |
| 10,758,230 | B2 | 9/2020 | Shelton, IV et al. |
| 10,758,232 | B2 | 9/2020 | Shelton, IV et al. |
| 10,758,233 | B2 | 9/2020 | Scheib et al. |
| 10,758,259 | B2 | 9/2020 | Demmy et al. |
| 10,765,425 | B2 | 9/2020 | Yates et al. |
| 10,765,427 | B2 | 9/2020 | Shelton, IV et al. |
| 10,765,429 | B2 | 9/2020 | Leimbach et al. |
| 10,765,430 | B2 | 9/2020 | Wixey |
| 10,765,432 | B2 | 9/2020 | Moore et al. |
| 10,765,442 | B2 | 9/2020 | Strobl |
| 10,772,625 | B2 | 9/2020 | Shelton, IV et al. |
| 10,772,628 | B2 | 9/2020 | Chen et al. |
| 10,772,629 | B2 | 9/2020 | Shelton, IV et al. |
| 10,772,630 | B2 | 9/2020 | Wixey |
| 10,772,631 | B2 | 9/2020 | Zergiebel et al. |
| 10,772,632 | B2 | 9/2020 | Kostrzewski |
| 10,772,651 | B2 | 9/2020 | Shelton, IV et al. |
| 10,779,818 | B2 | 9/2020 | Zemlok et al. |
| 10,779,820 | B2 | 9/2020 | Harris et al. |

(56) References Cited

U.S. PATENT DOCUMENTS

| | | | |
|---|---|---|---|
| 10,779,821 | B2 | 9/2020 | Harris et al. |
| 10,779,822 | B2 | 9/2020 | Yates et al. |
| 10,779,823 | B2 | 9/2020 | Shelton, IV et al. |
| 10,779,824 | B2 | 9/2020 | Shelton, IV et al. |
| 10,779,825 | B2 | 9/2020 | Shelton, IV et al. |
| 10,779,826 | B2 | 9/2020 | Shelton, IV et al. |
| 10,779,903 | B2 | 9/2020 | Wise et al. |
| 10,780,539 | B2 | 9/2020 | Shelton, IV et al. |
| 10,786,248 | B2 | 9/2020 | Rousseau et al. |
| 10,786,253 | B2 | 9/2020 | Shelton, IV et al. |
| 10,786,255 | B2 | 9/2020 | Hodgkinson et al. |
| D898,767 | S | 10/2020 | Shah et al. |
| D899,455 | S | 10/2020 | Rondoni et al. |
| 10,792,038 | B2 | 10/2020 | Becerra et al. |
| 10,796,471 | B2 | 10/2020 | Leimbach et al. |
| 10,799,240 | B2 | 10/2020 | Shelton, IV et al. |
| 10,799,306 | B2 | 10/2020 | Robinson et al. |
| 10,806,448 | B2 | 10/2020 | Shelton, IV et al. |
| 10,806,449 | B2 | 10/2020 | Shelton, IV et al. |
| 10,806,450 | B2 | 10/2020 | Yates et al. |
| 10,806,451 | B2 | 10/2020 | Harris et al. |
| 10,806,453 | B2 | 10/2020 | Chen et al. |
| 10,806,479 | B2 | 10/2020 | Shelton, IV et al. |
| 10,813,638 | B2 | 10/2020 | Shelton, IV et al. |
| 10,813,639 | B2 | 10/2020 | Shelton, IV et al. |
| 10,813,640 | B2 | 10/2020 | Adams et al. |
| 10,813,641 | B2 | 10/2020 | Setser et al. |
| 10,813,683 | B2 | 10/2020 | Baxter, III et al. |
| 10,813,705 | B2 | 10/2020 | Hares et al. |
| 10,813,710 | B2 | 10/2020 | Grubbs |
| 10,820,939 | B2 | 11/2020 | Sartor |
| 10,828,028 | B2 | 11/2020 | Harris et al. |
| 10,828,030 | B2 | 11/2020 | Weir et al. |
| 10,828,032 | B2 | 11/2020 | Leimbach et al. |
| 10,828,033 | B2 | 11/2020 | Shelton, IV et al. |
| 10,828,089 | B2 | 11/2020 | Clark et al. |
| 10,835,245 | B2 | 11/2020 | Swayze et al. |
| 10,835,246 | B2 | 11/2020 | Shelton, IV et al. |
| 10,835,247 | B2 | 11/2020 | Shelton, IV et al. |
| 10,835,249 | B2 | 11/2020 | Schellin et al. |
| 10,835,251 | B2 | 11/2020 | Shelton, IV et al. |
| 10,835,330 | B2 | 11/2020 | Shelton, IV et al. |
| 10,842,357 | B2 | 11/2020 | Moskowitz et al. |
| 10,842,473 | B2 | 11/2020 | Scheib et al. |
| 10,842,488 | B2 | 11/2020 | Swayze et al. |
| 10,842,489 | B2 | 11/2020 | Shelton, IV |
| 10,842,490 | B2 | 11/2020 | DiNardo et al. |
| 10,842,491 | B2 | 11/2020 | Shelton, IV et al. |
| 10,842,492 | B2 | 11/2020 | Shelton, IV et al. |
| 10,842,523 | B2 | 11/2020 | Shelton, IV et al. |
| D904,612 | S | 12/2020 | Wynn et al. |
| D904,613 | S | 12/2020 | Wynn et al. |
| D906,355 | S | 12/2020 | Messerly et al. |
| 10,849,621 | B2 | 12/2020 | Whitfield et al. |
| 10,849,623 | B2 | 12/2020 | Dunki-Jacobs et al. |
| 10,849,697 | B2 | 12/2020 | Yates et al. |
| 10,856,866 | B2 | 12/2020 | Shelton, IV et al. |
| 10,856,867 | B2 | 12/2020 | Shelton, IV et al. |
| 10,856,868 | B2 | 12/2020 | Shelton, IV et al. |
| 10,856,869 | B2 | 12/2020 | Shelton, IV et al. |
| 10,856,870 | B2 | 12/2020 | Harris et al. |
| 10,863,981 | B2 | 12/2020 | Overmyer et al. |
| 10,863,984 | B2 | 12/2020 | Shelton, IV et al. |
| 10,863,986 | B2 | 12/2020 | Yates et al. |
| 10,869,663 | B2 | 12/2020 | Shelton, IV et al. |
| 10,869,664 | B2 | 12/2020 | Shelton, IV |
| 10,869,665 | B2 | 12/2020 | Shelton, IV et al. |
| 10,869,666 | B2 | 12/2020 | Shelton, IV et al. |
| 10,869,669 | B2 | 12/2020 | Shelton, IV et al. |
| 10,874,290 | B2 | 12/2020 | Walen et al. |
| 10,874,391 | B2 | 12/2020 | Shelton, IV et al. |
| 10,874,392 | B2 | 12/2020 | Scirica et al. |
| 10,874,393 | B2 | 12/2020 | Satti, III et al. |
| 10,874,396 | B2 | 12/2020 | Moore et al. |
| 10,874,399 | B2 | 12/2020 | Zhang |
| 10,874,474 | B2 | 12/2020 | Wu et al. |
| 10,879,275 | B2 | 12/2020 | Li et al. |
| D907,647 | S | 1/2021 | Siebel et al. |
| D907,648 | S | 1/2021 | Siebel et al. |
| D908,216 | S | 1/2021 | Messerly et al. |
| 10,881,339 | B2 | 1/2021 | Peyser et al. |
| 10,881,395 | B2 | 1/2021 | Merchant et al. |
| 10,881,396 | B2 | 1/2021 | Shelton, IV et al. |
| 10,881,398 | B2 | 1/2021 | Whitman et al. |
| 10,881,399 | B2 | 1/2021 | Shelton, IV et al. |
| 10,881,401 | B2 | 1/2021 | Baber et al. |
| 10,881,446 | B2 | 1/2021 | Strobl |
| 10,888,318 | B2 | 1/2021 | Parihar et al. |
| 10,888,321 | B2 | 1/2021 | Shelton, IV et al. |
| 10,888,322 | B2 | 1/2021 | Morgan et al. |
| 10,888,323 | B2 | 1/2021 | Chen et al. |
| 10,888,325 | B2 | 1/2021 | Harris et al. |
| 10,888,328 | B2 | 1/2021 | Shelton, IV et al. |
| 10,888,329 | B2 | 1/2021 | Moore et al. |
| 10,888,330 | B2 | 1/2021 | Moore et al. |
| 10,888,369 | B2 | 1/2021 | Messerly et al. |
| 10,892,899 | B2 | 1/2021 | Shelton, IV et al. |
| 10,893,853 | B2 | 1/2021 | Shelton, IV et al. |
| 10,893,863 | B2 | 1/2021 | Shelton, IV et al. |
| 10,893,864 | B2 | 1/2021 | Harris et al. |
| 10,893,867 | B2 | 1/2021 | Leimbach et al. |
| 10,898,183 | B2 | 1/2021 | Shelton, IV et al. |
| 10,898,184 | B2 | 1/2021 | Yates et al. |
| 10,898,185 | B2 | 1/2021 | Overmyer et al. |
| 10,898,186 | B2 | 1/2021 | Bakos et al. |
| 10,898,190 | B2 | 1/2021 | Yates et al. |
| 10,898,193 | B2 | 1/2021 | Shelton, IV et al. |
| 10,898,194 | B2 | 1/2021 | Moore et al. |
| 10,898,195 | B2 | 1/2021 | Moore et al. |
| 10,903,685 | B2 | 1/2021 | Yates et al. |
| D910,847 | S | 2/2021 | Shelton, IV et al. |
| 10,905,415 | B2 | 2/2021 | DiNardo et al. |
| 10,905,418 | B2 | 2/2021 | Shelton, IV et al. |
| 10,905,420 | B2 | 2/2021 | Jasemian et al. |
| 10,905,422 | B2 | 2/2021 | Bakos et al. |
| 10,905,423 | B2 | 2/2021 | Baber et al. |
| 10,905,426 | B2 | 2/2021 | Moore et al. |
| 10,905,427 | B2 | 2/2021 | Moore et al. |
| 10,911,515 | B2 | 2/2021 | Biasi et al. |
| 10,912,559 | B2 | 2/2021 | Harris et al. |
| 10,912,562 | B2 | 2/2021 | Dunki-Jacobs et al. |
| 10,912,575 | B2 | 2/2021 | Shelton, IV et al. |
| 10,918,364 | B2 | 2/2021 | Applegate et al. |
| 10,918,380 | B2 | 2/2021 | Morgan et al. |
| 10,918,385 | B2 | 2/2021 | Overmyer et al. |
| 10,918,386 | B2 | 2/2021 | Shelton, IV et al. |
| 10,919,156 | B2 | 2/2021 | Roberts et al. |
| 10,925,600 | B2 | 2/2021 | McCuen |
| 10,925,605 | B2 | 2/2021 | Moore et al. |
| D914,878 | S | 3/2021 | Shelton, IV et al. |
| 10,932,772 | B2 | 3/2021 | Shelton, IV et al. |
| 10,932,774 | B2 | 3/2021 | Shelton, IV |
| 10,932,775 | B2 | 3/2021 | Shelton, IV et al. |
| 10,932,778 | B2 | 3/2021 | Smith et al. |
| 10,932,779 | B2 | 3/2021 | Vendely et al. |
| 10,932,784 | B2 | 3/2021 | Mozdzierz et al. |
| 10,932,804 | B2 | 3/2021 | Scheib et al. |
| 10,932,806 | B2 | 3/2021 | Shelton, IV et al. |
| 10,932,872 | B2 | 3/2021 | Shelton, IV et al. |
| 10,944,728 | B2 | 3/2021 | Wiener et al. |
| 10,945,727 | B2 | 3/2021 | Shelton, IV et al. |
| 10,945,728 | B2 | 3/2021 | Morgan et al. |
| 10,945,729 | B2 | 3/2021 | Shelton, IV et al. |
| 10,945,731 | B2 | 3/2021 | Baxter, III et al. |
| 10,952,708 | B2 | 3/2021 | Scheib et al. |
| 10,952,726 | B2 | 3/2021 | Chowaniec |
| 10,952,727 | B2 | 3/2021 | Giordano et al. |
| 10,952,728 | B2 | 3/2021 | Shelton, IV et al. |
| 10,952,759 | B2 | 3/2021 | Messerly et al. |
| 10,952,767 | B2 | 3/2021 | Kostrzewski et al. |
| 10,959,722 | B2 | 3/2021 | Morgan et al. |
| 10,959,725 | B2 | 3/2021 | Kerr et al. |
| 10,959,726 | B2 | 3/2021 | Williams et al. |
| 10,959,727 | B2 | 3/2021 | Hunter et al. |

(56) References Cited

U.S. PATENT DOCUMENTS

| | | | |
|---|---|---|---|
| 10,959,731 | B2 | 3/2021 | Casasanta, Jr. et al. |
| 10,959,744 | B2 | 3/2021 | Shelton, IV et al. |
| 10,959,797 | B2 | 3/2021 | Licht et al. |
| D917,500 | S | 4/2021 | Siebel et al. |
| 10,966,627 | B2 | 4/2021 | Shelton, IV et al. |
| 10,966,717 | B2 | 4/2021 | Shah et al. |
| 10,966,718 | B2 | 4/2021 | Shelton, IV et al. |
| 10,966,791 | B2 | 4/2021 | Harris et al. |
| 10,973,515 | B2 | 4/2021 | Harris et al. |
| 10,973,516 | B2 | 4/2021 | Shelton, IV et al. |
| 10,973,517 | B2 | 4/2021 | Wixey |
| 10,973,519 | B2 | 4/2021 | Weir et al. |
| 10,973,520 | B2 | 4/2021 | Shelton, IV et al. |
| 10,980,534 | B2 | 4/2021 | Yates et al. |
| 10,980,535 | B2 | 4/2021 | Yates et al. |
| 10,980,536 | B2 | 4/2021 | Weaner et al. |
| 10,980,537 | B2 | 4/2021 | Shelton, IV et al. |
| 10,980,538 | B2 | 4/2021 | Nalagatla et al. |
| 10,980,539 | B2 | 4/2021 | Harris et al. |
| 10,980,560 | B2 | 4/2021 | Shelton, IV et al. |
| 10,983,646 | B2 | 4/2021 | Yoon et al. |
| 10,987,102 | B2 | 4/2021 | Gonzalez et al. |
| 10,987,178 | B2 | 4/2021 | Shelton, IV et al. |
| 10,993,713 | B2 | 5/2021 | Shelton, IV et al. |
| 10,993,715 | B2 | 5/2021 | Shelton, IV et al. |
| 10,993,716 | B2 | 5/2021 | Shelton, IV et al. |
| 10,993,717 | B2 | 5/2021 | Shelton, IV et al. |
| 11,000,274 | B2 | 5/2021 | Shelton, IV et al. |
| 11,000,275 | B2 | 5/2021 | Shelton, IV et al. |
| 11,000,277 | B2 | 5/2021 | Giordano et al. |
| 11,000,278 | B2 | 5/2021 | Shelton, IV et al. |
| 11,000,279 | B2 | 5/2021 | Shelton, IV et al. |
| 11,005,291 | B2 | 5/2021 | Calderoni |
| 11,006,951 | B2 | 5/2021 | Giordano et al. |
| 11,006,955 | B2 | 5/2021 | Shelton, IV et al. |
| 11,007,004 | B2 | 5/2021 | Shelton, IV et al. |
| 11,007,022 | B2 | 5/2021 | Shelton, IV et al. |
| 11,013,511 | B2 | 5/2021 | Huang et al. |
| 11,013,552 | B2 | 5/2021 | Widenhouse et al. |
| 11,013,563 | B2 | 5/2021 | Shelton, IV et al. |
| 11,020,016 | B2 | 6/2021 | Wallace et al. |
| 11,020,112 | B2 | 6/2021 | Shelton, IV et al. |
| 11,020,113 | B2 | 6/2021 | Shelton, IV et al. |
| 11,020,114 | B2 | 6/2021 | Shelton, IV et al. |
| 11,020,115 | B2 | 6/2021 | Scheib et al. |
| 11,020,172 | B2 | 6/2021 | Garrison |
| 11,026,678 | B2 | 6/2021 | Overmyer et al. |
| 11,026,680 | B2 | 6/2021 | Shelton, IV et al. |
| 11,026,684 | B2 | 6/2021 | Shelton, IV et al. |
| 11,026,687 | B2 | 6/2021 | Shelton, IV et al. |
| 11,026,712 | B2 | 6/2021 | Shelton, IV et al. |
| 11,026,713 | B2 | 6/2021 | Stokes et al. |
| 11,026,751 | B2 | 6/2021 | Shelton, IV et al. |
| 11,033,267 | B2 | 6/2021 | Shelton, IV et al. |
| 11,039,834 | B2 | 6/2021 | Harris et al. |
| 11,039,836 | B2 | 6/2021 | Shelton, IV et al. |
| 11,039,837 | B2 | 6/2021 | Shelton, IV et al. |
| 11,039,849 | B2 | 6/2021 | Bucciaglia et al. |
| 11,045,189 | B2 | 6/2021 | Yates et al. |
| 11,045,191 | B2 | 6/2021 | Shelton, IV et al. |
| 11,045,192 | B2 | 6/2021 | Harris et al. |
| 11,045,196 | B2 | 6/2021 | Olson et al. |
| 11,045,197 | B2 | 6/2021 | Shelton, IV et al. |
| 11,045,199 | B2 | 6/2021 | Mozdzierz et al. |
| 11,045,270 | B2 | 6/2021 | Shelton, IV et al. |
| D925,563 | S | 7/2021 | Melvin et al. |
| 11,051,807 | B2 | 7/2021 | Shelton, IV et al. |
| 11,051,810 | B2 | 7/2021 | Harris et al. |
| 11,051,811 | B2 | 7/2021 | Shelton, IV et al. |
| 11,051,813 | B2 | 7/2021 | Shelton, IV et al. |
| 11,051,836 | B2 | 7/2021 | Shelton, IV et al. |
| 11,051,840 | B2 | 7/2021 | Shelton, IV et al. |
| 11,051,873 | B2 | 7/2021 | Wiener et al. |
| 11,058,418 | B2 | 7/2021 | Shelton, IV et al. |
| 11,058,420 | B2 | 7/2021 | Shelton, IV et al. |
| 11,058,422 | B2 | 7/2021 | Harris et al. |
| 11,058,423 | B2 | 7/2021 | Shelton, IV et al. |
| 11,058,424 | B2 | 7/2021 | Shelton, IV et al. |
| 11,058,425 | B2 | 7/2021 | Widenhouse et al. |
| 11,058,426 | B2 | 7/2021 | Nalagatla et al. |
| 11,058,498 | B2 | 7/2021 | Shelton, IV et al. |
| 11,064,997 | B2 | 7/2021 | Shelton, IV et al. |
| 11,064,998 | B2 | 7/2021 | Shelton, IV |
| 11,065,000 | B2 | 7/2021 | Shankarsetty et al. |
| 11,065,048 | B2 | 7/2021 | Messerly et al. |
| 11,069,012 | B2 | 7/2021 | Shelton, IV et al. |
| 11,071,542 | B2 | 7/2021 | Chen et al. |
| 11,071,543 | B2 | 7/2021 | Shelton, IV et al. |
| 11,071,545 | B2 | 7/2021 | Baber et al. |
| 11,071,554 | B2 | 7/2021 | Parfett et al. |
| 11,071,560 | B2 | 7/2021 | Deck et al. |
| 11,076,853 | B2 | 8/2021 | Parfett et al. |
| 11,076,854 | B2 | 8/2021 | Baber et al. |
| 11,076,921 | B2 | 8/2021 | Shelton, IV et al. |
| 11,076,929 | B2 | 8/2021 | Shelton, IV et al. |
| 11,083,452 | B2 | 8/2021 | Schmid et al. |
| 11,083,453 | B2 | 8/2021 | Shelton, IV et al. |
| 11,083,454 | B2 | 8/2021 | Harris et al. |
| 11,083,455 | B2 | 8/2021 | Shelton, IV et al. |
| 11,083,456 | B2 | 8/2021 | Shelton, IV et al. |
| 11,083,457 | B2 | 8/2021 | Shelton, IV et al. |
| 11,083,458 | B2 | 8/2021 | Harris et al. |
| 11,090,045 | B2 | 8/2021 | Shelton, IV |
| 11,090,046 | B2 | 8/2021 | Shelton, IV et al. |
| 11,090,047 | B2 | 8/2021 | Shelton, IV et al. |
| 11,090,048 | B2 | 8/2021 | Fanelli et al. |
| 11,090,049 | B2 | 8/2021 | Bakos et al. |
| 11,090,075 | B2 | 8/2021 | Hunter et al. |
| 11,096,687 | B2 | 8/2021 | Flanagan et al. |
| 11,096,688 | B2 | 8/2021 | Shelton, IV et al. |
| 11,096,689 | B2 | 8/2021 | Overmyer et al. |
| 11,100,631 | B2 | 8/2021 | Yates et al. |
| 11,103,241 | B2 | 8/2021 | Yates et al. |
| 11,103,248 | B2 | 8/2021 | Shelton, IV et al. |
| 11,103,268 | B2 | 8/2021 | Shelton, IV et al. |
| 11,103,269 | B2 | 8/2021 | Shelton, IV et al. |
| 11,103,301 | B2 | 8/2021 | Messerly et al. |
| 11,109,858 | B2 | 9/2021 | Shelton, IV et al. |
| 11,109,859 | B2 | 9/2021 | Overmyer et al. |
| 11,109,860 | B2 | 9/2021 | Shelton, IV et al. |
| 11,109,866 | B2 | 9/2021 | Shelton, IV et al. |
| 11,109,878 | B2 | 9/2021 | Shelton, IV et al. |
| 11,109,925 | B2 | 9/2021 | Cooper et al. |
| 11,116,485 | B2 | 9/2021 | Scheib et al. |
| 11,116,502 | B2 | 9/2021 | Shelton, IV et al. |
| 11,116,594 | B2 | 9/2021 | Beardsley |
| 11,123,069 | B2 | 9/2021 | Baxter, III et al. |
| 11,123,070 | B2 | 9/2021 | Shelton, IV et al. |
| 11,129,611 | B2 | 9/2021 | Shelton, IV et al. |
| 11,129,613 | B2 | 9/2021 | Harris et al. |
| 11,129,615 | B2 | 9/2021 | Scheib et al. |
| 11,129,616 | B2 | 9/2021 | Shelton, IV et al. |
| 11,129,634 | B2 | 9/2021 | Scheib et al. |
| 11,129,636 | B2 | 9/2021 | Shelton, IV et al. |
| 11,129,666 | B2 | 9/2021 | Messerly et al. |
| 11,129,680 | B2 | 9/2021 | Shelton, IV et al. |
| 11,132,462 | B2 | 9/2021 | Shelton, IV et al. |
| 11,133,106 | B2 | 9/2021 | Shelton, IV et al. |
| 11,134,938 | B2 | 10/2021 | Timm et al. |
| 11,134,940 | B2 | 10/2021 | Shelton, IV et al. |
| 11,134,942 | B2 | 10/2021 | Harris et al. |
| 11,134,943 | B2 | 10/2021 | Giordano et al. |
| 11,134,944 | B2 | 10/2021 | Wise et al. |
| 11,134,947 | B2 | 10/2021 | Shelton, IV et al. |
| 11,135,352 | B2 | 10/2021 | Shelton, IV et al. |
| 11,141,152 | B2 | 10/2021 | Ingmanson et al. |
| 11,141,153 | B2 | 10/2021 | Shelton, IV et al. |
| 11,141,154 | B2 | 10/2021 | Shelton, IV et al. |
| 11,141,155 | B2 | 10/2021 | Shelton, IV |
| 11,141,156 | B2 | 10/2021 | Shelton, IV |
| 11,141,159 | B2 | 10/2021 | Scheib et al. |
| 11,141,160 | B2 | 10/2021 | Shelton, IV et al. |
| 11,147,547 | B2 | 10/2021 | Shelton, IV et al. |
| 11,147,549 | B2 | 10/2021 | Timm et al. |

(56) References Cited

U.S. PATENT DOCUMENTS

| | | | |
|---|---|---|---|
| 11,147,551 | B2 | 10/2021 | Shelton, IV |
| 11,147,553 | B2 | 10/2021 | Shelton, IV |
| 11,147,554 | B2 | 10/2021 | Aronhalt et al. |
| 11,154,296 | B2 | 10/2021 | Aronhalt et al. |
| 11,154,297 | B2 | 10/2021 | Swayze et al. |
| 11,154,298 | B2 | 10/2021 | Timm et al. |
| 11,154,299 | B2 | 10/2021 | Shelton, IV et al. |
| 11,154,300 | B2 | 10/2021 | Nalagatla et al. |
| 11,154,301 | B2 | 10/2021 | Beckman et al. |
| D936,684 | S | 11/2021 | Luo et al. |
| 11,160,551 | B2 | 11/2021 | Shelton, IV et al. |
| 11,160,553 | B2 | 11/2021 | Simms et al. |
| 11,160,601 | B2 | 11/2021 | Worrell et al. |
| 11,166,716 | B2 | 11/2021 | Shelton, IV et al. |
| 11,166,717 | B2 | 11/2021 | Shelton, IV et al. |
| 11,166,720 | B2 | 11/2021 | Giordano et al. |
| 11,166,772 | B2 | 11/2021 | Shelton, IV et al. |
| 11,166,773 | B2 | 11/2021 | Ragosta et al. |
| 11,172,580 | B2 | 11/2021 | Gaertner, II |
| 11,172,927 | B2 | 11/2021 | Shelton, IV |
| 11,172,929 | B2 | 11/2021 | Shelton, IV |
| 11,179,150 | B2 | 11/2021 | Yates et al. |
| 11,179,151 | B2 | 11/2021 | Shelton, IV et al. |
| 11,179,152 | B2 | 11/2021 | Morgan et al. |
| 11,179,153 | B2 | 11/2021 | Shelton, IV |
| 11,179,155 | B2 | 11/2021 | Shelton, IV et al. |
| 11,179,208 | B2 | 11/2021 | Yates et al. |
| 11,185,325 | B2 | 11/2021 | Shelton, IV et al. |
| 11,185,330 | B2 | 11/2021 | Huitema et al. |
| 11,191,539 | B2 | 12/2021 | Overmyer et al. |
| 11,191,540 | B2 | 12/2021 | Aronhalt et al. |
| 11,191,543 | B2 | 12/2021 | Overmyer et al. |
| 11,191,545 | B2 | 12/2021 | Vendely et al. |
| 11,197,668 | B2 | 12/2021 | Shelton, IV et al. |
| 11,197,670 | B2 | 12/2021 | Shelton, IV et al. |
| 11,197,671 | B2 | 12/2021 | Shelton, IV et al. |
| 11,197,672 | B2 | 12/2021 | Dunki-Jacobs et al. |
| 11,202,570 | B2 | 12/2021 | Shelton, IV et al. |
| 11,202,631 | B2 | 12/2021 | Shelton, IV et al. |
| 11,202,633 | B2 | 12/2021 | Harris et al. |
| 11,207,064 | B2 | 12/2021 | Shelton, IV et al. |
| 11,207,065 | B2 | 12/2021 | Harris et al. |
| 11,207,067 | B2 | 12/2021 | Shelton, IV et al. |
| 11,207,089 | B2 | 12/2021 | Kostrzewski et al. |
| 11,207,090 | B2 | 12/2021 | Shelton, IV et al. |
| 11,207,146 | B2 | 12/2021 | Shelton, IV et al. |
| 11,213,293 | B2 | 1/2022 | Worthington et al. |
| 11,213,294 | B2 | 1/2022 | Shelton, IV et al. |
| 11,213,302 | B2 | 1/2022 | Parfett et al. |
| 11,213,359 | B2 | 1/2022 | Shelton, IV et al. |
| 11,219,453 | B2 | 1/2022 | Shelton, IV et al. |
| 11,219,455 | B2 | 1/2022 | Shelton, IV et al. |
| 11,224,423 | B2 | 1/2022 | Shelton, IV et al. |
| 11,224,426 | B2 | 1/2022 | Shelton, IV et al. |
| 11,224,427 | B2 | 1/2022 | Shelton, IV et al. |
| 11,224,428 | B2 | 1/2022 | Scott et al. |
| 11,224,454 | B2 | 1/2022 | Shelton, IV et al. |
| 11,224,497 | B2 | 1/2022 | Shelton, IV et al. |
| 11,229,436 | B2 | 1/2022 | Shelton, IV et al. |
| 11,229,437 | B2 | 1/2022 | Shelton, IV et al. |
| 11,234,698 | B2 | 2/2022 | Shelton, IV et al. |
| 11,234,700 | B2 | 2/2022 | Ragosta et al. |
| 11,241,229 | B2 | 2/2022 | Shelton, IV et al. |
| 11,241,230 | B2 | 2/2022 | Shelton, IV et al. |
| 11,241,235 | B2 | 2/2022 | Shelton, IV et al. |
| 11,246,590 | B2 | 2/2022 | Swayze et al. |
| 11,246,592 | B2 | 2/2022 | Shelton, IV et al. |
| 11,246,616 | B2 | 2/2022 | Shelton, IV et al. |
| 11,246,618 | B2 | 2/2022 | Hall et al. |
| 11,246,678 | B2 | 2/2022 | Shelton, IV et al. |
| 11,253,254 | B2 | 2/2022 | Kimball et al. |
| 11,253,256 | B2 | 2/2022 | Harris et al. |
| D946,025 | S | 3/2022 | Vogler-Ivashchanka et al. |
| D946,617 | S | 3/2022 | Ahmed |
| 11,259,799 | B2 | 3/2022 | Overmyer et al. |
| 11,259,803 | B2 | 3/2022 | Shelton, IV et al. |
| 11,259,805 | B2 | 3/2022 | Shelton, IV et al. |
| 11,259,806 | B2 | 3/2022 | Shelton, IV et al. |
| 11,259,807 | B2 | 3/2022 | Shelton, IV et al. |
| 11,266,405 | B2 | 3/2022 | Shelton, IV et al. |
| 11,266,406 | B2 | 3/2022 | Leimbach et al. |
| 11,266,409 | B2 | 3/2022 | Huitema et al. |
| 11,266,410 | B2 | 3/2022 | Shelton, IV et al. |
| 11,266,468 | B2 | 3/2022 | Shelton, IV et al. |
| 11,272,927 | B2 | 3/2022 | Swayze et al. |
| 11,272,928 | B2 | 3/2022 | Shelton, IV |
| 11,272,931 | B2 | 3/2022 | Boudreaux et al. |
| 11,272,938 | B2 | 3/2022 | Shelton, IV et al. |
| 11,278,279 | B2 | 3/2022 | Morgan et al. |
| 11,278,280 | B2 | 3/2022 | Shelton, IV et al. |
| 11,278,284 | B2 | 3/2022 | Shelton, IV et al. |
| 11,278,288 | B2 | 3/2022 | Rector et al. |
| 11,284,890 | B2 | 3/2022 | Nalagatla et al. |
| 11,284,891 | B2 | 3/2022 | Shelton, IV et al. |
| 11,284,898 | B2 | 3/2022 | Baxter, III et al. |
| 11,284,953 | B2 | 3/2022 | Shelton, IV et al. |
| 11,291,440 | B2 | 4/2022 | Harris et al. |
| 11,291,441 | B2 | 4/2022 | Giordano et al. |
| 11,291,442 | B2 | 4/2022 | Wixey et al. |
| 11,291,443 | B2 | 4/2022 | Viola et al. |
| 11,291,444 | B2 | 4/2022 | Boudreaux et al. |
| 11,291,445 | B2 | 4/2022 | Shelton, IV et al. |
| 11,291,447 | B2 | 4/2022 | Shelton, IV et al. |
| 11,291,449 | B2 | 4/2022 | Swensgard et al. |
| 11,291,451 | B2 | 4/2022 | Shelton, IV |
| 11,291,465 | B2 | 4/2022 | Parihar et al. |
| 11,291,510 | B2 | 4/2022 | Shelton, IV et al. |
| 11,298,125 | B2 | 4/2022 | Ming et al. |
| 11,298,127 | B2 | 4/2022 | Shelton, IV |
| 11,298,128 | B2 | 4/2022 | Messerly et al. |
| 11,298,129 | B2 | 4/2022 | Bakos et al. |
| 11,298,130 | B2 | 4/2022 | Bakos et al. |
| 11,298,132 | B2 | 4/2022 | Shelton, IV et al. |
| 11,298,134 | B2 | 4/2022 | Huitema et al. |
| 11,304,695 | B2 | 4/2022 | Shelton, IV et al. |
| 11,304,696 | B2 | 4/2022 | Shelton, IV et al. |
| 11,304,697 | B2 | 4/2022 | Fanelli et al. |
| 11,304,699 | B2 | 4/2022 | Shelton, IV et al. |
| 11,304,704 | B2 | 4/2022 | Thomas et al. |
| 11,311,290 | B2 | 4/2022 | Shelton, IV et al. |
| 11,311,292 | B2 | 4/2022 | Shelton, IV et al. |
| 11,311,294 | B2 | 4/2022 | Swayze et al. |
| 11,311,295 | B2 | 4/2022 | Wingardner et al. |
| 11,311,342 | B2 | 4/2022 | Parihar et al. |
| D950,728 | S | 5/2022 | Bakos et al. |
| D952,144 | S | 5/2022 | Boudreaux |
| 11,317,910 | B2 | 5/2022 | Miller et al. |
| 11,317,912 | B2 | 5/2022 | Jenkins et al. |
| 11,317,913 | B2 | 5/2022 | Shelton, IV et al. |
| 11,317,915 | B2 | 5/2022 | Boudreaux et al. |
| 11,317,917 | B2 | 5/2022 | Shelton, IV et al. |
| 11,317,919 | B2 | 5/2022 | Shelton, IV et al. |
| 11,317,978 | B2 | 5/2022 | Cameron et al. |
| 11,324,501 | B2 | 5/2022 | Shelton, IV et al. |
| 11,324,503 | B2 | 5/2022 | Shelton, IV et al. |
| 11,324,506 | B2 | 5/2022 | Beckman et al. |
| 11,324,557 | B2 | 5/2022 | Shelton, IV et al. |
| 11,331,100 | B2 | 5/2022 | Boudreaux et al. |
| 11,331,101 | B2 | 5/2022 | Harris et al. |
| 11,337,691 | B2 | 5/2022 | Widenhouse et al. |
| 11,337,693 | B2 | 5/2022 | Hess et al. |
| 11,337,698 | B2 | 5/2022 | Baxter, III et al. |
| 11,344,299 | B2 | 5/2022 | Yates et al. |
| 11,344,303 | B2 | 5/2022 | Shelton, IV et al. |
| D954,736 | S | 6/2022 | Teague et al. |
| 11,350,843 | B2 | 6/2022 | Shelton, IV et al. |
| 11,350,916 | B2 | 6/2022 | Shelton, IV et al. |
| 11,350,928 | B2 | 6/2022 | Shelton, IV et al. |
| 11,350,929 | B2 | 6/2022 | Giordano et al. |
| 11,350,932 | B2 | 6/2022 | Shelton, IV et al. |
| 11,350,934 | B2 | 6/2022 | Bakos et al. |
| 11,350,935 | B2 | 6/2022 | Shelton, IV et al. |
| 11,350,938 | B2 | 6/2022 | Shelton, IV et al. |
| 11,357,503 | B2 | 6/2022 | Bakos et al. |

(56) References Cited

U.S. PATENT DOCUMENTS 11,361,176 B2 6/2022 Shelton, IV et al.
11,364,027 B2 6/2022 Harris et al.
11,364,046 B2 6/2022 Shelton, IV et al.
11,369,366 B2 6/2022 Scheib et al.
11,369,368 B2 6/2022 Shelton, IV et al.
11,369,376 B2 6/2022 Simms et al.
11,369,377 B2 6/2022 Boudreaux et al.
11,373,755 B2 6/2022 Shelton, IV et al.
11,376,001 B2 7/2022 Shelton, IV et al.
11,376,002 B2 7/2022 Shelton, IV et al.
11,376,082 B2 7/2022 Shelton, IV et al.
11,376,098 B2 7/2022 Shelton, IV et al.
11,382,625 B2 7/2022 Huitema et al.
11,382,626 B2 7/2022 Shelton, IV et al.
11,382,627 B2 7/2022 Huitema et al.
11,382,628 B2 7/2022 Baxter, III et al.
11,382,638 B2 7/2022 Harris et al.
11,382,697 B2 7/2022 Shelton, IV et al.
11,382,704 B2 7/2022 Overmyer et al.
11,389,160 B2 7/2022 Shelton, IV et al.
11,389,161 B2 7/2022 Shelton, IV et al.
11,389,162 B2 7/2022 Baber et al.
11,389,164 B2 7/2022 Yates et al.
11,395,651 B2 7/2022 Shelton, IV et al.
11,395,652 B2 7/2022 Parihar et al.
11,399,828 B2 8/2022 Swayze et al.
11,399,829 B2 8/2022 Leimbach et al.
11,399,831 B2 8/2022 Overmyer et al.
11,399,837 B2 8/2022 Shelton, IV et al.
11,406,377 B2 8/2022 Schmid et al.
11,406,378 B2 8/2022 Baxter, III et al.
11,406,380 B2 8/2022 Yates et al.
11,406,381 B2 8/2022 Parihar et al.
11,406,382 B2 8/2022 Shelton, IV et al.
11,406,386 B2 8/2022 Baber et al.
11,406,390 B2 8/2022 Shelton, IV et al.
11,406,442 B2 8/2022 Davison et al.
11,410,259 B2 8/2022 Harris et al.
11,413,041 B2 8/2022 Viola et al.
11,413,042 B2 8/2022 Shelton, IV et al.
11,413,102 B2 8/2022 Shelton, IV et al.
11,419,606 B2 8/2022 Overmyer et al.
11,419,630 B2 8/2022 Yates et al.
11,424,027 B2 8/2022 Shelton, IV
11,426,160 B2 8/2022 Shelton, IV et al.
11,426,167 B2 8/2022 Shelton, IV et al.
11,426,251 B2 8/2022 Kimball et al.
D962,980 S 9/2022 Frenkler et al.
D964,564 S 9/2022 Boudreaux
11,432,816 B2 9/2022 Leimbach et al.
11,432,819 B2 9/2022 Rector et al.
11,432,885 B2 9/2022 Shelton, IV et al.
11,439,391 B2 9/2022 Bruns et al.
11,439,470 B2 9/2022 Spivey et al.
11,446,029 B2 9/2022 Shelton, IV et al.
11,446,034 B2 9/2022 Shelton, IV et al.
11,452,526 B2 9/2022 Ross et al.
11,452,528 B2 9/2022 Leimbach et al.
D966,512 S 10/2022 Shelton, IV et al.
D967,421 S 10/2022 Shelton, IV et al.
11,457,918 B2 10/2022 Shelton, IV et al.
11,464,511 B2 10/2022 Timm et al.
11,464,512 B2 10/2022 Shelton, IV et al.
11,464,513 B2 10/2022 Shelton, IV et al.
11,464,514 B2 10/2022 Yates et al.
11,464,601 B2 10/2022 Shelton, IV et al.
11,471,155 B2 10/2022 Shelton, IV et al.
11,471,156 B2 10/2022 Shelton, IV et al.
11,471,157 B2 10/2022 Baxter, III et al.
11,478,241 B2 10/2022 Shelton, IV et al.
11,478,242 B2 10/2022 Shelton, IV et al.
11,478,244 B2 10/2022 DiNardo et al.
D969,849 S 11/2022 Stipech et al.
D971,232 S 11/2022 Siebel et al.
11,484,307 B2 11/2022 Hall et al.
11,484,309 B2 11/2022 Harris et al.
11,484,310 B2 11/2022 Shelton, IV et al.
11,484,311 B2 11/2022 Shelton, IV et al.
11,484,312 B2 11/2022 Shelton, IV et al.
11,490,889 B2 11/2022 Overmyer et al.
11,497,488 B2 11/2022 Leimbach et al.
11,497,489 B2 11/2022 Baxter, III et al.
11,497,492 B2 11/2022 Shelton, IV
11,497,499 B2 11/2022 Shelton, IV et al.
11,504,116 B2 11/2022 Schmid et al.
11,504,119 B2 11/2022 Shelton, IV et al.
11,504,122 B2 11/2022 Shelton, IV et al.
11,504,192 B2 11/2022 Shelton, IV et al.
11,510,671 B2 11/2022 Shelton, IV et al.
11,510,673 B1 11/2022 Chen et al.
11,510,741 B2 11/2022 Shelton, IV et al.
11,517,304 B2 12/2022 Yates et al.
11,517,306 B2 12/2022 Miller et al.
11,517,309 B2 12/2022 Bakos et al.
11,517,311 B2 12/2022 Lytle, IV et al.
11,517,315 B2 12/2022 Huitema et al.
11,517,325 B2 12/2022 Shelton, IV et al.
11,517,390 B2 12/2022 Baxter, III
11,523,821 B2 12/2022 Harris et al.
11,523,822 B2 12/2022 Shelton, IV et al.
11,523,823 B2 12/2022 Hunter et al.
11,523,824 B2 12/2022 Williams
11,523,859 B2 12/2022 Shelton, IV et al.
11,529,137 B2 12/2022 Shelton, IV et al.
11,529,138 B2 12/2022 Jaworek et al.
11,529,139 B2 12/2022 Shelton, IV et al.
11,529,140 B2 12/2022 Shelton, IV et al.
11,529,142 B2 12/2022 Leimbach et al.
11,534,162 B2 12/2022 Shelton, IV
11,534,259 B2 12/2022 Leimbach et al.
D974,560 S 1/2023 Shelton, IV et al.
D975,278 S 1/2023 Shelton, IV et al.
D975,850 S 1/2023 Shelton, IV et al.
D975,851 S 1/2023 Shelton, IV et al.
D976,401 S 1/2023 Shelton, IV et al.
11,540,824 B2 1/2023 Shelton, IV et al.
11,540,829 B2 1/2023 Shelton, IV et al.
11,547,403 B2 1/2023 Shelton, IV et al.
11,547,404 B2 1/2023 Shelton, IV et al.
11,553,911 B2 1/2023 Shelton, IV et al.
11,553,916 B2 1/2023 Vendely et al.
11,553,919 B2 1/2023 Shelton, IV et al.
11,553,971 B2 1/2023 Shelton, IV et al.
11,559,302 B2 1/2023 Timm et al.
11,559,303 B2 1/2023 Shelton, IV et al.
11,559,304 B2 1/2023 Boudreaux et al.
11,559,307 B2 1/2023 Shelton, IV et al.
11,559,308 B2 1/2023 Yates et al.
11,559,496 B2 1/2023 Widenhouse et al.
11,564,679 B2 1/2023 Parihar et al.
11,564,682 B2 1/2023 Timm et al.
11,564,686 B2 1/2023 Yates et al.
11,564,688 B2 1/2023 Swayze et al.
11,564,703 B2 1/2023 Shelton, IV et al.
11,564,756 B2 1/2023 Shelton, IV et al.
11,571,207 B2 2/2023 Shelton, IV et al.
11,571,210 B2 2/2023 Shelton, IV et al.
11,571,212 B2 2/2023 Yates et al.
11,571,214 B2 * 2/2023 Sun .................. A61B 17/07207
11,571,215 B2 2/2023 Shelton, IV et al.
11,571,231 B2 2/2023 Hess et al.
11,576,668 B2 2/2023 Shelton, IV et al.
11,576,672 B2 2/2023 Shelton, IV et al.
11,576,673 B2 2/2023 Shelton, IV
11,576,677 B2 2/2023 Shelton, IV et al.
11,583,274 B2 2/2023 Widenhouse et al.
11,583,277 B2 2/2023 Shelton, IV et al.
11,583,278 B2 2/2023 Shelton, IV et al.
11,583,279 B2 2/2023 Smith et al.
11,589,863 B2 2/2023 Weir et al.
11,589,865 B2 2/2023 Shelton, IV et al.
11,589,888 B2 2/2023 Shelton, IV et al.
D980,425 S 3/2023 Baxter, III
11,596,406 B2 3/2023 Huitema et al.

(56) References Cited

U.S. PATENT DOCUMENTS 11,602,340 B2 3/2023 Schmid et al.
11,602,346 B2 3/2023 Shelton, IV
11,602,366 B2 3/2023 Shelton, IV et al.
11,607,219 B2 3/2023 Shelton, IV et al.
11,607,239 B2 3/2023 Swensgard et al.
11,607,278 B2 3/2023 Shelton, IV et al.
11,612,393 B2 3/2023 Morgan et al.
11,612,394 B2 3/2023 Morgan et al.
11,612,395 B2 3/2023 Yates et al.
11,617,575 B2 4/2023 Yates et al.
11,617,576 B2 4/2023 Yates et al.
11,617,577 B2 4/2023 Huang
11,622,763 B2 4/2023 Parihar et al.
11,622,766 B2 4/2023 Shelton, IV
11,622,785 B2 4/2023 Hess et al.
11,627,959 B2 4/2023 Shelton, IV et al.
11,627,960 B2 4/2023 Shelton, IV et al.
11,628,006 B2 4/2023 Henderson et al.
11,633,183 B2 4/2023 Parihar et al.
11,633,185 B2 4/2023 Wilson et al.
D985,009 S 5/2023 Barrett et al.
D985,617 S 5/2023 Bahatyrevich et al.
11,638,581 B2 5/2023 Parihar et al.
11,638,582 B2 5/2023 Bakos et al.
11,638,583 B2 5/2023 Yates et al.
11,638,587 B2 5/2023 Shelton, IV et al.
11,642,125 B2 5/2023 Harris et al.
11,642,128 B2 5/2023 Shelton, IV et al.
11,648,005 B2 5/2023 Yates et al.
11,648,006 B2 5/2023 Timm et al.
11,648,008 B2 5/2023 Shelton, IV et al.
11,648,009 B2 5/2023 Jenkins
11,648,022 B2 5/2023 Shelton, IV
11,648,024 B2 5/2023 Shelton, IV et al.
11,653,914 B2 5/2023 Shelton, IV et al.
11,653,915 B2 5/2023 Shelton, IV et al.
11,653,917 B2 5/2023 Scott et al.
11,653,918 B2 5/2023 Swayze et al.
11,653,920 B2 5/2023 Shelton, IV et al.
11,659,023 B2 5/2023 Shelton, IV et al.
11,660,090 B2 5/2023 Bakos et al.
11,660,110 B2 5/2023 Shelton, IV et al.
11,660,163 B2 5/2023 Shelton, IV et al.
11,666,327 B2 6/2023 Whitman et al.
11,666,332 B2 6/2023 Giordano et al.
11,672,531 B2 6/2023 Timm et al.
11,672,532 B2 6/2023 Shelton, IV et al.
11,672,536 B2 6/2023 Shelton, IV et al.
11,672,605 B2 6/2023 Messerly et al.
11,678,877 B2 6/2023 Shelton, IV et al.
11,678,880 B2 6/2023 Shelton, IV et al.
11,678,881 B2 6/2023 Yates et al.
11,678,882 B2 6/2023 Shelton, IV et al.
11,684,360 B2 6/2023 Shelton, IV et al.
11,684,361 B2 6/2023 Yates et al.
11,684,365 B2 6/2023 Shelton, IV et al.
11,684,369 B2 6/2023 Shelton, IV et al.
11,684,434 B2 6/2023 Shelton, IV
11,690,615 B2 7/2023 Parihar et al.
11,690,623 B2 7/2023 Shelton, IV et al.
11,696,757 B2 7/2023 Shelton, IV et al.
11,696,759 B2 7/2023 Shelton, IV et al.
11,696,761 B2 7/2023 Shelton, IV
11,696,778 B2 7/2023 Shelton, IV et al.
11,701,110 B2 7/2023 Yates et al.
11,701,111 B2 7/2023 Shelton, IV et al.
11,701,113 B2 7/2023 Shelton, IV et al.
11,701,114 B2 7/2023 Shelton, IV et al.
11,701,115 B2 7/2023 Harris et al.
11,701,118 B2 7/2023 Viola et al.
11,707,273 B2 7/2023 Kerr et al.
11,712,244 B2 8/2023 Vendely et al.
11,712,303 B2 8/2023 Shelton, IV et al.
11,717,285 B2 8/2023 Yates et al.
11,717,289 B2 8/2023 Leimbach
11,717,291 B2 8/2023 Morgan et al.
11,717,294 B2 8/2023 Huitema et al.
11,717,297 B2 8/2023 Baber et al.
11,723,657 B2 8/2023 Shelton, IV et al.
11,723,658 B2 8/2023 Bakos et al.
11,723,662 B2 8/2023 Leimbach et al.
11,730,471 B2 8/2023 Worthington et al.
11,730,473 B2 8/2023 Creamer et al.
11,730,474 B2 8/2023 Shelton, IV
11,730,477 B2 8/2023 Smith et al.
11,737,749 B2 8/2023 Shelton, IV et al.
11,737,751 B2 8/2023 Shelton, IV et al.
11,737,754 B2 8/2023 Shelton, IV et al.
11,744,581 B2 9/2023 Shelton, IV et al.
11,744,583 B2 9/2023 Shelton, IV et al.
11,744,588 B2 9/2023 Beckman et al.
11,744,593 B2 9/2023 Shelton, IV et al.
11,744,603 B2 9/2023 Shelton, IV et al.
11,744,604 B2 9/2023 Shelton, IV et al.
11,749,877 B2 9/2023 Shelton, IV et al.
11,751,867 B2 9/2023 Shelton, IV et al.
11,751,869 B2 9/2023 Shelton, IV et al.
11,751,872 B2 9/2023 Zeiner et al.
11,751,937 B2 9/2023 Harlev et al.
11,759,202 B2 9/2023 Morgan et al.
11,759,208 B2 9/2023 Harris et al.
11,759,224 B2 9/2023 Shelton, IV et al.
11,766,257 B2 9/2023 Shelton, IV et al.
11,766,258 B2 9/2023 Shelton, IV et al.
11,766,259 B2 9/2023 Shelton, IV et al.
11,766,260 B2 9/2023 Harris et al.
11,771,419 B2 10/2023 Shelton, IV et al.
11,771,425 B2 10/2023 Swayze et al.
11,771,426 B2 10/2023 Giordano et al.
11,771,454 B2 10/2023 Swensgard et al.
11,839,376 B2 12/2023 Li et al.
2001/0000531 A1 4/2001 Casscells et al.
2001/0025183 A1 9/2001 Shahidi
2001/0025184 A1 9/2001 Messerly
2001/0030219 A1 10/2001 Green et al.
2001/0034530 A1 10/2001 Malackowski et al.
2001/0045442 A1 11/2001 Whitman
2002/0014510 A1 2/2002 Richter et al.
2002/0022810 A1 2/2002 Urich
2002/0022836 A1 2/2002 Goble et al.
2002/0022861 A1 2/2002 Jacobs et al.
2002/0023126 A1 2/2002 Flavin
2002/0029032 A1 3/2002 Arkin
2002/0029036 A1 3/2002 Goble et al.
2002/0042620 A1 4/2002 Julian et al.
2002/0045905 A1 4/2002 Gerbi et al.
2002/0054158 A1 5/2002 Asami
2002/0065535 A1 5/2002 Kneifel et al.
2002/0066764 A1 6/2002 Perry et al.
2002/0077660 A1 6/2002 Kayan et al.
2002/0082612 A1 6/2002 Moll et al.
2002/0087048 A1 7/2002 Brock et al.
2002/0087148 A1 7/2002 Brock et al.
2002/0091374 A1 7/2002 Cooper
2002/0095175 A1 7/2002 Brock et al.
2002/0099374 A1 7/2002 Pendekanti et al.
2002/0103494 A1 8/2002 Pacey
2002/0111621 A1 8/2002 Wallace et al.
2002/0111624 A1 8/2002 Witt et al.
2002/0116063 A1 8/2002 Giannetti et al.
2002/0117533 A1 8/2002 Milliman et al.
2002/0117534 A1 8/2002 Green et al.
2002/0127265 A1 9/2002 Bowman et al.
2002/0128633 A1 9/2002 Brock et al.
2002/0133236 A1 9/2002 Rousseau
2002/0134811 A1 9/2002 Napier et al.
2002/0135474 A1 9/2002 Sylliassen
2002/0138086 A1 9/2002 Sixto et al.
2002/0143340 A1 10/2002 Kaneko
2002/0151770 A1 10/2002 Noll et al.
2002/0156497 A1 10/2002 Nagase et al.
2002/0158593 A1 10/2002 Henderson et al.
2002/0161277 A1 10/2002 Boone et al.
2002/0165559 A1 11/2002 Grant et al.

(56) References Cited

U.S. PATENT DOCUMENTS

| | | | |
|---|---|---|---|
| 2002/0165562 | A1 | 11/2002 | Grant et al. |
| 2002/0177848 | A1 | 11/2002 | Truckai et al. |
| 2002/0185514 | A1 | 12/2002 | Adams et al. |
| 2002/0188170 | A1 | 12/2002 | Santamore et al. |
| 2002/0188287 | A1 | 12/2002 | Zvuloni et al. |
| 2003/0004610 | A1 | 1/2003 | Niemeyer et al. |
| 2003/0009193 | A1 | 1/2003 | Corsaro |
| 2003/0011245 | A1 | 1/2003 | Fiebig |
| 2003/0012805 | A1 | 1/2003 | Chen et al. |
| 2003/0018323 | A1 | 1/2003 | Wallace et al. |
| 2003/0028236 | A1 | 2/2003 | Gillick et al. |
| 2003/0040670 | A1 | 2/2003 | Govari |
| 2003/0045835 | A1 | 3/2003 | Anderson et al. |
| 2003/0045900 | A1 | 3/2003 | Hahnen et al. |
| 2003/0047230 | A1 | 3/2003 | Kim |
| 2003/0047582 | A1 | 3/2003 | Sonnenschein et al. |
| 2003/0050628 | A1 | 3/2003 | Whitman et al. |
| 2003/0050654 | A1 | 3/2003 | Whitman et al. |
| 2003/0066858 | A1 | 4/2003 | Holgersson |
| 2003/0078647 | A1 | 4/2003 | Vallana et al. |
| 2003/0083648 | A1 | 5/2003 | Wang et al. |
| 2003/0084983 | A1 | 5/2003 | Rangachari et al. |
| 2003/0093103 | A1 | 5/2003 | Malackowski et al. |
| 2003/0093160 | A1 | 5/2003 | Maksimovic et al. |
| 2003/0094356 | A1 | 5/2003 | Waldron |
| 2003/0096158 | A1 | 5/2003 | Takano et al. |
| 2003/0105475 | A1 | 6/2003 | Sancoff et al. |
| 2003/0114851 | A1 | 6/2003 | Truckai et al. |
| 2003/0121586 | A1 | 7/2003 | Mitra et al. |
| 2003/0129382 | A1 | 7/2003 | Treat |
| 2003/0135204 | A1 | 7/2003 | Lee et al. |
| 2003/0135388 | A1 | 7/2003 | Martucci et al. |
| 2003/0139741 | A1 | 7/2003 | Goble et al. |
| 2003/0144660 | A1 | 7/2003 | Mollenauer |
| 2003/0149406 | A1 | 8/2003 | Martineau et al. |
| 2003/0153908 | A1 | 8/2003 | Goble et al. |
| 2003/0153968 | A1 | 8/2003 | Geis et al. |
| 2003/0158463 | A1 | 8/2003 | Julian et al. |
| 2003/0163029 | A1 | 8/2003 | Sonnenschein et al. |
| 2003/0163085 | A1 | 8/2003 | Tanner et al. |
| 2003/0164172 | A1 | 9/2003 | Chumas et al. |
| 2003/0181800 | A1 | 9/2003 | Bonutti |
| 2003/0181900 | A1 | 9/2003 | Long |
| 2003/0190584 | A1 | 10/2003 | Heasley |
| 2003/0195387 | A1 | 10/2003 | Kortenbach et al. |
| 2003/0205029 | A1 | 11/2003 | Chapolini et al. |
| 2003/0212005 | A1 | 11/2003 | Petito et al. |
| 2003/0216619 | A1 | 11/2003 | Scirica et al. |
| 2003/0216732 | A1 | 11/2003 | Truckai et al. |
| 2003/0220541 | A1 | 11/2003 | Salisbury et al. |
| 2003/0236505 | A1 | 12/2003 | Bonadio et al. |
| 2004/0006335 | A1 | 1/2004 | Garrison |
| 2004/0006340 | A1 | 1/2004 | Latterell et al. |
| 2004/0007608 | A1 | 1/2004 | Ehrenfels et al. |
| 2004/0024457 | A1 | 2/2004 | Boyce et al. |
| 2004/0028502 | A1 | 2/2004 | Cummins |
| 2004/0030333 | A1 | 2/2004 | Goble |
| 2004/0034287 | A1 | 2/2004 | Hickle |
| 2004/0034357 | A1 | 2/2004 | Beane et al. |
| 2004/0044295 | A1 | 3/2004 | Reinert et al. |
| 2004/0044364 | A1 | 3/2004 | DeVries et al. |
| 2004/0049121 | A1 | 3/2004 | Yaron |
| 2004/0049172 | A1 | 3/2004 | Root et al. |
| 2004/0059362 | A1 | 3/2004 | Knodel et al. |
| 2004/0068161 | A1 | 4/2004 | Couvillon |
| 2004/0068224 | A1 | 4/2004 | Couvillon et al. |
| 2004/0068307 | A1 | 4/2004 | Goble |
| 2004/0070369 | A1 | 4/2004 | Sakakibara |
| 2004/0073222 | A1 | 4/2004 | Koseki |
| 2004/0078037 | A1 | 4/2004 | Batchelor et al. |
| 2004/0082952 | A1 | 4/2004 | Dycus et al. |
| 2004/0085180 | A1 | 5/2004 | Juang |
| 2004/0092967 | A1 | 5/2004 | Sancoff et al. |
| 2004/0092992 | A1 | 5/2004 | Adams et al. |
| 2004/0093020 | A1 | 5/2004 | Sinton |
| 2004/0093024 | A1 | 5/2004 | Lousararian et al. |
| 2004/0098040 | A1 | 5/2004 | Taniguchi et al. |
| 2004/0101822 | A1 | 5/2004 | Wiesner et al. |
| 2004/0102783 | A1 | 5/2004 | Sutterlin et al. |
| 2004/0108357 | A1 | 6/2004 | Milliman et al. |
| 2004/0110439 | A1 | 6/2004 | Chaikof et al. |
| 2004/0115022 | A1 | 6/2004 | Albertson et al. |
| 2004/0116952 | A1 | 6/2004 | Sakurai et al. |
| 2004/0119185 | A1 | 6/2004 | Chen |
| 2004/0122419 | A1 | 6/2004 | Neuberger |
| 2004/0122423 | A1 | 6/2004 | Dycus et al. |
| 2004/0133095 | A1 | 7/2004 | Dunki-Jacobs et al. |
| 2004/0133189 | A1 | 7/2004 | Sakurai |
| 2004/0143297 | A1 | 7/2004 | Ramsey |
| 2004/0147909 | A1 | 7/2004 | Johnston et al. |
| 2004/0153100 | A1 | 8/2004 | Ahlberg et al. |
| 2004/0158261 | A1 | 8/2004 | Vu |
| 2004/0164123 | A1 | 8/2004 | Racenet et al. |
| 2004/0166169 | A1 | 8/2004 | Malaviya et al. |
| 2004/0167572 | A1 | 8/2004 | Roth et al. |
| 2004/0181219 | A1 | 9/2004 | Goble et al. |
| 2004/0193189 | A1 | 9/2004 | Kortenbach et al. |
| 2004/0197367 | A1 | 10/2004 | Rezania et al. |
| 2004/0199181 | A1 | 10/2004 | Knodel et al. |
| 2004/0204735 | A1 | 10/2004 | Shiroff et al. |
| 2004/0218451 | A1 | 11/2004 | Said et al. |
| 2004/0222268 | A1 | 11/2004 | Bilotti et al. |
| 2004/0225186 | A1 | 11/2004 | Horne et al. |
| 2004/0230230 | A1 | 11/2004 | Lindstrom et al. |
| 2004/0231870 | A1 | 11/2004 | McCormick et al. |
| 2004/0232194 | A1 | 11/2004 | Pedicini et al. |
| 2004/0232197 | A1 | 11/2004 | Shelton, IV et al. |
| 2004/0232201 | A1 | 11/2004 | Wenchell et al. |
| 2004/0236352 | A1 | 11/2004 | Wang et al. |
| 2004/0239582 | A1 | 12/2004 | Seymour |
| 2004/0243147 | A1 | 12/2004 | Lipow |
| 2004/0243151 | A1 | 12/2004 | Demmy et al. |
| 2004/0243163 | A1 | 12/2004 | Casiano et al. |
| 2004/0247415 | A1 | 12/2004 | Mangone |
| 2004/0249366 | A1 | 12/2004 | Kunz |
| 2004/0254455 | A1 | 12/2004 | Iddan |
| 2004/0254566 | A1 | 12/2004 | Plicchi et al. |
| 2004/0254590 | A1 | 12/2004 | Hoffman et al. |
| 2004/0254680 | A1 | 12/2004 | Sunaoshi |
| 2004/0260315 | A1 | 12/2004 | Dell et al. |
| 2004/0267310 | A1 | 12/2004 | Racenet et al. |
| 2004/0267362 | A1 | 12/2004 | Hwang et al. |
| 2005/0010158 | A1 | 1/2005 | Brugger et al. |
| 2005/0010213 | A1 | 1/2005 | Stad et al. |
| 2005/0021078 | A1 | 1/2005 | Vleugels et al. |
| 2005/0023325 | A1 | 2/2005 | Gresham et al. |
| 2005/0032511 | A1 | 2/2005 | Malone et al. |
| 2005/0033136 | A1 | 2/2005 | Govari et al. |
| 2005/0033352 | A1 | 2/2005 | Zepf et al. |
| 2005/0044489 | A1 | 2/2005 | Yamagami et al. |
| 2005/0051163 | A1 | 3/2005 | Deem et al. |
| 2005/0054946 | A1 | 3/2005 | Krzyzanowski |
| 2005/0057225 | A1 | 3/2005 | Marquet |
| 2005/0058890 | A1 | 3/2005 | Brazell et al. |
| 2005/0059997 | A1 | 3/2005 | Bauman et al. |
| 2005/0067548 | A1 | 3/2005 | Inoue |
| 2005/0070925 | A1 | 3/2005 | Shelton et al. |
| 2005/0070929 | A1 | 3/2005 | Dalessandro et al. |
| 2005/0074593 | A1 | 4/2005 | Day et al. |
| 2005/0075561 | A1 | 4/2005 | Golden |
| 2005/0079088 | A1 | 4/2005 | Wirth et al. |
| 2005/0080342 | A1 | 4/2005 | Gilreath et al. |
| 2005/0085693 | A1 | 4/2005 | Belson et al. |
| 2005/0085838 | A1 | 4/2005 | Thompson et al. |
| 2005/0090709 | A1 | 4/2005 | Okada et al. |
| 2005/0090817 | A1 | 4/2005 | Phan |
| 2005/0096683 | A1 | 5/2005 | Ellins et al. |
| 2005/0108643 | A1 | 5/2005 | Schybergson et al. |
| 2005/0116673 | A1 | 6/2005 | Carl et al. |
| 2005/0119524 | A1 | 6/2005 | Sekine et al. |
| 2005/0120836 | A1 | 6/2005 | Anderson |
| 2005/0121390 | A1 | 6/2005 | Wallace et al. |
| 2005/0124855 | A1 | 6/2005 | Jaffe et al. |
| 2005/0125028 | A1 | 6/2005 | Looper et al. |

(56) References Cited

U.S. PATENT DOCUMENTS

| | | | |
|---|---|---|---|
| 2005/0125897 | A1 | 6/2005 | Wyslucha et al. |
| 2005/0129730 | A1 | 6/2005 | Pang et al. |
| 2005/0129735 | A1 | 6/2005 | Cook et al. |
| 2005/0130682 | A1 | 6/2005 | Takara et al. |
| 2005/0131173 | A1 | 6/2005 | McDaniel et al. |
| 2005/0131211 | A1 | 6/2005 | Bayley et al. |
| 2005/0131390 | A1 | 6/2005 | Heinrich et al. |
| 2005/0131436 | A1 | 6/2005 | Johnston et al. |
| 2005/0131457 | A1 | 6/2005 | Douglas et al. |
| 2005/0137454 | A1 | 6/2005 | Saadat et al. |
| 2005/0137455 | A1 | 6/2005 | Ewers et al. |
| 2005/0139635 | A1 | 6/2005 | Wukusick et al. |
| 2005/0139636 | A1 | 6/2005 | Schwemberger et al. |
| 2005/0143759 | A1 | 6/2005 | Kelly |
| 2005/0143769 | A1 | 6/2005 | White et al. |
| 2005/0145671 | A1 | 7/2005 | Viola |
| 2005/0145672 | A1 | 7/2005 | Schwemberger et al. |
| 2005/0150928 | A1 | 7/2005 | Kameyama et al. |
| 2005/0154258 | A1 | 7/2005 | Tartaglia et al. |
| 2005/0154406 | A1 | 7/2005 | Bombard et al. |
| 2005/0159778 | A1 | 7/2005 | Heinrich et al. |
| 2005/0165419 | A1 | 7/2005 | Sauer et al. |
| 2005/0169974 | A1 | 8/2005 | Tenerz et al. |
| 2005/0171522 | A1 | 8/2005 | Christopherson |
| 2005/0177176 | A1 | 8/2005 | Gerbi et al. |
| 2005/0177181 | A1 | 8/2005 | Kagan et al. |
| 2005/0177249 | A1 | 8/2005 | Kladakis et al. |
| 2005/0178813 | A1 | 8/2005 | Swayze et al. |
| 2005/0182298 | A1 | 8/2005 | Ikeda et al. |
| 2005/0182443 | A1 | 8/2005 | Jonn et al. |
| 2005/0184121 | A1 | 8/2005 | Heinrich |
| 2005/0186240 | A1 | 8/2005 | Ringeisen et al. |
| 2005/0187545 | A1 | 8/2005 | Hooven et al. |
| 2005/0191936 | A1 | 9/2005 | Marine et al. |
| 2005/0197859 | A1 | 9/2005 | Wilson et al. |
| 2005/0203550 | A1 | 9/2005 | Laufer et al. |
| 2005/0209614 | A1 | 9/2005 | Fenter et al. |
| 2005/0216055 | A1 | 9/2005 | Scirica et al. |
| 2005/0222587 | A1 | 10/2005 | Jinno et al. |
| 2005/0222611 | A1 | 10/2005 | Weitkamp |
| 2005/0222616 | A1 | 10/2005 | Rethy et al. |
| 2005/0222665 | A1 | 10/2005 | Aranyi |
| 2005/0228224 | A1 | 10/2005 | Okada et al. |
| 2005/0228446 | A1 | 10/2005 | Mooradian et al. |
| 2005/0230453 | A1 | 10/2005 | Viola |
| 2005/0240178 | A1 | 10/2005 | Morley et al. |
| 2005/0242950 | A1 | 11/2005 | Lindsay et al. |
| 2005/0245965 | A1 | 11/2005 | Orban, III et al. |
| 2005/0246881 | A1 | 11/2005 | Kelly et al. |
| 2005/0251063 | A1 | 11/2005 | Basude |
| 2005/0251110 | A1 | 11/2005 | Nixon |
| 2005/0256452 | A1 | 11/2005 | DeMarchi et al. |
| 2005/0256546 | A1 | 11/2005 | Vaisnys et al. |
| 2005/0258963 | A1 | 11/2005 | Rodriguez et al. |
| 2005/0261676 | A1 | 11/2005 | Hall et al. |
| 2005/0263563 | A1 | 12/2005 | Racenet et al. |
| 2005/0267455 | A1 | 12/2005 | Eggers et al. |
| 2005/0267464 | A1 | 12/2005 | Truckai et al. |
| 2005/0267529 | A1 | 12/2005 | Crockett et al. |
| 2005/0274034 | A1 | 12/2005 | Hayashida et al. |
| 2005/0283188 | A1 | 12/2005 | Loshakove et al. |
| 2005/0283226 | A1 | 12/2005 | Haverkost |
| 2006/0000867 | A1 | 1/2006 | Shelton et al. |
| 2006/0008504 | A1 | 1/2006 | Kerr et al. |
| 2006/0008787 | A1 | 1/2006 | Hayman et al. |
| 2006/0011698 | A1 | 1/2006 | Okada et al. |
| 2006/0015009 | A1 | 1/2006 | Jaffe et al. |
| 2006/0019056 | A1 | 1/2006 | Turner et al. |
| 2006/0020167 | A1 | 1/2006 | Sitzmann |
| 2006/0020258 | A1 | 1/2006 | Strauss et al. |
| 2006/0020272 | A1 | 1/2006 | Gildenberg |
| 2006/0020336 | A1 | 1/2006 | Liddicoat |
| 2006/0025812 | A1 | 2/2006 | Shelton |
| 2006/0041188 | A1 | 2/2006 | Dirusso et al. |
| 2006/0047275 | A1 | 3/2006 | Goble |
| 2006/0049229 | A1 | 3/2006 | Milliman et al. |
| 2006/0052824 | A1 | 3/2006 | Ransick et al. |
| 2006/0052825 | A1 | 3/2006 | Ransick et al. |
| 2006/0053951 | A1* | 3/2006 | Revelis .................... G05G 1/46 74/527 |
| 2006/0064086 | A1 | 3/2006 | Odom |
| 2006/0079735 | A1 | 4/2006 | Martone et al. |
| 2006/0079874 | A1 | 4/2006 | Faller et al. |
| 2006/0079879 | A1 | 4/2006 | Faller et al. |
| 2006/0086032 | A1 | 4/2006 | Valencic et al. |
| 2006/0087746 | A1 | 4/2006 | Lipow |
| 2006/0089535 | A1 | 4/2006 | Raz et al. |
| 2006/0089628 | A1 | 4/2006 | Whitman |
| 2006/0097026 | A1 | 5/2006 | Shelton, IV |
| 2006/0097699 | A1 | 5/2006 | Kamenoff |
| 2006/0100643 | A1 | 5/2006 | Laufer et al. |
| 2006/0100649 | A1 | 5/2006 | Hart |
| 2006/0106369 | A1 | 5/2006 | Desai et al. |
| 2006/0111711 | A1 | 5/2006 | Goble |
| 2006/0111723 | A1 | 5/2006 | Chapolini et al. |
| 2006/0111738 | A1 | 5/2006 | Wenchell |
| 2006/0116634 | A1 | 6/2006 | Shachar |
| 2006/0142656 | A1 | 6/2006 | Malackowski et al. |
| 2006/0142772 | A1 | 6/2006 | Ralph et al. |
| 2006/0144898 | A1 | 7/2006 | Bilotti et al. |
| 2006/0154546 | A1 | 7/2006 | Murphy et al. |
| 2006/0161050 | A1 | 7/2006 | Butler et al. |
| 2006/0161185 | A1 | 7/2006 | Saadat et al. |
| 2006/0167471 | A1 | 7/2006 | Phillips |
| 2006/0173290 | A1 | 8/2006 | Lavallee et al. |
| 2006/0173470 | A1 | 8/2006 | Oray et al. |
| 2006/0176031 | A1 | 8/2006 | Forman et al. |
| 2006/0176242 | A1 | 8/2006 | Jaramaz et al. |
| 2006/0178556 | A1 | 8/2006 | Hasser et al. |
| 2006/0180633 | A1 | 8/2006 | Emmons |
| 2006/0180634 | A1 | 8/2006 | Shelton et al. |
| 2006/0185682 | A1 | 8/2006 | Marczyk |
| 2006/0189440 | A1 | 8/2006 | Gravagne |
| 2006/0199999 | A1 | 9/2006 | Ikeda et al. |
| 2006/0201989 | A1 | 9/2006 | Ojeda |
| 2006/0206100 | A1 | 9/2006 | Eskridge et al. |
| 2006/0217729 | A1 | 9/2006 | Eskridge et al. |
| 2006/0226196 | A1 | 10/2006 | Hueil et al. |
| 2006/0226957 | A1 | 10/2006 | Miller et al. |
| 2006/0235368 | A1 | 10/2006 | Oz |
| 2006/0241666 | A1 | 10/2006 | Briggs et al. |
| 2006/0241691 | A1 | 10/2006 | Wilk |
| 2006/0244460 | A1 | 11/2006 | Weaver |
| 2006/0247584 | A1 | 11/2006 | Sheetz et al. |
| 2006/0252981 | A1 | 11/2006 | Matsuda et al. |
| 2006/0252990 | A1 | 11/2006 | Kubach |
| 2006/0252993 | A1 | 11/2006 | Freed et al. |
| 2006/0258904 | A1 | 11/2006 | Stefanchik et al. |
| 2006/0259073 | A1 | 11/2006 | Miyamoto et al. |
| 2006/0261763 | A1 | 11/2006 | Iott et al. |
| 2006/0263444 | A1 | 11/2006 | Ming et al. |
| 2006/0264831 | A1 | 11/2006 | Skwarek et al. |
| 2006/0264929 | A1 | 11/2006 | Goble et al. |
| 2006/0271042 | A1 | 11/2006 | Latterell et al. |
| 2006/0271102 | A1 | 11/2006 | Bosshard et al. |
| 2006/0282064 | A1 | 12/2006 | Shimizu et al. |
| 2006/0284730 | A1 | 12/2006 | Schmid et al. |
| 2006/0287576 | A1 | 12/2006 | Tsuji et al. |
| 2006/0289600 | A1 | 12/2006 | Wales et al. |
| 2006/0289602 | A1 | 12/2006 | Wales et al. |
| 2006/0291981 | A1 | 12/2006 | Viola et al. |
| 2007/0005045 | A1 | 1/2007 | Mintz et al. |
| 2007/0009570 | A1 | 1/2007 | Kim et al. |
| 2007/0010702 | A1 | 1/2007 | Wang et al. |
| 2007/0010838 | A1 | 1/2007 | Shelton et al. |
| 2007/0016235 | A1 | 1/2007 | Tanaka et al. |
| 2007/0016272 | A1 | 1/2007 | Thompson et al. |
| 2007/0018958 | A1 | 1/2007 | Tavakoli et al. |
| 2007/0026039 | A1 | 2/2007 | Drumheller et al. |
| 2007/0026040 | A1 | 2/2007 | Crawley et al. |
| 2007/0027459 | A1 | 2/2007 | Horvath et al. |
| 2007/0027468 | A1 | 2/2007 | Wales et al. |
| 2007/0027551 | A1 | 2/2007 | Farnsworth et al. |
| 2007/0034668 | A1 | 2/2007 | Holsten et al. |

(56) References Cited

U.S. PATENT DOCUMENTS

2007/0034669 A1 2/2007 de la Torre et al.
2007/0043338 A1 2/2007 Moll et al.
2007/0043384 A1 2/2007 Ortiz et al.
2007/0043387 A1 2/2007 Vargas et al.
2007/0049951 A1 3/2007 Menn
2007/0049966 A1 3/2007 Bonadio et al.
2007/0051375 A1 3/2007 Milliman
2007/0055228 A1 3/2007 Berg et al.
2007/0055305 A1 3/2007 Schnyder et al.
2007/0069851 A1 3/2007 Sung et al.
2007/0073341 A1 3/2007 Smith et al.
2007/0073389 A1 3/2007 Bolduc et al.
2007/0078328 A1 4/2007 Ozaki et al.
2007/0078484 A1 4/2007 Talarico et al.
2007/0084897 A1 4/2007 Shelton et al.
2007/0088376 A1 4/2007 Zacharias
2007/0090788 A1 4/2007 Hansford et al.
2007/0093869 A1 4/2007 Bloom et al.
2007/0102472 A1 5/2007 Shelton
2007/0102476 A1 5/2007 Shelton et al.
2007/0103437 A1 5/2007 Rosenberg
2007/0106113 A1 5/2007 Ravo
2007/0106317 A1 5/2007 Shelton et al.
2007/0118115 A1 5/2007 Artale et al.
2007/0134251 A1 6/2007 Ashkenazi et al.
2007/0135686 A1 6/2007 Pruitt et al.
2007/0135803 A1 6/2007 Belson
2007/0152612 A1 7/2007 Chen et al.
2007/0152829 A1 7/2007 Lindsay et al.
2007/0155010 A1 7/2007 Farnsworth et al.
2007/0162056 A1 7/2007 Gerbi et al.
2007/0170225 A1 7/2007 Shelton et al.
2007/0173687 A1 7/2007 Shima et al.
2007/0173813 A1 7/2007 Odom
2007/0173872 A1 7/2007 Neuenfeldt
2007/0175950 A1 8/2007 Shelton et al.
2007/0175951 A1 8/2007 Shelton et al.
2007/0175955 A1 8/2007 Shelton et al.
2007/0179476 A1 8/2007 Shelton et al.
2007/0179477 A1 8/2007 Danger
2007/0185545 A1 8/2007 Duke
2007/0187857 A1 8/2007 Riley et al.
2007/0190110 A1 8/2007 Pameijer et al.
2007/0191868 A1 8/2007 Theroux et al.
2007/0191915 A1 8/2007 Strother et al.
2007/0194079 A1 8/2007 Hueil et al.
2007/0194081 A1 8/2007 Hueil et al.
2007/0194082 A1 8/2007 Morgan et al.
2007/0197954 A1 8/2007 Keenan
2007/0198039 A1 8/2007 Jones et al.
2007/0203510 A1 8/2007 Bettuchi
2007/0207010 A1 9/2007 Caspi
2007/0207186 A1 9/2007 Scanlon et al.
2007/0208359 A1 9/2007 Hoffman
2007/0208375 A1 9/2007 Nishizawa et al.
2007/0213750 A1 9/2007 Weadock
2007/0221701 A1 9/2007 Ortiz et al.
2007/0225562 A1 9/2007 Spivey et al.
2007/0233163 A1 10/2007 Bombard et al.
2007/0243227 A1 10/2007 Gertner
2007/0244471 A1 10/2007 Malackowski
2007/0244496 A1 10/2007 Hellenkamp
2007/0246505 A1 10/2007 Pace-Floridia et al.
2007/0250093 A1 10/2007 Makower et al.
2007/0260132 A1 11/2007 Sterling
2007/0260242 A1 11/2007 Dycus et al.
2007/0262592 A1 11/2007 Hwang et al.
2007/0270660 A1 11/2007 Caylor et al.
2007/0270790 A1 11/2007 Smith et al.
2007/0275035 A1 11/2007 Herman et al.
2007/0276409 A1 11/2007 Ortiz et al.
2007/0279011 A1 12/2007 Jones et al.
2007/0286892 A1 12/2007 Herzberg et al.
2007/0290027 A1 12/2007 Maatta et al.
2007/0296286 A1 12/2007 Avenell
2008/0000941 A1 1/2008 Sonnenschein et al.
2008/0003196 A1 1/2008 Jonn et al.
2008/0007237 A1 1/2008 Nagashima et al.
2008/0015598 A1 1/2008 Prommersberger
2008/0021486 A1 1/2008 Oyola et al.
2008/0029570 A1 2/2008 Shelton et al.
2008/0029573 A1 2/2008 Shelton et al.
2008/0029574 A1 2/2008 Shelton et al.
2008/0029575 A1 2/2008 Shelton et al.
2008/0029576 A1 2/2008 Shelton et al.
2008/0030170 A1 2/2008 Dacquay et al.
2008/0039746 A1 2/2008 Hissong et al.
2008/0042861 A1 2/2008 Dacquay et al.
2008/0046000 A1 2/2008 Lee et al.
2008/0051833 A1 2/2008 Gramuglia et al.
2008/0064920 A1 3/2008 Bakos et al.
2008/0064921 A1 3/2008 Larkin et al.
2008/0065153 A1 3/2008 Allard et al.
2008/0069736 A1 3/2008 Mingerink et al.
2008/0071328 A1 3/2008 Haubrich et al.
2008/0077158 A1 3/2008 Haider et al.
2008/0078802 A1 4/2008 Hess et al.
2008/0081948 A1 4/2008 Weisenburgh et al.
2008/0082114 A1 4/2008 McKenna et al.
2008/0082125 A1 4/2008 Murray et al.
2008/0082126 A1 4/2008 Murray et al.
2008/0083807 A1 4/2008 Beardsley et al.
2008/0083811 A1 4/2008 Marczyk
2008/0085296 A1 4/2008 Powell et al.
2008/0086078 A1 4/2008 Powell et al.
2008/0091072 A1 4/2008 Omori et al.
2008/0094228 A1 4/2008 Welch et al.
2008/0108443 A1 5/2008 Jinno et al.
2008/0114250 A1 5/2008 Urbano et al.
2008/0125634 A1 5/2008 Ryan et al.
2008/0125749 A1 5/2008 Olson
2008/0126984 A1 5/2008 Fleishman et al.
2008/0128469 A1 6/2008 Dalessandro et al.
2008/0129253 A1 6/2008 Shiue et al.
2008/0135600 A1 6/2008 Hiranuma et al.
2008/0140088 A1 6/2008 Orban, III
2008/0140115 A1 6/2008 Stopek
2008/0140159 A1 6/2008 Bornhoft et al.
2008/0149682 A1 6/2008 Uhm
2008/0154299 A1 6/2008 Livneh
2008/0154335 A1 6/2008 Thrope et al.
2008/0169328 A1 7/2008 Shelton
2008/0169330 A1 7/2008 Shelton et al.
2008/0169332 A1 7/2008 Shelton et al.
2008/0169333 A1 7/2008 Shelton et al.
2008/0172087 A1 7/2008 Fuchs et al.
2008/0177392 A1 7/2008 Williams et al.
2008/0190989 A1 8/2008 Crews et al.
2008/0196253 A1 8/2008 Ezra et al.
2008/0196419 A1 8/2008 Dube
2008/0197167 A1 8/2008 Viola et al.
2008/0200755 A1 8/2008 Bakos
2008/0200762 A1 8/2008 Stokes et al.
2008/0200835 A1 8/2008 Monson et al.
2008/0200911 A1 8/2008 Long
2008/0200933 A1 8/2008 Bakos et al.
2008/0200934 A1 8/2008 Fox
2008/0206186 A1 8/2008 Butler et al.
2008/0208058 A1 8/2008 Sabata et al.
2008/0214967 A1 9/2008 Aranyi et al.
2008/0216704 A1 9/2008 Eisenbeis et al.
2008/0217376 A1 9/2008 Clauson et al.
2008/0234709 A1 9/2008 Houser
2008/0234866 A1 9/2008 Kishi et al.
2008/0237296 A1 10/2008 Boudreaux et al.
2008/0242939 A1 10/2008 Johnston
2008/0243088 A1 10/2008 Evans
2008/0243143 A1 10/2008 Kuhns et al.
2008/0249536 A1 10/2008 Stahler et al.
2008/0249608 A1 10/2008 Dave
2008/0255413 A1 10/2008 Zemlok et al.
2008/0255420 A1 10/2008 Lee et al.
2008/0255421 A1 10/2008 Hegeman et al.
2008/0255663 A1 10/2008 Akpek et al.

(56) References Cited

U.S. PATENT DOCUMENTS

2008/0262654 A1 10/2008 Omori et al.
2008/0269596 A1 10/2008 Revie et al.
2008/0281171 A1 11/2008 Fennell et al.
2008/0281332 A1 11/2008 Taylor
2008/0287944 A1 11/2008 Pearson et al.
2008/0293910 A1 11/2008 Kapiamba et al.
2008/0294179 A1 11/2008 Balbierz et al.
2008/0296343 A1 12/2008 Schall et al.
2008/0296346 A1 12/2008 Shelton, IV et al.
2008/0296347 A1 12/2008 Shelton, IV et al.
2008/0297287 A1 12/2008 Shachar et al.
2008/0298784 A1 12/2008 Kastner
2008/0300579 A1 12/2008 Broehl et al.
2008/0308504 A1 12/2008 Hallan et al.
2008/0308602 A1 12/2008 Timm et al.
2008/0308603 A1 12/2008 Shelton et al.
2008/0308607 A1 12/2008 Timm et al.
2008/0308608 A1 12/2008 Prommersberger
2008/0308807 A1 12/2008 Yamazaki et al.
2008/0312686 A1 12/2008 Ellingwood
2008/0312687 A1 12/2008 Blier
2008/0315829 A1 12/2008 Jones et al.
2009/0001121 A1 1/2009 Hess et al.
2009/0001130 A1 1/2009 Hess et al.
2009/0004455 A1 1/2009 Gravagna et al.
2009/0005809 A1 1/2009 Hess et al.
2009/0007014 A1 1/2009 Coomer et al.
2009/0012534 A1 1/2009 Madhani et al.
2009/0015195 A1 1/2009 Loth-Krausser
2009/0020958 A1 1/2009 Soul
2009/0030437 A1 1/2009 Houser et al.
2009/0043253 A1 2/2009 Podaima
2009/0048583 A1 2/2009 Williams et al.
2009/0048589 A1 2/2009 Takashino et al.
2009/0053288 A1 2/2009 Eskridge, Jr. et al.
2009/0057369 A1 3/2009 Smith et al.
2009/0069806 A1 3/2009 De La Mora Levy et al.
2009/0076506 A1 3/2009 Baker
2009/0076510 A1 3/2009 Bell et al.
2009/0078736 A1 3/2009 Van Lue
2009/0078739 A1 3/2009 Viola
2009/0081313 A1 3/2009 Aghion et al.
2009/0088659 A1 4/2009 Graham et al.
2009/0090763 A1 4/2009 Zemlok et al.
2009/0099579 A1 4/2009 Nentwick et al.
2009/0099876 A1 4/2009 Whitman
2009/0110533 A1 4/2009 Jinno
2009/0112234 A1 4/2009 Crainich et al.
2009/0114701 A1 5/2009 Zemlok et al.
2009/0118762 A1 5/2009 Crainch et al.
2009/0119011 A1 5/2009 Kondo et al.
2009/0120994 A1 5/2009 Murray et al.
2009/0131819 A1 5/2009 Ritchie et al.
2009/0132400 A1 5/2009 Conway
2009/0135280 A1 5/2009 Johnston et al.
2009/0138003 A1 5/2009 Deville et al.
2009/0143797 A1 6/2009 Smith et al.
2009/0143855 A1 6/2009 Weber et al.
2009/0149871 A9 6/2009 Kagan et al.
2009/0167548 A1 7/2009 Sugahara
2009/0171147 A1 7/2009 Lee et al.
2009/0177218 A1 7/2009 Young et al.
2009/0177226 A1 7/2009 Reinprecht et al.
2009/0181290 A1 7/2009 Baldwin et al.
2009/0188964 A1 7/2009 Orlov
2009/0192534 A1 7/2009 Ortiz et al.
2009/0196903 A1 8/2009 Kliman
2009/0198272 A1 8/2009 Kerver et al.
2009/0204108 A1 8/2009 Steffen
2009/0204109 A1 8/2009 Grove et al.
2009/0204126 A1 8/2009 Le
2009/0204925 A1 8/2009 Bhat et al.
2009/0206125 A1 8/2009 Huitema et al.
2009/0206126 A1 8/2009 Huitema et al.
2009/0206131 A1 8/2009 Weisenburgh, II et al.
2009/0206133 A1 8/2009 Morgan et al.
2009/0206137 A1 8/2009 Hall et al.
2009/0206139 A1 8/2009 Hall et al.
2009/0206141 A1 8/2009 Huitema et al.
2009/0206142 A1 8/2009 Huitema et al.
2009/0206143 A1 8/2009 Huitema et al.
2009/0218384 A1 9/2009 Aranyi
2009/0221993 A1 9/2009 Sohi et al.
2009/0227834 A1 9/2009 Nakamoto et al.
2009/0234273 A1 9/2009 Intoccia et al.
2009/0236401 A1 9/2009 Cole et al.
2009/0242610 A1 10/2009 Shelton, IV et al.
2009/0246873 A1 10/2009 Yamamoto et al.
2009/0247368 A1 10/2009 Chiang
2009/0247901 A1 10/2009 Zimmer
2009/0248100 A1 10/2009 Vaisnys et al.
2009/0253959 A1 10/2009 Yoshie et al.
2009/0255974 A1 10/2009 Viola
2009/0255977 A1 10/2009 Zemlok
2009/0261141 A1 10/2009 Stratton et al.
2009/0262078 A1 10/2009 Pizzi
2009/0264940 A1 10/2009 Beale et al.
2009/0270895 A1 10/2009 Churchill et al.
2009/0273353 A1 11/2009 Kroh et al.
2009/0277288 A1 11/2009 Doepker et al.
2009/0278406 A1 11/2009 Hoffman
2009/0287300 A1 11/2009 Dave et al.
2009/0290016 A1 11/2009 Suda
2009/0292283 A1 11/2009 Odom
2009/0306639 A1 12/2009 Nevo et al.
2009/0308907 A1 12/2009 Nalagatla et al.
2009/0318557 A1 12/2009 Stockel
2009/0318936 A1 12/2009 Harris et al.
2009/0325859 A1 12/2009 Ameer et al.
2010/0002013 A1 1/2010 Kagaya
2010/0005035 A1 1/2010 Carpenter et al.
2010/0012703 A1 1/2010 Calabrese et al.
2010/0015104 A1 1/2010 Fraser et al.
2010/0016853 A1 1/2010 Burbank
2010/0016888 A1 1/2010 Calabrese et al.
2010/0017715 A1 1/2010 Balassanian
2010/0023024 A1 1/2010 Zeiner et al.
2010/0030233 A1 2/2010 Whitman et al.
2010/0030239 A1 2/2010 Viola et al.
2010/0032179 A1 2/2010 Hanspers et al.
2010/0032470 A1 2/2010 Hess et al.
2010/0036370 A1 2/2010 Mirel et al.
2010/0036441 A1 2/2010 Procter
2010/0051668 A1 3/2010 Milliman et al.
2010/0057118 A1 3/2010 Dietz et al.
2010/0065604 A1 3/2010 Weng
2010/0069833 A1 3/2010 Wenderow et al.
2010/0069942 A1 3/2010 Shelton, IV
2010/0076433 A1 3/2010 Taylor et al.
2010/0076483 A1 3/2010 Imuta
2010/0076489 A1 3/2010 Stopek et al.
2010/0081883 A1 4/2010 Murray et al.
2010/0089970 A1* 4/2010 Smith ................ A61B 17/0686
227/175.1
2010/0094312 A1 4/2010 Ruiz Morales et al.
2010/0094340 A1 4/2010 Stopek et al.
2010/0094400 A1 4/2010 Bolduc et al.
2010/0100123 A1 4/2010 Bennett
2010/0100124 A1 4/2010 Calabrese et al.
2010/0106167 A1 4/2010 Boulnois et al.
2010/0116519 A1 5/2010 Gareis
2010/0122339 A1 5/2010 Boccacci
2010/0125786 A1 5/2010 Ozawa et al.
2010/0133317 A1 6/2010 Shelton, IV et al.
2010/0137990 A1 6/2010 Apatsidis et al.
2010/0138659 A1 6/2010 Carmichael et al.
2010/0145146 A1 6/2010 Melder
2010/0147921 A1 6/2010 Olson
2010/0147922 A1 6/2010 Olson
2010/0159435 A1 6/2010 Mueller et al.
2010/0168741 A1 7/2010 Sanai et al.
2010/0179022 A1 7/2010 Shirokoshi
2010/0180711 A1 7/2010 Kilibarda et al.
2010/0181364 A1 7/2010 Shelton, IV et al.

(56) References Cited

U.S. PATENT DOCUMENTS

| | | | |
|---|---|---|---|
| 2010/0187285 | A1 | 7/2010 | Harris et al. |
| 2010/0191255 | A1 | 7/2010 | Crainich et al. |
| 2010/0191262 | A1 | 7/2010 | Harris et al. |
| 2010/0191292 | A1 | 7/2010 | DeMeo et al. |
| 2010/0193566 | A1 | 8/2010 | Scheib et al. |
| 2010/0194541 | A1 | 8/2010 | Stevenson et al. |
| 2010/0198159 | A1 | 8/2010 | Voss et al. |
| 2010/0204717 | A1 | 8/2010 | Knodel |
| 2010/0204721 | A1 | 8/2010 | Young et al. |
| 2010/0217281 | A1 | 8/2010 | Matsuoka et al. |
| 2010/0218019 | A1 | 8/2010 | Eckhard |
| 2010/0222901 | A1 | 9/2010 | Swayze et al. |
| 2010/0228250 | A1 | 9/2010 | Brogna |
| 2010/0234687 | A1 | 9/2010 | Azarbarzin et al. |
| 2010/0241115 | A1 | 9/2010 | Benamou et al. |
| 2010/0241137 | A1 | 9/2010 | Doyle et al. |
| 2010/0243707 | A1 | 9/2010 | Olson et al. |
| 2010/0245102 | A1 | 9/2010 | Yokoi |
| 2010/0249497 | A1 | 9/2010 | Peine et al. |
| 2010/0249947 | A1 | 9/2010 | Lesh et al. |
| 2010/0256675 | A1 | 10/2010 | Romans |
| 2010/0258327 | A1 | 10/2010 | Esenwein et al. |
| 2010/0267525 | A1 | 10/2010 | Tanner |
| 2010/0267662 | A1 | 10/2010 | Fielder et al. |
| 2010/0274160 | A1 | 10/2010 | Yachi et al. |
| 2010/0291184 | A1 | 11/2010 | Clark et al. |
| 2010/0292540 | A1 | 11/2010 | Hess et al. |
| 2010/0298636 | A1 | 11/2010 | Castro et al. |
| 2010/0298642 | A1 | 11/2010 | Trusty et al. |
| 2010/0301097 | A1 | 12/2010 | Scirica et al. |
| 2010/0310623 | A1 | 12/2010 | Laurencin et al. |
| 2010/0312261 | A1 | 12/2010 | Suzuki et al. |
| 2010/0318085 | A1 | 12/2010 | Austin et al. |
| 2010/0325568 | A1 | 12/2010 | Pedersen et al. |
| 2010/0327041 | A1 | 12/2010 | Milliman et al. |
| 2010/0331856 | A1 | 12/2010 | Carlson et al. |
| 2011/0006101 | A1 | 1/2011 | Hall et al. |
| 2011/0009694 | A1 | 1/2011 | Schultz et al. |
| 2011/0009863 | A1 | 1/2011 | Marczyk et al. |
| 2011/0011916 | A1 | 1/2011 | Levine |
| 2011/0016960 | A1 | 1/2011 | Debrailly |
| 2011/0021871 | A1 | 1/2011 | Berkelaar |
| 2011/0022032 | A1 | 1/2011 | Zemlok et al. |
| 2011/0024477 | A1 | 2/2011 | Hall |
| 2011/0024478 | A1 | 2/2011 | Shelton, IV |
| 2011/0025311 | A1 | 2/2011 | Chauvin et al. |
| 2011/0028991 | A1 | 2/2011 | Ikeda et al. |
| 2011/0029003 | A1 | 2/2011 | Lavigne et al. |
| 2011/0029270 | A1 | 2/2011 | Mueglitz |
| 2011/0036891 | A1 | 2/2011 | Zemlok et al. |
| 2011/0046667 | A1 | 2/2011 | Culligan et al. |
| 2011/0052660 | A1 | 3/2011 | Yang et al. |
| 2011/0056717 | A1 | 3/2011 | Herisse |
| 2011/0060363 | A1 | 3/2011 | Hess et al. |
| 2011/0066156 | A1 | 3/2011 | McGahan et al. |
| 2011/0066243 | A1 | 3/2011 | Rivin et al. |
| 2011/0071473 | A1 | 3/2011 | Rogers et al. |
| 2011/0082538 | A1 | 4/2011 | Dahlgren et al. |
| 2011/0087276 | A1 | 4/2011 | Bedi et al. |
| 2011/0088921 | A1 | 4/2011 | Forgues et al. |
| 2011/0091515 | A1 | 4/2011 | Zilberman et al. |
| 2011/0095064 | A1 | 4/2011 | Taylor et al. |
| 2011/0095067 | A1 | 4/2011 | Ohdaira |
| 2011/0101069 | A1 | 5/2011 | Bombard et al. |
| 2011/0101794 | A1 | 5/2011 | Schroeder et al. |
| 2011/0112513 | A1 | 5/2011 | Hester et al. |
| 2011/0112517 | A1 | 5/2011 | Peine et al. |
| 2011/0112530 | A1 | 5/2011 | Keller |
| 2011/0114697 | A1 | 5/2011 | Baxter, III et al. |
| 2011/0118708 | A1 | 5/2011 | Burbank et al. |
| 2011/0118754 | A1 | 5/2011 | Dachs, II et al. |
| 2011/0125149 | A1 | 5/2011 | El-Galley et al. |
| 2011/0125176 | A1 | 5/2011 | Yates et al. |
| 2011/0127945 | A1 | 6/2011 | Yoneda |
| 2011/0129706 | A1 | 6/2011 | Takahashi et al. |
| 2011/0144764 | A1 | 6/2011 | Bagga et al. |
| 2011/0147433 | A1 | 6/2011 | Shelton, IV et al. |
| 2011/0160725 | A1 | 6/2011 | Kabaya et al. |
| 2011/0163146 | A1 | 7/2011 | Ortiz et al. |
| 2011/0172495 | A1 | 7/2011 | Armstrong |
| 2011/0174861 | A1 | 7/2011 | Shelton, IV et al. |
| 2011/0189957 | A1 | 8/2011 | Hocke |
| 2011/0192882 | A1 | 8/2011 | Hess et al. |
| 2011/0198381 | A1 | 8/2011 | McCardle et al. |
| 2011/0199225 | A1 | 8/2011 | Touchberry et al. |
| 2011/0218400 | A1 | 9/2011 | Ma et al. |
| 2011/0218550 | A1 | 9/2011 | Ma |
| 2011/0220381 | A1 | 9/2011 | Friese et al. |
| 2011/0224543 | A1 | 9/2011 | Johnson et al. |
| 2011/0225105 | A1 | 9/2011 | Scholer et al. |
| 2011/0230713 | A1 | 9/2011 | Kleemann et al. |
| 2011/0235168 | A1 | 9/2011 | Sander |
| 2011/0238044 | A1 | 9/2011 | Main et al. |
| 2011/0241597 | A1 | 10/2011 | Zhu et al. |
| 2011/0251606 | A1 | 10/2011 | Kerr |
| 2011/0256266 | A1 | 10/2011 | Orme et al. |
| 2011/0271186 | A1 | 11/2011 | Owens |
| 2011/0275901 | A1 | 11/2011 | Shelton, IV |
| 2011/0276083 | A1 | 11/2011 | Shelton, IV et al. |
| 2011/0278035 | A1 | 11/2011 | Chen |
| 2011/0278343 | A1 | 11/2011 | Knodel et al. |
| 2011/0279268 | A1 | 11/2011 | Konishi et al. |
| 2011/0285507 | A1 | 11/2011 | Nelson |
| 2011/0290856 | A1 | 12/2011 | Shelton, IV et al. |
| 2011/0290858 | A1 | 12/2011 | Whitman et al. |
| 2011/0292258 | A1 | 12/2011 | Adler et al. |
| 2011/0293690 | A1 | 12/2011 | Griffin et al. |
| 2011/0295295 | A1 | 12/2011 | Shelton, IV et al. |
| 2011/0295299 | A1 | 12/2011 | Braithwaite et al. |
| 2011/0313894 | A1 | 12/2011 | Dye et al. |
| 2011/0315413 | A1 | 12/2011 | Fisher et al. |
| 2012/0004636 | A1 | 1/2012 | Lo |
| 2012/0007442 | A1 | 1/2012 | Rhodes et al. |
| 2012/0008880 | A1 | 1/2012 | Toth |
| 2012/0010615 | A1 | 1/2012 | Cummings et al. |
| 2012/0016239 | A1 | 1/2012 | Barthe et al. |
| 2012/0016413 | A1 | 1/2012 | Timm et al. |
| 2012/0016467 | A1 | 1/2012 | Chen et al. |
| 2012/0018487 | A1 | 1/2012 | Bettuchi et al. |
| 2012/0029272 | A1 | 2/2012 | Shelton, IV et al. |
| 2012/0029550 | A1 | 2/2012 | Forsell |
| 2012/0033360 | A1 | 2/2012 | Hsu |
| 2012/0043100 | A1 | 2/2012 | Isobe et al. |
| 2012/0059286 | A1 | 3/2012 | Hastings et al. |
| 2012/0064483 | A1 | 3/2012 | Lint et al. |
| 2012/0074200 | A1 | 3/2012 | Schmid et al. |
| 2012/0078243 | A1 | 3/2012 | Worrell et al. |
| 2012/0078244 | A1 | 3/2012 | Worrell et al. |
| 2012/0080336 | A1 | 4/2012 | Shelton, IV et al. |
| 2012/0080344 | A1 | 4/2012 | Shelton, IV |
| 2012/0080478 | A1 | 4/2012 | Morgan et al. |
| 2012/0080491 | A1 | 4/2012 | Shelton, IV et al. |
| 2012/0080498 | A1 | 4/2012 | Shelton, IV et al. |
| 2012/0083836 | A1 | 4/2012 | Shelton, IV et al. |
| 2012/0086276 | A1 | 4/2012 | Sawyers |
| 2012/0095458 | A1 | 4/2012 | Cybulski et al. |
| 2012/0101488 | A1 | 4/2012 | Aldridge et al. |
| 2012/0109186 | A1 | 5/2012 | Parrott et al. |
| 2012/0116261 | A1 | 5/2012 | Mumaw et al. |
| 2012/0116262 | A1 | 5/2012 | Houser et al. |
| 2012/0116263 | A1 | 5/2012 | Houser et al. |
| 2012/0116265 | A1 | 5/2012 | Houser et al. |
| 2012/0116266 | A1 | 5/2012 | Houser et al. |
| 2012/0116381 | A1 | 5/2012 | Houser et al. |
| 2012/0118595 | A1 | 5/2012 | Pellenc |
| 2012/0123463 | A1 | 5/2012 | Jacobs |
| 2012/0125792 | A1 | 5/2012 | Cassivi |
| 2012/0130217 | A1 | 5/2012 | Kauphusman et al. |
| 2012/0132286 | A1 | 5/2012 | Lim et al. |
| 2012/0132663 | A1 | 5/2012 | Kasvikis et al. |
| 2012/0143173 | A1 | 6/2012 | Steege et al. |
| 2012/0143175 | A1 | 6/2012 | Hermann et al. |
| 2012/0171539 | A1 | 7/2012 | Rejman et al. |
| 2012/0175398 | A1 | 7/2012 | Sandborn et al. |

(56) References Cited

U.S. PATENT DOCUMENTS

2012/0190964 A1 7/2012 Hyde et al.
2012/0197239 A1 8/2012 Smith et al.
2012/0197272 A1 8/2012 Oray et al.
2012/0203213 A1 8/2012 Kimball et al.
2012/0211542 A1 8/2012 Racenet
2012/0220990 A1 8/2012 Mckenzie et al.
2012/0233298 A1 9/2012 Verbandt et al.
2012/0234895 A1 9/2012 O'Connor et al.
2012/0234897 A1 9/2012 Shelton, IV et al.
2012/0239068 A1 9/2012 Morris et al.
2012/0241494 A1 9/2012 Marczyk
2012/0241503 A1 9/2012 Baxter, III et al.
2012/0248169 A1 10/2012 Widenhouse et al.
2012/0251861 A1 10/2012 Liang et al.
2012/0253328 A1 10/2012 Cunningham et al.
2012/0256494 A1 10/2012 Kesler et al.
2012/0271327 A1 10/2012 West et al.
2012/0283707 A1 11/2012 Giordano et al.
2012/0286019 A1 11/2012 Hueil et al.
2012/0289811 A1 11/2012 Viola et al.
2012/0289979 A1 11/2012 Eskaros et al.
2012/0292367 A1 11/2012 Morgan et al.
2012/0296316 A1 11/2012 Imuta
2012/0296342 A1 11/2012 Haglund Wendelschafer
2012/0298722 A1 11/2012 Hess et al.
2012/0301498 A1 11/2012 Altreuter et al.
2012/0310254 A1 12/2012 Manzo et al.
2012/0312861 A1 12/2012 Gurumurthy et al.
2012/0316424 A1 12/2012 Stopek
2012/0330285 A1 12/2012 Hartoumbekis et al.
2012/0330329 A1 12/2012 Harris et al.
2013/0006227 A1 1/2013 Takashino
2013/0008937 A1 1/2013 Viola
2013/0012983 A1 1/2013 Kleyman
2013/0018400 A1 1/2013 Milton et al.
2013/0020375 A1 1/2013 Shelton, IV et al.
2013/0020376 A1 1/2013 Shelton, IV et al.
2013/0023861 A1 1/2013 Shelton, IV et al.
2013/0023910 A1 1/2013 Solomon et al.
2013/0023915 A1 1/2013 Mueller
2013/0026208 A1 1/2013 Shelton, IV et al.
2013/0026210 A1 1/2013 Shelton, IV et al.
2013/0030462 A1 1/2013 Keating et al.
2013/0041292 A1 2/2013 Cunningham
2013/0056522 A1 3/2013 Swensgard
2013/0057162 A1 3/2013 Pollischansky
2013/0068816 A1 3/2013 Mandakolathur Vasudevan et al.
2013/0069088 A1 3/2013 Speck et al.
2013/0075447 A1 3/2013 Weisenburgh, II et al.
2013/0087597 A1 4/2013 Shelton, IV et al.
2013/0090534 A1 4/2013 Burns et al.
2013/0096568 A1 4/2013 Justis
2013/0098968 A1 4/2013 Aranyi et al.
2013/0098970 A1 4/2013 Racenet et al.
2013/0106352 A1 5/2013 Nagamine
2013/0112729 A1 5/2013 Beardsley et al.
2013/0116669 A1 5/2013 Shelton, IV et al.
2013/0123816 A1 5/2013 Hodgkinson et al.
2013/0126202 A1 5/2013 Oomori et al.
2013/0131476 A1 5/2013 Siu et al.
2013/0131651 A1 5/2013 Strobl et al.
2013/0136969 A1 5/2013 Yasui et al.
2013/0153639 A1 6/2013 Hodgkinson et al.
2013/0153641 A1 6/2013 Shelton, IV et al.
2013/0158390 A1 6/2013 Tan et al.
2013/0162198 A1 6/2013 Yokota et al.
2013/0165908 A1 6/2013 Purdy et al.
2013/0169217 A1 7/2013 Watanabe et al.
2013/0172713 A1 7/2013 Kirschenman
2013/0172878 A1 7/2013 Smith
2013/0175315 A1 7/2013 Milliman
2013/0175317 A1 7/2013 Yates et al.
2013/0183769 A1 7/2013 Tajima
2013/0186936 A1 7/2013 Shelton, IV
2013/0211244 A1 8/2013 Nathaniel
2013/0214025 A1 8/2013 Zemlok et al.
2013/0215449 A1 8/2013 Yamasaki
2013/0231681 A1 9/2013 Robinson et al.
2013/0233906 A1 9/2013 Hess et al.
2013/0238021 A1 9/2013 Gross et al.
2013/0248575 A1* 9/2013 Marczyk .............. A61B 17/072
227/175.1
2013/0248578 A1 9/2013 Arteaga Gonzalez
2013/0253480 A1 9/2013 Kimball et al.
2013/0253499 A1 9/2013 Kimball et al.
2013/0256373 A1 10/2013 Schmid et al.
2013/0256380 A1 10/2013 Schmid et al.
2013/0267950 A1 10/2013 Rosa et al.
2013/0267978 A1 10/2013 Trissel
2013/0270322 A1 10/2013 Scheib et al.
2013/0277410 A1 10/2013 Fernandez et al.
2013/0284792 A1 10/2013 Ma
2013/0289565 A1 10/2013 Hassler, Jr.
2013/0293353 A1 11/2013 McPherson et al.
2013/0303845 A1 11/2013 Skula et al.
2013/0304084 A1 11/2013 Beira et al.
2013/0306704 A1 11/2013 Balbierz et al.
2013/0310849 A1 11/2013 Malkowski
2013/0327552 A1 12/2013 Lovelass et al.
2013/0331826 A1 12/2013 Steege
2013/0333910 A1 12/2013 Tanimoto et al.
2013/0334280 A1 12/2013 Krehel et al.
2013/0334283 A1 12/2013 Swayze et al.
2013/0334285 A1 12/2013 Swayze et al.
2013/0341374 A1 12/2013 Shelton, IV et al.
2014/0001231 A1 1/2014 Shelton, IV et al.
2014/0001234 A1 1/2014 Shelton, IV et al.
2014/0002322 A1 1/2014 Kanome et al.
2014/0005550 A1 1/2014 Lu et al.
2014/0005640 A1 1/2014 Shelton, IV et al.
2014/0005678 A1 1/2014 Shelton, IV et al.
2014/0005702 A1 1/2014 Timm et al.
2014/0005718 A1 1/2014 Shelton, IV et al.
2014/0008289 A1 1/2014 Williams et al.
2014/0014704 A1 1/2014 Onukuri et al.
2014/0014705 A1 1/2014 Baxter, III
2014/0014707 A1 1/2014 Onukuri et al.
2014/0018832 A1 1/2014 Shelton, IV
2014/0022283 A1 1/2014 Chan et al.
2014/0039549 A1 2/2014 Belsky et al.
2014/0041191 A1 2/2014 Knodel
2014/0048580 A1 2/2014 Merchant et al.
2014/0069240 A1 3/2014 Dauvin et al.
2014/0078715 A1 3/2014 Pickard et al.
2014/0081176 A1 3/2014 Hassan
2014/0088614 A1 3/2014 Blumenkranz
2014/0088639 A1 3/2014 Bartels et al.
2014/0094681 A1 4/2014 Valentine et al.
2014/0100554 A1 4/2014 Williams
2014/0100558 A1 4/2014 Schmitz et al.
2014/0107697 A1 4/2014 Patani et al.
2014/0110453 A1 4/2014 Wingardner et al.
2014/0115229 A1 4/2014 Kothamasu et al.
2014/0131418 A1 5/2014 Kostrzewski
2014/0131419 A1 5/2014 Bettuchi
2014/0135832 A1 5/2014 Park et al.
2014/0148803 A1 5/2014 Taylor
2014/0151433 A1 6/2014 Shelton, IV et al.
2014/0155916 A1 6/2014 Hodgkinson et al.
2014/0158747 A1 6/2014 Measamer et al.
2014/0166718 A1 6/2014 Swayze et al.
2014/0166723 A1 6/2014 Beardsley et al.
2014/0166724 A1 6/2014 Schellin et al.
2014/0166725 A1 6/2014 Schellin et al.
2014/0166726 A1 6/2014 Schellin et al.
2014/0175147 A1 6/2014 Manoux et al.
2014/0175150 A1 6/2014 Shelton, IV et al.
2014/0175152 A1 6/2014 Hess et al.
2014/0181710 A1 6/2014 Baalu et al.
2014/0183244 A1 7/2014 Duque et al.
2014/0188091 A1 7/2014 Vidal et al.
2014/0188101 A1 7/2014 Bales, Jr. et al.
2014/0188159 A1 7/2014 Steege
2014/0194874 A1 7/2014 Dietz et al.

(56) References Cited

U.S. PATENT DOCUMENTS

2014/0207124 A1 7/2014 Aldridge et al.
2014/0209658 A1 7/2014 Skalla et al.
2014/0215242 A1 7/2014 Jung
2014/0224857 A1 8/2014 Schmid
2014/0228632 A1 8/2014 Sholev et al.
2014/0228867 A1 8/2014 Thomas et al.
2014/0239047 A1 8/2014 Hodgkinson et al.
2014/0243865 A1 8/2014 Swayze et al.
2014/0246475 A1 9/2014 Hall et al.
2014/0248167 A1 9/2014 Sugimoto et al.
2014/0249557 A1 9/2014 Koch, Jr. et al.
2014/0249573 A1 9/2014 Arav
2014/0262408 A1 9/2014 Woodard
2014/0263535 A1 9/2014 Rajani et al.
2014/0263541 A1 9/2014 Leimbach et al.
2014/0263552 A1 9/2014 Hall et al.
2014/0263558 A1 9/2014 Hausen et al.
2014/0276720 A1 9/2014 Parihar et al.
2014/0276730 A1 9/2014 Boudreaux et al.
2014/0276776 A1 9/2014 Parihar et al.
2014/0284371 A1 9/2014 Morgan et al.
2014/0287703 A1 9/2014 Herbsommer et al.
2014/0288460 A1 9/2014 Ouyang et al.
2014/0291379 A1 10/2014 Schellin et al.
2014/0291383 A1 10/2014 Spivey et al.
2014/0299648 A1 10/2014 Shelton, IV et al.
2014/0303645 A1 10/2014 Morgan et al.
2014/0303660 A1 10/2014 Boyden et al.
2014/0330161 A1 11/2014 Swayze et al.
2014/0330298 A1 11/2014 Arshonsky et al.
2014/0330579 A1 11/2014 Cashman et al.
2014/0358163 A1 12/2014 Farin et al.
2014/0367445 A1 12/2014 Ingmanson et al.
2014/0371764 A1 12/2014 Oyola et al.
2014/0373003 A1 12/2014 Grez et al.
2014/0374130 A1 12/2014 Nakamura et al.
2014/0378950 A1 12/2014 Chiu
2014/0379000 A1 12/2014 Romo et al.
2015/0001272 A1 1/2015 Sniffin et al.
2015/0002089 A1 1/2015 Rejman et al.
2015/0022012 A1 1/2015 Kim et al.
2015/0025549 A1 1/2015 Kilroy et al.
2015/0025571 A1 1/2015 Suzuki et al.
2015/0034697 A1 2/2015 Mastri et al.
2015/0039010 A1 2/2015 Beardsley et al.
2015/0053737 A1 2/2015 Leimbach et al.
2015/0053743 A1 2/2015 Yates et al.
2015/0053746 A1 2/2015 Shelton, IV et al.
2015/0053748 A1 2/2015 Yates et al.
2015/0060516 A1 3/2015 Collings et al.
2015/0060519 A1 3/2015 Shelton, IV et al.
2015/0060520 A1 3/2015 Shelton, IV et al.
2015/0060521 A1 3/2015 Weisenburgh, II et al.
2015/0066000 A1 3/2015 An et al.
2015/0067582 A1 3/2015 Donnelly et al.
2015/0076208 A1 3/2015 Shelton, IV
2015/0076209 A1 3/2015 Shelton, IV et al.
2015/0076210 A1 3/2015 Shelton, IV et al.
2015/0076211 A1 3/2015 Irka et al.
2015/0080883 A1 3/2015 Haverkost et al.
2015/0082624 A1 3/2015 Craig et al.
2015/0083781 A1 3/2015 Giordano et al.
2015/0087952 A1 3/2015 Albert et al.
2015/0088127 A1 3/2015 Craig et al.
2015/0088547 A1 3/2015 Balram et al.
2015/0090760 A1 4/2015 Giordano et al.
2015/0090762 A1 4/2015 Giordano et al.
2015/0127021 A1 5/2015 Harris et al.
2015/0133957 A1 5/2015 Kostrzewski
2015/0134077 A1 5/2015 Shelton, IV et al.
2015/0150620 A1 6/2015 Miyamoto et al.
2015/0173749 A1 6/2015 Shelton, IV et al.
2015/0173756 A1 6/2015 Baxter, III et al.
2015/0173789 A1 6/2015 Baxter, III et al.
2015/0196295 A1 7/2015 Shelton, IV et al.
2015/0196299 A1 7/2015 Swayze et al.
2015/0201918 A1 7/2015 Kumar et al.
2015/0201932 A1 7/2015 Swayze et al.
2015/0201936 A1 7/2015 Swayze et al.
2015/0201937 A1 7/2015 Swayze et al.
2015/0201938 A1 7/2015 Swayze et al.
2015/0201939 A1 7/2015 Swayze et al.
2015/0201940 A1 7/2015 Swayze et al.
2015/0201941 A1 7/2015 Swayze et al.
2015/0202013 A1 7/2015 Teichtmann et al.
2015/0209045 A1 7/2015 Hodgkinson et al.
2015/0216605 A1 8/2015 Baldwin
2015/0222212 A1 8/2015 Iwata
2015/0223868 A1 8/2015 Brandt et al.
2015/0230697 A1 8/2015 Phee et al.
2015/0230794 A1 8/2015 Wellman et al.
2015/0230861 A1 8/2015 Woloszko et al.
2015/0231409 A1 8/2015 Racenet et al.
2015/0238118 A1 8/2015 Legassey et al.
2015/0272557 A1 10/2015 Overmyer et al.
2015/0272571 A1 10/2015 Leimbach et al.
2015/0272580 A1 10/2015 Leimbach et al.
2015/0272582 A1 10/2015 Leimbach et al.
2015/0272606 A1 10/2015 Nobis
2015/0297200 A1 10/2015 Fitzsimmons et al.
2015/0297222 A1 10/2015 Huitema et al.
2015/0297223 A1 10/2015 Huitema et al.
2015/0297225 A1 10/2015 Huitema et al.
2015/0297824 A1 10/2015 Cabiri et al.
2015/0303417 A1 10/2015 Koeder et al.
2015/0305743 A1 10/2015 Casasanta et al.
2015/0313594 A1 11/2015 Shelton, IV et al.
2015/0324317 A1 11/2015 Collins et al.
2015/0352699 A1 12/2015 Sakai et al.
2015/0366585 A1 12/2015 Lemay et al.
2015/0367497 A1 12/2015 Ito et al.
2015/0372265 A1 12/2015 Morisaku et al.
2015/0374372 A1 12/2015 Zergiebel et al.
2015/0374378 A1 12/2015 Giordano et al.
2016/0000437 A1 1/2016 Giordano et al.
2016/0000452 A1 1/2016 Yates et al.
2016/0029998 A1 2/2016 Brister et al.
2016/0030042 A1 2/2016 Heinrich et al.
2016/0030043 A1 2/2016 Fanelli et al.
2016/0030076 A1 2/2016 Faller et al.
2016/0034167 A1 2/2016 Wilson et al.
2016/0047423 A1 2/2016 Bodtker
2016/0051316 A1 2/2016 Boudreaux
2016/0066913 A1 3/2016 Swayze et al.
2016/0069449 A1 3/2016 Kanai et al.
2016/0074035 A1 3/2016 Whitman et al.
2016/0074040 A1 3/2016 Widenhouse et al.
2016/0081678 A1 3/2016 Kappel et al.
2016/0082161 A1 3/2016 Zilberman et al.
2016/0089175 A1 3/2016 Hibner et al.
2016/0099601 A1 4/2016 Leabman et al.
2016/0100838 A1* 4/2016 Beaupré ........... A61B 17/07207
227/175.1
2016/0118201 A1 4/2016 Nicholas et al.
2016/0132026 A1 5/2016 Wingardner et al.
2016/0135835 A1 5/2016 Onuma
2016/0135895 A1 5/2016 Faasse et al.
2016/0139666 A1 5/2016 Rubin et al.
2016/0174969 A1 6/2016 Kerr et al.
2016/0174983 A1 6/2016 Shelton, IV et al.
2016/0175021 A1 6/2016 Hassler, Jr.
2016/0183939 A1 6/2016 Shelton, IV et al.
2016/0183944 A1 6/2016 Swensgard et al.
2016/0192927 A1 7/2016 Kostrzewski
2016/0192960 A1 7/2016 Bueno et al.
2016/0199063 A1 7/2016 Mandakolathur Vasudevan et al.
2016/0199956 A1 7/2016 Shelton, IV et al.
2016/0220150 A1 8/2016 Sharonov
2016/0235494 A1 8/2016 Shelton, IV et al.
2016/0242783 A1 8/2016 Shelton, IV et al.
2016/0242855 A1 8/2016 Fichtinger et al.
2016/0249910 A1 9/2016 Shelton, IV et al.
2016/0249922 A1 9/2016 Morgan et al.
2016/0249929 A1 9/2016 Cappola et al.

(56) References Cited

U.S. PATENT DOCUMENTS

2016/0256159 A1 9/2016 Pinjala et al.
2016/0256184 A1 9/2016 Shelton, IV et al.
2016/0256221 A1 9/2016 Smith
2016/0256229 A1 9/2016 Morgan et al.
2016/0262745 A1 9/2016 Morgan et al.
2016/0262921 A1 9/2016 Balbierz et al.
2016/0270781 A1 9/2016 Scirica
2016/0287265 A1 10/2016 Macdonald et al.
2016/0287279 A1 10/2016 Bovay et al.
2016/0302820 A1 10/2016 Hibner et al.
2016/0310143 A1 10/2016 Bettuchi
2016/0314716 A1 10/2016 Grubbs
2016/0314717 A1 10/2016 Grubbs
2016/0345972 A1 12/2016 Beardsley et al.
2016/0367122 A1 12/2016 Ichimura et al.
2016/0374669 A1 12/2016 Overmyer et al.
2016/0374716 A1 12/2016 Kessler
2017/0000549 A1 1/2017 Gilbert et al.
2017/0007234 A1 1/2017 Chin et al.
2017/0007244 A1 1/2017 Shelton, IV et al.
2017/0007245 A1 1/2017 Shelton, IV et al.
2017/0007347 A1 1/2017 Jaworek et al.
2017/0020616 A1 1/2017 Vale et al.
2017/0035419 A1 2/2017 Decker et al.
2017/0055819 A1 3/2017 Hansen et al.
2017/0055980 A1 3/2017 Vendely et al.
2017/0056008 A1 3/2017 Shelton, IV et al.
2017/0056016 A1 3/2017 Barton et al.
2017/0056018 A1 3/2017 Zeiner et al.
2017/0066054 A1 3/2017 Birky
2017/0079642 A1 3/2017 Overmyer et al.
2017/0086829 A1 3/2017 Vendely et al.
2017/0086830 A1 3/2017 Yates et al.
2017/0086930 A1 3/2017 Thompson et al.
2017/0086932 A1 3/2017 Auld et al.
2017/0095252 A1 4/2017 Smith et al.
2017/0095922 A1 4/2017 Licht et al.
2017/0105727 A1 4/2017 Scheib et al.
2017/0105733 A1 4/2017 Scheib et al.
2017/0105786 A1 4/2017 Scheib et al.
2017/0106302 A1 4/2017 Cummings et al.
2017/0135711 A1 5/2017 Overmyer et al.
2017/0135717 A1 5/2017 Boudreaux et al.
2017/0135747 A1 5/2017 Broderick et al.
2017/0143336 A1 5/2017 Shah et al.
2017/0168187 A1 6/2017 Calderoni et al.
2017/0172382 A1 6/2017 Nir et al.
2017/0172549 A1 6/2017 Smaby et al.
2017/0172662 A1 6/2017 Panescu et al.
2017/0181803 A1 6/2017 Mayer-Ullmann et al.
2017/0182195 A1 6/2017 Wagner
2017/0182211 A1 6/2017 Raxworthy et al.
2017/0196558 A1 7/2017 Morgan et al.
2017/0196649 A1 7/2017 Yates et al.
2017/0202605 A1 7/2017 Shelton, IV et al.
2017/0202607 A1 7/2017 Shelton, IV et al.
2017/0202770 A1 7/2017 Friedrich et al.
2017/0224332 A1 8/2017 Hunter et al.
2017/0224428 A1 8/2017 Kopp
2017/0231628 A1 8/2017 Shelton, IV et al.
2017/0231629 A1 8/2017 Stopek et al.
2017/0238962 A1 8/2017 Hansen et al.
2017/0238991 A1 8/2017 Worrell et al.
2017/0242455 A1 8/2017 Dickens
2017/0245880 A1 8/2017 Honda et al.
2017/0245949 A1 8/2017 Randle
2017/0249431 A1 8/2017 Shelton, IV et al.
2017/0252060 A1 9/2017 Ellingson et al.
2017/0255799 A1 9/2017 Zhao et al.
2017/0258471 A1 9/2017 DiNardo et al.
2017/0262110 A1 9/2017 Polishchuk et al.
2017/0265774 A1 9/2017 Johnson et al.
2017/0281186 A1 10/2017 Shelton, IV et al.
2017/0296173 A1 10/2017 Shelton, IV et al.
2017/0303984 A1 10/2017 Malackowski
2017/0308665 A1 10/2017 Heck et al.
2017/0312042 A1 11/2017 Giordano et al.
2017/0319047 A1 11/2017 Poulsen et al.
2017/0319201 A1 11/2017 Morgan et al.
2017/0333034 A1 11/2017 Morgan et al.
2017/0333035 A1 11/2017 Morgan et al.
2017/0348010 A1 12/2017 Chiang
2017/0348042 A1 12/2017 Drochner et al.
2017/0348043 A1 12/2017 Wang et al.
2017/0354413 A1 12/2017 Chen et al.
2017/0358052 A1 12/2017 Yuan
2017/0360441 A1 12/2017 Sgroi
2018/0008265 A1 1/2018 Hatanaka et al.
2018/0036024 A1 2/2018 Allen, IV
2018/0036025 A1 2/2018 Drochner et al.
2018/0042610 A1 2/2018 Sgroi, Jr.
2018/0042689 A1 2/2018 Mozdzierz et al.
2018/0049738 A1 2/2018 Meloul et al.
2018/0049794 A1 2/2018 Swayze et al.
2018/0051780 A1 2/2018 Shelton, IV et al.
2018/0055501 A1 3/2018 Zemlok et al.
2018/0067004 A1 3/2018 Sgroi, Jr.
2018/0085117 A1 3/2018 Shelton, IV et al.
2018/0085120 A1 3/2018 Viola
2018/0092710 A1 4/2018 Bosisio et al.
2018/0114591 A1 4/2018 Pribanic et al.
2018/0116658 A1 5/2018 Aronhalt, IV et al.
2018/0125481 A1 5/2018 Yates et al.
2018/0125487 A1 5/2018 Beardsley
2018/0125488 A1 5/2018 Morgan et al.
2018/0125594 A1 5/2018 Beardsley
2018/0132849 A1 5/2018 Miller et al.
2018/0132850 A1 5/2018 Leimbach et al.
2018/0132926 A1 5/2018 Asher et al.
2018/0132952 A1 5/2018 Spivey et al.
2018/0133521 A1 5/2018 Frushour et al.
2018/0140299 A1 5/2018 Weaner et al.
2018/0146960 A1 5/2018 Shelton, IV et al.
2018/0153542 A1 6/2018 Shelton, IV et al.
2018/0153634 A1 6/2018 Zemlok et al.
2018/0161034 A1 6/2018 Scheib et al.
2018/0168572 A1 6/2018 Burbank
2018/0168574 A1 6/2018 Robinson et al.
2018/0168575 A1 6/2018 Simms et al.
2018/0168577 A1 6/2018 Aronhalt et al.
2018/0168579 A1 6/2018 Aronhalt et al.
2018/0168598 A1 6/2018 Shelton, IV et al.
2018/0168608 A1 6/2018 Shelton, IV et al.
2018/0168609 A1 6/2018 Fanelli et al.
2018/0168615 A1 6/2018 Shelton, IV et al.
2018/0168618 A1 6/2018 Scott et al.
2018/0168619 A1 6/2018 Scott et al.
2018/0168623 A1 6/2018 Simms et al.
2018/0168625 A1 6/2018 Posada et al.
2018/0168633 A1 6/2018 Shelton, IV et al.
2018/0168647 A1 6/2018 Shelton, IV et al.
2018/0168648 A1 6/2018 Shelton, IV et al.
2018/0168650 A1 6/2018 Shelton, IV et al.
2018/0168754 A1 6/2018 Overmyer
2018/0168756 A1 6/2018 Liao et al.
2018/0206904 A1 7/2018 Felder et al.
2018/0228490 A1 8/2018 Richard et al.
2018/0231111 A1 8/2018 Mika et al.
2018/0231475 A1 8/2018 Brown et al.
2018/0235609 A1 8/2018 Harris et al.
2018/0235617 A1 8/2018 Shelton, IV et al.
2018/0235618 A1 8/2018 Kostrzewski
2018/0235626 A1 8/2018 Shelton, IV et al.
2018/0236181 A1 8/2018 Marlin et al.
2018/0242970 A1 8/2018 Mozdzierz
2018/0247711 A1 8/2018 Terry
2018/0250002 A1 9/2018 Eschbach
2018/0271526 A1 9/2018 Zammataro
2018/0271553 A1 9/2018 Worrell
2018/0271604 A1 9/2018 Grout et al.
2018/0273597 A1 9/2018 Stimson
2018/0279994 A1 10/2018 Schaer et al.
2018/0280026 A1 10/2018 Zhang et al.
2018/0280073 A1 10/2018 Sanai et al.

(56) References Cited

U.S. PATENT DOCUMENTS

| | | | |
|---|---|---|---|
| 2018/0289370 | A1* | 10/2018 | Amariglio ........ A61B 17/07207 |
| 2018/0289371 | A1 | 10/2018 | Wang et al. |
| 2018/0296216 | A1 | 10/2018 | Shelton, IV et al. |
| 2018/0296290 | A1 | 10/2018 | Namiki et al. |
| 2018/0310995 | A1 | 11/2018 | Gliner et al. |
| 2018/0317905 | A1 | 11/2018 | Olson et al. |
| 2018/0317915 | A1 | 11/2018 | Mcdonald, II |
| 2018/0325514 | A1 | 11/2018 | Harris et al. |
| 2018/0333169 | A1 | 11/2018 | Leimbach et al. |
| 2018/0360456 | A1 | 12/2018 | Shelton, IV et al. |
| 2018/0368066 | A1 | 12/2018 | Howell et al. |
| 2018/0368844 | A1 | 12/2018 | Bakos et al. |
| 2018/0372806 | A1 | 12/2018 | Laughery et al. |
| 2018/0375165 | A1 | 12/2018 | Shelton, IV et al. |
| 2019/0000459 | A1 | 1/2019 | Shelton, IV et al. |
| 2019/0000461 | A1 | 1/2019 | Shelton, IV et al. |
| 2019/0000481 | A1 | 1/2019 | Harris et al. |
| 2019/0000533 | A1 | 1/2019 | Messerly et al. |
| 2019/0000535 | A1 | 1/2019 | Messerly et al. |
| 2019/0000536 | A1 | 1/2019 | Yates et al. |
| 2019/0006047 | A1 | 1/2019 | Gorek et al. |
| 2019/0008515 | A1 | 1/2019 | Beardsley et al. |
| 2019/0015102 | A1 | 1/2019 | Baber et al. |
| 2019/0015165 | A1 | 1/2019 | Giordano et al. |
| 2019/0017311 | A1 | 1/2019 | McGettrick et al. |
| 2019/0021733 | A1 | 1/2019 | Burbank |
| 2019/0029682 | A1 | 1/2019 | Huitema et al. |
| 2019/0029701 | A1 | 1/2019 | Shelton, IV et al. |
| 2019/0038281 | A1 | 2/2019 | Shelton, IV et al. |
| 2019/0038283 | A1 | 2/2019 | Shelton, IV et al. |
| 2019/0038285 | A1 | 2/2019 | Mozdzierz |
| 2019/0059890 | A1 | 2/2019 | Shelton, IV et al. |
| 2019/0059891 | A1 | 2/2019 | Shelton, IV et al. |
| 2019/0059984 | A1 | 2/2019 | Otrembiak et al. |
| 2019/0059986 | A1 | 2/2019 | Shelton, IV et al. |
| 2019/0076143 | A1 | 3/2019 | Smith |
| 2019/0090871 | A1 | 3/2019 | Shelton, IV et al. |
| 2019/0091183 | A1 | 3/2019 | Tomat et al. |
| 2019/0104919 | A1 | 4/2019 | Shelton, IV et al. |
| 2019/0105035 | A1 | 4/2019 | Shelton, IV et al. |
| 2019/0105036 | A1 | 4/2019 | Morgan et al. |
| 2019/0105037 | A1 | 4/2019 | Morgan et al. |
| 2019/0105039 | A1 | 4/2019 | Morgan et al. |
| 2019/0105044 | A1 | 4/2019 | Shelton, IV et al. |
| 2019/0110779 | A1 | 4/2019 | Gardner et al. |
| 2019/0110791 | A1 | 4/2019 | Shelton, IV et al. |
| 2019/0117220 | A1 | 4/2019 | Nativ et al. |
| 2019/0117224 | A1 | 4/2019 | Setser et al. |
| 2019/0117287 | A1 | 4/2019 | Nativ et al. |
| 2019/0122840 | A1 | 4/2019 | Zergiebel et al. |
| 2019/0125320 | A1 | 5/2019 | Shelton, IV et al. |
| 2019/0125336 | A1 | 5/2019 | Deck et al. |
| 2019/0125338 | A1 | 5/2019 | Shelton, IV et al. |
| 2019/0125342 | A1 | 5/2019 | Beardsley et al. |
| 2019/0125344 | A1 | 5/2019 | DiNardo et al. |
| 2019/0125361 | A1 | 5/2019 | Shelton, IV et al. |
| 2019/0125378 | A1 | 5/2019 | Shelton, IV et al. |
| 2019/0125432 | A1 | 5/2019 | Shelton, IV et al. |
| 2019/0125454 | A1 | 5/2019 | Stokes et al. |
| 2019/0125476 | A1 | 5/2019 | Shelton, IV et al. |
| 2019/0133422 | A1 | 5/2019 | Nakamura |
| 2019/0133577 | A1 | 5/2019 | Weadock et al. |
| 2019/0138770 | A1 | 5/2019 | Compaijen et al. |
| 2019/0142423 | A1 | 5/2019 | Satti, III et al. |
| 2019/0150925 | A1 | 5/2019 | Marczyk et al. |
| 2019/0151029 | A1 | 5/2019 | Robinson |
| 2019/0175847 | A1 | 6/2019 | Pocreva, III et al. |
| 2019/0183502 | A1 | 6/2019 | Shelton, IV et al. |
| 2019/0192147 | A1 | 6/2019 | Shelton, IV et al. |
| 2019/0192148 | A1 | 6/2019 | Shelton, IV et al. |
| 2019/0192151 | A1 | 6/2019 | Shelton, IV et al. |
| 2019/0192155 | A1 | 6/2019 | Shelton, IV et al. |
| 2019/0200844 | A1 | 7/2019 | Shelton, IV et al. |
| 2019/0200905 | A1 | 7/2019 | Shelton, IV et al. |
| 2019/0200906 | A1 | 7/2019 | Shelton, IV et al. |
| 2019/0200977 | A1 | 7/2019 | Shelton, IV et al. |
| 2019/0200981 | A1 | 7/2019 | Harris et al. |
| 2019/0200986 | A1 | 7/2019 | Shelton, IV et al. |
| 2019/0200987 | A1 | 7/2019 | Shelton, IV et al. |
| 2019/0200988 | A1 | 7/2019 | Shelton, IV |
| 2019/0200989 | A1 | 7/2019 | Burbank et al. |
| 2019/0200997 | A1 | 7/2019 | Shelton, IV et al. |
| 2019/0200998 | A1 | 7/2019 | Shelton, IV et al. |
| 2019/0201020 | A1 | 7/2019 | Shelton, IV et al. |
| 2019/0201024 | A1 | 7/2019 | Shelton, IV et al. |
| 2019/0201027 | A1 | 7/2019 | Shelton, IV et al. |
| 2019/0201029 | A1 | 7/2019 | Shelton, IV et al. |
| 2019/0201030 | A1 | 7/2019 | Shelton, IV et al. |
| 2019/0201034 | A1 | 7/2019 | Shelton, IV et al. |
| 2019/0201045 | A1 | 7/2019 | Yates et al. |
| 2019/0201079 | A1 | 7/2019 | Shelton, IV et al. |
| 2019/0201104 | A1 | 7/2019 | Shelton, IV et al. |
| 2019/0201112 | A1 | 7/2019 | Wiener et al. |
| 2019/0201113 | A1 | 7/2019 | Shelton, IV et al. |
| 2019/0201115 | A1 | 7/2019 | Shelton, IV et al. |
| 2019/0201118 | A1 | 7/2019 | Shelton, IV et al. |
| 2019/0201139 | A1 | 7/2019 | Shelton, IV et al. |
| 2019/0201140 | A1 | 7/2019 | Yates et al. |
| 2019/0201142 | A1 | 7/2019 | Shelton, IV et al. |
| 2019/0201146 | A1 | 7/2019 | Shelton, IV et al. |
| 2019/0201158 | A1 | 7/2019 | Shelton, IV et al. |
| 2019/0201594 | A1 | 7/2019 | Shelton, IV et al. |
| 2019/0205567 | A1 | 7/2019 | Shelton, IV et al. |
| 2019/0206555 | A1 | 7/2019 | Morgan et al. |
| 2019/0206561 | A1 | 7/2019 | Shelton, IV et al. |
| 2019/0206564 | A1 | 7/2019 | Shelton, IV et al. |
| 2019/0206569 | A1 | 7/2019 | Shelton, IV et al. |
| 2019/0209172 | A1 | 7/2019 | Shelton, IV et al. |
| 2019/0209247 | A1 | 7/2019 | Giordano et al. |
| 2019/0209248 | A1 | 7/2019 | Giordano et al. |
| 2019/0209249 | A1 | 7/2019 | Giordano et al. |
| 2019/0209250 | A1 | 7/2019 | Giordano et al. |
| 2019/0239873 | A1 | 8/2019 | Laurent et al. |
| 2019/0247048 | A1 | 8/2019 | Gasparovich et al. |
| 2019/0261982 | A1 | 8/2019 | Holsten |
| 2019/0261983 | A1 | 8/2019 | Granger et al. |
| 2019/0261984 | A1 | 8/2019 | Nelson et al. |
| 2019/0261987 | A1 | 8/2019 | Viola et al. |
| 2019/0262153 | A1 | 8/2019 | Tassoni et al. |
| 2019/0269400 | A1 | 9/2019 | Mandakolathur Vasudevan et al. |
| 2019/0269402 | A1 | 9/2019 | Murray et al. |
| 2019/0269428 | A1 | 9/2019 | Allen et al. |
| 2019/0274685 | A1 | 9/2019 | Olson et al. |
| 2019/0274716 | A1 | 9/2019 | Nott et al. |
| 2019/0282233 | A1 | 9/2019 | Burbank et al. |
| 2019/0290264 | A1 | 9/2019 | Morgan et al. |
| 2019/0290266 | A1 | 9/2019 | Scheib et al. |
| 2019/0290267 | A1 | 9/2019 | Baxter, III et al. |
| 2019/0290297 | A1 | 9/2019 | Haider et al. |
| 2019/0298353 | A1 | 10/2019 | Shelton, IV et al. |
| 2019/0298360 | A1 | 10/2019 | Shelton, IV et al. |
| 2019/0298361 | A1 | 10/2019 | Shelton, IV et al. |
| 2019/0298362 | A1 | 10/2019 | Shelton, IV et al. |
| 2019/0298381 | A1 | 10/2019 | Kreidler et al. |
| 2019/0307452 | A1 | 10/2019 | Shelton, IV et al. |
| 2019/0307453 | A1 | 10/2019 | Shelton, IV et al. |
| 2019/0307454 | A1 | 10/2019 | Shelton, IV et al. |
| 2019/0307456 | A1 | 10/2019 | Shelton, IV et al. |
| 2019/0314015 | A1 | 10/2019 | Shelton, IV et al. |
| 2019/0321062 | A1 | 10/2019 | Williams |
| 2019/0328387 | A1 | 10/2019 | Overmyer et al. |
| 2019/0388091 | A1 | 12/2019 | Eschbach et al. |
| 2020/0008802 | A1 | 1/2020 | Aronhalt et al. |
| 2020/0008809 | A1 | 1/2020 | Shelton, IV et al. |
| 2020/0008827 | A1 | 1/2020 | Dearden et al. |
| 2020/0015817 | A1 | 1/2020 | Harris et al. |
| 2020/0015836 | A1 | 1/2020 | Nicholas et al. |
| 2020/0015915 | A1 | 1/2020 | Swayze et al. |
| 2020/0030020 | A1 | 1/2020 | Wang et al. |
| 2020/0037939 | A1 | 2/2020 | Castagna et al. |
| 2020/0038016 | A1 | 2/2020 | Shelton, IV et al. |
| 2020/0038018 | A1 | 2/2020 | Shelton, IV et al. |
| 2020/0038021 | A1 | 2/2020 | Contini et al. |
| 2020/0046355 | A1 | 2/2020 | Harris et al. |

(56) References Cited

U.S. PATENT DOCUMENTS

2020/0046356 A1 2/2020 Baxter, III et al.
2020/0054320 A1 2/2020 Harris et al.
2020/0054321 A1 2/2020 Harris et al.
2020/0054329 A1 2/2020 Shelton, IV et al.
2020/0054332 A1 2/2020 Shelton, IV et al.
2020/0054333 A1 2/2020 Shelton, IV et al.
2020/0054334 A1 2/2020 Shelton, IV et al.
2020/0054355 A1 2/2020 Laurent et al.
2020/0060523 A1 2/2020 Matsuda et al.
2020/0060713 A1 2/2020 Leimbach et al.
2020/0061385 A1 2/2020 Schwarz et al.
2020/0085435 A1 3/2020 Shelton, IV et al.
2020/0085518 A1 3/2020 Giordano et al.
2020/0093484 A1 3/2020 Shelton, IV et al.
2020/0093506 A1 3/2020 Leimbach et al.
2020/0093550 A1 3/2020 Spivey et al.
2020/0107829 A1 4/2020 Shelton, IV et al.
2020/0113563 A1 4/2020 Gupta et al.
2020/0114505 A1 4/2020 Kikuchi
2020/0138507 A1 5/2020 Davison et al.
2020/0138534 A1 5/2020 Garcia Kilroy et al.
2020/0146166 A1 5/2020 Sgroi, Jr.
2020/0146741 A1 5/2020 Long et al.
2020/0187943 A1 6/2020 Shelton, IV et al.
2020/0197027 A1 6/2020 Hershberger et al.
2020/0205810 A1 7/2020 Posey et al.
2020/0205811 A1 7/2020 Posey et al.
2020/0205823 A1 7/2020 Vendely et al.
2020/0214706 A1 7/2020 Vendely et al.
2020/0214731 A1 7/2020 Shelton, IV et al.
2020/0229814 A1 7/2020 Amariglio et al.
2020/0237371 A1 7/2020 Huitema et al.
2020/0268377 A1 8/2020 Schmid et al.
2020/0268381 A1 8/2020 Roberts et al.
2020/0275927 A1 9/2020 Shelton, IV et al.
2020/0280219 A1 9/2020 Laughery et al.
2020/0289112 A1 9/2020 Whitfield et al.
2020/0289119 A1 9/2020 Viola et al.
2020/0305863 A1 10/2020 Yates et al.
2020/0305864 A1 10/2020 Yates et al.
2020/0305872 A1 10/2020 Weidner et al.
2020/0315623 A1 10/2020 Eisinger et al.
2020/0323526 A1 10/2020 Huang et al.
2020/0330181 A1 10/2020 Junger et al.
2020/0337706 A1 10/2020 Truckai et al.
2020/0337791 A1 10/2020 Shelton, IV et al.
2020/0345346 A1 11/2020 Shelton, IV et al.
2020/0345349 A1 11/2020 Kimball et al.
2020/0345352 A1 11/2020 Shelton, IV et al.
2020/0345353 A1 11/2020 Leimbach et al.
2020/0345356 A1 11/2020 Leimbach et al.
2020/0345357 A1 11/2020 Leimbach et al.
2020/0345359 A1 11/2020 Baxter, III et al.
2020/0345363 A1 11/2020 Shelton, IV et al.
2020/0345435 A1 11/2020 Traina
2020/0352562 A1 11/2020 Timm et al.
2020/0352569 A1 11/2020 Viola et al.
2020/0367886 A1 11/2020 Shelton, IV et al.
2020/0375585 A1 12/2020 Swayze et al.
2020/0375597 A1 12/2020 Shelton, IV et al.
2020/0390444 A1 12/2020 Harris et al.
2020/0397430 A1 12/2020 Patel et al.
2020/0397439 A1 12/2020 Eisinger
2020/0405292 A1 12/2020 Shelton, IV et al.
2020/0405302 A1 12/2020 Shelton, IV et al.
2020/0405304 A1 12/2020 Mozdzierz et al.
2020/0405306 A1 12/2020 Shelton, IV et al.
2020/0405307 A1 12/2020 Shelton, IV et al.
2020/0405308 A1 12/2020 Shelton, IV
2020/0405375 A1 12/2020 Shelton, IV et al.
2020/0405403 A1 12/2020 Shelton, IV et al.
2020/0410177 A1 12/2020 Shelton, IV
2021/0000466 A1 1/2021 Leimbach et al.
2021/0000467 A1 1/2021 Shelton, IV et al.
2021/0007742 A1 1/2021 Rector et al.
2021/0007826 A1 1/2021 Shafer et al.
2021/0015480 A1 1/2021 Shelton, IV et al.
2021/0045742 A1 2/2021 Shelton, IV et al.
2021/0052271 A1 2/2021 Harris et al.
2021/0059661 A1 3/2021 Schmid et al.
2021/0059662 A1 3/2021 Shelton, IV
2021/0059664 A1 3/2021 Hensel et al.
2021/0059670 A1 3/2021 Overmyer et al.
2021/0059672 A1 3/2021 Giordano et al.
2021/0059673 A1 3/2021 Shelton, IV et al.
2021/0068829 A1 3/2021 Miller et al.
2021/0068835 A1 3/2021 Shelton, IV et al.
2021/0077099 A1 3/2021 Shelton, IV et al.
2021/0077109 A1 3/2021 Harris et al.
2021/0084700 A1 3/2021 Daniels
2021/0085313 A1 3/2021 Morgan et al.
2021/0085315 A1 3/2021 Aronhalt et al.
2021/0085316 A1 3/2021 Harris et al.
2021/0085320 A1 3/2021 Leimbach et al.
2021/0085321 A1 3/2021 Shelton, IV et al.
2021/0085325 A1 3/2021 Shelton, IV et al.
2021/0093321 A1 4/2021 Auld et al.
2021/0093323 A1 4/2021 Scirica et al.
2021/0100541 A1 4/2021 Shelton, IV et al.
2021/0100982 A1 4/2021 Laby et al.
2021/0107031 A1 4/2021 Bales, Jr. et al.
2021/0121175 A1 4/2021 Yates et al.
2021/0128153 A1 5/2021 Sgroi
2021/0137522 A1 5/2021 Shelton, IV et al.
2021/0145441 A1 5/2021 Weir et al.
2021/0153866 A1 5/2021 Knapp et al.
2021/0177401 A1 6/2021 Abramek et al.
2021/0177411 A1 6/2021 Williams
2021/0177528 A1 6/2021 Cappelleri et al.
2021/0186492 A1 6/2021 Shelton, IV et al.
2021/0186497 A1 6/2021 Shelton, IV et al.
2021/0186499 A1 6/2021 Shelton, IV et al.
2021/0186501 A1 6/2021 Shelton, IV et al.
2021/0196265 A1 7/2021 Shelton, IV et al.
2021/0196269 A1 7/2021 Shelton, IV et al.
2021/0196270 A1 7/2021 Shelton, IV et al.
2021/0196425 A1 7/2021 Shelton, IV et al.
2021/0204941 A1 7/2021 Dewaele et al.
2021/0204951 A1 7/2021 Sgroi et al.
2021/0212671 A1 7/2021 Ramadan et al.
2021/0212776 A1 7/2021 Schmitt et al.
2021/0225140 A1 7/2021 Adachi et al.
2021/0228209 A1 7/2021 Shelton, IV et al.
2021/0244407 A1 8/2021 Shelton, IV et al.
2021/0244411 A1 8/2021 Smith et al.
2021/0251720 A1 8/2021 Jhaveri et al.
2021/0259681 A1 8/2021 Shelton, IV et al.
2021/0259687 A1 8/2021 Gonzalez et al.
2021/0259790 A1 8/2021 Kaiser
2021/0259986 A1 8/2021 Widenhouse et al.
2021/0259987 A1 8/2021 Widenhouse et al.
2021/0267589 A1 9/2021 Swayze et al.
2021/0267594 A1 9/2021 Morgan et al.
2021/0267595 A1 9/2021 Posada et al.
2021/0267596 A1 9/2021 Fanelli et al.
2021/0275053 A1 9/2021 Shelton, IV et al.
2021/0275172 A1 9/2021 Harris et al.
2021/0275173 A1 9/2021 Shelton, IV et al.
2021/0275175 A1 9/2021 Vadali et al.
2021/0282767 A1 9/2021 Shelton, IV et al.
2021/0282769 A1 9/2021 Baxter, III et al.
2021/0282776 A1 9/2021 Overmyer et al.
2021/0290226 A1 9/2021 Mandakolathur Vasudevan et al.
2021/0290231 A1 9/2021 Baxter, III et al.
2021/0290232 A1 9/2021 Harris et al.
2021/0290233 A1 9/2021 Shelton, IV et al.
2021/0290236 A1 9/2021 Moore et al.
2021/0290322 A1 9/2021 Traina
2021/0298745 A1 9/2021 Leimbach et al.
2021/0298746 A1 9/2021 Leimbach et al.
2021/0307744 A1 10/2021 Walcott et al.
2021/0307748 A1 10/2021 Harris et al.
2021/0313975 A1 10/2021 Shan et al.
2021/0315566 A1 10/2021 Yates et al.

(56) References Cited

U.S. PATENT DOCUMENTS

2021/0315570 A1 10/2021 Shelton, IV
2021/0315573 A1 10/2021 Shelton, IV et al.
2021/0315574 A1 10/2021 Shelton, IV et al.
2021/0315576 A1 10/2021 Shelton, IV et al.
2021/0315577 A1 10/2021 Shelton, IV et al.
2021/0322009 A1 10/2021 Huang et al.
2021/0330321 A1 10/2021 Leimbach et al.
2021/0338233 A1 11/2021 Shelton, IV et al.
2021/0338234 A1 11/2021 Shelton, IV et al.
2021/0338260 A1 11/2021 Le Rolland et al.
2021/0346082 A1 11/2021 Adams et al.
2021/0353284 A1 11/2021 Yang et al.
2021/0369271 A1 12/2021 Schings et al.
2021/0378669 A1 12/2021 Shelton, IV et al.
2021/0393366 A1 12/2021 Shelton, IV et al.
2021/0401487 A1 12/2021 Apostolopoulos et al.
2021/0401513 A1 12/2021 Apostolopoulos et al.
2022/0000478 A1 1/2022 Shelton, IV et al.
2022/0000479 A1 1/2022 Shelton, IV et al.
2022/0015760 A1 1/2022 Beardsley et al.
2022/0031315 A1 2/2022 Bakos et al.
2022/0031319 A1 2/2022 Witte et al.
2022/0031320 A1 2/2022 Hall et al.
2022/0031322 A1 2/2022 Parks
2022/0031323 A1 2/2022 Witte
2022/0031324 A1 2/2022 Hall et al.
2022/0031345 A1 2/2022 Witte
2022/0031346 A1 2/2022 Parks
2022/0031350 A1 2/2022 Witte
2022/0031351 A1 2/2022 Moubarak et al.
2022/0049593 A1 2/2022 Groover et al.
2022/0054125 A1 2/2022 Ji et al.
2022/0054130 A1 2/2022 Overmyer et al.
2022/0061642 A1 3/2022 Park et al.
2022/0061836 A1 3/2022 Parihar et al.
2022/0061843 A1 3/2022 Vendely et al.
2022/0061845 A1 3/2022 Shelton, IV et al.
2022/0061862 A1 3/2022 Shelton, IV et al.
2022/0071630 A1 3/2022 Swayze et al.
2022/0071631 A1 3/2022 Harris et al.
2022/0071632 A1 3/2022 Patel et al.
2022/0071635 A1 3/2022 Shelton, IV et al.
2022/0079580 A1 3/2022 Vendely et al.
2022/0079586 A1 3/2022 Shelton, IV et al.
2022/0079588 A1 3/2022 Harris et al.
2022/0079589 A1 3/2022 Harris et al.
2022/0079595 A1 3/2022 Huitema et al.
2022/0079596 A1 3/2022 Huitema et al.
2022/0104695 A1 4/2022 Russell
2022/0104814 A1 4/2022 Shelton, IV et al.
2022/0104816 A1 4/2022 Fernandes et al.
2022/0104820 A1 4/2022 Shelton, IV et al.
2022/0110673 A1 4/2022 Boronyak et al.
2022/0117602 A1 4/2022 Wise et al.
2022/0125472 A1 4/2022 Beckman et al.
2022/0133299 A1 5/2022 Baxter, III
2022/0133300 A1 5/2022 Leimbach et al.
2022/0133302 A1 5/2022 Zerkle et al.
2022/0133303 A1 5/2022 Huang
2022/0133304 A1 5/2022 Leimbach et al.
2022/0133310 A1 5/2022 Ross
2022/0133312 A1 5/2022 Huang
2022/0133318 A1 5/2022 Hudson et al.
2022/0142643 A1 5/2022 Shelton, IV et al.
2022/0151611 A1 5/2022 Shelton, IV et al.
2022/0151613 A1 5/2022 Vendely et al.
2022/0151614 A1 5/2022 Vendely et al.
2022/0151615 A1 5/2022 Shelton, IV et al.
2022/0151616 A1 5/2022 Shelton, IV et al.
2022/0160355 A1 5/2022 Harris et al.
2022/0160358 A1 5/2022 Wixey
2022/0167970 A1 6/2022 Aronhalt et al.
2022/0167972 A1 6/2022 Shelton, IV et al.
2022/0167973 A1 6/2022 Shelton, IV et al.
2022/0167977 A1 6/2022 Shelton, IV et al.
2022/0167979 A1 6/2022 Yates et al.
2022/0167981 A1 6/2022 Shelton, IV et al.
2022/0167982 A1 6/2022 Shelton, IV et al.
2022/0167995 A1 6/2022 Parfett et al.
2022/0168038 A1 6/2022 Shelton, IV et al.
2022/0175370 A1 6/2022 Shelton, IV et al.
2022/0175371 A1 6/2022 Hess et al.
2022/0175372 A1 6/2022 Shelton, IV et al.
2022/0175375 A1 6/2022 Harris et al.
2022/0175378 A1 6/2022 Leimbach et al.
2022/0175381 A1 6/2022 Scheib et al.
2022/0183685 A1 6/2022 Shelton, IV et al.
2022/0183687 A1 6/2022 Wixey et al.
2022/0202487 A1 6/2022 Shelton, IV et al.
2022/0211367 A1 7/2022 Schmid et al.
2022/0218332 A1 7/2022 Shelton, IV et al.
2022/0218336 A1 7/2022 Timm et al.
2022/0218338 A1 7/2022 Shelton, IV et al.
2022/0218344 A1 7/2022 Leimbach et al.
2022/0218345 A1 7/2022 Shelton, IV et al.
2022/0218346 A1 7/2022 Shelton, IV et al.
2022/0218347 A1 7/2022 Shelton, IV et al.
2022/0218348 A1 7/2022 Swensgard et al.
2022/0218349 A1 7/2022 Shelton, IV et al.
2022/0218350 A1 7/2022 Shelton, IV et al.
2022/0218351 A1 7/2022 Shelton, IV et al.
2022/0218376 A1 7/2022 Shelton, IV et al.
2022/0218381 A1 7/2022 Leimbach et al.
2022/0218382 A1 7/2022 Leimbach et al.
2022/0225986 A1 7/2022 Shelton, IV et al.
2022/0225993 A1 7/2022 Huitema et al.
2022/0225994 A1 7/2022 Setser et al.
2022/0226013 A1 7/2022 Hall et al.
2022/0233186 A1 7/2022 Timm et al.
2022/0233188 A1 7/2022 Timm et al.
2022/0233194 A1 7/2022 Baxter, III et al.
2022/0233195 A1 7/2022 Shelton, IV et al.
2022/0233257 A1 7/2022 Shelton, IV et al.
2022/0240928 A1 8/2022 Timm et al.
2022/0240929 A1 8/2022 Timm et al.
2022/0240930 A1 8/2022 Yates et al.
2022/0240936 A1 8/2022 Huitema et al.
2022/0240937 A1 8/2022 Shelton, IV et al.
2022/0265272 A1 8/2022 Li et al.
2022/0273293 A1 9/2022 Shelton, IV et al.
2022/0273294 A1 9/2022 Creamer et al.
2022/0273300 A1 9/2022 Shelton, IV et al.
2022/0273303 A1 9/2022 Creamer et al.
2022/0273304 A1 9/2022 Shelton, IV et al.
2022/0273306 A1 9/2022 Shelton, IV et al.
2022/0273307 A1 9/2022 Shelton, IV et al.
2022/0273308 A1 9/2022 Shelton, IV et al.
2022/0287711 A1 9/2022 Ming et al.
2022/0296230 A1 9/2022 Adams et al.
2022/0296231 A1 9/2022 Adams et al.
2022/0296232 A1 9/2022 Adams et al.
2022/0296237 A1 9/2022 Bakos et al.
2022/0304679 A1 9/2022 Bakos et al.
2022/0304680 A1 9/2022 Shelton, IV et al.
2022/0304681 A1 9/2022 Shelton, IV et al.
2022/0304682 A1 9/2022 Shelton, IV et al.
2022/0304683 A1 9/2022 Shelton, IV et al.
2022/0304684 A1 9/2022 Bakos et al.
2022/0304685 A1 9/2022 Bakos et al.
2022/0304686 A1 9/2022 Shelton, IV et al.
2022/0304687 A1 9/2022 Shelton, IV et al.
2022/0304688 A1 9/2022 Shelton, IV et al.
2022/0304689 A1 9/2022 Shelton, IV
2022/0304690 A1 9/2022 Baxter, III et al.
2022/0304715 A1 9/2022 Shelton, IV
2022/0313253 A1 10/2022 Shelton, IV et al.
2022/0313263 A1 10/2022 Huitema et al.
2022/0313619 A1 10/2022 Schmid et al.
2022/0323067 A1 10/2022 Overmyer et al.
2022/0323070 A1 10/2022 Ross et al.
2022/0330940 A1 10/2022 Shelton, IV et al.
2022/0338870 A1 10/2022 Swayze et al.
2022/0346774 A1 11/2022 Hess et al.
2022/0346775 A1 11/2022 Hess et al.

(56) References Cited

U.S. PATENT DOCUMENTS

| | | | |
|---|---|---|---|
| 2022/0346776 | A1 | 11/2022 | Aronhalt et al. |
| 2022/0346781 | A1 | 11/2022 | Shelton, IV et al. |
| 2022/0346783 | A1 | 11/2022 | Shelton, IV et al. |
| 2022/0346785 | A1 | 11/2022 | Aronhalt et al. |
| 2022/0354492 | A1 | 11/2022 | Baril |
| 2022/0354493 | A1 | 11/2022 | Shelton, IV et al. |
| 2022/0354495 | A1 | 11/2022 | Baxter, III et al. |
| 2022/0361879 | A1 | 11/2022 | Baxter, III et al. |
| 2022/0370069 | A1 | 11/2022 | Simms et al. |
| 2022/0378418 | A1 | 12/2022 | Huang et al. |
| 2022/0378424 | A1 | 12/2022 | Huang et al. |
| 2022/0378425 | A1 | 12/2022 | Huang et al. |
| 2022/0378426 | A1 | 12/2022 | Huang et al. |
| 2022/0378427 | A1 | 12/2022 | Huang et al. |
| 2022/0378428 | A1 | 12/2022 | Shelton, IV et al. |
| 2022/0378435 | A1 | 12/2022 | Dholakia et al. |
| 2022/0387030 | A1 | 12/2022 | Shelton, IV et al. |
| 2022/0387031 | A1 | 12/2022 | Yates et al. |
| 2022/0387032 | A1 | 12/2022 | Huitema et al. |
| 2022/0387033 | A1 | 12/2022 | Huitema et al. |
| 2022/0387034 | A1 | 12/2022 | Huitema et al. |
| 2022/0387035 | A1 | 12/2022 | Huitema et al. |
| 2022/0387036 | A1 | 12/2022 | Huitema et al. |
| 2022/0387037 | A1 | 12/2022 | Huitema et al. |
| 2022/0387038 | A1 | 12/2022 | Huitema et al. |
| 2022/0387125 | A1 | 12/2022 | Leimbach et al. |
| 2023/0016171 | A1 | 1/2023 | Yates et al. |
| 2023/0018950 | A1 | 1/2023 | Shelton, IV et al. |
| 2023/0055711 | A1 | 2/2023 | Chen et al. |
| 2023/0088531 | A1 | 3/2023 | Hall et al. |
| 2023/0094712 | A1 | 3/2023 | Shelton, IV et al. |
| 2023/0120983 | A1 | 4/2023 | Stokes et al. |
| 2023/0121131 | A1 | 4/2023 | Swayze et al. |
| 2023/0121658 | A1 | 4/2023 | Stokes et al. |
| 2023/0133811 | A1 | 5/2023 | Huang |
| 2023/0134883 | A1 | 5/2023 | Leimbach |
| 2023/0135070 | A1 | 5/2023 | Shelton, IV et al. |
| 2023/0135282 | A1 | 5/2023 | Schings et al. |
| 2023/0135811 | A1 | 5/2023 | Guest |
| 2023/0138314 | A1 | 5/2023 | Jenkins |
| 2023/0138743 | A1 | 5/2023 | Ross et al. |
| 2023/0165582 | A1 | 6/2023 | Harris et al. |
| 2023/0165584 | A1 | 6/2023 | Leimbach et al. |
| 2023/0172607 | A1 | 6/2023 | DiNardo et al. |
| 2023/0200831 | A1 | 6/2023 | Swensgard et al. |
| 2023/0210525 | A1 | 7/2023 | Shelton, IV et al. |
| 2023/0218296 | A1 | 7/2023 | Yates et al. |
| 2023/0240677 | A1 | 8/2023 | Ming et al. |
| 2023/0240678 | A1 | 8/2023 | Overmyer et al. |
| 2023/0255631 | A1 | 8/2023 | Vendely et al. |
| 2023/0270438 | A1 | 8/2023 | Jaworek et al. |
| 2023/0277175 | A1 | 9/2023 | Shelton, IV et al. |
| 2023/0285021 | A1 | 9/2023 | Shelton, IV |

FOREIGN PATENT DOCUMENTS

| | | | |
|---|---|---|---|
| AU | 2012268848 | A1 | 1/2013 |
| AU | 2011218702 | B2 | 6/2013 |
| AU | 2012200178 | B2 | 7/2013 |
| BR | 112013007744 | A2 | 6/2016 |
| BR | 112013027777 | A2 | 1/2017 |
| CA | 1015829 | A | 8/1977 |
| CA | 1125615 | A | 6/1982 |
| CA | 2520413 | A1 | 3/2007 |
| CA | 2725181 | A1 | 11/2007 |
| CA | 2851239 | A1 | 11/2007 |
| CA | 2550059 | C | 8/2008 |
| CA | 2664874 | A1 | 11/2009 |
| CA | 2813230 | A1 | 4/2012 |
| CA | 2940510 | A1 | 8/2015 |
| CA | 2698728 | C | 8/2016 |
| CN | 1163558 | A | 10/1997 |
| CN | 2488482 | Y | 5/2002 |
| CN | 1634601 | A | 7/2005 |
| CN | 2716900 | Y | 8/2005 |
| CN | 2738962 | Y | 11/2005 |
| CN | 1777406 | A | 5/2006 |
| CN | 2785249 | Y | 5/2006 |
| CN | 2796654 | Y | 7/2006 |
| CN | 2868212 | Y | 2/2007 |
| CN | 200942099 | Y | 9/2007 |
| CN | 200984209 | Y | 12/2007 |
| CN | 200991269 | Y | 12/2007 |
| CN | 201001747 | Y | 1/2008 |
| CN | 101143105 | A | 3/2008 |
| CN | 201029899 | Y | 3/2008 |
| CN | 101188900 | A | 5/2008 |
| CN | 101203085 | A | 6/2008 |
| CN | 101273908 | A | 10/2008 |
| CN | 101378791 | A | 3/2009 |
| CN | 101401736 | A | 4/2009 |
| CN | 101507635 | A | 8/2009 |
| CN | 101522120 | A | 9/2009 |
| CN | 101669833 | A | 3/2010 |
| CN | 101716090 | A | 6/2010 |
| CN | 101721236 | A | 6/2010 |
| CN | 101756727 | A | 6/2010 |
| CN | 101828940 | A | 9/2010 |
| CN | 101856250 | A | 10/2010 |
| CN | 101873834 | A | 10/2010 |
| CN | 201719298 | U | 1/2011 |
| CN | 102038532 | A | 5/2011 |
| CN | 201879759 | U | 6/2011 |
| CN | 201949071 | U | 8/2011 |
| CN | 102217961 | A | 10/2011 |
| CN | 102217963 | A | 10/2011 |
| CN | 102243850 | A | 11/2011 |
| CN | 102247182 | A | 11/2011 |
| CN | 102247183 | A | 11/2011 |
| CN | 101779977 | B | 12/2011 |
| CN | 102309352 | A | 1/2012 |
| CN | 101912284 | B | 7/2012 |
| CN | 102125450 | B | 7/2012 |
| CN | 202313537 | U | 7/2012 |
| CN | 202397539 | U | 8/2012 |
| CN | 202426586 | U | 9/2012 |
| CN | 102743201 | A | 10/2012 |
| CN | 202489990 | U | 10/2012 |
| CN | 102228387 | B | 11/2012 |
| CN | 102835977 | A | 12/2012 |
| CN | 202568350 | U | 12/2012 |
| CN | 103037781 | A | 4/2013 |
| CN | 103083053 | A | 5/2013 |
| CN | 103391037 | A | 11/2013 |
| CN | 203328751 | U | 12/2013 |
| CN | 103505264 | A | 1/2014 |
| CN | 103584893 | A | 2/2014 |
| CN | 103635150 | A | 3/2014 |
| CN | 103690212 | A | 4/2014 |
| CN | 103764046 | A | 4/2014 |
| CN | 203564285 | U | 4/2014 |
| CN | 203564287 | U | 4/2014 |
| CN | 203597997 | U | 5/2014 |
| CN | 103829981 | A | 6/2014 |
| CN | 103829983 | A | 6/2014 |
| CN | 103860221 | A | 6/2014 |
| CN | 103908313 | A | 7/2014 |
| CN | 203693685 | U | 7/2014 |
| CN | 203736251 | U | 7/2014 |
| CN | 103981635 | A | 8/2014 |
| CN | 104027145 | A | 9/2014 |
| CN | 203815517 | U | 9/2014 |
| CN | 102783741 | B | 10/2014 |
| CN | 102973300 | B | 10/2014 |
| CN | 104321021 | A | 1/2015 |
| CN | 204092074 | U | 1/2015 |
| CN | 104337556 | A | 2/2015 |
| CN | 204158440 | L | 2/2015 |
| CN | 204158441 | U | 2/2015 |
| CN | 102469995 | B | 3/2015 |
| CN | 104422849 | A | 3/2015 |
| CN | 104586463 | A | 5/2015 |
| CN | 204520822 | U | 8/2015 |
| CN | 204636451 | U | 9/2015 |

(56) References Cited

FOREIGN PATENT DOCUMENTS

| | | | |
|---|---|---|---|
| CN | 103860225 | B | 3/2016 |
| CN | 103750872 | B | 5/2016 |
| CN | 105682566 | A | 6/2016 |
| CN | 105919642 | A | 9/2016 |
| CN | 103648410 | B | 10/2016 |
| CN | 105997173 | A | 10/2016 |
| CN | 106344091 | A | 1/2017 |
| CN | 104921730 | B | 9/2017 |
| CN | 104349800 | B | 11/2017 |
| CN | 107635483 | A | 1/2018 |
| CN | 208625784 | U | 3/2019 |
| DE | 273689 | C | 5/1914 |
| DE | 1775926 | A | 1/1972 |
| DE | 3036217 | A1 | 4/1982 |
| DE | 3210466 | A1 | 9/1983 |
| DE | 3709067 | A1 | 9/1988 |
| DE | 19534043 | A1 | 3/1997 |
| DE | 19851291 | A1 | 1/2000 |
| DE | 19924311 | A1 | 11/2000 |
| DE | 20016423 | U1 | 2/2001 |
| DE | 20112837 | U1 | 10/2001 |
| DE | 20121753 | U1 | 4/2003 |
| DE | 202004012389 | U1 | 9/2004 |
| DE | 10314072 | A1 | 10/2004 |
| DE | 102004014011 | A1 | 10/2005 |
| DE | 102004041871 | A1 | 3/2006 |
| DE | 102004063606 | A1 | 7/2006 |
| DE | 202007003114 | U1 | 6/2007 |
| DE | 102010013150 | A1 | 9/2011 |
| DE | 102012213322 | A1 | 1/2014 |
| DE | 102013101158 | A1 | 8/2014 |
| EM | 002220467-0008 | | 4/2013 |
| EP | 0000756 | A1 | 2/1979 |
| EP | 0122046 | A1 | 10/1984 |
| EP | 0129442 | B1 | 11/1987 |
| EP | 0251444 | A1 | 1/1988 |
| EP | 0255631 | A1 | 2/1988 |
| EP | 0169044 | B1 | 6/1991 |
| EP | 0541950 | A1 | 5/1993 |
| EP | 0548998 | A1 | 6/1993 |
| EP | 0594148 | A1 | 4/1994 |
| EP | 0646357 | A1 | 4/1995 |
| EP | 0505036 | B1 | 5/1995 |
| EP | 0669104 | A1 | 8/1995 |
| EP | 0516544 | B1 | 3/1996 |
| EP | 0705571 | A1 | 4/1996 |
| EP | 0528478 | B1 | 5/1996 |
| EP | 0770355 | A1 | 5/1997 |
| EP | 0625335 | B1 | 11/1997 |
| EP | 0879742 | A1 | 11/1998 |
| EP | 0650701 | B1 | 3/1999 |
| EP | 0923907 | A1 | 6/1999 |
| EP | 0484677 | B2 | 7/2000 |
| EP | 1034747 | A1 | 9/2000 |
| EP | 1034748 | A1 | 9/2000 |
| EP | 0726632 | B1 | 10/2000 |
| EP | 1053719 | A1 | 11/2000 |
| EP | 1055399 | A1 | 11/2000 |
| EP | 1055400 | A1 | 11/2000 |
| EP | 1064882 | A1 | 1/2001 |
| EP | 1080694 | A1 | 3/2001 |
| EP | 1090592 | A1 | 4/2001 |
| EP | 1095627 | A1 | 5/2001 |
| EP | 0806914 | B1 | 9/2001 |
| EP | 1157666 | A1 | 11/2001 |
| EP | 1234587 | A1 | 8/2002 |
| EP | 1284120 | A1 | 2/2003 |
| EP | 0717967 | B1 | 5/2003 |
| EP | 0869742 | B1 | 5/2003 |
| EP | 1374788 | A1 | 1/2004 |
| EP | 1407719 | A2 | 4/2004 |
| EP | 0996378 | B1 | 6/2004 |
| EP | 1558161 | A1 | 8/2005 |
| EP | 0880338 | B1 | 10/2005 |
| EP | 1158917 | B1 | 11/2005 |
| EP | 1344498 | B1 | 11/2005 |
| EP | 1330989 | B1 | 12/2005 |
| EP | 1632191 | A2 | 3/2006 |
| EP | 1082944 | B1 | 5/2006 |
| EP | 1253866 | B1 | 7/2006 |
| EP | 1723914 | A1 | 11/2006 |
| EP | 1285633 | B1 | 12/2006 |
| EP | 1011494 | B1 | 1/2007 |
| EP | 1767163 | A1 | 3/2007 |
| EP | 1837041 | A1 | 9/2007 |
| EP | 0922435 | B1 | 10/2007 |
| EP | 1599146 | B1 | 10/2007 |
| EP | 1330201 | B1 | 6/2008 |
| EP | 2039302 | A2 | 3/2009 |
| EP | 1719461 | B1 | 6/2009 |
| EP | 2116196 | A2 | 11/2009 |
| EP | 2153793 | A2 | 2/2010 |
| EP | 1769754 | B1 | 6/2010 |
| EP | 1627605 | B1 | 12/2010 |
| EP | 2316345 | A1 | 5/2011 |
| EP | 1962711 | B1 | 2/2012 |
| EP | 2486862 | A2 | 8/2012 |
| EP | 2486868 | A2 | 8/2012 |
| EP | 2517638 | A1 | 10/2012 |
| EP | 2529671 | A2 | 12/2012 |
| EP | 2606812 | A1 | 6/2013 |
| EP | 2649948 | A1 | 10/2013 |
| EP | 2649949 | A1 | 10/2013 |
| EP | 2668910 | A2 | 12/2013 |
| EP | 2687164 | A2 | 1/2014 |
| EP | 2713902 | A1 | 4/2014 |
| EP | 2743042 | A2 | 6/2014 |
| EP | 2764827 | A2 | 8/2014 |
| EP | 2777524 | A2 | 9/2014 |
| EP | 2789299 | A1 | 10/2014 |
| EP | 2842500 | A1 | 3/2015 |
| EP | 2853220 | A1 | 4/2015 |
| EP | 2878274 | A1 | 6/2015 |
| EP | 2298220 | B1 | 6/2016 |
| EP | 2510891 | B1 | 6/2016 |
| EP | 3031404 | A1 | 6/2016 |
| EP | 3047806 | A1 | 7/2016 |
| EP | 3078334 | A1 | 10/2016 |
| EP | 2364651 | B1 | 11/2016 |
| EP | 2747235 | B1 | 11/2016 |
| EP | 3095399 | A2 | 11/2016 |
| EP | 3120781 | A2 | 1/2017 |
| EP | 3135225 | A2 | 3/2017 |
| EP | 2789299 | B1 | 5/2017 |
| EP | 3225190 | A2 | 10/2017 |
| EP | 3235445 | A1 | 10/2017 |
| EP | 3326548 | A1 | 5/2018 |
| EP | 3363378 | A1 | 8/2018 |
| EP | 3409216 | A1 | 12/2018 |
| EP | 3476301 | A1 | 5/2019 |
| EP | 3476334 | A1 | 5/2019 |
| EP | 3275378 | B1 | 7/2019 |
| EP | 3505095 | A1 | 7/2019 |
| EP | 3791810 | A1 | 3/2021 |
| ES | 1070456 | U | 9/2009 |
| FR | 459743 | A | 11/1913 |
| FR | 999646 | A | 2/1952 |
| FR | 1112936 | A | 3/1956 |
| FR | 2598905 | A1 | 11/1987 |
| FR | 2689749 | B1 | 7/1994 |
| FR | 2765794 | A1 | 1/1999 |
| FR | 2815842 | A1 | 5/2002 |
| GB | 939929 | A | 10/1963 |
| GB | 1210522 | A | 10/1970 |
| GB | 1217159 | A | 12/1970 |
| GB | 1339394 | A | 12/1973 |
| GB | 2024012 | A | 1/1980 |
| GB | 2109241 | A | 6/1983 |
| GB | 2090534 | B | 6/1984 |
| GB | 2272159 | A | 5/1994 |
| GB | 2336214 | A | 10/1999 |
| GB | 2509523 | A | 7/2014 |
| GR | 930100110 | A | 11/1993 |
| JP | S4711908 | Y1 | 5/1972 |

(56) References Cited

FOREIGN PATENT DOCUMENTS

| | | | |
|---|---|---|---|
| JP | S5033988 | U | 4/1975 |
| JP | S5367286 | A | 6/1978 |
| JP | S56112235 | A | 9/1981 |
| JP | S60113007 | A | 6/1985 |
| JP | S62170011 | U | 10/1987 |
| JP | S6333137 | A | 2/1988 |
| JP | S63270040 | A | 11/1988 |
| JP | S63318824 | A | 12/1988 |
| JP | H0129503 | B2 | 6/1989 |
| JP | H02106189 | A | 4/1990 |
| JP | H0378514 | U | 8/1991 |
| JP | H0385009 | U | 8/1991 |
| JP | H0489041 | A | 3/1992 |
| JP | H04215747 | A | 8/1992 |
| JP | H04131860 | U | 12/1992 |
| JP | H0584252 | A | 4/1993 |
| JP | H05123325 | A | 5/1993 |
| JP | H05226945 | A | 9/1993 |
| JP | H0630945 | A | 2/1994 |
| JP | H0636757 | A | 2/1994 |
| JP | H06237937 | A | 8/1994 |
| JP | H06304176 | A | 11/1994 |
| JP | H06327684 | A | 11/1994 |
| JP | H079622 | U | 2/1995 |
| JP | H07124166 | A | 5/1995 |
| JP | H07163573 | A | 6/1995 |
| JP | H07255735 | A | 10/1995 |
| JP | H07285089 | A | 10/1995 |
| JP | H0833642 | A | 2/1996 |
| JP | H08164141 | A | 6/1996 |
| JP | H08182684 | A | 7/1996 |
| JP | H08507708 | A | 8/1996 |
| JP | H08229050 | A | 9/1996 |
| JP | H08289895 | A | 11/1996 |
| JP | H0950795 | A | 2/1997 |
| JP | H09-323068 | A | 12/1997 |
| JP | H10118090 | A | 5/1998 |
| JP | H10-200699 | A | 7/1998 |
| JP | H10296660 | A | 11/1998 |
| JP | 2000014632 | A | 1/2000 |
| JP | 2000033071 | A | 2/2000 |
| JP | 2000112002 | A | 4/2000 |
| JP | 2000166932 | A | 6/2000 |
| JP | 2000171730 | A | 6/2000 |
| JP | 2000210299 | A | 8/2000 |
| JP | 2000271141 | A | 10/2000 |
| JP | 2000287987 | A | 10/2000 |
| JP | 2000325303 | A | 11/2000 |
| JP | 2001-69758 | A | 3/2001 |
| JP | 2001087272 | A | 4/2001 |
| JP | 2001208655 | A | 8/2001 |
| JP | 2001514541 | A | 9/2001 |
| JP | 2001276091 | A | 10/2001 |
| JP | 2002051974 | A | 2/2002 |
| JP | 2002054903 | A | 2/2002 |
| JP | 2002085415 | A | 3/2002 |
| JP | 2002143078 | A | 5/2002 |
| JP | 2002153481 | A | 5/2002 |
| JP | 2002528161 | A | 9/2002 |
| JP | 2002314298 | A | 10/2002 |
| JP | 2003135473 | A | 5/2003 |
| JP | 2003521301 | A | 7/2003 |
| JP | 3442423 | B2 | 9/2003 |
| JP | 2003300416 | A | 10/2003 |
| JP | 2004147701 | A | 5/2004 |
| JP | 2004162035 | A | 6/2004 |
| JP | 2004229976 | A | 8/2004 |
| JP | 2005013573 | A | 1/2005 |
| JP | 2005080702 | A | 3/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005187954 | A | 7/2005 |
| JP | 2005211455 | A | 8/2005 |
| JP | 2005328882 | A | 12/2005 |
| JP | 2005335432 | A | 12/2005 |
| JP | 2005342267 | A | 12/2005 |
| JP | 3791856 | B2 | 6/2006 |
| JP | 2006187649 | A | 7/2006 |
| JP | 2006218228 | A | 8/2006 |
| JP | 2006281405 | A | 10/2006 |
| JP | 2006291180 | A | 10/2006 |
| JP | 2006346445 | A | 12/2006 |
| JP | 2007-97252 | A | 4/2007 |
| JP | 2007289715 | A | 11/2007 |
| JP | 2007304057 | A | 11/2007 |
| JP | 2007306710 | A | 11/2007 |
| JP | D1322057 | | 2/2008 |
| JP | 2008154804 | A | 7/2008 |
| JP | 2008220032 | A | 9/2008 |
| JP | 2009507526 | A | 2/2009 |
| JP | 2009189838 | A | 8/2009 |
| JP | 2009189846 | A | 8/2009 |
| JP | 2009207260 | A | 9/2009 |
| JP | 2009226028 | A | 10/2009 |
| JP | 2009538684 | A | 11/2009 |
| JP | 2009539420 | A | 11/2009 |
| JP | D1383743 | | 2/2010 |
| JP | 2010065594 | A | 3/2010 |
| JP | 2010069307 | A | 4/2010 |
| JP | 2010069310 | A | 4/2010 |
| JP | 2010098844 | A | 4/2010 |
| JP | 2010214128 | A | 9/2010 |
| JP | 2011072574 | A | 4/2011 |
| JP | 4722849 | B2 | 7/2011 |
| JP | 4728996 | B2 | 7/2011 |
| JP | 2011524199 | A | 9/2011 |
| JP | 2011200665 | A | 10/2011 |
| JP | D1432094 | | 12/2011 |
| JP | 1433631 | S | 2/2012 |
| JP | 2012115542 | A | 6/2012 |
| JP | 2012143283 | A | 8/2012 |
| JP | 5154710 | B1 | 2/2013 |
| JP | 2013099551 | A | 5/2013 |
| JP | 2013126430 | A | 6/2013 |
| JP | D1481426 | | 9/2013 |
| JP | 2013541982 | A | 11/2013 |
| JP | 2013541983 | A | 11/2013 |
| JP | 2013541997 | A | 11/2013 |
| JP | 2014018667 | A | 2/2014 |
| JP | D1492363 | | 2/2014 |
| JP | 2014121599 | A | 7/2014 |
| JP | 2014171879 | A | 9/2014 |
| JP | 1517663 | S | 2/2015 |
| JP | 2015512725 | A | 4/2015 |
| JP | 2015513956 | A | 5/2015 |
| JP | 2015513958 | A | 5/2015 |
| JP | 2015514471 | A | 5/2015 |
| JP | 2015516838 | A | 6/2015 |
| JP | 2015521524 | A | 7/2015 |
| JP | 2015521525 | A | 7/2015 |
| JP | 2016007800 | A | 1/2016 |
| JP | 2016508792 | A | 3/2016 |
| JP | 2016512057 | A | 4/2016 |
| JP | 2016518914 | A | 6/2016 |
| JP | 2016530949 | A | 10/2016 |
| JP | 2017513563 | A | 6/2017 |
| JP | 1601498 | S | 4/2018 |
| JP | 2019513530 | A | 5/2019 |
| JP | 2020501797 | A | 1/2020 |
| JP | D1677030 | S | 1/2021 |
| JP | D1696539 | S | 10/2021 |
| KR | 20100110134 | A | 10/2010 |
| KR | 20110003229 | A | 1/2011 |
| KR | 300631507 | | 3/2012 |
| KR | 300747646 | | 6/2014 |
| KR | 20180053811 | A | 5/2018 |
| RU | 1814161 | A1 | 5/1993 |
| RU | 1814161 | C | 5/1993 |
| RU | 2008830 | C1 | 3/1994 |
| RU | 2052979 | C1 | 1/1996 |

(56) References Cited

FOREIGN PATENT DOCUMENTS

| | | | |
|---|---|---|---|
| RU | 2066128 | C1 | 9/1996 |
| RU | 2069981 | C1 | 12/1996 |
| RU | 2098025 | C1 | 12/1997 |
| RU | 2104671 | C1 | 2/1998 |
| RU | 2110965 | C1 | 5/1998 |
| RU | 2141279 | C1 | 11/1999 |
| RU | 2144791 | C1 | 1/2000 |
| RU | 2161450 | C1 | 1/2001 |
| RU | 2181566 | C2 | 4/2002 |
| RU | 2187249 | C2 | 8/2002 |
| RU | 32984 | U1 | 10/2003 |
| RU | 2225170 | C2 | 3/2004 |
| RU | 42750 | U1 | 12/2004 |
| RU | 61114 | U1 | 2/2007 |
| RU | 61122 | U1 | 2/2007 |
| RU | 2430692 | C2 | 10/2011 |
| SU | 189517 | A | 1/1967 |
| SU | 297156 | A | 5/1971 |
| SU | 328636 | A | 9/1972 |
| SU | 511939 | A1 | 4/1976 |
| SU | 674747 | A1 | 7/1979 |
| SU | 728848 | A1 | 4/1980 |
| SU | 1009439 | A | 4/1983 |
| SU | 1042742 | A1 | 9/1983 |
| SU | 1271497 | A1 | 11/1986 |
| SU | 1333319 | A2 | 8/1987 |
| SU | 1377052 | A1 | 2/1988 |
| SU | 1377053 | A1 | 2/1988 |
| SU | 1443874 | A1 | 12/1988 |
| SU | 1509051 | A1 | 9/1989 |
| SU | 1561964 | A1 | 5/1990 |
| SU | 1708312 | A1 | 1/1992 |
| SU | 1722476 | A1 | 3/1992 |
| SU | 1752361 | A1 | 8/1992 |
| WO | WO-9308754 | A1 | 5/1993 |
| WO | WO-9315648 | A1 | 8/1993 |
| WO | WO-9420030 | A1 | 9/1994 |
| WO | WO-9517855 | A1 | 7/1995 |
| WO | WO-9520360 | A1 | 8/1995 |
| WO | WO-9623448 | A1 | 8/1996 |
| WO | WO-9635464 | A1 | 11/1996 |
| WO | WO-9639086 | A1 | 12/1996 |
| WO | WO-9639088 | A1 | 12/1996 |
| WO | WO-9724073 | A1 | 7/1997 |
| WO | WO-9734533 | A1 | 9/1997 |
| WO | WO-9827870 | A1 | 7/1998 |
| WO | WO-9903407 | A1 | 1/1999 |
| WO | WO-9903409 | A1 | 1/1999 |
| WO | WO-9948430 | A1 | 9/1999 |
| WO | WO-0024322 | A1 | 5/2000 |
| WO | WO-0024330 | A1 | 5/2000 |
| WO | WO-0036690 | A2 | 6/2000 |
| WO | WO-0053112 | A2 | 9/2000 |
| WO | WO-0024448 | A2 | 10/2000 |
| WO | WO-0057796 | A1 | 10/2000 |
| WO | WO-0105702 | A1 | 1/2001 |
| WO | WO-0154594 | A1 | 8/2001 |
| WO | WO-0158371 | A1 | 8/2001 |
| WO | WO-0162164 | A2 | 8/2001 |
| WO | WO-0162169 | A2 | 8/2001 |
| WO | WO-0191646 | A1 | 12/2001 |
| WO | WO-0219932 | A1 | 3/2002 |
| WO | WO-0226143 | A1 | 4/2002 |
| WO | WO-0236028 | A1 | 5/2002 |
| WO | WO-02065933 | A2 | 8/2002 |
| WO | WO-03055402 | A1 | 7/2003 |
| WO | WO-03094747 | A1 | 11/2003 |
| WO | WO-03079909 | A3 | 3/2004 |
| WO | WO-2004019803 | A1 | 3/2004 |
| WO | WO-2004032783 | A1 | 4/2004 |
| WO | WO-2004047626 | A1 | 6/2004 |
| WO | WO-2004047653 | A2 | 6/2004 |
| WO | WO-2004056277 | A1 | 7/2004 |
| WO | WO-2004078050 | A2 | 9/2004 |
| WO | WO-2004078051 | A2 | 9/2004 |
| WO | WO-2004096015 | A2 | 11/2004 |
| WO | WO-2006044581 | A2 | 4/2006 |
| WO | WO-2006051252 | A1 | 5/2006 |
| WO | WO-2006059067 | A1 | 6/2006 |
| WO | WO-2006073581 | A2 | 7/2006 |
| WO | WO-2006085389 | A1 | 8/2006 |
| WO | WO-2007015971 | A2 | 2/2007 |
| WO | WO-2007074430 | A1 | 7/2007 |
| WO | WO-2007129121 | A1 | 11/2007 |
| WO | WO-2007137304 | A2 | 11/2007 |
| WO | WO-2007142625 | A2 | 12/2007 |
| WO | WO-2008021969 | A2 | 2/2008 |
| WO | WO-2008061566 | A1 | 5/2008 |
| WO | WO-2008089404 | A2 | 7/2008 |
| WO | WO-2009005969 | A2 | 1/2009 |
| WO | WO-2009067649 | A2 | 5/2009 |
| WO | WO-2009091497 | A2 | 7/2009 |
| WO | WO-2010126129 | A1 | 11/2010 |
| WO | WO-2010134913 | A1 | 11/2010 |
| WO | WO-2011008672 | A2 | 1/2011 |
| WO | WO-2011044343 | A2 | 4/2011 |
| WO | WO-2012006306 | A2 | 1/2012 |
| WO | WO-2012013577 | A1 | 2/2012 |
| WO | WO-2012044606 | A2 | 4/2012 |
| WO | WO-2012061725 | A1 | 5/2012 |
| WO | WO-2012072133 | A1 | 6/2012 |
| WO | WO-2012166503 | A1 | 12/2012 |
| WO | WO-2013087092 | A1 | 6/2013 |
| WO | WO-2013151888 | A1 | 10/2013 |
| WO | WO-2014004209 | A2 | 1/2014 |
| WO | WO-2014113438 | A1 | 7/2014 |
| WO | WO-2014175894 | A1 | 10/2014 |
| WO | WO-2015032797 | A1 | 3/2015 |
| WO | WO-2015076780 | A1 | 5/2015 |
| WO | WO-2015137040 | A1 | 9/2015 |
| WO | WO-2015138760 | A1 | 9/2015 |
| WO | WO-2015187107 | A1 | 12/2015 |
| WO | WO-2016100682 | A1 | 6/2016 |
| WO | WO-2016107448 | A1 | 7/2016 |
| WO | WO-2017138905 | A1 | 8/2017 |
| WO | WO-2018011664 | A1 | 1/2018 |
| WO | WO-2019036490 | A1 | 2/2019 |
| WO | WO-2019130087 | A1 | 7/2019 |
| WO | WO-2019130089 | A1 | 7/2019 |
| WO | WO-2019208902 | A1 | 10/2019 |
| WO | WO-2021189234 | A1 | 9/2021 |
| WO | WO-2022249091 | A1 | 12/2022 |
| WO | WO-2022249094 | A1 | 12/2022 |

OTHER PUBLICATIONS

ASTM procedure D2240-05, "Standard Test Method for Rubber Property-Durometer Hardness," (Published Apr. 2010).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

Disclosed Anonymously, "Motor-Driven Surgical Stapler Improvements," Research Disclosure Database No. 526041, Published: Feb. 2008.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).

(56) References Cited

OTHER PUBLICATIONS

Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Covidien Brochure, "Endo GIA™ Ultra Universal Stapler," (2010), 2 pages.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Peppas, Editor "Hydrogels in Medicine and Pharmacy, " vol. I, Fundamentals, CRC Press, 1986.
Young, "Microcellular foams via phase separation," Journal of Vacuum Science & Technology A 4(3), (May/Jun. 1986).
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.
http://ninpgan.net/publications/51-100/89.pdf; 2004, Ning Pan, On Uniqueness of Fibrous Materials, Design & Nature II. Eds: Colins, M. and Brebbia, C. WIT Press, Boston, 493-504.
Solorio et al., "Gelatin Microspheres Crosslinked with Genipin for Local Delivery of Growth Factors," J. Tissue Eng. Regen. Med. (2010), 4(7): pp. 514-523.
Covidien iDrive™ Ultra in Service Reference Card, "iDrive™ Ultra Powered Stapling Device," (4 pages).
Covidien iDrive™ Ultra Powered Stapling System ibrochure, "The Power of iDrive™ Ultra Powered Stapling System and Tri-Staple™ Technology," (23 pages).
Covidien "iDrive™ Ultra Powered Stapling System, A Guide for Surgeons," (6 pages).
Covidien "iDrive™ Ultra Powered Stapling System, Cleaning and Sterilization Guide," (2 pages).
Covidien Brochure "iDrive™ Ultra Powered Stapling System," (6 pages).
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Pitt et al., "Attachment of Hyaluronan to Metallic Surfaces," J. Biomed. Mater. Res. 68A: pp. 95-106, 2004.
Indian Standard: Automotive Vehicles—Brakes and Braking Systems (IS 11852-1:2001), Mar. 1, 2001.
Patrick J. Sweeney: "RFID for Dummies", Mar. 11, 2010, pp. 365-365, XP055150775, ISBN: 978-1-11-805447-5, Retrieved from the Internet: URL: books.google.de/books?isbn=1118054474 [retrieved on Nov. 4, 2014]—book not attached.
Allegro MicroSystems, LLC, Automotive Full Bridge MOSFET Driver, A3941-DS, Rev. 5, 21 pages, http://www.allegromicro.com/~/media/Files/Datasheets/A3941-Datasheet_ashx?la=en.
Data Sheet of LM4F230H5QR, 2007.
Seils et al., Covidien Summary: Clinical Study "UCONN Biodynamics: Final Report on Results," (2 pages).
Byrne et al., "Molecular Imprinting Within Hydrogels," Advanced Drug Delivery Reviews, 54 (2002) pp. 149-161.
Fast, Versatile Blackfin Processors Handle Advanced RFID Reader Applications; Analog Dialogue: vol. 40—Sep. 2006; http://www.analog.com/library/analogDialogue/archives/40-09/rfid.pdf; Wayback Machine to Feb. 15, 2012.
Chen et al., "Elastomeric Biomaterials for Tissue Engineering," Progress in Polymer Science 38 (2013), pp. 584-671.
Matsuda, "Thermodynamics of Formation of Porous Polymeric Membrane from Solutions," Polymer Journal, vol. 23, No. 5, pp. 435-444 (1991).
Covidien Brochure, "Endo GIA™ Black Reload with Tri-Staple™ Technology," (2012), 2 pages.
Biomedical Coatings, Fort Wayne Metals, Research Products Corporation, obtained online at www.fwmetals.com on Jun. 21, 2010 (1 page).
The Sodem Aseptic Battery Transfer Kit, Sodem Systems, 2000, 3 pages.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.
Serial Communication Protocol; Michael Lemmon Feb. 1, 2009; http://www3.nd.edu/~lemmon/courses/ee224/web-manual/web-manual/lab12/node2.html; Wayback Machine to Apr. 29, 2012.
Lyon et al. "The Relationship Between Current Load and Temperature for Quasi-Steady State and Transient Conditions," SPIE—International Society for Optical Engineering. Proceedings, vol. 4020, (pp. 62-70), Mar. 30, 2000.
Anonymous: "Sense & Control Application Note Current Sensing Using Linear Hall Sensors," Feb. 3, 2009, pp. 1-18. Retrieved from the Internet: URL: http://www.infineon.com/dgdl/Current_Sensing_Rev.1.1.pdf?fileId=db3a304332d040720132d939503e5f17 [retrieved on Oct. 18, 2016].
Mouser Electronics, "LM317M 3-Terminal Adjustable Regulator with Overcurrent/Overtemperature Self Protection", Mar. 31, 2014 (Mar. 31, 2014), XP0555246104, Retrieved from the Internet: URL: http://www.mouser.com/ds/2/405/lm317m-440423.pdf, pp. 1-8.
Mouser Electronics, "LM317 3-Terminal Adjustable Regulator with Overcurrent/Overtemperature Self Protection", Sep. 30, 2016 (Sep. 30, 2016), XP0555246104, Retrieved from the Internet: URL: http://www.mouser.com/ds/2/405/lm317m-440423.pdf, pp. 1-9.
Cuper et al., "The Use of Near-Infrared Light for Safe and Effective Visualization of Subsurface Blood Vessels to Facilitate Blood Withdrawal in Children," Medical Engineering & Physics, vol. 35, No. 4, pp. 433-440 (2013).
Yan et al, Comparison of the effects of Mg—6Zn and Ti—3Al—2.5V alloys on TGF-β/TNF-α/VEGF/b-FGF in the healing of the intestinal track in vivo, Biomed. Mater. 9 (2014), 11 pages.
Pellicer et al. "On the biodegradability, mechanical behavior, and cytocompatibility of amorphous Mg72Zn23Ca5 and crystalline Mg70Zn23Ca5Pd2 alloys as temporary implant materials," J Biomed Mater Res Part A ,2013:101A:502-517.
Anonymous, Analog Devices Wiki, Chapter 11: The Current Mirror, Aug. 20, 2017, 22 pages. https://wiki.analog.com/university/courses/electronics/text/chapter-11?rev=1503222341.
Yan et al., "Comparison of the effects of Mg—6Zn and titanium on intestinal tract in vivo," J Mater Sci: Mater Med (2013), 11 pages.
Brar et al., "Investigation of the mechanical and degradation properties of Mg—Sr and Mg—Zn—Sr alloys for use as potential biodegradable implant materials," J. Mech. Behavior of Biomed. Mater. 7 (2012) pp. 87-95.
Texas Instruments: "Current Recirculation and Decay Modes," Application Report SLVA321—Mar. 2009; Retrieved from the Internet: URL:http://www.ti.com/lit/an/slva321/slva321 [retrieved on Apr. 25, 2017], 7 pages.
Qiu Li Loh et al.: "Three-Dimensional Scaffolds for Tissue Engineering Applications: Role of Porosity and Pore Size", Tissue Engineering Part B—Reviews, vol. 19, No. 6, Dec. 1, 2013, pp. 485-502.
Gao et al., "Mechanical Signature Enhancement of Response Vibrations in the Time Lag Domain," Fifth International Congress on Sound and Vibration, Dec. 15-18, 1997, pp. 1-8.
Trendafilova et al., "Vibration-based Methods for Structural and Machinery Fault Diagnosis Based on Nonlinear Dynamics Tools," In: Fault Diagnosis in Robotic and Industrial Systems, IConcept Press LTD, 2012, pp. 1-29.
Youtube.com; video by Fibran (retrieved from URL https://www.youtube.com/watch?v=vN2Qjt51gFQ); (Year: 2018).

(56) References Cited

OTHER PUBLICATIONS

Foot and Ankle: Core Knowledge in Orthopaedics; by DiGiovanni MD, Elsevier; (p. 27, left column heading "Materials for Soft Orthoses", 7th bullet point); (Year: 2007).
Lee, Youbok, "Antenna Circuit Design for RFID Applications," 2003, pp. 1-50, DS00710C, Microchip Technology Inc., Available: http://ww1.microchip.com/downloads/en/AppNotes/00710c.pdf.
Kawamura, Atsuo, et al. "Wireless Transmission of Power and Information Through One High-Frequency Resonant AC Link Inverter for Robot Manipulator Applications," Journal, May/Jun. 1996, pp. 503-508, vol. 32, No. 3, IEEE Transactions on Industry Applications.
Honda HS1332AT and ATD Model Info, powerequipment.honda.com [online], published on or before Mar. 22, 2016, [retrieved on May 31, 2019], retrieved from the Internet [URL: https://powerequipment.honda.com/snowblowers/models/hss1332at-hss1332atd] {Year: 2016).
Slow Safety Sign, shutterstock.com [online], published on or before May 9, 2017, [retrieved on May 31, 2019], retrieved from the https://www.shutterstock.com/image-victor/slow-safety-sign-twodimensional-turtle-symbolizing-. . . see PDF in file for full URL] (Year: 2017).
Warning Sign Beveled Buttons, by Peter, flarestock.com [online], published on or before Jan. 1, 2017, [retrieved on Jun. 4, 2019], retrieved from the Internet [URL: https://www.flarestock.com/stock-images/warning-sign-beveled-buttons/70257] (Year: 2017).
Arrow Sign Icon Next Button, by Blan-k, shutterstock.com [online], published on or before Aug. 6, 2014, [retrieved on Jun. 4, 2019], retrieved from the Internet [URL:https://www.shutterstock.com/de/image-vector/arrow-sign-icon-next-button-navigation-207700303?irgwc=1&utm . . . see PDF in file for full URL] (Year: 2014).
Elite Icons, by smart/icons, iconfinder.com [online], published on Aug. 18, 2016, [retrieved on Jun. 4, 2019], retrieved from the Internet [URL: https://www.iconfinder.com/iconsets/elite] (Year: 2016).
Tutorial overview of inductively coupled RFID Systems, UPM, May 2003, pp. 1-7, UPM Rafsec,<http://cdn.mobiusconsulting.com/papers/rfidsystems.pdf>.
Schroeter, John, "Demystifying UHF Gen 2 RFID, HF RFID," *Online Article*, Jun. 2, 2008, pp. 1-3, <https://www.edn.com/design/industrial-control/4019123/Demystifying-UHF-Gen-2-RFID-HF-RFID>.
Adeeb, et al., "An Inductive Link-Based Wireless Power Transfer System for Biomedical Applications," Research Article, Nov. 14, 2011, pp. 1-12, vol. 2012, *Article ID 879294, Hindawi Publishing Corporation*.
Pushing Pixels (GIF), published on dribble.com, 2013.
Sodium stearate C18H35NaO2, Chemspider Search and Share Chemistry, Royal Society of Chemistry, pp. 1-3, 2015, http://www.chemspider.com/Chemical-Structure.12639.html, accessed May 23, 2016.
NF Monographs: Sodium Stearate, U.S. Pharmacopeia, http://www.pharmacopeia.cn/v29240/usp29nf24s0_m77360.html, accessed May 23, 2016.
Fischer, Martin H, "Colloid-Chemical Studies on Soaps", The Chemical Engineer, pp. 184-193, Aug. 1919.
V.K. Ahluwalia and Madhuri Goyal, A Textbook of Organic Chemistry, Section 19.11.3, p. 356, 2000.
A.V. Kasture and S.G. Wadodkar, Pharmaceutical Chemistry-II: Second Year Diploma in Pharmacy, Nirali Prakashan, p. 339, 2007.
Forum discussion regarding "Speed is Faster", published on Oct. 1, 2014 and retrieved on Nov. 8, 2019 from URL https://english.stackexchange.com/questions/199018/how-is-that-correct-speed-is-faster-or-prices-are-cheaper (Year: 2014).
"Understanding the Requirements of ISO/IEC 14443 for Type B Proximity Contactless Identification Cards," retrieved from https://www.digchip.com/application-notes/22/15746.php on Mar. 2, 2020, pp. 1-28 (Nov. 2005).
Jauchem, J.R., "Effects of low-level radio-frequency (3 kHz to 300 GHz) enery on human cardiovascular, reproductive, immune, and other systems: A review of the recent literatured," Int. J. Hyg. Environ. Health 211 (2008) 1-29.
Sandvik, "Welding Handbook," https://www.meting.rs/wp-content/uploads/2018/05/welding-handbook.pdf, retrieved on Jun. 22, 2020. pp. 5-6.
Ludois, Daniel C., "Capacitive Power Transfer for Rotor Field Current in Synchronous Machines," IEEE Transactions on Power Electronics, Institute of Electrical and Electronics Engineers, USA, vol. 27, No. 11, Nov. 1, 2012, pp. 4638-4645.
Rotary Systems: Sealed Slip Ring Categories, Rotary Systems, May 22, 2017, retrieved from the internet: http://web.archive.org/we/20170522174710/http:/rotarysystems.com: 80/slip-rings/sealed/, retrieved on Aug. 12, 2020, pp. 1-2.
IEEE Std 802.3-2012 (Revision of IEEE Std 802.3-2008, published Dec. 28, 2012.
"ATM-MPLS Network Interworking Version 2.0, af-aic-0178.001" ATM Standard, The ATM Forum Technical Committee, published Aug. 2003.
Yang et al.; "4D printing reconfigurable, deployable and mechanically tunable metamaterials," Material Horizions, vol. 6, pp. 1244-1250 (2019).
"Council Directive 93/42/EEC of Jun. 14, 1993 Concerning Medical Devices," Official Journal of the European Communities, L&C. Ligislation and Competition, S, No. L 169, Jun. 14, 1993, pp. 1-43.
Arjo Loeve et al., Scopes Too Flexible . . . and Too Stiff, 2010, IEEE Pulse, Nov./Dec. 2010 (Year: 2010), 16 pages.
Molina, "Low Level Reader Protocol (LLRP)," Oct. 13, 2010, pp. 1-198.
Makerbot, 10 Advantages of 3D Printing, 2020 (retrieved via the wayback machine), Makerbot.com (Year: 2020).
U.S. Appl. No. 62/798,651, filed Jan. 30, 2019.
U.S. Appl. No. 62/840,602, filed Apr. 30, 2019.

* cited by examiner (Position 1) Jaw Closure

| | | |
|---|---|---|
| LED 1 | N.C. | N.C. |
| LED 2 | N.C. | N.C. |
| LED 3 | H | L |
| LED 4 | L | H |

(Position 2) Firing

| | | |
|---|---|---|
| LED 1 | H | L |
| LED 2 | L | H |
| LED 3 | N.C. | N.C. |
| LED 4 | N.C. | N.C. |

SURGICAL INSTRUMENT COMPRISING A FIRING DRIVE INCLUDING A SELECTABLE LEVERAGE MECHANISM

CROSS-REFERENCE TO RELATED APPLICATION

This application is a divisional application claiming priority under 35 U.S.C. § 121 to U.S. patent application Ser. No. 17/208,362, entitled STAPLE CARTRIDGE COMPRISING A FIRING LOCKOUT, filed Mar. 22, 2021, which issued on Nov. 28, 2023 as U.S. Pat. No. 11,826,042, the entire disclosure of which is hereby incorporated by reference herein.

BACKGROUND

The present invention relates to surgical instruments and, in various arrangements, to surgical stapling and cutting instruments and staple cartridges for use therewith that are designed to staple and cut tissue.

BRIEF DESCRIPTION OF THE DRAWINGS

Various features of the embodiments described herein, together with advantages thereof, may be understood in accordance with the following description taken in conjunction with the accompanying drawings as follows.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Figure 1:
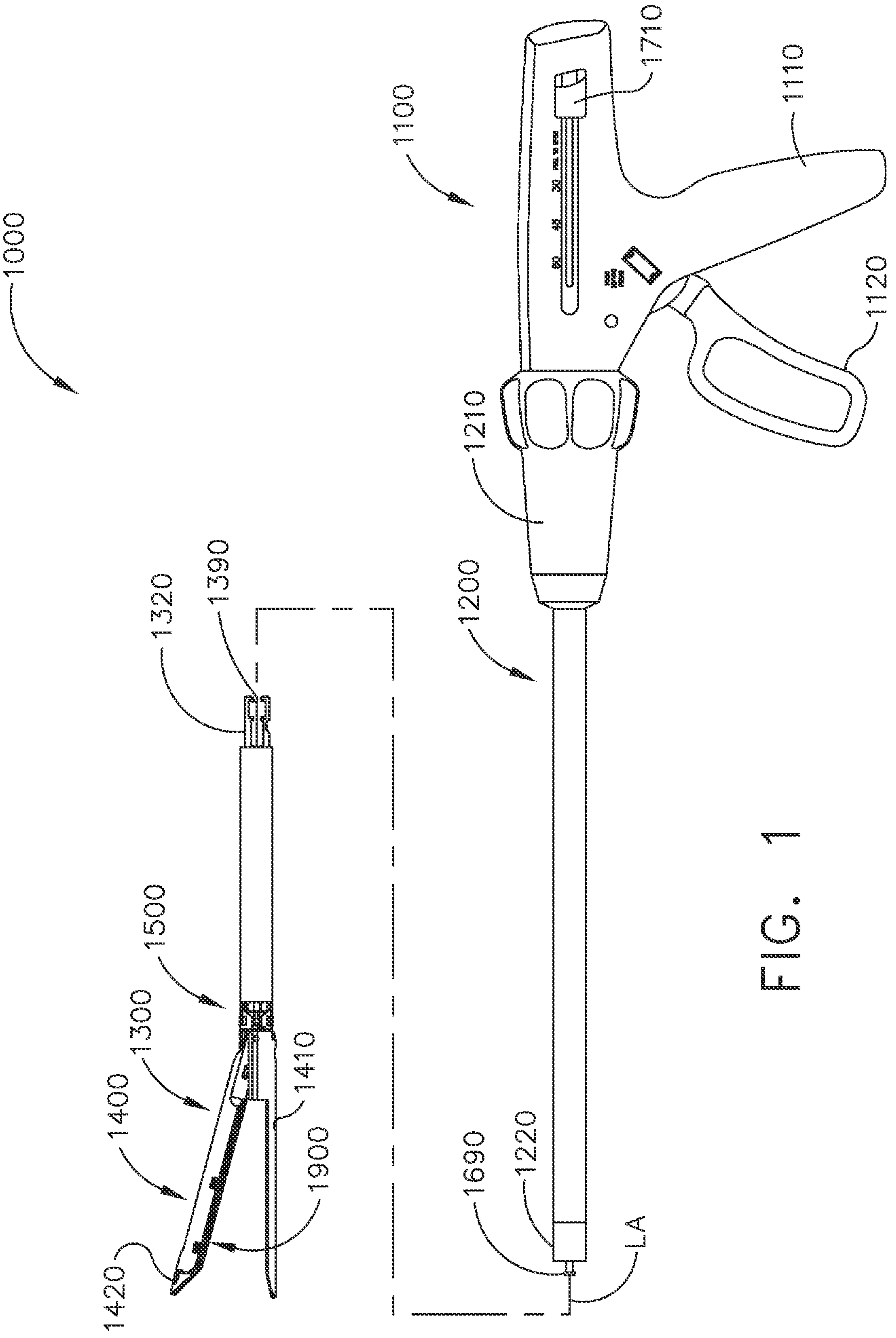
FIG. 1 is an elevational view of a surgical stapling instrument in accordance with at least one embodiment.

Applicant of the present application also owns the following U.S. Patent Applications that were filed on Mar. 22, 2021, and which are each herein incorporated by reference in their respective entireties:

- U.S. patent application Ser. No. 17/208,339, entitled METHOD OF SHIFTING A SURGICAL STAPLING INSTRUMENT, now U.S. Patent Application Publication No. 2022/0296230;
- U.S. patent application Ser. No. 17/208,347, entitled STAPLING INSTRUMENT COMPRISING A PULSED MOTOR-DRIVEN FIRING RACK, now U.S. Patent Application Publication No. 2022/0296231;

U.S. patent application Ser. No. 17/208,357, entitled SURGICAL STAPLING INSTRUMENT COMPRISING A RETRACTION SYSTEM, now U.S. Pat. No. 11,737,749;

U.S. patent application Ser. No. 17/208,380, entitled STAPLE CARTRIDGE COMPRISING STAPLES CONFIGURED TO APPLY DIFFERENT TISSUE COMPRESSION, now U.S. Pat. No. 11,717,291;

U.S. patent application Ser. No. 17/208,385, entitled STAPLE CARTRIDGE COMPRISING A FIRING LOCKOUT, now U.S. Pat. No. 11,723,658;

U.S. patent application Ser. No. 17/208,390, entitled STAPLE CARTRIDGE COMPRISING AN IMPLANTABLE LAYER, now U.S. Pat. No. 11,759,202; and U.S. patent application Ser. No. 17/208,397, entitled STAPLING INSTRUMENT COMPRISING TISSUE COMPRESSION SYSTEMS, now U.S. Patent Application Publication No. 2022/0296237.

Applicant of the present application also owns the following U.S. Patent Applications that were filed on Feb. 26, 2021 and which are each herein incorporated by reference in their respective entireties:

U.S. patent application Ser. No. 17/186,269, entitled METHOD OF POWERING AND COMMUNICATING WITH A STAPLE CARTRIDGE;

U.S. patent application Ser. No. 17/186,273, entitled METHOD OF POWERING AND COMMUNICATING WITH A STAPLE CARTRIDGE;

U.S. patent application Ser. No. 17/186,276, entitled ADJUSTABLE COMMUNICATION BASED ON AVAILABLE BANDWIDTH AND POWER CAPACITY;

U.S. patent application Ser. No. 17/186,283, entitled ADJUSTMENT TO TRANSFER PARAMETERS TO IMPROVE AVAILABLE POWER;

U.S. patent application Ser. No. 17/186,345, entitled MONITORING OF MANUFACTURING LIFECYCLE;

U.S. patent application Ser. No. 17/186,350, entitled MONITORING OF MULTIPLE SENSORS OVER TIME TO DETECT MOVING CHARACTERISTICS OF TISSUE;

U.S. patent application Ser. No. 17/186,353, entitled MONITORING OF INTERNAL SYSTEMS TO DETECT AND TRACK CARTRIDGE MOTION STATUS;

U.S. patent application Ser. No. 17/186,357, entitled DISTAL COMMUNICATION ARRAY TO TUNE FREQUENCY OF RF SYSTEMS;

U.S. patent application Ser. No. 17/186,364, entitled STAPLE CARTRIDGE COMPRISING A SENSOR ARRAY;

U.S. patent application Ser. No. 17/186,373, entitled STAPLE CARTRIDGE COMPRISING A SENSING ARRAY AND A TEMPERATURE CONTROL SYSTEM;

U.S. patent application Ser. No. 17/186,378, entitled STAPLE CARTRIDGE COMPRISING AN INFORMATION ACCESS CONTROL SYSTEM;

U.S. patent application Ser. No. 17/186,407, entitled STAPLE CARTRIDGE COMPRISING A POWER MANAGEMENT CIRCUIT;

U.S. patent application Ser. No. 17/186,421, entitled STAPLING INSTRUMENT COMPRISING A SEPARATE POWER ANTENNA AND A DATA TRANSFER ANTENNA;

U.S. patent application Ser. No. 17/186,438, entitled SURGICAL INSTRUMENT SYSTEM COMPRISING A POWER TRANSFER COIL; and U.S. patent application Ser. No. 17/186,451, entitled STAPLING INSTRUMENT COMPRISING A SIGNAL ANTENNA.

Applicant of the present application also owns the following U.S. Patent Applications that were filed on Oct. 29, 2020 and which are each herein incorporated by reference in their respective entireties:

U.S. patent application Ser. No. 17/084,179, entitled SURGICAL INSTRUMENT COMPRISING A RELEASABLE CLOSURE DRIVE LOCK;

U.S. patent application Ser. No. 17/084,190, entitled SURGICAL INSTRUMENT COMPRISING A STOWED CLOSURE ACTUATOR STOP;

U.S. patent application Ser. No. 17/084,198, entitled SURGICAL INSTRUMENT COMPRISING AN INDICATOR WHICH INDICATES THAT AN ARTICULATION DRIVE IS ACTUATABLE;

U.S. patent application Ser. No. 17/084,205, entitled SURGICAL INSTRUMENT COMPRISING AN ARTICULATION INDICATOR;

U.S. patent application Ser. No. 17/084,258, entitled METHOD FOR OPERATING A SURGICAL INSTRUMENT;

U.S. patent application Ser. No. 17/084,206, entitled SURGICAL INSTRUMENT COMPRISING AN ARTICULATION LOCK;

U.S. patent application Ser. No. 17/084,215, entitled SURGICAL INSTRUMENT COMPRISING A JAW ALIGNMENT SYSTEM;

U.S. patent application Ser. No. 17/084,229, entitled SURGICAL INSTRUMENT COMPRISING SEALABLE INTERFACE;

U.S. patent application Ser. No. 17/084,180, entitled SURGICAL INSTRUMENT COMPRISING A LIMITED TRAVEL SWITCH;

U.S. Design Patent Application Ser. No. 29/756,615, Applications entitled SURGICAL STAPLING ASSEMBLY;

U.S. Design Patent Application Ser. No. 29/756,620, entitled SURGICAL STAPLING ASSEMBLY;

U.S. patent application Ser. No. 17/084,188, entitled SURGICAL INSTRUMENT COMPRISING A STAGED VOLTAGE REGULATION START-UP SYSTEM; and U.S. patent application Ser. No. 17/084,193, entitled SURGICAL INSTRUMENT COMPRISING A SENSOR CONFIGURED TO SENSE WHETHER AN ARTICULATION DRIVE OF THE SURGICAL INSTRUMENT IS ACTUATABLE.

Applicant of the present application also owns the following U.S. Patent Applications that were filed on Apr. 11, 2020 and which are each herein incorporated by reference in their respective entireties:

U.S. patent application Ser. No. 16/846,303, entitled METHODS FOR STAPLING TISSUE USING A SURGICAL INSTRUMENT, now U.S. Patent Application Publication No. 2020/0345353;

U.S. patent application Ser. No. 16/846,304, entitled ARTICULATION ACTUATORS FOR A SURGICAL INSTRUMENT, now U.S. Patent Application Publication No. 2020/0345354;

U.S. patent application Ser. No. 16/846,305, entitled ARTICULATION DIRECTIONAL LIGHTS ON A SURGICAL INSTRUMENT, now U.S. Patent Application Publication No. 2020/0345446;

U.S. patent application Ser. No. 16/846,307, entitled SHAFT ROTATION ACTUATOR ON A SURGICAL INSTRUMENT, now U.S. Patent Application Publication No. 2020/0345349;

U.S. patent application Ser. No. 16/846,308, entitled ARTICULATION CONTROL MAPPING FOR A SURGICAL INSTRUMENT, now U.S. Patent Application Publication No. 2020/0345355;

U.S. patent application Ser. No. 16/846,309, entitled INTELLIGENT FIRING ASSOCIATED WITH A SURGICAL INSTRUMENT, now U.S. Patent Application Publication No. 2020/0345356;

U.S. patent application Ser. No. 16/846,310, entitled INTELLIGENT FIRING ASSOCIATED WITH A SURGICAL INSTRUMENT, now U.S. Patent Application Publication No. 2020/0345357;

U.S. patent application Ser. No. 16/846,311, entitled ROTATABLE JAW TIP FOR A SURGICAL INSTRUMENT, now U.S. Patent Application Publication No. 2020/0345358;

U.S. patent application Ser. No. 16/846,312, entitled TISSUE STOP FOR A SURGICAL INSTRUMENT, now U.S. Patent Application Publication No. 2020/0345359; and U.S. patent application Ser. No. 16/846,313, entitled ARTICULATION PIN FOR A SURGICAL INSTRUMENT, now U.S. Patent Application Publication No. 2020/0345360.

Applicant of the present application owns the following U.S. Patent Applications that were filed on Jun. 26, 2019 and which are each herein incorporated by reference in their respective entireties:

U.S. patent application Ser. No. 16/453,273, entitled METHOD FOR PROVIDING AN AUTHENTICATION LOCKOUT IN A SURGICAL STAPLER WITH A REPLACEABLE CARTRIDGE, now U.S. Patent Application Publication No. 2020/0261080;

U.S. patent application Ser. No. 16/453,283, entitled SURGICAL STAPLING ASSEMBLY WITH CARTRIDGE BASED RETAINER CONFIGURED TO UNLOCK A FIRING LOCKOUT, now U.S. Patent Application Publication No. 2020/0261081;

U.S. patent application Ser. No. 16/453,289, entitled SURGICAL STAPLING ASSEMBLY WITH CARTRIDGE BASED RETAINER CONFIGURED TO UNLOCK A CLOSURE LOCKOUT, now U.S. Patent Application Publication No. 2020/0261082;

U.S. patent application Ser. No. 16/453,302, entitled UNIVERSAL CARTRIDGE BASED KEY FEATURE THAT UNLOCKS MULTIPLE LOCKOUT ARRANGEMENTS IN DIFFERENT SURGICAL STAPLERS, now U.S. Patent Application Publication No. 2020/0261075;

U.S. patent application Ser. No. 16/453,310, entitled STAPLE CARTRIDGE RETAINERS WITH FRANGIBLE RETENTION FEATURES AND METHODS OF USING SAME, now U.S. Patent Application Publication No. 2020/0261083;

U.S. patent application Ser. No. 16/453,330, entitled STAPLE CARTRIDGE RETAINER WITH FRANGIBLE AUTHENTICATION KEY, now U.S. Patent Application Publication No. 2020/0261084;

U.S. patent application Ser. No. 16/453,335, entitled STAPLE CARTRIDGE RETAINER WITH RETRACTABLE AUTHENTICATION KEY, now U.S. Patent Application Publication No. 2020/0261078;

U.S. patent application Ser. No. 16/453,343, entitled STAPLE CARTRIDGE RETAINER SYSTEM WITH AUTHENTICATION KEYS, now U.S. Patent Application Publication No. 2020/0261085;

U.S. patent application Ser. No. 16/453,355, entitled INSERTABLE DEACTIVATOR ELEMENT FOR SURGICAL STAPLER LOCKOUTS, now U.S. Patent Application Publication No. 2020/0261086;

U.S. patent application Ser. No. 16/453,369, entitled DUAL CAM CARTRIDGE BASED FEATURE FOR UNLOCKING A SURGICAL STAPLER LOCKOUT, now U.S. Patent Application Publication No. 2020/0261076;

U.S. patent application Ser. No. 16/453,391, entitled STAPLE CARTRIDGES WITH CAM SURFACES CONFIGURED TO ENGAGE PRIMARY AND SECONDARY PORTIONS OF A LOCKOUT OF A SURGICAL STAPLING DEVICE, now U.S. Patent Application Publication No. 2020/0261077;

U.S. patent application Ser. No. 16/453,413, entitled SURGICAL STAPLE CARTRIDGES WITH MOVABLE AUTHENTICATION KEY ARRANGEMENTS, now U.S. Patent Application Publication No. 2020/0261087;

U.S. patent application Ser. No. 16/453,423, entitled DEACTIVATOR ELEMENT FOR DEFEATING SURGICAL STAPLING DEVICE LOCKOUTS, now U.S. Patent Application Publication No. 2020/0261088; and U.S. patent application Ser. No. 16/453,429, entitled SURGICAL STAPLE CARTRIDGES WITH INTEGRAL AUTHENTICATION KEYS, now U.S. Patent Application Publication No. 2020/0261089.

Applicant of the present application owns the following U.S. Design Patent Applications that were filed on Jun. 25, 2019, each of which is herein incorporated by reference in its entirety:

U.S. Design Patent Application Ser. No. 29/696,066, entitled SURGICAL STAPLE CARTRIDGE RETAINER WITH FIRING SYSTEM AUTHENTICATION KEY;

U.S. Design Patent Application Ser. No. 29/696,067, entitled SURGICAL STAPLE CARTRIDGE RETAINER WITH CLOSURE SYSTEM AUTHENTICATION KEY; and U.S. Design Patent Application Ser. No. 29/696,072, entitled SURGICAL STAPLE CARTRIDGE.

The entire disclosure of U.S. Provisional Patent Application Ser. No. 62/866,208, entitled STAPLE CARTRIDGES WITH FEATURES FOR DEFEATING LOCKOUTS IN SURGICAL STAPLING DEVICES, filed Jun. 25, 2019, is hereby incorporated by reference herein.

The entire disclosure of U.S. Provisional Patent Application Ser. No. 62/840,715, entitled SURGICAL INSTRUMENT COMPRISING AN ADAPTIVE CONTROL SYSTEM, filed Apr. 30, 2019, is hereby incorporated by reference herein.

Applicant of the present application owns the following U.S. Patent Applications that were filed on Feb. 21, 2019 and which are each herein incorporated by reference in their respective entireties:

- U.S. patent application Ser. No. 16/281,658, entitled METHODS FOR CONTROLLING A POWERED SURGICAL STAPLER THAT HAS SEPARATE ROTARY CLOSURE AND FIRING SYSTEMS, now U.S. Patent Application Publication No. 2019/0298350;
- U.S. patent application Ser. No. 16/281,670, entitled STAPLE CARTRIDGE COMPRISING A LOCKOUT KEY CONFIGURED TO LIFT A FIRING MEMBER, now U.S. Patent Application Publication No. 2019/0298340;
- U.S. patent application Ser. No. 16/281,675, entitled SURGICAL STAPLERS WITH ARRANGEMENTS FOR MAINTAINING A FIRING MEMBER THEREOF IN A LOCKED CONFIGURATION UNLESS A COMPATIBLE CARTRIDGE HAS BEEN INSTALLED THEREIN, now U.S. Patent Application Publication No. 2019/0298354;
- U.S. patent application Ser. No. 16/281,685, entitled SURGICAL INSTRUMENT COMPRISING CO-OPERATING LOCKOUT FEATURES, now U.S. Patent Application Publication No. 2019/0298341;
- U.S. patent application Ser. No. 16/281,693, entitled SURGICAL STAPLING ASSEMBLY COMPRISING A LOCKOUT AND AN EXTERIOR ACCESS ORIFICE TO PERMIT ARTIFICIAL UNLOCKING OF THE LOCKOUT, now U.S. Patent Application Publication No. 2019/0298342;
- U.S. patent application Ser. No. 16/281,704, entitled SURGICAL STAPLING DEVICES WITH FEATURES FOR BLOCKING ADVANCEMENT OF A CAMMING ASSEMBLY OF AN INCOMPATIBLE CARTRIDGE INSTALLED THEREIN, now U.S. Patent Application Publication No. 2019/0298356;
- U.S. patent application Ser. No. 16/281,707, entitled STAPLING INSTRUMENT COMPRISING A DEACTIVATABLE LOCKOUT, now U.S. Patent Application Publication No. 2019/0298347;
- U.S. patent application Ser. No. 16/281,741, entitled SURGICAL INSTRUMENT COMPRISING A JAW CLOSURE LOCKOUT, now U.S. Patent Application Publication No. 2019/0298357;
- U.S. patent application Ser. No. 16/281,762, entitled SURGICAL STAPLING DEVICES WITH CARTRIDGE COMPATIBLE CLOSURE AND FIRING LOCKOUT ARRANGEMENTS, now U.S. Patent Application Publication No. 2019/0298343;
- U.S. patent application Ser. No. 16/281,666, entitled SURGICAL STAPLING DEVICES WITH IMPROVED ROTARY DRIVEN CLOSURE SYSTEMS, now U.S. Patent Application Publication No. 2019/0298352;
- U.S. patent application Ser. No. 16/281,672, entitled SURGICAL STAPLING DEVICES WITH ASYMMETRIC CLOSURE FEATURES, now U.S. Patent Application Publication No. 2019/0298353;
- U.S. patent application Ser. No. 16/281,678, entitled ROTARY DRIVEN FIRING MEMBERS WITH DIFFERENT ANVIL AND CHANNEL ENGAGEMENT FEATURES, now U.S. Patent Application Publication No. 2019/0298355; and
- U.S. patent application Ser. No. 16/281,682, entitled SURGICAL STAPLING DEVICE WITH SEPARATE ROTARY DRIVEN CLOSURE AND FIRING SYSTEMS AND FIRING MEMBER THAT ENGAGES BOTH JAWS WHILE FIRING, now U.S. Patent Application Publication No. 2019/0298346.

Applicant of the present application owns the following U.S. Provisional Patent Applications that were filed on Feb. 19, 2019 and which are each herein incorporated by reference in their respective entireties:

- U.S. Provisional Patent Application Ser. No. 62/807,310, entitled METHODS FOR CONTROLLING A POWERED SURGICAL STAPLER THAT HAS SEPARATE ROTARY CLOSURE AND FIRING SYSTEMS;
- U.S. Provisional Patent Application Ser. No. 62/807,319, entitled SURGICAL STAPLING DEVICES WITH IMPROVED LOCKOUT SYSTEMS; and
- U.S. Provisional Patent Application Ser. No. 62/807,309, entitled SURGICAL STAPLING DEVICES WITH IMPROVED ROTARY DRIVEN CLOSURE SYSTEMS.

Applicant of the present application owns the following U.S. Provisional Patent Applications, filed on Mar. 28, 2018, each of which is herein incorporated by reference in its entirety:

- U.S. Provisional Patent Application Ser. No. 62/649,302, entitled INTERACTIVE SURGICAL SYSTEMS WITH ENCRYPTED COMMUNICATION CAPABILITIES;
- U.S. Provisional Patent Application Ser. No. 62/649,294, entitled DATA STRIPPING METHOD TO INTERROGATE PATIENT RECORDS AND CREATE ANONYMIZED RECORD;
- U.S. Provisional Patent Application Ser. No. 62/649,300, entitled SURGICAL HUB SITUATIONAL AWARENESS;
- U.S. Provisional Patent Application Ser. No. 62/649,309, entitled SURGICAL HUB SPATIAL AWARENESS TO DETERMINE DEVICES IN OPERATING THEATER;
- U.S. Provisional Patent Application Ser. No. 62/649,310, entitled COMPUTER IMPLEMENTED INTERACTIVE SURGICAL SYSTEMS;
- U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;
- U.S. Provisional Patent Application Ser. No. 62/649,296, entitled ADAPTIVE CONTROL PROGRAM UPDATES FOR SURGICAL DEVICES;
- U.S. Provisional Patent Application Ser. No. 62/649,333, entitled CLOUD-BASED MEDICAL ANALYTICS FOR CUSTOMIZATION AND RECOMMENDATIONS TO A USER;
- U.S. Provisional Patent Application Ser. No. 62/649,327, entitled CLOUD-BASED MEDICAL ANALYTICS FOR SECURITY AND AUTHENTICATION TRENDS AND REACTIVE MEASURES;
- U.S. Provisional Patent Application Ser. No. 62/649,315, entitled DATA HANDLING AND PRIORITIZATION IN A CLOUD ANALYTICS NETWORK;
- U.S. Provisional Patent Application Ser. No. 62/649,313, entitled CLOUD INTERFACE FOR COUPLED SURGICAL DEVICES;
- U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Provisional Patent Applications, filed on Mar. 30, 2018, which is herein incorporated by reference in its entirety:

U.S. Provisional Patent Application Ser. No. 62/650,887, entitled SURGICAL SYSTEMS WITH OPTIMIZED SENSING CAPABILITIES.

Applicant of the present application owns the following U.S. Patent Applications, filed on Dec. 4, 2018, which is herein incorporated by reference in its entirety:

U.S. patent application Ser. No. 16/209,423, entitled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981.

Applicant of the present application owns the following U.S. Patent Applications that were filed on Aug. 20, 2018 and which are each herein incorporated by reference in their respective entireties:

U.S. patent application Ser. No. 16/105,101, entitled METHOD FOR FABRICATING SURGICAL STAPLER ANVILS, now U.S. Patent Application Publication No. 2020/0054323;

U.S. patent application Ser. No. 16/105,183, entitled REINFORCED DEFORMABLE ANVIL TIP FOR SURGICAL STAPLER ANVIL, now U.S. Pat. No. 10,912,559;

U.S. patent application Ser. No. 16/105,150, entitled SURGICAL STAPLER ANVILS WITH STAPLE DIRECTING PROTRUSIONS AND TISSUE STABILITY FEATURES, now U.S. Patent Application Publication No. 2020/0054326;

U.S. patent application Ser. No. 16/105,098, entitled FABRICATING TECHNIQUES FOR SURGICAL STAPLER ANVILS, now U.S. Patent Application Publication No. 2020/0054322;

U.S. patent application Ser. No. 16/105,140, entitled SURGICAL STAPLER ANVILS WITH TISSUE STOP FEATURES CONFIGURED TO AVOID TISSUE PINCH, now U.S. Pat. No. 10,779,821;

U.S. patent application Ser. No. 16/105,081, entitled METHOD FOR OPERATING A POWERED ARTICULATABLE SURGICAL INSTRUMENT, now U.S. Patent Application Publication No. 2020/0054320;

U.S. patent application Ser. No. 16/105,094, entitled SURGICAL INSTRUMENTS WITH PROGRESSIVE JAW CLOSURE ARRANGEMENTS, now U.S. Patent Application Publication No. 2020/0054321;

U.S. patent application Ser. No. 16/105,097, entitled POWERED SURGICAL INSTRUMENTS WITH CLUTCHING ARRANGEMENTS TO CONVERT LINEAR DRIVE MOTIONS TO ROTARY DRIVE MOTIONS, now U.S. Patent Application Publication No. 2020/0054328;

U.S. patent application Ser. No. 16/105,104, entitled POWERED ARTICULATABLE SURGICAL INSTRUMENTS WITH CLUTCHING AND LOCKING ARRANGEMENTS FOR LINKING AN ARTICULATION DRIVE SYSTEM TO A FIRING DRIVE SYSTEM, now U.S. Pat. No. 10,842,492;

U.S. patent application Ser. No. 16/105,119, entitled ARTICULATABLE MOTOR POWERED SURGICAL INSTRUMENTS WITH DEDICATED ARTICULATION MOTOR ARRANGEMENTS, now U.S. Patent Application Publication No. 2020/0054330;

U.S. patent application Ser. No. 16/105,160, entitled SWITCHING ARRANGEMENTS FOR MOTOR POWERED ARTICULATABLE SURGICAL INSTRUMENTS, now U.S. Pat. No. 10,856,870; and U.S. Design Patent Application Ser. No. 29/660,252, entitled SURGICAL STAPLER ANVILS.

Applicant of the present application owns the following U.S. Patent Applications and U.S. Patents that are each herein incorporated by reference in their respective entireties:

U.S. patent application Ser. No. 15/386,185, entitled SURGICAL STAPLING INSTRUMENTS AND REPLACEABLE TOOL ASSEMBLIES THEREOF, now U.S. Pat. No. 10,639,035;

U.S. patent application Ser. No. 15/386,230, entitled ARTICULATABLE SURGICAL STAPLING INSTRUMENTS, now U.S. Patent Application Publication No. 2018/0168649;

U.S. patent application Ser. No. 15/386,221, entitled LOCKOUT ARRANGEMENTS FOR SURGICAL END EFFECTORS, now U.S. Pat. No. 10,835,247;

U.S. patent application Ser. No. 15/386,209, entitled SURGICAL END EFFECTORS AND FIRING MEMBERS THEREOF, now U.S. Pat. No. 10,588,632;

U.S. patent application Ser. No. 15/386,198, entitled LOCKOUT ARRANGEMENTS FOR SURGICAL END EFFECTORS AND REPLACEABLE TOOL ASSEMBLIES, now U.S. Pat. No. 10,610,224;

U.S. patent application Ser. No. 15/386,240, entitled SURGICAL END EFFECTORS AND ADAPTABLE FIRING MEMBERS THEREFOR, now U.S. Patent Application Publication No. 2018/0168651;

U.S. patent application Ser. No. 15/385,939, entitled STAPLE CARTRIDGES AND ARRANGEMENTS OF STAPLES AND STAPLE CAVITIES THEREIN, now U.S. Pat. No. 10,835,246;

U.S. patent application Ser. No. 15/385,941, entitled SURGICAL TOOL ASSEMBLIES WITH CLUTCHING ARRANGEMENTS FOR SHIFTING BETWEEN CLOSURE SYSTEMS WITH CLOSURE STROKE REDUCTION FEATURES AND ARTICULATION AND FIRING SYSTEMS, now U.S. Pat. No. 10,736,629;

U.S. patent application Ser. No. 15/385,943, entitled SURGICAL STAPLING INSTRUMENTS AND STAPLE-FORMING ANVILS, now U.S. Pat. No. 10,667,811;

U.S. patent application Ser. No. 15/385,950, entitled SURGICAL TOOL ASSEMBLIES WITH CLOSURE STROKE REDUCTION FEATURES, now U.S. Pat. No. 10,588,630;

U.S. patent application Ser. No. 15/385,945, entitled STAPLE CARTRIDGES AND ARRANGEMENTS OF STAPLES AND STAPLE CAVITIES THEREIN, now U.S. Pat. No. 10,893,864;

U.S. patent application Ser. No. 15/385,946, entitled SURGICAL STAPLING INSTRUMENTS AND STAPLE-FORMING ANVILS, now U.S. Patent Application Publication No. 2018/0168633;

U.S. patent application Ser. No. 15/385,951, entitled SURGICAL INSTRUMENTS WITH JAW OPENING FEATURES FOR INCREASING A JAW OPENING DISTANCE, now U.S. Pat. No. 10,568,626;

U.S. patent application Ser. No. 15/385,953, entitled METHODS OF STAPLING TISSUE, now U.S. Pat. No. 10,675,026;

U.S. patent application Ser. No. 15/385,954, entitled FIRING MEMBERS WITH NON-PARALLEL JAW ENGAGEMENT FEATURES FOR SURGICAL END EFFECTORS, now U.S. Pat. No. 10,624,635;

U.S. patent application Ser. No. 15/385,955, entitled SURGICAL END EFFECTORS WITH EXPANDABLE TISSUE STOP ARRANGEMENTS, now U.S. Pat. No. 10,813,638;

U.S. patent application Ser. No. 15/385,948, entitled SURGICAL STAPLING INSTRUMENTS AND STAPLE-FORMING ANVILS, now U.S. Patent Application Publication No. 2018/0168584;

U.S. patent application Ser. No. 15/385,956, entitled SURGICAL INSTRUMENTS WITH POSITIVE JAW OPENING FEATURES, now U.S. Pat. No. 10,588,631;

U.S. patent application Ser. No. 15/385,958, entitled SURGICAL INSTRUMENTS WITH LOCKOUT ARRANGEMENTS FOR PREVENTING FIRING SYSTEM ACTUATION UNLESS AN UNSPENT STAPLE CARTRIDGE IS PRESENT, now U.S. Pat. No. 10,639,034;

U.S. patent application Ser. No. 15/385,947, entitled STAPLE CARTRIDGES AND ARRANGEMENTS OF STAPLES AND STAPLE CAVITIES THEREIN, now U.S. Pat. No. 10,568,625;

U.S. patent application Ser. No. 15/385,896, entitled METHOD FOR RESETTING A FUSE OF A SURGICAL INSTRUMENT SHAFT, now U.S. Patent Application Publication No. 2018/0168597;

U.S. patent application Ser. No. 15/385,898, entitled STAPLE-FORMING POCKET ARRANGEMENT TO ACCOMMODATE DIFFERENT TYPES OF STAPLES, now U.S. Pat. No. 10,537,325;

U.S. patent application Ser. No. 15/385,899, entitled SURGICAL INSTRUMENT COMPRISING IMPROVED JAW CONTROL, now U.S. Pat. No. 10,758,229;

U.S. patent application Ser. No. 15/385,901, entitled STAPLE CARTRIDGE AND STAPLE CARTRIDGE CHANNEL COMPRISING WINDOWS DEFINED THEREIN, now U.S. Pat. No. 10,667,809;

U.S. patent application Ser. No. 15/385,902, entitled SURGICAL INSTRUMENT COMPRISING A CUTTING MEMBER, now U.S. Pat. No. 10,888,322;

U.S. patent application Ser. No. 15/385,904, entitled STAPLE FIRING MEMBER COMPRISING A MISSING CARTRIDGE AND/OR SPENT CARTRIDGE LOCKOUT, now U.S. Pat. No. 10,881,401;

U.S. patent application Ser. No. 15/385,905, entitled FIRING ASSEMBLY COMPRISING A LOCKOUT, now U.S. Pat. No. 10,695,055;

U.S. patent application Ser. No. 15/385,907, entitled SURGICAL INSTRUMENT SYSTEM COMPRISING AN END EFFECTOR LOCKOUT AND A FIRING ASSEMBLY LOCKOUT, now U.S. Patent Application Publication No. 2018/0168608;

U.S. patent application Ser. No. 15/385,908, entitled FIRING ASSEMBLY COMPRISING A FUSE, now U.S. Patent Application Publication No. 2018/0168609;

U.S. patent application Ser. No. 15/385,909, entitled FIRING ASSEMBLY COMPRISING A MULTIPLE FAILED-STATE FUSE, now U.S. Patent Application Publication No. 2018/0168610;

U.S. patent application Ser. No. 15/385,920, entitled STAPLE-FORMING POCKET ARRANGEMENTS, now U.S. Pat. No. 10,499,914;

U.S. patent application Ser. No. 15/385,913, entitled ANVIL ARRANGEMENTS FOR SURGICAL STAPLERS, now U.S. Patent Application Publication No. 2018/0168614;

U.S. patent application Ser. No. 15/385,914, entitled METHOD OF DEFORMING STAPLES FROM TWO DIFFERENT TYPES OF STAPLE CARTRIDGES WITH THE SAME SURGICAL STAPLING INSTRUMENT, now U.S. Patent Application Publication No. 2018/0168615;

U.S. patent application Ser. No. 15/385,893, entitled BILATERALLY ASYMMETRIC STAPLE-FORMING POCKET PAIRS, now U.S. Pat. No. 10,682,138;

U.S. patent application Ser. No. 15/385,929, entitled CLOSURE MEMBERS WITH CAM SURFACE ARRANGEMENTS FOR SURGICAL INSTRUMENTS WITH SEPARATE AND DISTINCT CLOSURE AND FIRING SYSTEMS, now U.S. Pat. No. 10,667,810;

U.S. patent application Ser. No. 15/385,911, entitled SURGICAL STAPLERS WITH INDEPENDENTLY ACTUATABLE CLOSING AND FIRING SYSTEMS, now U.S. Pat. No. 10,448,950;

U.S. patent application Ser. No. 15/385,927, entitled SURGICAL STAPLING INSTRUMENTS WITH SMART STAPLE CARTRIDGES, now U.S. Patent Application Publication No. 2018/0168625;

U.S. patent application Ser. No. 15/385,917, entitled STAPLE CARTRIDGE COMPRISING STAPLES WITH DIFFERENT CLAMPING BREADTHS, now U.S. Patent Application Publication No. 2018/0168617;

U.S. patent application Ser. No. 15/385,900, entitled STAPLE-FORMING POCKET ARRANGEMENTS COMPRISING PRIMARY SIDEWALLS AND POCKET SIDEWALLS, now U.S. Pat. No. 10,898,186;

U.S. patent application Ser. No. 15/385,931, entitled NO-CARTRIDGE AND SPENT CARTRIDGE LOCKOUT ARRANGEMENTS FOR SURGICAL STAPLERS, now U.S. Patent Application Publication No. 2018/0168627;

U.S. patent application Ser. No. 15/385,915, entitled FIRING MEMBER PIN ANGLE, now U.S. Pat. No. 10,779,823;

U.S. patent application Ser. No. 15/385,897, entitled STAPLE-FORMING POCKET ARRANGEMENTS COMPRISING ZONED FORMING SURFACE GROOVES, now U.S. Patent Application Publication No. 2018/0168598;

U.S. patent application Ser. No. 15/385,922, entitled SURGICAL INSTRUMENT WITH MULTIPLE FAILURE RESPONSE MODES, now U.S. Pat. No. 10,426,471;

U.S. patent application Ser. No. 15/385,924, entitled SURGICAL INSTRUMENT WITH PRIMARY AND SAFETY PROCESSORS, now U.S. Pat. No. 10,758,230;

U.S. patent application Ser. No. 15/385,910, entitled ANVIL HAVING A KNIFE SLOT WIDTH, now U.S. Pat. No. 10,485,543;
U.S. patent application Ser. No. 15/385,903, entitled CLOSURE MEMBER ARRANGEMENTS FOR SURGICAL INSTRUMENTS, now U.S. Pat. No. 10,617,414;
U.S. patent application Ser. No. 15/385,906, entitled FIRING MEMBER PIN CONFIGURATIONS, now U.S. Pat. No. 10,856,868;
U.S. patent application Ser. No. 15/386,188, entitled STEPPED STAPLE CARTRIDGE WITH ASYMMETRICAL STAPLES, now U.S. Pat. No. 10,537,324;
U.S. patent application Ser. No. 15/386,192, entitled STEPPED STAPLE CARTRIDGE WITH TISSUE RETENTION AND GAP SETTING FEATURES, now U.S. Pat. No. 10,687,810;
U.S. patent application Ser. No. 15/386,206, entitled STAPLE CARTRIDGE WITH DEFORMABLE DRIVER RETENTION FEATURES, now U.S. Patent Application Publication No. 2018/0168586;
U.S. patent application Ser. No. 15/386,226, entitled DURABILITY FEATURES FOR END EFFECTORS AND FIRING ASSEMBLIES OF SURGICAL STAPLING INSTRUMENTS, now U.S. Patent Application Publication No. 2018/0168648;
U.S. patent application Ser. No. 15/386,222, entitled SURGICAL STAPLING INSTRUMENTS HAVING END EFFECTORS WITH POSITIVE OPENING FEATURES, now U.S. Patent Application Publication No. 2018/0168647;
U.S. patent application Ser. No. 15/386,236, entitled CONNECTION PORTIONS FOR DEPOSABLE LOADING UNITS FOR SURGICAL STAPLING INSTRUMENTS, now U.S. Patent Application Publication No. 2018/0168650;
U.S. patent application Ser. No. 15/385,887, entitled METHOD FOR ATTACHING A SHAFT ASSEMBLY TO A SURGICAL INSTRUMENT AND, ALTERNATIVELY, TO A SURGICAL ROBOT, now U.S. Pat. No. 10,835,245;
U.S. patent application Ser. No. 15/385,889, entitled SHAFT ASSEMBLY COMPRISING A MANUALLY-OPERABLE RETRACTION SYSTEM FOR USE WITH A MOTORIZED SURGICAL INSTRUMENT SYSTEM, now U.S. Patent Application Publication No. 2018/0168590;
U.S. patent application Ser. No. 15/385,890, entitled SHAFT ASSEMBLY COMPRISING SEPARATELY ACTUATABLE AND RETRACTABLE SYSTEMS, now U.S. Pat. No. 10,675,025;
U.S. patent application Ser. No. 15/385,891, entitled SHAFT ASSEMBLY COMPRISING A CLUTCH CONFIGURED TO ADAPT THE OUTPUT OF A ROTARY FIRING MEMBER TO TWO DIFFERENT SYSTEMS, now U.S. Patent Application Publication No. 2018/0168592;
U.S. patent application Ser. No. 15/385,892, entitled SURGICAL SYSTEM COMPRISING A FIRING MEMBER ROTATABLE INTO AN ARTICULATION STATE TO ARTICULATE AN END EFFECTOR OF THE SURGICAL SYSTEM, now U.S. Pat. No. 10,918,385;
U.S. patent application Ser. No. 15/385,894, entitled SHAFT ASSEMBLY COMPRISING A LOCKOUT, now U.S. Pat. No. 10,492,785;
U.S. patent application Ser. No. 15/385,895, entitled SHAFT ASSEMBLY COMPRISING FIRST AND SECOND ARTICULATION LOCKOUTS, now U.S. Pat. No. 10,542,982;
U.S. patent application Ser. No. 15/385,916, entitled SURGICAL STAPLING SYSTEMS, now U.S. Patent Application Publication No. 2018/0168575;
U.S. patent application Ser. No. 15/385,918, entitled SURGICAL STAPLING SYSTEMS, now U.S. Patent Application Publication No. 2018/0168618;
U.S. patent application Ser. No. 15/385,919, entitled SURGICAL STAPLING SYSTEMS, now U.S. Patent Application Publication No. 2018/0168619;
U.S. patent application Ser. No. 15/385,921, entitled SURGICAL STAPLE CARTRIDGE WITH MOVABLE CAMMING MEMBER CONFIGURED TO DISENGAGE FIRING MEMBER LOCKOUT FEATURES, now U.S. Pat. No. 10,687,809;
U.S. patent application Ser. No. 15/385,923, entitled SURGICAL STAPLING SYSTEMS, now U.S. Patent Application Publication No. 2018/0168623;
U.S. patent application Ser. No. 15/385,925, entitled JAW ACTUATED LOCK ARRANGEMENTS FOR PREVENTING ADVANCEMENT OF A FIRING MEMBER IN A SURGICAL END EFFECTOR UNLESS AN UNFIRED CARTRIDGE IS INSTALLED IN THE END EFFECTOR, now U.S. Pat. No. 10,517,595;
U.S. patent application Ser. No. 15/385,926, entitled AXIALLY MOVABLE CLOSURE SYSTEM ARRANGEMENTS FOR APPLYING CLOSURE MOTIONS TO JAWS OF SURGICAL INSTRUMENTS, now U.S. Patent Application Publication No. 2018/0168577;
U.S. patent application Ser. No. 15/385,928, entitled PROTECTIVE COVER ARRANGEMENTS FOR A JOINT INTERFACE BETWEEN A MOVABLE JAW AND ACTUATOR SHAFT OF A SURGICAL INSTRUMENT, now U.S. Patent Application Publication No. 2018/0168578;
U.S. patent application Ser. No. 15/385,930, entitled SURGICAL END EFFECTOR WITH TWO SEPARATE COOPERATING OPENING FEATURES FOR OPENING AND CLOSING END EFFECTOR JAWS, now U.S. Patent Application Publication No. 2018/0168579;
U.S. patent application Ser. No. 15/385,932, entitled ARTICULATABLE SURGICAL END EFFECTOR WITH ASYMMETRIC SHAFT ARRANGEMENT, now U.S. Patent Application Publication No. 2018/0168628;
U.S. patent application Ser. No. 15/385,933, entitled ARTICULATABLE SURGICAL INSTRUMENT WITH INDEPENDENT PIVOTABLE LINKAGE DISTAL OF AN ARTICULATION LOCK, now U.S. Pat. No. 10,603,036;
U.S. patent application Ser. No. 15/385,934, entitled ARTICULATION LOCK ARRANGEMENTS FOR LOCKING AN END EFFECTOR IN AN ARTICULATED POSITION IN RESPONSE TO ACTUATION OF A JAW CLOSURE SYSTEM, now U.S. Pat. No. 10,582,928;
U.S. patent application Ser. No. 15/385,935, entitled LATERALLY ACTUATABLE ARTICULATION LOCK ARRANGEMENTS FOR LOCKING AN END EFFECTOR OF A SURGICAL INSTRUMENT IN AN ARTICULATED CONFIGURATION, now U.S. Pat. No. 10,524,789;

U.S. patent application Ser. No. 15/385,936, entitled ARTICULATABLE SURGICAL INSTRUMENTS WITH ARTICULATION STROKE AMPLIFICATION FEATURES, now U.S. Pat. No. 10,517,596;

U.S. patent application Ser. No. 14/318,996, entitled FASTENER CARTRIDGES INCLUDING EXTENSIONS HAVING DIFFERENT CONFIGURATIONS, now U.S. Patent Application Publication No. 2015/0297228;

U.S. patent application Ser. No. 14/319,006, entitled FASTENER CARTRIDGE COMPRISING FASTENER CAVITIES INCLUDING FASTENER CONTROL FEATURES, now U.S. Pat. No. 10,010,324;

U.S. patent application Ser. No. 14/318,991, entitled SURGICAL FASTENER CARTRIDGES WITH DRIVER STABILIZING ARRANGEMENTS, now U.S. Pat. No. 9,833,241;

U.S. patent application Ser. No. 14/319,004, entitled SURGICAL END EFFECTORS WITH FIRING ELEMENT MONITORING ARRANGEMENTS, now U.S. Pat. No. 9,844,369;

U.S. patent application Ser. No. 14/319,008, entitled FASTENER CARTRIDGE COMPRISING NON-UNIFORM FASTENERS, now U.S. Pat. No. 10,299,792;

U.S. patent application Ser. No. 14/318,997, entitled FASTENER CARTRIDGE COMPRISING DEPLOYABLE TISSUE ENGAGING MEMBERS, now U.S. Pat. No. 10,561,422;

U.S. patent application Ser. No. 14/319,002, entitled FASTENER CARTRIDGE COMPRISING TISSUE CONTROL FEATURES, now U.S. Pat. No. 9,877,721;

U.S. patent application Ser. No. 14/319,013, entitled FASTENER CARTRIDGE ASSEMBLIES AND STAPLE RETAINER COVER ARRANGEMENTS, now U.S. Patent Application Publication No. 2015/0297233; and U.S. patent application Ser. No. 14/319,016, entitled FASTENER CARTRIDGE INCLUDING A LAYER ATTACHED THERETO, now U.S. Pat. No. 10,470,768.

Applicant of the present application owns the following U.S. Patent Applications that were filed on Jun. 24, 2016 and which are each herein incorporated by reference in their respective entireties:

U.S. patent application Ser. No. 15/191,775, entitled STAPLE CARTRIDGE COMPRISING WIRE STAPLES AND STAMPED STAPLES, now U.S. Patent Application Publication No. 2017/0367695;

U.S. patent application Ser. No. 15/191,807, entitled STAPLING SYSTEM FOR USE WITH WIRE STAPLES AND STAMPED STAPLES, now U.S. Pat. No. 10,702,270;

U.S. patent application Ser. No. 15/191,834, entitled STAMPED STAPLES AND STAPLE CARTRIDGES USING THE SAME, now U.S. Pat. No. 10,542,979;

U.S. patent application Ser. No. 15/191,788, entitled STAPLE CARTRIDGE COMPRISING OVERDRIVEN STAPLES, now U.S. Pat. No. 10,675,024; and U.S. patent application Ser. No. 15/191,818, entitled STAPLE CARTRIDGE COMPRISING OFFSET LONGITUDINAL STAPLE ROWS, now U.S. Pat. No. 10,893,863.

Applicant of the present application owns the following U.S. Patent Applications that were filed on Jun. 24, 2016 and which are each herein incorporated by reference in their respective entireties:

U.S. Design Patent Application Ser. No. 29/569,218, entitled SURGICAL FASTENER, now U.S. Design Patent No. D826,405;

U.S. Design Patent Application Ser. No. 29/569,227, entitled SURGICAL FASTENER, now U.S. Design Patent No. D822,206;

U.S. Design Patent Application Ser. No. 29/569,259, entitled SURGICAL FASTENER CARTRIDGE, now U.S. Design Patent No. D847,989; and U.S. Design Patent Application Ser. No. 29/569,264, entitled SURGICAL FASTENER CARTRIDGE, now U.S. Design Patent No. D850,617.

Applicant of the present application owns the following patent applications that were filed on Apr. 1, 2016 and which are each herein incorporated by reference in their respective entirety:

U.S. patent application Ser. No. 15/089,325, entitled METHOD FOR OPERATING A SURGICAL STAPLING SYSTEM, now U.S. Patent Application Publication No. 2017/0281171;

U.S. patent application Ser. No. 15/089,321, entitled MODULAR SURGICAL STAPLING SYSTEM COMPRISING A DISPLAY, now U.S. Pat. No. 10,271,851;

U.S. patent application Ser. No. 15/089,326, entitled SURGICAL STAPLING SYSTEM COMPRISING A DISPLAY INCLUDING A RE-ORIENTABLE DISPLAY FIELD, now U.S. Pat. No. 10,433,849;

U.S. patent application Ser. No. 15/089,263, entitled SURGICAL INSTRUMENT HANDLE ASSEMBLY WITH RECONFIGURABLE GRIP PORTION, now U.S. Pat. No. 10,307,159;

U.S. patent application Ser. No. 15/089,262, entitled ROTARY POWERED SURGICAL INSTRUMENT WITH MANUALLY ACTUATABLE BAILOUT SYSTEM, now U.S. Pat. No. 10,357,246;

U.S. patent application Ser. No. 15/089,277, entitled SURGICAL CUTTING AND STAPLING END EFFECTOR WITH ANVIL CONCENTRIC DRIVE MEMBER, now U.S. Pat. No. 10,531,874;

U.S. patent application Ser. No. 15/089,296, entitled INTERCHANGEABLE SURGICAL TOOL ASSEMBLY WITH A SURGICAL END EFFECTOR THAT IS SELECTIVELY ROTATABLE ABOUT A SHAFT AXIS, now U.S. Pat. No. 10,413,293;

U.S. patent application Ser. No. 15/089,258, entitled SURGICAL STAPLING SYSTEM COMPRISING A SHIFTABLE TRANSMISSION, now U.S. Pat. No. 10,342,543;

U.S. patent application Ser. No. 15/089,278, entitled SURGICAL STAPLING SYSTEM CONFIGURED TO PROVIDE SELECTIVE CUTTING OF TISSUE, now U.S. Pat. No. 10,420,552;

U.S. patent application Ser. No. 15/089,284, entitled SURGICAL STAPLING SYSTEM COMPRISING A CONTOURABLE SHAFT, now U.S. Patent Application Publication No. 2017/0281186;

U.S. patent application Ser. No. 15/089,295, entitled SURGICAL STAPLING SYSTEM COMPRISING A TISSUE COMPRESSION LOCKOUT, now U.S. Pat. No. 10,856,867;

U.S. patent application Ser. No. 15/089,300, entitled SURGICAL STAPLING SYSTEM COMPRISING AN UNCLAMPING LOCKOUT, now U.S. Pat. No. 10,456,140;

U.S. patent application Ser. No. 15/089,196, entitled SURGICAL STAPLING SYSTEM COMPRISING A JAW CLOSURE LOCKOUT, now U.S. Pat. No. 10,568,632;

U.S. patent application Ser. No. 15/089,203, entitled SURGICAL STAPLING SYSTEM COMPRISING A JAW ATTACHMENT LOCKOUT, now U.S. Pat. No. 10,542,991;

U.S. patent application Ser. No. 15/089,210, entitled SURGICAL STAPLING SYSTEM COMPRISING A SPENT CARTRIDGE LOCKOUT, now U.S. Pat. No. 10,478,190;

U.S. patent application Ser. No. 15/089,324, entitled SURGICAL INSTRUMENT COMPRISING A SHIFTING MECHANISM, now U.S. Pat. No. 10,314,582;

U.S. patent application Ser. No. 15/089,335, entitled SURGICAL STAPLING INSTRUMENT COMPRISING MULTIPLE LOCKOUTS, now U.S. Pat. No. 10,485,542;

U.S. patent application Ser. No. 15/089,339, entitled SURGICAL STAPLING INSTRUMENT, now U.S. Patent Application Publication No. 2017/0281173;

U.S. patent application Ser. No. 15/089,253, entitled SURGICAL STAPLING SYSTEM CONFIGURED TO APPLY ANNULAR ROWS OF STAPLES HAVING DIFFERENT HEIGHTS, now U.S. Pat. No. 10,413,297;

U.S. patent application Ser. No. 15/089,304, entitled SURGICAL STAPLING SYSTEM COMPRISING A GROOVED FORMING POCKET, now U.S. Pat. No. 10,285,705;

U.S. patent application Ser. No. 15/089,331, entitled ANVIL MODIFICATION MEMBERS FOR SURGICAL STAPLERS, now U.S. Pat. No. 10,376,263;

U.S. patent application Ser. No. 15/089,336, entitled STAPLE CARTRIDGES WITH ATRAUMATIC FEATURES, now U.S. Pat. No. 10,709,446;

U.S. patent application Ser. No. 15/089,312, entitled CIRCULAR STAPLING SYSTEM COMPRISING AN INCISABLE TISSUE SUPPORT, now U.S. Patent Application Publication No. 2017/0281189;

U.S. patent application Ser. No. 15/089,309, entitled CIRCULAR STAPLING SYSTEM COMPRISING ROTARY FIRING SYSTEM, now U.S. Pat. No. 10,675,021; and U.S. patent application Ser. No. 15/089,349, entitled CIRCULAR STAPLING SYSTEM COMPRISING LOAD CONTROL, now U.S. Pat. No. 10,682,136.

Applicant of the present application also owns the U.S. Patent Applications identified below which were filed on Dec. 30, 2015 which are each herein incorporated by reference in their respective entirety:

U.S. patent application Ser. No. 14/984,488, entitled MECHANISMS FOR COMPENSATING FOR BATTERY PACK FAILURE IN POWERED SURGICAL INSTRUMENTS, now U.S. Pat. No. 10,292,704;

U.S. patent application Ser. No. 14/984,525, entitled MECHANISMS FOR COMPENSATING FOR DRIVETRAIN FAILURE IN POWERED SURGICAL INSTRUMENTS, now U.S. Pat. No. 10,368,865; and U.S. patent application Ser. No. 14/984,552, entitled SURGICAL INSTRUMENTS WITH SEPARABLE MOTORS AND MOTOR CONTROL CIRCUITS, now U.S. Pat. No. 10,265,068.

Applicant of the present application also owns the U.S. Patent Applications identified below which were filed on Feb. 9, 2016, which are each herein incorporated by reference in their respective entirety:

U.S. patent application Ser. No. 15/019,220, entitled SURGICAL INSTRUMENT WITH ARTICULATING AND AXIALLY TRANSLATABLE END EFFECTOR, now U.S. Pat. No. 10,245,029;

U.S. patent application Ser. No. 15/019,228, entitled SURGICAL INSTRUMENTS WITH MULTIPLE LINK ARTICULATION ARRANGEMENTS, now U.S. Pat. No. 10,433,837;

U.S. patent application Ser. No. 15/019,196, entitled SURGICAL INSTRUMENT ARTICULATION MECHANISM WITH SLOTTED SECONDARY CONSTRAINT, now U.S. Pat. No. 10,413,291;

U.S. patent application Ser. No. 15/019,206, entitled SURGICAL INSTRUMENTS WITH AN END EFFECTOR THAT IS HIGHLY ARTICULATABLE RELATIVE TO AN ELONGATE SHAFT ASSEMBLY, now U.S. Pat. No. 10,653,413;

U.S. patent application Ser. No. 15/019,215, entitled SURGICAL INSTRUMENTS WITH NON-SYMMETRICAL ARTICULATION ARRANGEMENTS, now U.S. Patent Application Publication No. 2017/0224332;

U.S. patent application Ser. No. 15/019,227, entitled ARTICULATABLE SURGICAL INSTRUMENTS WITH SINGLE ARTICULATION LINK ARRANGEMENTS, now U.S. Patent Application Publication No. 2017/0224334;

U.S. patent application Ser. No. 15/019,235, entitled SURGICAL INSTRUMENTS WITH TENSIONING ARRANGEMENTS FOR CABLE DRIVEN ARTICULATION SYSTEMS, now U.S. Pat. No. 10,245,030;

U.S. patent application Ser. No. 15/019,230, entitled ARTICULATABLE SURGICAL INSTRUMENTS WITH OFF-AXIS FIRING BEAM ARRANGEMENTS, now U.S. Pat. No. 10,588,625; and U.S. patent application Ser. No. 15/019,245, entitled SURGICAL INSTRUMENTS WITH CLOSURE STROKE REDUCTION ARRANGEMENTS, now U.S. Pat. No. 10,470,764.

Applicant of the present application also owns the U.S. Patent Applications identified below which were filed on Feb. 12, 2016, which are each herein incorporated by reference in their respective entirety:

U.S. patent application Ser. No. 15/043,254, entitled MECHANISMS FOR COMPENSATING FOR DRIVETRAIN FAILURE IN POWERED SURGICAL INSTRUMENTS, now U.S. Pat. No. 10,258,331;

U.S. patent application Ser. No. 15/043,259, entitled MECHANISMS FOR COMPENSATING FOR DRIVETRAIN FAILURE IN POWERED SURGICAL INSTRUMENTS, now U.S. Pat. No. 10,448,948;

U.S. patent application Ser. No. 15/043,275, entitled MECHANISMS FOR COMPENSATING FOR DRIVETRAIN FAILURE IN POWERED SURGICAL INSTRUMENTS, now U.S. Patent Application Publication No. 2017/0231627; and U.S. patent application Ser. No. 15/043,289, entitled MECHANISMS FOR COMPENSATING FOR DRIVETRAIN FAILURE IN POWERED SURGICAL INSTRUMENTS, now U.S. Patent Application Publication No. 2017/0231628.

Applicant of the present application owns the following Patent Applications that were filed on Jun. 18, 2015 and which are each herein incorporated by reference in their respective entirety:

- U.S. patent application Ser. No. 14/742,925, entitled SURGICAL END EFFECTORS WITH POSITIVE JAW OPENING ARRANGEMENTS, now U.S. Pat. No. 10,182,818;
- U.S. patent application Ser. No. 14/742,941, entitled SURGICAL END EFFECTORS WITH DUAL CAM ACTUATED JAW CLOSING FEATURES, now U.S. Pat. No. 10,052,102;
- U.S. patent application Ser. No. 14/742,933, entitled SURGICAL STAPLING INSTRUMENTS WITH LOCKOUT ARRANGEMENTS FOR PREVENTING FIRING SYSTEM ACTUATION WHEN A CARTRIDGE IS SPENT OR MISSING, now U.S. Pat. No. 10,154,841;
- U.S. patent application Ser. No. 14/742,914, entitled MOVABLE FIRING BEAM SUPPORT ARRANGEMENTS FOR ARTICULATABLE SURGICAL INSTRUMENTS, now U.S. Pat. No. 10,405,863;
- U.S. patent application Ser. No. 14/742,900, entitled ARTICULATABLE SURGICAL INSTRUMENTS WITH COMPOSITE FIRING BEAM STRUCTURES WITH CENTER FIRING SUPPORT MEMBER FOR ARTICULATION SUPPORT, now U.S. Pat. No. 10,335,149;
- U.S. patent application Ser. No. 14/742,885, entitled DUAL ARTICULATION DRIVE SYSTEM ARRANGEMENTS FOR ARTICULATABLE SURGICAL INSTRUMENTS, now U.S. Pat. No. 10,368,861; and
- U.S. patent application Ser. No. 14/742,876, entitled PUSH/PULL ARTICULATION DRIVE SYSTEMS FOR ARTICULATABLE SURGICAL INSTRUMENTS, now U.S. Pat. No. 10,178,992.

Applicant of the present application owns the following Patent Applications that were filed on Mar. 6, 2015 and which are each herein incorporated by reference in their respective entirety:

- U.S. patent application Ser. No. 14/640,746, entitled POWERED SURGICAL INSTRUMENT, now U.S. Pat. No. 9,808,246;
- U.S. patent application Ser. No. 14/640,795, entitled MULTIPLE LEVEL THRESHOLDS TO MODIFY OPERATION OF POWERED SURGICAL INSTRUMENTS, now U.S. Pat. No. 10,441,279;
- U.S. patent application Ser. No. 14/640,832, entitled ADAPTIVE TISSUE COMPRESSION TECHNIQUES TO ADJUST CLOSURE RATES FOR MULTIPLE TISSUE TYPES, now U.S. Pat. No. 10,687,806;
- U.S. patent application Ser. No. 14/640,935, entitled OVERLAID MULTI SENSOR RADIO FREQUENCY (RF) ELECTRODE SYSTEM TO MEASURE TISSUE COMPRESSION, now U.S. Pat. No. 10,548,504;
- U.S. patent application Ser. No. 14/640,831, entitled MONITORING SPEED CONTROL AND PRECISION INCREMENTING OF MOTOR FOR POWERED SURGICAL INSTRUMENTS, now U.S. Pat. No. 9,895,148;
- U.S. patent application Ser. No. 14/640,859, entitled TIME DEPENDENT EVALUATION OF SENSOR DATA TO DETERMINE STABILITY, CREEP, AND VISCOELASTIC ELEMENTS OF MEASURES, now U.S. Pat. No. 10,052,044;
- U.S. patent application Ser. No. 14/640,817, entitled INTERACTIVE FEEDBACK SYSTEM FOR POWERED SURGICAL INSTRUMENTS, now U.S. Pat. No. 9,924,961;
- U.S. patent application Ser. No. 14/640,844, entitled CONTROL TECHNIQUES AND SUB-PROCESSOR CONTAINED WITHIN MODULAR SHAFT WITH SELECT CONTROL PROCESSING FROM HANDLE, now U.S. Pat. No. 10,045,776;
- U.S. patent application Ser. No. 14/640,837, entitled SMART SENSORS WITH LOCAL SIGNAL PROCESSING, now U.S. Pat. No. 9,993,248;
- U.S. patent application Ser. No. 14/640,765, entitled SYSTEM FOR DETECTING THE MIS-INSERTION OF A STAPLE CARTRIDGE INTO A SURGICAL STAPLER, now U.S. Pat. No. 10,617,412;
- U.S. patent application Ser. No. 14/640,799, entitled SIGNAL AND POWER COMMUNICATION SYSTEM POSITIONED ON A ROTATABLE SHAFT, now U.S. Pat. No. 9,901,342; and
- U.S. patent application Ser. No. 14/640,780, entitled SURGICAL INSTRUMENT COMPRISING A LOCKABLE BATTERY HOUSING, now U.S. Pat. No. 10,245,033.

Applicant of the present application owns the following Patent Applications that were filed on Feb. 27, 2015, and which are each herein incorporated by reference in their respective entirety:

- U.S. patent application Ser. No. 14/633,576, entitled SURGICAL INSTRUMENT SYSTEM COMPRISING AN INSPECTION STATION, now U.S. Pat. No. 10,045,779;
- U.S. patent application Ser. No. 14/633,546, entitled SURGICAL APPARATUS CONFIGURED TO ASSESS WHETHER A PERFORMANCE PARAMETER OF THE SURGICAL APPARATUS IS WITHIN AN ACCEPTABLE PERFORMANCE BAND, now U.S. Pat. No. 10,180,463;
- U.S. patent application Ser. No. 14/633,560, entitled SURGICAL CHARGING SYSTEM THAT CHARGES AND/OR CONDITIONS ONE OR MORE BATTERIES, now U.S. Patent Application Publication No. 2016/0249910;
- U.S. patent application Ser. No. 14/633,566, entitled CHARGING SYSTEM THAT ENABLES EMERGENCY RESOLUTIONS FOR CHARGING A BATTERY, now U.S. Pat. No. 10,182,816;
- U.S. patent application Ser. No. 14/633,555, entitled SYSTEM FOR MONITORING WHETHER A SURGICAL INSTRUMENT NEEDS TO BE SERVICED, now U.S. Pat. No. 10,321,907;
- U.S. patent application Ser. No. 14/633,542, entitled REINFORCED BATTERY FOR A SURGICAL INSTRUMENT, now U.S. Pat. No. 9,931,118;
- U.S. patent application Ser. No. 14/633,548, entitled POWER ADAPTER FOR A SURGICAL INSTRUMENT, now U.S. Pat. No. 10,245,028;
- U.S. patent application Ser. No. 14/633,526, entitled ADAPTABLE SURGICAL INSTRUMENT HANDLE, now U.S. Pat. No. 9,993,258;
- U.S. patent application Ser. No. 14/633,541, entitled MODULAR STAPLING ASSEMBLY, now U.S. Pat. No. 10,226,250; and
- U.S. patent application Ser. No. 14/633,562, entitled SURGICAL APPARATUS CONFIGURED TO TRACK AN END-OF-LIFE PARAMETER, now U.S. Pat. No. 10,159,483.

Applicant of the present application owns the following patent applications that were filed on Dec. 18, 2014 and which are each herein incorporated by reference in their respective entirety:

- U.S. patent application Ser. No. 14/574,478, entitled SURGICAL INSTRUMENT SYSTEMS COMPRISING AN ARTICULATABLE END EFFECTOR AND MEANS FOR ADJUSTING THE FIRING STROKE OF A FIRING MEMBER, now U.S. Pat. No. 9,844,374;
- U.S. patent application Ser. No. 14/574,483, entitled SURGICAL INSTRUMENT ASSEMBLY COMPRISING LOCKABLE SYSTEMS, now U.S. Pat. No. 10,188,385;
- U.S. patent application Ser. No. 14/575,139, entitled DRIVE ARRANGEMENTS FOR ARTICULATABLE SURGICAL INSTRUMENTS, now U.S. Pat. No. 9,844,375;
- U.S. patent application Ser. No. 14/575,148, entitled LOCKING ARRANGEMENTS FOR DETACHABLE SHAFT ASSEMBLIES WITH ARTICULATABLE SURGICAL END EFFECTORS, now U.S. Pat. No. 10,085,748;
- U.S. patent application Ser. No. 14/575,130, entitled SURGICAL INSTRUMENT WITH AN ANVIL THAT IS SELECTIVELY MOVABLE ABOUT A DISCRETE NON-MOVABLE AXIS RELATIVE TO A STAPLE CARTRIDGE, now U.S. Pat. No. 10,245,027;
- U.S. patent application Ser. No. 14/575,143, entitled SURGICAL INSTRUMENTS WITH IMPROVED CLOSURE ARRANGEMENTS, now U.S. Pat. No. 10,004,501;
- U.S. patent application Ser. No. 14/575,117, entitled SURGICAL INSTRUMENTS WITH ARTICULATABLE END EFFECTORS AND MOVABLE FIRING BEAM SUPPORT ARRANGEMENTS, now U.S. Pat. No. 9,943,309;
- U.S. patent application Ser. No. 14/575,154, entitled SURGICAL INSTRUMENTS WITH ARTICULATABLE END EFFECTORS AND IMPROVED FIRING BEAM SUPPORT ARRANGEMENTS, now U.S. Pat. No. 9,968,355;
- U.S. patent application Ser. No. 14/574,493, entitled SURGICAL INSTRUMENT ASSEMBLY COMPRISING A FLEXIBLE ARTICULATION SYSTEM, now U.S. Pat. No. 9,987,000; and
- U.S. patent application Ser. No. 14/574,500, entitled SURGICAL INSTRUMENT ASSEMBLY COMPRISING A LOCKABLE ARTICULATION SYSTEM, now U.S. Pat. No. 10,117,649.

Applicant of the present application owns the following patent applications that were filed on Mar. 1, 2013 and which are each herein incorporated by reference in their respective entirety:

- U.S. patent application Ser. No. 13/782,295, entitled ARTICULATABLE SURGICAL INSTRUMENTS WITH CONDUCTIVE PATHWAYS FOR SIGNAL COMMUNICATION, now U.S. Pat. No. 9,700,309;
- U.S. patent application Ser. No. 13/782,323, entitled ROTARY POWERED ARTICULATION JOINTS FOR SURGICAL INSTRUMENTS, now U.S. Pat. No. 9,782,169;
- U.S. patent application Ser. No. 13/782,338, entitled THUMBWHEEL SWITCH ARRANGEMENTS FOR SURGICAL INSTRUMENTS, now U.S. Patent Application Publication No. 2014/0249557;
- U.S. patent application Ser. No. 13/782,499, entitled ELECTROMECHANICAL SURGICAL DEVICE WITH SIGNAL RELAY ARRANGEMENT, now U.S. Pat. No. 9,358,003;
- U.S. patent application Ser. No. 13/782,460, entitled MULTIPLE PROCESSOR MOTOR CONTROL FOR MODULAR SURGICAL INSTRUMENTS, now U.S. Pat. No. 9,554,794;
- U.S. patent application Ser. No. 13/782,358, entitled JOYSTICK SWITCH ASSEMBLIES FOR SURGICAL INSTRUMENTS, now U.S. Pat. No. 9,326,767;
- U.S. patent application Ser. No. 13/782,481, entitled SENSOR STRAIGHTENED END EFFECTOR DURING REMOVAL THROUGH TROCAR, now U.S. Pat. No. 9,468,438;
- U.S. patent application Ser. No. 13/782,518, entitled CONTROL METHODS FOR SURGICAL INSTRUMENTS WITH REMOVABLE IMPLEMENT PORTIONS, now U.S. Patent Application Publication No. 2014/0246475;
- U.S. patent application Ser. No. 13/782,375, entitled ROTARY POWERED SURGICAL INSTRUMENTS WITH MULTIPLE DEGREES OF FREEDOM, now U.S. Pat. No. 9,398,911; and
- U.S. patent application Ser. No. 13/782,536, entitled SURGICAL INSTRUMENT SOFT STOP, now U.S. Pat. No. 9,307,986.

Applicant of the present application also owns the following patent applications that were filed on Mar. 14, 2013 and which are each herein incorporated by reference in their respective entirety:

- U.S. patent application Ser. No. 13/803,097, entitled ARTICULATABLE SURGICAL INSTRUMENT COMPRISING A FIRING DRIVE, now U.S. Pat. No. 9,687,230;
- U.S. patent application Ser. No. 13/803,193, entitled CONTROL ARRANGEMENTS FOR A DRIVE MEMBER OF A SURGICAL INSTRUMENT, now U.S. Pat. No. 9,332,987;
- U.S. patent application Ser. No. 13/803,053, entitled INTERCHANGEABLE SHAFT ASSEMBLIES FOR USE WITH A SURGICAL INSTRUMENT, now U.S. Pat. No. 9,883,860;
- U.S. patent application Ser. No. 13/803,086, entitled ARTICULATABLE SURGICAL INSTRUMENT COMPRISING AN ARTICULATION LOCK, now U.S. Patent Application Publication No. 2014/0263541;
- U.S. patent application Ser. No. 13/803,210, entitled SENSOR ARRANGEMENTS FOR ABSOLUTE POSITIONING SYSTEM FOR SURGICAL INSTRUMENTS, now U.S. Pat. No. 9,808,244;
- U.S. patent application Ser. No. 13/803,148, entitled MULTI-FUNCTION MOTOR FOR A SURGICAL INSTRUMENT, now U.S. Pat. No. 10,470,762;
- U.S. patent application Ser. No. 13/803,066, entitled DRIVE SYSTEM LOCKOUT ARRANGEMENTS FOR MODULAR SURGICAL INSTRUMENTS, now U.S. Pat. No. 9,629,623;
- U.S. patent application Ser. No. 13/803,117, entitled ARTICULATION CONTROL SYSTEM FOR ARTICULATABLE SURGICAL INSTRUMENTS, now U.S. Pat. No. 9,351,726;
- U.S. patent application Ser. No. 13/803,130, entitled DRIVE TRAIN CONTROL ARRANGEMENTS FOR MODULAR SURGICAL INSTRUMENTS, now U.S. Pat. No. 9,351,727; and U.S. patent application Ser. No. 13/803,159, entitled METHOD AND SYSTEM FOR OPERATING A SURGICAL INSTRUMENT, now U.S. Pat. No. 9,888,919.

Applicant of the present application also owns the following patent application that was filed on Mar. 7, 2014 and is herein incorporated by reference in its entirety:

U.S. patent application Ser. No. 14/200,111, entitled CONTROL SYSTEMS FOR SURGICAL INSTRUMENTS, now U.S. Pat. No. 9,629,629.

Applicant of the present application also owns the following patent applications that were filed on Mar. 26, 2014 and are each herein incorporated by reference in their respective entirety:

U.S. patent application Ser. No. 14/226,106, entitled POWER MANAGEMENT CONTROL SYSTEMS FOR SURGICAL INSTRUMENTS, now U.S. Patent Application Publication No. 2015/0272582;

U.S. patent application Ser. No. 14/226,099, entitled STERILIZATION VERIFICATION CIRCUIT, now U.S. Pat. No. 9,826,977;

U.S. patent application Ser. No. 14/226,094, entitled VERIFICATION OF NUMBER OF BATTERY EXCHANGES/PROCEDURE COUNT, now U.S. Patent Application Publication No. 2015/0272580;

U.S. patent application Ser. No. 14/226,117, entitled POWER MANAGEMENT THROUGH SLEEP OPTIONS OF SEGMENTED CIRCUIT AND WAKE UP CONTROL, now U.S. Pat. No. 10,013,049;

U.S. patent application Ser. No. 14/226,075, entitled MODULAR POWERED SURGICAL INSTRUMENT WITH DETACHABLE SHAFT ASSEMBLIES, now U.S. Pat. No. 9,743,929;

U.S. patent application Ser. No. 14/226,093, entitled FEEDBACK ALGORITHMS FOR MANUAL BAILOUT SYSTEMS FOR SURGICAL INSTRUMENTS, now U.S. Pat. No. 10,028,761;

U.S. patent application Ser. No. 14/226,116, entitled SURGICAL INSTRUMENT UTILIZING SENSOR ADAPTATION, now U.S. Patent Application Publication No. 2015/0272571;

U.S. patent application Ser. No. 14/226,071, entitled SURGICAL INSTRUMENT CONTROL CIRCUIT HAVING A SAFETY PROCESSOR, now U.S. Pat. No. 9,690,362;

U.S. patent application Ser. No. 14/226,097, entitled SURGICAL INSTRUMENT COMPRISING INTERACTIVE SYSTEMS, now U.S. Pat. No. 9,820,738;

U.S. patent application Ser. No. 14/226,126, entitled INTERFACE SYSTEMS FOR USE WITH SURGICAL INSTRUMENTS, now U.S. Pat. No. 10,004,497;

U.S. patent application Ser. No. 14/226,133, entitled MODULAR SURGICAL INSTRUMENT SYSTEM, now U.S. Patent Application Publication No. 2015/0272557;

U.S. patent application Ser. No. 14/226,081, entitled SYSTEMS AND METHODS FOR CONTROLLING A SEGMENTED CIRCUIT, now U.S. Pat. No. 9,804,618;

U.S. patent application Ser. No. 14/226,076, entitled POWER MANAGEMENT THROUGH SEGMENTED CIRCUIT AND VARIABLE VOLTAGE PROTECTION, now U.S. Pat. No. 9,733,663;

U.S. patent application Ser. No. 14/226,111, entitled SURGICAL STAPLING INSTRUMENT SYSTEM, now U.S. Pat. No. 9,750,499; and U.S. patent application Ser. No. 14/226,125, entitled SURGICAL INSTRUMENT COMPRISING A ROTATABLE SHAFT, now U.S. Pat. No. 10,201,364.

Applicant of the present application also owns the following patent applications that were filed on Sep. 5, 2014 and which are each herein incorporated by reference in their respective entirety:

U.S. patent application Ser. No. 14/479,103, entitled CIRCUITRY AND SENSORS FOR POWERED MEDICAL DEVICE, now U.S. Pat. No. 10,111,679;

U.S. patent application Ser. No. 14/479,119, entitled ADJUNCT WITH INTEGRATED SENSORS TO QUANTIFY TISSUE COMPRESSION, now U.S. Pat. No. 9,724,094;

U.S. patent application Ser. No. 14/478,908, entitled MONITORING DEVICE DEGRADATION BASED ON COMPONENT EVALUATION, now U.S. Pat. No. 9,737,301;

U.S. patent application Ser. No. 14/478,895, entitled MULTIPLE SENSORS WITH ONE SENSOR AFFECTING A SECOND SENSOR'S OUTPUT OR INTERPRETATION, now U.S. Pat. No. 9,757,128;

U.S. patent application Ser. No. 14/479,110, entitled POLARITY OF HALL MAGNET TO IDENTIFY CARTRIDGE TYPE, now U.S. Pat. No. 10,016,199;

U.S. patent application Ser. No. 14/479,098, entitled SMART CARTRIDGE WAKE UP OPERATION AND DATA RETENTION, now U.S. Pat. No. 10,135,242;

U.S. patent application Ser. No. 14/479,115, entitled MULTIPLE MOTOR CONTROL FOR POWERED MEDICAL DEVICE, now U.S. Pat. No. 9,788,836; and U.S. patent application Ser. No. 14/479,108, entitled LOCAL DISPLAY OF TISSUE PARAMETER STABILIZATION, now U.S. Patent Application Publication No. 2016/0066913.

Applicant of the present application also owns the following patent applications that were filed on Apr. 9, 2014 and which are each herein incorporated by reference in their respective entirety:

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/248,581, entitled SURGICAL INSTRUMENT COMPRISING A CLOSING DRIVE AND A FIRING DRIVE OPERATED FROM THE SAME ROTATABLE OUTPUT, now U.S. Pat. No. 9,649,110;

U.S. patent application Ser. No. 14/248,595, entitled SURGICAL SYSTEM COMPRISING FIRST AND SECOND DRIVE SYSTEMS, now U.S. Pat. No. 9,844,368;

U.S. patent application Ser. No. 14/248,588, entitled POWERED LINEAR SURGICAL STAPLER, now U.S. Pat. No. 10,405,857;

U.S. patent application Ser. No. 14/248,591, entitled SURGICAL INSTRUMENT COMPRISING A GAP SETTING SYSTEM, now U.S. Pat. No. 10,149,680;

U.S. patent application Ser. No. 14/248,584, entitled MODULAR MOTOR DRIVEN SURGICAL INSTRUMENTS WITH ALIGNMENT FEATURES FOR ALIGNING ROTARY DRIVE SHAFTS WITH SURGICAL END EFFECTOR SHAFTS, now U.S. Pat. No. 9,801,626;

U.S. patent application Ser. No. 14/248,587, entitled POWERED SURGICAL STAPLER, now U.S. Pat. No. 9,867,612;

U.S. patent application Ser. No. 14/248,586, entitled DRIVE SYSTEM DECOUPLING ARRANGEMENT FOR A SURGICAL INSTRUMENT, now U.S. Pat. No. 10,136,887; and U.S. patent application Ser. No. 14/248,607, entitled MODULAR MOTOR DRIVEN SURGICAL INSTRUMENTS WITH STATUS INDICATION ARRANGEMENTS, now U.S. Pat. No. 9,814,460.

Applicant of the present application also owns the following patent applications that were filed on Apr. 16, 2013 and which are each herein incorporated by reference in their respective entirety:

U.S. Provisional Patent Application Ser. No. 61/812,365, entitled SURGICAL INSTRUMENT WITH MULTIPLE FUNCTIONS PERFORMED BY A SINGLE MOTOR;

U.S. Provisional Patent Application Ser. No. 61/812,376, entitled LINEAR CUTTER WITH POWER;

U.S. Provisional Patent Application Ser. No. 61/812,382, entitled LINEAR CUTTER WITH MOTOR AND PISTOL GRIP;

U.S. Provisional Patent Application Ser. No. 61/812,385, entitled SURGICAL INSTRUMENT HANDLE WITH MULTIPLE ACTUATION MOTORS AND MOTOR CONTROL; and U.S. Provisional Patent Application Ser. No. 61/812,372, entitled SURGICAL INSTRUMENT WITH MULTIPLE FUNCTIONS PERFORMED BY A SINGLE MOTOR.

Applicant of the present application owns the following U.S. Provisional Patent Applications, filed on Dec. 28, 2017, the disclosure of each of which is herein incorporated by reference in its entirety:

U.S. Provisional Patent Application Ser. No. 62/611,341, entitled INTERACTIVE SURGICAL PLATFORM;

U.S. Provisional Patent Application Ser. No. 62/611,340, entitled CLOUD-BASED MEDICAL ANALYTICS; and U.S. Provisional Patent Application Ser. No. 62/611,339, entitled ROBOT ASSISTED SURGICAL PLATFORM.

Applicant of the present application owns the following U.S. Provisional Patent Applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. Patent Applications, filed on Mar. 29, 2018, each of which is herein incorporated by reference in its entirety:

U.S. patent application Ser. No. 15/940,641, entitled INTERACTIVE SURGICAL SYSTEMS WITH ENCRYPTED COMMUNICATION CAPABILITIES, now U.S. Patent Application Publication No. 2019/0207911;

U.S. patent application Ser. No. 15/940,648, entitled INTERACTIVE SURGICAL SYSTEMS WITH CONDITION HANDLING OF DEVICES AND DATA CAPABILITIES, now U.S. Patent Application Publication No. 2019/0206004;

U.S. patent application Ser. No. 15/940,656, entitled SURGICAL HUB COORDINATION OF CONTROL AND COMMUNICATION OF OPERATING ROOM DEVICES, now U.S. Patent Application Publication No. 2019/0201141;

U.S. patent application Ser. No. 15/940,666, entitled SPATIAL AWARENESS OF SURGICAL HUBS IN OPERATING ROOMS, now U.S. Patent Application Publication No. 2019/0206551;

U.S. patent application Ser. No. 15/940,670, entitled COOPERATIVE UTILIZATION OF DATA DERIVED FROM SECONDARY SOURCES BY INTELLIGENT SURGICAL HUBS, now U.S. Patent Application Publication No. 2019/0201116;

U.S. patent application Ser. No. 15/940,677, entitled SURGICAL HUB CONTROL ARRANGEMENTS, now U.S. Patent Application Publication No. 2019/0201143;

U.S. patent application Ser. No. 15/940,632, entitled DATA STRIPPING METHOD TO INTERROGATE PATIENT RECORDS AND CREATE ANONYMIZED RECORD, now U.S. Patent Application Publication No. 2019/0205566;

U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS, now U.S. Patent Application Publication No. 2019/0200863;

U.S. patent application Ser. No. 15/940,645, entitled SELF DESCRIBING DATA PACKETS GENERATED AT AN ISSUING INSTRUMENT, now U.S. Pat. No. 10,892,899;

U.S. patent application Ser. No. 15/940,649, entitled DATA PAIRING TO INTERCONNECT A DEVICE MEASURED PARAMETER WITH AN OUTCOME, now U.S. Patent Application Publication No. 2019/0205567;

U.S. patent application Ser. No. 15/940,654, entitled SURGICAL HUB SITUATIONAL AWARENESS, now U.S. Patent Application Publication No. 2019/0201140;

U.S. patent application Ser. No. 15/940,663, entitled SURGICAL SYSTEM DISTRIBUTED PROCESSING, now U.S. Patent Application Publication No. 2019/0201033;

U.S. patent application Ser. No. 15/940,668, entitled AGGREGATION AND REPORTING OF SURGICAL HUB DATA, now U.S. Patent Application Publication No. 2019/0201115;

U.S. patent application Ser. No. 15/940,671, entitled SURGICAL HUB SPATIAL AWARENESS TO DETERMINE DEVICES IN OPERATING THEATER, now U.S. Patent Application Publication No. 2019/0201104;

U.S. patent application Ser. No. 15/940,686, entitled DISPLAY OF ALIGNMENT OF STAPLE CARTRIDGE TO PRIOR LINEAR STAPLE LINE, now U.S. Patent Application Publication No. 2019/0201105;

U.S. patent application Ser. No. 15/940,700, entitled STERILE FIELD INTERACTIVE CONTROL DISPLAYS, now U.S. Patent Application Publication No. 2019/0205001;

U.S. patent application Ser. No. 15/940,629, entitled COMPUTER IMPLEMENTED INTERACTIVE SURGICAL SYSTEMS, now U.S. Patent Application Publication No. 2019/0201112;

U.S. patent application Ser. No. 15/940,704, entitled USE OF LASER LIGHT AND RED-GREEN-BLUE COLORATION TO DETERMINE PROPERTIES OF BACK SCATTERED LIGHT, now U.S. Patent Application Publication No. 2019/0206050;

U.S. patent application Ser. No. 15/940,722, entitled CHARACTERIZATION OF TISSUE IRREGULARITIES THROUGH THE USE OF MONO-CHROMATIC LIGHT REFRACTIVITY, now U.S. Patent Application Publication No. 2019/0200905; and U.S. patent application Ser. No. 15/940,742, entitled DUAL CMOS ARRAY IMAGING, now U.S. Patent Application Publication No. 2019/0200906.

Applicant of the present application owns the following U.S. Patent Applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES, now U.S. Patent Application Publication No. 2019/0206003;

U.S. patent application Ser. No. 15/940,653, entitled ADAPTIVE CONTROL PROGRAM UPDATES FOR SURGICAL HUBS, now U.S. Patent Application Publication No. 2019/0201114;

U.S. patent application Ser. No. 15/940,660, entitled CLOUD-BASED MEDICAL ANALYTICS FOR CUSTOMIZATION AND RECOMMENDATIONS TO A USER, now U.S. Patent Application Publication No. 2019/0206555;

U.S. patent application Ser. No. 15/940,679, entitled CLOUD-BASED MEDICAL ANALYTICS FOR LINKING OF LOCAL USAGE TRENDS WITH THE RESOURCE ACQUISITION BEHAVIORS OF LARGER DATA SET, now U.S. Patent Application Publication No. 2019/0201144;

U.S. patent application Ser. No. 15/940,694, entitled CLOUD-BASED MEDICAL ANALYTICS FOR MEDICAL FACILITY SEGMENTED INDIVIDUALIZATION OF INSTRUMENT FUNCTION, now U.S. Patent Application Publication No. 2019/0201119;

U.S. patent application Ser. No. 15/940,634, entitled CLOUD-BASED MEDICAL ANALYTICS FOR SECURITY AND AUTHENTICATION TRENDS AND REACTIVE MEASURES, now U.S. Patent Application Publication No. 2019/0201138;

U.S. patent application Ser. No. 15/940,706, entitled DATA HANDLING AND PRIORITIZATION IN A CLOUD ANALYTICS NETWORK, now U.S. Patent Application Publication No. 2019/0206561; and U.S. patent application Ser. No. 15/940,675, entitled CLOUD INTERFACE FOR COUPLED SURGICAL DEVICES, now U.S. Pat. No. 10,849,697.

Applicant of the present application owns the following U.S. Patent Applications, filed on Mar. 29, 2018, each of which is herein incorporated by reference in its entirety:

U.S. patent application Ser. No. 15/940,627, entitled DRIVE ARRANGEMENTS FOR ROBOT-ASSISTED SURGICAL PLATFORMS, now U.S. Patent Application Publication No. 2019/0201111;

U.S. patent application Ser. No. 15/940,637, entitled COMMUNICATION ARRANGEMENTS FOR ROBOT-ASSISTED SURGICAL PLATFORMS, now U.S. Patent Application Publication No. 2019/0201139;

U.S. patent application Ser. No. 15/940,642, entitled CONTROLS FOR ROBOT-ASSISTED SURGICAL PLATFORMS, now U.S. Patent Application Publication No. 2019/0201113;

U.S. patent application Ser. No. 15/940,676, entitled AUTOMATIC TOOL ADJUSTMENTS FOR ROBOT-ASSISTED SURGICAL PLATFORMS, now U.S. Patent Application Publication No. 2019/0201142;

U.S. patent application Ser. No. 15/940,680, entitled CONTROLLERS FOR ROBOT-ASSISTED SURGICAL PLATFORMS, now U.S. Patent Application Publication No. 2019/0201135;

U.S. patent application Ser. No. 15/940,683, entitled COOPERATIVE SURGICAL ACTIONS FOR ROBOT-ASSISTED SURGICAL PLATFORMS, now U.S. Patent Application Publication No. 2019/0201145;

U.S. patent application Ser. No. 15/940,690, entitled DISPLAY ARRANGEMENTS FOR ROBOT-ASSISTED SURGICAL PLATFORMS, now U.S. Patent Application Publication No. 2019/0201118; and U.S. patent application Ser. No. 15/940,711, entitled SENSING ARRANGEMENTS FOR ROBOT-ASSISTED SURGICAL PLATFORMS, now U.S. Patent Application Publication No. 2019/0201120.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The second jaw is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. The end effector is rotatable about an articulation axis extending through the articulation joint. Other embodiments are envisioned which do not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing member. The firing member is configured to contact the sled and push the sled toward the distal end. The longitudinal slot defined in the cartridge body is configured to receive the firing member. The anvil also includes a slot configured to receive the firing member. The firing member further comprises a first cam which engages the first jaw and a second cam which engages the second jaw. As the firing member is advanced distally, the first cam and the second cam can control the distance, or tissue gap, between the deck of the staple cartridge and the anvil. The firing member also comprises a knife configured to incise the tissue captured intermediate the staple cartridge and the anvil. It is desirable for the knife to be positioned at least partially proximal to the ramped surfaces such that the staples are ejected ahead of the knife.

Figure 2:
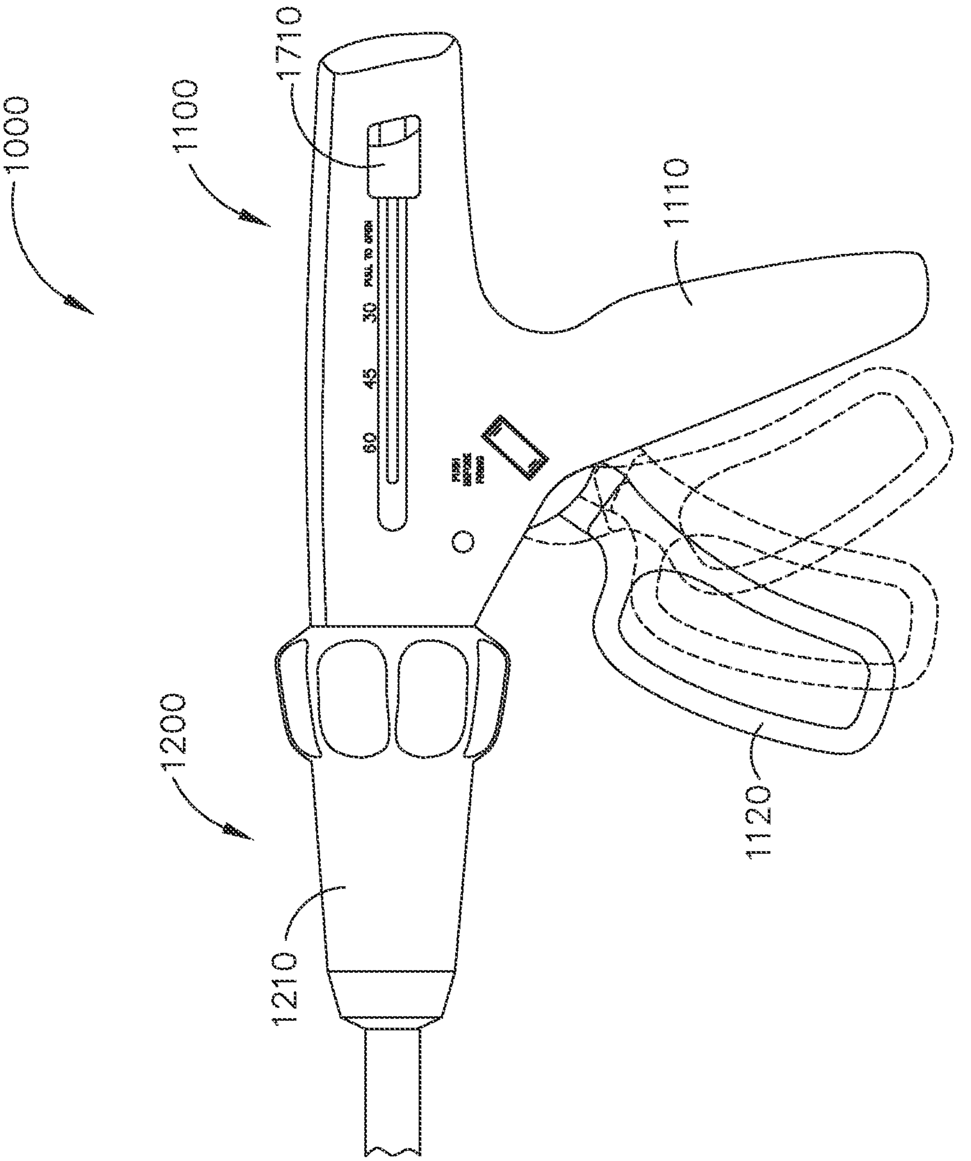
FIG. 2 is an elevational view of a handle of the surgical stapling instrument of FIG. 1.

A stapling instrument 1000 is illustrated in FIG. 1. The stapling instrument 1000 comprises a handle 1100, a shaft 1200 extending from the handle 1100, and a loading unit 1300 that is removably attachable to the shaft 1200. The shaft 1200 comprises a distal connection 1220 that is releasably attached to a proximal connection end 1320 of the loading unit 1300. The entire disclosure of U.S. Pat. No. 5,865,361, entitled SURGICAL STAPLING APPARATUS, which issued on Feb. 2, 1999 is incorporated by reference herein. The loading unit 1300 further comprises an end effector 1400 and an articulation joint 1500. The end effector 1400 comprises an anvil jaw 1410 and a cartridge jaw 1420. The cartridge jaw 1420 is configured to receive a staple cartridge, such as staple cartridge 1900, for example, and is rotatable between an open unclamped position and a closed clamped position relative to the anvil jaw 1410. In various other embodiments, the anvil jaw 1410 is rotatable relative to the cartridge jaw 1420. In either embodiment, the stapling instrument 1000 comprises a firing drive actuatable to close the end effector 1400 and, during a separate actuation (or actuations), fire the staples from the staple cartridge 1900. Referring to FIG. 1, the firing drive includes a firing trigger 1120 which, when actuated (FIG. 2), advances a firing rod 1690 distally. When the loading unit 1300 is attached to the shaft 1200, the firing rod 1690 is coupled to a firing member 1390 of the loading unit 1300 which is advanced distally by the firing rod 1690 when the firing rod 1690 is advanced distally.

Further to the above, the firing trigger 1120 is actuated a first time to advance the firing rod 1690 and the firing member 1390 distally to close the end effector 1400. When the firing trigger 1120 is actuated toward a grip 1110 of the handle 1100, the firing trigger 1120 compresses a trigger spring, such as a torsion spring, for example, between the firing trigger 1120 and a frame of the handle 1100. The firing trigger 1120 is then released and the trigger spring returns the firing trigger 1120 back into its unactuated position. Notably, the firing rod 1690 and the firing member 1390 are not retracted proximally when the firing trigger 1120 is returned to its unactuated position. Instead, the firing rod 1690 and the firing member 1390 remain in their distally-advanced positions. The firing drive further comprises a retraction knob 1710 coupled to the firing rod 1690. If the clinician is unsatisfied with the positioning of the jaws 1410 and 1420 on the patient tissue, the clinician can pull the retraction knob 1710 proximally to manually retract the firing rod 1690 and the firing member 1390 proximally and open the end effector 1400. In at least one embodiment, the end effector 1400 comprises one or more springs, such as coil springs, for example, positioned between the jaws 1410 and 1420 such that the springs push the end effector 1400 open when the firing member 1390 is retracted by the firing rod 1690.

If the clinician is satisfied with the position of the jaws 1410 and 1420 on the patient tissue, further to the above, the clinician can depress a mode switch, which is discussed further below. When depressed, the mode switch electronically and/or mechanically shifts the stapling instrument 1000 from a closure mode to a staple firing mode. As a result, a second actuation of the firing trigger 1120 drives the firing rod 1690 and firing member 1390 distally through a firing stroke to eject staples from the staple cartridge 1900. In at least one embodiment, the staple firing stroke is about 15 mm, for example. In some embodiments, a 15 mm staple firing stroke is sufficient to fire all of the staples of the staple cartridge 1900 while, in other embodiments, more than one staple firing stroke is needed to fire all of the staples from the staple cartridge 1900. In such multi-stroke embodiments, the firing trigger 1120 is releasable after the second actuation and then reactuated a third time to produce a second staple firing stroke. Like the first staple firing stroke, the second staple firing stroke is also about 15 mm. In various embodiments, the firing trigger 1120 is actuatable to produce a third staple firing stoke and/or a fourth staple firing stroke, or as many firing strokes that are needed, to fire all of the staples of the staple cartridge 1900. Regardless of the number of staple firing strokes needed to fully fire the staple cartridge 1900, the clinician can pull the retraction actuator 1710 proximally after less than all of the staple firing strokes have been completed to open the end effector 1400 and remove the stapling instrument 1000 from the patient. The entire disclosure of U.S. Pat. No. 10,433,842, entitled SURGICAL HANDLE ASSEMBLY, which issued on Oct. 8, 2019, is incorporated by reference herein.

Further to the above, an entire staple firing stroke can be comprised of multiple staple firing actuations, especially in embodiments comprising a reciprocating mechanism such as those discussed below, for example. That said, in various instances, each staple firing actuation can be referred to as a staple firing stroke even though each such staple firing stroke does not fire all of the staples of a staple cartridge. In such instances, such staple firing strokes are part of an entire staple firing stroke to eject all of the staples from a staple cartridge.

Figure 3:
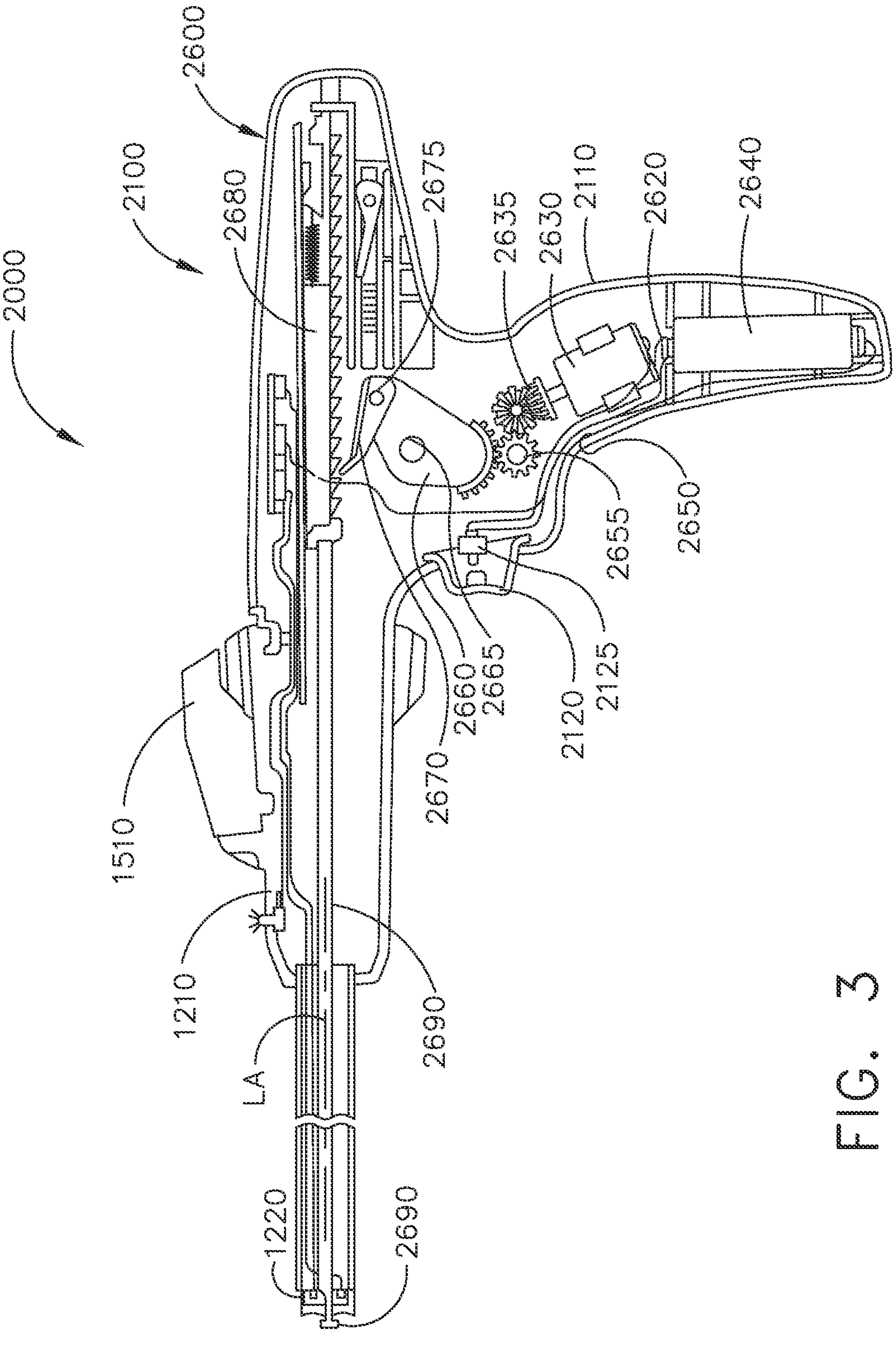
FIG. 3 is an elevational view of a surgical stapling instrument in accordance with at least one embodiment illustrated with some components removed.

A surgical stapling instrument 2000 is illustrated in FIG. 3. The stapling instrument 2000 is similar to the stapling instrument 1000 in many respects which will not be discussed herein for the sake of brevity. The stapling instrument 2000 comprises a handle 2100 and a firing drive 2600. The handle 2100 comprises a grip 2110 and a firing actuator 2120 which includes an actuatable switch 2125. The firing drive 2600 comprises an electric motor 2630 and a battery 2640 configured to supply power to the electric motor 2630 through an electronic circuit 2620 that is controlled by the firing actuator 2120. The electric motor 2630 is mounted in the handle 2100 and comprises a rotatable motor output 2635 operably engaged with a gear train 2650 of the drive system 2600. The gear train 2650 comprises a drive gear 2655 operably engaged with a drive crank 2660 of the drive system 2600 which is rotatably mounted to the handle 2100 about a pivot 2665. The drive crank 2660 comprises a gear portion comprising gear teeth meshingly engaged with the drive gear 2655 and is rotatable about the pivot 2665 by the drive gear 2655. The drive system 2600 further comprises a pawl 2670 and a firing rack 2680. The pawl 2670 is rotatably connected to the drive crank 2660 about a pin 2675 and comprises a drive tooth 2672 configured to engage a longitudinal array of ratchet teeth 2682 defined on the bottom of the firing rack 2680 and drive the firing rack 2680 distally along longitudinal axis LA during a firing stroke.

As discussed above, the electronic circuit 2620 controls the operation of the electric motor 2630 in response to inputs from the firing actuator 2120. In various embodiments, the motor 2630 comprises a direct current (DC) motor, for example, but can comprise any suitable motor. In various embodiments, the electronic circuit 2620 comprises a microprocessor comprising at least one input gate in communication with the firing actuator switch 2125 and at least one output gate in communication with a relay configured to control the supply of power from the battery 2640 to the electric motor 2630. Although not illustrated in FIG. 3, the electronic circuit 2620 comprises electrical conductors, wires, and/or flex circuits, for example, which connect the components of the electronic circuit such as the motor 2630 and the battery 2640, for example. In certain embodiments, the electronic circuit 2620 does not comprise a microprocessor and, instead, relies on switch logic to control the operation of the electric motor 2630. Such embodiments may be advantageous when the stapling instrument 2000 is exposed to a harsh sterilization process, for example. Thus, while the discussion provided below is presented using an embodiment including a microprocessor, the reader should appreciate that an equivalent analog circuit could be used to perform the same functions and operations discussed herein.

Figure 4:
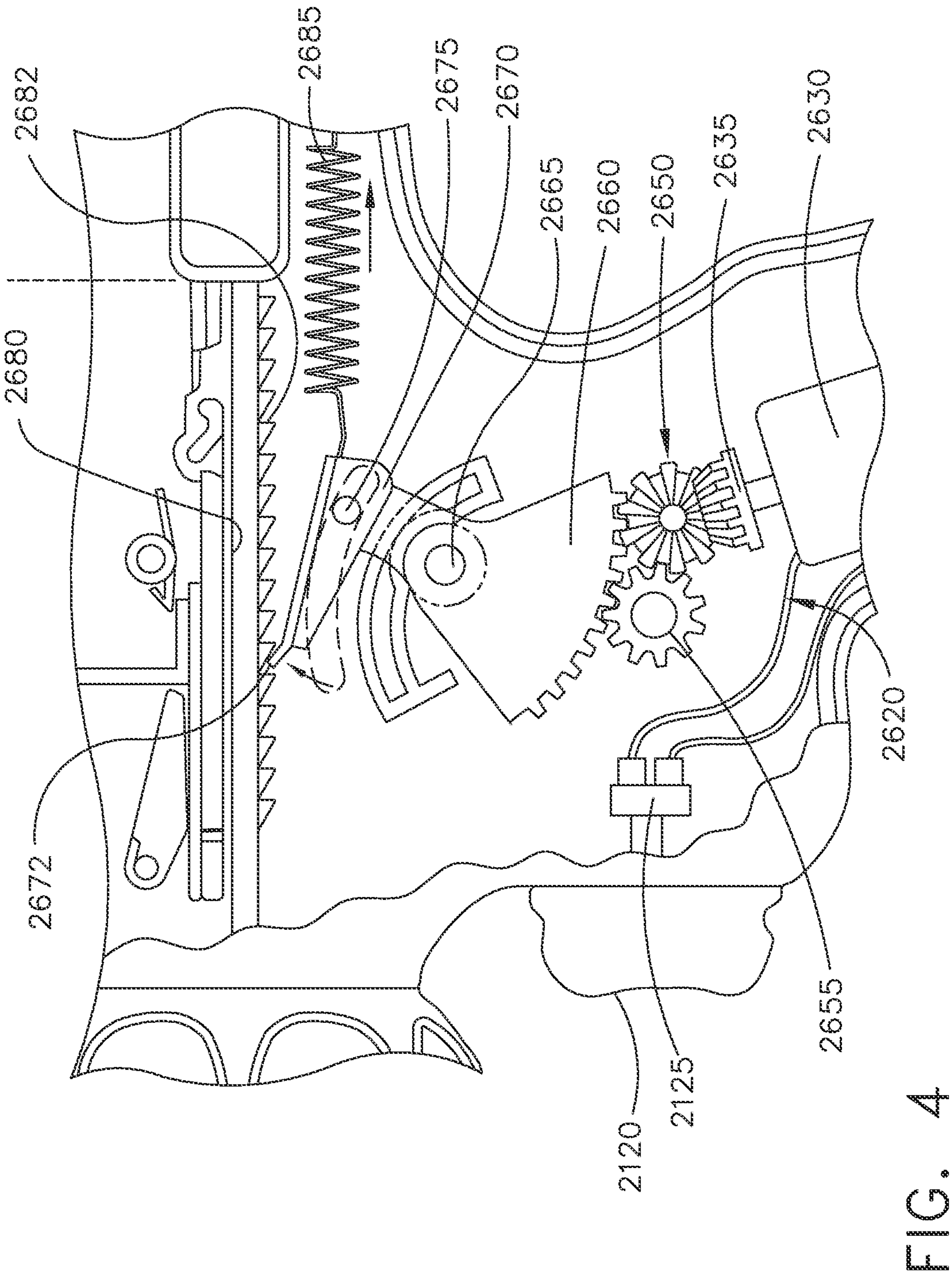
FIG. 4 is a detail view of a staple firing system of the surgical stapling instrument of FIG. 3.
Figure 5:
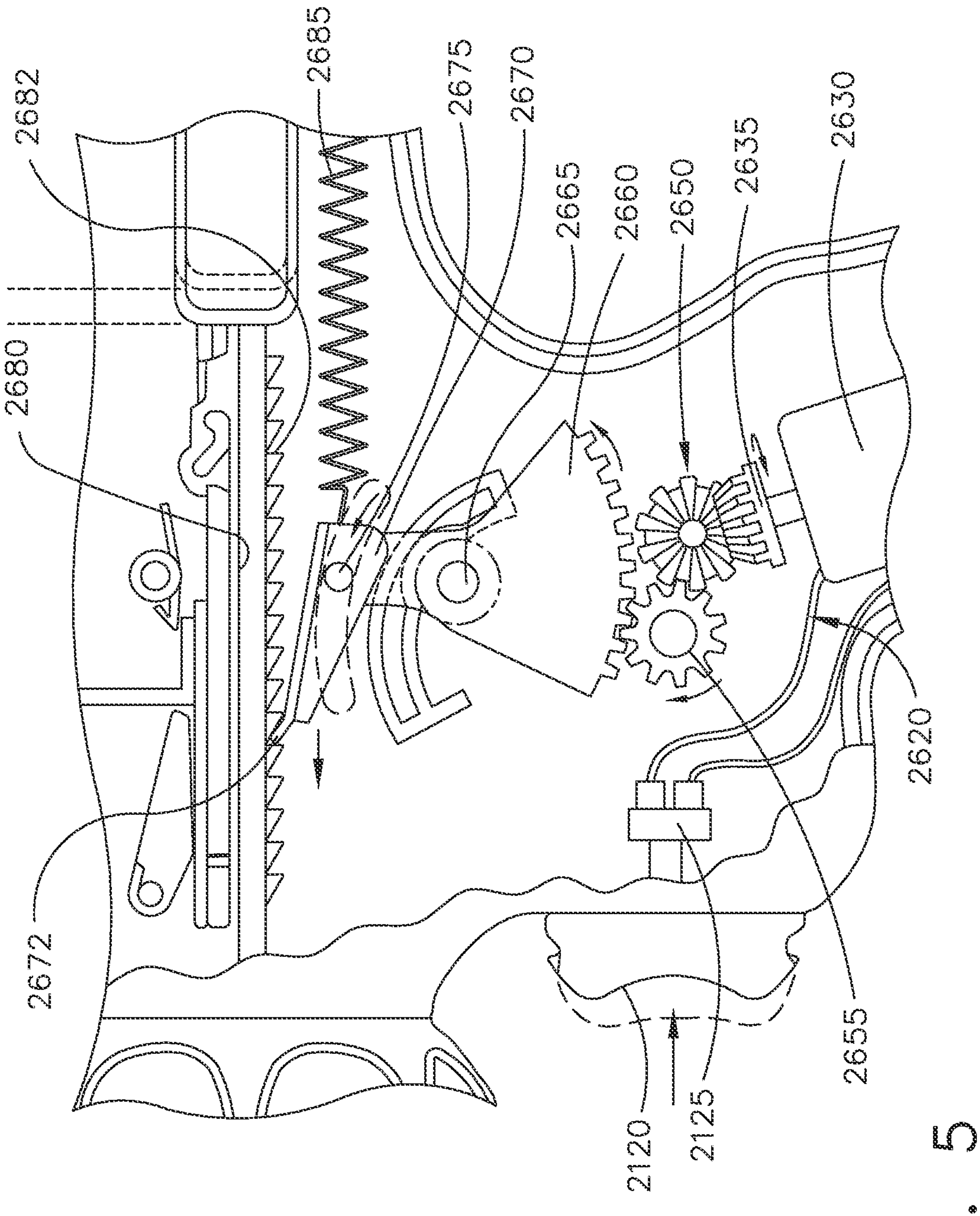
FIG. 5 is a detail view of the staple firing system of FIG. 4 illustrating a first actuation of the staple firing system.

In use, referring to FIG. 4, the firing actuator 2120 is actuated a first time to close the end effector 1400 of the stapling instrument 2000. The actuation of the firing actuator 2120 closes the switch 2125 which is detected by the microprocessor. In response, the microprocessor applies a voltage potential to the electric motor 2630 from the battery 2640 to rotate the motor output 2635 in a first direction and drive the pawl 2670 distally. The firing drive comprises a pawl spring 2685 mounted to the pawl 2670 and the frame of the handle 2100 which applies a biasing force to the pawl 2670 to bias the drive tooth 2672 into engagement with the ratchet teeth 2682 defined on the firing rack 2680. When the pawl 2670 is advanced distally in response to the first actuation of the firing actuator 2120, referring to FIG. 5, the pawl 2670 drives the firing rack 2680 distally which, in turn, drives the firing rod 1690 and the firing member 1390 distally to close the end effector 1400. Stated another way, the pawl 2670, the firing rack 2680, the firing rod 1690, and the firing member 1390 are all advanced distally a closure stroke in response to the first actuation of the firing actuator 2120.

Figure 6:
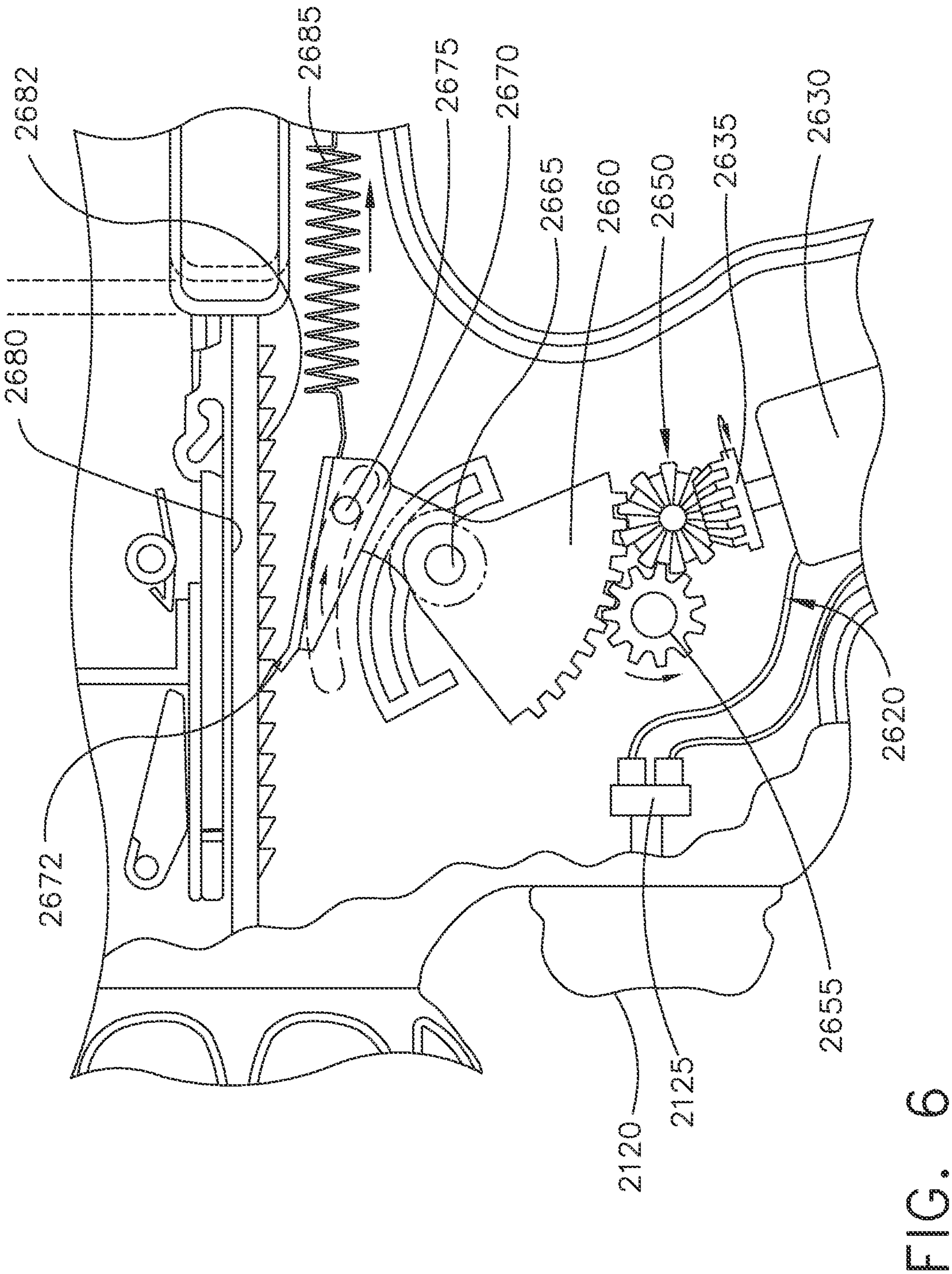
FIG. 6 is a detail view of the staple firing system of FIG. 4 illustrating a pawl of the staple firing system being retracted after the first actuation.

After the microprocessor determines that the closure stroke is complete, further to the above, the microprocessor stops the motor 2630 by disconnecting the voltage potential from the battery 2640. At such point, referring to FIG. 6, the pawl spring 2685, which was resiliently stretched when the pawl 2670 was advanced distally through the closure stroke, resiliently contracts and pulls the pawl 2670 proximally back into its unactuated position. Notably, the ratchet teeth 2682 defined on the firing rack 2680 are shaped to permit the drive tooth 2672 of the pawl 2670 to slide proximally relative to the ratchet teeth 2682 when the pawl 2670 is retracted. In such instances, the pawl spring 2685 can backdrive the electric motor 2630. In various alternative embodiments, the microprocessor can reverse the polarity of the voltage potential being applied to the motor 2630 to operate the motor output 2635 in an opposite direction to drive the pawl 2670 proximally. Such embodiments can be useful to overcome the inertia of the gear train 2650. Also, in such embodiments, the firing drive can include a beginning-of-stroke sensor in communication with the microprocessor which is closed when the pawl 2670 is retracted back into its unactuated position. When the beginning-of-stroke sensor is closed, the microprocessor disconnects the voltage polarity from the motor 2630.

As discussed above, the microprocessor is configured to determine when the closure stroke is complete. In various embodiments, the firing drive further comprises an encoder in communication with the microprocessor which is configured to monitor and count the rotations of the motor output 2635. In at least one such embodiment, a magnetic element is positioned on and/or within the motor output 2635 and the encoder is configured to detect the disturbances in a magnetic field created by the encoder when the motor output 2635 is rotated. Once the rotation count reaches a predetermined count threshold, the microprocessor disconnects and/or reverses the polarity being applied to the motor 2630. In various embodiments, the firing drive comprises an end-of-stroke sensor in communication with the microprocessor that is closed by the pawl 2670 when the pawl 2670 reaches the end of its stroke. The microprocessor is configured to sense the closure of the end-of-stroke sensor and, in response, disconnect and/or reverse the polarity being applied to the motor 2630.

Figure 7:
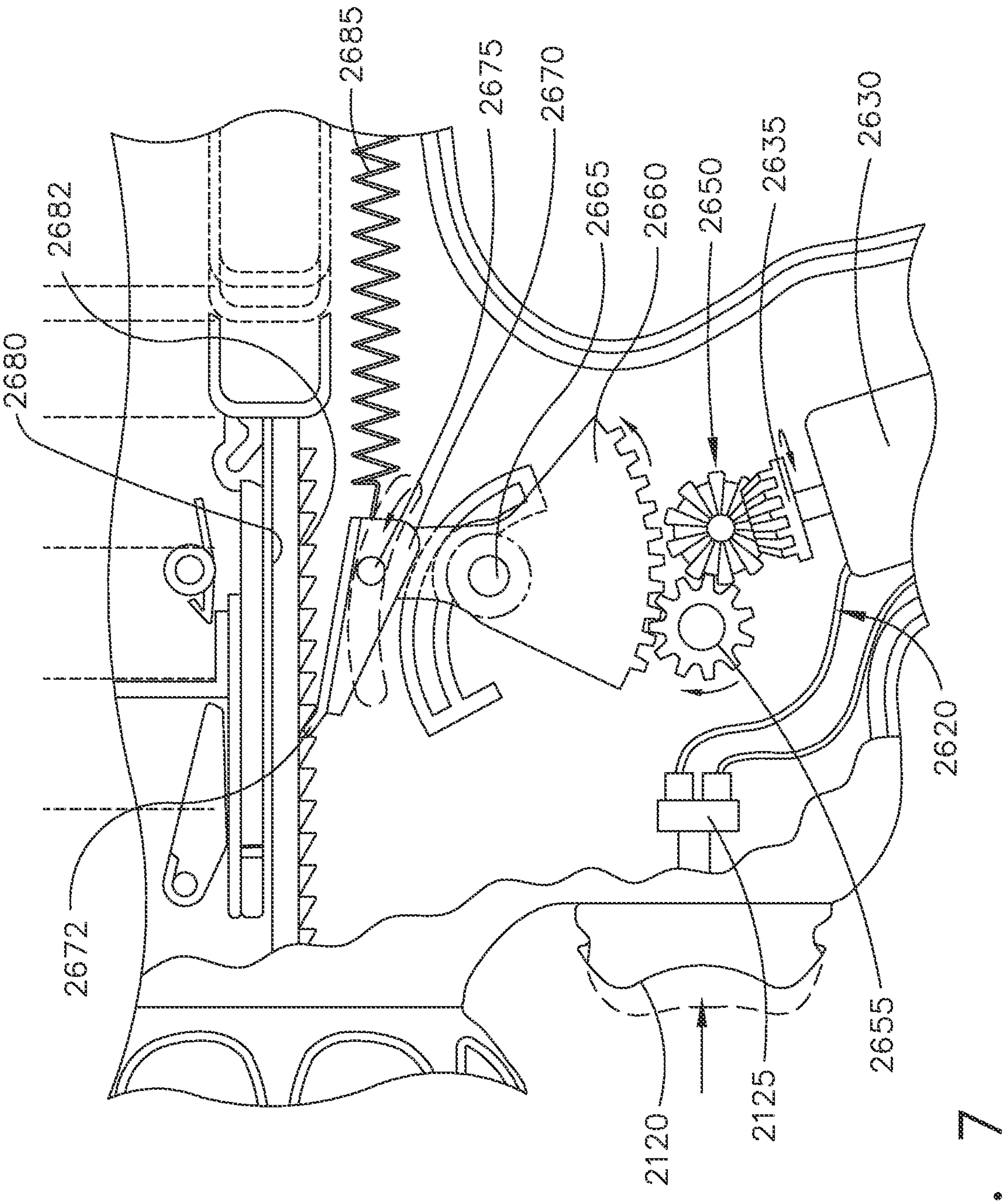
FIG. 7 is a detail view of the staple firing system of FIG. 4 illustrating a second actuation of the staple firing system.

After the pawl 2670 has been reset after the closure stroke, the clinician may decide to re-open the end effector 1400 by pulling the retraction knob 1710 proximally or initiate the staple firing stroke. To initiate the staple firing stroke, the clinician must first depress a mode switch in communication with the microprocessor, which is discussed further below. If the mode switch is not depressed, the microprocessor and motor 2630 are not responsive to a subsequent actuation of the firing actuator 2120. After the mode switch is depressed, referring to FIG. 7, the microprocessor and motor 2630 are responsive to a subsequent actuation of the firing actuator 2120. In such instances, the motor output 2635 is rotated in the first direction once again to drive the pawl 2670 distally through a second actuation stroke. In this actuation stroke, the pawl 2670 drives the firing member 1390 partially through the staple cartridge 1900 to eject staples therefrom. Once the pawl 2670 reaches the end of the second actuation stroke, the pawl 2670 closes the end-of-stroke switch and the microprocessor reverses the polarity of the voltage being applied to the electric motor 2630 such that the direction of the motor output 2635 is reversed and the pawl 2670 is retracted. This process is repeated automatically until either the microprocessor determines that the maximum number of staple firing strokes has been performed or the clinician releases the firing actuator 2120. In various instances, each staple firing stroke is about 15 mm, for example, and in embodiments configured to deploy a 60 mm staple pattern, for example, the maximum number of staple firing strokes is four. In such instances, the pawl 2670 would be reciprocated once for the closure stroke and then four times to deploy the staples.

If the clinician releases the firing actuator 2120 prior to the maximum number of staple firing strokes being reached, further to the above, the microprocessor disconnects the voltage polarity from the electric motor 2630. In various embodiments, the inertia of the gear train 2650 holds the pawl 2670 in position and the firing drive is held in a paused condition. In certain embodiments, in such instances, the microprocessor can apply a voltage potential to the electric motor 2630 that is sufficient to temporarily hold the pawl 2670 in position. If the clinician no longer wishes to continue deploying the staples, the clinician can pull the retraction knob 1710 proximally to retract the firing rack 2680 proximally. To reset the stapling firing rive in such instances, the clinician can depress the mode switch once again which causes the microprocessor to return the pawl 2670 back into its unactuated position. If the clinician wishes to continue deploying the staples, on the other hand, the clinician can re-depress the firing actuator 2120 to re-start the motor 2630.

Figure 9:
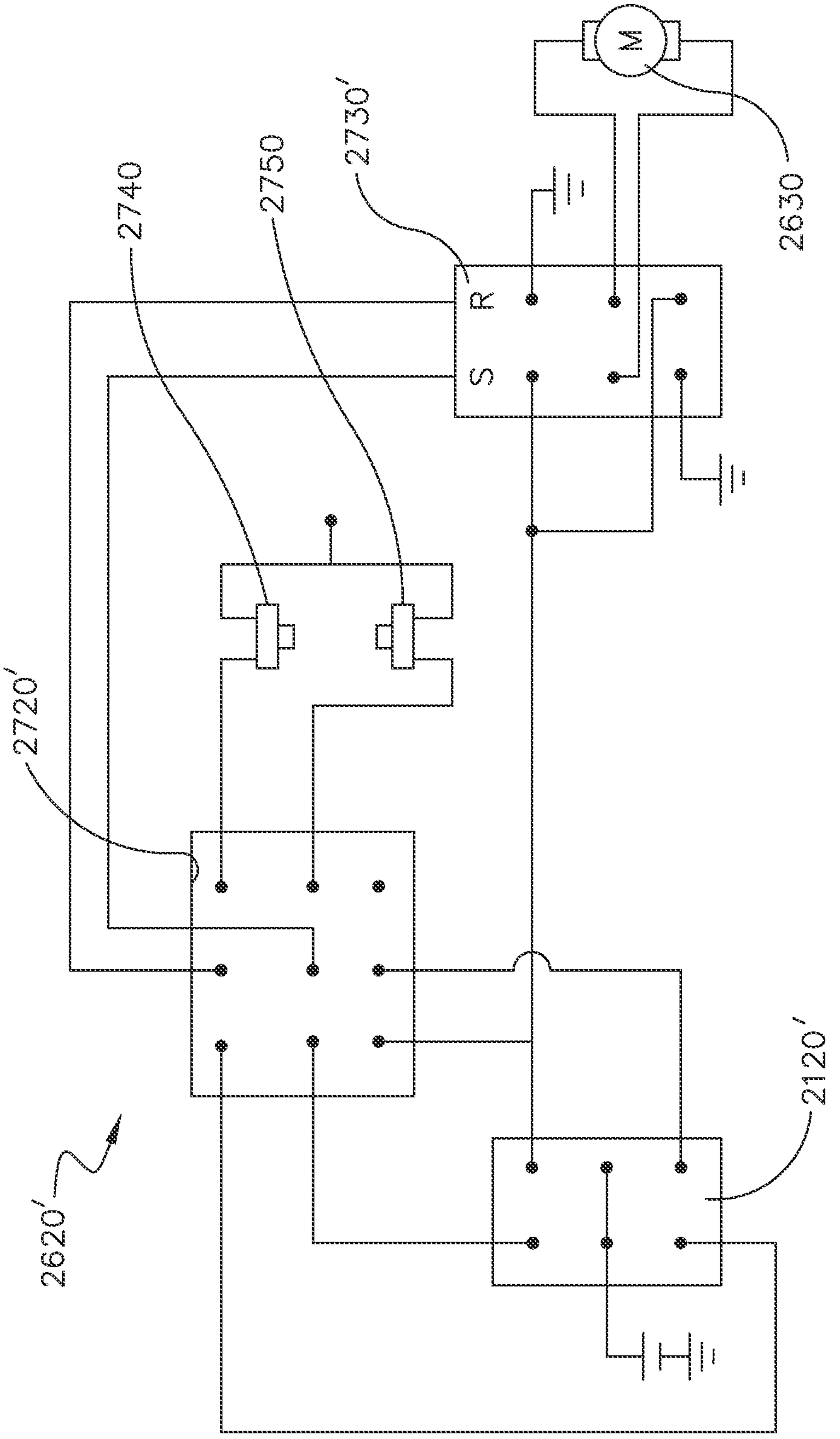
FIG. 9 is a schematic of a control circuit in accordance with at least one embodiment.

As discussed above, the stapling instrument 2000 can comprise an analog control circuit for controlling the above-described series of operations. Referring to FIG. 9, the stapling instrument 2000 can comprise a control circuit 2620' configured to control the operation of the motor 2630. The control circuit 2620' comprises a firing actuator 2120', a mode switch 2720', and a relay 2730'. The firing actuator 2120' comprises a mom-off-mom switch, for example, in communication with the mode switch 2720' and the relay 2730'. The relay 2730' comprises a set/re-set function capable of reversing the voltage polarity applied to the motor 2630. The control circuit 2620' further comprises an end-of-stroke switch 2740 and a beginning-of-stroke switch 2750. In various instances, the operation of the motor 2630 is changed or interrupted if one or both of the switches 2740 and 2750 is opened, for example. In at least one such embodiment, the end-of-stroke switch 2740 is opened by the firing rack 2680 when the firing rack 2680 has been advanced through the maximum number of staple firing actuations. Similarly, in at least one such embodiment, the beginning-of-stroke switch 2750 is opened by the firing rack 2680 when the firing rack 2680 has been returned to its proximal unactuated position.

Figure 8:
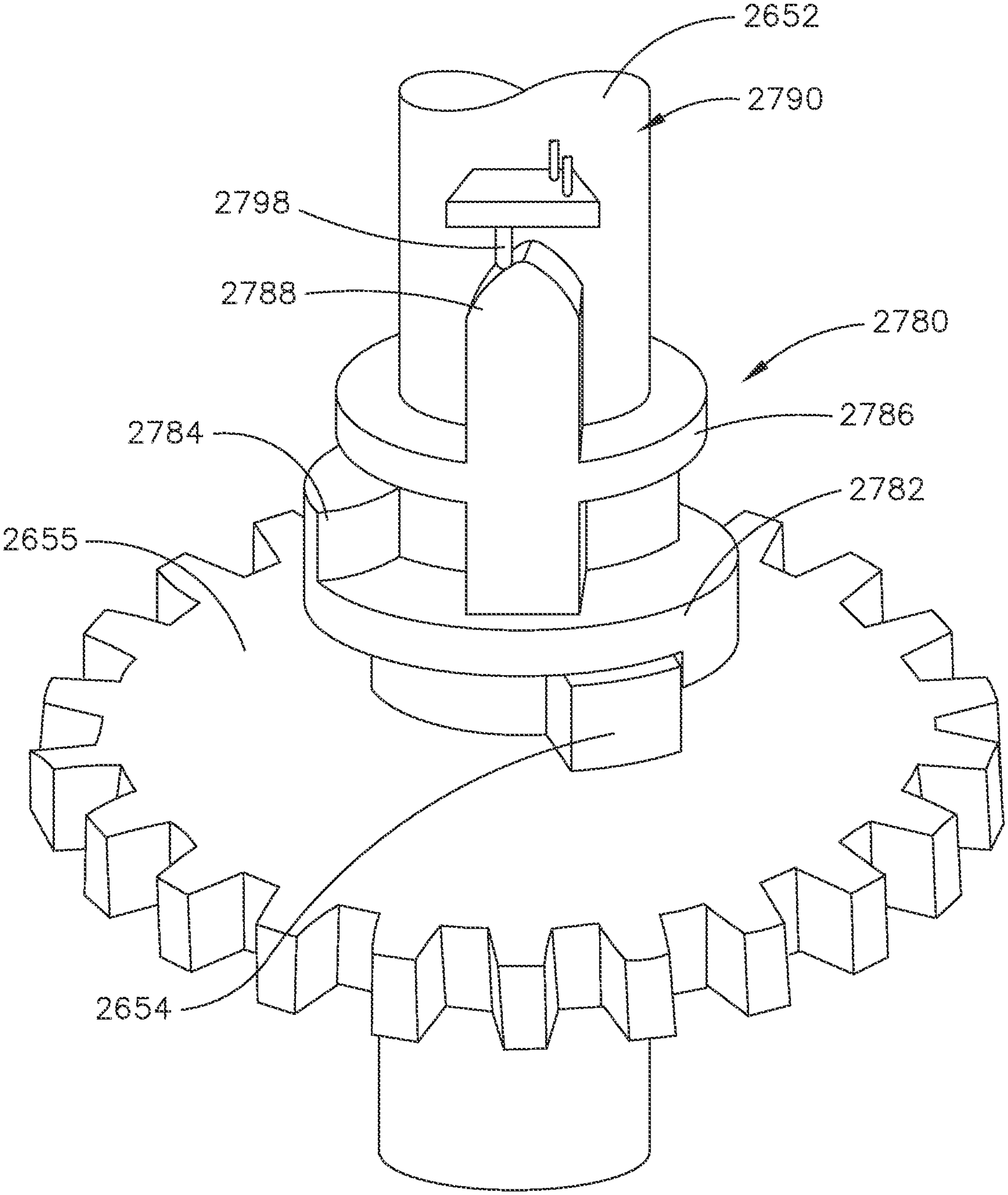
FIG. 8 is a perspective view of an end-of-stroke sensor in accordance with at least one embodiment.

Further to the above, referring to FIG. 8, the surgical instrument 2000 can comprise an end-of-stroke switch 2790 that is closed by the drive gear 2655 at the end of an actuation stroke of the pawl 2670. The drive gear 2655 is fixedly mounted to a gear shaft 2652 and the drive gear 2655 is rotatably mounted in the handle 2100 about the gear shaft 2652. The gear shaft 2652 comprises a switch key 2654 extending therefrom which, during an initial portion of the drive gear 2655 rotation, is not in contact with a ring stack 2780 including a first switch ring 2782 and a second switch ring 2786 which are rotatably supported by the gear shaft 2652 and do not rotate with the gear shaft 2652 during the initial rotation of the drive gear 2655. As the drive gear 2655 is rotated, however, the switch key 2654 contacts the first switch ring 2782 and, as a result, the first switch ring 2782 and the gear shaft 2652 begin to rotate together. Notably, though, the second switch ring 2786 does not immediately rotate with the first switch ring 2782 and the gear shaft 2652; rather, the first switch ring 2782 and the gear shaft 2652 rotate relative to the second switch ring 2786 until a drive shoulder 2784 of the first switch ring 2782 contacts the second switch ring 2786. At such point, the gear shaft 2652, the first switch ring 2782, and the second switch ring 2786 rotate together until a switch key 2788 of the second switch ring 2786 contacts a switch element 2798 of the end-of-stroke switch 2790 and closes the end-of-stroke switch 2790. The pawl 2670 reaching the end of its actuation stroke coincides with the closure of the end-of-stroke switch 2790 and the closure of the end-of-stroke switch 2790 reverses the motor 2630 to retract the pawl 2670.

Referring again to FIG. 3, the motor 2630 of the stapling instrument 2000 is positioned in the grip 2110 of the handle 2100. In various other embodiments, the motor 2630 is positioned proximally relative to the grip 2110 within the handle 2100. In at least one such embodiment, the motor 2630 can drive a jack screw arrangement to move the firing rack 2680.

Figure 12:
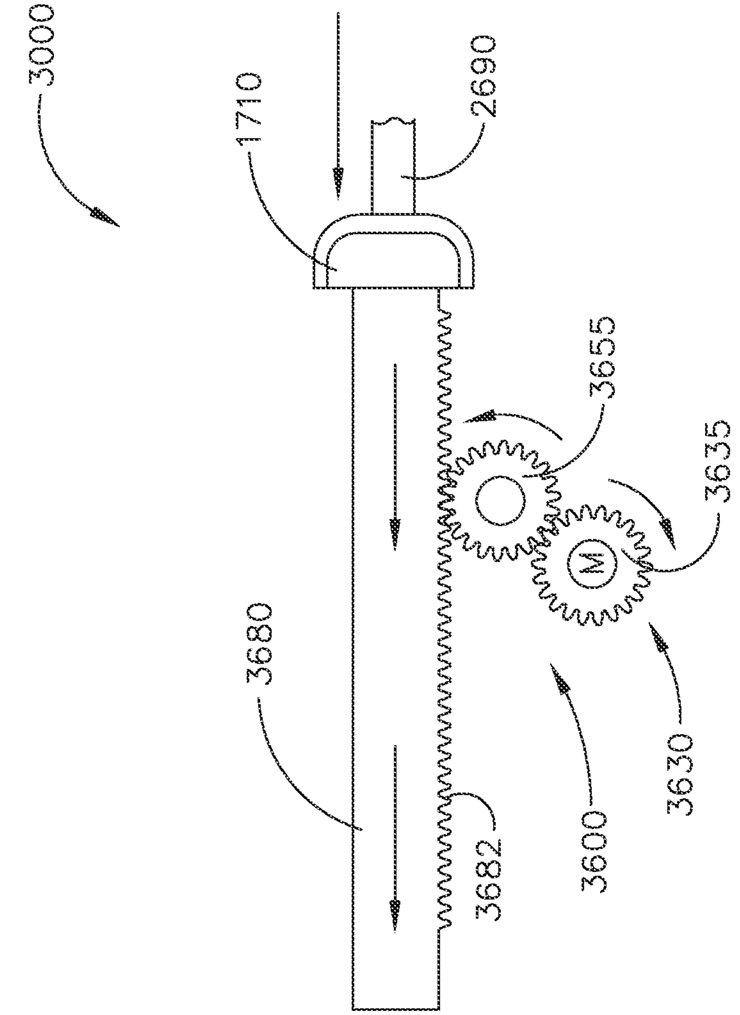
FIG. 12 illustrates a motor-driven firing drive in accordance with at least one embodiment.

A stapling instrument 3000 is illustrated in FIG. 12. The stapling instrument 3000 comprises a motor-driven firing system that does not use a pawl. Instead, the firing drive 3600 of the stapling instrument 3000 comprises an electric motor 3630 including a gear output 3635, a drive gear 3655 operably intermeshed with the gear output 3635, and a firing rack 3680 including a longitudinal array of gear teeth 3682 intermeshed with the drive gear 3655. In use, a first voltage polarity is applied to the motor 3630 to rotate the gear output 3635 in a first direction and a second, or opposite, voltage polarity is applied to the motor 3630 to rotate the gear output 3635 in a second, or opposite, direction. The firing rack 3680 and the firing rod 2690 are driven distally when the motor 3630 is operated in the first direction and retracted proximally when the motor 3630 is operated in the second direction.

Further to the above, the stapling instrument 3000 comprises a control circuit including a firing actuator 2120 comprising a firing actuation switch 2125 that, when actuated, closes a sub-circuit that applies the first voltage polarity to the motor 3630 to advance the firing rack 3670 through a closure stroke to close the end effector 1400. The stapling instrument 3000 further comprises an end-of-closure-stroke switch that is opened when the firing rack 3680 reaches the end of the closure stroke to stop the electric motor 3630. The stapling instrument 3000 also comprises a second, or reverse, actuation switch that, when actuated, closes a sub-circuit that applies the second voltage polarity to the motor 3630 to retract the firing rack 3680 and the firing rod 2690 and open the end effector 1400. Once the end effector 1400 is closed and the clinician is satisfied with the position of the end effector 1400 on the patient tissue, the clinician can depress a mode switch of the control circuit that, when depressed, re-closes the end-of-closure-stroke switch such that the motor 3630 is responsive to the firing actuator switch 2125 once again. When the firing actuator 2120 is re-actuated by the clinician, at such point, the motor 3630 is operated in the first direction once again to advance the firing rack 3680 and the firing rod 2690 distally to perform the staple firing stroke. The stapling instrument 3000 further comprises an end-of-firing-stroke switch that is opened when the firing rack 3680 reaches the end of the staple firing stroke to stop the electric motor 3630. To retract the firing rack 3680 and the firing rod 2690 back into their unfired position, the clinician can depress the reverse actuation switch to apply the opposite voltage polarity to the electric motor 3630.

Figure 12B:
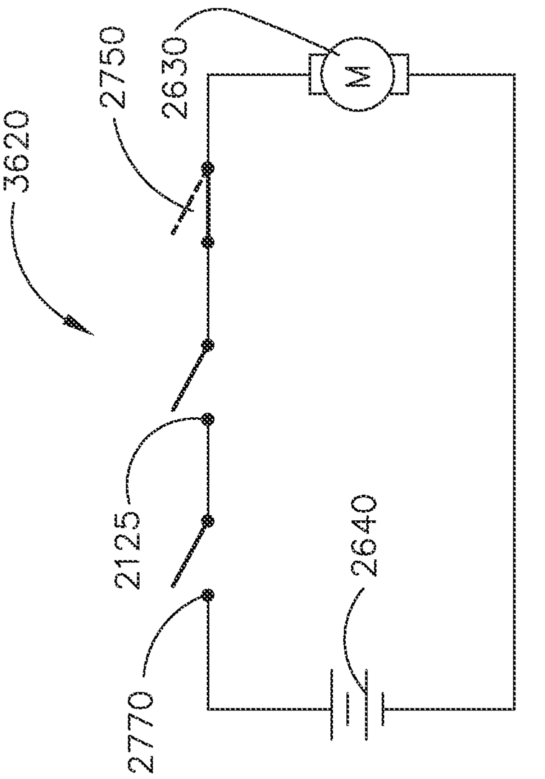
FIG. 12B illustrates the control circuit of FIG. 12A in a different switch state.
Figure 12A:
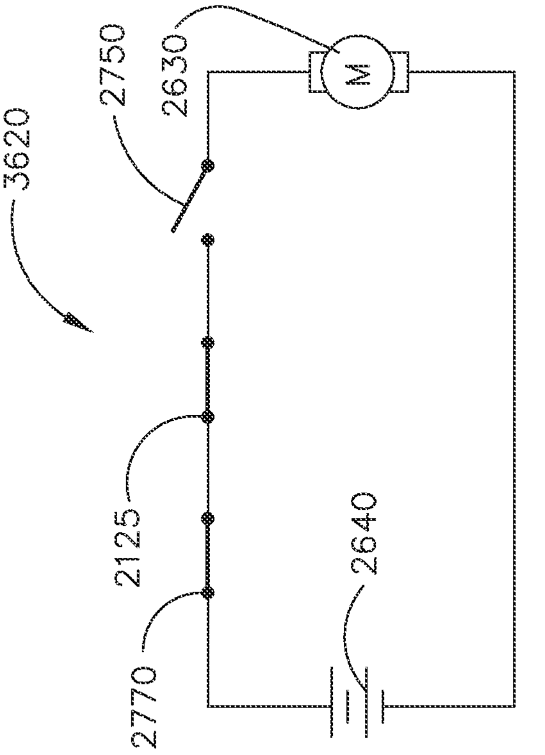
FIG. 12A is a schematic of a control circuit in accordance with at least one embodiment.

As discussed above, the motor 3630 is responsive to the actuation switch 2125 of the firing actuator 2120 being closed. FIG. 12A depicts a staple firing circuit 3620 including the actuation switch 2125 and the motor 3630 with the actuation switch 2125 being in a closed, or actuated, condition. The control circuit 3620 further comprises a clamp, or end-of-closure-stroke, switch 2770 and an end-of-firing-stroke switch 2750. When the end effector 1400 is in an open, or unclamped, configuration, as illustrated in FIG. 12B, the clamp switch 2770 is in an open condition thereby decoupling the battery 2640 from the electric motor 3630 and preventing the staple firing stroke from being performed even if the actuation switch 2125 is closed, or actuated, by the clinician. When the end effector 1400 is in a closed, or clamped, configuration, the clamp switch 2770 is closed. The end-of-firing-stroke switch 2750 is in a normally-closed condition and is opened by the firing drive at the end of the staple firing stroke, as discussed above, which opens the firing circuit to stop the electric motor 3630.

In various alternative embodiments, the motor 3630 is operated in a first direction in response to the firing actuator 2120 being actuated to perform the staple firing stroke. The motor 3630 continues to turn so long as the firing actuator 2120 is depressed and the firing rack 3680 is driven distally until the teeth 3682 of the firing rack 3680 run off the drive gear 3655. At such point, the staple firing stroke is complete and the firing rack 3680 is no longer advanced distally by the motor 3630 even though the firing actuator 2120 is depressed. To reset the staple firing system, the firing actuator 2120 is released and the retraction handle 1710 is pulled proximally to retract the firing rack 3680 and the firing rod 2690 back into their unfired positions. In such instances, pulling the firing rack 3680 proximally will, absent other considerations, backdrive the motor 3630. In at least one embodiment, the drive gear 3655 can be biased out of engagement with the firing rack 3680 as the firing rack 3680 is retracted proximally and then re-engaged with the firing rack 3680 after the firing rack 3680 has been returned to its proximal unfired position. In at least one embodiment, the handle of the surgical instrument comprises an actuator, such as a toggle switch, for example, that is actuated to disengage the drive gear 3655 from the firing rack 3680 before the retraction stroke of the firing rack 3680 and then switched back after the retraction stroke of the firing rack 3680 is completed.

In various embodiments, a surgical stapling instrument comprises an actuator including an actuator switch and an electric motor 3630 operated by the actuator which drives the firing rack 3680 distally from a proximal unfired position when the actuator switch is closed. The stapling instrument further comprises an end-of-stroke switch which, when opened by the firing rack 3680 at the end of the staple firing stroke, automatically reverses the operation of the electric motor 3630 to retract the firing rack 3680 proximally. The stapling instrument further comprises a beginning-of-stroke switch which is opened by the firing rack 3680 when the firing rack 3680 is returned to its proximal unfired position to stop the electric motor 3630. In various alternative embodiments, the switch logic of such a stapling instrument can comprise one or more normally-open switches instead of a normally-closed switch. In any event, the staple firing stroke is stopped when the actuator is released by the clinician. If the clinician desires to return the firing rack 3680 back into its proximal unfired position without finishing the staple firing stroke, the clinician can retract the firing rack 3680 proximally by the retraction handle 1710.

Figure 10:
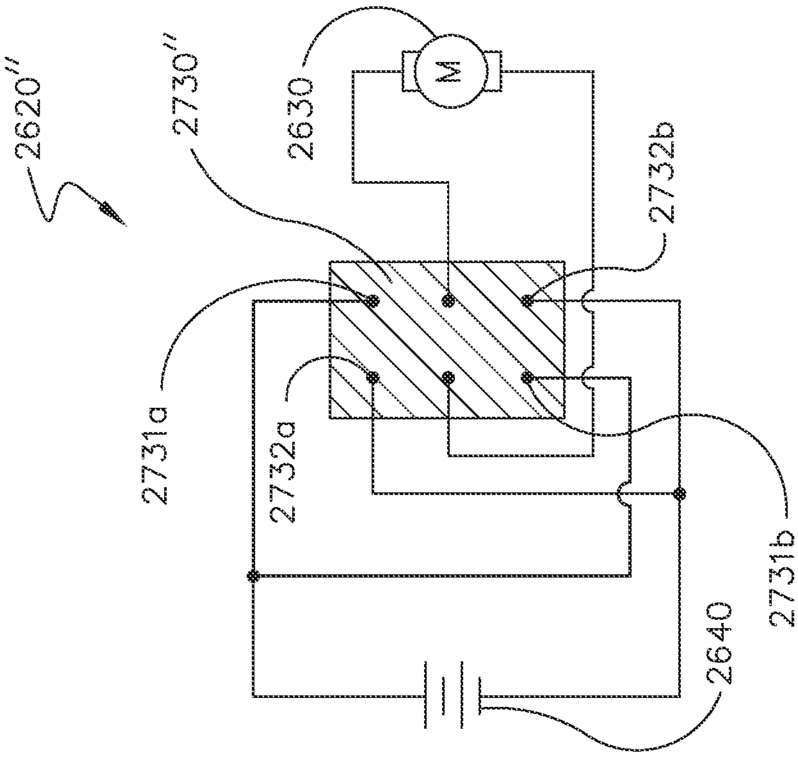
FIG. 10 is a schematic of a control circuit in accordance with at least one embodiment.

In various embodiments, referring to FIG. 10, a stapling instrument can comprise a control circuit 2620". The control circuit 2620" comprises a double pole, double throw momentary switch 2730" configured to control the operation of the motor 2630. The momentary switch 2730" comprises a mom-off-mom switch that is switchable from an off state to a first on-state and a second-on state, but any suitable switch could be used. In the first on-state of the momentary switch 2730", a first voltage polarity is applied to the motor 2630 from the battery 2640 which advances the firing rack 2680 distally. In the second on-state of the momentary switch 2730", a second, or opposite, voltage polarity is applied to the motor 2630 from the battery 2640 which retracts the firing rack 2680 proximally.

Figure 11:
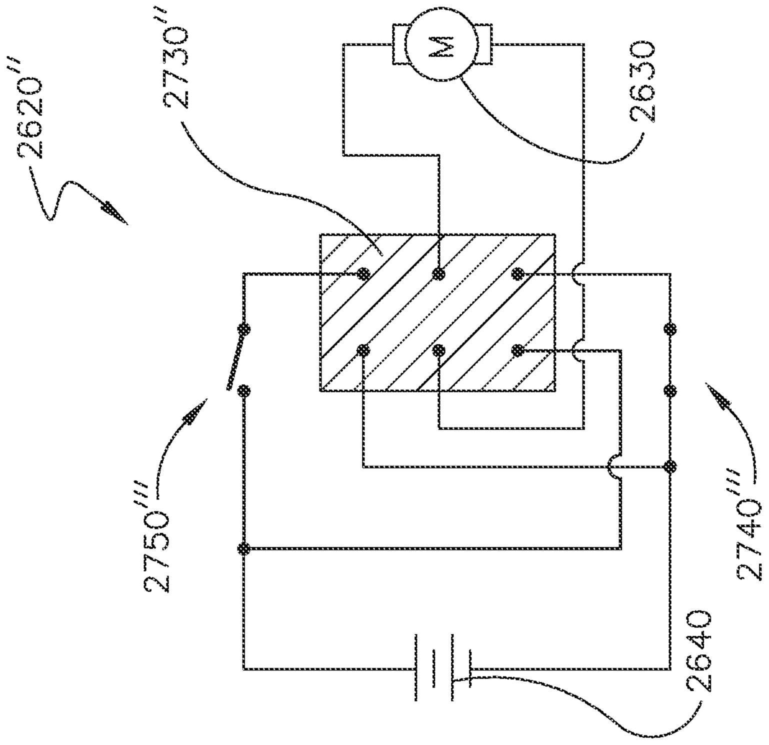
FIG. 11 is a schematic of a control circuit in accordance with at least one embodiment.

A control circuit 2620'", which is similar to the control circuit 2620" in many respects, is illustrated in FIG. 11. In addition to the above, the control circuit 2620'" further comprises a normally-closed end-of-firing-stroke switch 2750'" which is opened by the firing rack 2680 when the firing rack 2680 reaches the end of the staple firing stroke. In such instances, further to the above, the power supplied to the motor 2630 from the battery 2640 is disconnected at the end of the staple firing stroke. At such point, the motor 2630 is no longer responsive to the first on-state of the momentary switch 2730". That said, the motor 2630 is responsive to the second on-state of the momentary switch 2730". In order to retract the firing rack 2680 back into its unactuated position, the clinician must close the second on-state of the momentary switch 2730" to operate the motor 2630 in reverse. Notably, the control circuit 2620'" further comprises a normally-closed switch 2740'" that is opened when the firing rack 2680 has been fully retracted. When the switch 2740'" is opened by the firing rack 2680, the circuit connecting the motor 2630 to the battery 2640 is opened and the motor 2630 is no longer responsive to the second on-state of the momentary switch 2730".

In various instances, further to the above, the switch 2750'" is resettable so that the stapling instrument can be used to perform a second staple firing stroke after the spent staple cartridge in the end effector 1400 has been replaced with an unspent staple cartridge. In at least one embodiment, the switch 2750'" is manually reset. In at least one embodiment, the switch 2750'" comprises a biasing element, or feature, configured to automatically reset the switch 2750'" when the firing rack 2680 is retracted. In embodiments including a microprocessor, the switch 2750'" can be electronically reset. In at least one embodiment, seating an unspent staple cartridge in the end effector 1400 can be sensed by the microprocessor which then resets the switch 2750"". Similarly, the switch 2740'" is resettable so that the firing rack 2680 can be retracted by the motor 2630 after the second staple firing stroke. In at least one embodiment, the switch 2740'" is manually reset. In at least one embodiment, the switch 2740'" comprises a biasing element, or feature, configured to automatically reset the switch 2740'" when the firing rack 2680 is advanced distally to perform the second staple firing stroke. In embodiments including a microprocessor, the switch 2740'" can be electronically reset. In at least one embodiment, seating an unspent staple cartridge in the end effector 1400 can be sensed by the microprocessor which then resets the switch 2740"".

Figure 13A:
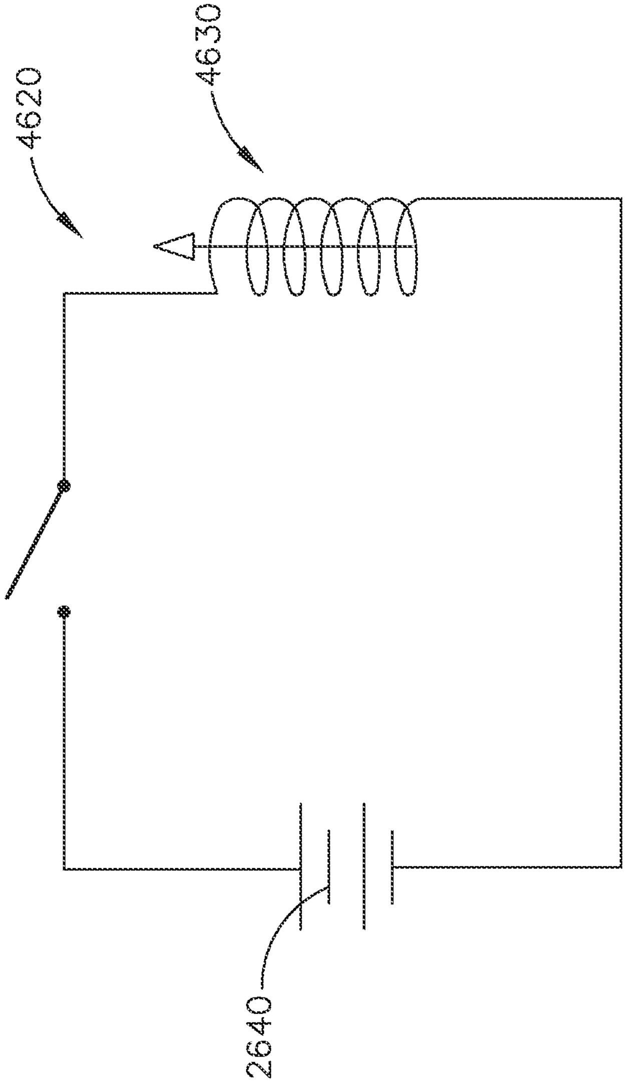
FIG. 13A is a control circuit of the firing drive of FIG. 13.
Figure 13:
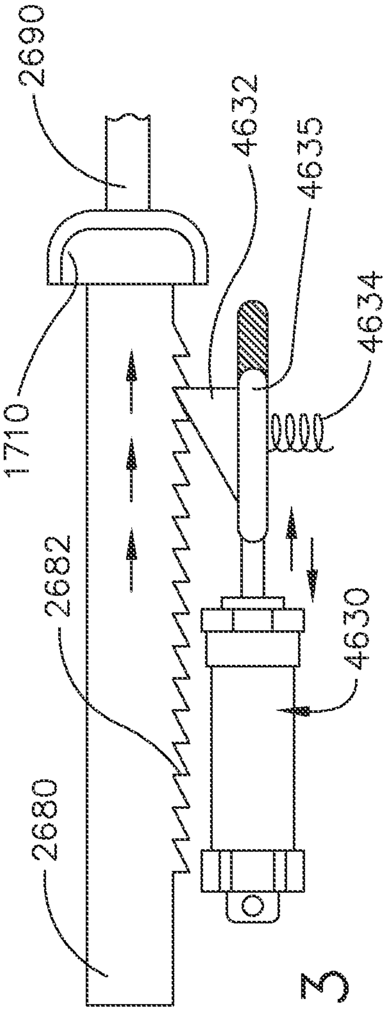
FIG. 13 illustrates a solenoid-driven firing drive in accordance with at least one embodiment.
Figure 14:
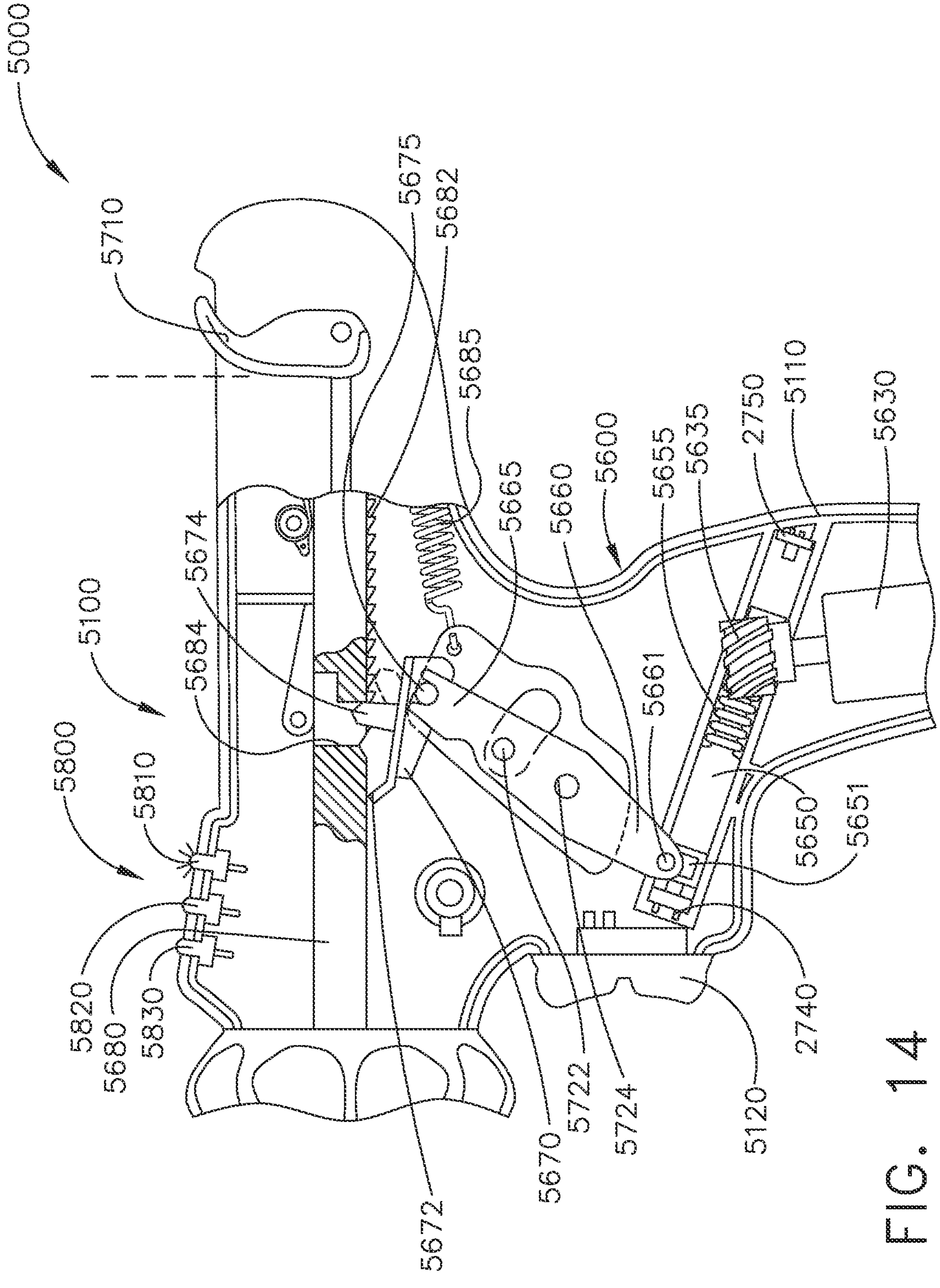
FIG. 14 is an elevational view of a surgical stapling instrument in accordance with at least one embodiment illustrated with some components removed.

A firing drive including a ratcheting solenoid mechanism is illustrated in FIGS. 13 and 13A. The firing drive comprises a solenoid 4630 including a linear actuator 4635 which is moved proximally and distally by the solenoid 4630, depending on the voltage polarity applied to the solenoid 4630. When a first voltage polarity is applied to the solenoid, the linear actuator 4635 is advanced distally. Notably, the linear actuator 4635 comprises a slot and a pawl element 4632 movably seated within the slot which is biased into engagement with the firing rack 2680 by a biasing element, such as a spring 4634, for example, contained in the linear actuator 4635. When the linear actuator 4635 is advanced distally, the pawl element 4632 is engaged with the pawl teeth 2682 defined in the bottom of the firing rack 2680 which drives the firing rack 2680 distally. At the end of the actuation stroke of the solenoid 4630, a second, or opposite, voltage polarity is applied to the solenoid 4630 to retract the linear actuator 4635 proximally. In such instances, the pawl element 4632 can slide relative to the pawl teeth 2682 defined in the firing rack 2680. Once the linear actuator 4635 has been retracted, the first voltage polarity can be applied to the solenoid once again to perform another actuation stroke. This process can be repeated until the closing stroke and/or staple firing stroke has been completed. In various instances, further to the above, the first actuation stroke of the linear actuator 4635 closes the end effector 1400 and the second actuation stroke, and any subsequent actuation strokes, fire the staples from the staple cartridge, for example.

In various embodiments, a surgical stapling instrument can comprise an electric motor including a rotatable output, a drive gear operably engaged with the rotatable output, and a pawl pivotably mounted to the drive gear. The pawl is engaged with a longitudinal rack of ratchet teeth defined on a firing rack and is configured to drive the firing rack distally when the drive gear is rotated in a first direction and slide relative to the firing rack when the drive gear is rotated in an opposite direction. To advance the firing rack through a staple firing stroke, the voltage polarity applied to the electric motor is repeatedly flipped between a positive polarity and a negative polarity to drive the gear back and forth within a drive range that is less than a full rotation of the drive gear.

Figure 15:
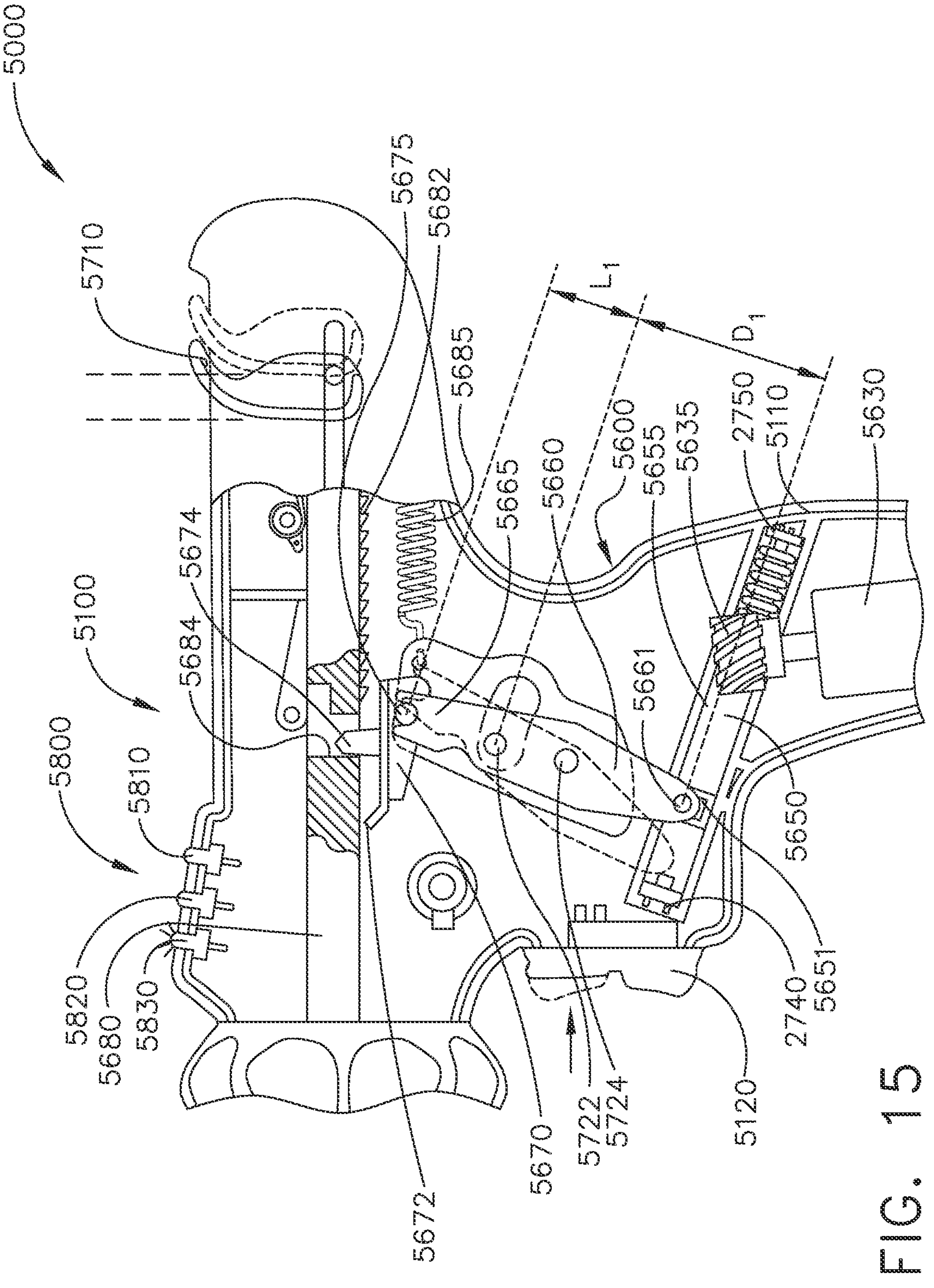
FIG. 15 is an elevational view of the stapling instrument of FIG. 14 illustrating a firing drive in a closed configuration.

A surgical stapling instrument 5000 including a handle 5100 and a firing drive 5600 is illustrated in FIGS. 14-18. The stapling instrument 5000 is similar to the stapling instruments 1000 and 2000 and other stapling instrument disclosed herein in many respects, most of which will not be discussed herein for the sake of brevity. The firing dive 5600 comprises an electric motor 5630 including a helical gear output 5635 meshingly engaged with a rack of teeth 5655 defined on a slideable rack 5650. When a first polarity is applied to the motor 5630 owing to the actuation of a firing actuator 5120, the motor 5630 is rotated in a first direction which drives the rack 5650 from an unactuated position (FIG. 14) to an actuated position (FIG. 15). Similar to the above, the stapling instrument 5000 comprises an end-of-actuation sensor 2750 which changes state in response to the rack 5650 reaching its fully-actuated position to stop the motor 5630. The firing drive 5600 further comprises a drive crank 5660 pivotably mounted to the handle 5100 about one of a first pivot 5722 and a second pivot 5724, as discussed further below. The drive crank 5660 is coupled to the rack 5650 at a connection which allows the rack 5650 to drive the drive crank 5660 about its pivot and, at the same time, permit the drive crank 5660 to rotate relative to the rack 5650. In at least one instance, the drive crank 5660 comprises a pin 5661 which extends into a pin slot 5651 defined in the rack 5650 which permits such relative motion therebetween. The firing drive 5600 further comprises a pawl 5670 rotatably supported in a seat defined in the opposite end of the drive crank 5660 about a pawl pin 5675. The firing drive 5600 also comprises a firing rack 5680 which is slid distally by the pawl 5670, as discussed below.

Figure 16:
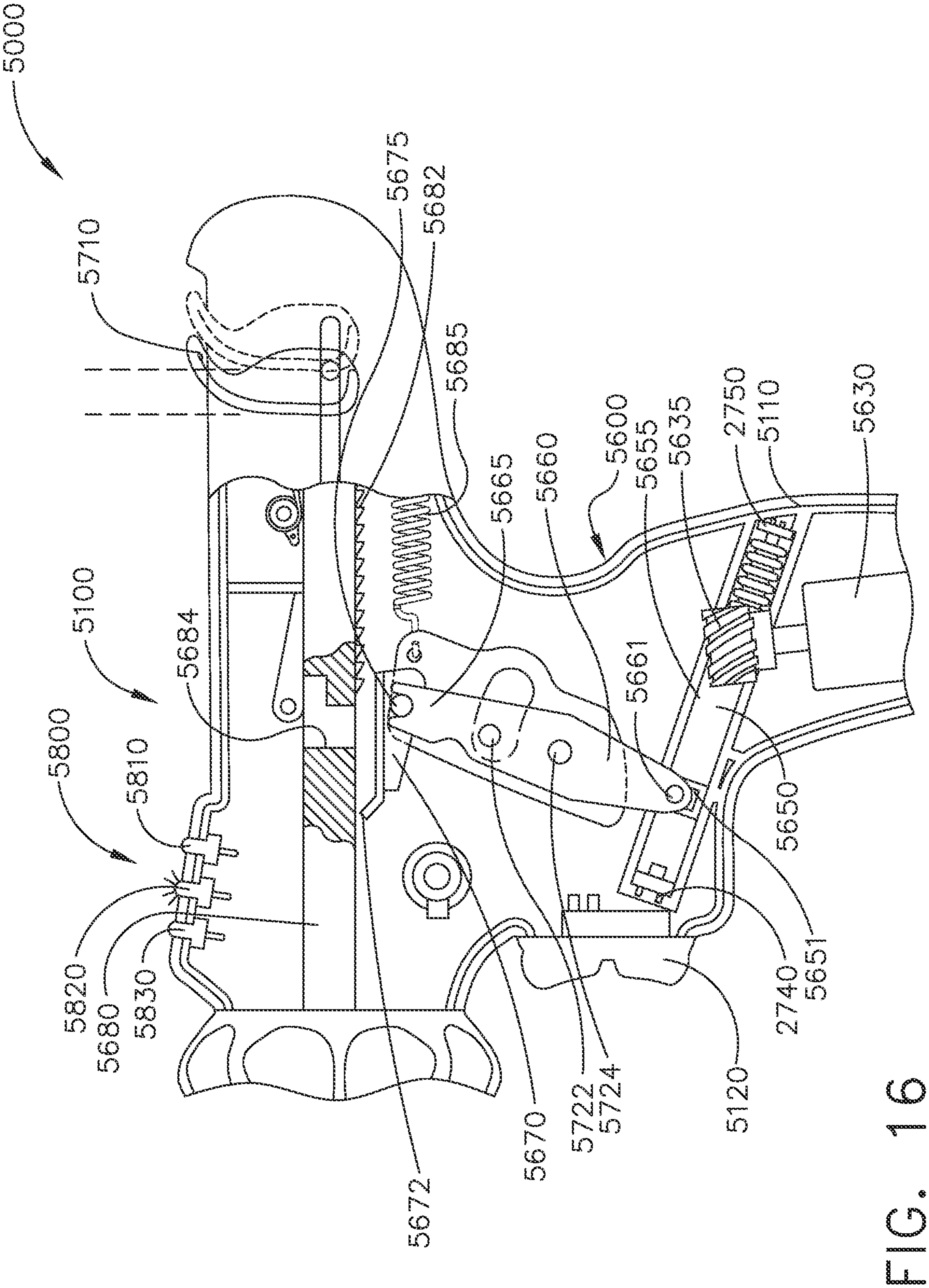
FIG. 16 is an elevational view of the stapling instrument of FIG. 14 illustrating the firing drive in a staple firing mode.
Figure 17:
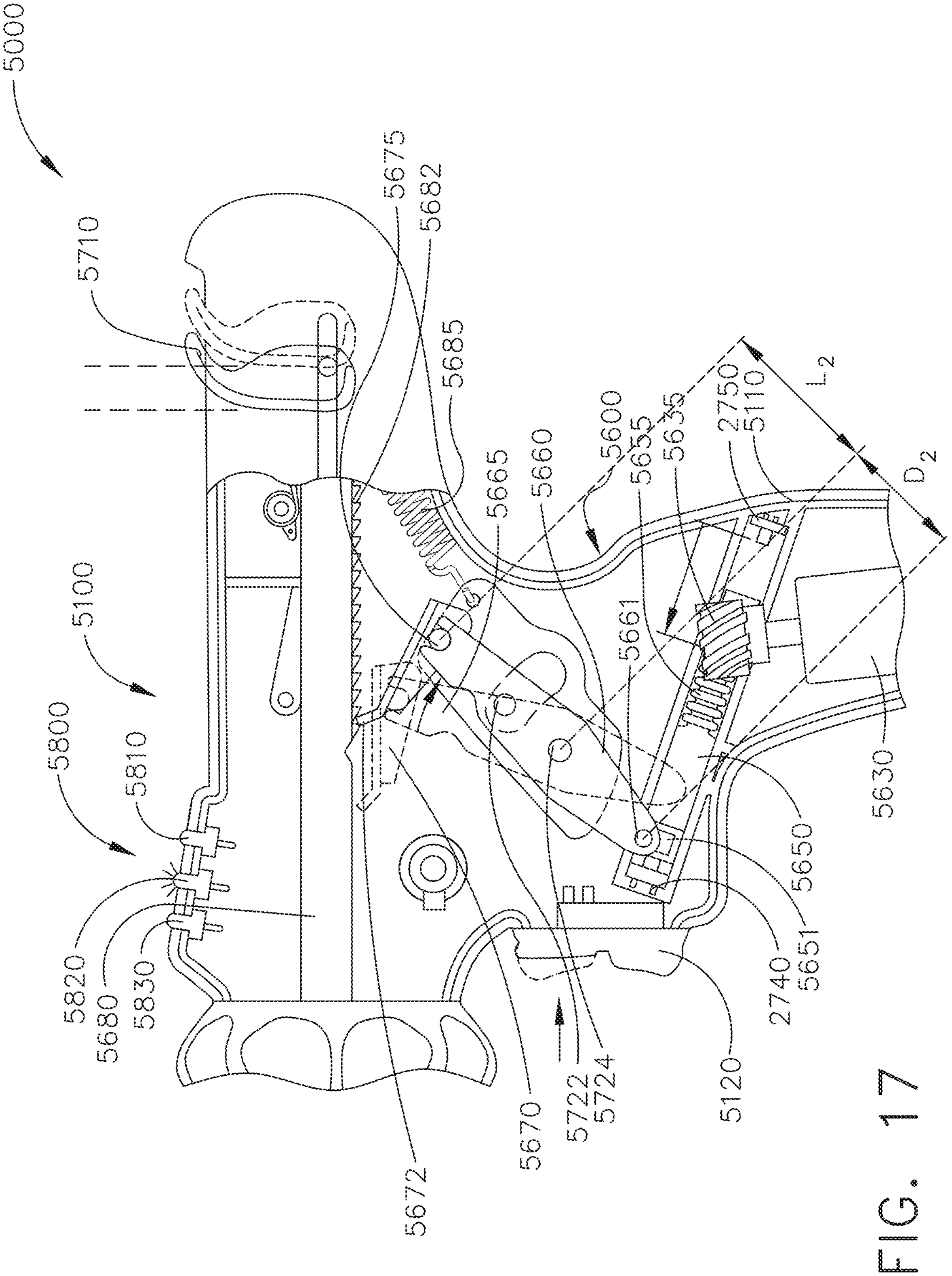
FIG. 17 is an elevational view of the stapling instrument of FIG. 14 illustrating the firing drive being retracted before performing a staple firing actuation.
Figure 18:
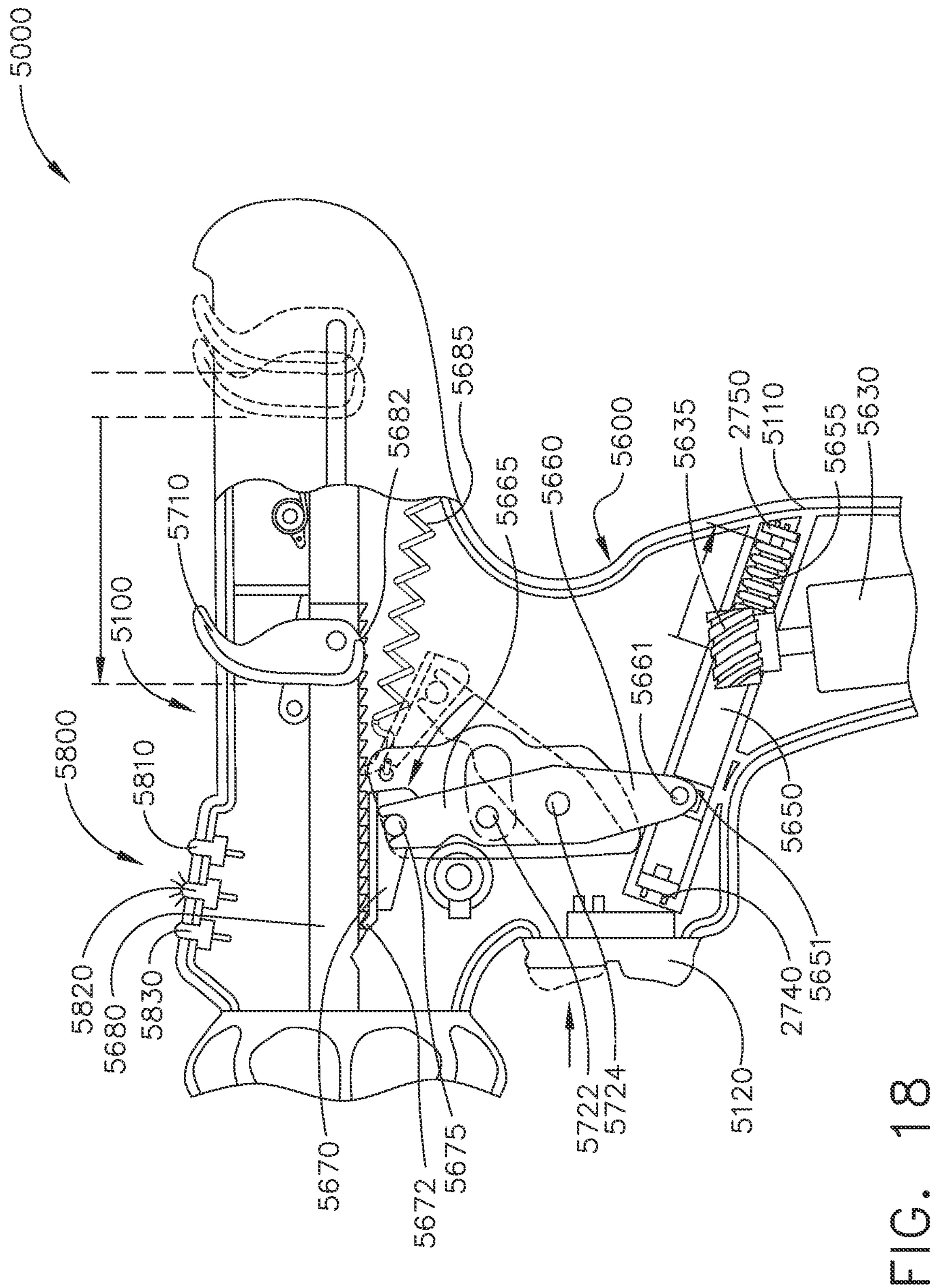
FIG. 18 is an elevational view of the stapling instrument of FIG. 14 illustrating the firing drive during the staple firing actuation.

Further to the above, the pawl 5670 comprises two drive teeth—a closure tooth 5674 and a staple firing tooth 5672. The closure tooth 5674 is in an extended position (FIGS. 14 and 15) during the initial actuation of the firing drive 5600 and a retracted position (FIGS. 16-18) after the initial actuation. When the closure tooth 5674 is in its extended position, referring to FIG. 14, the closure tooth 5674 extends into a closure drive aperture 5684 defined in the firing rack 5680 and, when the pawl 5670 is advanced distally during the initial actuation, referring to FIG. 15, the closure tooth 5674 pushes the firing rack 5680 and the firing rod 2690 distally through a closure stroke to close the end effector 1400. At such point, the electric motor 5630 is operated in a second, or opposite, direction to drive the rack 5650 back into its unactuated position, as illustrated in FIG. 16. Similar to the above, the stapling instrument 5000 comprises a beginning-of-actuation sensor 2740 which changes state in response to the rack 5650 reaching its fully-retracted position to stop the motor 5630. Notably, the closure tooth 5674 is in its retracted position when the pawl 5670 is reset by the rack 5650. In this embodiment, the closure tooth 5674 is pivotably coupled to the pawl 5670 and, when the pawl 5670 is retracted proximally after the initial actuation, the closure tooth 5674 contacts a backwall of the closure drive aperture 5684 and is rotated, or flipped, downwardly into its retracted position. In various alternative embodiments, a pawl tooth actuator in communication with a controller of the surgical instrument 5000 controls the position of the closure tooth 5674.

Referring again to FIG. 14, the drive crank 5660 further comprises a plate 5665 mounted thereto. The plate 5665 is mounted to the drive crank 5660 such that the plate 5665 rotates with the drive crank 5660. The firing drive 5600 further comprises a retraction spring 5685—coupled to the plate 5665 and the frame of the handle 5100—which resiliently stretches when the drive crank 5660 is rotated distally to drive the pawl 5670 through an actuation stroke. At the end of the actuation stroke, as discussed above, an end-of-actuation switch is opened and power is no longer supplied to the motor 5630. As also discussed above, an opposite polarity can be applied to the motor 5630 to drive the drive crank 5660 and the pawl 5670 proximally after the actuation stroke. That said, the retraction spring 5685 can resiliently contract to pull the drive crank 5660 and pawl 5670 proximally after the actuation stroke without the motor 5630 being operated in reverse. In such instances, the proximal movement, or retraction, of the drive crank 5660 and the pawl 5670 can be limited by a physical stop in the handle 5100. In any event, the motor 5630 can be actuated a second time to advance the drive crank 5660 and pawl 5670 distally once again. During the second actuation, however, the closure tooth 5674 is in its retracted position and not engaged with the firing rack 5680. Instead, referring to FIG. 17, the staple firing tooth 5672 of the pawl 5670 is engaged with the ratchet teeth 5682 defined on the bottom of the firing rack 5680. Thus, during the second actuation, the pawl 5670 drives the firing rack 5680 distally via the staple firing tooth 5672 to eject staples from the staple cartridge. The reciprocation of the pawl 5670 can be repeated until all of the staples from the staple cartridge have been ejected. In various embodiments, two actuations, or reciprocations, of the pawl 5670 eject all of the staples while, in other embodiments, all of the staples of the staple cartridge are ejected as a result of four actuations of the pawl 5670, for example. In various embodiments, a separate actuation of the firing actuator 5120 is required to perform each actuation of the firing drive 5600. In other embodiments, a first actuation of the firing actuator 5120 performs the initial, or closure, actuation while a second actuation of the firing actuator 5120 performs all of the staple firing actuations sequentially unless the firing actuator 5120 is released.

Further to the above, the stapling instrument 5000 transitions between from an end effector closure mode to a staple firing mode between the first, or closure, actuation of the motor 5630 and the second, or staple firing, actuation of the motor 5630. Further to the above, the stapling instrument 5000 comprises a mode switch which must be depressed by a clinician after the closure actuation to place the stapling instrument 5000 in the staple firing mode such that the stapling instrument is responsive to a second actuation of the firing actuator 5120 to perform the staple firing actuation. If the clinician does not depress the mode switch after the closure actuation, the motor 5630 is not responsive to the second actuation of the firing actuator 5120. The stapling instrument 5000 further comprises a controller, such as a processor, for example, in communication with the switches and/or sensors of the stapling instrument 5000.

The stapling instrument 5000 also comprises a status indicator array 5800 in communication with the processor. The status indicator array 5800 comprises a first indicator 5810, a second status indicator 5820, and a third status indicator 5830, but could comprise any suitable number of indicators. Each status indicator 5810, 5820, and 5830 comprises a light emitting diode (LED), for example, in communication with the processor. In at least one embodiment, the stapling instrument 5000 comprises a sensor configured to detect the presence of an unspent staple cartridge in the end effector 1400 in communication with the processor. If an unspent staple cartridge seated in the end effector 1400 is detected by the processor, the processor applies a voltage potential to the first status indicator 5810 to illuminate the first status indicator 5810. If an unspent staple cartridge is not detected by the processor, the processor does not apply a voltage potential to the first status indicator 5810. In at least one embodiment, the stapling instrument 5000 can comprise a sensor in communication with the processor which is configured to detect the attachment of a loading unit 1300 to the stapling instrument. If a loading unit 1300 is detected by the sensor, the processor applies a voltage potential to the second status indicator 5820 to illuminate the second status indicator 5820. If a loading unit 1300 is not detected by the sensor, the processor does not apply a voltage potential to the second status indicator 5820.

Further to the above, the stapling instrument 5000 further comprises a sensor configured to detect the closure of the end effector 1400 in communication with the processor. If the processor determines that the end effector 1400 is closed, or at least sufficiently closed, the processor applies a voltage potential to the third status indicator 5830 to illuminate the third status indicator 5830. If the processor determines that the end effector 1400 is open, the processor does not apply a voltage potential to the third status indicator 5830. In addition, the mode switch is in communication with the processor and the processor is configured to determine whether or not the mode switch has been depressed. If the processor determines that the mode switch has been depressed, the processor applies a voltage potential to a fourth status indicator to illuminate the fourth status indicator. If the processor does not determine that the mode switch has been depressed, the processor does not apply a voltage potential to the fourth status indicator.

When the stapling instrument 5000 is in its end effector closure mode (FIGS. 14 and 15), the drive crank 5660 is rotatable about the first pivot 5722. When the stapling instrument 5000 is in its staple firing mode (FIGS. 17 and 18), the drive crank 5660 is instead rotatable about the second pivot 5724. The first pivot 5722 comprises a first pin that extends into a first pin aperture defined in the drive crank 5660 when the mode switch is in an unactuated position. Notably, the second pivot 5724 is not engaged with the drive crank 5660 when the mode switch is in the unactuated position. The second pivot 5724 comprises a second pin that extends into a second pin aperture defined in the drive crank 5660 when the mode switch is in an actuated position. Notably, the first pivot 5722 is not engaged with the drive crank 5660 when the mode switch is in the actuated position. In at least one embodiment, the mode switch comprises a rocker switch having two positions—a first position in which the first pivot 5722 is engaged with the drive crank 5660 and a second position in which the second pivot 5724 is engaged with the drive crank 5660. In at least one embodiment, the mode switch is in communication with a first solenoid and a second solenoid. When the mode switch is in its first position, the first solenoid is actuated to extend the first pin and, when the mode switch is in its second position, the second solenoid is actuated to extend the second pin.

When the mode switch is in its first position and the stapling instrument 5000 is in its end effector closure mode, referring to FIG. 15, the drive crank 5660 defines two torque arms about the first pivot 5722. More specifically, a first torque arm D1 is defined between the pin 5661 and the first pivot 5722 and a second torque arm L1 is defined between the first pivot 5722 and the pawl pin 5675. Notably, the first torque arm D1 is longer than the second torque arm L1. When the mode switch is in its second position and the stapling instrument 5000 is in its staple firing mode, referring to FIG. 17, the drive crank 5660 defines two torque arms about the second pivot 5724. More specifically, a first torque arm D2 is defined between the pin 5661 and the second pivot 5724 and a second torque arm L2 is defined between the second pivot 5724 and the pawl pin 5675. Notably, the first torque arm D1 is longer than the second torque arm D2. Also, notably, the torque arm L2 is longer than the torque arm L1. As a result of the above, the staple-firing actuations of the pawl 5670 and the firing rack 5680 are longer than the end effector closing actuation of the pawl 5670 and the firing rack 5680. Such an arrangement is useful as a short closure actuation allows the end effector 1400 to be closed quickly and longer staple firing actuations may reduce the number of pawl reciprocations that are needed to complete the entire staple firing stroke.

Further to the above, referring to FIG. 16, the stapling instrument 5000 is switched from its closure mode to its staple firing mode after the closure actuation has been completed but before the driver crank 5660 and the pawl 5670 are retracted. In this position, the first pin aperture in the drive crank 5660 is aligned with the first pivot 5722 and the second pin aperture in the drive crank 5660 is aligned with the second pivot 5724. As a result, this particular position of the drive crank 5660 can be used to switch from the first pivot 5722 to the second pivot 5724 and, likewise, from the second pivot 5724 back to the first pivot 5722. That said, any other suitable position of the drive crank 5660 can be used to switch between the first pivot and the second pivot in other embodiments. In at least one embodiment, the mode switch is in communication with the control system of the stapling instrument 5000 and the control system is not responsive to the mode switch until after the closure stroke has been completed. That said, various other embodiments are envisioned in which the stapling instrument 5000 is switchable from a first state to a second state between any two actuations of the stapling instrument 5000. In such embodiments, for instance, the controller can switch the stapling instrument 5000 from a first, or low, leverage state to a second, or high, leverage state in which a larger drive force is transmitted to the firing rack 5680 during a subsequent actuation than during a previous actuation. In at least one such embodiment, the clinician can sense that the force being transmitted to the staple firing member is high and then selectively actuate an actuator in communication with the controller which, in response, stops the reciprocation of the driver crank 5660 and the pawl 5670 in the transition position and switches the stapling instrument from the first state to the second state. Once the stapling instrument has been switched into its second state by the controller, the controller is responsive to the firing actuator 5120 to finish the staple firing stroke.

In various embodiments, further to the above, the controller of a stapling instrument is configured to automatically switch the stapling instrument from a first state to a second state between the pawl reciprocations of a staple firing stroke. In at least one such embodiment, the controller comprises a sensing system configured to sense the force being transmitted through the firing rack 5680 to the firing rod 5690 and the firing member 1390 which is configured to switch the stapling instrument from the first state to the second state when the force exceeds a predetermined force threshold. In at least one embodiment, the sensing system comprises a load cell sensor configured to directly measure the force being transmitted through the firing rack 5680. In at least one embodiment, the sensing system comprises a strain gauge mounted to the firing rack 5680 configured to measure the strain in the firing rack 5680 which is a proxy for the force being transmitted through the firing rack 5680. In such instances, the sensing system switches the stapling instrument from the first state to the second state when the measured strain exceeds a predetermined strain threshold. In at least one embodiment the sensing system comprises a current sensor configured to measure the current through the electric motor 5630 which is a proxy for the force being transmitted through the firing rack 5680. In such instances, the sensing system switches the stapling instrument from the first state to the second state when the measured current exceeds a predetermined current threshold. In any event, in the second state of the stapling instrument, the stapling instrument transmits a larger firing load to the firing rack 5680 for the remainder of the staple firing stroke. In various embodiments, the controller is configured to switch the stapling instrument back into the first state when the sensed firing load, or a sensed parameter related to the firing load, falls below the corresponding threshold.

Figure 19:
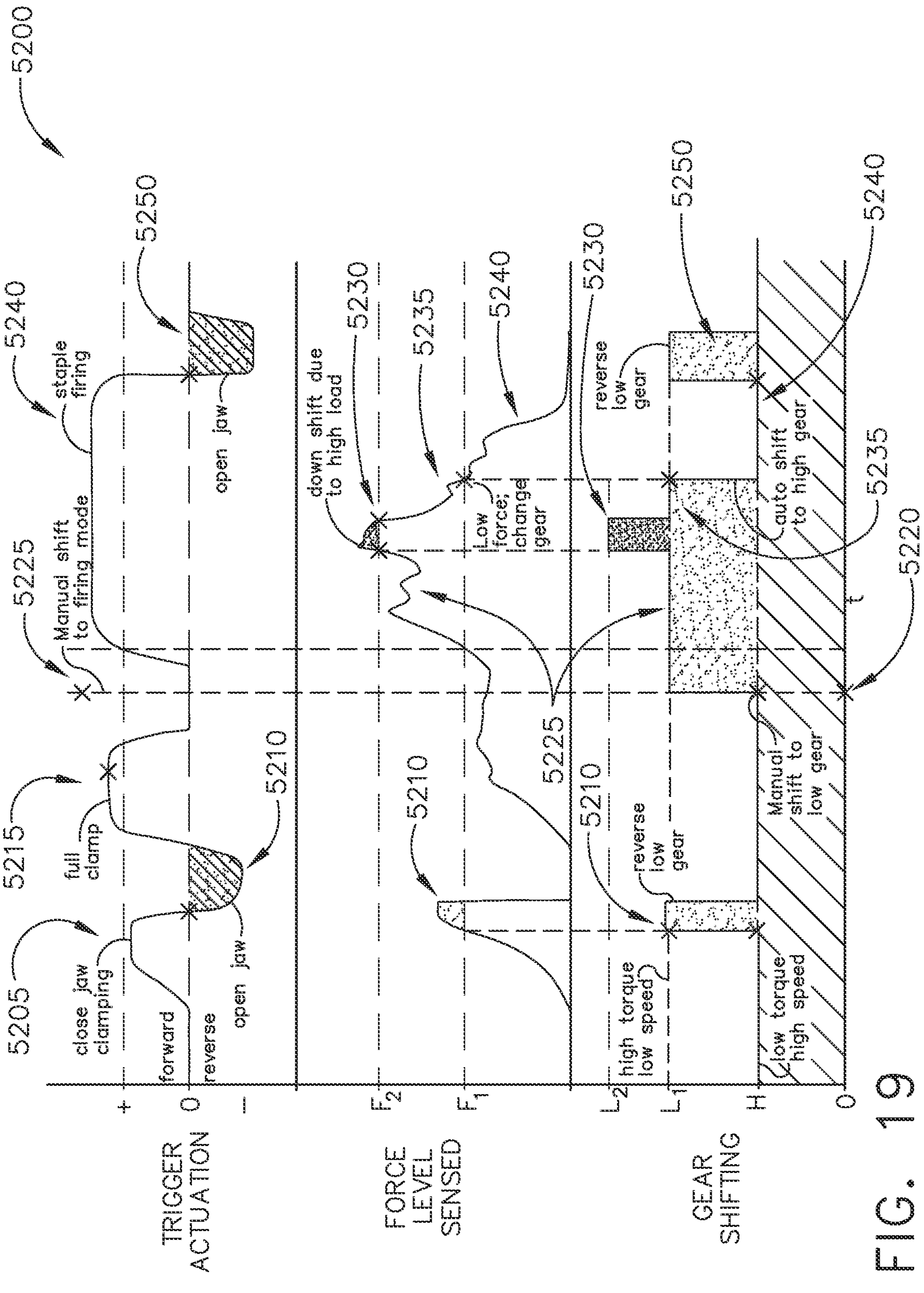
FIG. 19 is a graph depicting the operation of a stapling instrument comprising a firing drive including a shiftable transmission in accordance with at least one embodiment.

In various embodiments, referring to FIG. 19, a firing drive of a stapling instrument can comprise a transmission including a high speed, low torque gear or gear set (a "high speed gear H") and a low speed, high torque gear or gear set (a "low speed gear L"). In at least one such embodiment, the low speed gear L comprises a first low speed gear L1 and the stapling instrument further comprises a second low speed gear L2. The second low speed gear L2 is slower than the first low speed gear L1 and has a higher torque than the first low speed gear L1. That said, a transmission can comprise any suitable number of gears or gear sets. In use, the stapling instrument shifts between the high speed gear H, the first low speed gear L1, and the second low speed gear L2. The transmission comprises an automatic transmission configured to shift from the high speed gear H to the first low speed gear L1 when the force transmitted through the firing drive exceeds a first force threshold F1. The automatic transmission is also configured to shift from the first low speed gear L1 to the second low speed gear L2 when the force transmitted through the firing drive exceeds a second force threshold F2. FIG. 19 comprises a graph 5200 describing the operational steps of the stapling instrument and the transmission shifting during those operational steps, as described further below.

At step 5205, further to the above, the firing trigger of the stapling instrument is closed to clamp the end effector. Neither force threshold F1 nor force threshold F2 are exceeded during step 5205 and, as a result, the transmission remains in its high speed gear H. If the force threshold F1 had been exceeded during step 5205, the transmission would have shifted from the high speed gear H to the first low speed gear L1. If the force threshold F2 had been exceeded during step 5205, the transmission would have shifted to the second low speed gear L2. At step 5210, the motor is operated in reverse and the end effector is unclamped. During step 5210, the force threshold F1 was exceeded and the transmission shifted from the high speed gear H to the first low speed gear L1. Notably, the force threshold F2 was not exceeded during step 5210 and, thus, the transmission did not shift into the second low speed gear L2. If the force threshold F2 had been exceeded during step 5210, then the transmission would have shifted into the second low speed gear L2. During step 5215, the end effector is re-closed. Notably, the step 5215 is operationally similar to the step 5205; however, the step 5215 may be operationally different owing to changes in the fluid content of the tissue being clamped. Also, notably, the operation of the surgical instrument does not require steps 5210 and 5215. Instead, steps 5210 and 5215 can be skipped and the operation of the surgical instrument can skip from step 5205 to step 5220 which comprises shifting the stapling instrument from the end effector closure mode to the staple firing mode, which is discussed below.

Once step 5220 is complete, further to the above, the staple firing stroke can be initiated which is represented by step 5225. During the staple firing stroke, the firing force can fluctuate greatly. At step 5225, the firing force has exceeded the force threshold F1, but not the force threshold F2. As such, the transmission is in the first low speed gear L1 at the outset of the staple firing stroke. At step 5230, the firing force has exceeded the force threshold F2 and, as a result, the transmission is in the second low speed gear L2. The firing force can increase as the result of the tissue cutting knife of the firing member and/or the staples passing through tough, dense, and/or thick tissue, for example, during the staple firing stroke. At step 5235, the firing force fell back below the force threshold F2 but remained above the force threshold F1 and, as a result, the transmission shifted into the first low speed gear L1. Had the firing force fallen back below the force threshold F1, the transmission would have shifted in the high speed gear H, as it did during step 5240 which is at the end of the staple firing stroke. That said, the firing force may not always drop below the force threshold F1 at the end of the staple firing stroke and, in such instances, the transmission would not shift into the high speed gear H. In fact, it's possible for the firing force to exceed the force threshold F2 at the end of the staple firing stroke which would cause the transmission to shift into the second low gear L2. That said, embodiments are envisioned in which the controller of the stapling instrument holds the transmission in a particular gear during a particular part of the staple firing stroke. For instance, embodiments are envisioned in which the firing drive moves slowly during the beginning and/or end of the staple firing stroke resulting in a "soft start" and/or "soft stop" to the staple firing stroke. In such embodiments, the stapling instrument may be in the first low speed gear L1 or the second low speed gear L2 at the beginning and/or end of the firing stroke regardless of the measured firing force. In any event, the tissue cutting knife is retracted after the staple firing stroke has been completed such that the end effector can be re-opened which is represented by step 5250. Notably, the transmission is in the first low speed gear L1 during step 5250 despite the fact that there is very little force being transmitted through the firing drive. Similar to the above, in this embodiment, the stapling instrument controller can hold the transmission in the first low speed gear L1, for example, when the tissue cutting knife is being retracted. The entire disclosures of U.S. Pat. No. 9,028,529, entitled MOTORIZED SURGICAL INSTRUMENT, which issued on May 12, 2015 and U.S. Pat. No. 8,602,287, entitled MOTOR DRIVEN SURGICAL CUTTING INSTRUMENT, which issued on Dec. 10, 2013 are incorporated by reference herein.

Figure 20:
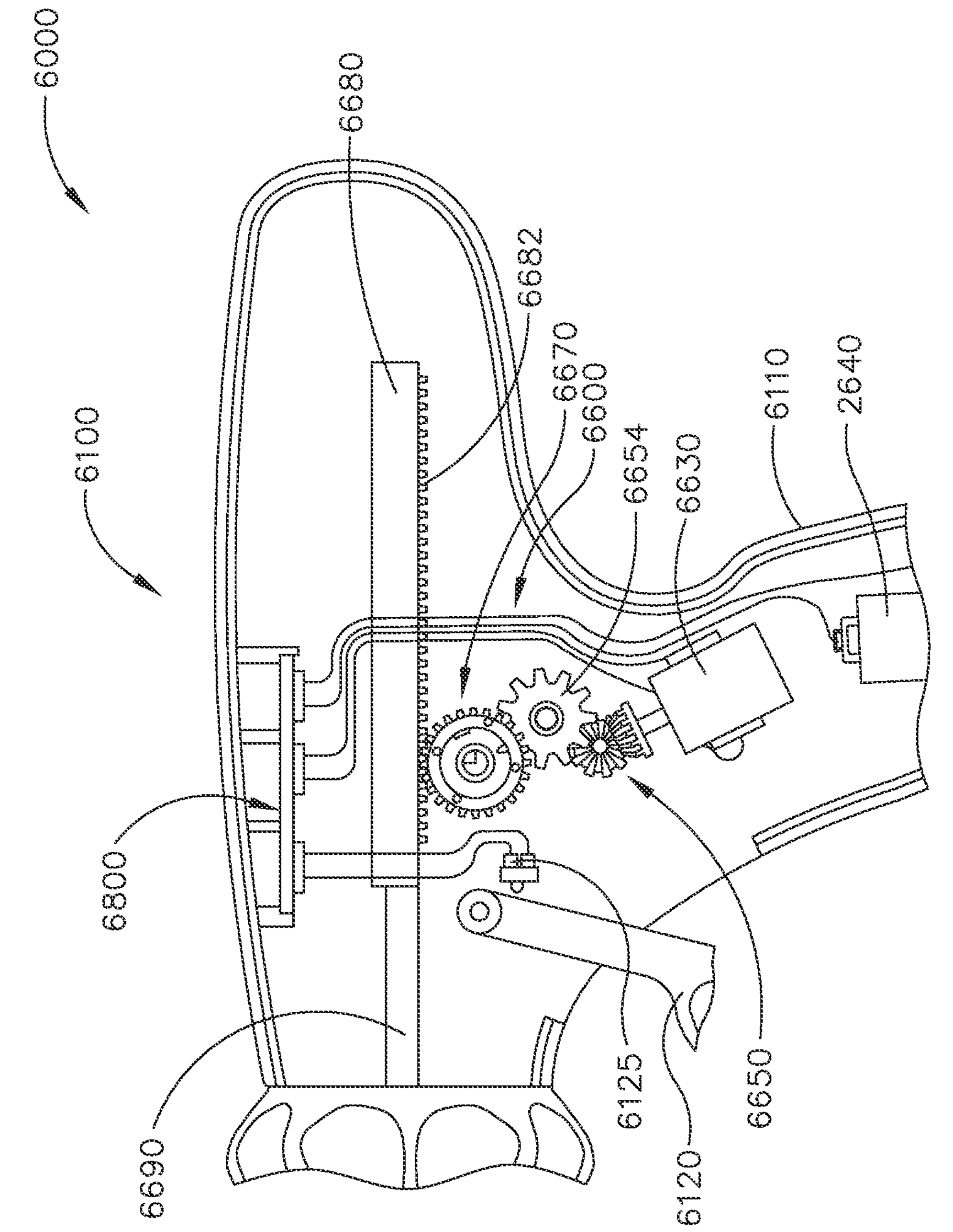
FIG. 20 is a partial cross-sectional view of a stapling instrument comprising a firing drive including a slip clutch in accordance with at least one embodiment.

As discussed above, a stapling instrument can comprise a shifting device to increase the firing force being transmitted through a firing drive. In some instances, though, the increased firing force may exceed the strength of one or more components in the firing drive. In various embodiments, a firing drive can comprise a slip clutch to limit the force transmitted by the firing drive. One such stapling instrument, i.e., stapling instrument 6000, is illustrated in FIG. 20. The stapling instrument 6000 is similar to the stapling instruments 1000 and 2000 and other stapling instruments disclosed herein in many respects, most of which will not be discussed herein for the sake of brevity. The stapling instrument 6000 comprises a handle 6100, a firing drive 6600, and a controller 6800. The handle 6000 comprises a grip 6110 and a rotatable firing trigger 6120. The firing drive 6600 comprises a motor 6630, a gear train 6650 operably engaged with the motor 6630, a slip clutch 6670 operably engaged with a drive gear 6654 of the gear train 6650, a firing rack 6680 operably engaged with the slip clutch 6670, and a firing rod 6690 mounted to and translatable with the firing rack 6680. The controller 6800 is in communication with the motor 6630, a battery 2640, and a firing trigger switch 6125 which is closed by the firing trigger 6120 when the firing trigger 6120 is actuated. When the controller 6800 detects that the firing trigger switch 6125 has been closed, the controller 6800 supplies power to the electric motor 6630 from the battery 2640.

Figure 20A:
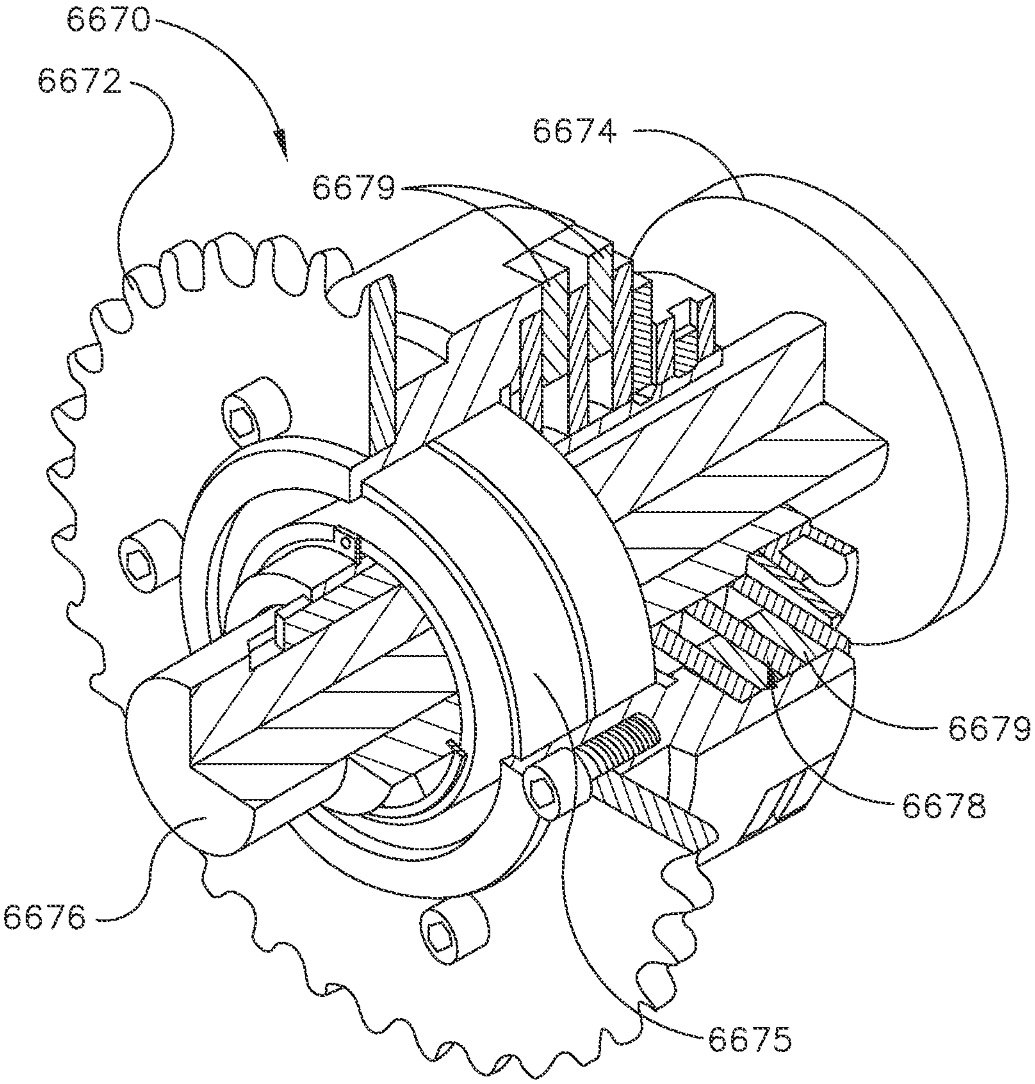
FIG. 20A is a cross-sectional view of the slip clutch of FIG. 20.

Further to the above, referring to FIG. 20A, the slip clutch 6670 comprises an input gear 6674 including a full circumference of gear teeth (not illustrated) operably engaged with the drive gear 6654 of the gear train 6650. The slip clutch 6670 further comprises an output gear 6672 operably engaged with a longitudinal array of teeth 6682 defined on the bottom of the firing rack 6680. The slip clutch 6670 further comprises a shaft 6676 and a bearing 6675 which rotatably supports the shaft 6676. The input gear 6674 is fixedly mounted to the shaft 6676 such that the rotation of the input gear 6674 is transmitted to the shaft 6676. The slip clutch 6670 further comprises an array of annular clutch plates 6678 mounted to the shaft 6676 and an array of annular friction plates 6679 mounted to the output gear 6672 which are engaged with the clutch plates 6678. When the static friction threshold between the clutch plates 6678 and the friction plates 6679 is not exceeded, the output gear 6672 rotates with the shaft 6676 and the input gear 6674. On the other hand, the clutch plates 6678, the shaft 6676, and the input gear 6674 slip relative to the friction plates 6679 and the output gear 6672 when the static friction threshold between the clutch plates 6678 and the friction plates 6679 has been exceeded. As a result, the firing force that can be transmitted to the firing rack 6680 is limited by the slip clutch 6670.

Further to the above, a surgical stapling instrument can comprise any suitable force limiting device to prevent the staple firing drive from being overloaded. In at least one such embodiment the bottom of the firing rack comprises a rough surface and the gear drive comprises a friction wheel including a grit perimeter in contact with the rough surface. When the force transmitted from the friction wheel to the firing rack is below the static friction threshold, the friction wheel drives the firing rack proximally or distally depending on the direction in which the friction wheel is rotated. When the force transmitted from the friction wheel to the firing rack exceeds the static friction threshold, the friction wheel slips relative to the firing rack and does not drive the firing rack.

Figure 21:
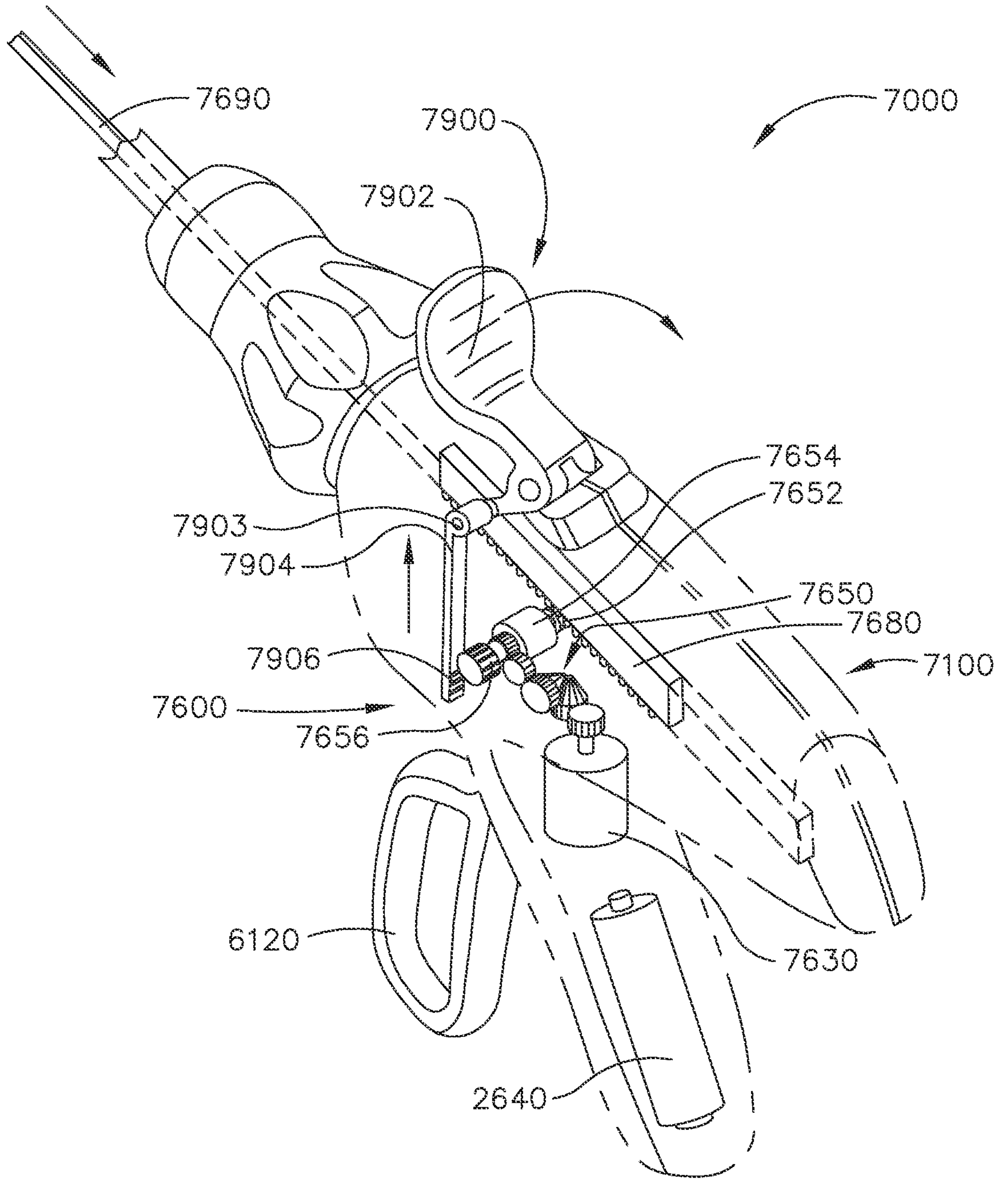
FIG. 21 is a partial perspective view of a stapling instrument comprising a bailout drive in accordance with at least one embodiment.

A stapling instrument 7000 is illustrated in FIG. 21 and is similar to the stapling instruments 1000 and 2000 and other stapling instruments disclosed herein in many respects, most of which are not discussed herein for the sake of brevity. The stapling instrument 7000 comprises a handle 7100 and a firing drive 7600. The firing drive 7600 comprises an electric motor 7630, a gear train 7650, a firing rack 7680, and a firing rod 7690 mounted to the firing rack 7680. The gear train 7650 comprises a planetary gear arrangement 7654 operably coupled to an output of the electric motor 7630 and a drive gear 7652 which operably couples the planetary gear arrangement 7654 to the firing rack 7680. The motor 7630 is operated in a first direction when a first voltage potential is supplied to the motor 7630 from a battery 2640 in response to an actuation of a firing actuator 6120. In such instances, the gear train 7650 drives the firing rack 7680 and firing rod 7690 distally. The motor 7630 is operated in an opposite direction when an opposite polarity is applied to the motor 7630 from the battery 2640. In such instances, the gear train 7650 drives the firing rack 7680 and the firing rod 7690 proximally. In various instances, however, the motor 7630 may fail and/or the battery 2640 may not be able to suitably supply power the motor 7630 to retract the firing rack 7680 and the firing rod 7690. As such, the stapling instrument 7000 further comprises a manually-driven bailout drive 7900 which is operable to retract the firing rack 7680 and firing rod 7690 proximally, as discussed below.

The bailout drive 7900, referring again to FIG. 21, comprises a bailout lever 7902 rotatably mounted to a housing of the handle 7100 and a bailout rack 7904 coupled to the bailout lever 7902 at a pin joint 7903 which transmits the motion of the bailout lever 7902 to the bailout rack 7904. The bailout rack 7904 comprises an array of teeth 7906 defined thereon which are meshingly engaged with a bailout gear 7656 of the gear drive 7650. When the bailout lever 7902 is in a stowed position, i.e., in a position lying flat against the handle housing, the bailout rack 7904 is not engaged with the bailout gear 7656. In such instances, the bailout gear 7656 rotates relative to the bailout rack 7904 when the gear drive 7650 is driven by the electric motor 7630. When the bailout lever 7902 is moved out of its stowed position, i.e., rotated away from the handle housing, the bailout lever 7902 is rotated into an engaged position in which the bailout rack 7904 is engaged with the bailout gear 7656. At such point, the bailout lever 7902 is rotatably cranked from its engaged position to an actuated position to drive the bailout rack 7904 upwardly and rotate the bailout gear 7656. Notably, the bailout gear 7656 and the planetary gear arrangement 7654 are driven by a common input shaft in the gear train 7650 such that, when the bailout gear 7656 is driven by the rack 7904, the bailout gear 7656 drives the planetary gear arrangement 7654 which drives the firing rack 7680 and firing rod 7690 proximally. In such instances, the tissue cutting knife in the end effector 1400 is retracted proximally such that the end effector 1400 can be opened and released from the patient tissue. In various embodiments, a single actuation of the bailout lever 7902 sufficiently opens the end effector 1400. In other embodiments, the bailout lever 7902 is ratcheted back and forth to sufficiently retract the tissue cutting knife. In at least one embodiment, the rack teeth 7906 comprise ratchet teeth which slide over the bailout gear 7656 when the bailout rack 7904 is retracted. In at least one embodiment, the rack 7680 lifts away from the bailout gear 7656 when the bailout lever 7656 is rotated from its actuated position back into its engaged position and then re-engages with the bailout gear 7656 when the bailout 7656 is re-actuated. In at least one embodiment, the rack teeth 7906 comprise gear teeth which are operably intermeshed with the teeth of the bailout gear 7656 and, in this embodiment, the bailout gear 7656 comprises a ratchet face engaged with the input shaft extending into the planetary gear arrangement 7654. As a result of the ratchet face being driveable in only one direction, the bailout gear 7656 is not driven by the electric motor 7630 but is driveable by the bailout drive. In any event, the actuation of the bailout drive 7900 does not destroy the firing drive 7600 and, as a result, the stapling instrument 7000 can be used once again once the issue that required the bailout drive 7900 to be used is resolved.

Figure 22:
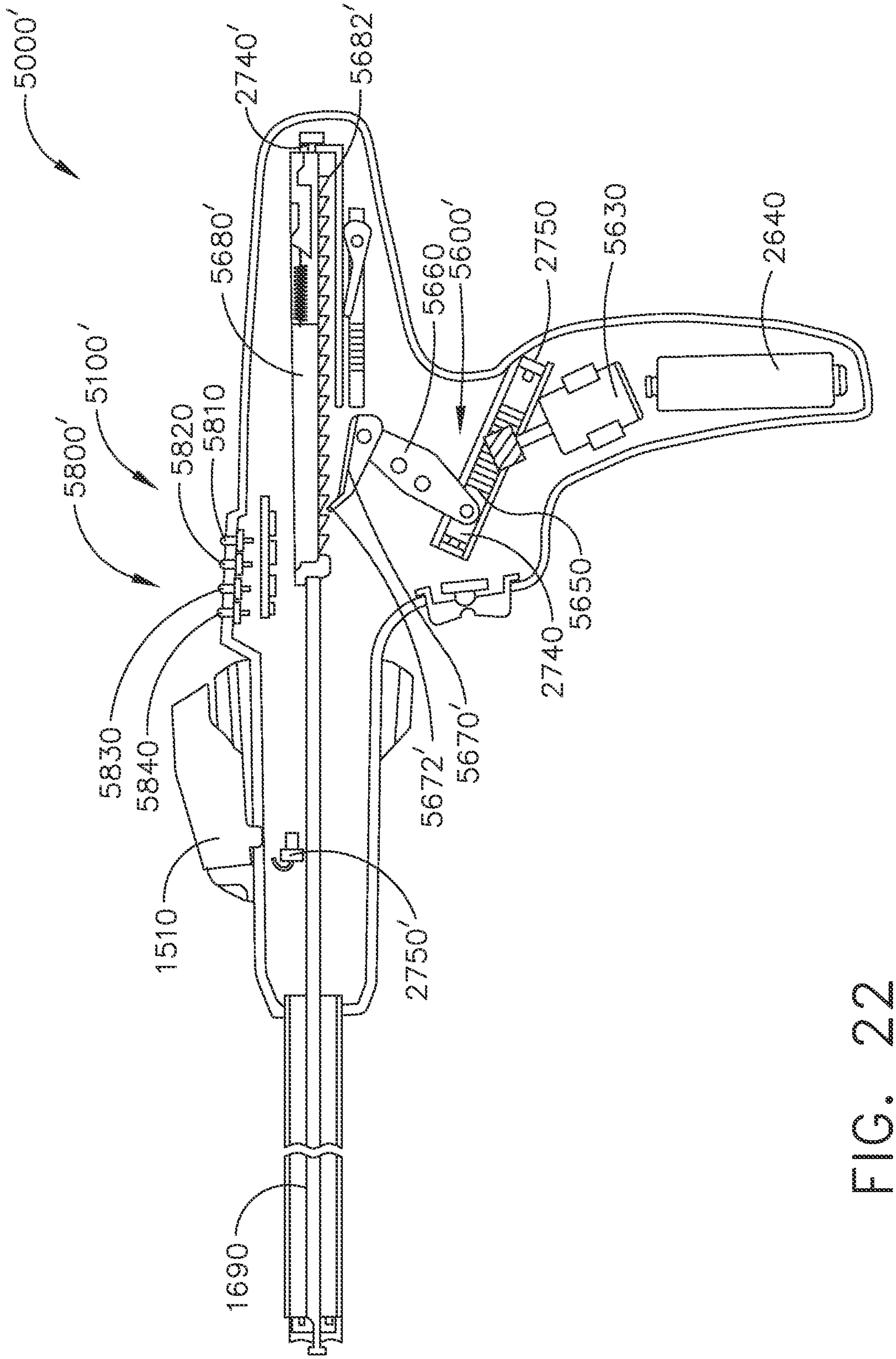
FIG. 22 is a partial elevational view of a stapling instrument in accordance with at least one embodiment illustrated with some components removed.

In various embodiments, a stapling instrument can comprise a firing drive configured to advance and retract a firing rack and bailout drive configured to retract the firing rack. In at least one such embodiment, the firing drive comprises a firing gear drive operably engaged with the firing rack which drives and/or retracts the firing rack in response to a rotational input. The bailout drive comprises a bailout gear drive which is selectively engageable with the firing drive. More specifically, the stapling instrument comprises a shiftable gear which is shiftable between a first position in which the A stapling instrument 5000' is illustrated in FIG. 22 and is similar to the stapling instruments 1000 and 5000 and other stapling instruments disclosed herein in many respects, most of which will not be discussed herein for the sake of brevity. The stapling instrument 5000' comprises a handle 5100' including a firing drive 5600' which includes the motor 5630 powered by the battery 2640, the rack 5650 which is driven by the motor 5630, and the drive crank 5660 which is driven by the rack 5650. The firing drive 5600' is operated in a similar manner to that of the firing drive 5600, but the firing drive 5600' further comprises a pawl 5670' instead of the pawl 5670 and a firing rack 5680' instead of a firing rack 5680. Unlike the pawl 5670, the pawl 5670' comprises a single drive tooth 5672' which engages a longitudinal array of ratchet teeth 5682' defined on the bottom of the firing rack 5680' to drive the firing rack 5680' distally during every actuation, or reciprocation, of the pawl 5670'.

Figure 22A:
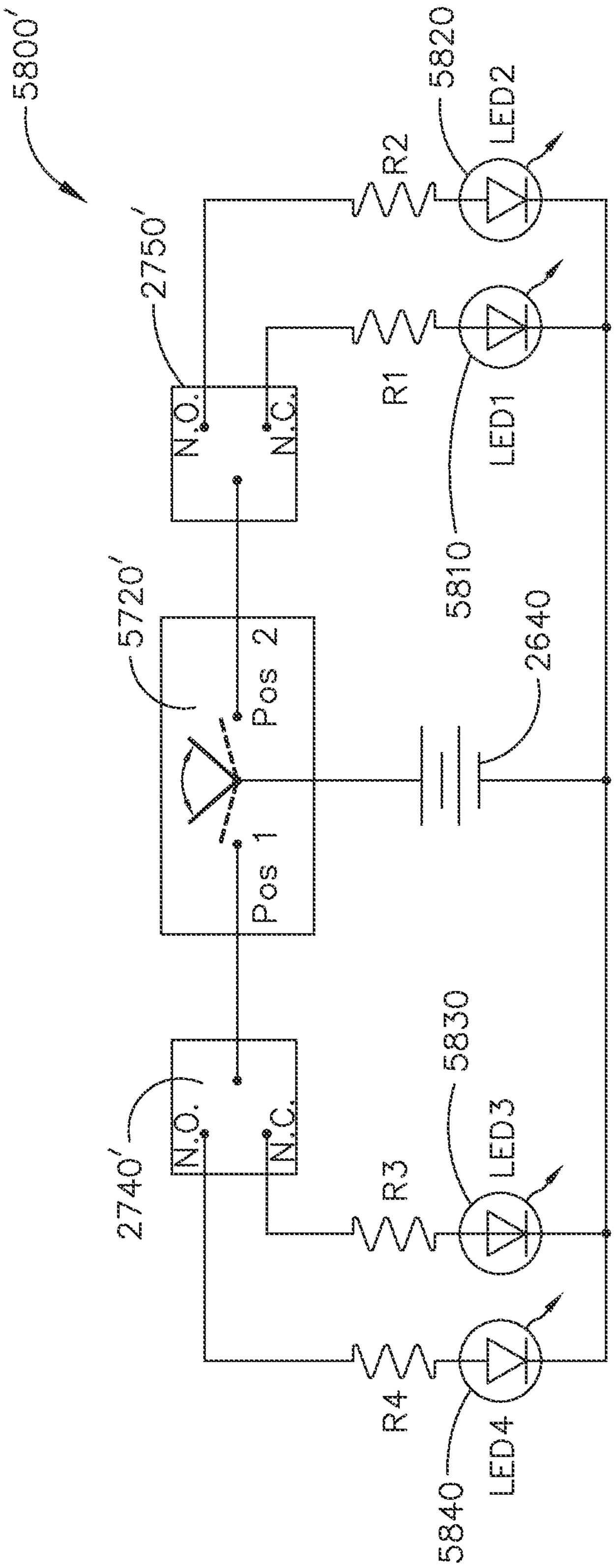
FIG. 22A is a schematic of an indicator system of the stapling instrument of FIG. 22.

Further to the above, the stapling instrument 5000' further comprises a control system including an indicator array 5800' configured to indicate the status of the stapling instrument 5000'. The indicator array 5800' comprises four indicator lights 5810, 5820, 5830, and 5840, but could comprise any suitable number of indicator lights. The control system further comprises a proximal switch 2740' and a distal switch 2750'. When the firing rack 5680' is in its proximal-most, unactuated, position (FIG. 22), the firing rack 5680' is in contact with the proximal switch 2740' which holds the proximal switch 2740' in an open state. The stapling instrument 5000' further comprises a mode switch 5720' in communication with the indicator array 5800' that is switchable between a first position to place the stapling instrument 5000' in an end effector closure mode and a second position to place the stapling instrument 5000' in a staple firing mode. When the mode switch 5720' is in its first position and the firing rack 5680' is in its proximal-most position, referring now to FIG. 22A, the indicator light 5840 is illuminated by the battery 2640. When the firing rack 5680' is advanced distally to perform the closure stroke, the firing rack 5680' disengages from the proximal switch 2740' which allows the proximal switch 2740' to close. In such instances, the indicator light 5840 is no longer illuminated and, instead, the indicator light 5830 is illuminated. This change in the indicator lights indicates to the clinician that the end effector 1400 is closed. Once the mode switch 2740' is shifted to its second position, neither of the indicator lights 5830 and 5840 are illuminated and, instead, the indicator light 5810 is illuminated owing to the distal switch 2750' being in a normally-closed condition. At the end of the staple firing stroke, the firing rack 5680' contacts the distal switch 2750' and opens the distal switch 2750'. In such instances, the indicator light 5810 is no longer illuminated and, instead, the indicator light 5820 is illuminated. This change in the indicator lights indicates to the clinician that the staple firing stroke has been completed.

In various embodiments, a surgical stapling instrument comprises a firing drive including an electric motor and a firing rack driven distally by the electric motor to perform a closure stroke and then a staple firing stroke. In at least one embodiment, the firing drive further comprises a closure actuator and a separate firing actuator in communication with a processor of the stapling instrument. When the closure actuator is actuated to close the end effector, the electric motor is rotated in a first direction to drive the firing rack distally. When the end effector is closed, the processor stops the electric motor. That said, the processor is not responsive to an actuation of the firing actuator while the end effector is open. After the end effector has been closed, the processor is no longer responsive to an actuation of the closure actuator. To open the end effector, at such point, the firing rack is retraced proximally when a retraction knob extending from the firing rack is pulled proximally. Once the end effector has been closed, the processor is now responsive to an actuation of the firing actuator to operate the electric motor in the first direction to perform the staple firing stroke. Once the staple firing stroke has been completed, the processor stops the electric motor. Once the electric motor has been stopped—either at the end of the staple firing stroke or before the end of the staple firing stroke—the firing rack can be retracted proximally by the retraction knob to re-open the end effector. In various embodiments, the stapling instrument comprises a retraction actuator in communication with the processor that, when actuated, operates the electric motor in an opposite direction to retract the firing rack and open the end effector.

In various embodiments, a surgical stapling instrument comprises two firing drives—a manually-driven closure drive and a motor-driven staple firing drive. The manually-driven closure drive comprises a rotatable trigger and a firing rack. The trigger is engaged with the firing rack such that an actuation of the trigger drives the firing rack distally through a closure stroke. When the trigger is rotated into its actuated position, the trigger is releasably held in its actuated position by a trigger lock. If the clinician wants to re-open the end effector, the clinician can release the trigger lock and allow a trigger spring to bias the trigger back into its unactuated position and drive the firing rack proximally. The motor-driven staple firing drive comprises an electric motor configured to drive the firing rack distally through a staple firing stroke once the firing rack has been moved through the closure stroke. The closure stroke moves the firing rack from a proximal unactuated position in which the firing rack is not operably engaged with the electric motor to an actuated position in which the firing rack is operably engaged with the electric motor. At such point, a firing actuator in communication with the electric motor is actuatable to operate the electric motor to drive the firing rack through the staple firing stroke. In at least one embodiment, the electric motor is controlled by a processor and, prior to the end effector being closed, the processor is not responsive to an actuation of the firing actuator. Once the end effector has been closed, the processor is responsive to the firing actuator. In any event, the closure trigger is disengaged from the firing rack once the end effector has been closed. In such instances, as a result, the staple firing stroke is performed without the closure trigger being operably engaged with the firing rack. Once the staple firing stroke has been completed, the processor automatically operates the electric motor in an opposite direction to retract the firing rack. Alternatively, a retraction knob extending from the firing rack can be pulled proximally to retract the firing rack. When the firing rack is retracted back to the actuated position, i.e., the position between the closure stroke and the staple firing stroke, the firing rack is re-engaged with the closure trigger. Once the firing trigger is re-engaged with the closure trigger, the closure trigger can be released to drive the firing rack back into its unactuated position to re-open the end effector.

Further to the above, a manually-driven closure system allows the clinician to feel the clamping load being applied to the tissue captured within the end effector via the trigger. If the clamping load is high, for instance, the clinician can feel the force needed to clamp the end effector thereby giving the clinician an intuitive feel of what is occurring in the end effector. That said, the force needed to drive the firing rack distally to fire the staples and cut the tissue is often very high, or at least high enough that some clinicians may struggle to advance the firing rack distally with a manual trigger. A motor-driven staple firing drive can alleviate this issue and make the stapling instrument easy to operate by all clinicians.

In various embodiments, a surgical stapling instrument comprises a pneumatic firing drive. The firing drive comprises an air pump in communication with an air reservoir configured to store compressed air supplied to the air reservoir from the air pump. The firing drive further comprises a normally-closed valve in communication with the air reservoir and a linear air piston. The linear air piston comprises a firing rod that is moved distally when the valve is opened by a rotatable trigger. The linear air piston further comprises a pawl rotatably mounted to the firing rod. When the firing rod is driven distally, the pawl drives a firing rack of the firing drive distally through an actuation stroke. When the valve is re-closed, the compressed air in the air piston is exhausted through the valve and the firing rod and the pawl are retracted proximally by a compression spring positioned in the linear air piston. In such instances, the pawl slides proximally relative to the firing rack back into an unactuated position. At such point, the valve can be re-opened to drive the pawl and firing rack distally through another actuation stroke. In various instances, the first actuation stroke can comprise a closure stroke to close the end effector and the second actuation stroke can comprise a staple firing stroke. In such instances, the firing drive can be actuated as many times as needed to fire all of the staples from the staple cartridge.

Figure 23:
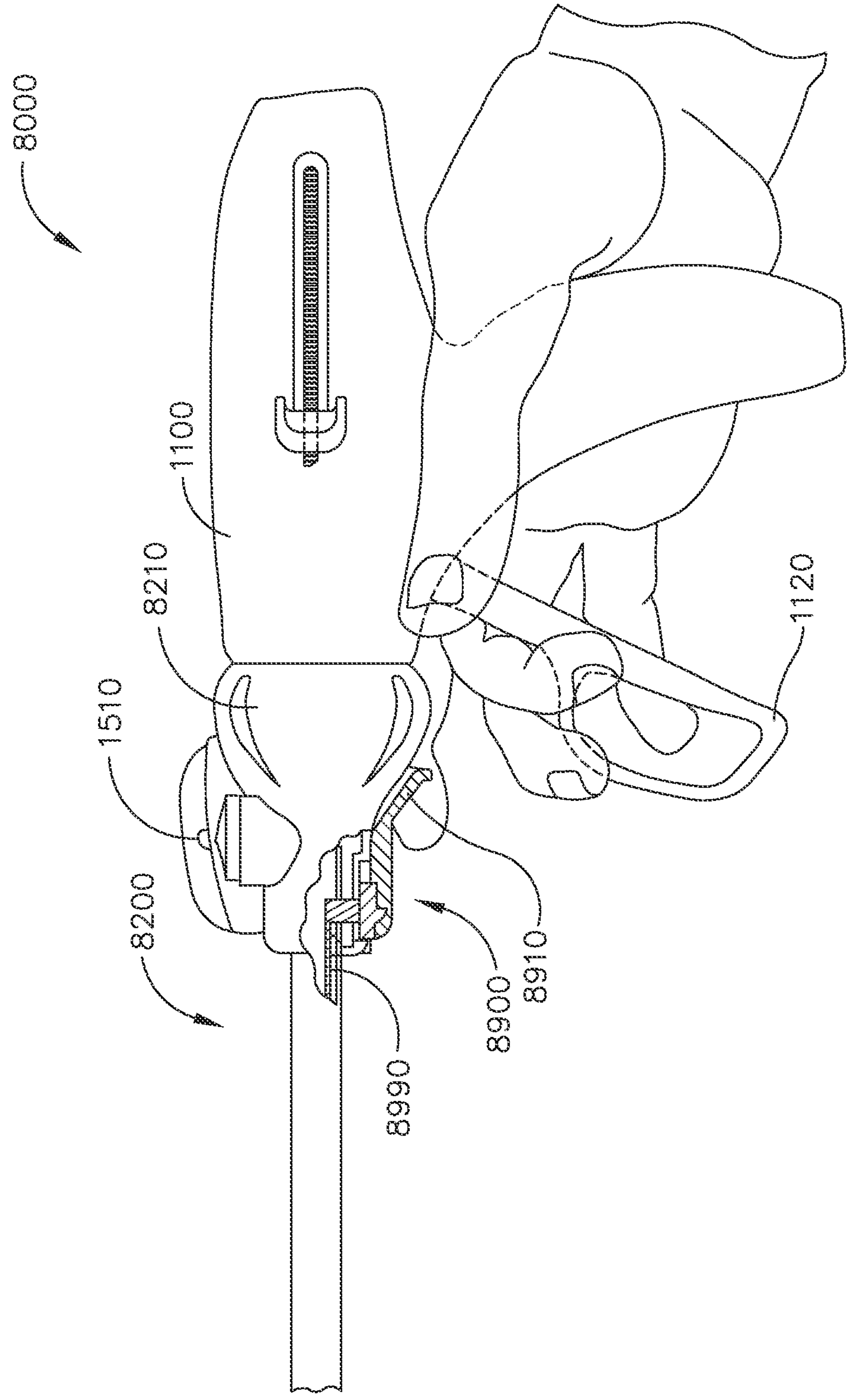
FIG. 23 is a partial elevational view of a stapling instrument comprising a loading unit release actuator in accordance with at least one embodiment.

Referring again to FIG. 1, the loading unit 1300 is removably attachable to the shaft 1200 of the stapling instrument 1000. In various instances, the loading unit 1300 comprises a lock that releasably locks the loading unit 1300 to the shaft 1200. When the stapling instrument 1000 is not positioned in the patient, a clinician can easily move the lock from a locked position to an unlocked position and detach the loading unit 1300 from the shaft 1200. If, however, the loading unit 1300 is positioned in a patient, such as through a trocar or tube, for example, the clinician may not be able to access the lock to disconnect the loading unit 1300 from the shaft 1200. As a result, the options for a clinician to resolve a failure in the stapling instrument 1000 may be limited. Referring to FIG. 23, a stapling instrument 8000 comprises a handle 1100 and a shaft 8200 that is rotatably coupled to the shaft 8200 about a rotation joint positioned within a nozzle grip 8210 of the shaft 8200. Similar to the stapling instrument 1000, the stapling instrument 8000 comprises a loading unit that is releasably attachable to the shaft 8200. The stapling instrument 8000 further comprises a loading unit lock release 8900 which is configured to unlock the loading unit from the shaft 8200. Notably, the lock release 8900 is supported by the shaft 8200 adjacent the handle 1100. More specifically, the lock release 8900 comprises an actuator 8910 slideably mounted to the nozzle grip 8210 such that a clinician holding the handle 1100 can access the actuator 8910 with the same hand and pull the actuator 8910 proximally. The lock release 8900 further comprises an elongate lock bar 8990 including a first end mounted to the actuator 8910 and a second end releasably engaged with the loading unit lock. When the actuator 8910 is in its unactuated position, the loading unit is locked to the shaft 8200. When the actuator 8910 is slid into its actuated position, the loading unit lock is unlocked and the shaft 8200 can be detached from the loading unit. In at least one embodiment, the loading unit lock is rotatable between a locked position and an unlocked position when the actuator 8910 is moved proximally. The lock release 8900 further comprises a spring configured to bias the actuator 8910 back into its actuated position when the clinician releases the actuator 8910. As a result of the above, a clinician can easily unlock the loading unit from the shaft 8200 to resolve a failure in the stapling instrument 8000, such as when the tissue cutting knife in the loading unit becomes stuck during the staple firing stroke and/or cannot otherwise be retracted.

Figure 24:
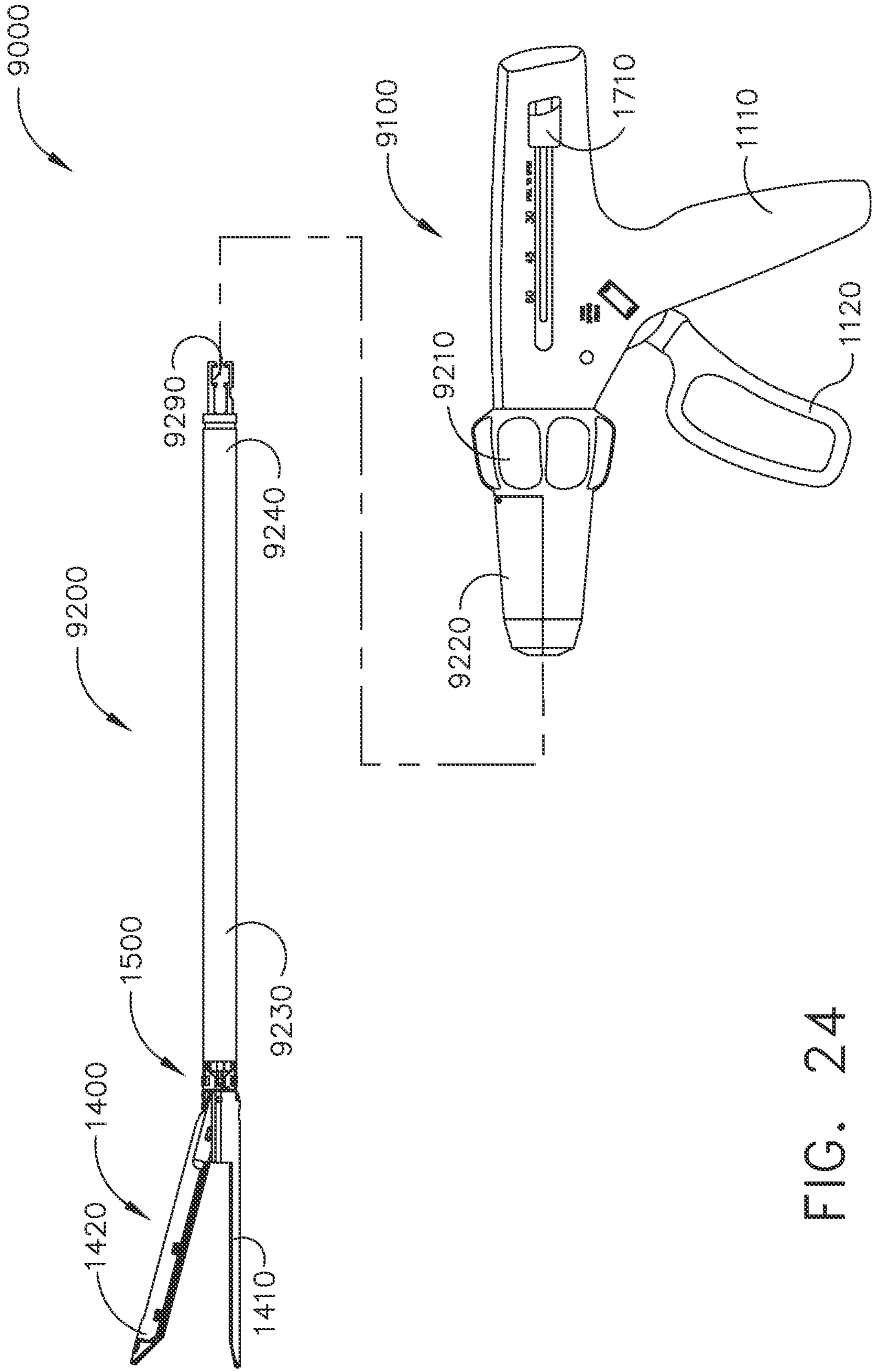
FIG. 24 is an elevational view of a stapling instrument comprising a detachable shaft in accordance with at least one embodiment.

As discussed above, a stapling instrument can comprise a loading unit that is removably attached to a shaft of the stapling instrument. A stapling instrument 9000 is illustrated in FIG. 24 and is similar to the stapling instruments 1000, 2000, and 8000 in many respects, most of which will not be discussed herein for the sake of brevity. The stapling instrument 9000 comprises a handle 9100 and a releasable shaft assembly 9200. The shaft assembly 9200 comprises an end effector 1400, an articulation joint 1500, an elongate portion 9230 extending proximally from the articulation joint 1500, and a proximal attachment end 9240 configured to be attached to a rotatable nozzle grip 9210 of the handle 9100. The nozzle grip 9210 comprises a door, or hatch, 9220 that is rotatable from a closed position to an open position. When the door 9220 is in its closed position, a clinician cannot access the interconnection between the proximal attachment end 9240 and the handle 9100. When the door 9220 is in its open position, however, a clinician can access the interconnection between the proximal attachment end 9240 and the handle 9100 and decouple the shaft assembly 9200 from the handle 9100. The shaft assembly 9200 comprises a shaft frame that is disengageable from a frame of the handle 9100. The shaft assembly 9200 further comprises a firing member 9290 that is disengageable from a firing rack in the handle 9100 and an articulation actuator that is disengageable from an articulation input actuator 1510 (FIG. 23) supported on the nozzle grip 9210. When the shaft assembly 9200 is detached from the handle 9100, the clinician can pull on the proximal end of the firing member 9290 to retract the firing member 9290 proximally and open the end effector 1400. Such an arrangement can be particularly useful in situations where the end effector 1400 has been inserted into a patient through a trocar, or tube, and the end effector 1400 is stuck on the patient tissue, for example. In such instances, the firing member 9290 is accessible from outside of the patient and the trocar. The entire disclosure of U.S. Pat. No. 7,624,902, entitled SURGICAL STAPLING APPARATUS, which issued on Dec. 1, 2009 is incorporated by reference herein. A linear pull bailout, such as those described herein, for example, is usable with the stapling instruments disclosed in U.S. Pat. No. 7,624,902, among others. In any event, the shaft assembly 9200 can be re-assembled to the handle 9100 and re-used once the issue that required the bailout to be used is resolved.

Figure 25:
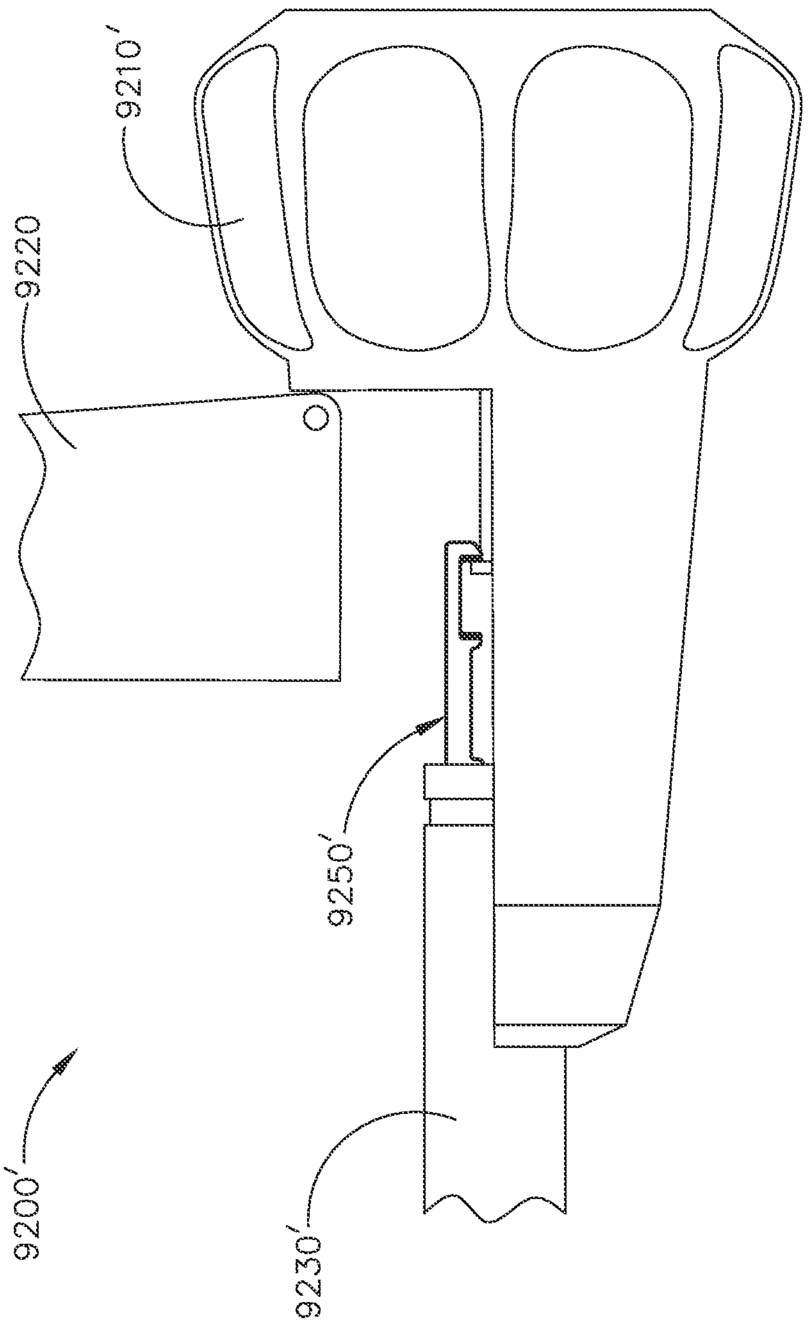
FIG. 25 illustrates a proximal end of a detachable shaft in an open configuration in accordance with at least one embodiment.
Figure 25A:
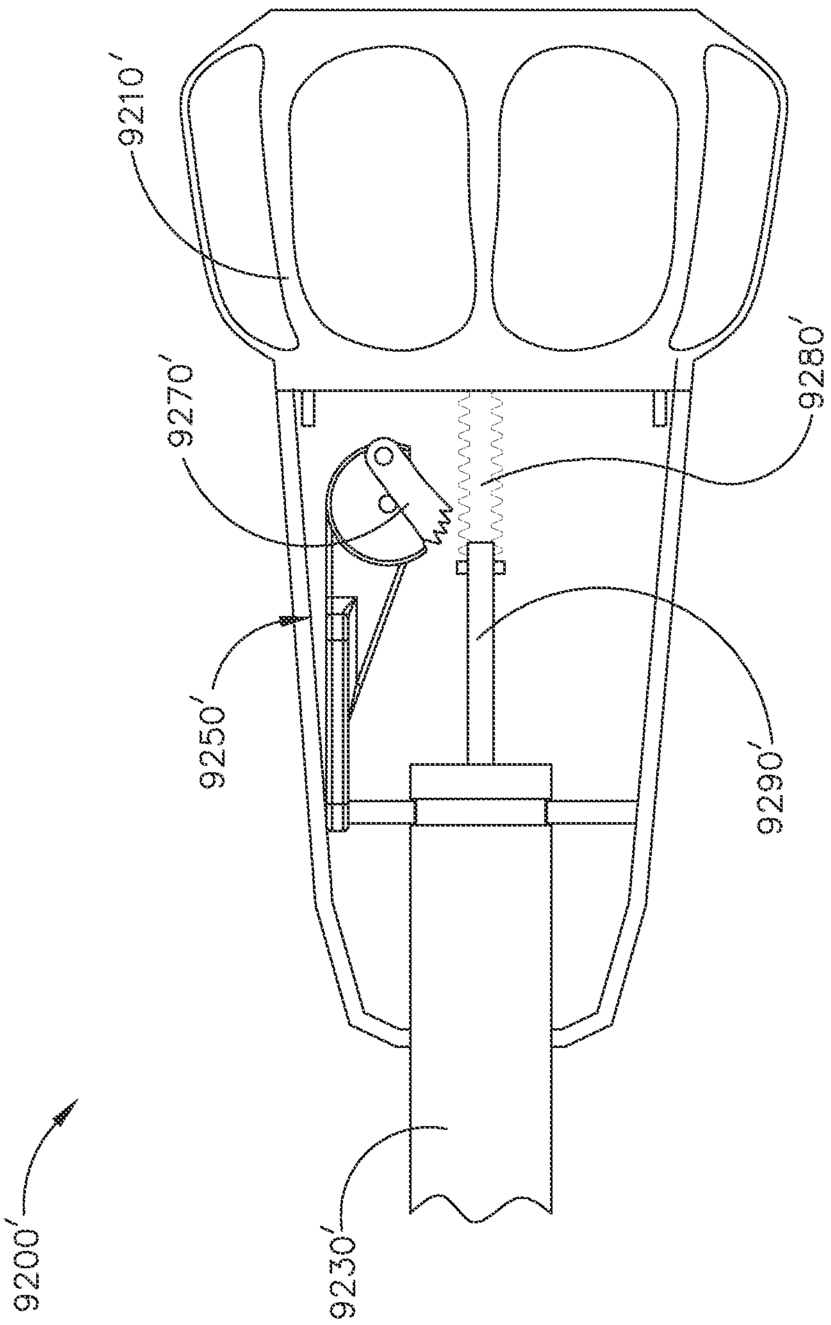
FIG. 25A is a top view of the proximal shaft end of FIG. 25.

In various alternative embodiments, referring to FIG. 25, a shaft assembly 9200' comprises a nozzle grip 9210' and an elongate portion 9230' mounted to the nozzle grip 9210' where the nozzle grip 9210' is releasably attachable to a handle. Similar to the handle nozzle grip 9210, the shaft nozzle grip 9210' comprises an openable door, or hatch, 9220 rotatably mounted to the nozzle grip 9210'. When the door 9220 is open, referring primarily to FIG. 25A, the clinician has access to a bailout mechanism 9250' which is actuatable to engage a ratchet pawl 9270' with a longitudinal rack 9280' defined on the proximal end of a firing member 9290' extending through the shaft 9200'. Thus, when the shaft assembly 9200' has been detached from the handle, the clinician can manually drive the firing member 9290' proximally by ratcheting the bailout mechanism 9250' and open the end effector 1400. The shaft assembly 9200' can be re-assembled to the handle and re-used once the issue that required the bailout to be used is resolved.

Figure 26:
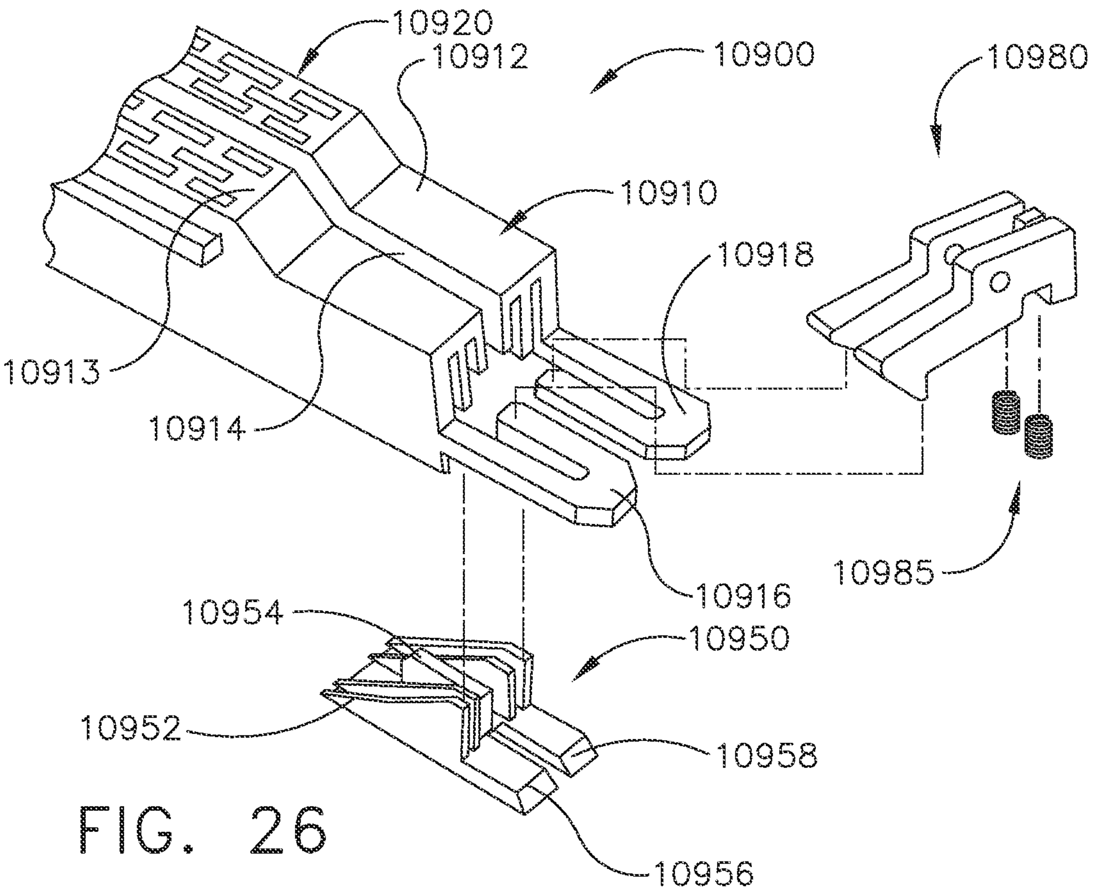
FIG. 26 is a partial exploded view of a staple cartridge in accordance with at least one embodiment.
Figure 26A:
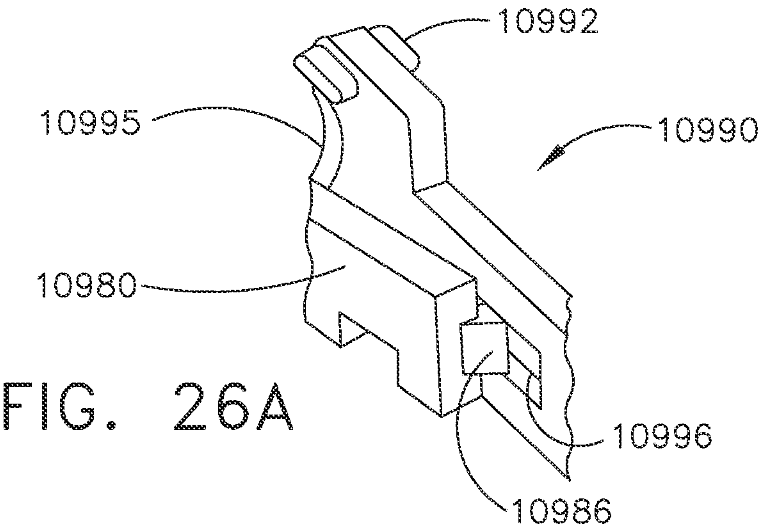
FIG. 26A is a partial perspective view of a firing member in a locked condition.

A staple cartridge 10900 for use with a stapling instrument is illustrated in FIG. 26. The staple cartridge 10900 comprises a cartridge body 10910 including a proximal end 10912, a distal end, a deck 10913 extending between the proximal end 10912 and the distal end, and longitudinal rows of staple cavities 10920 defined in the deck 10913. The cartridge body 10910 further comprises a longitudinal slot 10914 extending from the proximal end 10912 toward the distal end. The staple cavities 10920 are arranged in three longitudinal rows on each side of the longitudinal slot

10914, although embodiments are envisioned in which the staple cavities 10920 are arranged in two longitudinal rows on each side of the longitudinal slot 10914. That said, the staple cavities 10920 can be arranged in any suitable number of longitudinal rows and/or oriented in any suitable manner. A staple is removably stored in each staple cavity 10920; however, alternative embodiments are envisioned in which a staple is not positioned in each staple cavity 10920. In at least one such embodiment, the outermost rows of staple cavities 10920 do not have a staple in each staple cavity 10920. Such an embodiment may provide a more flexible staple line in the stapled tissue. The cartridge body 10910 further comprises lock supports 10916 and 10918 extending proximally from the proximal end 10912, which are discussed in greater detail further below.

Figure 27:
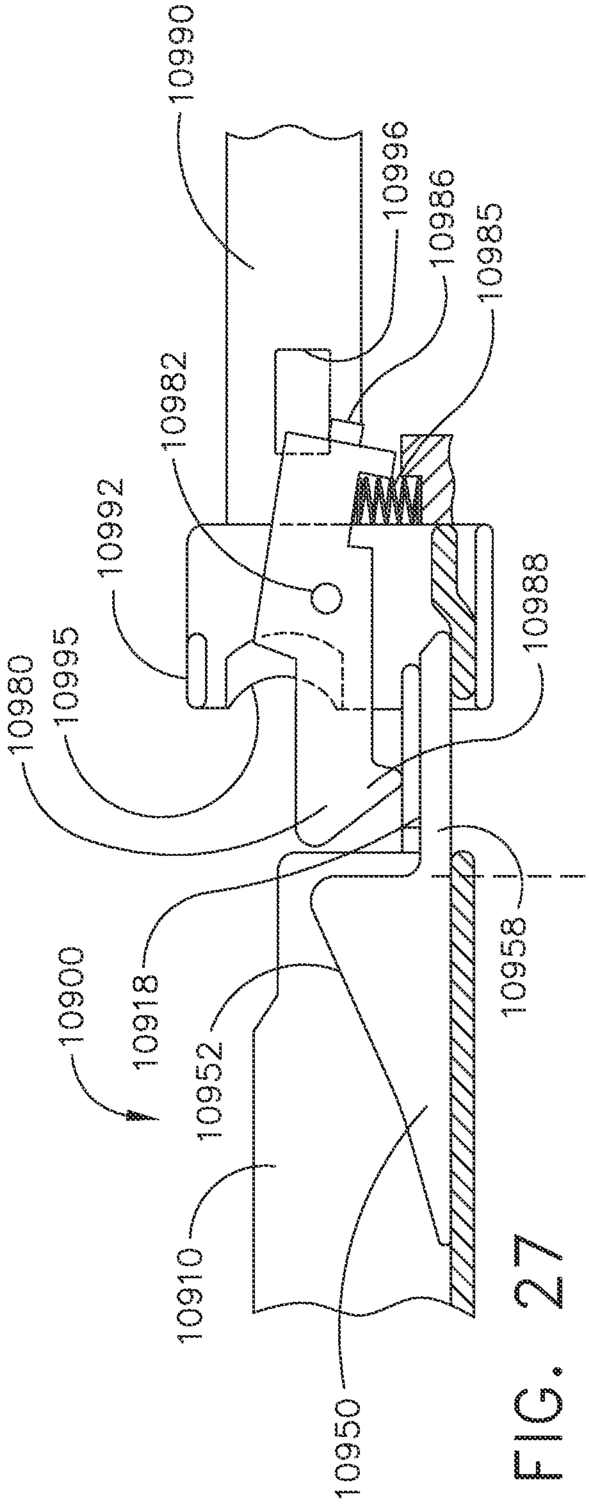
FIG. 27 is a partial cross-sectional view of the staple cartridge of FIG. 26 and the firing member of FIG. 26A in an unlocked condition.

The staple cartridge 10900 further comprises staple drivers and a sled 10950. The sled 10950 is positioned in the cartridge body 10910 and is movable from a proximal unfired position to a distal fired position by a firing member 10990 during a staple firing stroke. The sled 10950 comprises a center portion 10954 positioned in the longitudinal slot 10914 and ramps 10952 positioned on opposite sides of the central portion 10954. As the sled 10950 is progressed distally by the firing member 10990 during the staple firing stroke, the ramps 10952 contact the staple drivers and drive the staple drivers and the staples toward an anvil of the stapling instrument positioned opposite the staple cartridge 10900. The sled 10950 further comprises lock supports 10956 and 10958 extending proximally therefrom. When the sled 10950 is in its proximal unfired position, referring to FIG. 27, the lock support 10956 of the sled 10950 extends under the lock support 10916 of the cartridge body 10910 and, similarly, the lock support 10958 of the sled 10950 extends under the lock support 10918 of the cartridge body 10910. In such instances, the sled lock supports 10956 and 10958 co-operate with the cartridge lock supports 10916 and 10918 to hold a firing lockout of the stapling instrument in an unlocked position. More specifically, the firing lockout comprises two lock arms 10980 rotatably mounted to a shaft of the stapling instrument about pivot pins 10982 which are held in an unlocked position by the lock supports 10916, 10918, 10956, and 10958 when the sled 10950 is in its proximal unfired position, as illustrated in FIG. 27. In such instances, the distal ends 10988 of the lock arms 10980 are held in position by the lock supports 10916, 10918, 10956, and 10958 against a biasing force applied to their proximal ends by springs 10985 compressed between the lock arms 10980 and a shaft frame of the stapling instrument. Moreover, each lock arm 10980 further comprises an inwardly-extending lock 10986 that, in such instances, is not engaged with a lock window 10996 defined in the firing member 10990 and, as a result, the firing member 10990 can be moved distally to push the sled 10950 through the staple firing stroke.

Figure 28:
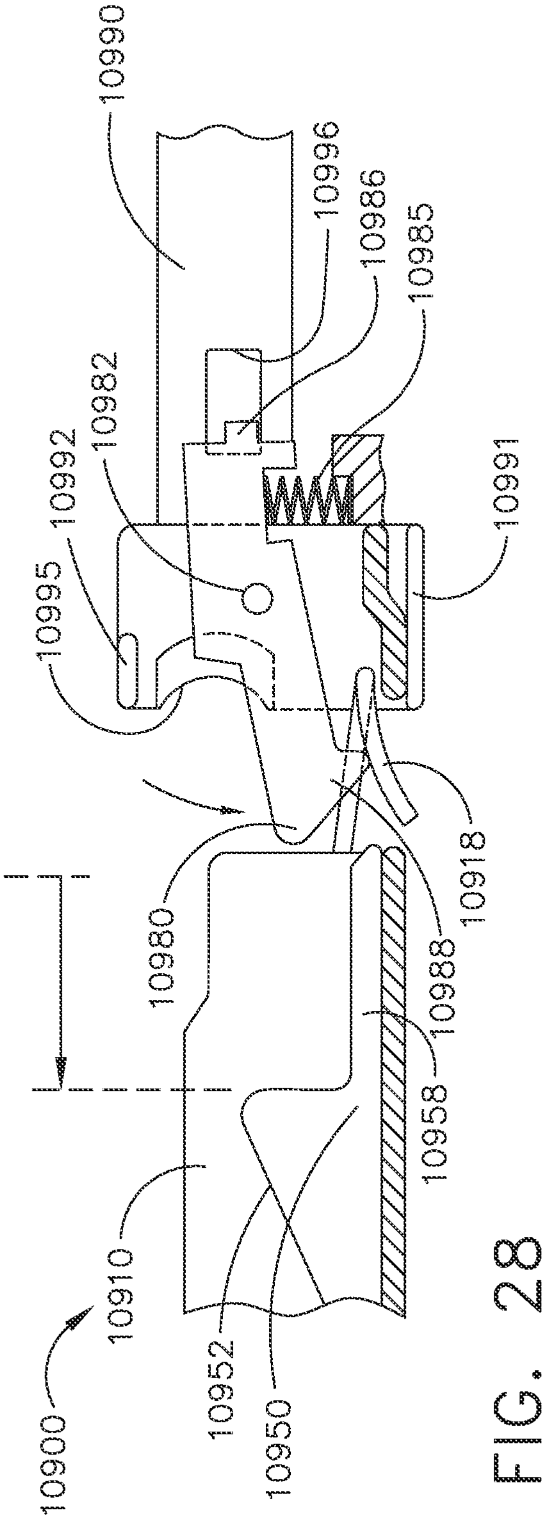
FIG. 28 is a partial cross-sectional view of the staple cartridge of FIG. 26 and the firing member of FIG. 26A in the locked condition of FIG. 26A.

When the sled 10950 is advanced distally during the staple firing stroke, referring to FIG. 28, the sled lock supports 10956 and 10958 are no longer positioned under the cartridge lock supports 10916 and 10918. The cartridge lock supports 10916 and 10918 are not strong enough by themselves to support the lock arms 10980 in their unlocked positions owing to the biasing forces being applied to the proximal ends of the lock arms 10980 by the springs 10985. As such, the cartridge lock supports 10916 and 10918, which comprise cantilevers, deflect downwardly under the load being applied thereto thereby allowing the lock arms 10980 to rotate into the locked positions. Notably, at this point, the firing member 10990 has already been advanced distally, at least partially, and the lock windows 10996 defined in the firing member 10990 are no longer aligned with the inwardly-extending locks 10986 of the lock arms 10980. As such, the distal movement of the firing member 10990 during the rest of the staple firing stroke is unimpeded by the lock arms 10980. When the firing member 10990 is retracted back into its unactuated position after the staple firing stroke, however, the inwardly-extending locks 10986 of the lock arms 10980 swing into the lock windows 10996 of the firing member 10990. In such instances, the lock arms 10980 provide a gate that prevents the firing member 10990 from being advanced distally through another staple firing stroke through the now-spent staple cartridge 10900 positioned in the cartridge jaw. In order to reset the stapling instrument so that it can be used once again, the spent staple cartridge 10900 must be removed from the cartridge jaw and replaced with another unspent staple cartridge 10900. In such instances, the lock arms 10980 are rotated back into their unlocked positions by the lock supports 10916, 10918, 10956, and 10958 of the new, or unspent, staple cartridge 10900. The reader should appreciate that this lockout system serves as both a spent cartridge lockout and as a missing cartridge lockout. The entire disclosure of U.S. Pat. No. 9,566,064, entitled SURGICAL STAPLING APPARATUS, which issued on Feb. 14, 2017 is incorporated by reference herein.

Further to the above, the sled lock supports 10956 and 10958 are in contact with the cartridge lock supports 10916 and 10918 when the sled 10950 is in its proximal unfired position. In such instances, the cartridge lock supports 10916 and 10918 releasably hold the sled 10950 in its proximal unfired position until the sled 10950 is pushed distally by the firing member 10990 owing to frictional resistance between the cartridge lock supports 10916 and 10918 and the sled lock supports 10956 and 10958, respectively. Such an arrangement can prevent, or at least inhibit, the sled 10950 from being moved distally accidentally prior to the staple firing stroke.

Figure 26B:
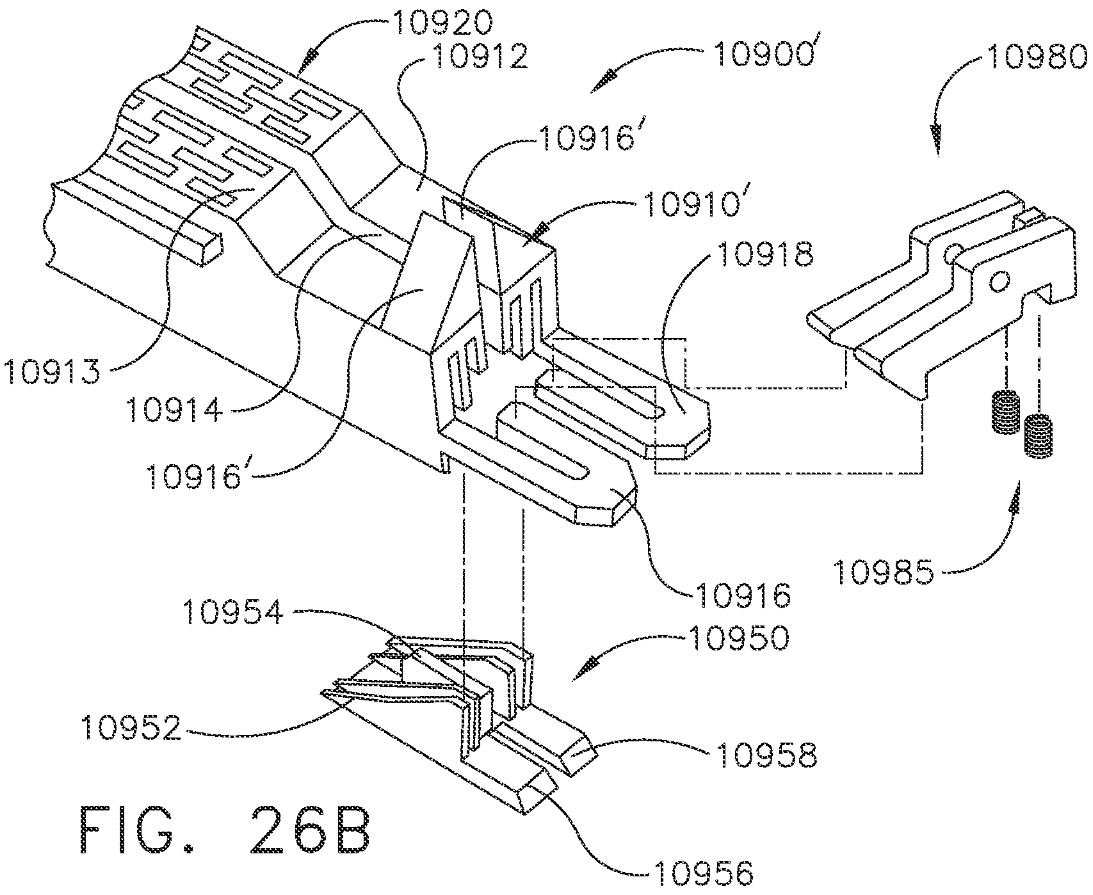
FIG. 26B is a partial exploded view of a staple cartridge in accordance with at least one embodiment.
Figure 26C:
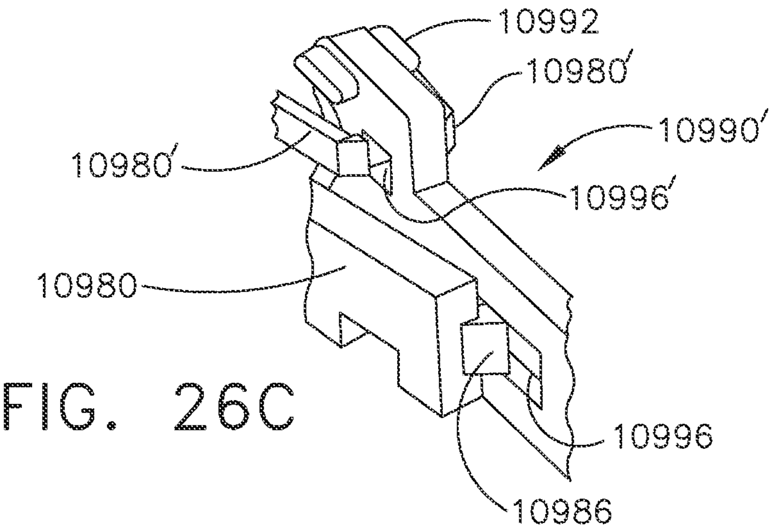
FIG. 26C is a partial perspective view of a firing member in a locked condition by two sets of lockouts.

In various embodiments, further to the above, the lock arms 10980 can also serve as a closure lockout. More specifically, as discussed above, the firing member 10990 is advanceable distally to close the end effector of the surgical instrument and then advanceable distally again to perform a staple firing stroke. If the firing member 10990 is not unlocked by the staple cartridge 10900 as discussed above, then the lock arms 10980 would be engaged with the firing member 10990 at the outset of the closure stroke and, as a result, the firing member 10990 would not be advanceable distally to close the end effector. In various alternative embodiments, the lock windows 10996 defined in the firing member 10990 are sized and configured to permit the firing member 10990 to move distally far enough to close the end effector even if the lock arms 10980 have not been moved into their unlocked positions by an unfired staple cartridge 10900. In such embodiments, referring to FIGS. 26B and 26C, the stapling instrument can further comprise a separate closure lockout which prevents the end effector from closing if a staple cartridge is missing from the stapling instrument, as discussed further below.

In various embodiments, a surgical instrument can further comprise lock arms 10980' which are rotatable between a locked position in which they are engaged with a sidewall of a lock window 10986' defined in a firing member 10990' and an unlocked position in which the lock arms 10980' are not engaged with the firing member 10990'. A staple cartridge 10900', which is similar to the staple cartridge 10900 in many respects, comprises closure keys 10916' extending from a cartridge body 10910' of the staple cartridge 10900' which can engage the lock arms 10986' and move the lock arms 10986' into their unlocked position. In at least one embodiment, the closure keys 10916' of the staple cartridge 10900' unlock the lock arms 10986' when the staple cartridge 10900' is seated in the surgical instrument. At such point, the firing member 10990' is in an unlocked closure state and can be advanced distally to perform a closure stroke to close the end effector. That said, whether or not the firing member 10990' is an unlocked firing state to then perform a staple firing stroke is determined by the position of the lock arms 10980, as discussed above.

In various alternative embodiments, further to the above, the closure keys 10916' do not automatically unlock the lock arms 10980' when the staple cartridge 10900' is seated in the surgical instrument. Instead, the closure keys 10916' can engage the lock arms 10980' when the cartridge jaw supporting the staple cartridge 10990' is moved toward its closed, or clamped, position. In such embodiments, the lock window 10996' defined in the firing member 10990' is sized and configured to permit some initial distal movement of the firing member 10990' when the closure stroke is initiated and, if the closure keys 10916' engage and unlock the lock arms 10980' during this initial movement, the firing member 10990' enters into its unlocked closure state and can be advanced distally to complete the closure stroke. If, however, the staple cartridge seated in the cartridge jaw does not comprise the closure keys 10916', the lock arms 10980' are not unlocked by the initial movement of the firing member 10990' and the lock arms 10980' will stop the firing member 10990' from completing the closure stroke. Such an arrangement can prevent incompatible staple cartridges from being used with a surgical instrument.

Figure 29:
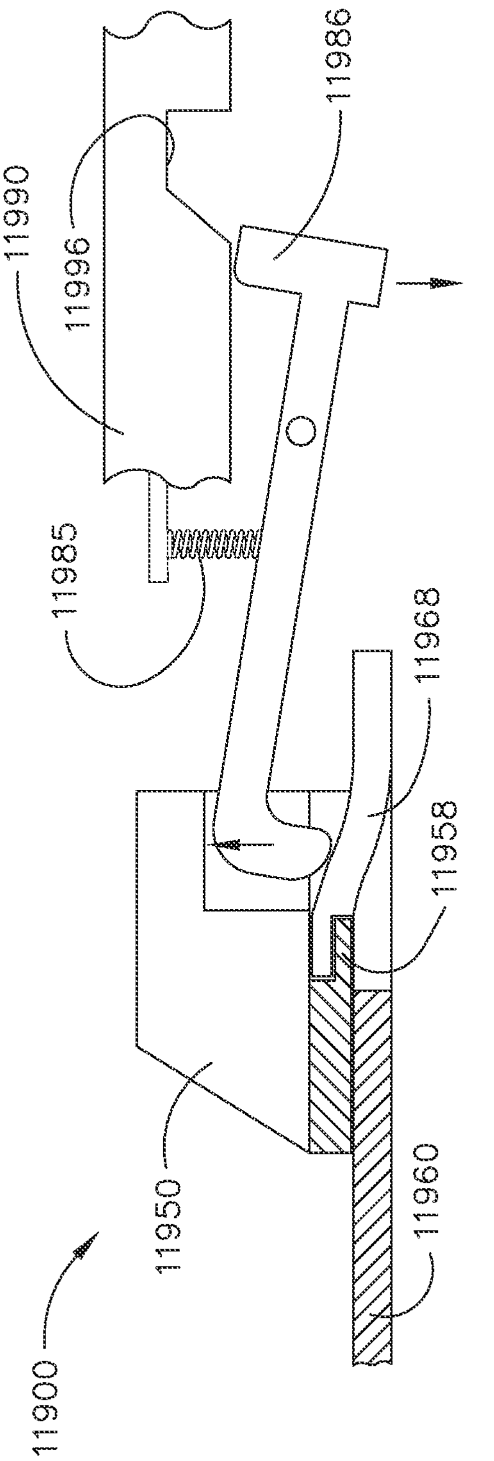
FIG. 29 is a partial cross-sectional view of a staple cartridge and a firing member in an unlocked condition in accordance with at least one embodiment.
Figure 30:
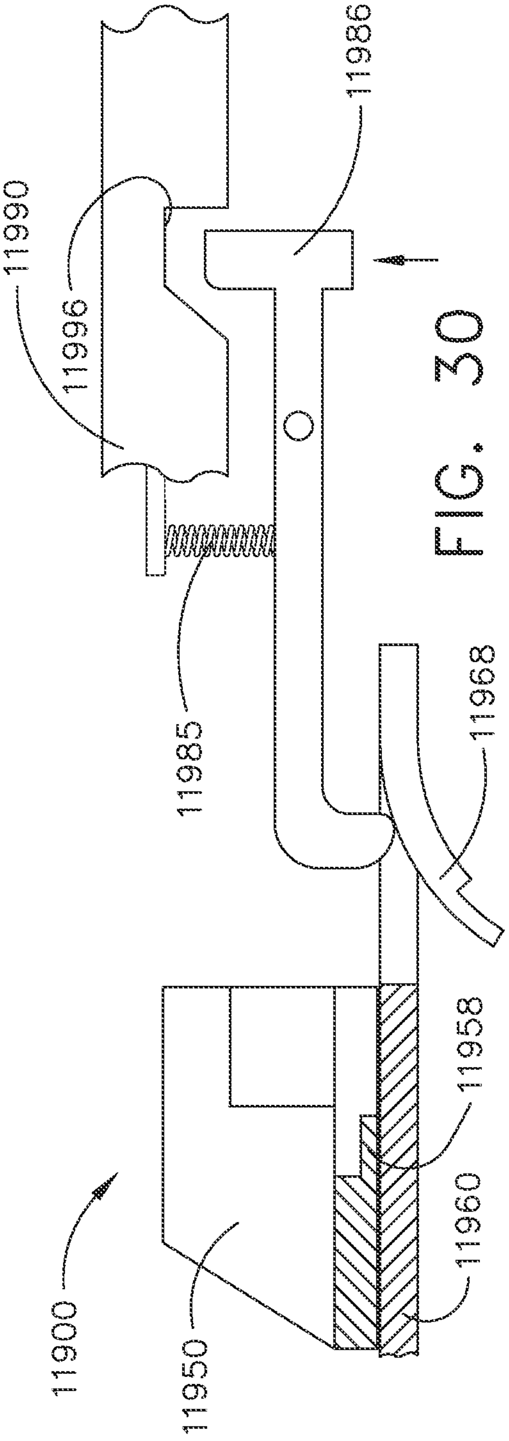
FIG. 30 is a partial cross-sectional view of the staple cartridge and firing member of FIG. 29 illustrating the firing member in a locked condition.

The firing lockout discussed above in connection with FIGS. 26-26C keys off of the presence of the sled 10950 being positioned in the proximal end of the staple cartridge 10900 when the staple firing stroke is initiated. Another embodiment is illustrated in FIG. 29 which comprises a staple cartridge 11900 for use with a stapling instrument comprising a firing lockout. The staple cartridge 11900 comprises a cartridge body, staple drivers, and staples removably stored in staple cavities defined in the cartridge body. The staple cartridge 11900 further comprises a sled 11950 including a lock support 11958 that is moved from a proximal unfired position (FIG. 29) to a distal fired position (FIG. 30) by a tissue cutting knife 11990 of the stapling instrument during a staple firing stroke. The staple cartridge 11900 further comprises a pan 11960 attached to the cartridge body which prevents the staple drivers and/or staples from falling out of the bottom of the cartridge body. The pan 11960 comprises a lock support 11968 which sits on top of the lock support 11958 of the sled 11950 when the sled 11950 is in its proximal unfired position (FIG. 29). In such instances, the pan lock support 11968 and the sled lock support 11958 co-operate to hold a lock arm 11980 of the stapling instrument in an unlocked position against a biasing force being applied to the lock arm 11980 by a biasing spring 11985 positioned intermediate the lock arm 11980 and a frame of the stapling instrument. In such instances, a lock end 11986 of the lock arm 11980 is not positioned in a lock notch 11996 defined in the tissue cutting knife 11990 and, as a result, the tissue cutting knife 11990 can be moved distally through the staple firing stroke. When the sled 11950 is moved distally by the tissue cutting knife 11990, referring to FIG. 30, the sled lock support 11958 no longer supports the pan lock support 11968 and, as a result, the biasing spring 11985 pushes the lock arm 11980 downwardly which bends, or deflects, the pan lock support 11968 downwardly. At such point, the lock notch 11996 is no longer aligned with the lock end 11986 of the lock arm 11980 and, as a result, the lock end 11986 is pushed against the bottom of the tissue cutting knife 11990 by the spring 11985 throughout the remainder of the staple firing stroke. When the tissue cutting knife 11990 is retracted, however, the lock notch 11996 is re-aligned with the lock end 11986 which is pushed into the lock notch 11996 by the spring 11985. In such instances, the tissue cutting knife 11990 is locked from being advanced distally through another staple firing stroke without the spent staple cartridge 11900 being replaced with an unspent staple cartridge 11900. The reader should appreciate that this lockout system serves as both a spent cartridge lockout and as a missing cartridge lockout.

Figure 31:
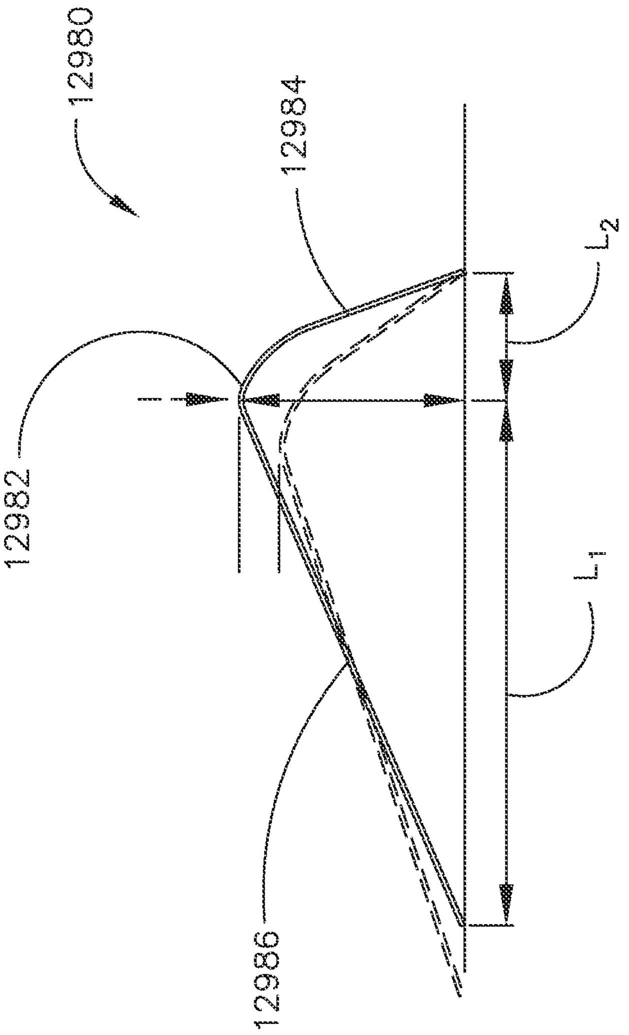
FIG. 31 illustrates a spent cartridge/missing cartridge lockout in accordance with at least one embodiment.
Figures 31A, 31B, 31C, 31D:
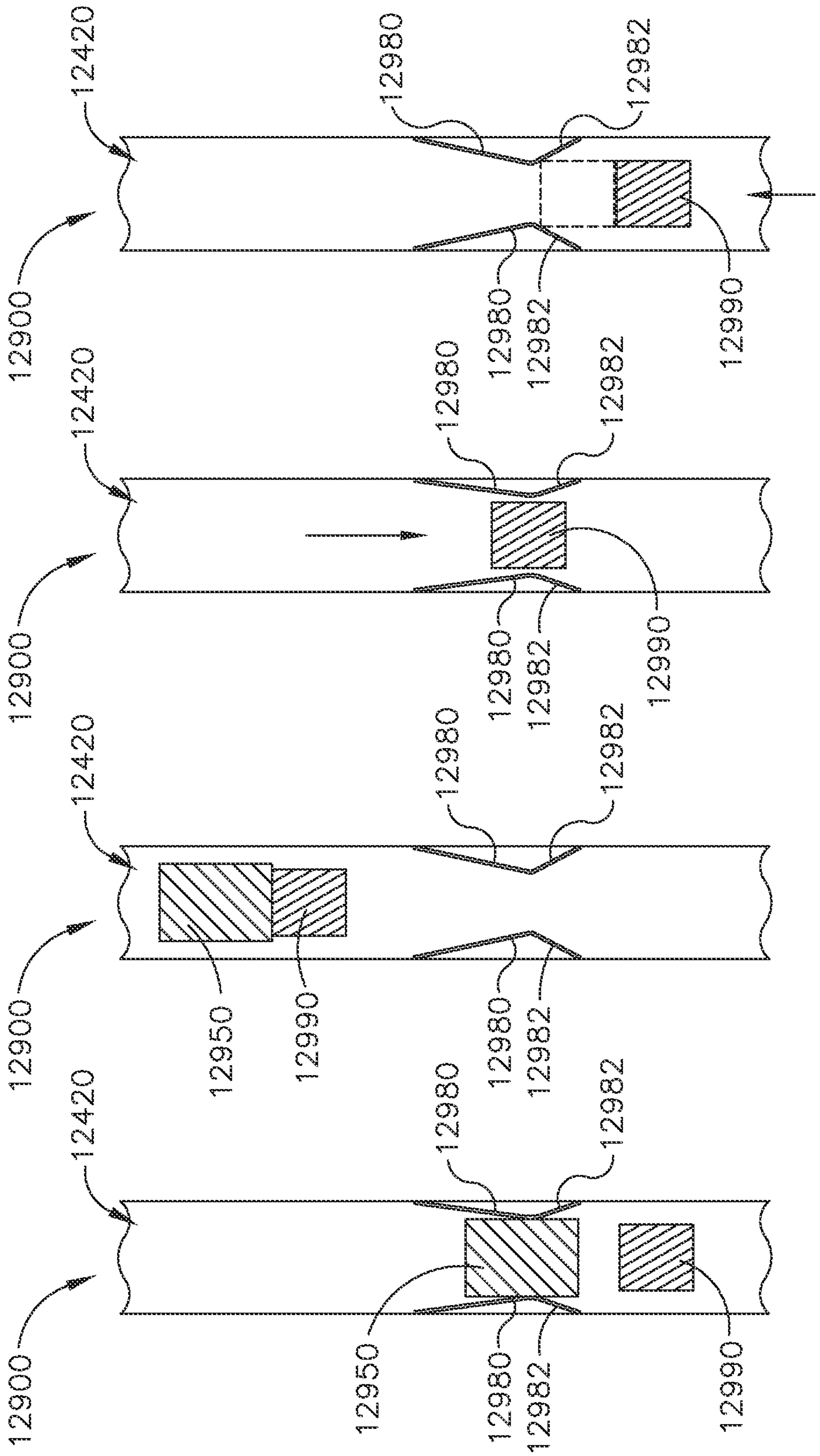
FIG. 31A illustrates a staple cartridge including a sled holding the lockout of FIG. 31 in an unlocked condition.
FIG. 31B illustrates the sled of FIG. 31A being advanced distally through a staple firing stroke by a firing member.
FIG. 31C illustrates the firing member of FIG. 31B being retracted after the staple firing stroke.
FIG. 31D illustrates the lockout of FIG. 31 in a locked condition preventing the firing member from being moved through another firing stroke.

A staple cartridge 12900 comprising a spent cartridge lockout is illustrated in FIGS. 31-31D. The staple cartridge 12900 comprises a cartridge body including longitudinal rows of staple cavities, staples positioned within the staple cavities, and a sled 12950 movable from a proximal unfired position (FIG. 31A) to a distal fired position (FIG. 31B) to eject the staples from the staple cavities. The staple cartridge 12900 is seatable in a cartridge jaw 12420 of a stapling instrument such that the sled 12950 is positioned in front of a tissue cutting knife 12990 of the stapling instrument. When the sled 12950 is in its proximal unfired position, referring to FIG. 31A, the sled 12950 is held in position between two springs 12980 extending from the cartridge body positioned on opposite sides of the sled 12950. Referring to FIG. 31, each spring 12980 comprises an apex 12982, a proximal side 12984 on the proximal side of the apex 12982, and a distal side 12986 on the distal side of the apex 12982. When the sled 12950 is in its proximal unfired position, as illustrated in FIG. 31A, the sled 12950 is wedged between the apexes 12982 of the springs 12980 and compresses the springs 12980 laterally. Stated another way, the sled 12950 holds open a larger opening between the springs 12980 such that the tissue cutting knife 12990 can move between the springs 12980 to push the sled 12950 distally through the staple firing stroke, which is illustrated in FIG. 31B. During the staple firing stroke, the springs 12980 resiliently return to their unflexed states to partially close the gap between the apexes 12982 of the springs 12980 owing to the absence of the sled 12950 positioned therebetween. After the staple firing stroke, referring to FIG. 31C, the tissue cutting knife 12990 is retracted proximally until it contacts the distal sides 12986 of the springs 12980. The distal sides 12986 are angled, or sloped, such that the tissue cutting knife 12990 can deflect the springs 12980 laterally as the tissue cutting knife 12990 is retracted proximally until the tissue cutting knife 12990 passes by the springs 12980. At such point, the springs 12980 resiliently return to their unflexed configurations to partially close the gap between the spring apexes 12988, as illustrated in FIG. 31D. Notably, the sled 12950 is not retracted proximally with the tissue cutting knife 12990 and, as such, the sled 12950 is not positioned to expand the gap between the spring axes 12982 after the staple firing stroke. If the tissue cutting knife 12990 is advanced distally once again without replacing the now-spent staple cartridge 12900, the tissue cutting knife 12990 contacts the proximal sides 12984 of the springs 12980 in their unflexed state and, owing to slope or angle of the proximal sides 12984, the tissue cutting knife 12990 is unable to pass by the springs 12980. Such an arrangement, as a result, provides a spent cartridge lockout. When the spent staple cartridge is replaced with an unspent staple cartridge, the tissue cutting knife 12990 can be advanced distally through another staple firing stroke.

As described above, referring again to FIG. 31, the proximal sides 12984 of the springs 12980 and the distal sides 12986 of the springs 12980 extend at different angles. More specifically, the distal sides 12986 extend at more shallow angles than the proximal sides 12984. Another way of describing this arraignment is that the distal sides 12986 have a length L1 which is longer than the length L2 of the proximal sides 12984. In various embodiments, the springs 12980 are comprised of metal, for example. In at least one such embodiment, the springs 12980 are part of a metal pan extending under and attached to the staple cartridge 12900. In another embodiment, the springs 12980 comprise metal inserts in a plastic cartridge body of the staple cartridge 12900. In various other embodiments, the springs 12980 are comprised of plastic and are integrally formed with a plastic cartridge body of the staple cartridge 12900, for example.

Figure 32:
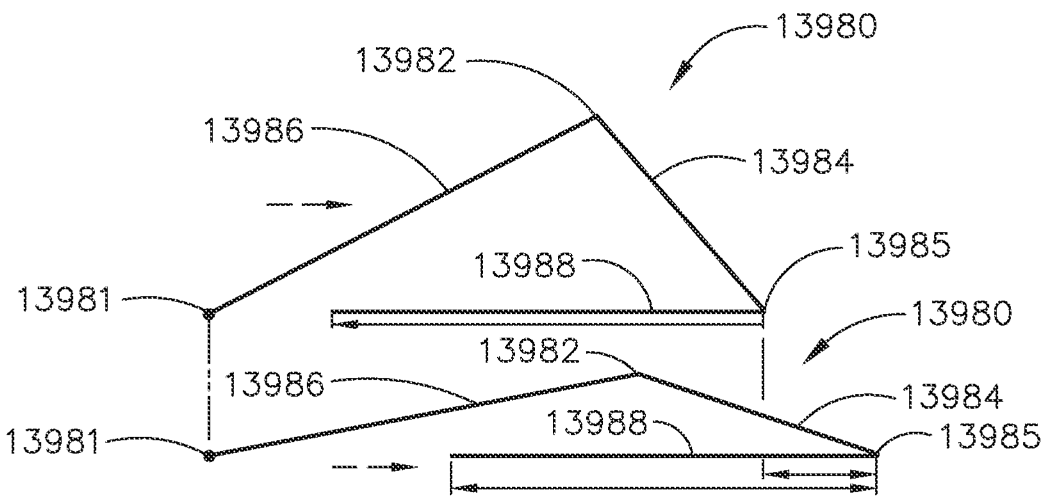
FIG. 32 illustrates a spent cartridge/missing cartridge lockout in accordance with at least one embodiment.
Figure 33:
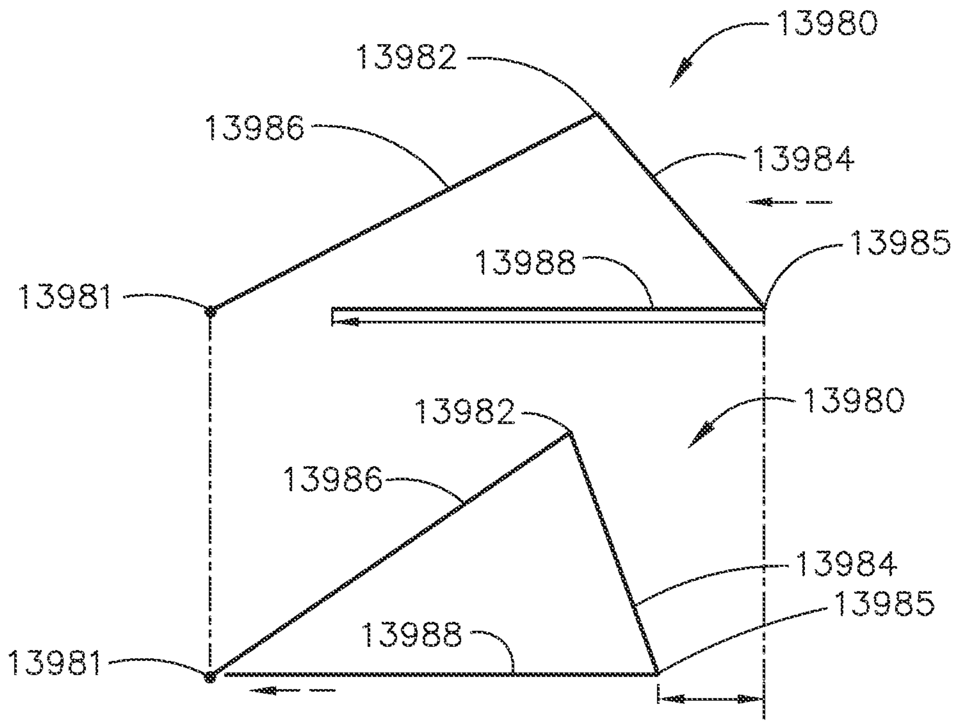
FIG. 33 illustrates the lockout of FIG. 32 in a locked condition.

An alternative spent cartridge lockout comprising springs 13980 is illustrated in FIG. 32. The springs 13980 are connected to the cartridge body and/or the pan of the staple cartridge at a pivot 13981 and, similar to the springs 12980, are held in a compressed state by the sled 12950 when the sled 12950 is in its proximal unfired position such that the tissue cutting knife 12990 can pass between the springs 13980 to push the sled 12950 through its staple firing stroke. Each spring 13980 comprises a proximal link 13984 and a distal link 13986 connected at an apex 13982 of the spring 13980. The apex 13982 comprises a pivot joint connecting the proximal link 13984 and the distal link 13986. In at least one embodiment, the apex 13982 includes a score or notch in the body of the spring 13980 which allows the links 13984 and 13986 to pivot relative to one another. Each spring 13980 further comprises a base link 13988 pivotably mounted to the proximal link 13984 at a pivot 13985. Similar to the above, the pivot 13985 can comprise a score or notch in the body of the spring 13980, for example. Notably, the base link 13988 comprises a free end which is unconnected to any other portion of the staple cartridge that allows the base link 13988 to slide relative to the cartridge body. When the tissue cutting knife 12990 is retracted after the staple firing stroke, referring to FIG. 32, the tissue cutting knife 12990 passes over the pivots 13981 and contacts the distal links 13986. Owing to the free ends of the base links 13988, the springs 13980 collapse to permit the tissue cutting knife 12990 to be retracted to its proximal unfired position. In such instances, the base links 13988 slide proximally to accommodate this change in the configuration of the springs 13980. Once the tissue cutting knife 12990 is retracted past the springs 13980, the springs 13980 resiliently return to their unflexed shape. If the spent staple cartridge is not replaced and the tissue cutting knife 12990 is advanced distally once again, referring to FIG. 33, the tissue cutting knife 12990 contacts the proximal links 13984 of the springs 13980 and pushes the base links 13988 distally which, in turn, pushes the opposing apexes 13982 toward one another to close the gap between the springs 13980 to prevent the tissue cutting knife 12990 from being moved through the spent staple cartridge. When the spent staple cartridge is replaced with an unspent staple cartridge, the tissue cutting knife 12990 can be advanced distally through another staple firing stroke.

In various embodiments, as discussed above, a spent staple cartridge is replaceable with an unspent staple cartridge. In certain embodiments, referring to FIG. 1, a staple cartridge, such as staple cartridge 1900, for example, is snap-fit into the cartridge jaw 1420. In at least one such embodiment, the staple cartridge 1900 is positioned between the anvil jaw 1410 and the cartridge jaw 1420 with the pan of the staple cartridge 1900 facing toward the cartridge jaw 1420 and the deck of the staple cartridge 1900 generally facing the anvil jaw 1410. With the proximal end of the staple cartridge 1900 being aligned with the proximal end of the cartridge jaw 1420 and the distal nose of the staple cartridge 1900 extending from the distal end of the cartridge jaw 1420, the clinician pushes down on the deck of the staple cartridge 1900 to seat the staple cartridge 1900 in the cartridge jaw 1420. In many instances, a considerable amount of force is needed to insert the staple cartridge 1900 into the cartridge jaw 1420. To remove the staple cartridge 1900 from the cartridge jaw 1420, an impact force is often applied to the nose of the staple cartridge 1900 to dislodge the staple cartridge 1900 from its snap-fit arrangement with the cartridge jaw 1420. Although this design is suitable for its intended purpose, improvements to this design are discussed below.

Figure 34:
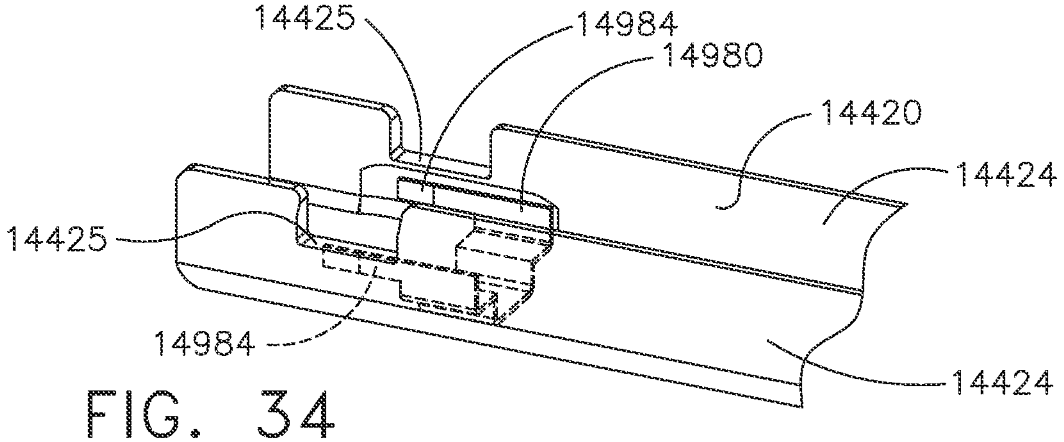
FIG. 34 is a partial perspective view of a stapling instrument including a cartridge lock configured to lock a staple cartridge into a cartridge jaw in accordance with at least one embodiment.
Figure 35:
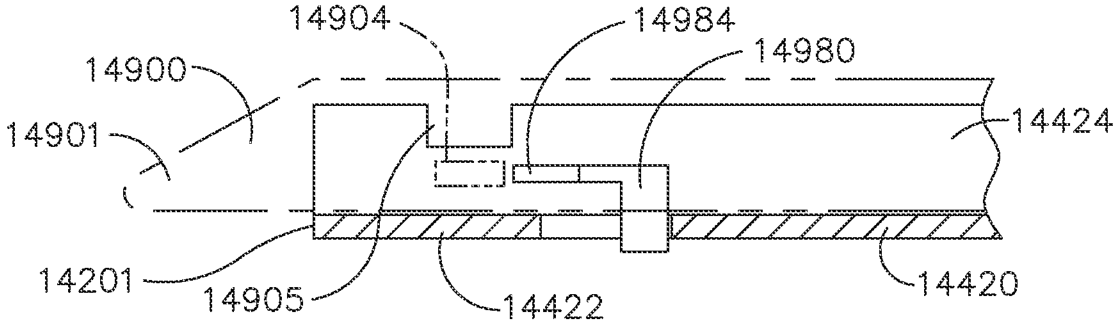
FIG. 35 is a partial cross-sectional view of a staple cartridge seated in the cartridge jaw of FIG. 34 illustrating the cartridge lock of FIG. 34 in an unlocked state.
Figure 36:
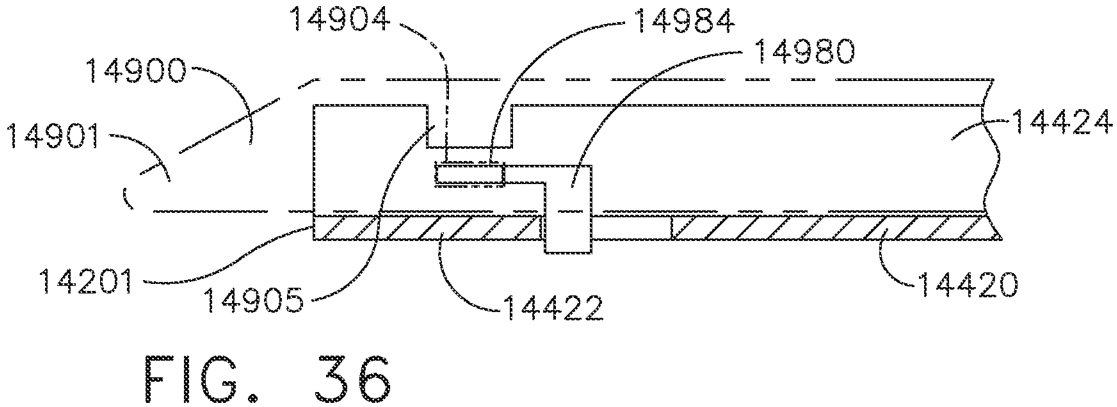
FIG. 36 is a partial cross-sectional view illustrating the cartridge lock of FIG. 34 in a locked state.

Referring to FIGS. 34-36, a stapling instrument comprises a cartridge jaw 14420 configured to releasably receive a staple cartridge 14900 therein. Similar to the cartridge jaw 1420, the cartridge jaw 14420 comprises a bottom wall 14422 and opposing lateral sidewalls 14424 extending upwardly from the bottom wall 14422. The walls 14422 and 14424 are comprised of metal, such as stainless steel, for example, but could be comprised of any suitable metal. The staple cartridge 14900 is configured to be closely received between the lateral sidewalls 14420 when the staple cartridge 14900 is seated in the cartridge jaw 14420 such that there is no relative lateral movement between the staple cartridge 14900 and the cartridge jaw 14420. In various instances, there is a line-to-line lateral fit between the staple cartridge 14900 and the cartridge jaw 14420 with little, if any, clearance therebetween. The cartridge jaw 14420 further comprises alignment notches 14425 defined in the lateral sidewalls 14424 which are configured to closely receive alignment projections 14905 extending from the staple cartridge 14900. The alignment notches 14425 and the alignment projections 14905 are sized and configured to co-operatively align the staple cartridge 14900 longitudinally within the cartridge jaw 14420. Moreover, the alignment notches 14425 and the alignment projections 14905 are sized and configured such that there is no relative longitudinal movement between the staple cartridge 14900 and the cartridge jaw 14420. In various instances, there is a line-to-line fit between the alignment notches 14425 and the cartridge jaw 14420 with little, if any, clearance therebetween. In various instances, further to the below, the fit between the staple cartridge 14900 and the cartridge jaw 14420 may be a slight friction fit and/or a zero-insertion-force (ZIF) fit.

Figure 37:
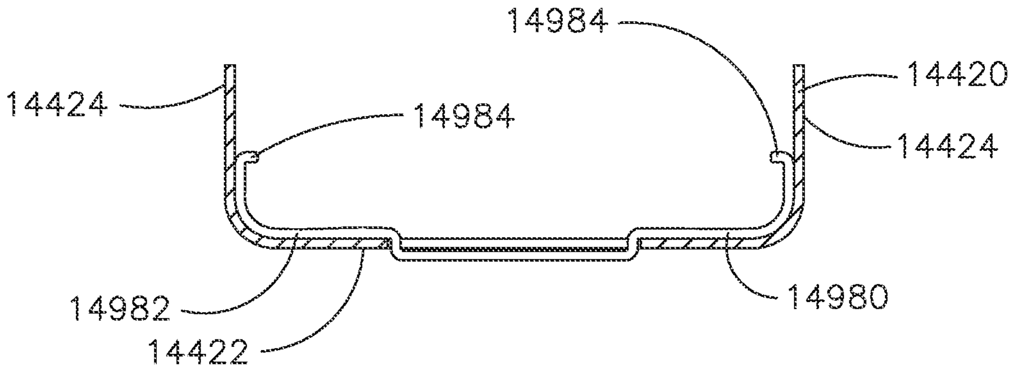
FIG. 37 is a cross-sectional end view of the cartridge jaw of FIG. 34.
Figure 38:
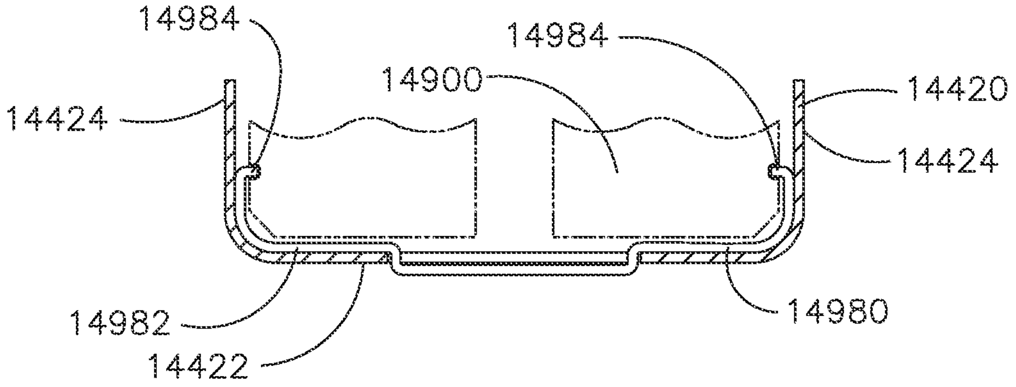
FIG. 38 is a cross-sectional end view of the staple cartridge of FIG. 35 locked in the cartridge jaw of FIG. 34.

Further to the above, the cartridge jaw 14420 further comprises a cartridge lock, such as cartridge lock 14980, for example, which is configured to lock the staple cartridge 14900 into the cartridge jaw 14420. The cartridge lock 14980 is slideable between an unlocked position (FIG. 35) and a locked position (FIG. 36) to engage the cartridge lock 14980 with the staple cartridge 14900 after the staple cartridge 14900 has been positioned in the cartridge jaw 14420. The cartridge lock 14980 comprises a base 14982 (FIGS. 37 and 38) slideable along the base wall 14422 of the cartridge jaw 14420 and lock arms 14984 extending distally therefrom. The cartridge lock 14980 is comprised of stamped stainless steel, for example, but could be comprised of any suitable material. When the cartridge lock 14980 is moved from its unlocked position (FIG. 35) to its locked position (FIG. 36), the lock arms 14984 engage lock windows 14904 defined in the staple cartridge 14900. In various embodiments, the cartridge lock 14980 further comprises a biasing spring configured to push the cartridge lock into its locked position. In at least one embodiment, the lateral sidewalls 14424 of the cartridge jaw 14420 comprise cam features which cam the lock arms 14984 into the lock windows 14904. In at least one embodiment, the lock arms 14984 are resiliently flexed outwardly when the staple cartridge 14900 is seated in the cartridge jaw 14420 and then relax inwardly into the lock windows 14904 when the cartridge lock 14980 is moved into its locked position. To unlock the staple cartridge 14900 and remove the staple cartridge 14900 from the cartridge jaw 14420, the cartridge lock 14980 is pulled proximally into its unlocked position to disengage the cartridge lock 14980 from the staple cartridge 14900. Such an arrangement can avoid the need to apply an impact force to the staple cartridge 14900 to remove the staple cartridge 14900 from the cartridge jaw 14420.

As discussed herein, a firing member, such as a tissue cutting knife, for example, is movable distally to close an end effector of a stapling instrument and then movable distally once again to perform a staple firing stroke. Referring to FIGS. 27 and 28 once again, the firing member 10990 comprises a first cam 10991 configured to engage a cartridge jaw, such as cartridge jaw 1420, for example, and a second cam 10992 configured to engage an anvil jaw, such as anvil jaw 1410, for example. When the firing member 10990 is advanced distally from an unactuated position, the firing member 10990 contacts the anvil jaw 1410 and the cartridge jaw 1420 to close the end effector 1400. In such instances, the cams 10991 and 10992 co-operatively work together during a closure stroke to move the cartridge jaw 1420 from an open, unclamped position to a closed, clamped position. To re-open the end effector 1400, the firing member 10990 is retracted proximally to disengage the cam 10991 from the cartridge jaw 1420 so that the cartridge jaw 1420 can be re-opened. Once the end effector 1400 is closed and the clinician is satisfied with the positon of the end effector 1400 on the patient tissue, the firing member 10990 is moved distally once again to perform the staple firing stroke. Notably, the cams 10991 and 10992 co-operate to the hold the cartridge jaw 1420 in position relative to the anvil jaw 1410 during the staple firing stroke. Also, notably, various embodiments are envisioned in which the anvil jaw 1410 rotates relative to the cartridge jaw 1420 between an open position and a closed position and the above-described arrangement is applicable to such embodiments.

Figure 39:
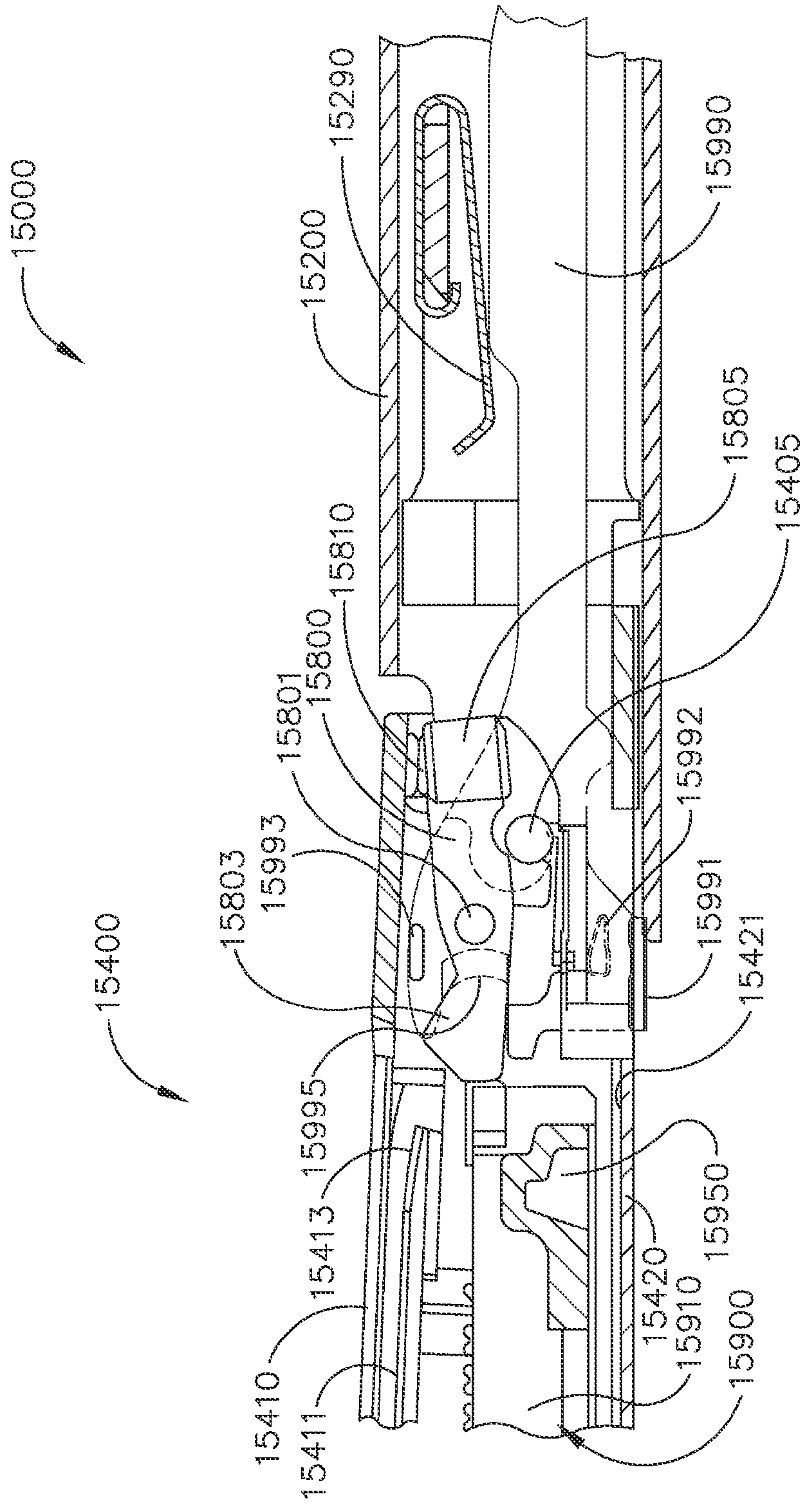
FIG. 39 is a partial cross-sectional view of a surgical stapling instrument comprising a firing member that has been moved distally to close an anvil jaw in accordance with at least one embodiment.
Figure 40:
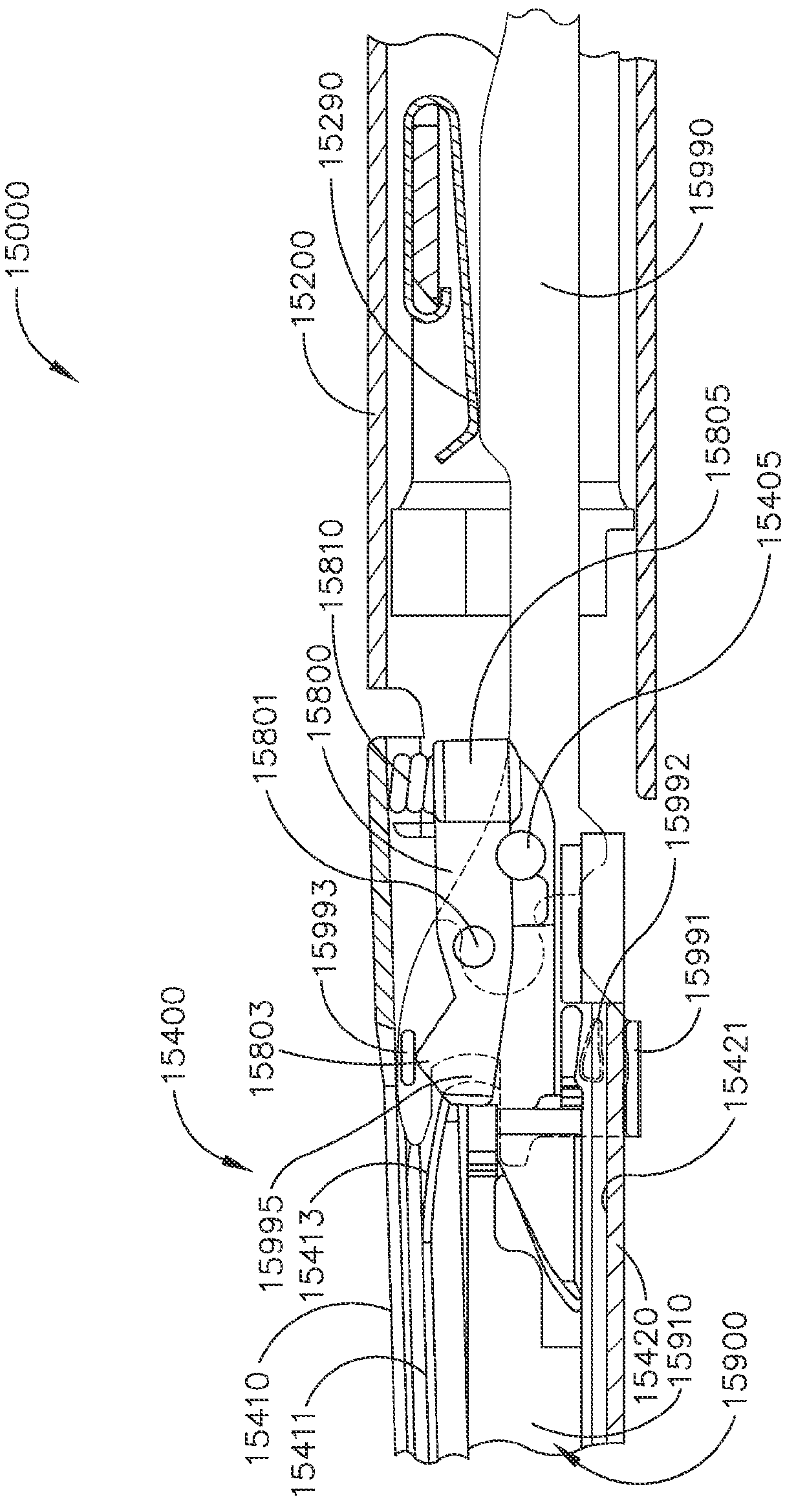
FIG. 40 is a partial cross-sectional view of the stapling instrument of FIG. 39 illustrating the firing member advanced distally to drive the anvil jaw downwardly.
Figure 41:
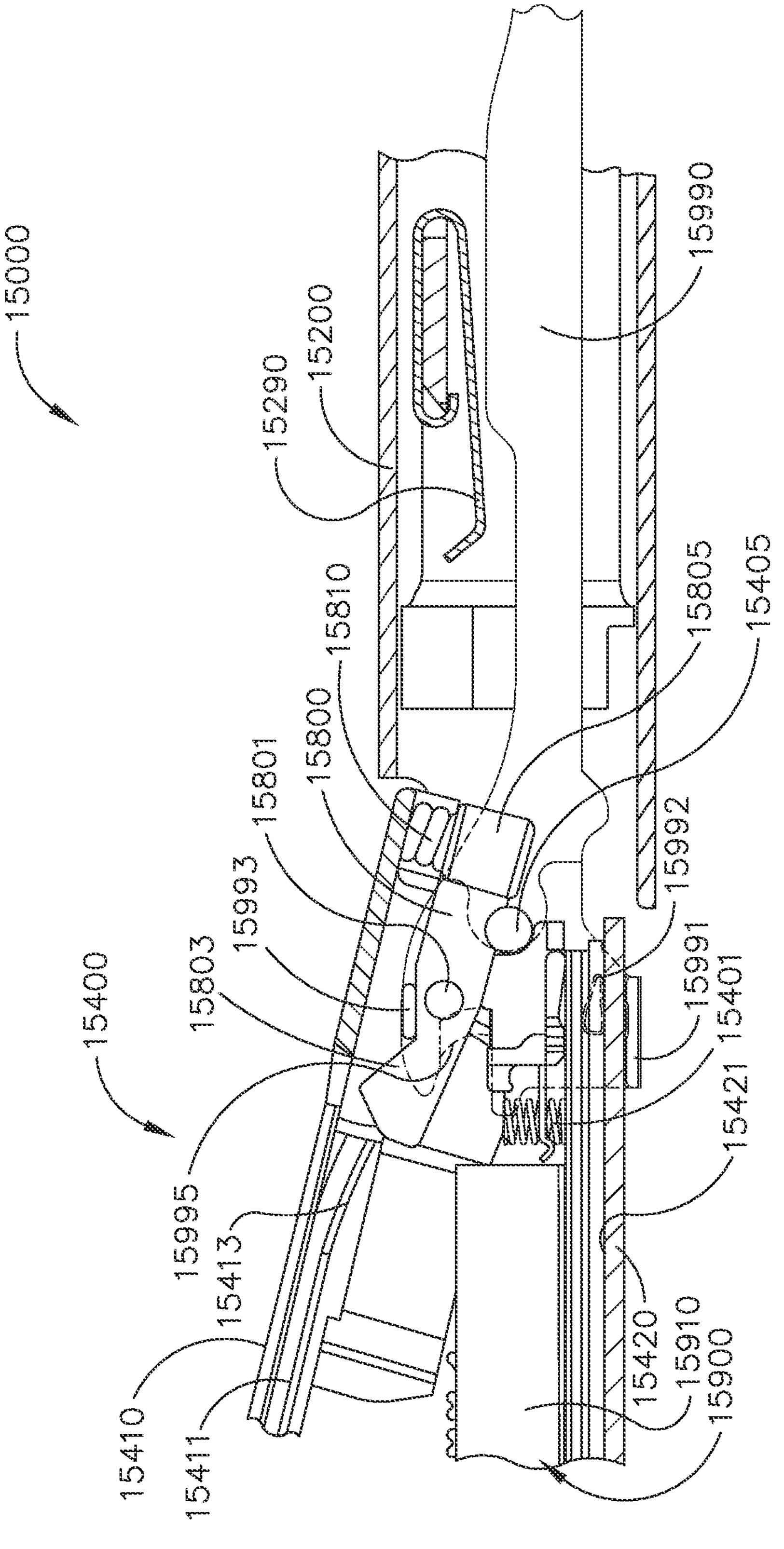
FIG. 41 is a partial cross-sectional view of the anvil jaw of FIG. 39 in an open position after the firing member has been retracted following a staple firing stroke.

A stapling instrument 15000 is illustrated in FIGS. 39-41 and is similar to stapling instruments 1000 and 2000 and/or other stapling instruments disclosed herein in many respects, most of which will not be discussed herein for the sake of brevity. Referring to FIG. 29, the stapling instrument 15000 comprises a shaft 15200, an end effector 15400, and a staple cartridge 15900 positioned in the end effector 15400. The staple cartridge 15900 comprises a cartridge body 15910 including staple cavities, staples removably stored in the staple cavities, staple drivers, and a sled 15950 movable from a proximal unfired position (FIG. 39) to a distal fired position (FIG. 41) during a staple firing stroke. The end effector 15400 comprises a cartridge jaw 15420 and an anvil jaw 15410 rotatable relative to the cartridge jaw 15420 about a jaw pivot 15405 between an open, unclamped position and a closed, clamped position. The stapling instrument 15000 further comprises a firing drive including a tissue cutting knife 15990 which is movable distally during a closure stroke to close the end effector 15400 and then movable distally once again during the staple firing stroke to push the sled 15950 distally and eject the staples from the staple cavities. The tissue cutting knife 15990 comprises a cartridge cam 15991, an anvil cam 15993, and a tissue cutting edge 15995 positioned intermediate the cartridge cam 15991 and the anvil cam 15993, and is discussed in greater detail below.

The stapling instrument 15000 further comprises a tissue compression lever 15800 which is engaged by the tissue cutting knife 15990 during the closure stroke to close the anvil jaw 15410. The tissue compression lever 15800 is rotatably mounted to a frame of the shaft 15200 about a pivot 15801 and comprises a distal end 15803 which extends distally relative to the pivot 15801 and a proximal end 15805 which extends proximally relative to the pivot 15801. When the anvil jaw 15410 is in its open position, the tissue cutting knife 15990 is not engaged with the tissue compression lever 15800. When the tissue cutting knife 15990 is advanced distally during the closure stroke, referring to FIG. 39, the anvil cam 15993 of the tissue cutting knife 15990 contacts the distal end 15803 of the tissue compression lever 15800 and rotates the distal end 15803 downwardly. This rotation of the tissue compression lever 15800 causes the proximal end 15805 of the tissue compression lever 15800 to rotate upwardly. A spring 15810 is positioned intermediate the anvil jaw 15410 and the proximal end 15805 of the tissue compression lever 15800 at location which is proximal to the jaw pivot 15405. Another spring 15290 pushes the tissue cutting knife 15990 downwardly to hold the tissue cutting knife 15990 in contact with the compression lever 15800. As a result of the above, the distal movement of the tissue cutting knife 15990 rotates the tissue compression lever 15800 in a direction which, not only pushes the anvil jaw 15410 closed as illustrated in FIG. 39, but pushes the anvil jaw 15410 into an over-compressed orientation as illustrated in FIG. 40. Such over-compression of the tissue occurs before the staple firing stroke and advantageously pushes some of the fluid contained in the tissue clamped between the jaws 15410 and 15420 into the adjacent tissue. In many instances, the clinician may pause for about 10 seconds, for example after the closure stroke before performing the staple firing stroke to permit more fluid to flow out of the tissue. As a result of the above, the tissue may be thinner when it is stapled and/or the deformation of the staples against the anvil 15410 may be more consistent.

Further to the above, the anvil jaw 15410 comprises a longitudinal slot 15411 defined therein which is configured to receive the anvil cam 15993 of the tissue cutting knife 15990 during the staple firing stroke. The longitudinal slot 15411 comprises a proximal ramp 15413 positioned adjacent to the distal end 15803 of the tissue compression lever 15800 when the anvil jaw 15410 is in a closed position after the closure stroke. At the outset of the staple firing stroke, the tissue cutting knife 15990 moves distally such that the anvil cam 15993 of the tissue cutting knife 15990 disengages from the tissue compression lever 15800 and contacts the proximal ramp 15413 of the longitudinal slot 15411. At such point, the pre-compression provided by the tissue compression lever 15800 is relieved and the compression of the tissue during the staple firing stroke is controlled by the anvil cam 15993 which slides along the bottom surface of the slot 15411 and the cartridge cam 15991 which slides along the bottom surface of the anvil jaw 15420. In such instances, the cams 15991 and 15993 co-operatively control the position of the anvil jaw 15410 relative to the staple cartridge 15900 and, also, co-operatively control the staple forming gap between the forming pockets in the anvil jaw 15410 and the drivers in the staple cartridge 15900 as the drivers are lifted toward the anvil jaw 15410 during the staple firing stroke. The tissue cutting knife 15990 also comprises a lateral flange 15992 which extends into a longitudinal slot 15421 defined in the cartridge jaw 15420 which can also assist in controlling the relative positioning of the anvil jaw 15410 and the cartridge jaw 15420. When the tissue cutting knife 15990 is retracted after the staple firing stroke, referring to FIG. 41, the anvil cam 15993 of the tissue cutting knife 15990 exits the longitudinal slot 15411, contacts the tissue compression lever 15880, and then disengages from the tissue compression lever 15880 as the tissue cutting knife 15990 is reset into its proximal unactuated position. At such point, the anvil jaw 15410 is pushed open by one or more jaw opening springs 15401 (FIG. 41) positioned intermediate the anvil jaw 15410 and the cartridge jaw 15420 that were resiliently compressed during the closure stroke.

The entire disclosures of U.S. Pat. No. 7,143,923, entitled SURGICAL STAPLING INSTRUMENT HAVING A FIRING LOCKOUT FOR AN UNCLOSED ANVIL, which issued on Dec. 5, 2006; U.S. Pat. No. 7,044,352, SURGICAL STAPLING INSTRUMENT HAVING A SINGLE LOCKOUT MECHANISM FOR PREVENTION OF FIRING, which issued on May 16, 2006; U.S. Pat. No. 7,000,818, SURGICAL STAPLING INSTRUMENT HAVING SEPARATE DISTINCT CLOSING AND FIRING SYSTEMS, which issued on Feb. 21, 2006; U.S. Pat. No. 6,988,649, SURGICAL STAPLING INSTRUMENT HAVING A SPENT CARTRIDGE LOCKOUT, which issued on Jan. 24, 2006; and U.S. Pat. No. 6,978,921, SURGICAL STAPLING INSTRUMENT INCORPORATING AN E-BEAM FIRING MECHANISM, which issued on Dec. 27, 2005, are incorporated by reference herein.

Figure 42:
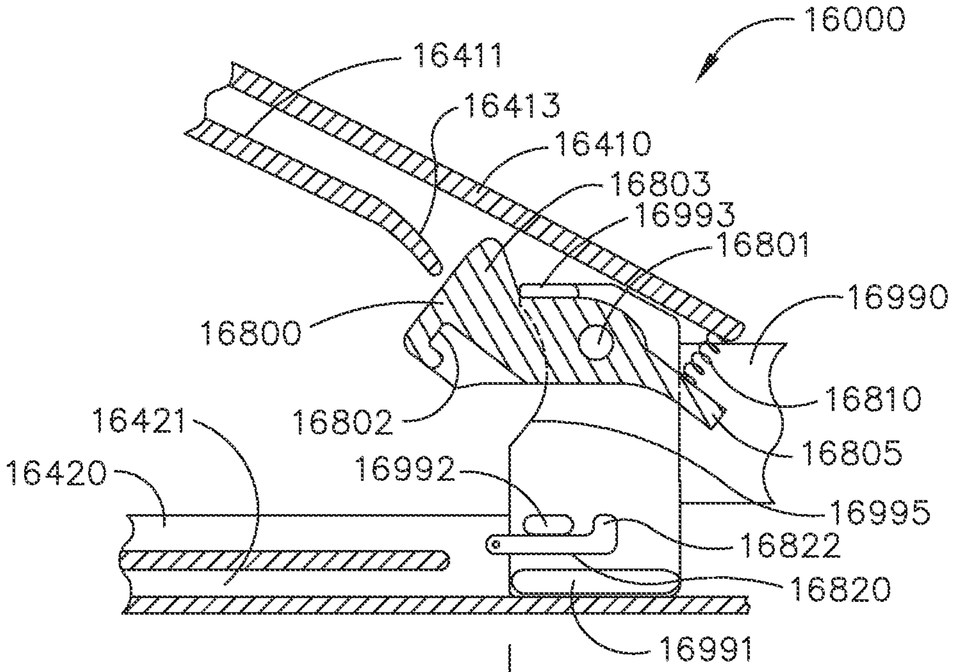
FIG. 42 is a partial cross-sectional view of an end effector of a surgical stapling instrument in accordance with at least one embodiment illustrated in an open configuration.
Figure 43:
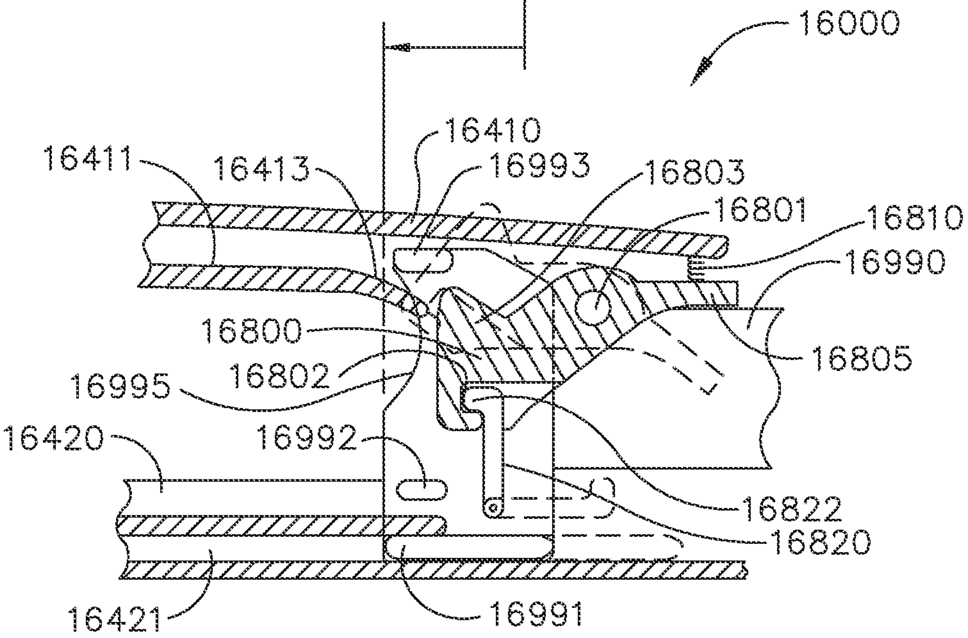
FIG. 43 is a partial cross-sectional view of the end effector of FIG. 42 illustrated in a closed configuration.

Further to the above, referring now to FIGS. 42 and 43, a stapling instrument 16000 comprises a cartridge jaw 16420 and an anvil jaw 16410 rotatable relative to the cartridge jaw 16420. The stapling instrument 16000 further comprises a tissue cutting knife 16990 movable distally from a proximal unfired position (FIG. 42) to a distal position (FIG. 43) to perform a closure stroke and then a distal fired position to perform a staple firing stroke. The stapling instrument 16000 also comprises a tissue compression lever 16800 which, similar to the tissue compression lever 15800, is contacted by the tissue cutting knife 16990 to close the anvil jaw 16410 and apply a compression force to the tissue captured between the anvil jaw 16410 and the staple cartridge seated in the cartridge jaw 16420. Also similar to the tissue compression lever 15800, the tissue compression lever 16800 is rotatably coupled to the shaft of the stapling instrument 16000 about a pivot 16801 and comprises a distal end 16803 and a proximal end 16805. The tissue cutting knife 16990 comprises an anvil cam 16993 and, at the outset of the closure stroke, referring to FIG. 43, the anvil cam 16993 contacts the distal end 16803 of the tissue compression lever 16800 to rotate the tissue compression lever 16800 and apply a closing force to the anvil jaw 16993 via a compression spring 16810. Notably, as illustrated in FIG. 43, the anvil cam 16993 has moved distally off of the tissue compression lever 16800 by the end of the closure stroke and does not hold the tissue compression lever 16800 in its rotated position. Instead, as also illustrated in FIG. 43, the distal advancement of the tissue cutting knife 16990 to perform the closure stroke releases a spring-loaded closure latch 16820 which engages the tissue compression lever 16800 and holds the tissue compression lever 16800 in its rotated position and, as a result, holds the anvil jaw 16410 in its closed position. The latch 16820 is rotatably mounted to the frame of the stapling instrument 16000 and is held in an unlocked position (FIG. 42) by a lateral shoulder 16992 extending from the tissue cutting knife 16990 when the tissue cutting knife 16990 is in its proximal unactuated position. During the close stroke, the lateral shoulder 16992 disengages from the latch 16820 which, owing to a spring force applied to the latch 16820 by a torsion spring, for example, the latch 16820 rotates into a locked position (FIG. 42) in which a lock 16822 extending from the latch 16820 engages a lock shoulder 16802 defined in the tissue compression lever 16800. At such point, the latch 16820 is able to hold the anvil jaw 16410 in its closed position while the anvil cam 16993 of the tissue cutting knife 16900 transfers off of the tissue compression lever 16800 onto a ramp 16413 of a longitudinal slot 16411 defined in the anvil jaw 16410. Notably, the latch 16820 holds the tissue compression lever 16800 in a position which is distal to the jaw pivot connecting the anvil jaw 16410 and the cartridge jaw 16420.

Further to the above, the tissue cutting knife 16990 further comprises a cartridge cam 16991 that enters into a longitudinal slot 16421 defined in the cartridge jaw 16420 during the closure stroke of the tissue cutting knife 16990. As the tissue cutting knife 16990 is advanced distally through a staple firing stroke, the anvil cam 16993 and the cartridge cam 16991 co-operate to hold the anvil jaw 16410 in its closed position. That said, the latch 16820 also holds the anvil jaw 16410 in its closed position and provides a second jaw holding mechanism. When the tissue cutting knife 16990 is retracted proximally after the staple firing stroke, the lateral shoulder 16992 extending from the tissue cutting knife 16990 contacts the latch 16820 and pushes the latch 16820 back into its unlocked position (FIG. 42). At such point, the anvil jaw 16410 is no longer locked in position by the latch 16820 and/or the anvil cam 16993 and, as a result, the anvil jaw 16410 can be re-opened.

Further to the above, the shape and configuration of the longitudinal slot 16421 defined in the cartridge jaw 16420 is constant, or at least substantially constant, along the length thereof. Similarly, the shape and configuration of the longitudinal slot 16411 defined in the anvil jaw 16410 is constant, or at least substantially constant, along the length thereof. In this embodiment, the anvil cam 16991 and the cartridge cam 16992 co-operate to hold the anvil jaw 16410 at a fixed, or an at least substantially fixed, distance relative to the cartridge jaw 16420 during the staple firing stroke.

Figure 44:
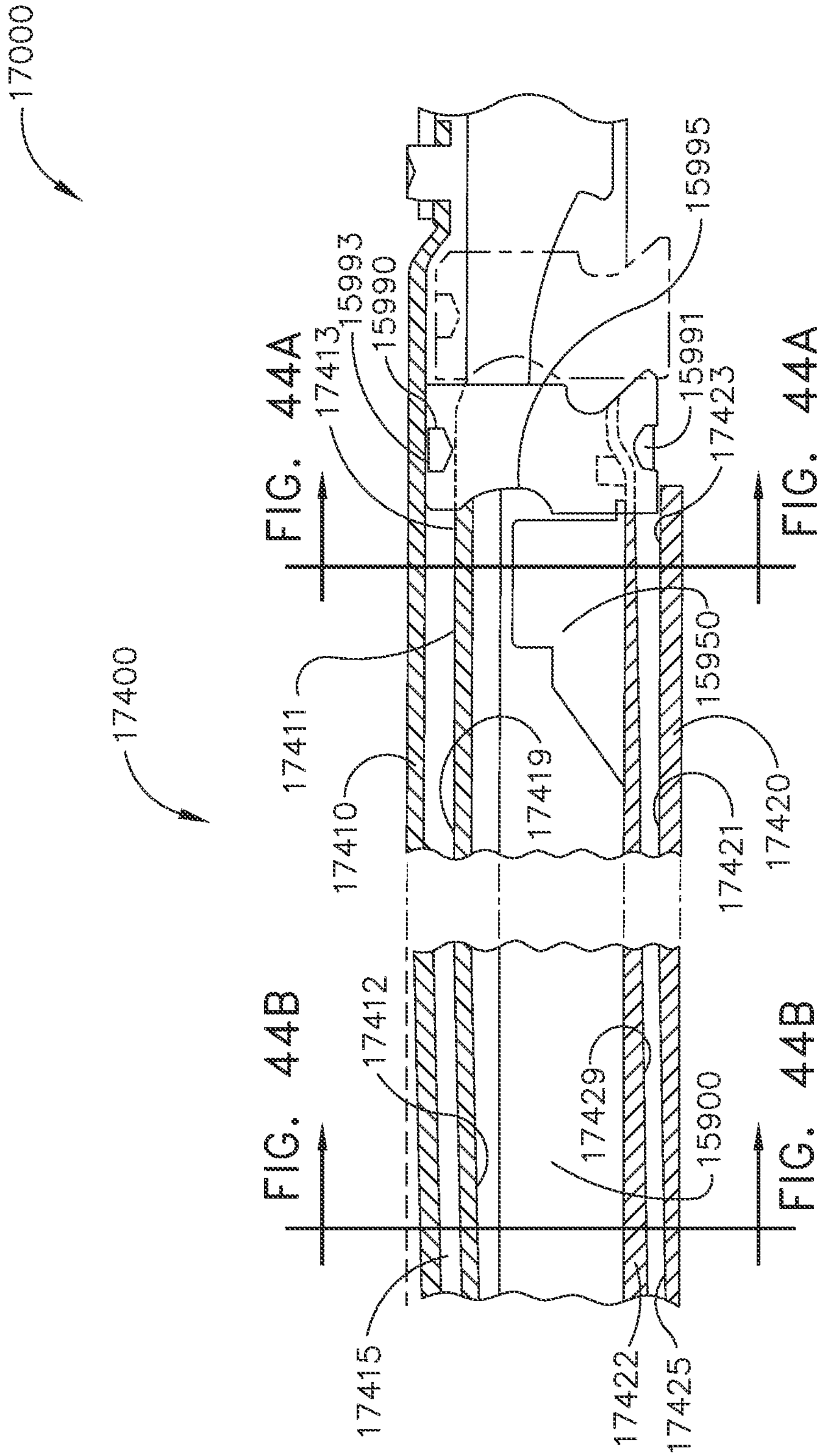
FIG. 44 is a partial cross-sectional view of an end effector in accordance with at least one embodiment.

A stapling instrument 17000 is illustrated in FIG. 44 and is similar to the stapling instruments 1000 and 2000 and other stapling instruments disclosed herein in many respects, most of which will not be discussed herein out of the sake of brevity. The stapling instrument 17000 comprises an end effector 17400 including a cartridge jaw 17420 and an anvil jaw 17410, a staple cartridge 15900, for example, positioned in the cartridge jaw 17420, and a firing drive including a tissue cutting knife 15990. The cartridge jaw 17420 is pivotably coupled to the anvil jaw 17410 and is movable relative to the anvil jaw 17410 from an open position to a closed position during the closure stroke of the tissue cutting knife 15990. The anvil jaw 17410 comprises a longitudinal slot 17411 defined therein which is configured to receive an anvil cam 15993 of the tissue cutting knife 15990 during the staple firing stroke of the tissue cutting knife 15990. The anvil longitudinal slot 17411 comprises a proximal end 17413 and a distal end 17415 and a cam surface 17419 extending between the proximal end 17413 and the distal end 17415. When the tissue cutting knife 15990 is advanced distally through the staple firing stroke, the anvil cam 15993 slides along the cam surface 17419 of the anvil jaw 17410.

Similar to the above, the cartridge jaw 17420 comprises a longitudinal slot 17421 defined therein which is configured to receive a cartridge cam 15991 of the tissue cutting knife 15990 during the staple firing stroke. The cartridge longitudinal slot 17421 comprises a proximal end 17423 and a distal end 17425 and a cam surface 17429 extending between the proximal end 17423 and the distal end 17425. When the tissue cutting knife 15990 is advanced distally through the staple firing stroke, the cartridge cam 15991 slides along the cam surface 17429 of the cartridge jaw 17420. In various instances, the tissue compressed between the anvil jaw 17410 and the staple cartridge 15900 provides a resilient spring force to the anvil jaw 17410 and the staple cartridge 15900 which acts to push the jaws 17410 and 17420 away from one another. Owing to the cams 15991 and 15993 of the tissue cutting knife 15990, however, the relative position of the jaws 17410 and 17420 is constrained by the tissue cutting knife 15990.

Figure 44A:
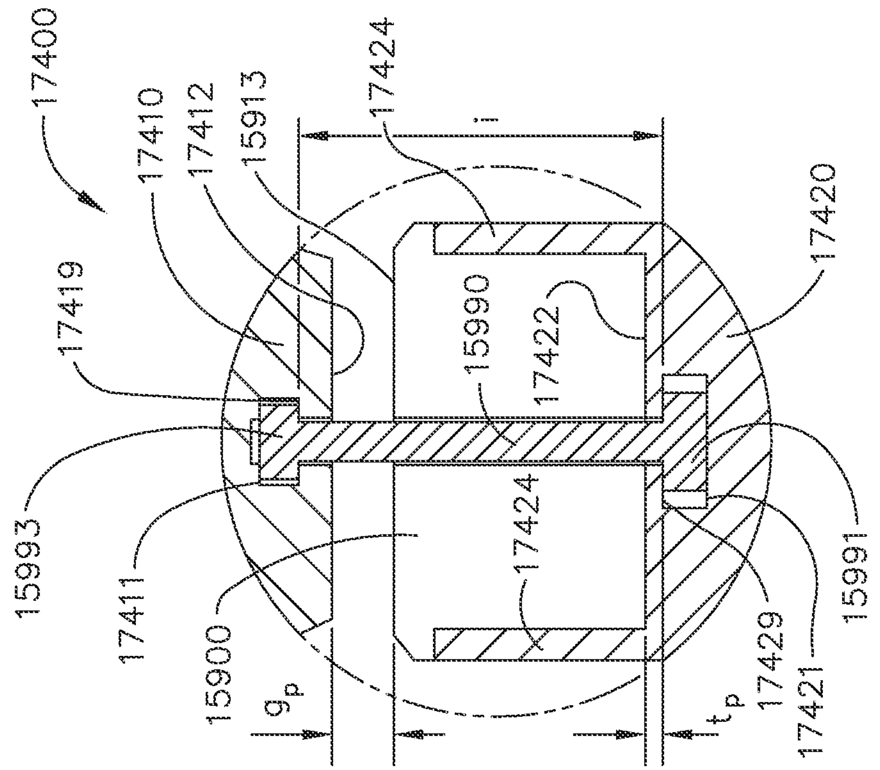
FIG. 44A is a cross-sectional view of the end effector of FIG. 44 taken along line 44A-44A in FIG. 44.
Figure 44B:
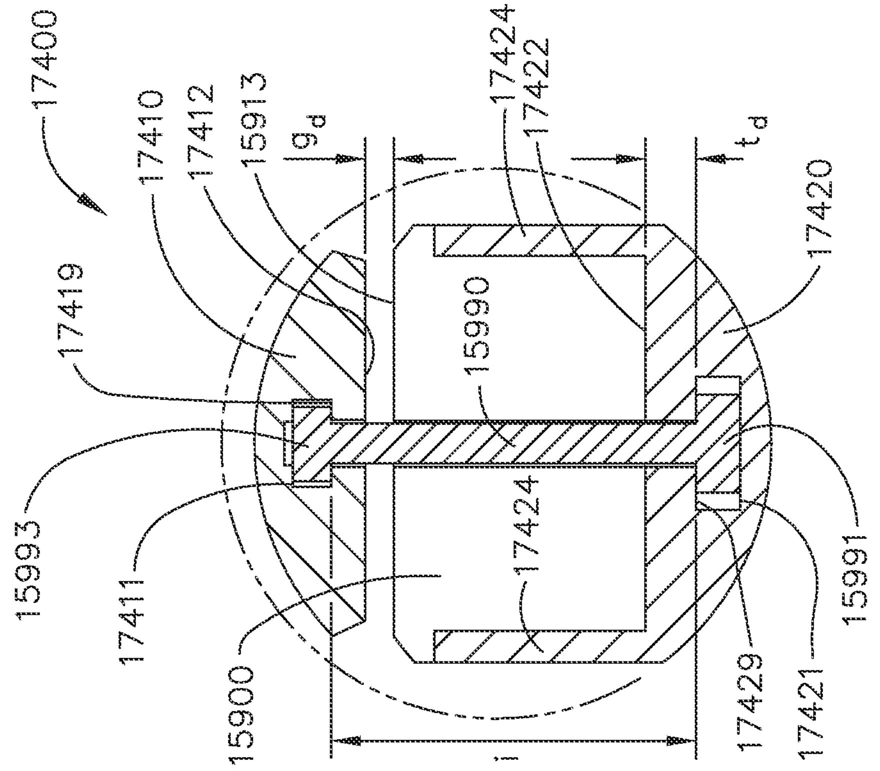
FIG. 44B is a cross-sectional view of the end effector of FIG. 44 taken along line 44B-44B in FIG. 44.

Further to the above, referring to FIGS. 44-44B, the cartridge jaw 17420 comprises a bottom wall 17422 configured to support the staple cartridge 15900 and lateral sidewalls 17424 extending upwardly from the bottom wall 17422 which are sized and configured to closely receive the staple cartridge 15900 therebetween. The staple cartridge 15900 further comprises a tissue supporting deck 15913 which faces the anvil jaw 17410 when the cartridge jaw 17420 is in its closed, or clamped, position, as illustrated in FIGS. 44-44B. The anvil jaw 17410 comprises a tissue supporting portion 17412 which is positioned opposite the deck 15913 of the staple cartridge 15900 and comprises longitudinal rows of staple forming pockets defined therein configured to deform the staples ejected from the staple cartridge 15900 during the staple firing stroke. Notably, referring primarily to FIG. 44, the tissue supporting portion 17412 also defines the longitudinal cam surface 17419 and comprises a constant thickness, or an at least substantially constant thickness, along the longitudinal length thereof. Also, notably, the bottom wall 17422 of the cartridge jaw 17420 defines the longitudinal cam surface 17429 and comprises a thickness that is not constant along the longitudinal length thereof. Rather, the thickness of the bottom wall 17422 is thinner at the proximal end 17423 and thicker at the distal end 17425. The thickness of the bottom wall 17422 tapers linearly, or at least substantially linearly, between the proximal end 17423 and the distal end 17425. That said, the thickness of the bottom wall 17422 can taper in any suitable manner. Owing to this arrangement, the distance between the anvil jaw cam surface 17419 and the cartridge jaw cam surface 17429 would change along the longitudinal length of the end effector 17400 for a given position of the cartridge jaw 17420. In many instances, however, the cartridge jaw 17420 moves relative to the anvil jaw 17410 during the staple firing stroke owing to the compressed tissue positioned between the staple cartridge 15900 and the anvil jaw 17410. During the staple firing stroke, the sloped longitudinal cam surface 17429 of the cartridge jaw 17420 causes the tissue cutting knife 15990 to draw the cartridge jaw 15420 toward the anvil jaw 15410 and narrow the gap, i.e., the tissue gap, between the staple cartridge 15900 and the anvil jaw 15410. This movement of the cartridge jaw 17420 can be readily noticed when comparing FIG. 44A, which depicts the beginning of the staple firing stroke, and FIG. 44B, which depicts the end of the staple firing stroke. As can be seen in FIGS. 44A and 44B, the tissue gap $g_p$ closes significantly. Such an arrangement applies a larger clamping force and/or clamping pressure to the tissue at the distal end of the end effector 15400 as the staple firing stroke progresses which can inhibit the tissue from being pushed out the distal end of the end effector 15400. Moreover, such an arrangement can compensate for situations where the anvil jaw 17410 flexes away from the cartridge jaw 17420 during the staple firing stroke.

Further to the above, referring again to FIGS. 44-44B, the height of the anvil longitudinal slot 17411 narrows along the length thereof. That said, the height of the cartridge longitudinal slot 17421 also narrows along the length thereof but the thickness of the cartridge support 17422 increases along the length thereof. Various other embodiments are envisioned in which the thickness of the cartridge support 17422 increases along the longitudinal length thereof but the height of the longitudinal slot 17421 does not change, or at least substantially change. Whether or not the longitudinal slots 17411 and 17421 are tapered, various embodiments are envisioned in which one or both of the longitudinal slots 17411 and 17421 comprise enlarged proximal openings so that they can reliably receive the tissue cutting member cams 15993 and 15991, respectively. In various instances, the anvil jaw cam 15993 is longitudinally longer than the cartridge jaw cam 15991. Such an arrangement can reliably hold the tissue cutting edge 15995 in alignment with the tissue captured between the staple cartridge 15900 and the anvil jaw 17410. In embodiments where the anvil jaw 17410 is rotatable and the cartridge jaw 17420 does not rotate, the cartridge jaw cam 15991 can be longer than the anvil jaw cam 15993 to achieve the same result. That said, the cams 15991 and 15993 can comprise any suitable length and/or configuration. The entire disclosure of U.S. Pat. No. 9,844,369, entitled SURGICAL END EFFECTORS WITH FIRING ELEMENT MONITORING ARRANGEMENTS, which issued on Dec. 19, 2017 is incorporated by reference herein.

Referring again to FIGS. 44A and 44B, the cartridge jaw 17420 defines a closed-bottom channel. In at least one embodiment, the bottom of the cartridge channel below the tissue cutting knife 15990 is entirely closed along the entire bottom of the cartridge jaw 17420. In such instances, the cartridge jaw 17420 is quite stiff and does not bend, or at least substantially bend, during the staple firing stroke. In at least one such embodiment, the bottom of the cartridge channel can be considered closed even though viewing windows are defined in the cartridge channel which can be used by a clinician to observe the position of the tissue cutting knife 15990. In other embodiments, the bottom of the cartridge channel is open, i.e., a longitudinal slot is defined therein which opens to the bottom of the cartridge jaw 17420 such that a portion of the tissue cutting knife 15990 is positioned outside of the cartridge jaw 17420. The reader should appreciate that an open cartridge channel may not be as stiff as a closed cartridge channel. In at least one embodiment, a portion of the sled extends down into the longitudinal slot of an open cartridge channel so as to stiffen the cartridge jaw 17420. The entire disclosure of U.S. Patent Application Publication No. 2015/0297228, entitled FASTENER CARTRIDGES INCLUDING EXTENSIONS HAVING DIFFERENT CONFIGURATIONS, which published on Oct. 22, 2015 is incorporated by reference herein.

As discussed above, a staple cartridge can be configured to fire three longitudinal rows of staples on each side of an incision made in patient tissue during a staple firing stroke. In various instances, the staple cartridge, and the stapling instrument used to fire the staples from the staple cartridge, is configured to deform all of the staples to the same, or at least substantially the same, deformed height. In other instances, the staple cartridge and the stapling instrument are configured to deform the staples to different formed heights. In at least one such instance, the staple cartridge and the stapling instrument are configured to fire six longitudinal rows of staples—three rows on each side of the incision—such that the innermost two rows of staples are deformed to a first height, the intermediate rows of staples adjacent the innermost two rows are deformed to a second height that is larger than the first deformed height, and the outermost rows of staples are deformed to a third height that is larger than the second deformed height. Such different deformed heights can be created in a number of different ways. For instance, the staple forming pockets in the anvil of the stapling instrument can be shallower in the innermost rows of forming pockets and deeper in the intermediate rows of forming pockets. Similarly, the staple forming pockets in the anvil can be deeper in the outermost rows of forming pockets than the intermediate rows of forming pockets. Also, for instance, the staple drivers that drive the innermost rows of staples can lift the innermost staples closer to the anvil than the intermediate staple drivers. Similarly, the staple drivers that drive the intermediate rows of staples can lift the intermediate staples closer to the anvil than the outermost staple drivers. In at least one such embodiment, the innermost staple drivers, the intermediate staple drivers, and the outermost staple drivers are unconnected to one another. In other embodiments, some of the staple drivers are connected to one another. In at least one such embodiment, an innermost staple driver, an intermediate staple driver, and an outermost staple driver are connected to one another such that they are lifted together by the cartridge sled. The entire disclosures of U.S. Pat. No. 8,317,070, entitled SURGICAL STAPLING DEVICES THAT PRODUCE FORMED STAPLES HAVING DIFFERENT LENGTHS, which issued on Nov. 27, 2012, International Publication No. 2003/094747, entitled SURGICAL STAPLER AND DISPOSABLE LOADING UNIT HAVING DIFFERENT SIZE STAPLES, and U.S. Patent Application Publication No. 2010/0243707, entitled SURGICAL STAPLING APPARATUS, which published on Sep. 30, 2010 are incorporated by reference herein.

Regardless of how the staples are deformed into different deformed heights during the staple firing stroke, further to the above, the innermost staples—which are deformed to a shorter deformed height than the intermediate staples—can apply a larger clamping pressure to the patient tissue than the intermediate staples. Similarly, the intermediate staples—which are deformed to a shorter deformed height than the outermost staples—can apply a larger clamping pressure to the patient tissue than the outermost staples. As a result of the above, the innermost staples and the intermediate staples can seal, or at least substantially seal, the incised margin of the patient tissue while the larger outermost staples can support the patient tissue while affording some flexibility to the tissue captured within the staples. As discussed above, the innermost staples are deformed to a first deformed height, the intermediate staples are deformed to a second deformed height that is taller than the first deformed height, and the outermost staples are deformed to a third deformed height that is taller than the second deformed height. These first, second, and third deformed heights are set during the staple firing stroke, but it should be understood that these deformed heights may increase, or grow, slightly after the stapled tissue is released from between the jaws of the stapling instrument. This phenomenon can be referred to as "spring back" and is the result of the internal pressure created within the captured tissue and the resiliency of the metal staples, among other things. That said, even after the spring back has increased the deformed heights of the innermost staples, the intermediate staples, and the outermost staples, the deformed innermost staples are still shorter than the deformed intermediate staples and, likewise, the deformed intermediate staples are shorter than the deformed outermost staples. For easy reference, the deformed height of the staples immediately after they are deformed can be called the "as-formed height" and the deformed height of the staples after they have relaxed—owing to spring back—can be called the "post-formed height".

Figure 46:
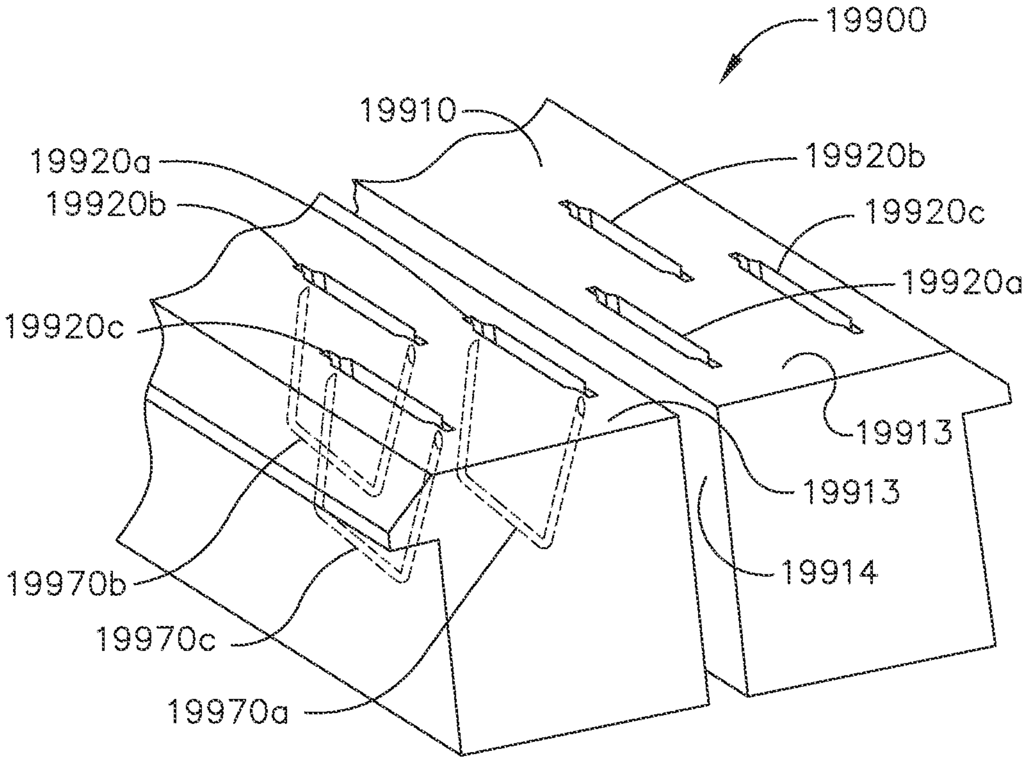
FIG. 46 is a partial perspective view of a staple cartridge in accordance with at least one embodiment.

Further to the above, a staple cartridge 19900 is illustrated in FIG. 46 and is similar to the staple cartridge 1900 and other staple cartridges disclosed herein in many respects, most of which are not discussed herein for the sake of brevity. The staple cartridge 19900 comprises a cartridge body 19910 including a deck 19913 configured to support patient tissue, a longitudinal slot 19914 configured to receive a tissue cutting knife, and longitudinal rows of staple cavities 19920*a*, 19920*b*, and 19920*c* defined in the deck 19913 on each side of the longitudinal slot 19914. The longitudinal rows of staple cavities 19920*a* adjacent the longitudinal slot 19914 comprise the innermost staple cavities, the longitudinal rows of staple cavities 19920*b* comprise intermediate staple cavities, and the longitudinal rows of staple cavities 19920*c* comprise the outermost staple cavities. The staple cartridge 19900 further comprises first staples 19970*a* removably positioned in the innermost staple cavities 19920*a*, second staples 19970*b* removably positioned in the intermediate staple cavities 19920*b*, and third staples 19970*c* removably positioned in the outermost staple cavities 19920*c*. In at least one embodiment, the first staples 19970*a* have a first unformed height, the second staples 19970*b* have a second unformed height, and the third staples 19970*c* have a third unformed height where the first unformed height, the second unformed height, and third unformed height are the same. The reader should appreciate that the staples 19970*a*, 19970*b*, and 19970*c* have the same unformed height despite variations to the unformed heights owing to manufacturing tolerances. For instance, in at least one embodiment, the staples 19970*a*, 19970*b*, and 19970*c* have the same unformed height when their unformed heights fall between 3.8 mm and 4.2 mm, for example. In another embodiment, the staples 19970*a*, 19970*b*, and 19970*c* have the same unformed height when their unformed heights fall between 1.9 mm and 2.1 mm, for example. In various alternative embodiments, the first unformed height is shorter than the second unformed height, and the second unformed height is shorter than the third unformed height. In at least one such embodiment, the first unformed height is about 2.0 mm, the second unformed height is about 3.0 mm, and the third unformed height is about 4.0 mm, for example.

Figure 46A:
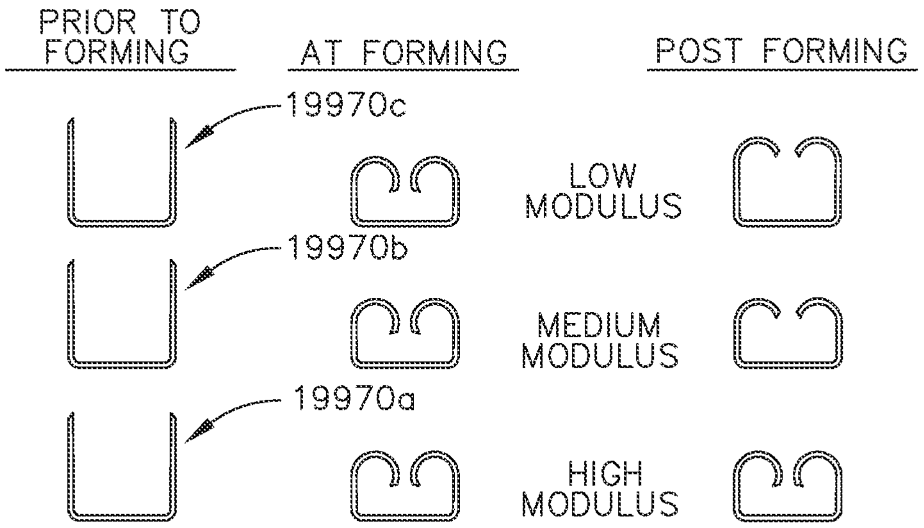
FIG. 46A is a diagram depicting the staples of the staple cartridge of FIG. 46 as they are deformed and after they are deformed.

Further to the above, FIG. 46A depicts the progression of the first staples 19970*a*, the second staples 19970*b*, and the third staples 19970*c* from their unformed heights to their as-formed heights and then to their post-formed heights. Notably, the staple cartridge 19900 is usable with a stapling instrument which is configured to co-operatively deform the first staples 19970*a*, the second staples 19970*b*, and the third staples 19970*c* to the same formed height. The reader should appreciate that, owing to manufacturing tolerances and/or variances in tissue thickness and density, that the staples 19970*a*, 19970*b*, and 19970*c* will not all be deformed to the exact same height. Rather, the staples 19970*a*, 19970*b*, and 19970*c* are deformed to the same formed height when their formed heights fall within the same range of heights. For instance, the staples 19970*a*, 19970*b*, and 19970*c* are deformed to the same formed height when their formed heights are within a range of 1.90 mm-2.10 mm, for example. In other instances, the staples 19970*a*, 19970*b*, and 19970*c* are deformed to the same formed height when their formed heights are within a range of 1.35 mm-1.65 mm, for example. That said, any suitable formed height, or formed height range, can be used.

Notably, referring again to FIG. 46A, the first staples 19970*a* do not relax much, if at all, between their as-formed height and their post-formed height. That said, the second staples 19970*b* relax a larger amount between their as-formed height and their post-formed height than the first staples 19970*a*. Moreover, the third staples 19970*c* relax a larger amount between their as-formed height and their post-formed height than the second staples 19970*b*. Stated another way, the first staples 19970*a*, the second staples 19970*b*, and the third staples 19970*c* relax to different post-formed heights even though their as-formed heights are the same. In various instances, these different post-formed heights occur owing to the softness, or compliance, of the metal used to make the first staples 19970*a*, the second staples 19970*b*, and the third staples 19970*c*. In at least one such instance, the second staples 19970*b* have less annealing than the first staples 19970*a*, and the third staples 19970*c* have less annealing than the second staples 19970*b*, for example, thereby making the third staples 19970*c* softer than the second staples 19970*b* and the second staples 19970*b* softer than the first staples 19970*a*.

Further to the above, various embodiments are envisioned in which the first staples 19970*a*, 19970*b*, and 19970*c* have the same as-formed heights but different post-formed heights regardless of whether the staples 19970*a*, 19970*b*, and 19970*c* have the same unformed height or different unformed heights. In various embodiments, the staples 19970*a*, 19970*b*, and 19970*c* are comprised of stainless steel, titanium, and/or Nitinol—an alloy of nickel and titanium, for example. That said, embodiments are envisioned in which the first staples 19970*a* are comprised of a first material, the second staples 19970*b* are comprised of a second material, and third staples 19970*c* are comprised of a third material such that the first staples 19970*a*, the second staples 19970*b*, and the third staples 19970*c* can relax from the same as-formed heights to different post-formed heights. In at least one embodiment, the first staples 19970*a* are comprised of a material having a first modulus of elasticity, the second staples 19970*b* are comprised of a material have a second modulus of elasticity which is lower than the first modulus of elasticity, and the third staples 19970*c* are comprised of a material having a third modulus of elasticity which is lower than the second modulus of elasticity. In at least one embodiment, the first staples 19970*a* are comprised of a material having a first stiffness, the second staples 19970*b* are comprised of a material have a second stiffness which is lower than the first stiffness, and the third staples 19970*c* are comprised of a material having a third stiffness which is lower than the second stiffness.

Figure 46B:
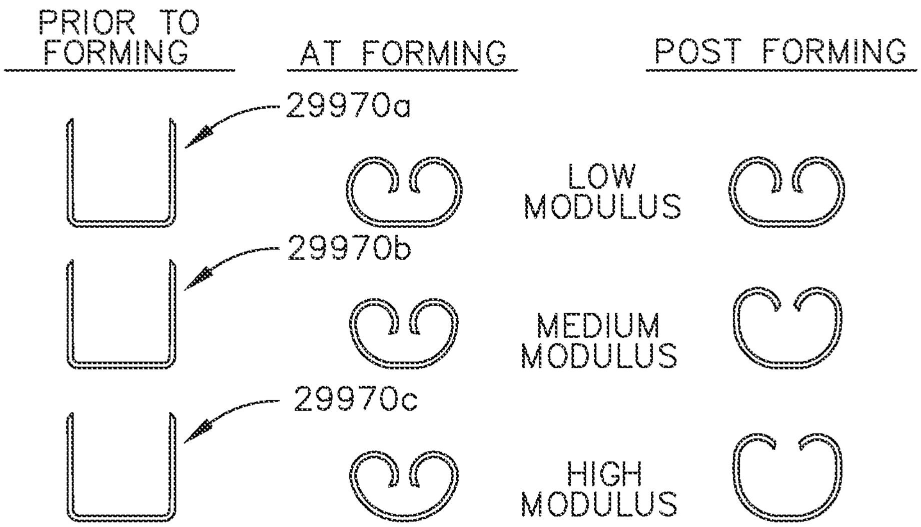
FIG. 46B is a diagram depicting staples as they are deformed and after they are deformed in accordance with at least one embodiment.

In various alternative embodiments, referring now to FIG. 46B, the staple cartridge 19900 can comprise first staples 29970*a*, second staples 29970*b*, and staples 29970*c* having the same unformed shape. Notably, the first staples 29970*a*, second staples 29970*b*, and third staples 29970*c* have different as-formed shapes. In their as-formed shapes, the radius between the base of the first staples 29970*a* and the legs of the first staples 29970*a* have a first radius, the radius between the base of the second staples 29970*b* and the legs of the second staples 29970*b* have a second radius which is smaller than the first radius, and the radius between the base of the third staples 29970*c* and the legs of the third staples 29970*c* have a third radius which is smaller than the second radius. Owing to the radii of the as-formed staple shapes and the materials of the staples 29970*a*, 29970*b*, and 29970*c*, the third staples 29970*c* have more spring back than the second staples 29970*b*, and the second staples 29970*b* have more spring back than the first staples 29970*a* which result in different post-formed shapes for the staples 29970*a*, 29970*b*, and 29970*c*. In various instances, the first staple forming pockets, the second forming pockets, and the third forming pockets of the anvil comprise different configurations which can produce the different as-formed shapes of the staples 29970*a*, 29970*b*, and 29970*c*. In at least one embodiment, the ratio of the entry radius to the exit radius of a staple forming pocket determines the as-formed shape of a staple. For instance, when the entry radius and the exit radius of a forming pocket are about the same, i.e. 1:1, the forming pocket deforms the staple to a large continuous radius. In at least one embodiment, staples that are deformed into a large continuous radius have little, if any, spring back. Such forming pockets can be suitable to deform an inner row of staples, for example. When the entry radius and the exit radius have a ratio of about 3:1, the deformed staples have a sharper radius and a larger spring back. Such forming pockets can be suitable to deform an outer row of staples, for example.

Figure 48:
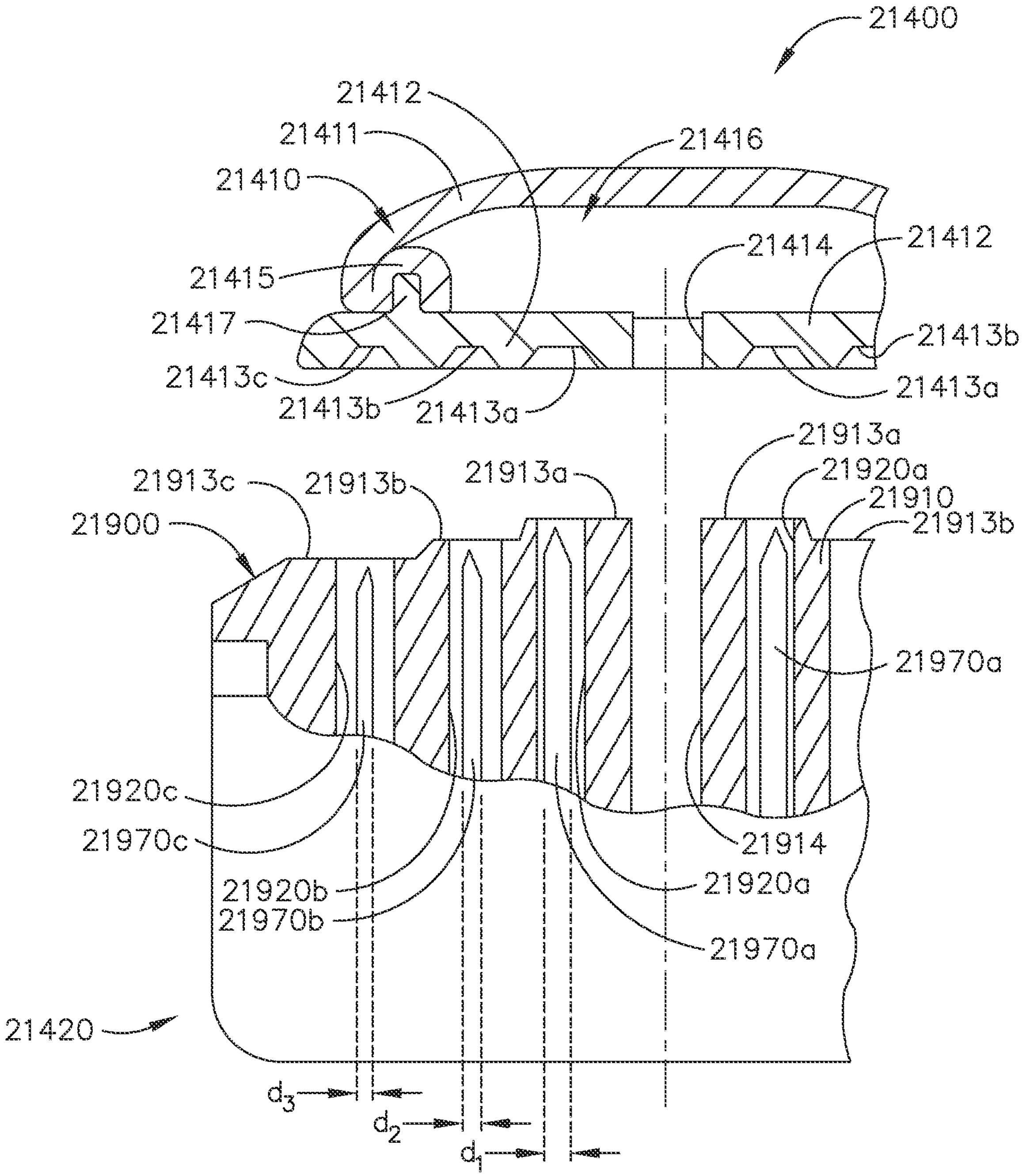
FIG. 48 is a partial cross-sectional view of an anvil jaw and a staple cartridge in accordance with at least one embodiment.

An end effector 21400 of a stapling instrument is illustrated in FIG. 48 and is similar to the other end effectors disclosed herein in many respects, many of which will not be discussed herein for the sake of brevity. The end effector 21400 comprises an anvil jaw 21410, a cartridge jaw 21420, and a staple cartridge 21900 positioned in the cartridge jaw 21420. The anvil jaw 21410 comprises a cap, or cover, 21411 and tissue support plates 21412 welded to the cap 21411. Each support plate 21412 comprises a longitudinal lateral flange 21417 extending therefrom which is positioned in a longitudinal slot, or rolled gutter, 21415 defined in a folded lateral lip of the cap 21411. In various instances, the longitudinal lateral flanges 21417 are press-fit into their respective longitudinal slots 21415 and then welded into place. In at least one instance, openings, or apertures, are defined in the cap 21411 which allow the lateral flanges 21417 to be directly welded to the cap 21411 so that the support plates 21412 are held securely in position relative to the cap 21411. The support plates 21412 are positioned and arranged such that a longitudinal slot 21414 is defined between the support plates 21412 and such that a longitudinal cavity 21416 is defined between the support plates 21412 and the cap 21411. The longitudinal slot 21414 and the longitudinal cavity 21416 are sized and configured to receive a tissue cutting knife therein. Each support plate 21412 comprises a longitudinal row of first, or innermost, staple forming pockets 21413*a* defined therein, a longitudinal row of second, or intermediate, staple forming pockets 21413*b* defined therein, and a longitudinal row of third, or outermost, staple forming pockets 21413*c* defined therein.

Further to the above, the staple cartridge 21900 comprises a cartridge body 21900 including a deck configured to support patient tissue, a longitudinal slot 21914 at least partially extending between first and second sides of the deck, and longitudinal rows of staple cavities 21920*a*, 21920*b*, and 21920*c* defined therein which are registered with the staple forming pockets 21413*a*, 21413*b*, and 21413*c*, respectively. Each side of the deck comprises a first, or inner, longitudinal step 21913*a* adjacent the longitudinal slot 21914, a second, or intermediate, longitudinal step 21913*b* extending alongside the first longitudinal step 21913*a*, and a third, or outer, longitudinal step 21913*c* extending alongside the second longitudinal step 21913*b*. Notably, the inner longitudinal step 21913*a* is closer to the anvil jaw 21410 than the longitudinal steps 21913*b* and 21913*c* and, owing to its height, the longitudinal step 21913*a* applies a larger clamping pressure to the patient tissue captured between the staple cartridge 21900 and the anvil jaw 21410 than the longitudinal steps 21913*b* and 21913*c*. Similarly, the intermediate longitudinal step 21913*b* is closer to the anvil jaw 21410 than the longitudinal step 21913*c* and, owing to its height, the longitudinal step 21913*b* applies a larger clamping pressure to the patient tissue captured between the staple cartridge 21900 and the anvil jaw 21410 than the longitudinal step 21913*c*. Such an arrangement can hold the patient tissue tightly alongside the longitudinal slot 21914 such that the tissue cutting knife passing through the longitudinal slot 21914 does not push and/or disorient the patient tissue during the staple firing stroke. Such an arrangement also provides relief to the patient tissue at the lateral edges of the end effector 21400 so that the patient tissue does not rip or tear.

Figure 49:
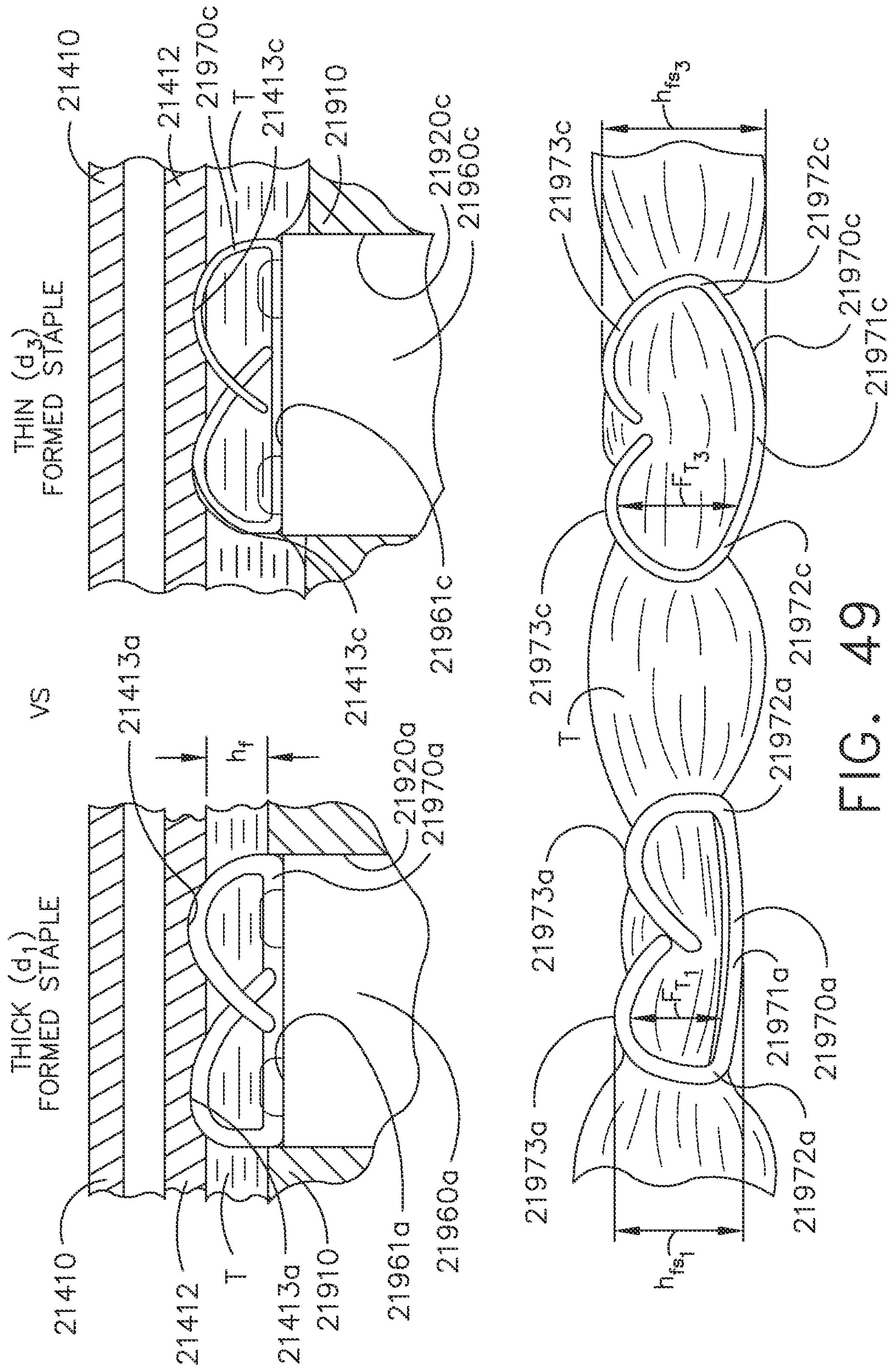
FIG. 49 is a diagram illustrating the staples of the staple cartridge of FIG. 48.

Further to the above, the staple cartridge 21900 further comprises first staples 21970*a* positioned in the first staple cavities 21920*a*, second staples 21970*b* positioned in second staple cavities 21920*b*, and third staples 21970*c* positioned in third staple cavities 21920*c*. The first staples 21970*a* are comprised of wire having a first diameter, the second staples 21970*b* are comprised of wire having a second diameter that is smaller than the first diameter, and the third staples 21970*c* are comprised of wire having a third diameter than is smaller than the second diameter. During the staple firing stroke, the first staples 21970*a* are deformed against their respective anvil forming pockets 21413*a*, the second staples 21970*b* are deformed against their respective anvil forming pockets 21413*b*, and the third staples 21970*c* are deformed against their respective forming pockets 21413*c*. In this embodiment, the staples 21970*a*, 21970*b*, and 21970*c* are all deformed to the same as-formed height, but spring back to different post-formed heights. More specifically, the first staples 21970*a* have a first post-formed height, the second staples 21970*b* have a second post-formed height which is taller than the first post-formed height, and the third staples 21970*c* have a third post-formed height which is taller than the second post-formed height. This arrangement is represented in FIG. 49 and can provide variable lateral compression within the tissue. As can be seen in FIG. 49, the staple cartridge 21900 comprises first staple drivers 21960*a* which fire the first staples 21970*a* to the same deformed height that the third staple drivers 21960*c* fire the third staples 21970*c*. The forming height of the staples is determined by the distance between the driver cradles 21961*a* and 21961*c* and the staple forming pockets 21413*a* and 21413*c*, respectively. As can also be seen in FIG. 49, each first staple 21970*a* comprises a base 21971*a*, legs 21973*a* extending from the base 21971*a*, and radiused portions 21972*a* connecting the legs 21973*a* to the base 21971*a*. Similarly, each third staple 21970*c* comprises a base 21971*c*, legs 21973*c* extending from the base 21971*c*, and radiused portions 21972*c* connecting the legs 21973*c* to the base 21971*c*. Notably, the radiused portions 21972*c* are the same size as the radiused portions 21972*a* in their as-fired configurations but the radiused portions 21972*c* are larger than the radiused portions 21972*a* after the staples reach their post-fired configurations.

As discussed above, a tissue cutting knife is advanced distally through a staple cartridge to eject the staples therefrom during a staple firing stroke. More specifically, in various embodiments, the tissue cutting knife contacts a sled stored in the staple cartridge which is pushed distally by the tissue cutting knife during the staple firing stroke. During the staple firing stroke, the sled contacts staple drivers contained within the staple cartridge which push, or fire, the staples upwardly toward the an anvil positioned opposite the staple cartridge. Notably, the sled contacts and lifts the proximal-most staple drivers first and then sequentially contacts and lifts the staple drivers positioned distally with respect to the proximal-most staple drivers until the distal-most staple drivers are contacted and lifted by the sled. As the sled is moved distally, however, the sled disengages from the drivers that it has just lifted to their fired positions. Thus, the time in which the sled is in contact with an individual staple driver may be brief as the sled lifts the staple driver to its fired position and then moves on. Thus, the staples spend very little time under compression (TUC) during the staple firing stroke. Staples that spend very little time under compression may undergo what can be described as a brief impact force that creates a large amount of plastic yielding within the staples. On the other hand, staples that spend a lot of time under compression may receive less of an impact force spike thereby resulting in less plastic yielding within the staples. Staples that undergo more plastic yielding tend to have less spring back than staples that undergo less plastic yielding. As discussed further below, the sled of a staple cartridge can be configured to create more plastic yielding within certain staples, or less plastic yielding within other staples, to create a desired arrangement of post-formed staple heights.

Figure 45:
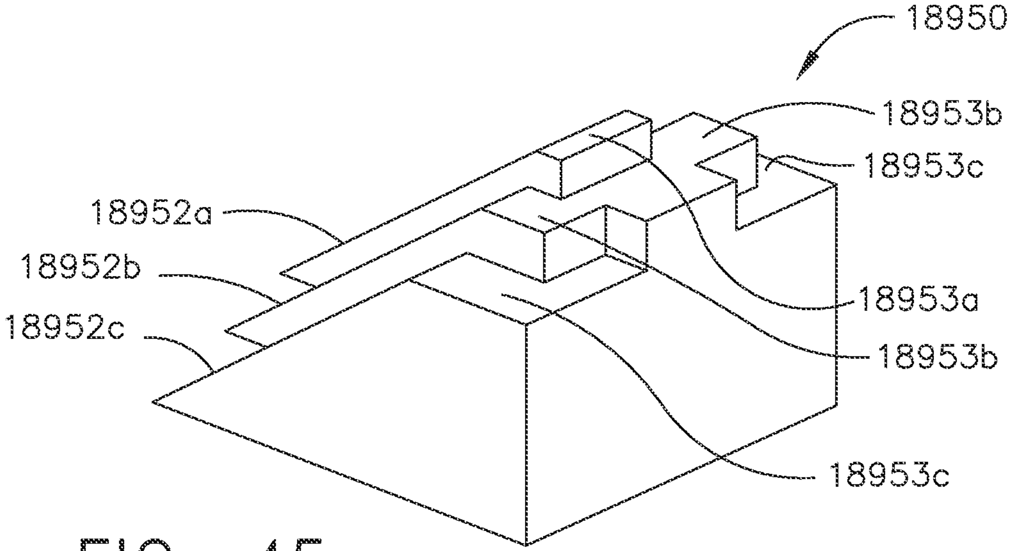
FIG. 45 is a perspective view of a sled in accordance with at least one embodiment.
Figure 45A:
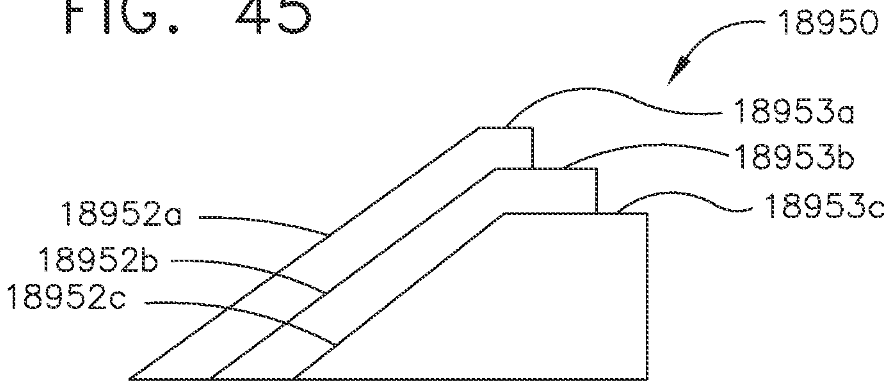
FIG. 45A is an elevational view of the sled of FIG. 45.
Figure 45B:
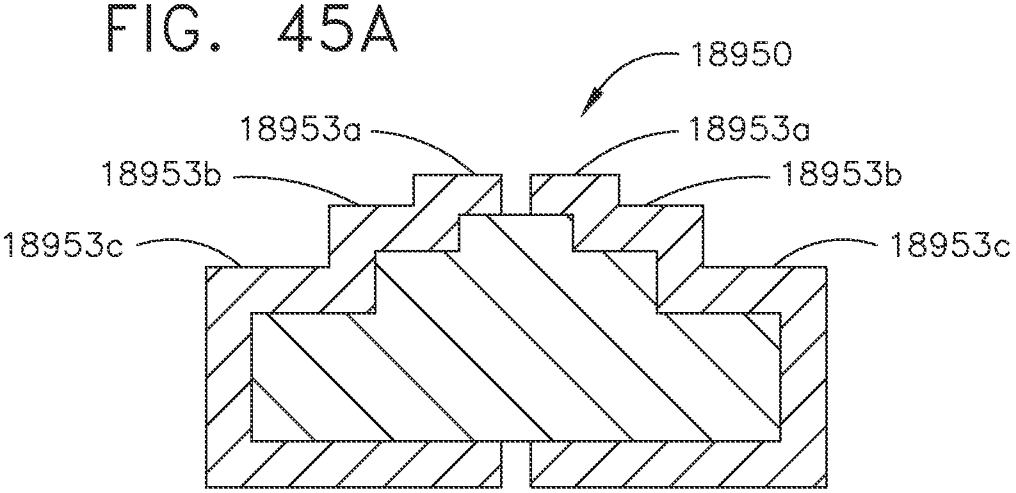
FIG. 45B is a cross-sectional view of the sled of FIG. 45.

In various embodiments, referring to FIGS. 45-45B, a sled, such as sled 18950, for example, comprises a first ramp 18952*a* which engages and lifts the first staple drivers 21960*a*, second ramps 18952*b* which engage and lift the second staple drivers, and third ramps 18952*c* which engage and lift the third staple drivers 21960*c*. At the top of each ramp 18952*a*, 18952*b*, and 18952*c* is a forming plateau which defines the fully-formed position of the staple drivers being lifted by the ramps 18952*a*, 18952*b*, and 18952*c*. More specifically, the sled 18950 comprises a first forming plateau 18953*a* aligned with the first ramp 18952*a*, a second forming plateau 18953*b* aligned with each second ramp 18952*b*, and a third forming plateau 18953*c* aligned with each third ramp 18952*c*. When the first staple driver 21960*a* reaches the top of the first ramp 18952*a*, for example, the first staple driver 21960*a* slides along the first forming plateau 18953*a* and then falls off the back of the sled 18950 as the sled 18950 is advanced distally through its staple firing stroke. Similarly, the second staple drivers 21960*b* slide along their respective second forming plateaus 18953*b* and then fall off the back of the sled 18950 as the sled 18950 is advanced distally through its staple firing stroke. Likewise, the third staple drivers 21960*c* slide along their respective third forming plateaus 18953*c* and then fall off the back of the sled 18950 as the sled 18950 is advanced distally through its staple firing stroke. Notably, the first forming plateau 18953*a* is shorter than the second forming plateaus 18953*b* and, as a result, the first staples may have more plastic yielding and less spring back than the second staples. Similarly, the second forming plateaus 18953*b* are shorter than the third forming plateaus 18953*c* and, as a result, the second staples may have more plastic yielding and less spring back than the third staples.

Controlling the time under compression, as discussed above, can be used to allow staples which have been deformed to the same as-formed height to have different post-formed heights. That said, the sled 18950 is also configured to deform the first staples, the second staples, and the third staples to different as-formed heights. For instance, the first forming plateau 18953*a* is higher than the second forming plateaus 18953*b* which means that the sled 18950 can lift the first staples to a higher forming height than the second staples and, in various instances, make the deformed first staples smaller than the deformed second staples. Similarly, the second forming plateaus 18953*b* are higher than the third forming plateaus 18953*c* which means that the sled 18950 can lift the second staples to a higher forming height than the third staples and, in various instances, make the deformed second staples smaller than the deformed third staples. In various instances, referring to FIG. 45B, the sled 18950 is comprised of an inner core and an outer layer surrounding the inner core. In at least one instance, the inner core can be comprised of a first material selected for its ability to withstand high forces without substantially deflecting and the outer layer can be comprised of a second material selected for its lubriciousness to reduce the friction forces between the sled 18950 and the staple drivers, for example.

Figure 47:
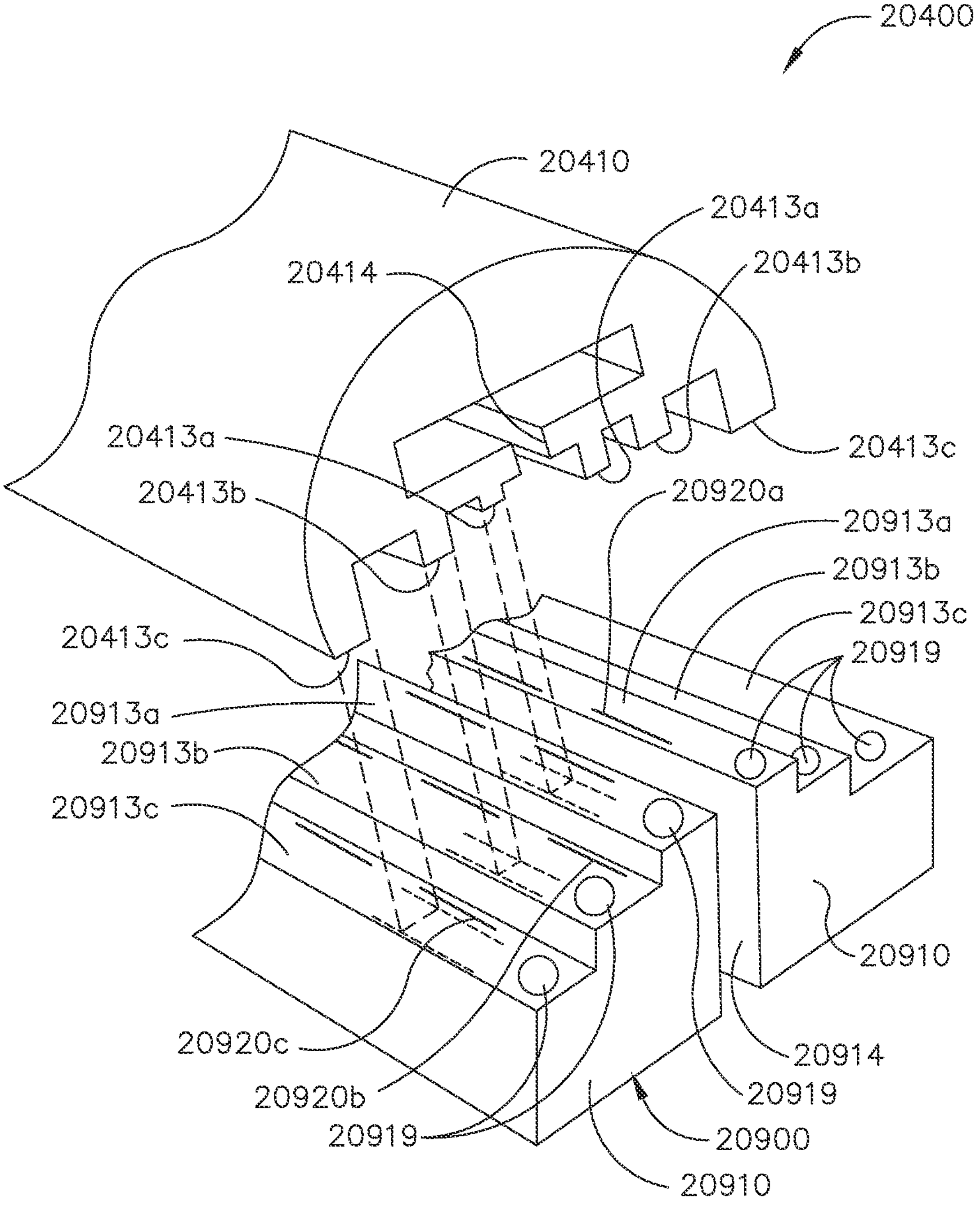
FIG. 47 is a partial cross-sectional perspective view of an anvil jaw and a staple cartridge in accordance with at least one embodiment illustrated with some components removed.

An end effector 20400 is illustrated in FIG. 47 and is similar to the end effector 21400 and other end effectors disclosed herein in many respects, most of which will not be discussed herein for the sake of brevity. The end effector 20400 comprises an anvil jaw 20410, a cartridge jaw, and a staple cartridge 20900 seated in the cartridge jaw. The staple cartridge 20900 comprises a cartridge body 20910 including a longitudinal slot 20914 at least partially extending between first and second sides of the deck, and longitudinal rows of staple cavities 20920*a*, 20920*b*, and 20920*c* defined therein. Each side of the deck comprises a first, or inner, longitudinal step 20913*a* adjacent the longitudinal slot 20914, a second, or intermediate, longitudinal step 20913*b* extending alongside the first longitudinal step 20913*a*, and a third, or outer, longitudinal step 20913*c* extending alongside the second longitudinal step 20913*b*. The staple cavities 20920*a* comprise openings defined in the first longitudinal steps 20913*a*, the staple cavities 20920*b* comprise openings defined in the second longitudinal steps 20913*b*, and the staple cavities 20920*c* comprise openings defined in the third longitudinal steps 20913*c*. Notably, the inner longitudinal step 20913*a* is closer to the anvil jaw 20410 than the longitudinal steps 20913*b* and 20913*c* and, owing to its height, the longitudinal step 20913*a* applies a larger clamping pressure to the patient tissue captured between the staple cartridge 20900 and the anvil jaw 20410 than the longitudinal steps 20913*b* and 20913*c*. Similarly, the intermediate longitudinal step 20913*b* is closer to the anvil jaw 20410 than the longitudinal step 20913*c* and, owing to its height, the longitudinal step 20913*b* applies a larger clamping pressure to the patient tissue captured between the staple cartridge 20900 and the anvil jaw 20410 than the longitudinal step 20913*c*. Such an arrangement can hold the patient tissue tightly alongside the longitudinal slot 20914 such that the tissue cutting knife passing through the longitudinal slot 20914 does not push and/or disorient the patient tissue during the staple firing stroke. Such an arrangement also provides relief to the patient tissue at the lateral edges of the end effector 20400 so that the patient tissue does not rip or tear.

In addition to or in lieu of the above, the tissue supporting surface of an anvil jaw can comprise longitudinal steps to create a tighter tissue gap along the tissue cut line and a wider tissue gap along the lateral outer edges of the end effector. Such an arrangement can also position the staple forming pockets of the anvil to create smaller as-deformed inner staples along the tissue cut line, larger intermediate as-deformed staples adjacent the inner staples, and outer as-deformed staples which are larger than the intermediate as-deformed staples, for example.

Further to the above, the anvil 20410 comprises a longitudinal slot 20414 defined therein which, like the longitudinal slot 20914, is configured to receive a tissue cutting knife. The anvil 20410 further comprises concentration features configured to concentrate the tissue forces between the anvil jaw 20410 and the staple cartridge 20900. For instance, the anvil 20410 comprises longitudinal concentration features 20413*a*, 20413*b*, and 20413*c* defined on both sides of the longitudinal slot 20914. The longitudinal concentration features 20413*a* are aligned with the first longitudinal steps 20913*a* of the staple cartridge 20900 when the anvil jaw 20410 is in its closed position; however, the concentration features 20413*a* do not extend over the entire width of the first longitudinal steps 20913*a*. As a result, the tissue gap between the anvil 20410 and the staple cartridge 20900 is narrow immediately under the concentration features 20413*a* which increases the compression being applied to the tissue immediately under and surrounding the concentration features 20413*a*. Similarly, the longitudinal concentration features 20413*b* are aligned with the second longitudinal steps 20913*b* of the staple cartridge 20900 when the anvil jaw 20410 is in its closed position; however, the concentration features 20413*b* do not extend over the entire width of the second longitudinal steps 20913*b*. As a result, the tissue gap between the anvil 20410 and the staple cartridge 20900 is narrow immediately under the concentration features 20413*b* which increases the compression being applied to the tissue immediately under and surrounding the concentration features 20413*b*. Likewise, the longitudinal concentration features 20413*a* are aligned with the third longitudinal steps 20913*c* of the staple cartridge 20900 when the anvil jaw 20410 is in its closed position; however, the concentration features 20413*c* do not extend over the entire width of the third longitudinal steps 20913*c*. As a result, the tissue gap between the anvil 20410 and the staple cartridge 20900 is narrow immediately under the concentration features 20413*c* which increases the compression being applied to the tissue immediately under and surrounding the concentration features 20413*c*.

Referring again to FIG. 47, each concentration feature 20413*a* has a first lateral width, each concentration feature 20413*b* has a second lateral width which is wider than the first lateral width, and each concentration feature 20413*c* has a third lateral width which is wider than the second lateral width. As a result, the force concentration under the concentration features 20413*a* is greater than the force concentration under the concentration features 20413*b*. Similarly, as a result, the force concentration under the concentration features 20413*b* is greater than the force concentration under the concentration features 20413*c*. As a result of the above, the first staples deployed from the first staple cavities 20420*a* will have a shorter post-fired height than the second staples deployed from the second staple cavities 20420*b*. Similarly, as a result of the above, the second staples deployed from the second staple cavities 20420*b* will have a shorter post-fired height than the third staples deployed from the third staple cavities 20420*c*.

Further to the above, a tissue cutting knife is moved through the staple cartridge 20900 to fire the staples stored therein during a staple firing stroke. In many instances, the tissue cutting knife is very sharp and/or the patient tissue is not very tough and/or dense. In such instances, the tissue cutting knife easily passes through the patient tissue without displacing the tissue distally. In other instances, the tissue cutting knife may not easily cut the tissue and may push some of the patient tissue captured within the end effector 20400 out of the distal end of the end effector 20400, thereby resulting in less tissue being stapled during the staple firing stroke. Referring again to FIG. 47, the cartridge body 20910 comprises distal tissue stops positioned at the distal end of the staple cartridge 20900 which prevent, or at least inhibit, the tissue from flowing distally out of the end effector 20400. The distal tissue stops comprise bumps, or domes, positioned at the distal ends of the longitudinal steps 20913*a*, 20913*b*, and 20913*c*, but could comprise any suitable configuration. The cartridge body 20910 comprises distal tissue stops 20919*a* positioned at the distal ends of the longitudinal steps 20913*a*, distal tissue stops 20919*b* positioned at the distal ends of the longitudinal steps 20913*b*, and distal tissue stops 20919*c* positioned at the distal ends of the longitudinal steps 20913*a*.

In various embodiments, further to the above, a staple cartridge can comprise a distal wall which can block the distal migration or flow of the tissue out of the end effector. In at least one embodiment, the perimeter of the staple cartridge is raised to control both longitudinal and lateral tissue flow. In various embodiments, the perimeter of the staple cartridge, including the distal end, for example, comprises a rough surface, or texture, which can prevent, or at least inhibit, the flow of the tissue out of the end effector. In at least one such embodiment, the rough surface texture around the perimeter of the cartridge deck can be about 10 times as rough as the rest of the deck surface, for example.

Figure 58:
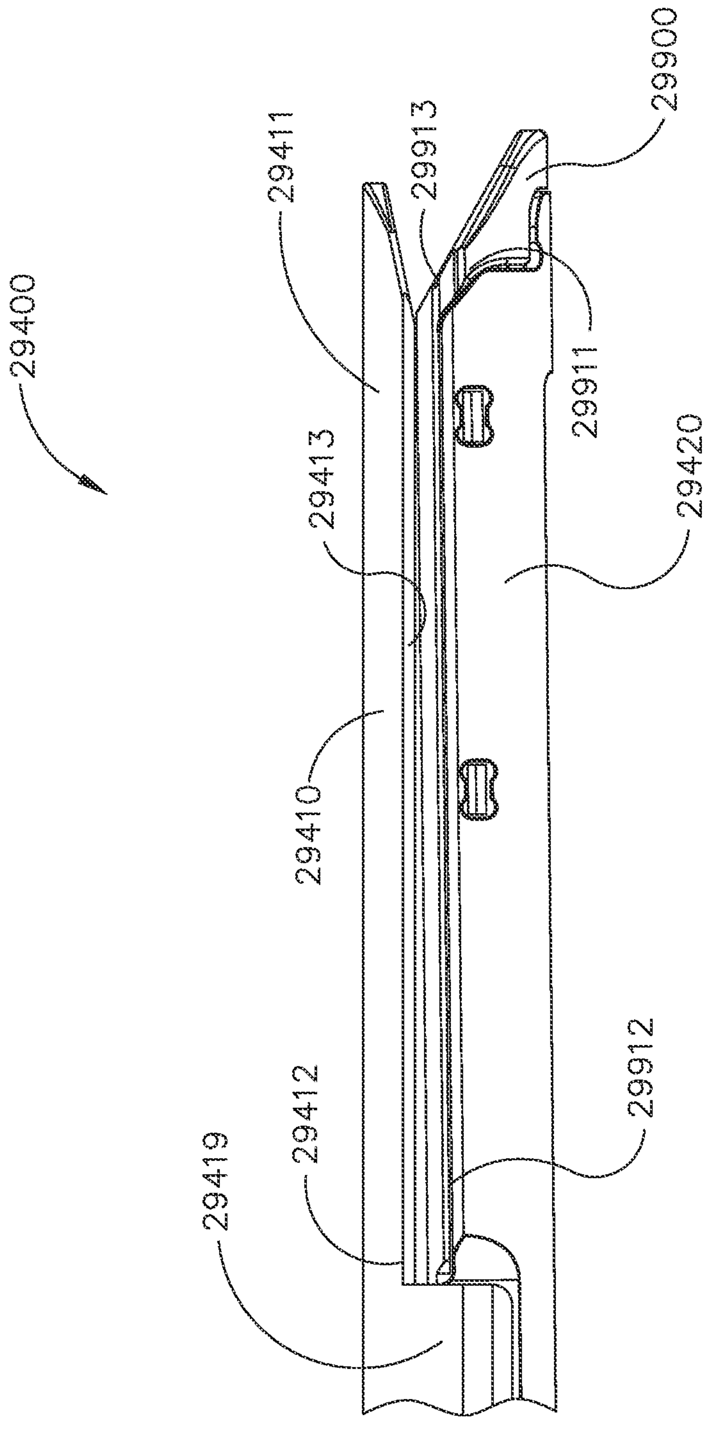
FIG. 58 is a partial elevational view of an end effector including an anvil jaw and a staple cartridge in accordance with at least one embodiment.
Figure 59:
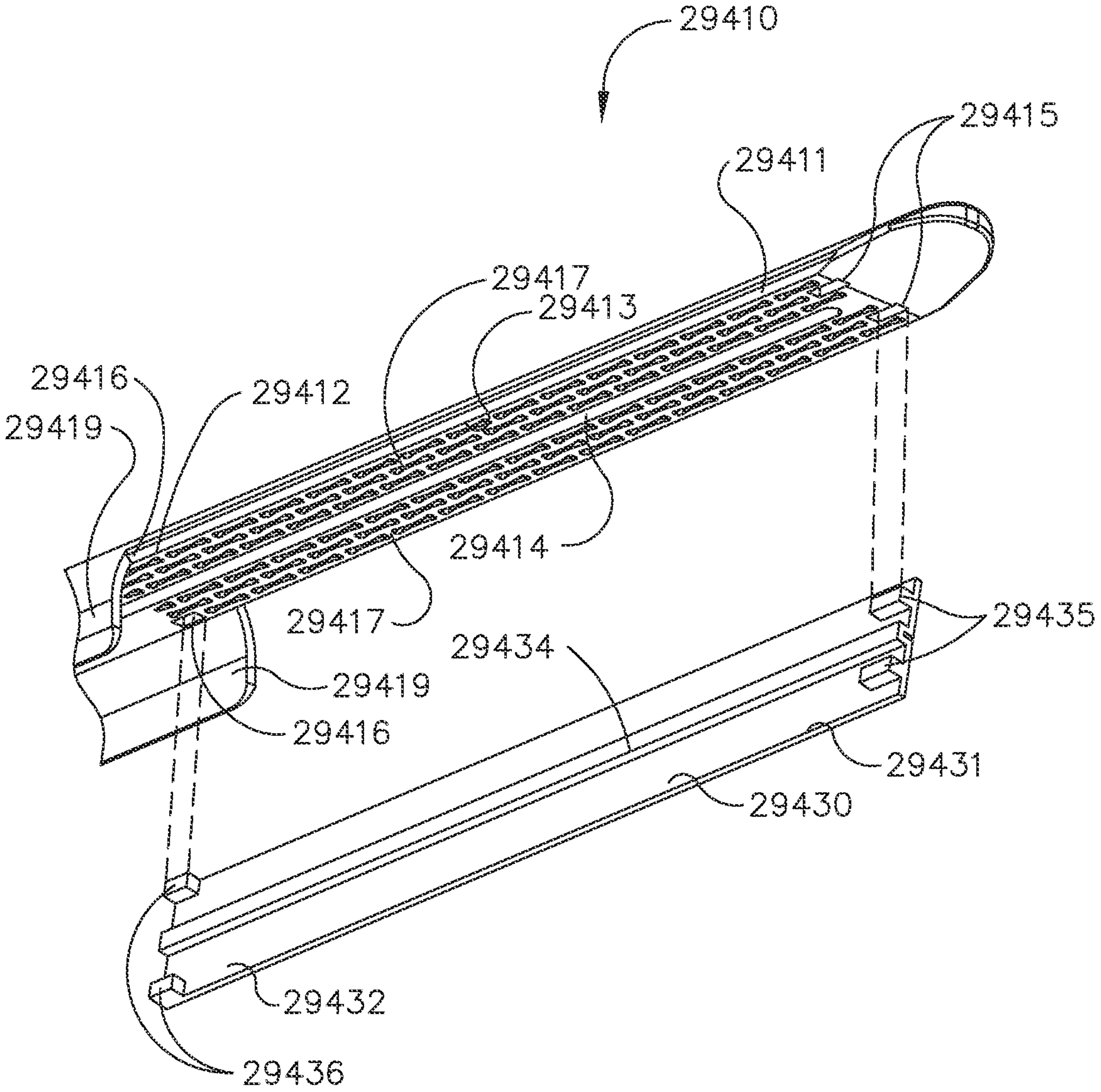
FIG. 59 is a partial perspective view of the anvil jaw of FIG. 58 including a detachable adjunct in accordance with at least one embodiment.

In various embodiments, referring now to FIG. 58, an end effector 29400 of a stapling instrument comprises an anvil jaw 29410 and a cartridge jaw 29420. The anvil jaw 29410 comprises a proximal end 29412 and a distal end 29411 where the proximal end 29412 is rotatably mounted to the cartridge jaw 29420 and is rotatable relative to the cartridge jaw 29420 between an open, or unclamped, position and a closed, or clamped, position (FIG. 58). Referring to FIG. 59, the anvil jaw 29410 further comprises a flat, or an at least substantially flat, tissue compression surface 29417 extending between the proximal end 29412 and the distal end 29411, a longitudinal slot 29414 extending from the proximal end 29412 toward the distal end 29411 which is configured to receive a tissue cutting knife, and longitudinal rows of staple forming pockets 29313 defined on opposite sides of the longitudinal slot 29414. The anvil jaw 29410 further comprises proximal tissue stops 29414 extending downwardly toward the cartridge jaw 29420, which are discussed further below.

Figure 60:
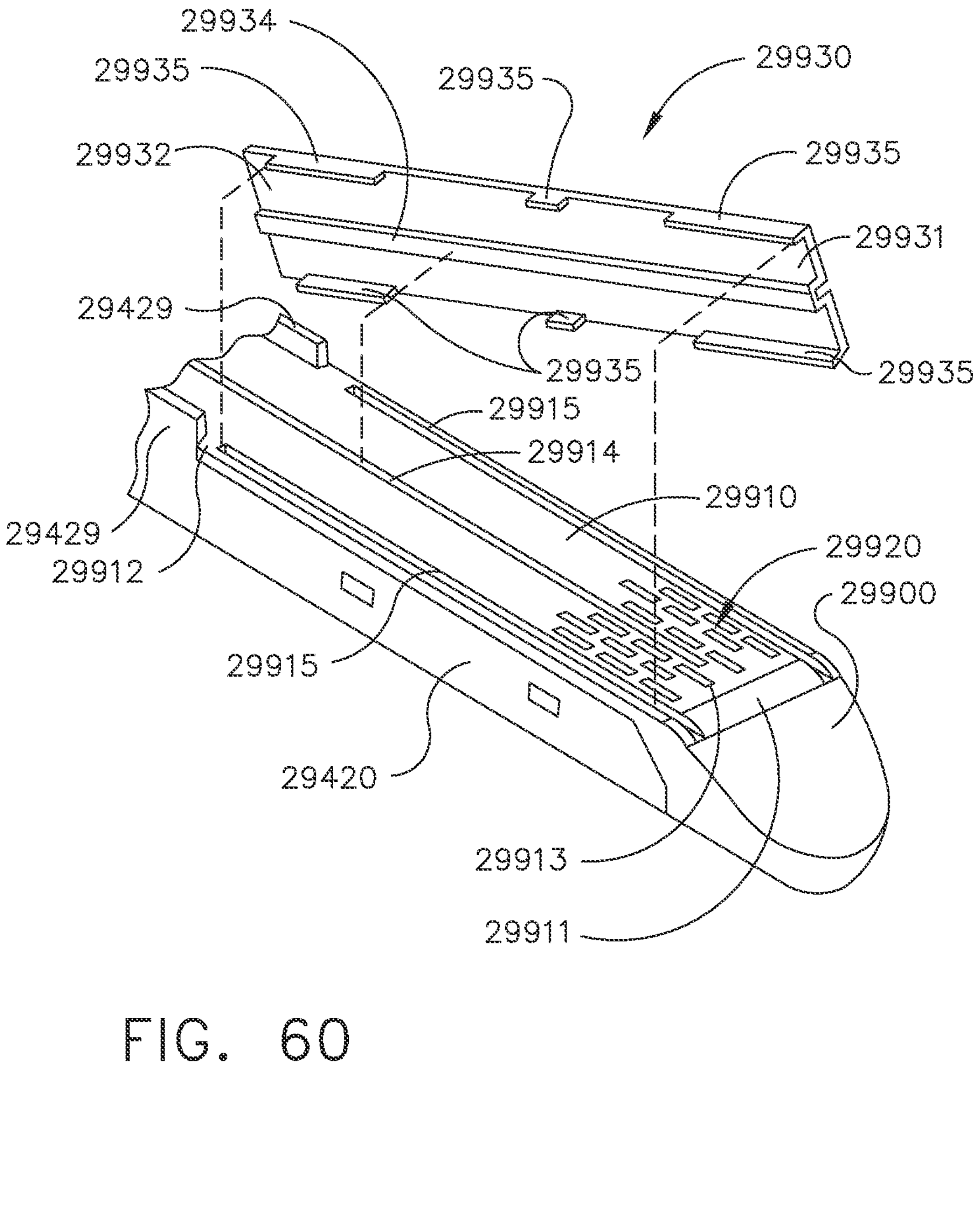
FIG. 60 is a partial perspective view of the staple cartridge of FIG. 58 comprising a detachable adjunct seated in a cartridge jaw in accordance with at least one embodiment.
Figure 61:
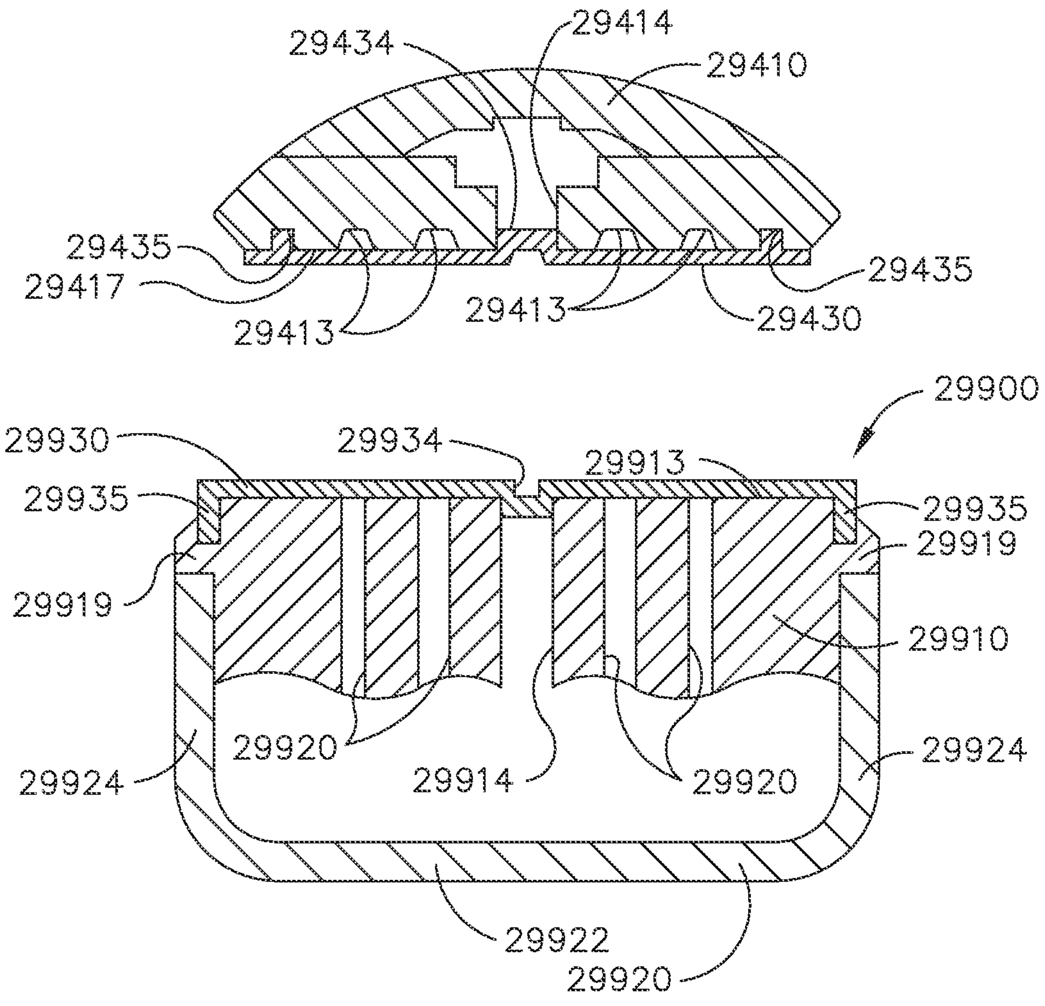
FIG. 61 is a cross-sectional view of the end effector of FIG. 58.

Referring to FIG. 61, the cartridge jaw 29420 comprises a bottom wall 29922 and lateral sidewalls 29924 extending therefrom which define a channel configured to receive a staple cartridge therein. Referring to FIGS. 58 and 60, the end effector 29400 further comprises a staple cartridge 29900 seated in the channel defined by the cartridge jaw 29420. The staple cartridge 29900 comprises a cartridge body 29910 including a proximal end 29912 and a distal end 29911, a deck 29913 extending between the proximal end 29912 and the distal end 29911 which is configured to support patient tissue, and a longitudinal slot 29914 extending from the proximal end 29912 toward the distal end 29911 which is configured to receive the tissue cutting knife. Referring again to FIG. 61, the staple cartridge 29900 is configured to be closely received between the lateral sidewalls 29924 of the cartridge jaw 29420. Moreover, the cartridge body 29910 comprises lateral support flanges 29919 extending therefrom which are in contact with the top surfaces of the lateral sidewalls 29924 which support the staple cartridge 29900 within the cartridge jaw 29420. Referring again to FIG. 60, the staple cartridge 29900 further comprises longitudinal rows of staple cavities 29920 defined in the cartridge body 29910 on opposite sides of the longitudinal slot 29914 which contain staples removably stored therein. During a staple firing stroke, the staples are ejected from the staple cavities 29920 by the tissue cutting knife and deformed against the staple forming pockets 29913 of the anvil jaw 29910.

Further to the above, referring to FIG. 60, the cartridge jaw 29420 further comprises proximal tissue stops 29429 extending upwardly toward the anvil jaw 29410. Referring to FIG. 58, the anvil tissue stops 29419 and the cartridge tissue stops 29429 co-operate to prevent patient tissue from moving proximally into the end effector 29400 where the tissue may accidentally contact the tissue cutting knife in its proximal unactuated position. Moreover, the anvil tissue stops 29419 and the cartridge tissue stops 29429 co-operate to keep the patient tissue over the staple cavities 29920 defined in the staple cartridge 29900 such that the proximal-most tissue captured within the end effector 29400 is stapled during the staple firing stroke. The reader should note that the staple cavities 29220 extend proximally to and/or proximally past the proximal tissue stops 29429, even though this is not depicted in FIG. 60. Similarly, the reader should note that the staple forming pockets 29413 defined in the anvil jaw 29410 extend proximally to and/or proximally past the proximal tissue stops 29419. The reader should also note, referring to FIG. 58, that the camber of the tissue compression surface 29417 of the anvil jaw 29410 is angled downwardly toward the staple cartridge 29900 to prevent, or at least inhibit, the tissue captured between the anvil jaw 29410 and the staple cartridge 29900 from flowing out of the distal end of the end effector 29400.

Further to the above, referring to FIGS. 59 and 61, the end effector 29400 further comprises an implantable layer, or adjunct, 29430 releasably attached to the anvil jaw 29410. The implantable layer 29430 comprises a longitudinal rib 29434 extending therefrom which is positioned in the longitudinal slot 29414 defined in the anvil jaw 29410. The longitudinal rib 29434 is sized and configured such that rib 29434 is compressed between the sidewalls of the longitudinal slot 29414. Such an arrangement releasably retains the implantable layer 29430 to the anvil jaw 29410. That said, the tissue cutting knife progressively transects the implantable layer 29430 through the longitudinal rib 29434 as the tissue cutting knife is progressed through the staple firing stroke to release the rib 29434 from the longitudinal slot 29414. Notably, the implantable layer 29430 covers all of the tissue forming pockets 29413 of the anvil jaw 29410, but other embodiments are envisioned in which less than all of the staple forming pockets 29413 are covered by the implantable layer 29430. In addition to or in lieu of the longitudinal rib 29434 to secure the implantable layer 29430 to the anvil jaw 29410, the implantable layer 29430 comprises distal retention members 29435 extending from a distal end 29431 of the implantable layer 29430 which are press-fit and releasably received within distal retention apertures 29415 defined in the anvil jaw 29410. Similarly, the implantable layer 29430 comprises proximal retention members 29436 extending from a proximal end 29432 of the implantable layer 29430 which are press-fit within proximal retention apertures 29416 defined in the anvil jaw 29410. During the staple firing stroke, the staples ejected from the staple cartridge 29900 penetrate the patient tissue and the implantable layer 29430 and then capture the implantable layer 29430 against the patient tissue as the staples are deformed against the staple forming pockets 29413. After the staple firing stroke has been completed and the end effector 29400 is opened, the implantable layer 29430 releases from the anvil jaw 29410 and remains with the stapled patient tissue.

Further to the above, referring to FIGS. 60 and 61, the end effector 29400 further comprises an implantable layer, or adjunct, 29930 releasably attached to the cartridge jaw 29420. The implantable layer 29930 comprises a longitudinal rib 29934 extending therefrom which is positioned in the longitudinal slot 29914 defined in the cartridge body 29910. The longitudinal rib 29934 is sized and configured such that the rib 29934 is compressed between the sidewalls of the longitudinal slot 29914. Such an arrangement releasably retains the implantable layer 29930 to the cartridge jaw 29420. That said, the tissue cutting knife progressively transects the implantable layer 29930 through the longitudinal rib 29934 as the tissue cutting knife is progressed through the staple firing stroke to release the rib 29934 from the slot 29914. Notably, the implantable layer 29930 covers all of the staple cavities 29920 of the staple cartridge 29900, but other embodiments are envisioned in which less than all of the staple cavities 29920 are covered by the implantable layer 29930. In addition to or in lieu of the longitudinal rib 29934 to secure the implantable layer 29930 to the cartridge body 29910, the implantable layer 29930 comprises retention members 29935 extending from a distal end 29931, a proximal end 29932, and an intermediate portion of the implantable layer 29930 which are press-fit and releasably received within longitudinal retention slots 29915 defined in the lateral sides of the cartridge jaw 29910. During the staple firing stroke, the staples ejected from the staple cartridge 29900 penetrate the implantable layer 29930 and the patient tissue and then capture the implantable layer 29930 against the patient tissue as the staples are deformed against the staple forming pockets 29413. After the staple firing stroke has been completed and the end effector 29400 is opened, the implantable layer 29930 releases from the cartridge body 29910 and remains with the stapled patient tissue.

Further to the above, referring again to FIG. 60, the longitudinal retention slots 29915 comprise open ends at the distal end 29911 of the cartridge body 29910. The open ends of the retention slots 29915 are configured to receive the retention members 29935 when the implantable layer 29930 is slid, or assembled, longitudinally onto the cartridge body 29910 from the distal end 29911 of the cartridge body 29910. Such distal openings also assist in the implantable layer 29930 detaching from the cartridge body 29910. More specifically, the end effector 29400 is often pulled longitudinally away from the stapled tissue after the end effector 29400 has been opened and, in such instances, the retention slots 29915, and their distal openings, are aligned with this commonly-used motion of the end effector 29400.

The implantable layers 29430 and 29930 provide several benefits. In various instances, the implantable layers 29430 and 29930 buttress the patient tissue being stapled which prevents, or at least inhibits, the patient tissue from tearing, especially when the patient tissue is thin, for example. Also, in various instances, the implantable layers 29430 and 29930 are comprised of a compressible material and can compensate for changes in tissue thickness within a line of implanted staples. Moreover, in various instances, the implantable layers 29430 and 29930 can prevent, or at least inhibit, the implanted staples from pulling through the patient tissue. These benefits can be obtained, in varying degrees, if both the implantable layers 29430 and 29930 are implanted against the patient tissue or if only one of the implantable layers 29430 and 29930 are implanted against the patient tissue. The entire disclosure of U.S. Pat. No. 8,740,037, entitled COMPRESSIBLE FASTENER CARTRIDGE, filed on Sep. 30, 2010, is incorporated by reference herein.

Further to the above, the press-fit and/or friction fit between the retention members 29935 and the retention slots 29915 prevents, or at least inhibits, the implantable layer 29930 from sliding relative to the cartridge body 29910 when the end effector 29400 is positioned relative to the patient tissue and also when the tissue cutting knife is advanced through the patient tissue during the staple firing stroke. Among other things, the interaction between the retention members 29935 and the retention slots 29915 prevents the implantable layer 29930 from sliding laterally and/or longitudinally relative to the cartridge body 29910.

Referring again to FIG. 58, the distal tip 29411 of the anvil jaw 29410 is cambered downwardly toward the distal nose 29911 of the staple cartridge 29900 when the anvil jaw 29410 is in its clamped position. As a result, the tissue gap between the anvil jaw 29410 and the staple cartridge 29900 may be small at the distal end of the end effector 29400. In such instances, the distal end of the end effector 29400 can be used as a dissector to grasp and move tissue, for example.

In various embodiments, the distal tip 29411 of the anvil jaw 29410 is movable relative to the main body of the anvil jaw 29410. In at least one such embodiment, the main body defines a guide rail and the distal tip 29411 is slideable along the guide rail. When the anvil jaw 29410 is closed and the distal tip 29411 contacts the tissue, the distal tip 29411 can slide along the rail in reaction to the clamping force being applied to the tissue. In at least one embodiment, the rail extends longitudinally and the distal tip 29411 slides distally along the longitudinal rail to expand the tissue gap between the distal ends of the anvil jaw 29410 and the staple cartridge 29900. In at least one embodiment, the rail extends vertically and the distal tip 29411 slides along the vertical rail to expand the tissue gap between the distal ends of the anvil jaw 29410 and the staple cartridge 29900. In either event, the anvil jaw 29410 further comprises a spring connecting the distal tip 29411 to the main body of the anvil jaw 29410 which biases the distal tip 29411 back into its undisplaced position when the anvil jaw 29410 is re-opened. As a result of the above, the sliding distal tip 29411 can reduce the possibility of the tissue being pinched between the anvil jaw 29410 and the staple cartridge 29900. Moreover, the displacement of the distal tip 29411 can provide a visual indicator to the clinician that the tissue between the anvil jaw 29410 and the staple cartridge 29900 has been sufficiently compressed.

In addition to or in lieu of the above, the distal nose 29911 of the staple cartridge 29900 is movable relative to the main body of the cartridge body 29910. In at least one such embodiment, the cartridge body 29910 defines a guide rail and the distal nose 29911 is slideable along the guide rail. When the anvil jaw 29410 is closed, the cartridge nose 29911 can slide inwardly along the rail in reaction to the clamping force being applied to the tissue. In at least one embodiment, the rail extends longitudinally and the distal nose 29911 slides distally along the longitudinal rail to expand the tissue gap between the distal ends of the anvil jaw 29410 and the staple cartridge 29900. The entire disclosures of U.S. Pat. No. 9,039,736, entitled SURGICAL STAPLING DEVICE WITH DISSECTING TIP, which issued on May 26, 2015, U.S. Pat. No. 8,136,711, entitled DISSECTION TIP AND INTRODUCER FOR SURGICAL INSTRUMENT, which issued on Mar. 20, 2012, U.S. Pat. No. 8,714,429, entitled DISSECTING TIP FOR SURGI- CAL STAPLER, which issued on May 6, 2014, and European Patent No. EP 2,913,010, entitled INTRODUCER ASSEMBLY FOR A SURGICAL FASTENER APPLYING APPARATUS are incorporated by reference herein.

Figure 61A:
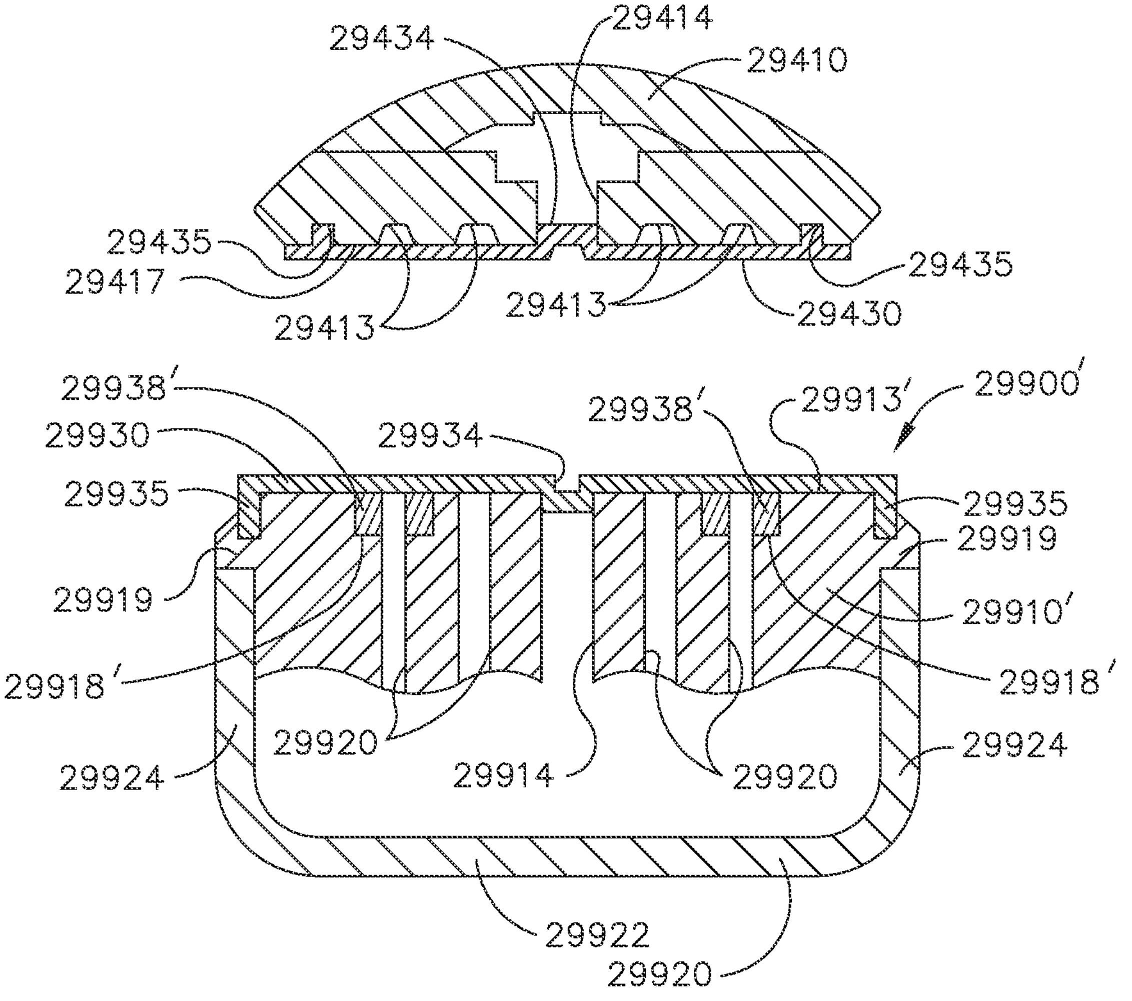
FIG. 61A is cross-sectional view of an end effector in accordance with at least one embodiment.

A staple cartridge 29900' is illustrated in FIG. 61A and is similar to the staple cartridge 29900 in many respects, most of which will not be discussed herein for the sake of brevity. The staple cartridge 29900' comprises a cartridge body 29910' and an implantable layer 29930' releasably attached to the cartridge body 29910'. The cartridge body 29910' comprises a deck 29913' and recesses, or dwells, 29918' defined therein which surround at least some of the openings of the staple cavities 29920 defined in the deck 29913'. The implantable layer 29930' comprises projections, or swells, 29938' extending therefrom which are positioned in the recesses 29918' which resist relative lateral and longitudinal sliding motion between the implantable layer 29930' and the cartridge body 29910'. The recesses 29918' comprise crescent-shaped pockets, but could comprise any suitable shape, and the projections 29938' are shaped and configured to complement or match the recesses 29918'. Such an arrangement can create an undulating or wavy top surface of the deck 29913', for example.

Figure 61B:
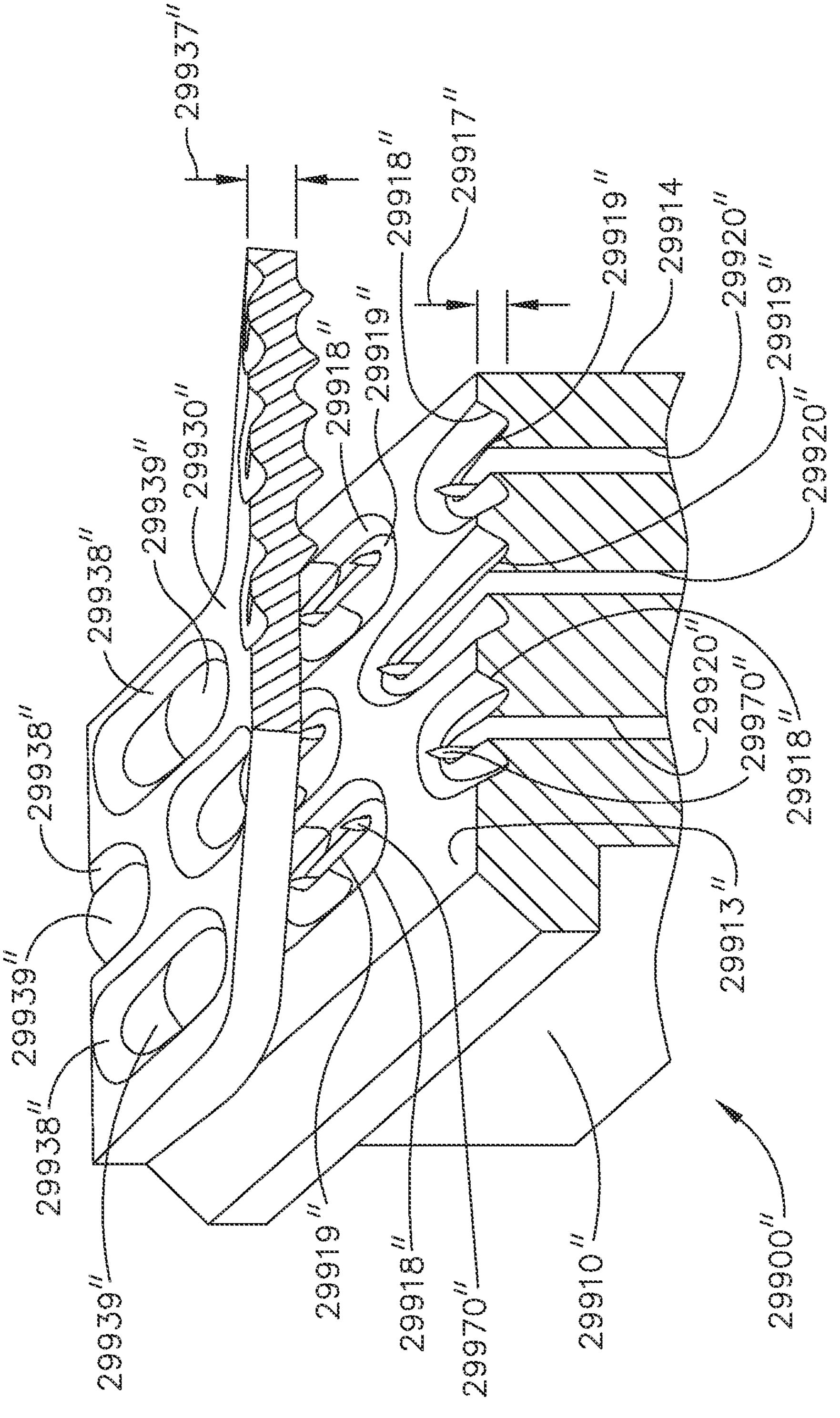
FIG. 61B is a partial cross-sectional view of a staple cartridge in accordance with at least one embodiment.

A staple cartridge 29900" is illustrated in FIG. 61B and is similar to the staple cartridges 29900 and 29900' in many respects, most of which will not be discussed herein for the sake of brevity. The staple cartridge 29900" comprises a cartridge body 29910" and an implantable layer 29930" releasably connected to the cartridge body 29910". The cartridge body 29910" comprises a deck 29913" and recesses 29918" defined therein which surround the openings of the staple cavities 29920 defined in the deck 29913". Each recess 29918" comprises a rounded profile and sloped walls. In at least one such embodiment, the recesses 29918" do not comprise vertical walls. The cartridge body 29910" further comprises a dimple 29919" extending upwardly from the bottom of each recess 29918". Similar to the recesses 29918", the dimples 29919" surround the openings of the staple cavities 29920 defined in the deck 29913" and comprise sloped walls. In at least one such embodiment, the dimples 29919" do not comprise vertical walls.

The implantable layer 29930" comprises recesses 29938" defined therein which define bumps that extend into the recesses 29918" defined in the cartridge body 29910". The implantable layer 29930" further comprises dimples 29939" in the recesses 29938" which are aligned, or at least substantially aligned, with the staples 29970" positioned in the staple cavities 29920. In at least one such embodiment, the tips of the staple legs are embedded in the dimples 29939" of the implantable layer 29930" when the staples 29970" are stored in their unfired positions in the staple cavities 29920. In other embodiments, the tips of the staple legs are positioned just below the dimples 29939" when the staples 29970" are stored in their unfired positions.

Further to the above, referring again to FIG. 61B, the implantable layer 29930" comprises a thickness 29937" and is comprised of a malleable material, for example. Notably, the thickness 29937" may or may not be constant across the entire implantable layer 29930". The height of the dimples 29919" is less than the thickness 29937" of the implantable layer 29930". Moreover, the recesses 29918" defined in the cartridge body 29910" have a depth 29917" which is larger than the height of the dimples 29919". As a result, the dimples 29919" do not extend above the deck 29913". That said, the layer 29930" is in contact with the dimples 29919" which prevents, or at least inhibits, the layer 29930" from sliding laterally and/or longitudinally relative to the cartridge deck 29910".

Figure 54:
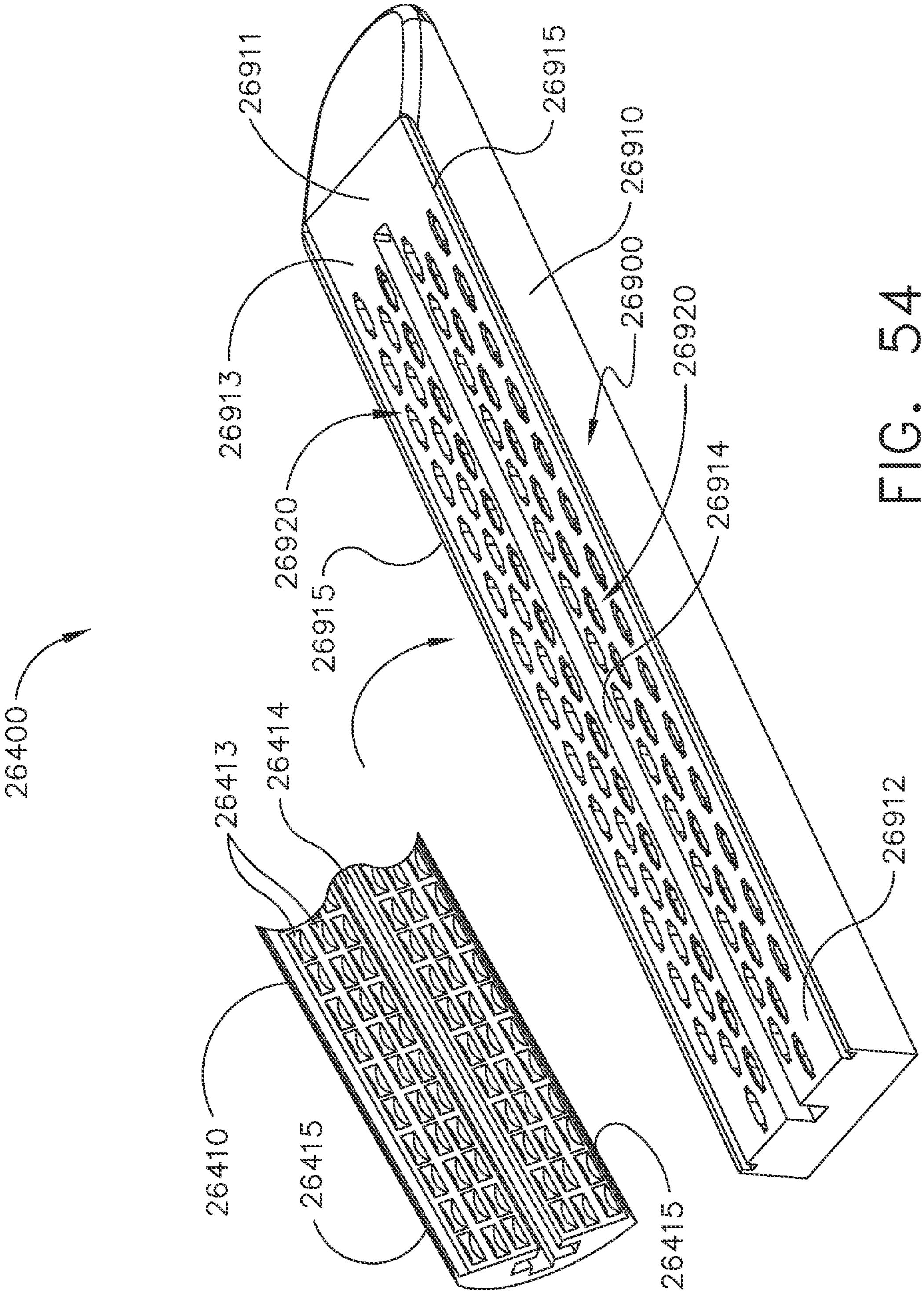
FIG. 54 is a partial cross-sectional view of a staple cartridge and an anvil in accordance with at least one embodiment.
Figure 55:
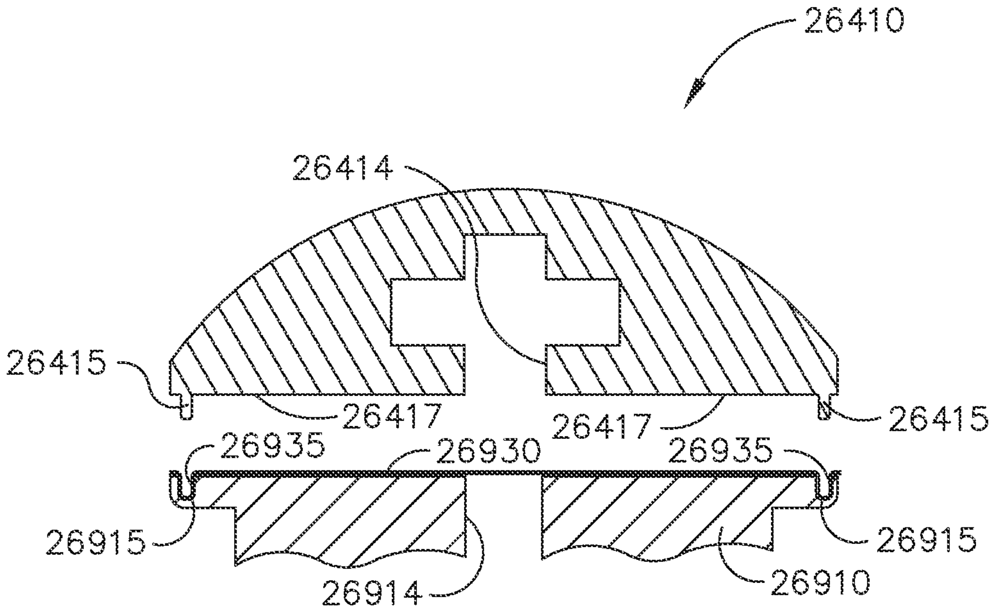
FIG. 55 is a partial cross-sectional view of an anvil jaw and a staple cartridge in accordance with at least one embodiment.

Referring now to FIGS. 54 and 55, an end effector 26400 comprises an anvil jaw 26410 and a cartridge jaw comprising a staple cartridge 26900 positioned therein. The anvil jaw 26410 comprises a longitudinal slot 26414 which is configured to receive a tissue cutting knife. The anvil jaw 26410 further comprises a tissue compression surface 26417 and longitudinal rows of staple forming pockets 26413 defined in the tissue compression surface 26417. The staple cartridge 26900 comprises a cartridge body 26910 including a proximal end 26912 and a distal end 26911, a deck 26913 extending between the proximal end 26912 and the distal end 26911 which is configured to support patient tissue, and a longitudinal slot 26914 extending from the proximal end 26912 toward the distal end 26911 which is configured to receive the tissue cutting knife. The staple cartridge 26900 further comprises longitudinal rows of staple cavities 26920 defined in the deck 26913 on opposite sides of the longitudinal slot 26914 which contain staples removably stored therein. During a staple firing stroke, the staples are ejected from the staple cavities 26920 by the tissue cutting knife and deformed against the staple forming pockets 26913 of the anvil jaw 26910.

Figure 55A:
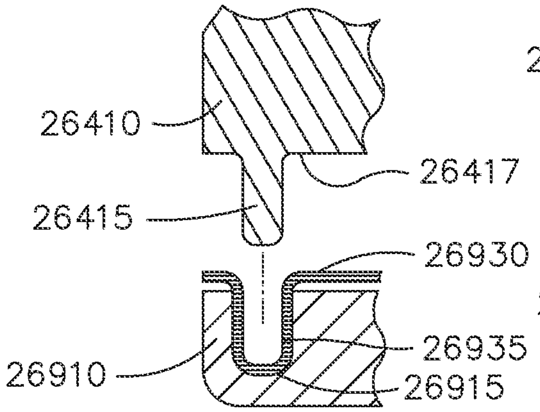
FIG. 55A is a detail view of the anvil jaw and staple cartridge of FIG. 55.

Further to the above, the staple cartridge 26900 further comprises an implantable layer 26930 releasably attached to the cartridge body 26910. The cartridge body 26910 comprises longitudinal retention slots 26915 defined therein which, similar to the above, comprise open distal ends which permit the implantable layer 26930 to be slid longitudinally onto the cartridge body 26910 when assembling the implantable layer 26930 onto the cartridge body 26910 and/or slid longitudinally off of the cartridge body 26910 after implanting the layer 26930 against the patient tissue. The implantable layer 26930 comprises lateral retention folds 26935 extending longitudinally along the lateral sides thereof which are positioned within and releasably secured within the longitudinal retention slots 26915. When the end effector 26400 is clamped against patient tissue, in various instances, the tissue may flow into the retention slots 26915 onto the retention folds 26935 which, absent other considerations, may loosen the grip of the end effector jaws on this portion of the patient tissue. Referring primarily to FIG. 55A, the anvil jaw 26410 comprises longitudinal rails 26415 defined thereon which are aligned with the retention slots 26915 and are configured to push the patient tissue into the retention slots 26915 and improve the grip of the end effector jaws onto the patient tissue.

Figure 55B:
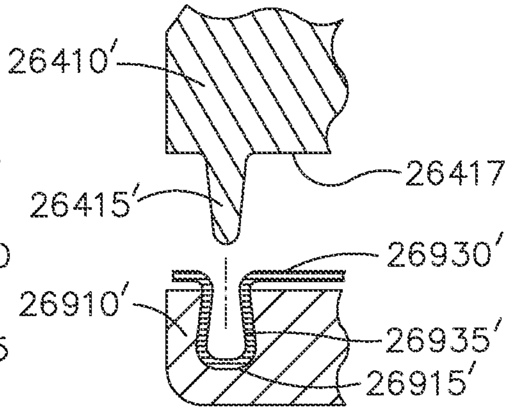
FIG. 55B is a detail view of an alternative embodiment to FIG. 55.

Referring again to FIG. 55A, the opposing sidewalls of the retentions slots 26915 are vertical and the lateral retention folds 26935 comprise a corresponding configuration to that of the retention slots 26915. Similarly, the longitudinal rails 26415 comprise vertical sidewalls which correspond to the vertical sidewalls of the retention slots 26915. An alternative embodiment is illustrated in FIG. 55B which comprises a cartridge body 26910' including a longitudinal retention slot 26915', an implantable layer 26930' including a lateral retention fold 26935' releasably secured within the retention slot 26915', and an anvil jaw 26410' comprising a longitudinal rail 26415' configured to grip the patient tissue when the anvil jaw 26410' is in a closed position. Notably, the opposing sidewalls of the retention slot 26915' are not vertical; rather, the opposing sidewalls of the retention slot 26915' are angled inwardly. The lateral retention fold 26935' comprises a corresponding configuration to that of the retention slot 26915' and the longitudinal rail 26415' comprises a tapered configuration which can improve the tissue grip of the anvil jaw 26410'.

Figure 56:
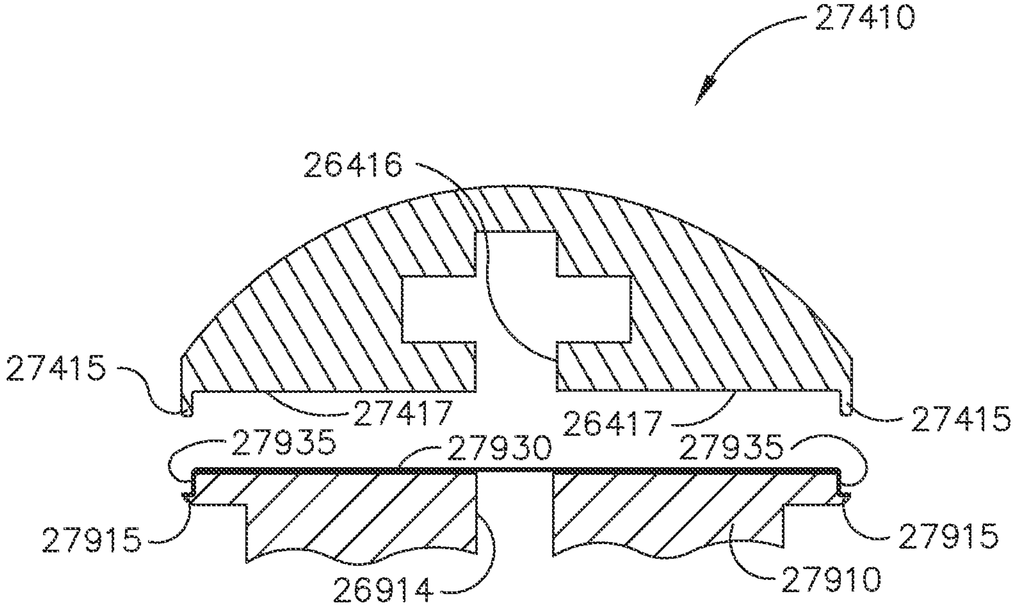
FIG. 56 is a partial cross-sectional view of an anvil jaw and a staple cartridge in accordance with at least one embodiment.
Figure 56A:
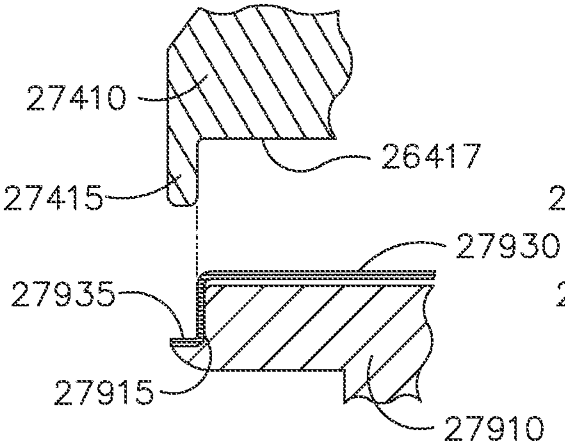
FIG. 56A is a detail view of the anvil jaw and staple cartridge of FIG. 56.
Figure 56B:
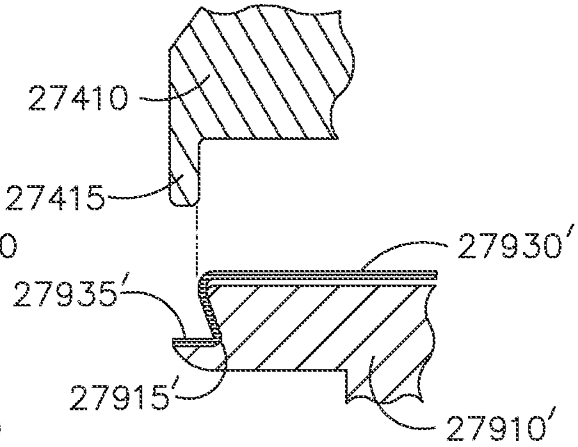
FIG. 56B is a detail view of an alternative embodiment to FIG. 56.

An alternative embodiment is illustrated in FIGS. 56 and 56A which comprises a cartridge body 27910 including longitudinal retention notches 27915, an implantable layer 27930 including lateral retention folds 27935 releasably secured within the retention notches 27915, and an anvil jaw 27410 comprising longitudinal rails 27415 configured to grip the patient tissue when the anvil jaw 27410 is in a closed position. Notably, the sidewalls of the retention notches 27915 are vertical. The lateral retention folds 27935 comprise a corresponding configuration to that of the retention slots 27915 and the longitudinal rails 27415 comprise vertical sidewalls which correspond to the sidewalls of the retention notches 27915. An alternative embodiment is illustrated in FIG. 56B which comprises a cartridge body 27910' including a longitudinal retention notch 27915', an implantable layer 27930' including a lateral retention fold 27935' releasably secured within the retention notch 27915', and an anvil jaw 27410 comprising a longitudinal rail 27415 configured to grip the patient tissue when the anvil jaw 27410 is in a closed position. Notably, the sidewall of the retention notch 27915' is not vertical, rather, the sidewall of the retention notch 27915' is angled inwardly. The lateral retention fold 27935' comprises a corresponding configuration to that of the retention notch 27915'. Such an arrangement can improve the retention of the implantable layer 27930' to the cartridge body 27910'.

Figure 57:
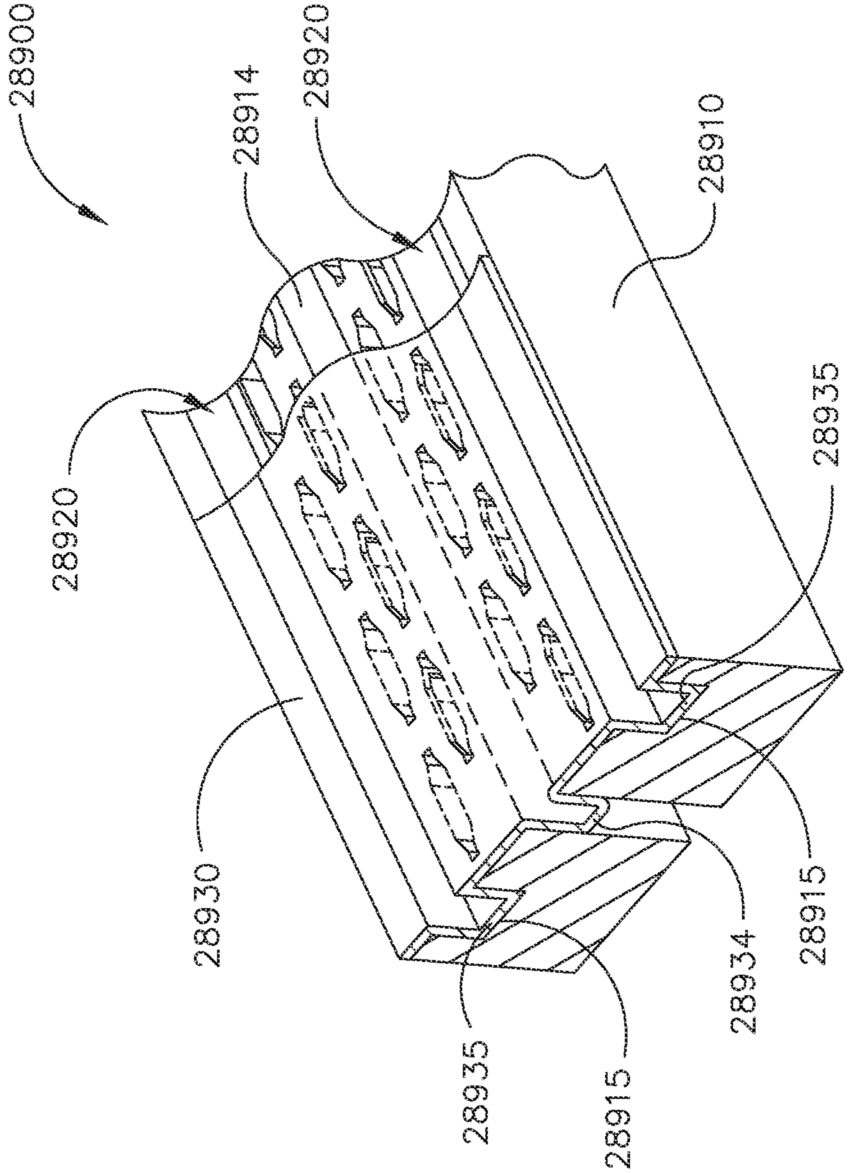
FIG. 57 is a partial cross-sectional view of a staple cartridge in accordance with at least one embodiment.

Referring to FIG. 57, a staple cartridge 28900 comprises a cartridge body 28910 and an implantable layer 28930 releasably attached thereto. The cartridge body 28910 comprises a longitudinal slot 28914 defined therein and longitudinal rows of staple cavities 28920 on opposite sides of the longitudinal slot 28914. The implantable layer 28930 comprises a longitudinal fold 28934 press-fit and/or friction-fit into the longitudinal slot 28914 which releasably holds the implantable layer 28930 to the cartridge body 28910.

Further to the above, the cartridge body 28910 further comprises longitudinal channels 28915 defined in the deck of the cartridge body 28910. More specifically, each side of the cartridge deck comprises a longitudinal channel 28915 which defines a lower portion of the cartridge deck aligned with the outer rows of staple cavities 28920. Each side of the cartridge deck further comprises an inner longitudinal row of staple cavities 28920 and an intermediate row of staple cavities 28920 defined in an upper portion of the cartridge deck. The implantable layer 28930 comprises longitudinal folds 28935 press-fit and/or friction-fit into the longitudinal channels 28915 which releasably hold the implantable layer 28930 to the cartridge body 28910. In various embodiments, the staple drivers configured to fire the staples stored in the outer longitudinal rows 28920 may not lift the outer staples to the same height as the inner and intermediate staples. In at least one such embodiment, the as-deformed size of the outer staples is larger than the as-deformed size of the inner staples and the intermediate staples. In at least one other embodiment, the outer staples are deformed to the same as-formed height as the inner staples and intermediate staples despite having a lower recessed deck.

Figure 50:
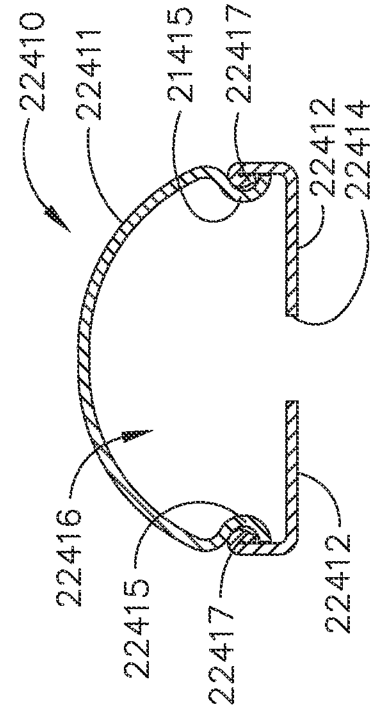
FIG. 50 is a cross-sectional view of an anvil jaw in accordance with at least one embodiment.

An anvil jaw 22410 of a stapling instrument is illustrated in FIG. 50 and is similar to the other anvil jaws disclosed herein in many respects, many of which will not be discussed herein for the sake of brevity. The anvil jaw 22410 comprises a cap, or cover, 22411 and tissue support plates 22412 welded to the cap 22411. Each support plate 22412 comprises a longitudinal lateral rib 22417 folded therein which is positioned in a longitudinal recess, or gutter, 22415 defined in a folded lateral lip of the cap 22411. In various instances, the longitudinal lateral ribs 22417 are press-fit into their respective longitudinal recesses 22415 and then welded into place. As a result of the above, the anvil jaw 22410 is stiff and resists bending during the staple firing stroke. The support plates 22412 are positioned and arranged such that a longitudinal slot 22414 is defined between the support plates 22412 and such that a longitudinal cavity 22416 is defined between the support plates 22412 and the cap 22411. The longitudinal slot 22414 and the longitudinal cavity 22416 are sized and configured to receive a tissue cutting knife therein. Each support plate 22412 comprises a longitudinal row of first, or innermost, staple forming pockets defined therein, a longitudinal row of second, or intermediate, staple forming pockets defined therein, and a longitudinal row of third, or outermost, staple forming pockets defined therein.

Figure 51:
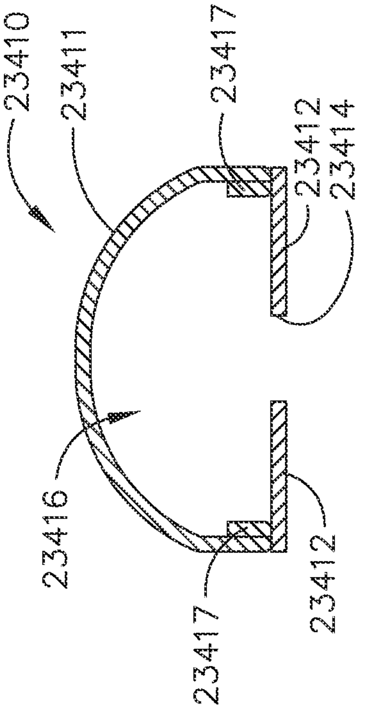
FIG. 51 is a cross-sectional view of an anvil jaw in accordance with at least one embodiment.

An anvil jaw 23410 of a stapling instrument is illustrated in FIG. 51 and is similar to the other anvil jaws disclosed herein in many respects, many of which will not be discussed herein for the sake of brevity. The anvil jaw 23410 comprises a cap, or cover, 23411 and tissue support plates 23412 welded to the cap 23411. Each support plate 23412 comprises a longitudinal lateral flange 23417 extending therefrom which abuts the cap 23411. In at least one instance, openings, or apertures, are defined in the cap 23411 which allow the lateral flanges 23417 to be directly welded to the cap 23411 so that the support plates 23412 are held securely in position relative to the cap 23411. As a result of the above, the anvil jaw 23410 is stiff and resists bending during the staple firing stroke. The support plates 23412 are positioned and arranged such that a longitudinal slot 23414 is defined between the support plates 23412 and such that a longitudinal cavity 23416 is defined between the support plates 23412 and the cap 23411. The longitudinal slot 23414 and the longitudinal cavity 23416 are sized and configured to receive a tissue cutting knife therein. Each support plate 23412 comprises a longitudinal row of first, or innermost, staple forming pockets defined therein, a longitudinal row of second, or intermediate, staple forming pockets defined therein, and a longitudinal row of third, or outermost, staple forming pockets defined therein.

Figure 52:
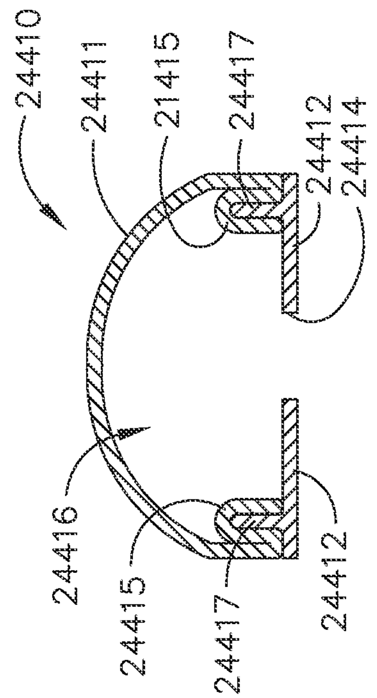
FIG. 52 is a cross-sectional view of an anvil jaw in accordance with at least one embodiment.
Figure 52A:
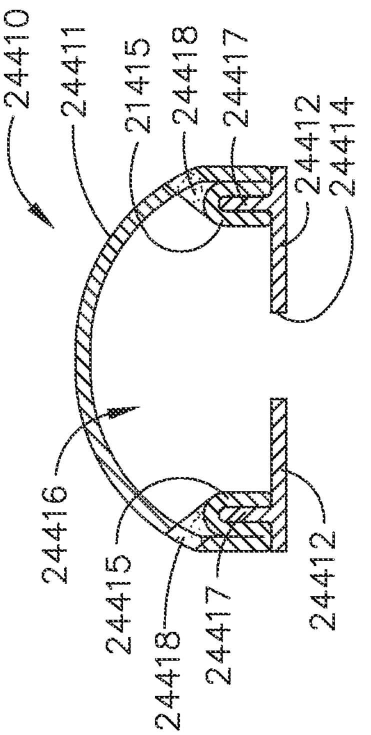
FIG. 52A is a cross-sectional view of the anvil jaw of FIG. 52 after the components of the anvil jaw have been welded.

An anvil jaw 24410 of a stapling instrument is illustrated in FIGS. 52 and 52A and is similar to the other anvil jaws disclosed herein in many respects, many of which will not be discussed herein for the sake of brevity. The anvil jaw 24410 comprises a cap, or cover, 24411 and tissue support plates 24412 welded to the cap 24411. Each support plate 24412 comprises a longitudinal lateral flange 24417 extending therefrom which is received in a folded lateral slot, or gutter, 24415 defined in the cap 24411. In at least one instance, openings, or apertures, are defined in the cap 24411 which allow the lateral flanges 24417 to be directly welded to the cap 24411 via welds 24418 so that the support plates 24412 are held securely in position relative to the cap 24411. As a result of the above, the anvil jaw 24410 is stiff and resists bending during the staple firing stroke. The support plates 24412 are positioned and arranged such that a longitudinal slot 24414 is defined between the support plates 24412 and such that a longitudinal cavity 24416 is defined between the support plates 24412 and the cap 24411. The longitudinal slot 24414 and the longitudinal cavity 24416 are sized and configured to receive a tissue cutting knife therein. Each support plate 24412 comprises a longitudinal row of first, or innermost, staple forming pockets defined therein, a longitudinal row of second, or intermediate, staple forming pockets defined therein, and a longitudinal row of third, or outermost, staple forming pockets defined therein.

Figure 53:
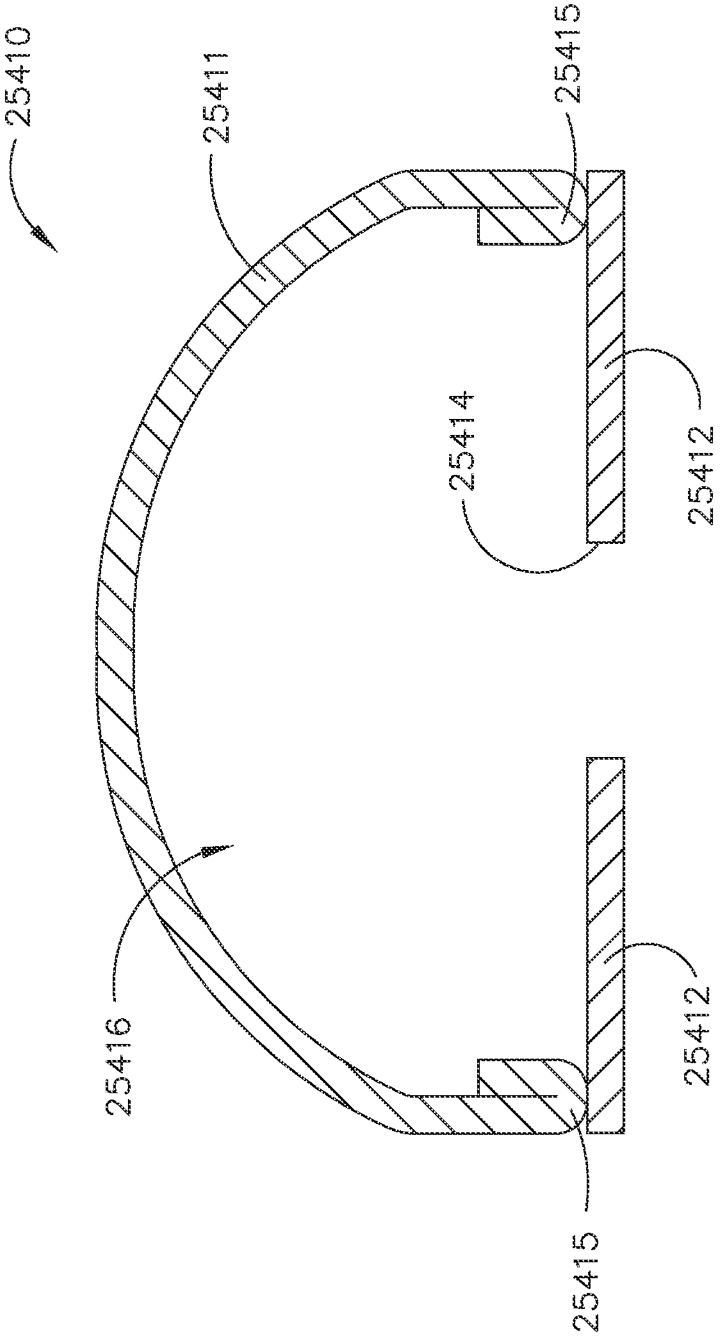
FIG. 53 is a cross-sectional view of an anvil jaw in accordance with at least one embodiment.

An anvil jaw 25410 of a stapling instrument is illustrated in FIG. 53 and is similar to the other anvil jaws disclosed herein in many respects, many of which will not be discussed herein for the sake of brevity. The anvil jaw 25410 comprises a cap, or cover, 25411 and tissue support plates 25412 welded to the cap 25411 along the folded edges 25415 of the cap 25411. In at least one instance, openings, or apertures, are defined in the cap 25411 which allow the support plates 25412 to be directly welded to the cap 25411 so that the support plates 25412 are held securely in position relative to the cap 25411. As a result of the above, the anvil jaw 25410 is stiff and resists bending during the staple firing stroke. The support plates 25412 are positioned and arranged such that a longitudinal slot 25414 is defined between the support plates 25412 and such that a longitudinal cavity 25416 is defined between the support plates 25412 and the cap 25411. The longitudinal slot 25414 and the longitudinal cavity 25416 are sized and configured to receive a tissue cutting knife therein. Each support plate 25412 comprises a longitudinal row of first, or innermost, staple forming pockets defined therein, a longitudinal row of second, or intermediate, staple forming pockets defined therein, and a longitudinal row of third, or outermost, staple forming pockets defined therein.

Figure 62:
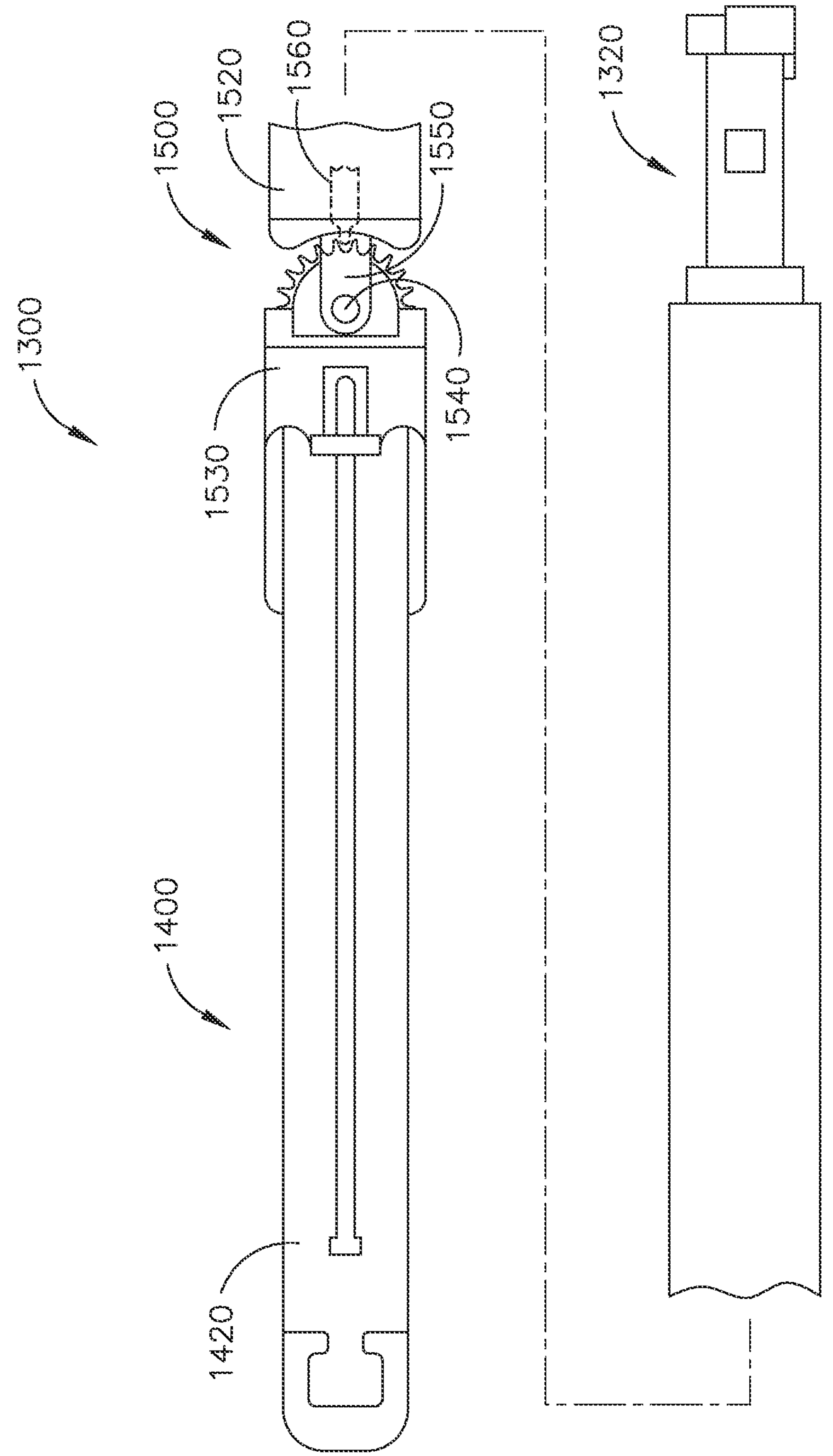
FIG. 62 is an elevational view of a loading unit comprising an articulation joint in accordance with at least one embodiment.
Figure 63:
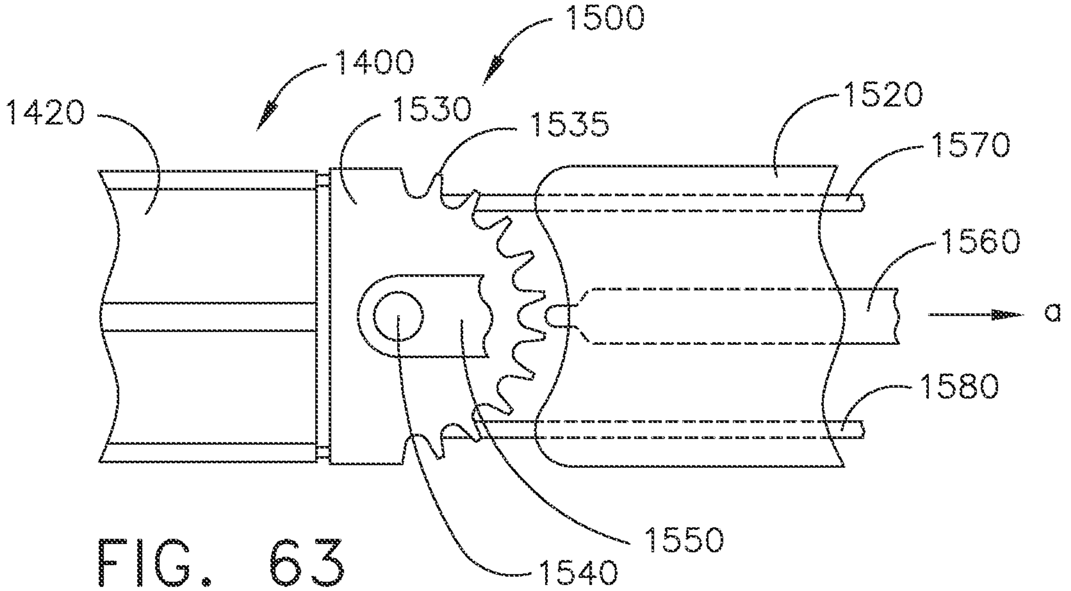
FIG. 63 is a detail view of the articulation joint of FIG. 62 illustrated in an unarticulated condition.
Figure 64:
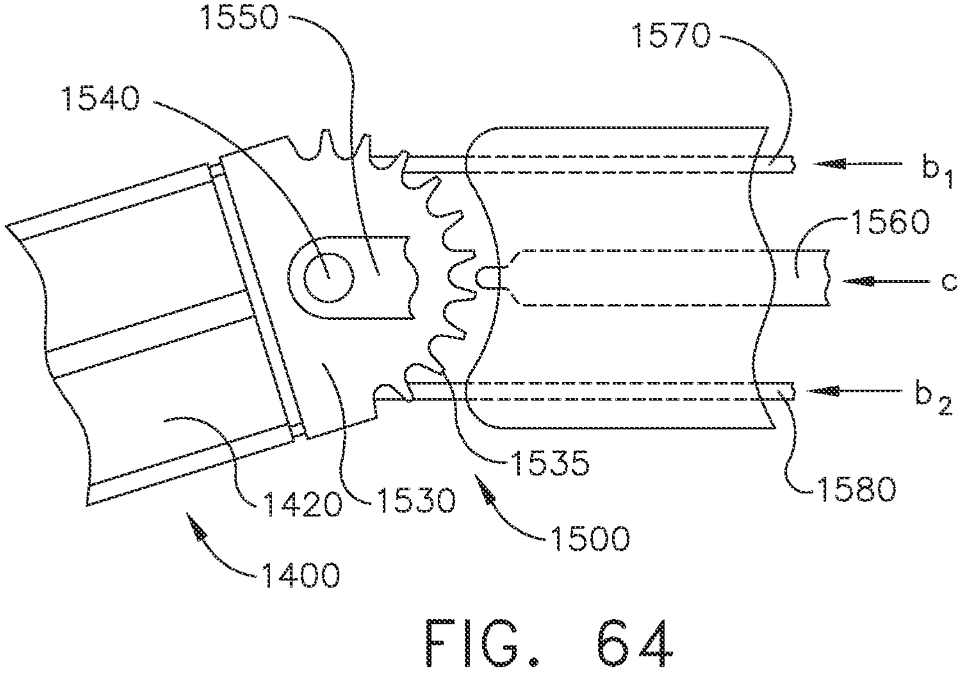
FIG. 64 is a detail view of the articulation joint of FIG. 62 illustrated in an articulated condition.

As mentioned above, referring again to FIG. 1, the loading unit 1300 comprises an articulation joint 1500. Referring now to FIG. 62, the loading unit 1300 comprises a proximal shaft portion 1520 and a distal shaft portion 1530 connected by two links 1550 that pin the distal shaft portion 1530 to the proximal shaft portion 1520 but permit the distal shaft portion 1530 to rotate, or articulate, relative to the proximal shaft portion 1520, as illustrated in FIG. 64. The distal end of each link 1550 is pinned to the distal shaft portion 1530 by a pin 1540 and, similarly, the proximal end of each link 1550 is pinned to the proximal shaft portion 1520 by another pin 1540. The loading unit 1300 further comprises a first articulation actuator 1570 connected to a first side of the distal shaft portion 1530 and a second articulation actuator 1580 connected to a second side of the distal shaft portion 1530. The loading unit 1300 further comprises an articulation lock 1560 configured to be engaged with an annular array of lock teeth 1535 defined on the distal shaft portion 1530 when the articulation lock 1560 is in a locked position and disengaged from the distal shaft portion 1530 when the articulation lock 1560 is in an unlocked position (FIGS. 63 and 64). When the articulation lock 1560 is in its unlocked position (FIGS. 63 and 64), one or both of the articulation actuators 1570 can be pushed and/or pulled to articulate the end effector 1400 of the loading unit about the articulation joint 1500. In various embodiments, the articulation actuators 1560 and 1570 are coupled to an articulation input actuator 1510 (FIG. 3) which is rotatable in a first direction to push the first articulation actuator 1570 distally and pull the second articulation actuator 1580 proximally to rotate the end effector 1400 in a first direction and, similarly, rotatable in a second direction to pull the first articulation actuator 1570 proximally and push the second articulation actuator 1580 distally to rotate the end effector 1400 in a second direction. When the clinician is satisfied with the orientation of the end effector 1400, the clinician can move the articulation lock 1560 into its locked position to prevent the end effector 1400 from rotating. The entire disclosures of U.S. Pat. No. 9,186,142, entitled SURGICAL INSTRUMENT END EFFECTOR ARTICULATION DRIVE WITH PINION AND OPPOSING RACKS, and U.S. Pat. No. 8,353,437, entitled SURGICAL STAPLING INSTRUMENT WITH A GEARED RETURN MECHANISM, which issued on Jan. 15, 2013 are incorporated herein by reference.

Figure 65:
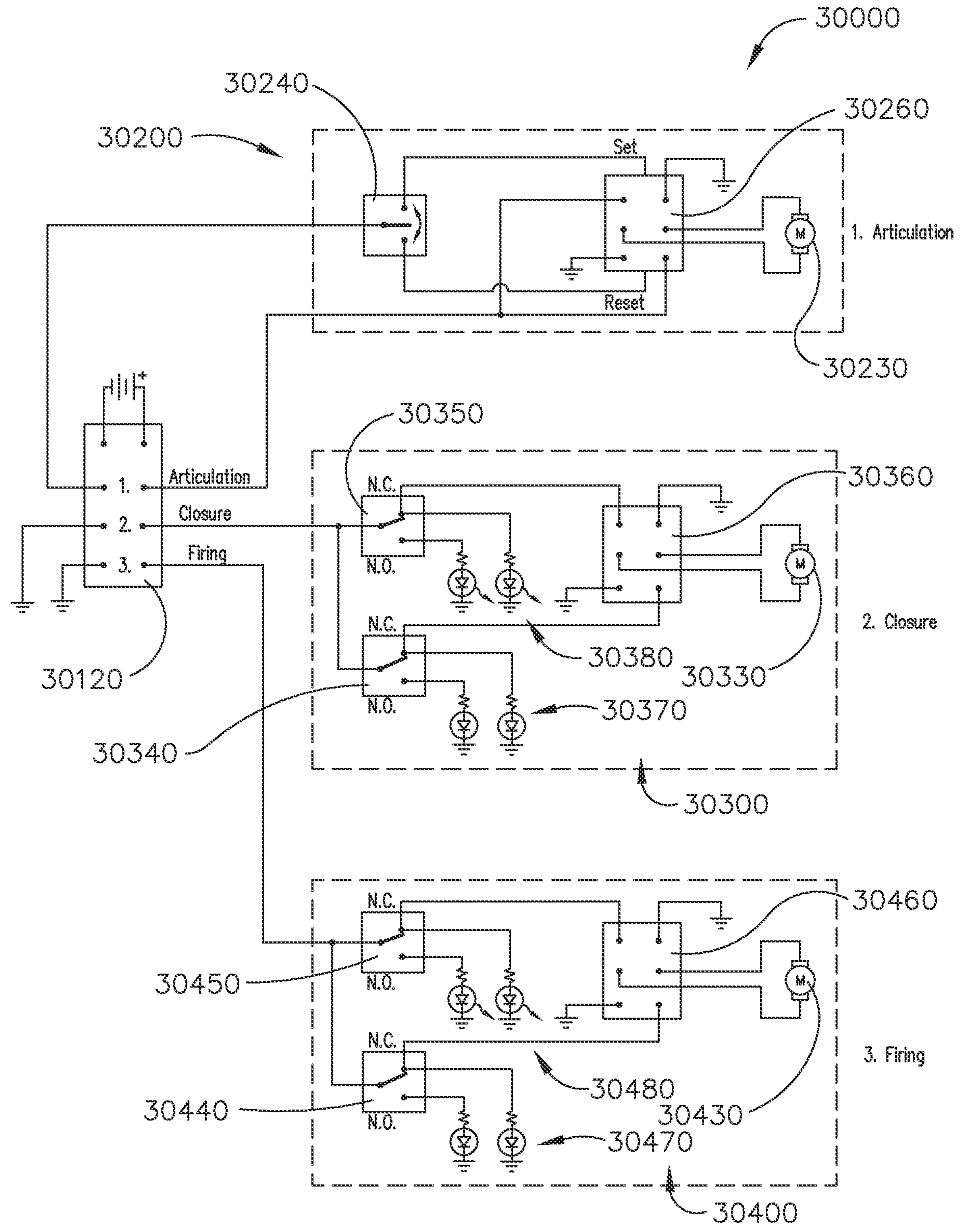
FIG. 65 is a control schematic of a stapling instrument in accordance with at least one embodiment.

A schematic representation of a surgical stapling instrument 30000 is illustrated in FIG. 65. The stapling instrument 30000 comprises three independent motor-driven actuation systems—a first actuation system 30200 for articulating an end effector of the stapling instrument 30000, a second actuation system 30300 for closing the end effector, and a third actuation system 30400 for performing a staple firing stroke. The stapling instrument 30000 further comprises a three-position switch 30120 for controlling the actuation systems 30200, 30300, and 30400. When the switch 30120 is in a first position, power from a power source, such as a battery, for example, is available to operate the first, or articulation, actuation system 30200. The articulation actuation system 30200 comprises an electric motor 30230 that is controlled by a directional switch 30240 and a relay switch 30260 with a set-reset function. When the switch 30120 is in a second position, power from the power source is available to operate the second, or closure, actuation system 30300. The closure actuation system 30300 comprises an electric motor 30330 that is controlled by an end-of-travel sensor 30340, a beginning-of-travel sensor 30350, and a momentary switch 30360. The closure actuation system 30300 further comprises indicator arrays 30370 and 30380 which comprise light emitting diodes (LEDs) that indicate the status of the closure actuation system. When the switch 30120 is in a third position, power from the power source is available to operate the third, or staple firing, actuation system 30400. The staple firing actuation system 30400 comprises an electric motor 30430 that is controlled by an end-of-travel sensor 30440, a beginning-of-travel sensor 30450, and a momentary switch 30460. The staple firing actuation system 30400 further comprises indicator arrays 30470 and 30480 which comprise light emitting diodes (LEDs) that indicate the status of the staple firing actuation system.

Figure 66:
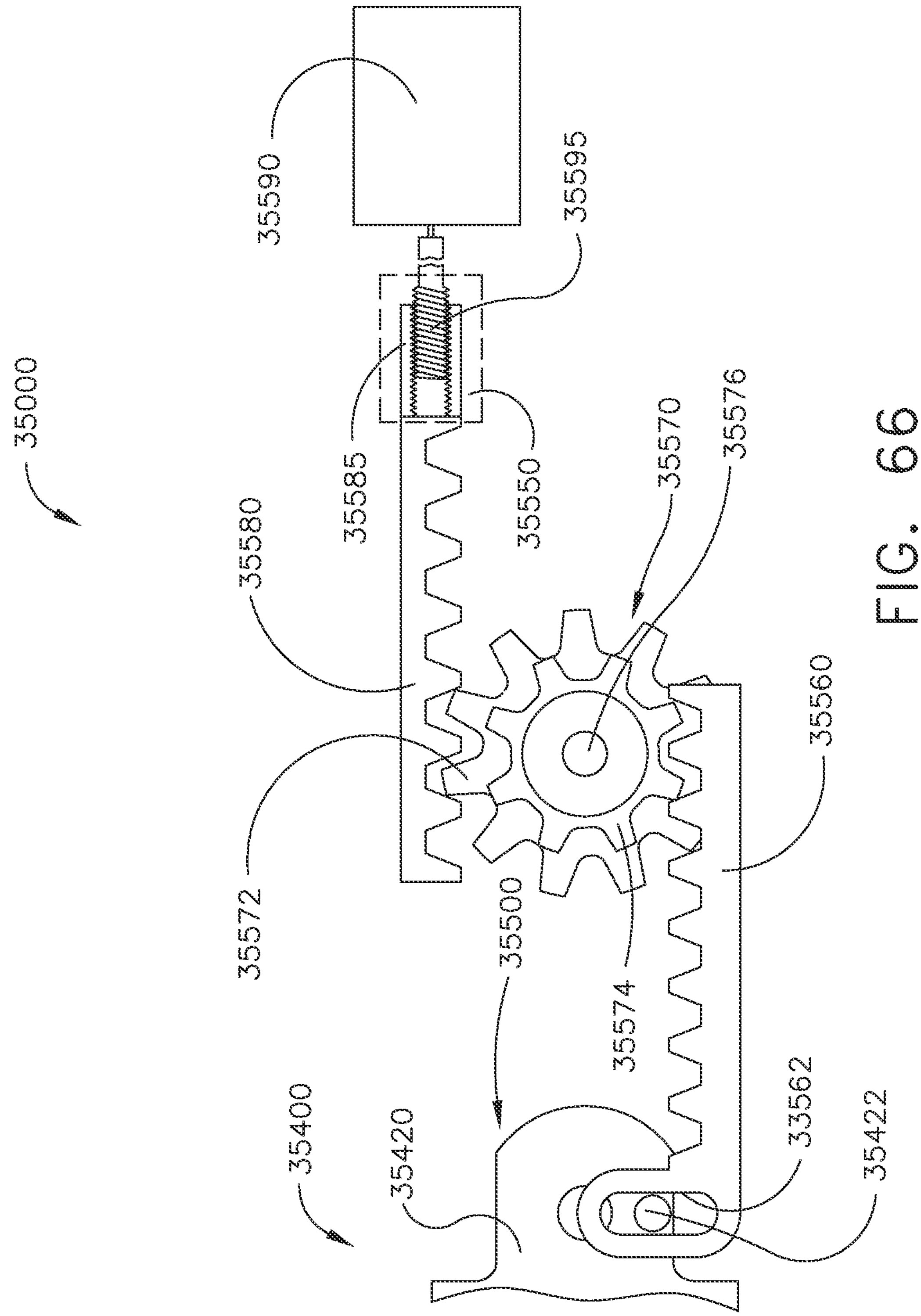
FIG. 66 is a schematic of a stapling instrument comprising an articulation joint and an articulation drive including a load limiting interface.

Further to the above, a surgical stapling instrument 35000 comprising an independent articulation system is illustrated in FIG. 66. The stapling instrument 35000 is similar to the stapling instruments 1000, 2000, 30000 and other stapling instruments disclosed herein. The stapling instrument 35000 comprises an end effector 35400 which is rotatable about an articulation joint 35500 by a motor-driven articulation drive. The articulation drive comprises an electric motor 35590 comprising a rotatable output 35595. The rotatable output 35595 comprises a helical or worm gear, for example, but can comprise any suitable configuration. The rotatable output 35595 is nested within a threaded socket 35585 of a proximal articulation drive rod 35580 and, when the rotatable output 35595 is rotated in a first direction, the proximal articulation drive rod 35580 is advanced distally to articulate the end effector 35400 in a first direction. Similarly, the proximal articulation drive rod 35580 is retracted proximally to articulate the end effector 35400 in a second direction when the rotatable output 35595 is rotated in a second, or opposite direction. As discussed in greater detail below, the motion of the proximal articulation drive rod 35580 is transmitted to the end effector 35400 by a transfer gear 35570 and a distal articulation rod 35570.

Further to the above, the proximal articulation drive rod 35580 comprises a rack of teeth operably engaged with a first gear perimeter 35572 of the transfer gear 35570 such that the longitudinal motion of the proximal articulation drive rod 35580 rotates the transfer gear 35570. The transfer gear 35570 is rotatably mounted to a shaft frame of the stapling instrument 35000 about a pin 35576 and further comprises a second gear perimeter 35574 operably engaged with the distal articulation drive rod 35560 such that the rotation of the transfer gear 35570 translates the distal articulation drive rod 35560. The distal articulation drive rod 35560 comprises an elongate opening 35562 defined therein including a sidewall which is configured to transmit the translation of the distal articulation drive rod 35560 to a frame 35420 of the end effector 35400 through a drive pin 35422 that extends from the frame 35420 and extends into the elongate opening 35562. Notably, the distal articulation drive rod 35560 extends across the articulation joint 35500 and, as a result, the translation of the distal articulation drive rod 35560 rotates the end effector 35400 about the articulation joint 35500.

As discussed above, the rotatable output 35595 of the motor 35590 is nested within the threaded socket 35585 of the proximal articulation drive rod 35580 to transfer the rotational motion of the output 35595 to the proximal articulation drive rod 35580. Notably, though, the threaded socket 35585 does not entirely enclose the rotatable output 35595. Instead, the threaded socket 35585 only engages half, or about half, of the rotatable output 35595. As a result, it is possible for the threaded socket 35585 and the rotatable output 35595 to disengage from one another when the load transmitted therebetween exceeds a threshold. Such instances can occur when the motion of the end effector 35400 is blocked, for example, and the force needed to drive the end effector 35400 increases above the amount of force ordinarily needed to articulate the end effector 35400, which is usually low. When the threaded socket 35585 disconnects from the rotatable output 35595, the articulation drive is no longer driven by the motor 35590. The articulation drive further comprises an elastic sleeve 35550 surrounding or encompassing the interface between the threaded socket 35585 and the rotatable output 35595 that is configured to re-seat or re-engage the threaded socket 35585 and the rotatable output 35595 when the load transmitted through the firing drive falls back below the threshold. The elastic sleeve 35550 is comprised of rubber, for example, but could be comprised of any suitable material. When the threaded socket 35585 decouples from the rotatable output 35595, the elastic sleeve 35550 resiliently expands to accommodate the decoupling of the threaded socket 35585 and acts to resiliently contract to re-engage the threaded socket 35585 with the rotatable output 35595.

In various embodiments, further to the above, an articulation drive system can comprise one or more resilient features engaged with, or engageable with, the end effector 35400 which resist, but permit, the rotation of the end effector 35400. Such resilient features can prevent, or at least inhibit, small unintentional movements of the end effector 35400.

In various embodiments, further to the above, a surgical stapling instrument can comprise one motor that is operable to drive more than one drive system of the stapling instrument. In at least one such embodiment, the stapling instrument is switchable between a first configuration in which the motor is operable to drive the articulation drive system and a second configuration in which the motor is operable to drive the staple firing drive system, for example. The entire disclosure of U.S. Pat. No. 9,101,358, entitled ARTICULATABLE SURGICAL INSTRUMENT COMPRISING A FIRING DRIVE, which issued on Aug. 11, 2015, is incorporated by reference herein. The entire disclosure of U.S. Pat. No. 5,865,361, entitled SURGICAL STAPLING APPARATUS, which issued on Feb. 2, 2019, is incorporated by reference herein.

As discussed above, referring again to FIG. 1, the shaft 1200 of the stapling instrument 1000 is rotatable relative to the handle 1100 about a longitudinal axis. More specifically, the stapling instrument 1000 comprises a rotation joint positioned within the nozzle of the shaft that permits the shaft 1200 to rotate relative to the handle 1100. In various instances, a considerable amount of friction can be present within the rotation joint which prevents, or at least inhibits, the shaft 1200 from unintentionally rotating relative to the handle 1100. In at least one embodiment, the shaft 1200 comprises a spring-loaded lock element biased into engagement with the handle 1100 which holds the shaft 1200 in position relative to the handle 1100. The handle 1100 comprises a circumferential ring of lock recesses extending around the outer housing which are each configured to receive the spring-loaded lock element therein. The interaction between the spring-loaded lock element and a lock recess resists the rotation of the shaft 1200 relative to the handle 1100. This resistance can be overcome by the clinician to rotate the shaft 1200 without having to release, or hold open, the spring-loaded lock element. That said, the clinician can hold open the spring-loaded lock element to freely rotate the shaft 1200 relative to the handle 1100. In various alternative embodiments, the spring-loaded lock element is mounted to the handle 1100 and the circumferential ring of lock recesses is defined on the outer housing of the shaft 1200.

The surgical instrument systems described herein have been described in connection with the deployment and deformation of staples; however, the embodiments described herein are not so limited. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083;

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A surgical stapling instrument, comprising:

an end effector, comprising:

a first jaw;

a second jaw rotatable relative to the first jaw between an open position and a closed position; and a staple cartridge comprising staples removably stored therein; and a firing drive, comprising:

a rack comprising teeth;

a motor comprising a rotatable output;

a pawl configured to drive the rack distally; and a crank operably coupled to the pawl, wherein the crank is selectively rotatable by the rotatable output about:

a first pivot, wherein a first length is defined between the first pivot and the pawl; and a second pivot, wherein a second length is defined between the second pivot and the pawl, and wherein the second length is different than the first length;

wherein the second jaw is rotatable toward the closed position based on the crank rotating about the first pivot, and wherein the staples are deployable from the staple cartridge based on the crank rotating about the second pivot.

2. The surgical stapling instrument of claim 1, further comprising:
- a shaft extending from the end effector; and
- a housing extending from the shaft.

3. The surgical stapling instrument of claim 2, wherein the housing comprises a handle.

4. The surgical stapling instrument of claim 1, wherein the crank defines:
- a first aperture at the first pivot; and
- a second aperture at the second pivot.

5. The surgical stapling instrument of claim 4, further comprising:
- a first pin;
- a second pin; and
- a mode switch, configurable between:
- a first state in which the first pin extends within the first aperture, wherein the crank is rotatable about the first pivot based on the mode switch being in the first state; and
- a second state in which the second pin extends within the second aperture, wherein the crank is rotatable about the second pivot based on the mode switch being in the second state.

6. The surgical stapling instrument of claim 5, further comprising a controller in operable communication with the motor and the mode switch.

7. The surgical stapling instrument of claim 1, further comprising a spring configured to resist rotation of the crank about the first pivot and the second pivot.

8. The surgical stapling instrument of claim 1, wherein the pawl is configured to drive the rack distally based on the crank rotating in a first direction, and wherein the pawl is configured to slide relative to the rack based on the crank rotating in a second direction.

9. A surgical stapling instrument, comprising:
- an end effector, comprising:
- a first jaw;
- a second jaw rotatable relative to the first jaw between an open position and a closed position; and
- a staple cartridge comprising staples removably stored therein; and
- a firing drive, comprising:
- a motor;
- a pawl; and
- a crank, wherein the pawl is driveable by the crank, and wherein the crank is selectively rotatable by the motor about:
- a first pivot, wherein a first length is defined between the first pivot and the pawl; and
- a second pivot, wherein a second length is defined between the second pivot and the pawl, and wherein the second length is different than the first length;
- wherein the second jaw is rotatable toward the closed position based on the crank rotating about the first pivot, and wherein the staples are deployable from the staple cartridge based on the crank rotating about the second pivot.

10. The surgical stapling instrument of claim 9, further comprising:
- a shaft extending from the end effector; and
- a housing extending from the shaft.

11. The surgical stapling instrument of claim 10, wherein the housing comprises a handle.

12. The surgical stapling instrument of claim 9, wherein the crank defines:
- a first aperture at the first pivot; and
- a second aperture at the second pivot.

13. The surgical stapling instrument of claim 12, further comprising:
- a first pin;
- a second pin; and
- a mode switch, configurable between:
- a first state in which the first pin extends within the first aperture, wherein the crank is rotatable about the first pivot based on the mode switch being in the first state; and
- a second state in which the second pin extends within the second aperture, wherein the crank is rotatable about the second pivot based on the mode switch being in the second state.

14. The surgical stapling instrument of claim 13, further comprising a controller in operable communication with the motor and the mode switch.

15. The surgical stapling instrument of claim 9, further comprising a spring configured to resist rotation of the crank about the first pivot and the second pivot.

16. The surgical stapling instrument of claim 9, wherein the pawl is configured to drive a rack distally based on the crank rotating in a first direction, and wherein the pawl is configured to slide relative to the rack based on the crank rotating in a second direction.

* * * * *